(12) United States Patent
Caferro et al.

(10) Patent No.: US 8,957,068 B2
(45) Date of Patent: Feb. 17, 2015

(54) 3-PYRIMIDIN-4-YL-OXAZOLIDIN-2-ONES AS INHIBITORS OF MUTANT IDH

(71) Applicants: Thomas Raymond Caferro, Abington, MA (US); Young Shin Cho, Cambridge, MA (US); Abran Q. Costales, El Cerrito, CA (US); Huangshu Lei, Chongqing (CN); Francois Lenoir, Waltham, MA (US); Julian Roy Levell, Arlington, MA (US); Gang Liu, Waltham, MA (US); Mark G. Palermo, Rindge, NH (US); Keith Bruce Pfister, San Ramon, CA (US); Martin Sendzik, San Mateo, CA (US); Cynthia Shafer, El Sobrante, CA (US); Michael David Shultz, Lexington, MA (US); Troy Smith, Nashua, NH (US); James Clifford Sutton, Pleasanton, CA (US); Bakary-Barry Toure, Weston, MA (US); Fan Yang, West Roxbury, MA (US); Qian Zhao, El Cerrito, CA (US)

(72) Inventors: Thomas Raymond Caferro, Abington, MA (US); Young Shin Cho, Cambridge, MA (US); Abran Q. Costales, El Cerrito, CA (US); Huangshu Lei, Chongqing (CN); Francois Lenoir, Waltham, MA (US); Julian Roy Levell, Arlington, MA (US); Gang Liu, Waltham, MA (US); Mark G. Palermo, Rindge, NH (US); Keith Bruce Pfister, San Ramon, CA (US); Martin Sendzik, San Mateo, CA (US); Cynthia Shafer, El Sobrante, CA (US); Michael David Shultz, Lexington, MA (US); Troy Smith, Nashua, NH (US); James Clifford Sutton, Pleasanton, CA (US); Bakary-Barry Toure, Weston, MA (US); Fan Yang, West Roxbury, MA (US); Qian Zhao, El Cerrito, CA (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 14/347,481

(22) PCT Filed: Sep. 26, 2012

(86) PCT No.: PCT/IB2012/055133
§ 371 (c)(1),
(2) Date: Mar. 26, 2014

(87) PCT Pub. No.: WO2013/046136
PCT Pub. Date: Apr. 4, 2013

(65) Prior Publication Data
US 2014/0235620 A1 Aug. 21, 2014

Related U.S. Application Data

(60) Provisional application No. 61/539,553, filed on Sep. 27, 2011.

(51) Int. Cl.
*C07D 413/04* (2006.01)
*C07D 413/14* (2006.01)
(Continued)

(52) U.S. Cl.
CPC ............ *C07D 413/14* (2013.01); *C07D 413/04* (2013.01);
(Continued)

(58) Field of Classification Search
USPC .......... 540/575; 544/122, 295, 296, 323, 324; 514/218, 235.8, 249, 252.19, 255.05, 514/275
See application file for complete search history.

(56) References Cited

U.S. PATENT DOCUMENTS

| | | |
|---|---|---|
| 3,975,384 A | 8/1976 | Narr et al. |
| 4,929,726 A | 5/1990 | Strekowski et al. |
| 5,358,945 A | 10/1994 | Mizuchi et al. |
| 5,786,355 A | 7/1998 | Konno et al. |

(Continued)

FOREIGN PATENT DOCUMENTS

| | | |
|---|---|---|
| AU | 2010291318 | 3/2011 |
| CN | 103483345 A | 1/2014 |

(Continued)

OTHER PUBLICATIONS

Ali et al., Essential role for the p110delta phosphoinositide 3-kinase in the allergic response. Nature. Oct. 21, 2004;431(7011):1007-11.
(Continued)

*Primary Examiner* — Deepak Rao
(74) *Attorney, Agent, or Firm* — Stephen Johnson

(57) ABSTRACT

The invention is directed to a compound of formula (I) or a pharmaceutically acceptable salt thereof, wherein $R^1$-$R^6$ are defined herein. The invention is also directed to compositions containing a compound of formula (I) and to the use of such compounds in the inhibition of mutant IDH proteins having a neomorphic activity. The invention is further directed to the use of a compound of formula (I) in the treatment of diseases or disorders associated with such mutant IDH proteins including, but not limited to, cell-proliferation disorders, such as cancer.

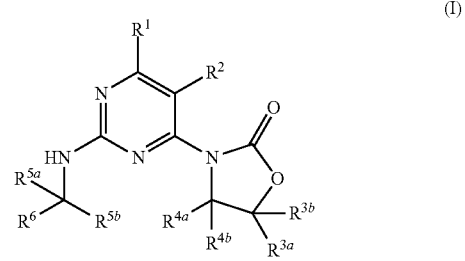

(I)

28 Claims, No Drawings

(51) Int. Cl.
*A61K 31/506* (2006.01)
*C07D 487/04* (2006.01)
*C07D 471/04* (2006.01)
*C07D 487/08* (2006.01)
*C07D 417/14* (2006.01)
*C07D 498/10* (2006.01)

(52) U.S. Cl.
CPC ........... *C07D 487/04* (2013.01); *C07D 471/04* (2013.01); *C07D 487/08* (2013.01); *C07D 417/14* (2013.01); *C07D 498/10* (2013.01)
USPC ... 514/218; 514/235.8; 514/249; 514/252.19; 514/255.05; 514/275; 540/575; 544/122; 544/295; 544/296; 544/323; 544/324

(56) References Cited

U.S. PATENT DOCUMENTS

| | | |
|---|---|---|
| 5,976,758 A | 11/1999 | Fukui et al. |
| 5,990,105 A | 11/1999 | Boes et al. |
| 6,251,900 B1 | 6/2001 | Kawashima et al. |
| 6,288,228 B1 | 9/2001 | Henkin et al. |
| 6,495,558 B1 | 12/2002 | Armistead et al. |
| 6,599,926 B2 | 7/2003 | Pinto et al. |
| 6,603,000 B2 | 8/2003 | Yee et al. |
| 6,743,788 B2 | 6/2004 | Cirillo et al. |
| 6,846,928 B2 | 1/2005 | Bebbington et al. |
| 7,045,519 B2 | 5/2006 | Nuss et al. |
| 7,091,343 B2 | 8/2006 | Bebbington et al. |
| 7,179,826 B2 | 2/2007 | Bebbington et al. |
| 7,423,148 B2 | 9/2008 | Nuss et al. |
| 7,566,712 B2 | 7/2009 | Bakthavatchalam et al. |
| 7,652,009 B2 | 1/2010 | Kim et al. |
| 7,767,669 B2 | 8/2010 | Nuss et al. |
| 7,893,063 B2 | 2/2011 | Pass et al. |
| 7,957,951 B2 | 6/2011 | Foster et al. |
| 8,173,647 B2 | 5/2012 | Atallah et al. |
| 8,217,035 B2 | 7/2012 | Burger et al. |
| 8,563,549 B2 | 10/2013 | Burger et al. |
| 8,575,338 B2 | 11/2013 | Tsuzuki et al. |
| 2004/0002496 A1 | 1/2004 | Bebbington et al. |
| 2004/0009974 A1 | 1/2004 | Bebbington et al. |
| 2004/0009981 A1 | 1/2004 | Bebbington et al. |
| 2005/0014753 A1 | 1/2005 | Ding et al. |
| 2009/0018134 A1 | 1/2009 | Pike et al. |
| 2010/0048547 A1 | 2/2010 | Atallah et al. |
| 2010/0249126 A1 | 9/2010 | Burger et al. |
| 2011/0195966 A1 | 8/2011 | Garcia-Echeverria et al. |
| 2011/0288065 A1* | 11/2011 | Fujihara et al. .......... 514/210.02 |
| 2012/0225859 A1 | 9/2012 | Burger et al. |
| 2013/0123289 A1 | 5/2013 | Yang et al. |
| 2013/0143862 A1 | 6/2013 | Ashcraft et al. |
| 2013/0150368 A1 | 6/2013 | Ashcraft et al. |
| 2013/0225574 A1 | 8/2013 | Caravatti et al. |
| 2014/0135330 A1 | 5/2014 | Fairhurst et al. |

FOREIGN PATENT DOCUMENTS

| | | |
|---|---|---|
| CN | 103694218 A | 4/2014 |
| DE | 2341925 A1 | 3/1975 |
| EP | 0 330 263 A1 | 8/1989 |
| EP | 0 459 830 A1 | 12/1991 |
| EP | 0 767 170 B1 | 10/2002 |
| EP | 1 277 738 A1 | 1/2003 |
| EP | 1 277 741 A1 | 1/2003 |
| EP | 2 394 999 A1 | 12/2011 |
| EP | 2 560 488 A1 | 2/2013 |
| EP | 2 563 365 A1 | 3/2013 |
| GB | 0 581 334 A | 10/1946 |
| GB | 2 431 156 A | 4/2007 |
| JP | 49-021148 B | 2/1974 |
| JP | 49-021149 B | 2/1974 |
| JP | 11-158073 A2 | 6/1999 |
| JP | 2001-089452 A | 4/2001 |
| WO | 89/00599 A1 | 1/1989 |
| WO | 99/19305 A2 | 4/1999 |
| WO | 99/65897 A1 | 12/1999 |
| WO | 00/43373 A2 | 7/2000 |
| WO | 01/00207 A1 | 1/2001 |
| WO | 01/00213 A1 | 1/2001 |
| WO | 01/00214 A1 | 1/2001 |
| WO | 01/05783 A1 | 1/2001 |
| WO | 01/60816 A1 | 8/2001 |
| WO | WO 01/60816 * | 8/2001 |
| WO | 01/72745 A1 | 10/2001 |
| WO | 01/83456 A1 | 11/2001 |
| WO | 02/20495 A2 | 3/2002 |
| WO | 02/22606 A1 | 3/2002 |
| WO | 02/22608 A1 | 3/2002 |
| WO | 02/36586 A1 | 5/2002 |
| WO | 02/062766 A2 | 8/2002 |
| WO | 02/062789 A1 | 8/2002 |
| WO | 02/064096 A2 | 8/2002 |
| WO | 02/102313 A2 | 12/2002 |
| WO | 03/030909 A1 | 4/2003 |
| WO | 2004/000820 A2 | 12/2003 |
| WO | 2004/029204 A2 | 4/2004 |
| WO | 2004/032716 A2 | 4/2004 |
| WO | 2004/039788 A1 | 5/2004 |
| WO | 2004/048365 A1 | 6/2004 |
| WO | 2004/084824 A2 | 10/2004 |
| WO | 2004/092196 A2 | 10/2004 |
| WO | 2005/007648 A2 | 1/2005 |
| WO | 2005/009977 A1 | 2/2005 |
| WO | 2005/028444 A1 | 3/2005 |
| WO | 2005/099711 A1 | 10/2005 |
| WO | 2006/005914 A1 | 1/2006 |
| WO | 2006/026135 A2 | 3/2006 |
| WO | 2006/065872 A1 | 6/2006 |
| WO | 2006/071538 A2 | 7/2006 |
| WO | 2006/071960 A2 | 7/2006 |
| WO | 2006/078992 A2 | 7/2006 |
| WO | 2006/090167 A2 | 8/2006 |
| WO | 2006/113704 A2 | 10/2006 |
| WO | 2007/080382 A1 | 7/2007 |
| WO | 2007/084786 A1 | 7/2007 |
| WO | 2008/080937 A1 | 7/2008 |
| WO | WO 2008/080937 * | 7/2008 |
| WO | 2008/098058 A1 | 8/2008 |
| WO | 2009/007748 A2 | 1/2009 |
| WO | 2009/066084 A1 | 5/2009 |
| WO | 2009/109605 A1 | 9/2009 |
| WO | 2009/118324 A1 | 10/2009 |
| WO | 2009/120094 A2 | 10/2009 |
| WO | 2009/125870 A1 | 10/2009 |
| WO | 2010/020432 A2 | 2/2010 |
| WO | 2010/049481 A1 | 5/2010 |
| WO | 2010/052569 A2 | 5/2010 |
| WO | 2010/068863 A2 | 6/2010 |
| WO | 2010/090290 A1 | 8/2010 |
| WO | 2010/090344 A1 | 8/2010 |
| WO | 2010/105243 A1 | 9/2010 |
| WO | 2010/120094 A2 | 10/2010 |
| WO | 2010/135070 A1 | 11/2010 |
| WO | 2011/005119 A1 | 1/2011 |
| WO | 2011/017296 A1 | 2/2011 |
| WO | 2011/026835 A1 | 3/2011 |
| WO | 2011/031896 A2 | 3/2011 |
| WO | 2011/072174 A1 | 6/2011 |
| WO | 2011/114275 A1 | 9/2011 |
| WO | 2011/133888 A1 | 10/2011 |
| WO | 2011/143160 A2 | 11/2011 |
| WO | 2012/009678 A1 | 1/2012 |
| WO | 2012/044727 A2 | 4/2012 |
| WO | 2012/054535 A2 | 4/2012 |
| WO | 2012/055942 A1 | 5/2012 |
| WO | 2012/109423 A1 | 8/2012 |
| WO | 2012/171337 A1 | 12/2012 |
| WO | 2013/030368 A1 | 3/2013 |
| WO | 2013/052395 A1 | 4/2013 |
| WO | 2013/124826 A1 | 8/2013 |
| WO | 2013/173283 A1 | 11/2013 |

(56) References Cited

FOREIGN PATENT DOCUMENTS

| | | |
|---|---|---|
| WO | 2013/184621 A1 | 12/2013 |
| WO | 2014/028566 A1 | 2/2014 |
| WO | 2014/064058 A1 | 5/2014 |

OTHER PUBLICATIONS

Amary et al., Oilier disease and Maffucci syndrome are caused by somatic mosaic mutations of IDH1 and IDH2. Nat Genet. Nov. 6, 2011;43(12):1262-5.
Amine, Utilities of 4-(4'-Benzyl Phenyl)-6-Arylpyrimi-dine-2-Thiones for the synthesis of biologically active condensed and non-condensed hetero-cycles. Egypt J Chem. 1998;41(1-6):267-76.
Andrisano, Pyrimidine. IV. Bollettino Scientifico della Facolta di Chimica Industriale di Bologna. 1947;5:48-51.
Angelo et al., Synthesis and anti-filarial activity of N-[4-[[4-alkoxy-3 [(dialkylamino)methyl]phenyl]amino]-2-pyrimidinyl]-N'-phenylguanidines. J Med Chem. Sep. 1983;26(9):1258-67.
Balant et al., Metabolic Considerations in Pro-drug Design. Burger's Medicinal Chemistry and Drug Discovery. 1995;1:975-7.
Balss et al., Analysis of the IDH1 codon 132 mutation in brain tumors. Acta Neuropathol. Dec. 2008;116(6):597-602. E-pub. Nov. 5, 2008.
Banker et al., Modern Pharmaceuticals. 3rd Edition. Marcel Dekker, New York. 1996:451, 596.
Bennet et al., Part XIV, Oncology. Cecil Textbook of Medicine. 20th Edition. W.B. Saunders, Philadelphia. 1996:1004-10.
Brown et al., Some Heterocyclic Analogues of Stilbenes. J Chem Soc. Jan. 1984:2147-53.
Bundy et al., Synthesis of 2,4-diaminopyrrolo[2,3-d]pyrimidines via thermal fisher indolization. Pyrazole formation with ytterbium triflate catalysis. J Heterocyclic Chem. Nov.-Dec. 2000;37:1471-7.
Bundy et al., Synthesis of novel 2,4-diaminopyrrolo-[2,3-d]pyrimidines with antioxidant, neuroprotective, and antiasthma activity. J Med Chem. Oct. 13, 1995;38(21):4161-3.
Buonamici et al., Interfering with resistance to smoothened antagonists by inhibition of the PI3K pathway in medulloblastoma. Sci. Transl. Med. Sep. 29, 2010;2(51):1-8.
Burger et al., Identification of NVP-BKM120 as a Potent, Selective, Orally Bioavailable Class I PI3 Kinase Inhibitor for Treating Cancer. ACS Med Chem. Lett. 2011;2(10):774-9.
Cabaj et al., Bromine-medicated addition of nucleophiles to the electron-rich pyrimidine subunit of triazad. J Org Chem. Aug. 1994; 59:5090-2.
Caine et al., Coagulopathic complications in breast cancer. Cancer. Oct. 2003;98(8):1578-86.
Chen et al, Activation of the mammalian target of rapamycin signalling pathway in epidermal tumours and its correlation with cyclin-dependent kinase 2. British Journal of Dermatology Aug. 2009; 160, pp442-445.
Clayton et al., A crucial role for the p110delta subunit of phosphatidylinositol 3-kinase in b cell development and activation. J Exp. Med. Sep. 9, 2000;196(6):753-63.
Crowder et al., Treating breast cancer through novel inhibitors of the phosphatidylinositol 3'-kinase pathway. Breast Cancer Res. 2005;7(5):212-4.
Dang et al., Cancer-associated IDH1 mutations produce 2-hydroxyglutarate. Nature. Dec. 10, 2009;462(7274):739-44.
Dang et al., IDH mutations in glioma and acute myeloid leukemia. Trends Mol. Med. Sep. 2010;16(9):387-97. E-pub. Aug. 5, 2010.
Dario et al, Targeting of the Tumor Suppressor GRHL3 by a miR-21-Dependent Proto-Oncogenic Network Results in PTEN Loss and Tumorigenesis. Cancer Cell Nov. 2011; 20(5): 635-648.
Essawy et al., Some reactions of 4-(2-Methoxynaphthyl)-6-(P-Chlorophenyl) Pyrimidin-2 (1H)-One and its corresponding 2-Chloro derivative. Egypt J Chem. 1994;37(4):413-21.
Falco et al., 2:4-diaminopyrimidines—a new series of antimalarials. Br J Pharmacol Chemother. Jun. 1951;6(2):185-200.
Font et al., Development of an efficient and straightforward methodology toward the synthesis of molecularly diverse 2,6-disubstituted 3,4-dihydropyrimidin-4(3H)-ones. Synthesis. Sep. 13, 2002:1833-42.
Gaal et al., Isocitrate dehydrogenase mutations are rare in pheochromocytomas and paragangliomas. J Clin Endocrinol Metab. Mar. 2010;95(3):1274-8. E-pub. Nov. 13, 2009.
Golub et al., Molecular classification of cancer: class discovery and class prediction by gene expression monitoring. Science. Oct. 15, 1999;286(5439):531-7.
Gross et al., Cancer-associated metabolite 2-hydroxyglutarate accumulates in acute myelogenous leukemia with isocitrate dehydrogenase 1 and 2 mutations. J Exp Med. Feb. 15, 2010; 207(2):339-44. E-pub. Feb. 8, 2010.
Hayden et al., Frequent IDH1 mutations in supratentorial primitive neuroectodermal tumors (sPNET) of adults but not children. Cell Cycle. Jun. 1, 2009;8(11):1806-7. E-pub. Jun. 30, 2009.
Jackson et al., PI 3-kinase p110beta: a new target for antithrombotic therapy. Nat Med. May 2005;11(5):507-14.
Jaworska et al., SAR applicability domain. Review of Methods for Assessing the Applicabilty Domains of SARS and QSARS. Sep. 27, 2004:1-8.
Jou et al., Essential, nonredundant role for the phosphoinositide 3-kinase p110delta in signaling by the B-cell receptor complex, Mol .Cell Biol. Dec. 2002;22(24):8580-91.
Katiyar et al., Syntheses of 2,4,6-trisubstituted pyrimidine derivatives as a new class of antifilarial topoisomerase II inhibitors. Bioorg Med Chem Lett. Jan. 3, 2005;15(1):47-50.
Kidwai et al., Base catalyzed pyrimidine synthesis using microwave. Bull Korean Chem Society. Nov. 2003;24(11):1575-8.
Kothari et al., A facile one pot conversion of 3',5'-dibromo-4'-hydroxy substituted chalcones to pyrimidine derivatives and their antibacterial and herbicidal activity. Indian Journal of Heterocyclic Chemistry. Apr.-Jun. 1999;8(4)285-8.
Kowalewski et al., Unfused heterobicycles as amplifiers of phleomycin. IV 4,5'-bipyrimidines with dimethylamino and/or dimethylaminoethylamino substituents. Australian Journal of Chem. 1981; 34(12):2929-33.
Kranendijket et al., IDH2 mutations in patients with D-2-hydroxyglutaric aciduria. Science. Oct. 15, 2010; 330(6002):336. Epub Sep. 16, 2010.
Lala et al., Role of nitric oxide in tumor progression: lessons from experimental tumors. Cancer Metastasis Rev. Mar. 1998;17(1):91-106.
Li et al., PIK3CA mutations in breast cancer are associated with poor outcome. Breast Cancer Research and Treatment. Mar. 2006;96(1):91-5.
Mamaev et al., Reaction kinetics of substituted 2-chloropyrimidines with piperdine. Reaktsionnaya Sposobnost Organicheskikh Soedinenii. 1968;5(3):824-37.
Mikhaleva et al., Pyrimidines. 70. Relative reactivities of the chlorine atoms of 2,2',4-trichloro-4',5-dipyrimidinyl in its reaction with piperidine. Chemistry of Heterocyclic Compounds. Jun. 1979;15(6):671-6.
Mikhaleva et al., Pyrimidines. 70. Relative reactivity of the chlorine atoms of 2,2',4-trichloro-4',5-bipyrimidine in the reaction with piperidine. Khimiya Geterotsiklicheskikh Soedinenii. 1979; 6:821-6.
Ming et al, UVB-induced ERK/AKT-dependent PTEN suppression promotes survival of epidermal keratinocytes. Jan. 2010; 29(4): 492-502.
Mokrosz et al., 4-(3-furyl)-2-(4-methylpiperazino)pyrimidines: Potent 5-HT2A receptor antagonists. Bioorganic & Medicinal Chemistry Letters. Jul. 1997;7(13):1635-8.
Mokrosz et al., Structure-activity relationship studies of CNS agents. Part 25. 4,6-Di(heteroaryl)-2-(Nmethylpiperazino) pyrimidines as new, potent 5-HT2A receptor ligands: a verification of the topographic model. Archiv der Pharmazie. Sep. 1995; 328(9):659-66.
Nahta et al., Signal transduction inhibitors in the treatment of breast cancer. Curr. Med. Chem. Anticancer Agents. May 2003;3(3):201-16.
Ouf et al., Preparation of Some Methyl Pyrimidines Expected to be Antimetabolites. Egyptian Journal of Pharmaceutical Science. 1973;14(2):180-95.

(56) References Cited

OTHER PUBLICATIONS

Pansuriya et al., Somatic mosaic IDH1 and IDH2 mutations are associated with enchondroma and spindle cell hemangioma in Ollier disease and Maffucci syndrome. Nat Genet. Nov. 6, 2011;43(12):1256-61.

Patani et al., Bioisosterism: A Rational Approach in Drug Design. Chem Rev. Dec. 1996;96(8):3147-76.

Reif et al., Cutting edge: differential roles for phosphoinositide 3-kinases, p110gamma and p110delta, in lymphocyte chemotaxis and homing. J. Immunol. Aug. 15, 2004;173(4):2236-40.

Salasche, Epidemiology of actinic keratoses and squamous cell carcinoma. J Am Acad Dermatol Jan. 2000;42:S4-7.

Sellner et al., Increased levels of 2-hydroxyglutarate in AML patients with IDH1-R132H and IDH2-R140Q mutations. Eur. J. Haematol. Nov. 2010; 85(5):457-9.

Sharma et al., A convenient one-pot synthesis of 2-substituted-4,6-diaryl pyrimidines. Indian Journal of Chem 38B. Aug. 1999: 966-8.

Shibata et al., Mutant IDH1 confers an in vivo growth in a melanoma cell line with BRAF mutation. Am J Pathol. Mar. 2011; 178(3):1395-402.

Silverman, The Organic Chemistry of Drug Design and Drug Action. 2nd Edition. Elsevier Academic Press. Jan. 26, 2004:29-34.

Sukhwal et al., A new route to 2-piperidino-4,6-diarylpyrimidines. Indian Journal of Heterocyclic Chemistry. Jul.-Sep. 1994;4:67-8.

Tani et al., 2,4,6-Trisubstituted pyrimidines. JP 49021148. May 30, 1974.

U.S. Office Action for U.S. Appl. No. 14/069,400 mailed Feb. 28, 2014.

U.S. Office Action for U.S. Appl. No. 14/208,015 filed Mar. 13, 2014.

Voskoglou-Nomikos et al., Clinical predictive value of the in vitro cell line, human xenograft, and mouse allograft preclinical cancer models. Clin Cancer Res. Sep. 15, 2003;9(11):4227-39.

Wolff, Burger's Medicinal Chemistry and Drug Discovery. 5th Edition. Wiley, New York. 1995;1:975-7.

\* cited by examiner

SEQUENCE LISTING

<160> NUMBER OF SEQ ID NOS: 3

<210> SEQ ID NO 1
<211> LENGTH: 434
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 1

```
Met Ala His His His His His Ser Ala Leu Glu Val Leu Phe
1               5                   10                  15

Gln Gly Pro Gly Met Ser Lys Lys Ile Ser Gly Ser Val Val Glu
            20                  25                  30

Met Gln Gly Asp Glu Met Thr Arg Ile Ile Trp Glu Leu Ile Lys Glu
            35                  40                  45

Lys Leu Ile Phe Pro Tyr Val Glu Leu Asp Leu His Ser Tyr Asp Leu
    50                  55                  60

Gly Ile Glu Asn Arg Asp Ala Thr Asn Asp Gln Val Thr Lys Asp Ala
65                  70                  75                  80

Ala Glu Ala Ile Lys Lys His Asn Val Gly Val Lys Cys Ala Thr Ile
                85                  90                  95

Thr Pro Asp Glu Lys Arg Val Glu Glu Phe Lys Leu Lys Gln Met Trp
            100                 105                 110

Lys Ser Pro Asn Gly Thr Ile Arg Asn Ile Leu Gly Gly Thr Val Phe
        115                 120                 125

Arg Glu Ala Ile Ile Cys Lys Asn Ile Pro Arg Leu Val Ser Gly Trp
    130                 135                 140

Val Lys Pro Ile Ile Ile Gly His His Ala Tyr Gly Asp Gln Tyr Arg
145                 150                 155                 160

Ala Thr Asp Phe Val Val Pro Gly Pro Gly Lys Val Glu Ile Thr Tyr
                165                 170                 175

Thr Pro Ser Asp Gly Thr Gln Lys Val Thr Tyr Leu Val His Asn Phe
            180                 185                 190

Glu Glu Gly Gly Gly Val Ala Met Gly Met Tyr Asn Gln Asp Lys Ser
        195                 200                 205

Ile Glu Asp Phe Ala His Ser Ser Phe Gln Met Ala Leu Ser Lys Gly
    210                 215                 220

Trp Pro Leu Tyr Leu Ser Thr Lys Asn Thr Ile Leu Lys Lys Tyr Asp
225                 230                 235                 240

Gly Arg Phe Lys Asp Ile Phe Gln Glu Ile Tyr Asp Lys Gln Tyr Lys
                245                 250                 255

Ser Gln Phe Glu Ala Gln Lys Ile Trp Tyr Glu His Arg Leu Ile Asp
            260                 265                 270

Asp Met Val Ala Gln Ala Met Lys Ser Glu Gly Gly Phe Ile Trp Ala
        275                 280                 285

Cys Lys Asn Tyr Asp Gly Asp Val Gln Ser Asp Ser Val Ala Gln Gly
    290                 295                 300

Tyr Gly Ser Leu Gly Met Met Thr Ser Val Leu Val Cys Pro Asp Gly
305                 310                 315                 320

Lys Thr Val Glu Ala Glu Ala Ala His Gly Thr Val Thr Arg His Tyr
                325                 330                 335

Arg Met Tyr Gln Lys Gly Gln Glu Thr Ser Thr Asn Pro Ile Ala Ser
            340                 345                 350

Ile Phe Ala Trp Thr Arg Gly Leu Ala His Arg Ala Lys Leu Asp Asn
        355                 360                 365

Asn Lys Glu Leu Ala Phe Phe Ala Asn Ala Leu Glu Glu Val Ser Ile
    370                 375                 380

Glu Thr Ile Glu Ala Gly Phe Met Thr Lys Asp Leu Ala Ala Cys Ile
385                 390                 395                 400

Lys Gly Leu Pro Asn Val Gln Arg Ser Asp Tyr Leu Asn Thr Phe Glu
                405                 410                 415
```

Phe Met Asp Lys Leu Gly Glu Asn Leu Lys Ile Lys Leu Ala Gln Ala
                420                 425                 430

Lys Leu

<210> SEQ ID NO 2
<211> LENGTH: 417
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Gly Pro Gly Met Ser Lys Lys Ile Ser Gly Ser Val Val Glu Met
1               5                   10                  15

Gln Gly Asp Glu Met Thr Arg Ile Ile Trp Glu Leu Ile Lys Glu Lys
            20                  25                  30

Leu Ile Phe Pro Tyr Val Glu Leu Asp Leu His Ser Tyr Asp Leu Gly
        35                  40                  45

Ile Glu Asn Arg Asp Ala Thr Asn Asp Gln Val Thr Lys Asp Ala Ala
50                  55                  60

Glu Ala Ile Lys Lys His Asn Val Gly Val Lys Cys Ala Thr Ile Thr
65                  70                  75                  80

Pro Asp Glu Lys Arg Val Glu Glu Phe Lys Leu Lys Gln Met Trp Lys
                85                  90                  95

Ser Pro Asn Gly Thr Ile Arg Asn Ile Leu Gly Gly Thr Val Phe Arg
            100                 105                 110

Glu Ala Ile Ile Cys Lys Asn Ile Pro Arg Leu Val Ser Gly Trp Val
        115                 120                 125

Lys Pro Ile Ile Ile Gly His His Ala Tyr Gly Asp Gln Tyr Arg Ala
    130                 135                 140

Thr Asp Phe Val Val Pro Gly Pro Gly Lys Val Glu Ile Thr Tyr Thr
145                 150                 155                 160

Pro Ser Asp Gly Thr Gln Lys Val Thr Tyr Leu Val His Asn Phe Glu
                165                 170                 175

Glu Gly Gly Gly Val Ala Met Gly Met Tyr Asn Gln Asp Lys Ser Ile
            180                 185                 190

Glu Asp Phe Ala His Ser Ser Phe Gln Met Ala Leu Ser Lys Gly Trp
        195                 200                 205

Pro Leu Tyr Leu Ser Thr Lys Asn Thr Ile Leu Lys Lys Tyr Asp Gly
    210                 215                 220

Arg Phe Lys Asp Ile Phe Gln Glu Ile Tyr Asp Lys Gln Tyr Lys Ser
225                 230                 235                 240

Gln Phe Glu Ala Gln Lys Ile Trp Tyr Glu His Arg Leu Ile Asp Asp
                245                 250                 255

Met Val Ala Gln Ala Met Lys Ser Glu Gly Gly Phe Ile Trp Ala Cys
            260                 265                 270

Lys Asn Tyr Asp Gly Asp Val Gln Ser Asp Ser Val Ala Gln Gly Tyr
        275                 280                 285

Gly Ser Leu Gly Met Met Thr Ser Val Leu Val Cys Pro Asp Gly Lys
    290                 295                 300

Thr Val Glu Ala Glu Ala Ala His Gly Thr Val Thr Arg His Tyr Arg
305                 310                 315                 320

Met Tyr Gln Lys Gly Gln Glu Thr Ser Thr Asn Pro Ile Ala Ser Ile
                325                 330                 335

```
Phe Ala Trp Thr Arg Gly Leu Ala His Arg Ala Lys Leu Asp Asn Asn
            340                 345                 350

Lys Glu Leu Ala Phe Phe Ala Asn Ala Leu Glu Glu Val Ser Ile Glu
        355                 360                 365

Thr Ile Glu Ala Gly Phe Met Thr Lys Asp Leu Ala Ala Cys Ile Lys
    370                 375                 380

Gly Leu Pro Asn Val Gln Arg Ser Asp Tyr Leu Asn Thr Phe Glu Phe
385                 390                 395                 400

Met Asp Lys Leu Gly Glu Asn Leu Lys Ile Lys Leu Ala Gln Ala Lys
                405                 410                 415

Leu

<210> SEQ ID NO 3
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 3

His His His His His His
1               5
```

3-PYRIMIDIN-4-YL-OXAZOLIDIN-2-ONES AS INHIBITORS OF MUTANT IDH

SEQUENCE LISTING

The instant application contains a Sequence Listing which has been submitted electronically in ASCII format and is hereby incorporated by reference in its entirety. Said ASCII copy, created on Jun. 18, 2014, is named PAT054800-US-PCT_SL.txt and is 8,478 bytes in size.

FIELD OF THE INVENTION

The present invention is directed to novel 3-pyrimidinyl-4-yl-oxazolidin-2-one compounds, compositions containing these compounds, the use of such compounds in the inhibition of mutant IDH proteins having a neomorphic activity and in the treatment of diseases or disorders associated with such mutant IDH proteins including, but not limited to, cell-proliferation disorders, such as cancer.

BACKGROUND OF THE INVENTION

Isocitrate dehydrogenase (IDH) is a key family of enzymes found in cellular metabolism. They are $NADP^+/NAD^+$ and metal dependent oxidoreductases of the enzyme class EC 1.1.1.42. The wild type proteins catalyze the oxidative decarboxylation of isocitrate to alpha-ketoglutarate generating carbon dioxide and NADPH/NADH in the process. They are also known to convert oxalosuccinate into alpha-ketoglutarate. Mutations in IDH1 (cytosolic) and IDH2 (mitochondrial) have been identified in multiple cancer types including, but not limited to, glioma, glioblastoma multiforme, paraganglioma, supratentorial primordial neuroectodermal tumors, acute myeloid leukemia (AML), prostate cancer, thyroid cancer, colon cancer, chondrosarcoma, cholangiocarcinoma, peripheral T-cell lymphoma, and melanoma. (See L. Deng et al., Trends Mol. Med., 2010, 16, 387; T. Shibata et al., Am. J. Pathol., 2011, 178(3), 1395; Gaal et al., J. Clin. Endocrinol. Metab. 2010; Hayden et al., Cell Cycle, 2009; Balss et al., Acta Neuropathol., 2008). The mutations have been found at or near key residues in the active site: G97D, R100, R132, H133Q, and A134D for IDH1, and R140 and R172 for IDH2. (See L. Deng et al., Nature, 2009, 462, 739; L. Sellner et al., Eur. J. Haematol., 2011, 85, 457).

These mutant forms of IDH are shown to have a neomorphic activity (also known as a gain of function activity), reducing alpha-ketoglutarate to 2-hydroxyglutarate (2-HG). (See P. S. Ward et al., Cancer Cell, 2010, 17, 225) In general, production of 2-HG is enantiospecific, resulting in generation of the D-enantiomer (also known as R enantiomer or R-2-HG). Normal cells have low native levels of 2-HG, whereas cells harboring these mutations in IDH1 or IDH2 show significantly elevated levels of 2-HG. High levels of 2-HG have been detected in tumors harboring the mutations. For example, high levels of 2-HG have been detected in the plasma of patients with mutant IDH containing AML. (See S. Gross et al., J. Exp. Med., 2010, 207(2), 339). High levels of 2-HG are highly associated with tumorigenesis.

Mutant IDH2 is also associated with the rare neurometabolic disorder D-2-hydroxyglutaric aciduria type II (D-2-HGA type II). Germline mutations were found at R140 in IDH2 in 15 pateints having D-2-HGA type II. Patients having this disorder also have consistently increased levels of D-2-HG in their urine, plasma and cerebrospinal fluid. (See Kranendijk, M. et al., Science, 2010, 330, 336). Finally, patients with Oilier Disease and Mafucci Syndrome (two rare disorders that predispose to cartilaginous tumors) have been shown to be somatically mosaic for IDH1 and 2 mutations and exhibit high levels of D-2-HG. (See Amary et al., Nature Genetics, 2011 and Pansuriya et al., Nature Genetics, 2011).

Thus, there is a need for small molecule inhibitors of mutant IDH proteins having a neomorphic activity for the treatment of diseases and disorders associated with these proteins.

SUMMARY OF THE INVENTION

In one aspect, this invention provides for a compound of formula (I)

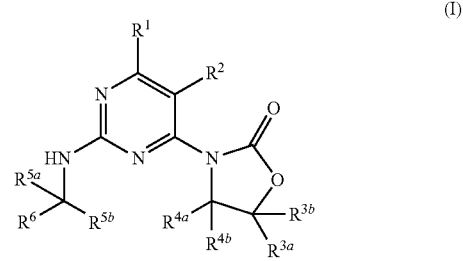

or a pharmaceutically acceptable salt thereof, wherein $R^1$-$R^6$ are defined herein.

In a second aspect, this invention provides for a pharmaceutical composition comprising a compound of formula (I), or a pharmaceutically acceptable salt thereof, and a pharmaceutically acceptable carrier or excipient.

In a third aspect, this invention provides for the use of a compound of formula (I), or a pharmaceutically acceptable salt thereof, as an inhibitor of a mutant IDH protein having a neomorphic activity such as reducing alpha-ketoglutarate to 2-hydroxyglutarate (2-HG neomorphic activity). Suitably, this invention provides for the use of a compound of formula (I), or a pharmaceutically acceptable salt thereof, as an inhibitor of mutant IDH1 having a neomorphic activity, such as 2-HG neomorphic activity, and/or mutant IDH2 having a neomorphic activity, such as 2-HG neomorphic activity. This invention further provides for the use of a compound of formula (I), or a pharmaceutically acceptable salt thereof, as an inhibitor of IDH1 having a mutation at residue 97, 100 or 132, for example G97D, R100Q, R132H, R132C, R132S, R132G, R132L, and R132V; and/or an inhibitor of IDH2 having a mutation at residue 140 or 172, for example R172K, R172M, R172S, R172G, and R172W.

In a fourth aspect, this invention provides for a method of treating a disease or disorder associated with a mutant IDH protein having a neomorphic activity comprising administration of an effective amount of a compound according to formula (I), or a pharmaceutically acceptable salt thereof, to a subject in need thereof. In one embodiment, the disease or disorder is a cell proliferation disorder, such as cancer. In another embodiment, the cancer is brain cancer, such as glioma, glioblastoma multiforme, paraganglioma, and supratentorial primordial neuroectodermal tumors (pNET); leukemia, such as acute myeloid leukemia (AML), myelodysplastic syndrome, and chronic myelogenous leukemia (CML); skin cancer, including melanoma; prostate cancer; thyroid cancer; colon cancer; lung cancer; sarcoma, including central chondrosarcoma, central and periosteal chondroma; and fibrosarcoma. In another embodiment the disease or disorder is D-2-hydroxyglutaric aciduria.

In a fifth aspect the invention provides for a compound of formula (I), or a pharmaceutically acceptable salt thereof, in combination with another therapeutic agent.

These and other aspects of the present invention are described further in the following detailed description of the invention.

DETAILED DESCRIPTION OF THE INVENTION

The present invention is directed to a compound of formula (I)

A compound of formula (I)

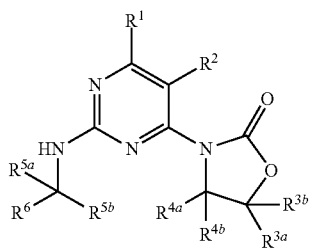

wherein:
$R^1$ and $R^2$ are each independently hydrogen, deuterium, halo, hydroxyl, $NH_2$, aryl, heteroaryl, or optionally substituted $C_{1-4}$ alkyl,
wherein said $C_{1-4}$ alkyl is optionally substituted with one to three substituents each independently selected from the group consisting of: halo, hydroxyl, and $NH_2$;
$R^{3a}$ is hydrogen, deuterium, $C_{1-6}$ alkyl, phenyl, or benzyl and $R^{3b}$ is hydrogen, deuterium, or $C_{1-6}$ alkyl; or
$R^{3a}$ and $R^{3b}$ are joined together forming an optionally substituted 3-7 membered cycloalkyl ring or an optionally substituted 4-7 membered heterocyclic ring,
wherein said cycloalkyl and heterocyclic rings are each optionally substituted with one or two substituents each independently selected from the group consisting of: halo, hydroxyl, oxo, $NH_2$, and $C_{1-3}$ alkyl;
$R^{4a}$ is hydrogen, $C_{1-6}$ alkyl, optionally substituted phenyl, optionally substituted benzyl, optionally substituted heteroaryl, or methylene-dibenzene,
wherein said phenyl, benzyl, and heteroaryl rings are optionally substituted with one to three substituents each independently selected from the group consisting of: halo, hydroxyl, cyano, nitro, $C_{1-4}$ alkoxy, $C_{1-3}$ haloalkyl, $C_{1-3}$ haloalkoxy, $C_{1-6}$ alkyl, $C_{3-6}$ cycloalkyl, phenyl, 5-6 membered heteroaryl, 5-6 membered heterocyclic, phenoxy, —$COOR^b$, —$SO_2R^b$, —$NHC(O)R^b$, and —$NR^bR^b$ and
$R^{4b}$ is hydrogen, deuterium, or $C_{1-3}$ alkyl; or
$R^{4a}$ and $R^{4b}$ are joined together forming an optionally substituted 3-7 membered cycloalkyl ring or an optionally substituted 4-7 membered heterocyclic ring,
wherein said cycloalkyl and heterocyclic rings are optionally substituted with one or two substituents each independently selected from the group consisting of: halo, hydroxyl, oxo, $NH_2$, and $C_{1-3}$ alkyl,
provided that only one of $R^{3a}$ and $R^{3b}$ and $R^{4a}$ and $R^{4b}$ are joined together forming a ring;
$R^{5a}$ is hydrogen or deuterium;
$R^{5b}$ is hydrogen, deuterium, methyl, ethyl, $CD_3$, $CF_3$, $CH_2F$, or $CHF_2$ and
$R^6$ is optionally substituted $C_{1-6}$ alkyl, optionally substituted aryl, optionally substituted heteroaryl, optionally substituted heterocyclic, or optionally substituted $C_{3-10}$ cycloalkyl, wherein said $C_{1-6}$ alkyl is optionally substituted with one substituent selected from the group consisting of hydroxyl, $C_{1-3}$ alkoxy and —$OR^a$,
wherein said aryl, heteroaryl, heterocyclic and $C_{3-10}$ cycloalkyl are optionally substituted with one to three substituents each independently selected from the group consisting of: halo; hydroxyl; cyano; nitro; $C_{1-4}$ alkoxy; $C_{1-3}$ haloalkyl; $C_{1-3}$ haloalkoxy; $C_{1-6}$ alkyl; $C_{3-6}$ cycloalkyl optionally substituted with one to three substituents each independently selected from the group consisting of: hydroxyl, cyano, $C_{1-3}$ alkyl, $C_{1-3}$ alkoxy, and $C_{1-3}$ haloalkyl; phenyl optionally substituted with one to three substituents each independently selected from the group consisting of: halo, hydroxyl, cyano, nitro, $C_{1-3}$ alkoxy, $C_{1-3}$ haloalkyl, $C_{1-3}$ haloalkoxy, $C_{1-6}$ alkyl, $C_{3-6}$ cycloalkyl, 5-6 membered heteroaryl, 5-6 membered heterocyclic, phenoxy, —$COOR^b$, —$SO_2R^b$, —$NHC(O)R^b$, and —$NR^bR^b$; 5-6 membered heteroaryl optionally substituted with one to three substituents each independently selected from the group consisting of: halo, hydroxyl, cyano, $C_{1-3}$ alkyl, $C_{1-3}$ alkoxy; 5-6 membered heterocyclic optionally substituted with one to three substituents each independently selected from the group consisting of: halo, hydroxyl, oxo, $NH_2$, and $C_{1-3}$ alkyl; —$CH_2R^a$; —$OR^a$; —$C(O)R^b$; —$NR^aR^b$; —$COOR^a$; —$SO_2R^a$; —$SO_2R^b$; $NHC(O)R^a$; —$NHC(O)R^b$; —$C(O)NR^aR^b$; —$C(O)NHR^b$; and —$SO_2NR^bR^b$; or
$R^{5b}$ and $R^6$ are joined together forming an optionally substituted $C_{3-7}$ cycloalkyl group or an optionally substituted group of formula (a):

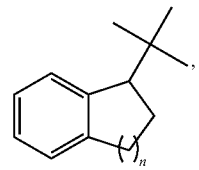

wherein n is 1, 2, or 3 and
said $C_{3-7}$ cycloalkyl and group of formula (a) are optionally substituted with one to three substituents each independently selected from the group consisting of: halo, hydroxyl, cyano, nitro, $C_{1-3}$ alkoxy, $C_{1-3}$ haloalkyl, $C_{1-3}$ haloalkoxy, $C_{1-6}$ alkyl, $C_{3-6}$ cycloalkyl, 5-6 membered heteroaryl, 5-6 membered heterocyclic, benzyloxy, —$COOR^b$, —$SO_2R^b$, —$NHC(O)R^b$, and —$NR^bR^b$;
each $R^a$ is independently optionally substituted phenyl, optionally substituted heteroaryl, optionally substituted heterocyclic, or optionally substituted $C_{3-7}$ cycloalkyl,
wherein said phenyl and heteroaryl are optionally substituted with one to three substituents each independently selected from the group consisting of halo, hydroxyl, cyano, nitro, $C_{1-3}$ alkoxy, $C_{1-3}$ haloalkyl, $C_{1-3}$ haloalkoxy, and $C_{1-3}$ alkyl,
wherein said heterocyclic is optionally substituted with one to three substituents each independently selected from the group consisting of halo, hydroxyl, oxo, $C_{1-3}$ alkoxy, $C_{1-3}$ haloalkyl, $C_{1-3}$ haloalkoxy, $C_{1-4}$ alkyl, $C_{3-5}$ cycloalkyl, —$C(O)R^b$, and —$NR^bR^b$; and
wherein said $C_{3-7}$ cycloalkyl is optionally substituted with one to three substituents each independently selected from the group consisting of halo, hydroxyl, oxo, $C_{1-3}$ alkoxy, $C_{1-3}$ haloalkyl, $C_{1-3}$ haloalkoxy, and $C_{1-3}$ alkyl; and
each $R^b$ is independently hydrogen or $C_{1-6}$ alkyl.

"Alkyl" refers to a monovalent saturated hydrocarbon chain having the specified number of carbon atoms. For example, $C_{1-6}$ alkyl refers to an alkyl group having from 1 to 6 carbon atoms. Alkyl groups may be optionally substituted with one or more substituents as defined in formula (I). Alkyl groups may be straight or branched. Representative branched alkyl groups have one, two, or three branches. Examples of alkyl groups include, but are not limited to, methyl, ethyl, propyl (n-propyl and isopropyl), butyl (n-butyl, isobutyl, sec-butyl, and t-butyl), pentyl (n-pentyl, isopentyl, and neopentyl), and hexyl.

"Alkoxy" refers to any alkyl moiety attached through an oxygen bridge (i.e. a —O—$C_{1-3}$ alkyl group wherein $C_{1-3}$ alkyl is as defined herein). Examples of such groups include, but are not limited to, methoxy, ethoxy, and propoxy.

"Aryl" refers to a hydrocarbon ring system having an aromatic ring. Aryl groups are monocyclic ring systems or bicyclic ring systems. Monocyclic aryl ring refers to phenyl. Bicyclic aryl rings refer to naphthyl and to rings wherein phenyl is fused to a $C_{5-7}$ cycloalkyl or $C_{5-7}$ cycloalkenyl ring as defined herein. Aryl groups may be optionally substituted with one or more substituents as defined in formula (I).

"Cycloalkyl" refers to a saturated hydrocarbon ring system having the specified number of carbon atoms. Cycloalkyl groups are monocyclic or bicyclic ring systems. For example, $C_{5-10}$ cycloalkyl refers to a cycloalkyl group having from 5 to 10 carbon atoms. Cycloalkyl groups may be optionally substituted with one or more substituents as defined in formula (I). Examples of cycloalkyl groups include, but are not limited to, cyclopropyl, cyclobutyl, cyclopentyl, cyclohexyl, cycloheptyl, and adamantanyl.

"Cycloalkenyl" refers to an unsaturated hydrocarbon ring system having the specified number of carbon atoms and having a carbon-carbon double bond within the ring. For example, $C_{5-7}$ cycloalkenyl refers to a cycloalkenyl group having from 5 to 7 carbon atoms. In certain embodiments, cycloalkenyl groups have one carbon-carbon double bond within the ring. In other embodiments, cycloalkeneyl groups have more than one carbon-carbon double bond within the ring. Cycloalkenyl rings are not aromatic. Cycloalkenyl groups may be optionally substituted with one or more substituents as defined in formula (I).

"Halo" refers to the halogen radicals fluoro, chloro, bromo, and iodo.

"Haloalkyl" refers to an alkyl group wherein at least one hydrogen atom attached to a carbon atom within the alkyl group is replaced with halo. The number of halo substituents includes, but is not limited to, 1, 2, 3, 4, 5, or 6 substituents. Haloalkyl includes, but is not limited to, monofluoromethyl, difluoroethyl, and trifluoromethyl.

"Haloalkoxy" refers to a haloalkyl moiety attached through an oxygen bridge (i.e. a —O—$C_{1-3}$ haloalkyl group wherein $C_{1-3}$ haloalkyl is as defined herein). An example of a haloalkoxy group is trifluoromethoxy.

"Heteroaryl" refers to an aromatic ring system containing from 1 to 5 heteroatoms. Heteroaryl groups containing more than one heteroatom may contain different heteroatoms. Heteroaryl groups may be optionally substituted with one or more substituents as defined in formula (I). Heteroaryl groups are monocyclic ring systems or are fused bicyclic ring systems. Monocyclic heteroaryl rings have from 5 to 6 ring atoms. Bicyclic heteroaryl rings have from 8 to 10 member atoms. Bicyclic heteroaryl rings include those ring systems wherein a heteroaryl ring is fused to a phenyl ring. Heteroaryl includes, but is not limited to, pyrrolyl, pyrazolyl, imidazolyl, oxazolyl, isoxazolyl, oxadiazolyl (including 1,3,4-oxadiazolyl and 1,2,4-oxadiazolyl), thiazolyl, isothiazolyl, thiadiazolyl, furanyl, furanzanyl, thienyl, triazolyl, pyridinyl (including 2-, 3-, and 4-pyridinyl), pyrimidinyl, pyridazinyl, pyrazinyl, trazinyl, tetrazinyl, tetrzolyl, indonyl, isoindolyl, indolizinyl, indazolyl, purinyl, quinolinyl, isoquinolinyl, quinoxalinyl, quinazolinyl, benzimidazolyl, benzopyranyl, benzopyranyl, benzoxazolyl, benzoisoxazolyl, benzofuranyl, benzothiazolyl, benzothienyl, naphthyridinyl, 1H-pyrrolo[2,3-b]pyridinyl, tetrazolo[1,5-a]pyridinyl, imidazo[2,1-b][1,3,4]thiadiazolyl and the like.

"Heteroatom" refers to a nitrogen, oxygen, or sulfur atom.

"Heterocyclic" refers to a 3 to 11 membered saturated or unsaturated monocyclic or bicyclic ring containing from 1 to 4 heteroatoms. Heterocyclic ring systems are not aromatic. Heterocyclic groups containing more than one heteroatom may contain different heteroatoms. Heterocyclic includes ring systems wherein a sulfur atom is oxidized to form SO or $SO_2$. Heterocyclic groups may be optionally substituted with one or more substituents as defined in formula (I). Heterocyclic groups are monocyclic, spiro, or fused or bridged bicyclic ring systems. Monocyclic heterocyclic rings have 3 to 7 ring atoms. Examples of monocyclic heterocyclic groups include oxtanyl, tetrahydrofuranyl, dihydrofuranyl, 1,4-dioxanyl, morpholinyl, 1,4-dithianyl, piperazinyl, piperidinyl, 1,3-dioxolanyl, imidazolidinyl, imidazolinyl, pyrrolinyl, pyrrolidinyl, tetrahydropyranyl, dihydropyranyl, oxathiolanyl, dithiolanyl, 1,3-dioxanyl, 1,3-dithianyl, oxathianyl, thiomorpholinyl, tetrahydro-thiopyran1,1-dioxide, 1,4-diazepanyl, and the like. Fused heterocyclic ring systems have from 8 to 11 ring atoms and include groups wherein a heterocyclic ring is fused to a phenyl ring, a heteroaryl ring or another heterocyclic ring. Examples of fused heterocyclic rings include 2,3-dihydrobenzo[b][1,4]dioxinyl, octahydro-pyrrolo[1,2-a]pyrazinyl, octahydro-pyrido[1,2-a]pyrazinyl, octahydro-pyrrolo[3,4-c]pyrrolyl, 5,6,7,8-tetrahydro-[1,2,4]triazolo[4,3-a]pyrazinyl, 5,6,7,8-tetrahydro-imidazo[1,2-a]pyrazinyl and the like. Examples of bridged heterocyclic groups include 3,8-diaza-bicyclo[3.2.1]octanyl, 3,8-diaza-bicyclo[4.2.0]octanyl and the like. Examples of spiro heterocyclic groups include 4,7-diaza-spiro[2.5]octanyl and the like.

"4-7 membered heterocyclic" refers to a heterocyclic group as defined above, having from 4 to 7 ring atoms and containing from 1 to 4 heteroatoms.

"5-6 membered heterocylic" refers to a heterocyclic group as defined above, having 5 or 6 ring atoms and containing from 1 to 4 heteroatoms.

"Optionally substituted" indicates that a group, such as an alkyl, cycloalkyl, heteroaryl, heterocyclic, phenyl, and benzyl may be unsubstituted or the group may be substituted with one or more substituents as defined in formula (I).

"Oxo" refers to a C=O group.

"Pharmaceutically acceptable" means a compound which is suitable for pharmaceutical use. Salts and solvates (e.g. hydrates and hydrates of salts) of compounds of the invention which are suitable for use in medicine are those where in the counterion or associated solvent is pharmaceutically acceptable. However, salts and solvates having non-pharmaceutically acceptable counterions or associated solvents are within the scope of the present invention, for example, for use as intermediates in the preparation of other compounds of the invention and their pharmaceutically acceptable salts and solvates.

"Substituted" in reference to a group such as alkyl, phenyl, benzyl, heteroaryl, and heterocyclic, indicates that one or more hydrogen atoms attached to an atom within the group is replaced with a substituent selected from the group of defined substituents. It should be understood that the term "substituted" includes the implicit provision that such substitution be in accordance with permitted valence of the substituted atom and the substituent, and that the substitution results in a stable compound (i.e. one that does not spontaneously undergo transformation, for example, by hydrolysis, rearrangement, cyclization, or elimination and that is sufficiently robust to survive isolation from a reaction mixture). When it is stated that a group may contain one or more substituents, one or more (as appropriate) atoms within the group may be substituted. In addition, a single atom within the group may be substituted with more than one substituent as long as such substitution is accordance with the permitted valence of the atom. Suitable substituents are defined for each substituted or optionally substituted group.

The skilled artisan will appreciate that salts, including pharmaceutically acceptable salts, of the compounds according to formula (I) may be prepared. These salts may be prepared in situ during the final isolation and purification of the compound, or by separately reacting the purified compound in its free acid or free base form with a suitable base or acid, respectively.

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulfonate, chloride/hydrochloride, chlortheophyllonate, citrate, ethandisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, sulfosalicylate, tartrate, tosylate and trifluoroacetate salts.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like. Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

The pharmaceutically acceptable salts of the present invention can be synthesized from a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

Solvates, including pharmaceutically acceptable solvates, of the compounds of formula (I) may also be prepared. "Solvate" refers to a complex of variable stoichiometry formed by a solute and solvent. Such solvents for the purpose of the invention may not interfere with the biological activity of the solute. Examples of suitable solvents include, but are not limited to, water, MeOH, EtOH, and AcOH. Solvates wherein water is the solvent molecule are typically referred to as hydrates. Hydrates include compositions containing stoichiometric amounts of water, as well as compositions containing variable amounts of water.

The compounds of formula (I), including salts and solvates thereof, may exist in crystalline forms, non-crystalline forms, or mixtures thereof. The compound or salt or solvate thereof may also exhibit polymorphism, i.e. the capacity of occurring in different crystalline forms. These different crystalline forms are typically known as "polymorphs". Polymorphs have the same chemical composition but differ in packing, geometrical arrangement, and other descriptive properties of crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, all of which may be used for identification. One of ordinary skill in the art will appreciate that different polymorphs may be produced, for example, by changing or adjusting the conditions used in crystallizing/recrystallizing a compound of formula (I).

The invention also includes various isomers of the compounds of formula (I). "Isomer" refers to compounds that have the same composition and molecular weight but differ in physical and/or chemical properties. The structural difference may be in constitution (geometric isomers) or in the ability to rotate the plane of polarized light (stereosiomers). With regard to stereoisomers, the compounds of formula (I) may have one or more asymmetric carbon atom and may occur as racemates, racemic mixtures and as individual enantiomers or diastereomers. All such isomeric forms are included within the present invention, including mixtures thereof. If the compound contains a double bond, the substituent may be in the E or Z configuration. If the compound contains a disubstituted cycloalkyl, the cycloalkyl substituent may have a cis- or trans-configuration. All tautomeric forms are also intended to be included.

Any asymmetric atom (e.g., carbon or the like) of a compound of formula (I) can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated double bonds may, if possible, be present in cis-(Z)- or trans-(E)-form.

Accordingly, as used herein a compound of formula (I) can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

The invention includes unlabeled forms as well as isotopically labeled forms of compounds of formula (I). Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^{2}H$, $^{3}H$, $^{11}C$, $^{13}C$, $^{14}C$, $^{15}N$, $^{18}F$, $^{31}P$, $^{32}P$, $^{35}S$, $^{36}Cl$, $^{125}I$ respectively. The invention includes various isotopically labeled compounds as defined herein, for example those into which radioactive isotopes, such as $^{3}H$ and $^{14}C$, or those into which non-radioactive isotopes, such as $^{2}H$ and $^{13}C$ are present. Such isotopically labelled compounds are useful in metabolic studies (with $^{14}C$), reaction kinetic studies (with, for example $^{2}H$ or $^{3}H$), detection or imaging techniques, such as positron emission tomography (PET) or single-photon emission computed tomography (SPECT) including drug or substrate tissue distribution assays, or in radioactive treatment of patients. In particular, an $^{18}F$ or labeled compound may be particularly desirable for PET or SPECT studies. Isotopically-labeled compounds of formula (I) can generally be prepared by conventional techniques known to those skilled in the art or by processes analogous to those described in the accompanying Examples and Preparations using an appropriate isotopically-labeled reagents in place of the non-labeled reagent previously employed.

Furthermore, substitution with heavier isotopes, particularly deuterium (i.e., $^{2}H$ or D) may afford certain therapeutic advantages resulting from greater metabolic stability, for example increased in vivo half-life or reduced dosage requirements or an improvement in therapeutic index. It is understood that deuterium in this context is regarded as a substituent of a compound of the formula (I). The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Representative Embodiments

Various embodiments of the invention are described herein. It will be recognized that features specified in each embodiment may be combined with other specified features to provide for further embodiments.

One embodiment of the present invention is a compound according to formula (I) wherein:
each $R^1$ and $R^2$ is independently hydrogen, deuterium, halo, hydroxyl, $NH_2$, aryl, heteroaryl, or optionally substituted $C_{1-4}$ alkyl,
  wherein said $C_{1-4}$ alkyl is optionally substituted with one to three substituents each independently selected from the group consisting of: halo, hydroxyl, and $NH_2$;
$R^{3a}$ is hydrogen, deuterium, $C_{1-6}$ alkyl, phenyl, or benzyl and
$R^{3b}$ is hydrogen, deuterium, or $C_{1-6}$ alkyl; or
$R^{3a}$ and $R^{3b}$ are joined together forming an optionally substituted 3-7 membered cycloalkyl ring or an optionally substituted 4-7 membered heterocyclic ring,
  wherein said cycloalkyl and heterocyclic rings are optionally substituted with one or two substituents each independently selected from the group consisting of: halo, hydroxyl, oxo, $NH_2$, and $C_{1-3}$ alkyl;
$R^{4a}$ is hydrogen, $C_{1-6}$ alkyl, optionally substituted phenyl, optionally substituted benzyl, optionally substituted heteroaryl, or methylene-dibenzene,
  wherein said phenyl, benzyl, and heteroaryl rings are optionally substituted with one to three substituents each independently selected from the group consisting of: halo, hydroxyl, cyano, nitro, $C_{1-3}$ alkoxy, $C_{1-3}$ haloalkyl, $C_{1-3}$ haloalkoxy, $C_{1-6}$ alkyl, $C_{3-6}$ cycloalkyl, 5-6 membered heteroaryl, 5-6 membered heterocyclic, phenoxy, $COOR^b$, $SO_2R^b$, $NHC(O)R^b$, and $NR^bR^b$ and
$R^{4b}$ is hydrogen, deuterium, or $C_{1-3}$ alkyl; or
$R^{4a}$ and $R^{4b}$ are joined together forming an optionally substituted 3-7 membered cycloalkyl ring or an optionally substituted 4-7 membered heterocyclic ring,
  wherein said cycloalkyl and heterocyclic rings are optionally substituted with one or two substituents each independently selected from the group consisting of: halo, hydroxyl, oxo, $NH_2$, and $C_{1-3}$ alkyl,
  provided that only one of $R^{3a}$ and $R^{3b}$ and $R^{4a}$ and $R^{4b}$ are joined together forming a ring;
$R^{5a}$ is hydrogen or deuterium;
$R^{5b}$ is hydrogen, deuterium, methyl, ethyl, $CD_3$, $CF_3$, $CH_2F$, or $CHF_2$ and
$R^6$ is optionally substituted $C_{1-6}$ alkyl, optionally substituted aryl, optionally substituted heteroaryl, optionally substituted heterocyclic, or optionally substituted $C_{5-10}$ cycloalkyl,
  wherein said $C_{1-6}$ alkyl is optionally substituted with one substituent selected from the group consisting of hydroxyl, $C_{1-3}$ alkoxy and —$OR^a$;
  wherein said aryl, heteroaryl, heterocyclic and $C_{5-10}$ cycloalkyl are optionally substituted with one to three substituents each independently selected from the group consisting of: halo; hydroxyl; cyano; nitro; $C_{1-3}$ alkoxy; $C_{1-3}$ haloalkyl; $C_{1-3}$ haloalkoxy; $C_{1-6}$ alkyl; $C_{3-6}$ cycloalkyl; phenyl optionally substituted with one to three substituents each independently selected from the group consisting of: halo, hydroxyl, cyano, nitro, $C_{1-3}$ alkoxy, $C_{1-3}$ haloalkyl, $C_{1-3}$ haloalkoxy, $C_{1-6}$ alkyl, $C_{3-6}$ cycloalkyl, 5-6 membered heteroaryl, 5-6 membered heterocyclic, phenoxy, COOR$^b$, SO$_2$R$^b$, NHC(O)R$^b$, and NR$^b$R$^b$; 5-6 membered heteroaryl; 5-6 membered heterocyclic optionally substituted with one to three substituents each independently selected from the group consisting of: halo, hydroxyl, oxo, NH$_2$, and C$_{1-3}$ alkyl; —CH$_2$R$^a$; —OR$^a$; —C(O)R$^a$; —NR$^a$R$^b$; —COOR$^a$; —SO$_2$R$^a$; NHC(O)R$^a$; and —SO$_2$NR$^b$R$^b$; or R$^{5b}$ and R$^6$ are joined together forming an optionally substituted C$_{3-7}$ cycloalkyl group or an optionally substituted group of formula (a):

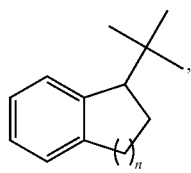

(a)

wherein n is 1, 2, or 3 and said C$_{3-7}$ cycloalkyl and group of formula (a) are optionally substituted with one to three substituents each independently selected from the group consisting of: halo, hydroxyl, cyano, nitro, C$_{1-3}$ alkoxy, C$_{1-3}$ haloalkyl, C$_{1-3}$ haloalkoxy, C$_{1-6}$ alkyl, C$_{3-6}$ cycloalkyl, 5-6 membered heteroaryl, 5-6 membered heterocyclic, benzyloxy, COOR$^b$, SO$_2$R$^b$, NHC(O)R$^b$, and NR$^b$R$^b$;

each R$^a$ is independently optionally substituted phenyl, optionally substituted heteroaryl, or optionally substituted 4-7 membered heterocyclic, wherein said phenyl and heteroaryl are optionally substituted with one to three substituents each independently selected from the group consisting of halo, hydroxyl, cyano, nitro, C$_{1-3}$ alkoxy, C$_{1-3}$ haloalkyl, C$_{1-3}$ haloalkoxy, and C$_{1-3}$ alkyl, wherein said 4-7 membered heterocyclic is optionally substituted with one to three substituents each independently selected from the group consisting of halo, hydroxyl, oxo, C$_{1-3}$ alkoxy, C$_{1-3}$ haloalkyl, C$_{1-3}$ haloalkoxy, and C$_{1-3}$ alkyl; and each R$^b$ is independently hydrogen or C$_{1-6}$ alkyl.

In another embodiment of the present invention R$^1$ is hydrogen, halo, or optionally substituted C$_{1-4}$ alkyl. Suitably R$^1$ is hydrogen, fluoro, chloro, or methyl. In another embodiment R$^1$ is hydrogen, fluoro or chloro. Suitably R$^1$ is hydrogen.

In another embodiment of the present invention R$^2$ is hydrogen, halo or optionally substituted C$_{1-4}$ alkyl. Suitably R$^2$ is hydrogen, fluoro, chloro, or methyl. In another embodiment R$^2$ is hydrogen or fluoro. In another embodiment of the present invention R$^2$ is hydrogen.

In another embodiment of the present invention R$^1$ and R$^2$ are both hydrogen.

In another embodiment of the present invention R$^{3a}$ is hydrogen, C$_{1-6}$ alkyl, or phenyl. Suitably R$^{3a}$ is hydrogen, methyl, or phenyl. Suitably R$^{3a}$ is hydrogen or methyl. Suitably R$^{3a}$ is hydrogen.

In another embodiment of the present invention R$^{3b}$ is hydrogen or methyl. Suitably R$^{3b}$ is hydrogen.

In another embodiment R$^{3a}$ and R$^{3b}$ are both hydrogen.

In another embodiment of the present invention R$^{3a}$ and R$^{3b}$ are joined together forming oxetanyl or tetrahydro-2H-pyranyl.

Another embodiment of the present invention is a compound according to formula (II).

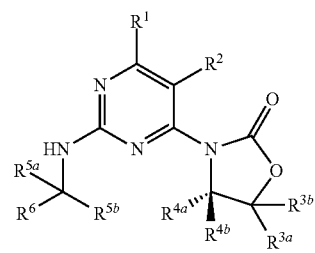

(II)

In another embodiment of the present invention R$^{4a}$ is hydrogen, C$_{1-6}$ alkyl, optionally substituted phenyl, optionally substituted benzyl, optionally substituted heteroaryl, or methylene-dibenzene, wherein said phenyl, benzyl, and heteroaryl rings are optionally substituted with one to three substituents each independently selected from the group consisting of: halo, hydroxyl, cyano, nitro, C$_{1-3}$ alkoxy, C$_{1-3}$ haloalkyl, C$_{1-3}$ haloalkoxy, C$_{1-6}$ alkyl, C$_{3-6}$ cycloalkyl, 5-6 membered heteroaryl, 5-6 membered heterocyclic, phenoxy, —COOR$^b$, —SO$_2$R$^b$, —NHC(O)R$^b$, and —NR$^b$R$^b$.

In another embodiment of the present invention R$^{4a}$ is hydrogen, C$_{1-4}$ alkyl, optionally substituted phenyl, optionally substituted benzyl, optionally substituted heteroaryl, or methylene-dibenzene. Suitably R$^{4a}$ is hydrogen, C$_{1-4}$ alkyl, optionally substituted phenyl, optionally substituted benzyl, optionally substituted pyridinyl, or methylene-dibenzene. More suitably R$^{4a}$ is hydrogen, methyl, isopropyl, isobutyl, t-butyl, phenyl, 4-methoxyphenyl, 4-fluorophenyl, benzyl, or methylene-dibenzene. In another embodiment R$^{4a}$ is hydrogen, methyl, ethyl, isopropyl, phenyl, 4-fluorophenyl, 4-methoxyphenyl, biphenyl, benzyl, or pyridinyl. Suitably R$^{4a}$ is isopropyl.

In another embodiment of the present invention R$^{4b}$ is hydrogen or methyl. Suitably R$^{4b}$ is hydrogen.

In another embodiment R$^{4a}$ is isopropyl and R$^{4b}$ is methyl. In another embodiment R$^{4a}$ is isopropyl and R$^{4b}$ is hydrogen.

In another embodiment of the present invention R$^{4a}$ and R$^{4b}$ are joined together forming cyclopentyl.

Another embodiment of the present invention is a compound according to formula (III).

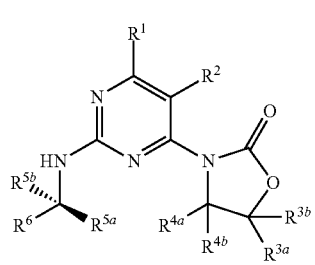

(III)

In another embodiment of the present invention R$^{5a}$ is hydrogen. In another embodiment R$^{5a}$ is deuterium.

In another embodiment of the present invention R$^{5b}$ is hydrogen, methyl, ethyl, or CF$_3$. Suitably R$^{5b}$ is methyl.

In another embodiment of the present invention R$^6$ is isopropyl, optionally substituted aryl, optionally substituted pyrazolyl, optionally substituted pyridinyl, 2,3-dihydrobenzofuranyl, 2,3-dihydrobenzo[b][1,4]dioxinyl, or optionally substituted C$_{5-10}$ cycloalkyl. Suitably R$^6$ is isopropyl, optionally substituted phenyl, optionally substituted naphthyl, pyrazolyl, pyridinyl, 2,3-dihydrobenzofuranyl, 2,3-dihydrobenzo[b][1,4]dioxinyl, or $C_{5-10}$ cycloalkyl, wherein said phenyl and naphthyl are each optionally substituted with one to three substituents each independently selected from the group consisting of: fluoro, chloro, bromo, hydroxy, cyano, methoxy, trifluoromethyl, methyl, t-butyl, phenyl, pyrrolyl, piperidinyl, 4-methylpiperazinyl, morpholinyl, phenoxy, and —SO$_2$NH$_2$.

In another embodiment of the present invention $R^6$ is optionally substituted heteroaryl, optionally substituted heterocyclic or optionally substituted $C_{5-10}$ cycloalkyl.

In another embodiment of the present invention $R^6$ is methyl, $C_{5-10}$ cycloalkyl, optionally substituted phenyl, optionally substituted pyridinyl, optionally substituted pyrimidinyl, optionally substituted pyridazinyl, optionally substituted pyrazinyl, optionally substituted triazolyl, optionally substituted pyrazolyl, optionally substituted thiazolyl, optionally substituted 1,3,4-oxadiazolyl, optionally substituted 1,2,4-oxadiazolyl, optionally substituted isoxazolyl, thienyl, oxazolyl, quinolinyl, optionally substituted benzimidazolyl, benzthiazolyl, benzoxazolyl, tetrazolo[1,5-a]pyridinyl, imidazo[2,1-b][1,3,4]thiadiazolyl, optionally substituted piperidinyl, optionally substituted piperazinyl, tetrahydrofuranyl, tetrahydropyranyl, optionally substituted tetrahydrothiopyran1,1-dioxide, 1H-pyrrolo[2,3-b]pyridinyl, 2,3-dihydro-benzo[1,4]dioxinyl, 5,6,7,8-tetrahydro-[1,2,4]trazolo[4,3-a]pyrazinyl, 4,5,6,7-tetrahydro-benzothiazolyl, or indolizinyl, wherein said phenyl, pyridinyl, pyrimidinyl, pyridazinyl, pyrazinyl, triazolyl, pyrazolyl, thiazolyl, 1,3,4-oxadiazolyl, 1,2,4-oxadiazolyl, isoxazolyl, benzimidazolyl, piperidinyl, piperazinyl, and tetrahydro-thiopyran1,1-dioxide are each optionally substituted with one or two substituents as defined in formula (I). Suitably $R^6$ is phenyl optionally substituted with one or two substituents. Suitably $R^6$ is optionally substituted 1,3,4-oxadiazolyl or 1,2,4-optionally substituted oxadiazolyl. Suitably $R^6$ is pyrimidinyl optionally substituted with one substituent.

In another embodiment $R^6$ is optionally substituted with one or two substituents each independently selected from the group consisting of: halo; hydroxy; nitro; $C_{1-4}$ alkoxy; $C_{1-3}$ haloalkyl; $C_{1-3}$ haloalkoxy; $C_{1-6}$ alkyl; $C_{3-6}$ cycloalkyl optionally substituted with one substituent selected from the group consisting of: cyano, $C_{1-3}$ alkyl, and $C_{1-3}$ alkoxy; phenyl optionally substituted with one or two substituents each independently selected from the group consisting of: fluoro, chloro, methyl, cyano, and methoxy; and 5-6 membered heteroaryl (for example, imidazolyl, pyrazolyl, trazolyl, and pyridinyl) optionally substituted with one or two methyl groups.

In another embodiment $R^6$ is substituted with one —CH$_2$R$^a$, —C(O)R$^a$, —NHC(O)R$^a$, —NHC(O)R$^b$, —C(O)NHR$^a$, —C(O)NHR$^b$, —OR$^a$, —NR$^a$R$^b$, —SO$_2$NR$^b$R$^b$, —SO$_2$R$^a$, or —SO$_2$R$^b$ group. Suitably $R^6$ is substituted with one —CH$_2$R$^a$, —C(O)R$^a$, or —OR$^a$ group.

In another embodiment $R^6$ is phenyl substituted with one fluoro or chloro group and one —CH$_2$R$^a$, —C(O)R$^a$, or —C(O)NHR$^a$ group wherein the —CH$_2$R$^a$, —C(O)R$^a$, or —C(O)NHR$^a$ group is in the para position of the phenyl ring. Suitably $R^6$ is phenyl substituted with one fluoro group and one —CH$_2$R$^a$, —C(O)R$^a$, or —C(O)NHR$^a$ group wherein the —CH$_2$R$^a$, —C(O)R$^a$, or —C(O)NHR$^a$ group is in the para position of the phenyl ring. In another embodiment $R^6$ is phenyl substituted with one —CH$_2$R$^a$, —C(O)R$^a$, or —C(O)NHR$^a$ group in the para position. In another embodiment $R^6$ is phenyl substituted by —CH$_2$R$^a$ in the para position.

In another embodiment $R^a$ is phenyl optionally substituted with one or two substituents each independently selected from the group consisting of fluoro, chloro and bromo.

In another embodiment $R^a$ is an optionally substituted 5-6 membered heteroaryl. Suitably $R^a$ is optionally substituted pyridinyl or optionally substituted pyrimidinyl. Suitably $R^a$ is pyridinyl or pyrimidinyl optionally substituted with one trifluoromethyl.

In another embodiment $R^a$ is $C_{5-7}$ cycloalkyl each of which is optionally substituted with one or two substituents each independently selected from the group consisting of fluoro, hydroxy, methyl, and $C_{1-3}$ haloalkoxy.

In another embodiment $R^a$ is optionally substituted heterocyclic. Suitably $R^a$ is piperidinyl, piperazinyl, morpholinyl, tetrahydropyranyl, tetrahydro-thiopyran1,1-dioxide, 1,4-diazepanyl, 4,7-diaza-spiro[2.5]octanyl, 3,8-diaza-bicyclo[3.2.1]octanyl, 3,8-diaza-bicyclo[4.2.0]octanyl, octahydro-pyrrolo[1,2-a]pyrazinyl, octahydro-pyrido[1,2-a]pyrazinyl, octahydro-pyrrolo[3,4-c]pyrrolyl, and 5,6,7,8-tetrahydro-imidazo[1,2-a]pyrazinyl each of which is optionally substituted with one to three substituents each independently selected from the group consisting of: hydroxy, fluoro, amino, dimethylamino, $C_{1-3}$ haloalkoxy, $C_{1-3}$ alkyl, and $C_{3-5}$ cycloalkyl. Suitably $R^a$ is piperidinyl, piperazinyl, or morpholinyl each of which is optionally substituted with one to three substituents each independently selected from the group consisting of: hydroxy, fluoro, amino, dimethylamino, $C_{1-3}$ haloalkoxy, $C_{1-3}$ alkyl, and $C_{3-5}$ cycloalkyl.

In another embodiment of the present invention $R^{5b}$ and $R^6$ are joined together forming an optionally substituted $C_{3-7}$ cycloalkyl group or an optionally substituted group of formula (a).

In another embodiment of the present invention each $R^b$ is independently hydrogen or methyl.

In another embodiment $R^1$ is hydrogen, $R^2$ is fluoro and $R^{3a}$, $R^{3b}$, $R^{4a}$ and $R^{4b}$ are each hydrogen.

Another embodiment of the present invention is a compound according to formula (IV).

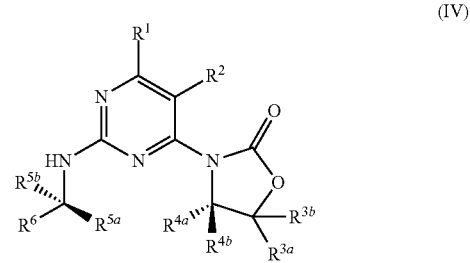

(IV)

Another embodiment of the present invention is a compound according to formula (V):

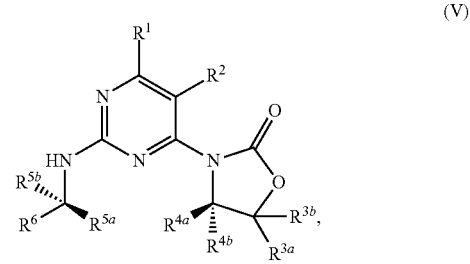

(V)

wherein $R^{4a}$ is phenyl and $R^{4b}$ is hydrogen.

Selected compounds of the present invention include:
(S)-4-isopropy-3-(2-(((S)-1-(4-(2-yl)phenyl)ethyl)amino) pyrimidin-4-yl)oxazolidin-2-one;
N-(4-((S)-1-(4-((S)-4-isopropyl-2-oxooxazolidin-3-yl)pyrimidin-2-ylamino)ethyl)phenyl)cyclohexanecarboxamide;
(S)-3-(2-(((S)-1-(3-fluoro-4-((4-methylpiperazin-1-yl)methyl)phenyl)ethyl)amino)pyrimidin-4-yl)-4-isopropyloxazolidin-2-one;
(S)-4-isopropyl-3-(2-(((S)-1-(4-((3,3,4-trimethylpiperazin-1-yl)methyl)phenyl)ethyl)amino)pyrimidin-4-yl)oxazolidin-2-one;
2-fluoro-N-(4-hydroxy-4-methylcyclohexyl)-4-((S)-1-((4-((S)-4-isopropyl-2-oxooxazolidin-3-yl)pyrimidin-2-yl)amino)ethyl)benzamide;
(S)-3-(2-((S)-1-(4-((4-amino-4-methylpiperidin-1-yl)methyl)phenyl)ethylamino)pyrimidin-4-yl)-4-isopropyloxazolidin-2-one;
(S)-3-(2-((S)-1-(4-((4-(dimethylamino)piperidin-1-yl)methyl)phenyl)ethylamino)pyrimidin-4-yl)-4-isopropyloxazolidin-2-one;
(S)-4-isopropyl-3-(2-((S)-1-(4-((4-methylpiperazin-1-yl)methyl)phenyl)ethylamino)pyrimidin-4-yl)oxazolidin-2-one;
(S)-4-isopropyl-4-methyl-3-(2-((S)-1-(4-((4-methylpiperazin-1-yl)methyl)phenyl)ethylamino)pyrimidin-4-yl)oxazolidin-2-one;
(S)-4-isopropyl-3-(2-((S)-1-(6-phenylpyridin-3-yl)ethylamino)pyrimidin-4-yl)oxazolidin-2-one;
(S)-3-(2-((S)-1-(4-benzoyl phenyl)ethylamino)pyrimidin-4-yl)-4-isopropyloxazolidin-2-one;
(S)-4-isopropyl-3-(2-(((S)-1-(5-phenyl-1,3,4-thiadiazol-2-yl)ethyl)amino)pyrimidin-4-yl)oxazolidin-2-one;
(4S)-4-isopropyl-3-(2-(1-(5-phenylpyrimidin-2-yl)ethylamino)pyrimidin-4-yl)oxazolidin-2-one;
3-(5-fluoro-2-((1-(5-(4-fluoro-3-methylphenyl)pyridin-2-yl)ethyl)amino)pyrimidin-4-yl)oxazolidin-2-one;
(S)-4-isopropyl-3-(2-(((S)-1-(1-(3-methoxyphenyl)-1H-pyrazol-4-yl)ethyl)amino)pyrimidin-4-yl)oxazolidin-2-one;
(S)-3-(2-(((S)-1-(5-(4-fluorophenyl)-1,3,4-oxadiazol-2-yl)ethyl)amino)pyrimidin-4-yl)-4-isopropyloxazolidin-2-one;
(S)-3-(2-(((S)-1-(3-(4-chlorophenyl)-1,2,4-oxadiazol-5-yl)ethyl)amino)pyrimidin-4-yl)-4-isopropyloxazolidin-2-one;
(S)-4-isopropyl-3-(2-(((S)-1-(3-(m-tolyl)-1,2,4-oxadiazol-5-yl)ethyl)amino)pyrimidin-4-yl)oxazolidin-2-one;
(S)-3-(2-(((S)-1-(3-(4-fluorophenyl)-1,2,4-oxadiazol-5-yl)ethyl)amino)pyrimidin-4-yl)-4-isopropyloxazolidin-2-one;
(S)-3-(2-((S)-1-(5-(4-fluoro-2-methylphenyl)pyrimidin-2-yl)ethylamino)pyrimidin-4-yl)-4-isopropyloxazolidin-2-one;
(S)-4-Isopropyl-3-{2-[(3-p-tolyl-[1,2,4]oxadiazol-5-ylmethyl)-amino]-pyrimidin-4-yl}-oxazolidin-2-one;
(S)-4-isopropyl-3-(2-((S)-1-(4-(1-methyl-1H-pyrazol-4-yl)phenyl)ethylamino)pyrimidin-4-yl)oxazolidin-2-one;
(S)-3-(2-((S)-1-(2-fluoro-4-isopropylphenyl)ethylamino)pyrimidin-4-yl)-4-isopropyloxazolidin-2-one;
(S)-3-(2-((S)-1-(4-isobutoxy-3-methylphenyl)ethylamino)pyrimidin-4-yl)-4-isopropyloxazolidin-2-one;
(S)-3-(2-(((S)-1-(4-isobutoxyphenyl)ethyl)amino)pyrimidin-4-yl)-4-isopropyloxazolidin-2-one;
(S)-3-(5-fluoro-2-(((S)-1-(4-isobutoxyphenyl)ethyl)amino)pyrimidin-4-yl)-4-isopropyloxazolidin-2-one;
2-fluoro-N-(trans-4-hydroxycyclohexyl)-4-((S)-1-(4-((S)-4-isopropyl-2-oxooxazolidin-3-yl)pyrimidin-2-ylamino)ethyl)benzamide;
(S)-3-(5-fluoro-2-((S)-1-(3-fluoro-4-(piperidine-1-carbonyl)phenyl)ethylamino)pyrimidin-4-yl)-4-isopropyloxazolidin-2-one;
N-cyclohexyl-2-fluoro-4-((S)-1-(5-fluoro-4-((S)-4-isopropyl-2-oxooxazolidin-3-yl)pyrimidin-2-ylamino)ethyl)benzamide;
N-cyclohexyl-2-fluoro-4-((S)-1-(4-((S)-4-isopropyl-2-oxooxazolidin-3-yl)pyrimidin-2-ylamino)ethyl)benzamide; and
(S)-3-(5-fluoro-2-((S)-1-(2-fluoro-4-(trifluoromethyl)phenyl)ethylamino)pyrimidin-4-yl)-4-isopropyloxazolidin-2-one.

Selected compounds of the present invention include:
(S)-3-(2-(((S)-1-(3-fluoro-4-((3,3,4-trimethylpiperazin-1-yl)methyl)phenyl)ethyl)amino)pyrimidin-4-yl)-4-isopropyloxazolidin-2-one;
(S)-3-(2-(((S)-1-(4-((4,4-difluoropiperidin-1-yl)methyl)phenyl)ethyl)amino)pyrimidin-4-yl)-4-isopropyloxazolidin-2-one;
(S)-3-(5-fluoro-2-(1-(4-phenoxyphenyl)ethylamino)pyrimidin-4-yl)oxazolidin-2-one;
(S)-3-(2-((S)-1-(4-(4-fluorophenoxy)phenyl)ethylamino)pyrimidin-4-yl)-4-isopropyloxazolidin-2-one;
(S)-3-(2-((S)-1-(4-(((2S,6R)-2,6-dimethylmorpholino)methyl)phenyl)ethylamino)pyrimidin-4-yl)-4-isopropyloxazolidin-2-one;
(S)-3-(2-(((S)-1-(3-(4-chlorophenyl)-1,2,4-oxadiazol-5-yl)ethyl)amino)pyrimidin-4-yl)-4-isopropyloxazolidin-2-one;
(S)-3-(2-(((S)-1-(5-(4-chlorophenyl)-1,2,4-oxadiazol-3-yl)ethyl)amino)pyrimidin-4-yl)-4-isopropyloxazolidin-2-one;
(S)-3-(2-((S)-1-(5-(4-fluoro-3-methylphenyl)pyridin-2-yl)ethylamino)pyrimidin-4-yl)-4-isopropyloxazolidin-2-one;
(S)-3-(2-((S)-1-(5-(4-fluorophenoxy)pyrimidin-2-yl)ethylamino)pyrimidin-4-yl)-4-isopropyloxazolidin-2-one;
(S)-3-(2-((S)-1-(5-(4-fluorophenoxy)pyrazin-2-yl)ethylamino)pyrimidin-4-yl)-4-isopropyloxazolidin-2-one;
(S)-4-isopropyl-3-(2-((S)-1-(5-(3-(trifluoromethyl)phenyl)pyrimidin-2-yl)ethylamino)pyrimidin-4-yl)oxazolidin-2-one; and
(S)-3-(2-((S)-1-(5-(4-fluoro-3-methylphenyl)pyrimidin-2-yl)ethylamino)pyrimidin-4-yl)-4-isopropyloxazolidin-2-one.

Selected compounds of the present invention include:
(S)-3-(2-(1-(3-(4-chlorophenyl)-1,2,4-oxadiazol-5-yl)ethylamino)-5-fluoropyrimidin-4-yl)-4,4-dimethyloxazolidin-2-one;
(S)-3-(6-chloro-2-(1-(3-(4-chlorophenyl)-1,2,4-oxadiazol-5-yl)ethylamino)pyrimidin-4-yl)oxazolidin-2-one;
(S)-3-(2-((S)-1-(2-fluoro-4-(1-methylcyclopropyl)phenyl)ethylamino)pyrimidin-4-yl)-4-isopropyloxazolidin-2-one;
(S)-3-(2-((S)-1-(2-fluoro-4-(trifluoromethyl)phenyl)ethylamino)pyrimidin-4-yl)-4-isopropyloxazolidin-2-one;
2-chloro-N-cyclopentyl-4-((S)-1-(4-((S)-4-isopropyl-2-oxooxazolidin-3-yl)pyrimidin-2-ylamino)ethyl)benzamide;
(S)-3-(2-((S)-1-(4-((3,3-difluoropiperidin-1-yl)methyl)phenyl)ethylamino)pyrimidin-4-yl)-4-isopropyloxazolidin-2-one;

(S)-3-(2-((S)-1-(4-(4,7-diazaspiro[2.5]octan-4-ylmethyl) phenyl)ethylamino)pyrimidin-4-yl)-4-isopropyloxazolidin-2-one;

(S)-3-(2-((S)-1-(4-((4-acetylpiperazin-1-yl)methyl)phenyl) ethylamino)pyrimidin-4-yl)-4-isopropyloxazolidin-2-one;

(S)-3-(2-(((S)-1-(4-isobutoxyphenyl)ethyl)amino)pyrimidin-4-yl)-4-isopropyloxazolidin-2-one;

(S)-3-(5-fluoro-2-(((S)-1-(4-isobutoxyphenyl)ethyl)amino) pyrimidin-4-yl)-4-isopropyloxazolidin-2-one; and 2-fluoro-N-(trans-4-hydroxycyclohexyl)-4-((S)-1-(4-((S)-4-isopropyl-2-oxooxazolidin-3-yl)pyrimidin-2-ylamino) ethyl)benzamide.

ENUMERATED EMBODIMENTS

Embodiment 1

A compound of formula (I)

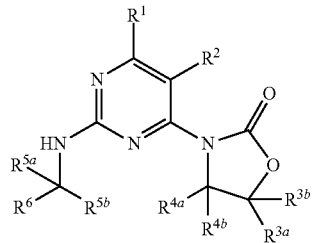

(I)

wherein:
each $R^1$ and $R^2$ is independently hydrogen, deuterium, halo, hydroxyl, $NH_2$, aryl, heteroaryl, or optionally substituted $C_{1-4}$ alkyl,
wherein said $C_{1-4}$ alkyl is optionally substituted with one to three substituents each independently selected from the group consisting of: halo, hydroxyl, and $NH_2$;
$R^{3a}$ is hydrogen, deuterium, $C_{1-6}$ alkyl, phenyl, or benzyl and $R^{3b}$ is hydrogen, deuterium, or $C_{1-6}$ alkyl; or
$R^{3a}$ and $R^{3b}$ are joined together forming an optionally substituted 3-7 membered cycloalkyl ring or an optionally substituted 4-7 membered heterocyclic ring,
wherein said cycloalkyl and heterocyclic rings are each optionally substituted with one or two substituents each independently selected from the group consisting of: halo, hydroxyl, oxo, $NH_2$, and $C_{1-3}$ alkyl;
$R^{4a}$ is hydrogen, $C_{1-6}$ alkyl, optionally substituted phenyl, optionally substituted benzyl, optionally substituted heteroaryl, or methylene-dibenzene,
wherein said phenyl, benzyl, and heteroaryl rings are optionally substituted with one to three substituents each independently selected from the group consisting of: halo, hydroxyl, cyano, nitro, $C_{1-3}$ alkoxy, $C_{1-3}$ haloalkyl, $C_{1-3}$ haloalkoxy, $C_{1-6}$ alkyl, $C_{3-6}$ cycloalkyl, 5-6 membered heteroaryl, 5-6 membered heterocyclic, phenoxy, $COOR^b$, $SO_2R^b$, $NHC(O)R^b$, and $NR^bR^b$ and
$R^{4b}$ is hydrogen, deuterium, or $C_{1-3}$ alkyl; or
$R^{4a}$ and $R^{4b}$ are joined together forming an optionally substituted 3-7 membered cycloalkyl ring or an optionally substituted 4-7 membered heterocyclic ring,
wherein said cycloalkyl and heterocyclic rings are optionally substituted with one or two substituents each independently selected from the group consisting of: halo, hydroxyl, oxo, $NH_2$, and $C_{1-3}$ alkyl, provided that only one of $R^{3a}$ and $R^{3b}$ and $R^{4a}$ and $R^{4b}$ are joined together forming a ring;

$R^{5a}$ is hydrogen or deuterium;

$R^{5b}$ is hydrogen, deuterium, methyl, ethyl, $CD_3$, $CF_3$, $CH_2F$, or $CHF_2$ and $R^6$ is optionally substituted $C_{1-6}$ alkyl, optionally substituted aryl, optionally substituted heteroaryl, optionally substituted heterocyclic, or optionally substituted $C_{5-10}$ cycloalkyl, wherein said $C_{1-6}$ alkyl is optionally substituted with one substituent selected from the group consisting of hydroxyl, $C_{1-3}$ alkoxy and $-OR^a$;

wherein said aryl, heteroaryl, heterocyclic and $C_{5-10}$ cycloalkyl are optionally substituted with one to three substituents each independently selected from the group consisting of: halo; hydroxyl; cyano; nitro; $C_{1-3}$ alkoxy; $C_{1-3}$ haloalkyl; $C_{1-3}$ haloalkoxy; $C_{1-6}$ alkyl; $C_{3-6}$ cycloalkyl; phenyl optionally substituted with one to three substituents each independently selected from the group consisting of: halo, hydroxyl, cyano, nitro, $C_{1-3}$ alkoxy, $C_{1-3}$ haloalkyl, $C_{1-3}$ haloalkoxy, $C_{1-6}$ alkyl, $C_{3-6}$ cycloalkyl, 5-6 membered heteroaryl, 5-6 membered heterocyclic, phenoxy, $COOR^b$, $SO_2R^b$, $NHC(O)R^b$, and $NR^bR^b$; 5-6 membered heteroaryl; 5-6 membered heterocyclic optionally substituted with one to three substituents each independently selected from the group consisting of: halo, hydroxyl, oxo, $NH_2$, and $C_{1-3}$ alkyl; $-CH_2R^a$; $-OR^a$; $-C(O)R^a$; $-NR^aR^b$; $-COOR^a$; $-SO_2R^a$; $NHC(O)R^a$; and $-SO_2NR^bR^b$; or $R^{5b}$ and $R^6$ are joined together forming an optionally substituted $C_{3-7}$ cycloalkyl group or an optionally substituted group of formula (a):

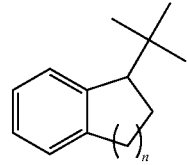

(a)

wherein n is 1, 2, or 3 and said $C_{3-7}$ cycloalkyl and group of formula (a) are optionally substituted with one to three substituents each independently selected from the group consisting of: halo, hydroxyl, cyano, nitro, $C_{1-3}$ alkoxy, $C_{1-3}$ haloalkyl, $C_{1-3}$ haloalkoxy, $C_{1-6}$ alkyl, $C_{3-6}$ cycloalkyl, 5-6 membered heteroaryl, 5-6 membered heterocyclic, benzyloxy, $COOR^b$, $SO_2R^b$, $NHC(O)R^b$, and $NR^bR^b$;

each $R^a$ is independently optionally substituted phenyl, optionally substituted heteroaryl, or optionally substituted 4-7 membered heterocyclic, wherein said phenyl and heteroaryl are optionally substituted with one to three substituents each independently selected from the group consisting of halo, hydroxyl, cyano, nitro, $C_{1-3}$ alkoxy, $C_{1-3}$ haloalkyl, $C_{1-3}$ haloalkoxy, and $C_{1-3}$ alkyl, wherein said 4-7 membered heterocyclic is optionally substituted with one to three substituents each independently selected from the group consisting of halo, hydroxyl, oxo, $C_{1-3}$ alkoxy, $C_{1-3}$ haloalkyl, $C_{1-3}$ haloalkoxy, and $C_{1-3}$ alkyl; and each $R^b$ is independently hydrogen or $C_{1-6}$ alkyl; or a pharmaceutically acceptable salt thereof.

Embodiment 2

The compound according to embodiment 1 wherein $R^2$ is hydrogen; or a pharmaceutically acceptable salt thereof.

Embodiment 3

The compound according to embodiment 2 wherein $R^1$ is hydrogen, halo, or optionally substituted $C_{1-4}$ alkyl; or a pharmaceutically acceptable salt thereof.

Embodiment 4

The compound according to embodiment 3 wherein $R^1$ is hydrogen, fluoro, chloro, or methyl; or a pharmaceutically acceptable salt thereof.

Embodiment 5

The compound according to embodiment 4 wherein $R^{3a}$ is hydrogen, $C_{1-6}$ alkyl, phenyl, or benzyl and $R^{3b}$ is hydrogen or $C_{1-6}$ alkyl; or a pharmaceutically acceptable salt thereof.

Embodiment 6

The compound according to embodiment 5 wherein $R^{3b}$ is hydrogen or methyl; or a pharmaceutically acceptable salt thereof.

Embodiment 7

The compound according to embodiment 6 wherein $R^{3a}$ is hydrogen, methyl, or phenyl; or a pharmaceutically acceptable salt thereof.

Embodiment 8

The compound according to embodiment 7 wherein $R^{4a}$ is hydrogen, $C_{1-6}$ alkyl, optionally substituted phenyl, optionally substituted benzyl, optionally substituted heteroaryl, or methylene-dibenzene, wherein said phenyl, benzyl, and heteroaryl rings are optionally substituted with one to three substituents each independently selected from the group consisting of: halo, hydroxyl, cyano, nitro, $C_{1-3}$ alkoxy, $C_{1-3}$ haloalkyl, $C_{1-3}$ haloalkoxy, $C_{1-6}$ alkyl, $C_{3-6}$ cycloalkyl, 5-6 membered heteroaryl, 5-6 membered heterocyclic, phenoxy, $COOR^b$, $SO_2R^b$, $NHC(O)R^b$, and $NR^bR^b$ and $R^{4b}$ is hydrogen or $C_{1-3}$ alkyl; or a pharmaceutically acceptable salt thereof.

Embodiment 9

The compound according to embodiment 8 wherein $R^{4b}$ is hydrogen or methyl; or a pharmaceutically acceptable salt thereof.

Embodiment 10

The compound according to embodiment 9 wherein $R^{4a}$ is hydrogen, $C_{1-4}$ alkyl, optionally substituted phenyl, optionally substituted benzyl, optionally substituted heteroaryl, or methylene-dibenzene; or a pharmaceutically acceptable salt thereof.

Embodiment 11

The compound according to embodiment 10 wherein $R^{4a}$ is hydrogen, methyl, isopropyl, isobutyl, t-butyl, phenyl, 4-methoxyphenyl, 4-fluorophenyl, benzyl, or methylene-dibenzene; or a pharmaceutically acceptable salt thereof.

Embodiment 12

The compound according to embodiment 11 wherein $R^{5a}$ is H; or a pharmaceutically acceptable salt thereof.

Embodiment 13

The compound according to embodiment 12 wherein $R^{5b}$ is hydrogen, methyl, ethyl, or $CF_3$.

Embodiment 14

The compound according to embodiment 13 wherein $R^6$ is isopropyl, optionally substituted aryl, optionally substituted pyrazolyl, optionally substituted pyridinyl, 2,3-dihydrobenzofuranyl, 2,3-dihydrobenzo[b][1,4]dioxinyl, or optionally substituted $C_{5-10}$ cycloalkyl; or a pharmaceutically acceptable salt thereof.

Embodiment 15

A pharmaceutical composition comprising a compound according to embodiment 1, or a pharmaceutically acceptable salt thereof, and a pharmaceutically acceptable carrier or excipient.

Embodiment 16

A method for the treatment of a disease or disorder associated with a mutant IDH protein having a neomorphic activity comprising administration of a therapeutically effective amount of a compound according to embodiment 1, or a pharmaceutically acceptable salt thereof, to subject in need of thereof.

Embodiment 17

A method for the treatment of a disease or disorder associated with a mutant IDH protein having a neomorphic activity comprising administration of a therapeutically effective amount of a compound according to embodiment 1, or a pharmaceutically acceptable salt thereof, and another therapeutic agent to subject in need of thereof.

General Synthetic Procedures

The compounds of the present invention may be made by a variety of methods, including standard chemistry. Suitable synthetic routes are depicted in the Schemes given below.

The compounds of formula (I) may be prepared by methods known in the art of organic synthesis as set forth in part by the following synthetic schemes. In the schemes described below, it is well understood that protecting groups for sensitive or reactive groups are employed where necessary in accordance with general principles or chemistry. Protecting groups are manipulated according to standard methods of organic synthesis (T. W. Greene and P. G. M. Wuts, "Protective Groups in Organic Synthesis", Third edition, Wiley, New York 1999). These groups are removed at a convenient stage of the compound synthesis using methods that are readily apparent to those skilled in the art. The selection processes, as well as the reaction conditions and order of their execution, shall be consistent with the preparation of compounds of formula (I).

Those skilled in the art will recognize if a stereocenter exists in the compounds of formula (I). Accordingly, the present invention includes both possible stereoisomers and includes not only racemic compounds but the individual enantiomers and/or diastereomers as well. When a compound is desired as a single enantiomer or diastereomer, it may be obtained by stereospecific synthesis or by resolution of the final product or any convenient intermediate. Resolution of the final product, an intermediate, or a starting material may be effected by any suitable method known in the art. See, for example, "Stereochemistry of Organic Compounds" by E. L. Eliel, S. H. Wilen, and L. N. Mander (Wiley-Interscience, 1994).

The compounds described herein may be made from commercially available starting materials or synthesized using known organic, inorganic, and/or enzymatic processes.

Scheme 1.

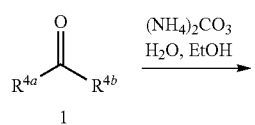

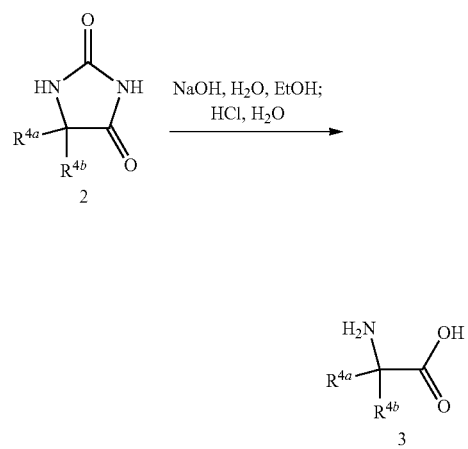

Non-commercial aminoacids can be prepared following the procedures of Scheme 1. Conversion of ketone 1 to the corresponding imidazolidine-2,4-dione 2 followed by hydrolysis provides aminoacid 3.

Scheme 2.

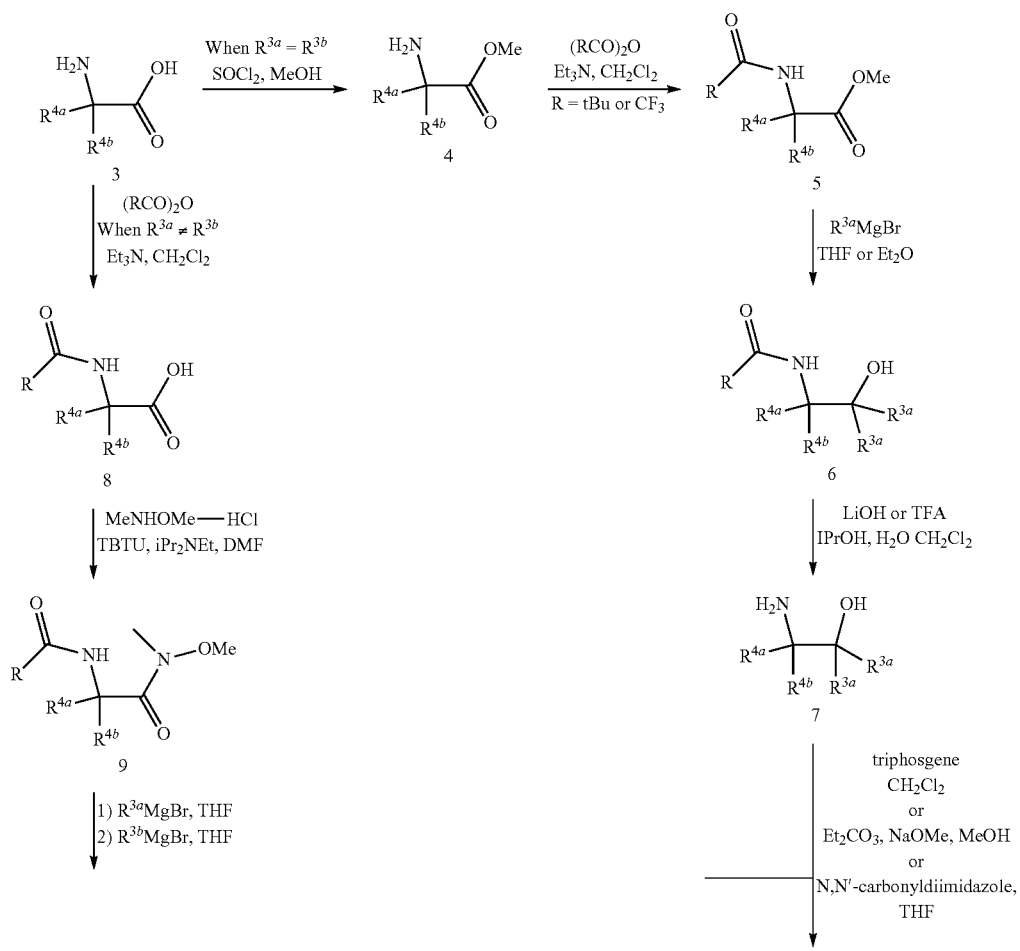

-continued

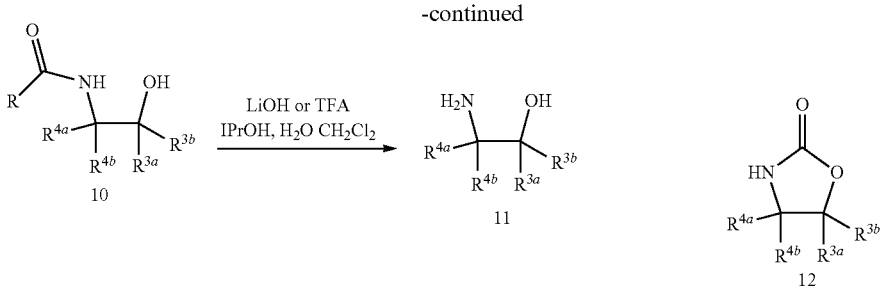

When aminoalcohol, precursor of oxazolidinone, is not commercially available, it can be prepared from aminoacid 3 following the procedures of Scheme 2. When $R^{3a}=R^{3b}$, protected aminoester 5 is treated with an appropriate Grignard reagent to give protected aminoalcohol 6 which goes through basic or acidic deprotection step. When $R^{3a}\neq R^{3b}$, protected aminoacid 8 is converted into Weinreb amide 9 which is treated with different Grignard reagents sequentially to provide protected aminoalcohol 10. Either basic or acidic deprotection of 10 gives 11. Insertion of CO unit into 7 or 11 to provide oxazolidinone 12 is accomplished with several reagents, including (but not limited to) triphosgene, $Et_2CO_3$ or N—N'-darbonyldiimidazole, as shown in Scheme 2.

Scheme 3.

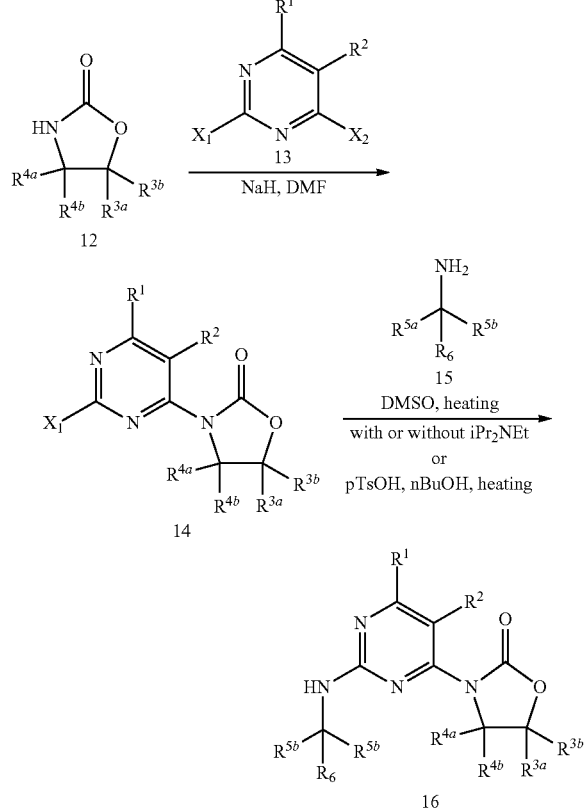

Oxazolidinone 12 is coupled with dihalogen-pyrimidine 13 in the presence of NaH and the resulting 14 is treated with primary amine 15 under several different reaction conditions as shown in Scheme 3 to provide 16.

Scheme 4.

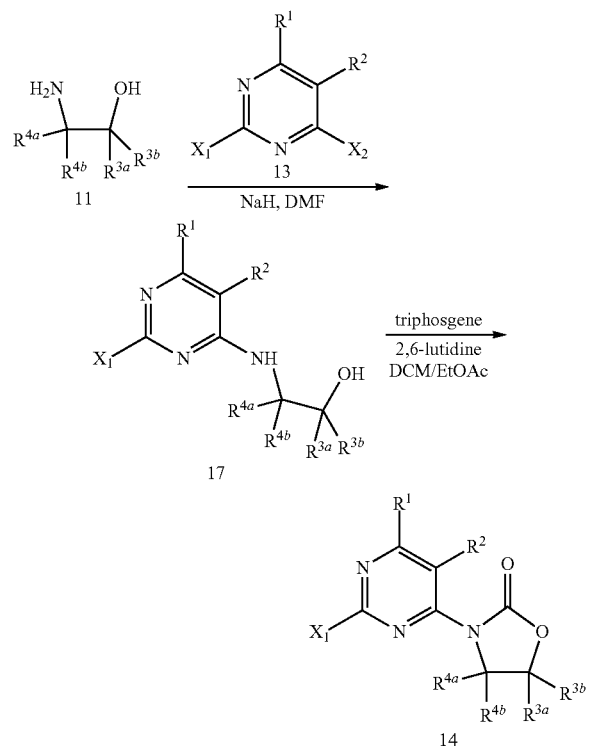

Alternately intermediate 14 can be prepared by coupling the amino alcohol 11 and dihalogen-pyrimidine 13 in the presence of a base such as diisopropylethyl amine resulting in intermediate 17 which can be treated with triphosgene in the presence of a base such as 2,6-lutidine resulting in intermediate 14.

Methods of Use

The compounds of the present invention are inhibitors of a mutant IDH protein having a neomorphic activity and are therefore useful in the treatment of diseases or disorders associated with such proteins including, but not limited to, cell proliferation disorders, such as cancer.

Examples of a mutant IDH protein having a neomorphic activity are mutant IDH1 and mutant IDH2. A neomorphic activity associated with mutant IDH1 and mutant IDH2 is the ability to produce 2-hydroxyglutarate (2-HG neomorphic activity), specifically R-2-HG (R-2-HG neomorphic activity). Mutations in IDH1 associated with 2-HG neomorphic activity, specifically R-2-HG neomorphic activity, include mutations at residues 97, 100, and 132, e.g. G97D, R100Q, R132H, R132C, R132S, R132G, R132L, and R132V. Mutations in IDH2 associated with 2-HG neoactivity, specifically R-2-HG neomorphic activity, include mutations at residues 140 and 172, e.g. R140Q, R140G, R172K, R172M, R172S, R172G, and R172W.

Cell-proliferation disorders associated with a mutant IDH protein having a neomorphic activity include, but are not limited to, cancer. Examples of such cancers include Acute Lymphoblastic Leukemia, Adult; Acute Lymphoblastic Leukemia, Childhood; Acute Myeloid Leukemia, Adult; Adrenocortical Carcinoma; Adrenocortical Carcinoma, Childhood; AIDS-Related Lymphoma; AIDS-Related Malignancies; Anal Cancer; Astrocytoma, Childhood Cerebellar; Astrocytoma, Childhood Cerebral; Bile Duct Cancer, Extrahepatic; Bladder Cancer; Bladder Cancer, Childhood; Bone Cancer, Osteosarcoma/Malignant Fibrous Histiocytoma; Brain Stem Glioma, Childhood; Brain Tumor, Adult; Brain Tumor, Brain Stem Glioma, Childhood; Brain Tumor, Cerebellar Astrocytoma, Childhood; Brain Tumor, Cerebral Astrocytoma/Malignant Glioma, Childhood; Brain Tumor, Ependymoma, Childhood; Brain Tumor, Medulloblastoma, Childhood; Brain Tumor, Supratentorial Primitive Neuroectodermal Tumors, Childhood; Brain Tumor, Visual Pathway and Hypothalamic Glioma, Childhood; Brain Tumor, Childhood (Other); Breast Cancer; Breast Cancer and Pregnancy; Breast Cancer, Childhood; Breast Cancer, Male; Bronchial Adenomas/Carcinoids, Childhood; Carcinoid Tumor, Childhood; Carcinoid Tumor, Gastrointestinal; Carcinoma, Adrenocortical; Carcinoma, Islet Cell; Carcinoma of Unknown Primary; Central Nervous System Lymphoma, Primary; Cerebellar Astrocytoma, Childhood; Cerebral Astrocytoma/Malignant Glioma, Childhood; Cervical Cancer; Childhood Cancers; Chronic Lymphocytic Leukemia; Chronic Myelogenous Leukemia; Chronic Myeloproliferative Disorders; Clear Cell Sarcoma of Tendon Sheaths; Colon Cancer; Colorectal Cancer, Childhood; Cutaneous T-Cell Lymphoma; Endometrial Cancer; Ependymoma, Childhood; Epithelial Cancer, Ovarian; Esophageal Cancer; Esophageal Cancer, Childhood; Ewing's Family of Tumors; Extracranial Germ Cell Tumor, Childhood; Extragonadal Germ Cell Tumor; Extrahepatic Bile Duct Cancer; Eye Cancer, Intraocular Melanoma; Eye Cancer, Retinoblastoma; Gallbladder Cancer; Gastric (Stomach) Cancer; Gastric (Stomach) Cancer, Childhood; Gastrointestinal Carcinoid Tumor; Germ Cell Tumor, Extracranial, Childhood; Germ Cell Tumor, Extragonadal; Germ Cell Tumor, Ovarian; Gestational Trophoblastic Tumor; Glioma, Childhood Brain Stem; Glioma, Childhood Visual Pathway and Hypothalamic; Hairy Cell Leukemia; Head and Neck Cancer; Hepatocellular (Liver) Cancer, Adult (Primary); Hepatocellular (Liver) Cancer, Childhood (Primary); Hodgkin's Lymphoma, Adult; Hodgkin's Lymphoma, Childhood; Hodgkin's Lymphoma During Pregnancy; Hypopharyngeal Cancer; Hypothalamic and Visual Pathway Glioma, Childhood; Intraocular Melanoma; Islet Cell Carcinoma (Endocrine Pancreas); Kaposi's Sarcoma; Kidney Cancer; Laryngeal Cancer; Laryngeal Cancer, Childhood; Leukemia, Acute Lymphoblastic, Adult; Leukemia, Acute Lymphoblastic, Childhood; Leukemia, Acute Myeloid, Adult; Leukemia, Acute Myeloid, Childhood; Leukemia, Chronic Lymphocytic; Leukemia, Chronic Myelogenous; Leukemia, Hairy Cell; Lip and Oral Cavity Cancer; Liver Cancer, Adult (Primary); Liver Cancer, Childhood (Primary); Lung Cancer, Non-Small Cell; Lung Cancer, Small Cell; Lymphoblastic Leukemia, Adult Acute; Lymphoblastic Leukemia, Childhood Acute; Lymphocytic Leukemia, Chronic; Lymphoma, AIDS-Related; Lymphoma, Central Nervous System (Primary); Lymphoma, Cutaneous T-Cell; Lymphoma, Hodgkin's, Adult; Lymphoma, Hodgkin's, Childhood; Lymphoma, Hodgkin's During Pregnancy; Lymphoma, Non-Hodgkin's, Adult; Lymphoma, Non-Hodgkin's, Childhood; Lymphoma, Non-Hodgkin's During Pregnancy; Lymphoma, Primary Central Nervous System; Macroglobulinemia, Waldenstrom's; Male Breast Cancer; Malignant Mesothelioma, Adult; Malignant Mesothelioma, Childhood; Malignant Thymoma; Medulloblastoma, Childhood; Melanoma; Melanoma, Intraocular; Merkel Cell Carcinoma; Mesothelioma, Malignant; Metastatic Squamous Neck Cancer with Occult Primary; Multiple Endocrine Neoplasia Syndrome, Childhood; Multiple Myeloma/Plasma Cell Neoplasm; Mycosis Fungoides; Myelodysplastic Syndromes; Myelogenous Leukemia, Chronic; Myeloid Leukemia, Childhood Acute; Myeloma, Multiple; Myeloproliferative Disorders, Chronic; Nasal Cavity and Paranasal Sinus Cancer; Nasopharyngeal Cancer; Nasopharyngeal Cancer, Childhood; Neuroblastoma; Non-Hodgkin's Lymphoma, Adult; Non-Hodgkin's Lymphoma, Childhood; Non-Hodgkin's Lymphoma During Pregnancy; Non-Small Cell Lung Cancer; Oral Cancer, Childhood; Oral Cavity and Lip Cancer; Oropharyngeal Cancer; steosarcoma/Malignant Fibrous Histiocytoma of Bone; Ovarian Cancer, Childhood; Ovarian Epithelial Cancer; Ovarian Germ Cell Tumor; Ovarian Low Malignant Potential Tumor; Pancreatic Cancer; Pancreatic Cancer, Childhood; Pancreatic Cancer, Islet Cell; Paranasal Sinus and Nasal Cavity Cancer; Parathyroid Cancer; Penile Cancer; Pheochromocytoma; Pineal and Supratentorial Primitive Neuroectodermal Tumors, Childhood; Pituitary Tumor; Plasma Cell Neoplasm/Multiple Myeloma; Pleuropulmonary Blastoma; Pregnancy and Breast Cancer; Pregnancy and Hodgkin's Lymphoma; Pregnancy and Non-Hodgkin's Lymphoma; Primary Central Nervous System Lymphoma; Primary Liver Cancer, Adult; Primary Liver Cancer, Childhood; Prostate Cancer; Rectal Cancer; Renal Cell (Kidney) Cancer; Renal Cell Cancer, Childhood; Renal Pelvis and Ureter, Transitional Cell Cancer; Retinoblastoma; Rhabdomyosarcoma, Childhood; Salivary Gland Cancer; Salivary Gland Cancer, Childhood; Sarcoma, Ewing's Family of Tumors; Sarcoma, Kaposi's; Sarcoma (Osteosarcoma)/Malignant Fibrous Histiocytoma of Bone; Sarcoma, Rhabdomyosarcoma, Childhood; Sarcoma, Soft Tissue, Adult; Sarcoma, Soft Tissue, Childhood; Sezary Syndrome; Skin Cancer; Skin Cancer, Childhood; Skin Cancer (Melanoma); Skin Carcinoma, Merkel Cell; Small Cell Lung Cancer; Small Intestine Cancer; Soft Tissue Sarcoma, Adult; Soft Tissue Sarcoma, Childhood; Squamous Neck Cancer with Occult Primary, Metastatic; Stomach (Gastric) Cancer; Stomach (Gastric) Cancer, Childhood; Supratentorial Primitive Neuroectodermal Tumors, Childhood; T-Cell Lymphoma, Cutaneous; Testicular Cancer; Thymoma, Childhood; Thymoma, Malignant; Thyroid Cancer; Thyroid Cancer, Childhood; Transitional Cell Cancer of the Renal Pelvis and Ureter; Trophoblastic Tumor, Gestational; Unknown Primary Site, Cancer of, Childhood; Unusual Cancers of Childhood; Ureter and Renal Pelvis, Transitional Cell Cancer; Urethral Cancer; Uterine Sarcoma; Vaginal Cancer; Visual Pathway and Hypothalamic Glioma, Childhood; Vulvar Cancer; Waldenstrom's Macro globulinemia; and Wilms' Tumor.

In another embodiment the cancer associated with a mutant IDH protein having a neomorphic activity is brain cancer, such as astrocytic tumor (e.g., pilocytic astrocytoma, subependymal giant-cell astrocytoma, diffuse astrocytoma, pleomorphic xanthoastrocytoma, anaplastic astrocytoma, astrocytoma, giant cell glioblastoma, glioblastoma, secondary glioblastoma, primary adult glioblastoma, and primary pediatric glioblastoma); oligodendroglial tumor (e.g., oligodendroglioma, and anaplastic oligodendroglioma); oligoastrocytic tumor (e.g., oligoastrocytoma, and anaplastic oligoastrocytoma); ependymoma (e.g., myxopapillary ependymoma, and anaplastic ependymoma); medulloblastoma; primitive neuroectodermal tumor, schwannoma, meningioma, meatypical meningioma, anaplastic meningioma; and pituitary adenoma. In another embodiment, the brain cancer is glioma, glioblastoma multiforme, paraganglioma, or suprantentorial primordial neuroectodermal tumors (sP-NET).

In another embodiment the cancer associated with a mutant IDH protein having a neomorphic activity is leukemia, such as acute myeloid leukemia (AML), myelodysplastic syndrome (MDS), chronic myelogenous leukemia (CML), myeloproliferative neoplasm (MPN), MDS.MPN including chronic myelomonocytic leukemia, post MDS AML, post MPN AML, post MDS/MPN AML, del(5q)-associated high risk MDS or AML, blast-phase chronic myelogenous leukemia, angioimmunoblastic lymphoma and acute lymphoblastic leukemia.

In another embodiment the cancer associated with a mutant IDH protein having a neomorphic activity is skin cancer, including melanoma.

In another embodiment the cancer associated with a mutant IDH protein having a neomorphic activity is prostate cancer, thyroid cancer, colon cancer, or lung cancer.

In another embodiment the cancer associated with a mutant IDH protein having a neomorphic activity is sarcoma, including central chondrosarcoma, central and periosteal chondroma, and fibrosarcoma.

In another embodiment the cancer associated with a mutant IDH protein having a neomorphic activity is cholangiocarcinoma.

Another disease or disorder associated with a mutant IDH protein having R-2-HG neomorphic activity is D-2-hydroxyglutaric aciduria.

Another disease or disorder associated with a mutant IDH protein having R-2-HG neomorphic activity is Diller disease and Mafucci syndrome.

As used herein the term "neomorphic activity" refers to a gain of novel activity of a protein that the wild-type protein does not have or does not exhibit to a significant degree. For example, a neomorphic activity associated with a mutant form of IDH1 and IDH2 is the ability to reduce alpha-ketoglutarate to 2-hydroxyglutarate (i.e. 2-HG, specifically R-2-HG). The wild type form of IDH1 and IDH2 does not have the ability to reduce alpha-ketoglutarate to 2-hydroxyglutarate (i.e. 2-HG, specifically R-2-HG) or if it does have this ability, it does not produce significant (i.e. harmful or disease causing) amounts of 2-HG.

As used herein, the term "subject" refers to an animal. Typically the animal is a mammal. A subject also refers to for example, primates (e.g., humans, male or female), cows, sheep, goats, horses, dogs, cats, rabbits, rats, mice, fish, birds and the like. In certain embodiments, the subject is a primate. In yet other embodiments, the subject is a human.

As used herein, the term "therapeutically effective amount" in reference to a compound of the invention means an amount of the compound sufficient to treat the subject's disease or condition, but low enough to avoid serious sides effects (at a reasonable benefit/risk ratio) within the scope of sound medical judgment. A therapeutically effective amount of a compound will vary with the particular compound chosen (e.g. consider the potency, efficacy, and half-life of the compound); the route of administration chosen; the condition being treated; the severity of the condition being treated; the age, size, weight, and physical condition of the subject being treated; the medical history of the subject being treated; the duration of the treatment; the nature of the concurrent therapy; the desired therapeutic effect; and like factors and can be routinely determined by the skilled artisan.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to preventing or delaying the onset or development or progression of the disease or disorder.

As used herein, a subject is "in need of" a treatment if such subject would benefit biologically, medically or in quality of life from such treatment.

The compounds of the present invention may be administered by any suitable route including oral and parenteral administration. Parenteral administration is typically by injection or infusion and includes intravenous, intramuscular, and subcontaneous injection or infusion.

The compounds of the invention may be administered once or according to a dosing regimen wherein a number of doses are administered at varying intervals of time for a given period of time. For example, doses may be administered one, two, three, or four times per day. Doses may be administered until the desired therapeutic effect is achieved or indefinitely to maintain the desired therapeutic effect. Suitable dosing regimens for a compound of the invention depend on the pharmacokinetic properties of that compound, such as absorption, distribution and half life which can be determined by the skilled artisan. In addition, suitable dosing regimens, including the duration such regimens are administered, for a compound of the invention depend on the disease or condition being treated, the severity of the disease or condition, the age and physical condition of the subject being treated, the medical history of the subject being treated, the nature of concurrent therapy, the desired therapeutic effect, and like factors within the knowledge and expertise of the skilled artisan. It will be further understood by such skilled artisans that suitable dosing regimens may require adjustment given an individual subject's response to the dosing regimen or over time as the individual subject needs change. Typical daily dosages may vary depending upon the particular route of administration chosen. Typical daily dosages for oral administration, to a human weighing approximately 70 kg would range from about 5 mg to about 500 mg of a compound of formula (I).

One embodiment of the present invention provides for a method of treating a disease or disorder associated with a mutant form of IDH having a neomorphic activity comprising administration of a therapeutically effective amount of a compound of formula (I) to a subject in need of treatment thereof. In one embodiment, the disease or disorder associated with a mutant form of IDH having a neomorphic activity is a cell proliferation disorder. In another embodiment, the cell proliferation disorder is cancer. In another embodiment, the cancer is a cancer associated with mutant IDH1 having 2-HG neomorphic activity or mutant IDH2 having 2-HG neomorphic activity. In another embodiment the neomorphic activity is R-2-HG neomorphic activity. In another embodiment the cancer is associated with mutant IDH1 having 2-HG or R-2-

HG neomorphic activity having a mutation at residues 97, 100, or 132, such as G97D, R100Q, R132H, R132C, R132S, R132G, R132L, and R132V. In another embodiment the cancer is associated with mutant IDH2 having 2-HG or R-2-HG neomorphic activity having a mutation at residues 140 or 172, e.g. R140Q, R140G, R172K, R172M, R172S, R172G, and R172W. In another embodiment the cancer is brain cancer, leukemia, skin cancer, prostate cancer, thyroid cancer, colon cancer, lung cancer or sarcoma. In another embodiment the cancer is glioma, glioblastoma multiforme, paraganglioma, suprantentorial primordial neuroectodermal tumors, acute myeloid leukemia, myelodysplastic syndrome, chronic myelogenous leukemia, melanoma, prostate, thyroid, colon, lung, central chondrosarcoma, central and periosteal chondroma tumors, fibrosarcoma, and cholangiocarcinoma.

Another embodiment of the present invention provides for a method of treating a disease or disorder associated with a mutant form of IDH having R-2-HG neomorphic activity comprising administration of a therapeutically effective amount of a compound according to formula (I) to a subject in need thereof wherein the disease or disorder is D-2-hydroxyglutaric aciduria, Ollier Disease, or Mafucci Syndrome.

Another embodiment of the present invention provides for the use of a compound of formula (I) in therapy. In a further embodiment the therapy is a disease or disorder associated with a mutant form of IDH having a neomorphic activity. In another embodiment the therapy is a cell proliferation disorder associated with a mutant form of IDH having a neomorphic activity. In another embodiment the therapy is cancer. In another embodiment the therapy is a cancer associated with a mutant IDH protein having a neomorphic activity, such as mutant IDH1 having 2-HG neomorphic activity or mutant IDH2 having 2-HG neomorphic activity. In another embodiment the neomorphic activity is R-2-HG neomorphic activity. In another embodiment the cancer is associated with mutant IDH1 having 2-HG or R-2-HG neomorphic activity having a mutation at residues 97, 100, or 132, such as G97D, R100Q, R132H, R132C, R132S, R132G, R132L, and R132V. In another embodiment the cancer is associated with mutant IDH2 having 2-HG or R-2-HG neomorphic activity having a mutation at residue at residues R140 or 172, e.g. R140Q, R140G, R172K, R172M, R172S, R172G, and R172W. In another embodiment the cancer is brain cancer, leukemia, skin cancer, prostate cancer, thyroid cancer, colon cancer, lung cancer or sarcoma. In another embodiment the cancer is glioma, glioblastoma multiforme, paraganglioma, suprantentorial primordial neuroectodermal tumors, acute myeloid leukemia, myelodysplastic syndrome, chronic myelogenous leukemia, melanoma, prostate, thyroid, colon, lung, central chondrosarcoma, central and periosteal chondroma tumors, fibrosarcoma, and cholangiocarcinoma.

Another embodiment of the present invention provides for the use of a compound of formula (I) in therapy wherein the therapy is D-2-hydroxyglutaric aciduria, Ollier Disease, or Mafucci Syndrome.

Another embodiment of the present invention provides for the use of a compound according to formula (I) in the manufacture of a medicament for the treatment of disease or disorder associated with a mutant form of IDH having a neomorphic activity. In one embodiment the disease or disorder associated with a mutant form of IDH having a neomorphic activity is a cell proliferation disorder. In another embodiment, the cell proliferation disorder is cancer. In another embodiment the cancer is a cancer associated with a mutant IDH protein having a neomorphic activity, such as mutant IDH1 having 2-HG neomorphic activity or mutant IDH2 having 2-HG neomorphic activity. In another embodiment the neomorphic activity is R-2-HG neomorphic activity. In another embodiment the cancer is associated with mutant IDH1 having 2-HG or R-2-HG neomorphic activity having a mutation at residues 97, 100, or 132, such as G97D, R100Q, R132H, R132C, R132S, R132G, R132L, and R132V. In another embodiment the cancer is associated with mutant IDH2 having 2-HG or R-2-HG neomorphic activity having a mutation at residue at residues 140 or 172, e.g. R140Q, R140G, R172K, R172M, R172S, R172G, and R172W. In another embodiment the cancer is brain cancer, leukemia, skin cancer, prostate cancer, thyroid cancer, colon cancer, lung cancer or sarcoma. In another embodiment the cancer is glioma, glioblastoma multiforme, paraganglioma, suprantentorial primordial neuroectodermal tumors, acute myeloid leukemia, myelodysplastic syndrome, chronic myelogenous leukemia, melanoma, prostate, thyroid, colon, lung, central chondrosarcoma, central and periosteal chondroma tumors, fibrosarcoma, and cholangiocarcinoma.

Another embodiment of the present invention provides for the use of a compound according to formula (I) in the manufacture of a medicament for the treatment of disease or disorder associated with a mutant form of IDH having R-2-HG neomorphic activity wherein the disease or disorder is D-2-hydroxyglutaric aciduria, Ollier Disease, or Mafucci Syndrome.

Compositions

In another aspect, the present invention provides a pharmaceutical composition comprising a compound of formula (I) and a pharmaceutically acceptable carrier or excipient.

The pharmaceutical compositions of the invention may be prepared and packaged in bulk form wherein a therapeutically effective amount of a compound of the invention can be extracted and then given to a subject, such as with powders or syrups. Alternatively, the pharmaceutical compositions of the invention may be prepared and packaged in unit dosage form wherein each physically discrete unit contains a therapeutically effective amount of a compound of the invention. When prepared in unit dosage form, the pharmaceutical compositions of the invention typically contain from about 5 mg to 500 mg of a compound of formula (I).

As used herein the term "pharmaceutically acceptable carrier or excipient" means a pharmaceutically acceptable material, composition or vehicle that, for example, are involved in giving form or consistency to the pharmaceutical composition. Each excipient must be compatible with the other ingredients of the pharmaceutical composition when commingled such that interactions which would substantially reduce the efficacy of the compound of the invention when administered to a subject and interactions which would result in pharmaceutical compositions that are not pharmaceutically acceptable are avoided. In addition, each excipient must, of course, be of sufficiently high purity to render it pharmaceutically acceptable.

The compound of the invention and the pharmaceutically acceptable carrier or excipient(s) will typically be formulated into a dosage form adapted for administration to the subject by the desired route of administration. For example, dosage forms include those adapted for (1) oral administration such as tablets, capsules, caplets, pills, troches, powders, syrups, elixirs, suspensions, solutions, emulsions, sachets, and cachets; and (2) parenteral administration such as sterile solutions, suspensions, and powders for reconstitution. Suitable pharmaceutically acceptable excipients will vary depending upon the particular dosage form chosen. In addition, suitable pharmaceutically acceptable excipients may be chosen for a particular function that they may serve in the composition. For example, certain pharmaceutically acceptable excipients may be chosen for their ability to facilitate the production of uniform dosage forms. Certain pharmaceutically acceptable excipients may be chosen for their ability to facilitate the production of stable dosage forms. Certain pharmaceutically acceptable excipients may be chosen for their ability to facilitate the carrying or transporting of the compound or compounds of the invention, once administered to the subject, from one organ or portion of the body to another organ or another portion of the body. Certain pharmaceutically acceptable excipients may be chosen for their ability to enhance patient compliance.

Suitable pharmaceutically acceptable excipients include the following types of excipients: diluents, lubricants, binders, disintegrants, fillers, glidants, granulating agents, coating agents, wetting agents, solvents, co-solvents, suspending agents, emulsifiers, sweeteners, flavoring agents, flavor masking agents, coloring agents, anti-caking agents, hemectants, chelating agents, plasticizers, viscosity increasing agents, antioxidants, preservatives, stabilizers, surfactants, and buffering agents.

Skilled artisans possess the knowledge and skill in the art to enable them to select suitable pharmaceutically acceptable carriers and excipients in appropriate amounts for the use in the invention. In addition, there are a number of resources available to the skilled artisan, which describe pharmaceutically acceptable carriers and excipients and may be useful in selecting suitable pharmaceutically acceptable carriers and excipients. Examples include *Remington's Pharmaceutical Sciences* (Mack Publishing Company), *The Handbook of Pharmaceutical Additives* (Gower Publishing Limited), and *The Handbook of Pharmaceutical Excipients* (the American Pharmaceutical Association and the Pharmaceutical Press).

The pharmaceutical compositions of the invention are prepared using techniques and methods known to those skilled in the art. Some methods commonly used in the art are described in *Remington's Pharmaceutical Sciences* (Mack Publishing Company).

In one aspect, the invention is directed to a solid oral dosage form such as a tablet or capsule comprising a therapeutically effective amount of a compound of the invention and a diluent or filler. Suitable diluents and fillers include lactose, sucrose, dextrose, mannitol, sorbitol, starch (e.g. corn starch, potato starch, and pre-gelatinized starch), cellulose and its derivatives, (e.g. microcrystalline cellulose), calcium sulfate, and dibasic calcium phosphate. The oral solid dosage form may further comprise a binder. Suitable binders include starch (e.g. corn starch, potato starch, and pre-gelatinized starch) gelatin, acacia, sodium alginate, alginic acid, tragacanth, guar gum, povidone, and cellulose and its derivatives (e.g. microcrystalline cellulose). The oral solid dosage form may further comprise a disintegrant. Suitable disintegrants include crospovidone, sodium starch glycolate, croscarmelose, alginic acid, and sodium carboxymethyl cellulose. The oral solid dosage form may further comprise a lubricant. Suitable lubricants include stearic acid, magnesium stearate, calcium stearate, and talc.

Where appropriate, dosage unit formulations for oral administration can be microencapsulated. The composition can also be prepared to prolong or sustain the release as, for example, by coating or embedding particulate material in polymers, wax, or the like.

The compounds of the invention may also be coupled with soluble polymers as targetable drug carriers. Such polymers can include polyvinylpyrrolidone, pyrancopolymer, polyhydroxypropylmethacrylamidephenol, polyhydroxyethylaspartamidephenol, or polyethyleneoxidepolylysine substituted with palmitoyl residues. Furthermore, the compounds of the invention may be coupled to a class of biodegradable polymers useful in achieving controlled release of a drug, for example polylactic acid, polepsilon caprolactone, polyhydroxy butyric acid, polyorthoesters, polyacetals, polydihydropyrans, polycyanacrylates and cross-linked or amphipathic block copolymers of hydrogels.

In another aspect, the invention is directed to a liquid oral dosage form. Oral liquids such as solution, syrups and elixirs can be prepared in dosage unit form so that a given quantity contains a predetermined amount of a compound of the invention. Syrups can be prepared by dissolving the compound of the invention in a suitably flavored aqueous solution; while elixirs are prepared through the use of a non-toxic alcoholic vehicle. Suspensions can be formulated by dispersing the compound of the invention in a non-toxic vehicle. Solubilizers and emulsifiers such as ethoxylated isostearyl alcohols and polyoxy ethylene sorbitol ethers, preservatives, flavor additives such as peppermint oil or other natural sweeteners or saccharin or other artificial sweeteners and the like can also be added.

In another aspect, the invention is directed to parenteral administration. Pharmaceutical compositions adapted for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The compositions may be presented in unit-dose or multi-dose containers, for example sealed ampoules and vials, and may be stored in a freeze dried (lyophilized) condition requiring only the addition of the sterile liquid carrier, for example water for injections, immediately prior to use. Extemporaneous injection solutions and suspensions may be prepared from sterile powders, granules and tablets.

Combinations

The compound of the present invention may be administered either simultaneously with, or before or after, one or more other therapeutic agent(s). The compound of the present invention may be administered separately, by the same or different route of administration, or together in the same pharmaceutical composition as the other agent(s).

In one embodiment, the invention provides a product comprising a compound of formula (I) and at least one other therapeutic agent as a combined preparation for simultaneous, separate or sequential use in therapy. In one embodiment, the therapy is the treatment of a disease or disorder associated with a mutant form of IDH. Products provided as a combined preparation include a composition comprising the compound of formula (I) and the other therapeutic agent(s) together in the same pharmaceutical composition, or the compound of formula (I) and the other therapeutic agent(s) in separate form, e.g. in the form of a kit.

In one embodiment, the invention provides a pharmaceutical composition comprising a compound of formula (I) and another therapeutic agent(s). Optionally, the pharmaceutical composition may comprise a pharmaceutically acceptable excipient, as described above.

In one embodiment, the invention provides a kit comprising two or more separate pharmaceutical compositions, at least one of which contains a compound of formula (I). In one embodiment, the kit comprises means for separately retaining said compositions, such as a container, divided bottle, or divided foil packet. An example of such a kit is a blister pack, as typically used for the packaging of tablets, capsules and the like.

The kit of the invention may be used for administering different dosage forms, for example, oral and parenteral, for administering the separate compositions at different dosage intervals, or for titrating the separate compositions against one another. To assist compliance, the kit of the invention typically comprises directions for administration.

In the combination therapies of the invention, the compound of the invention and the other therapeutic agent may be manufactured and/or formulated by the same or different manufacturers. Moreover, the compound of the invention and the other therapeutic agent may be brought together into a combination therapy: (i) prior to release of the combination product to physicians (e.g. in the case of a kit comprising the compound of the invention and the other therapeutic agent); (ii) by the physician themselves (or under the guidance of the physician) shortly before administration; (iii) in the patient themselves, e.g. during sequential administration of the compound of the invention and the other therapeutic agent.

Accordingly, the invention provides the use of a compound of formula (I) for treating a disease or disorder associated with a mutant form of IDH, wherein the medicament is prepared for administration with another therapeutic agent. The invention also provides the use of another therapeutic agent for treating a disease or disorder associated with a mutant form of IDH, wherein the medicament is administered with a compound of formula (I).

The invention also provides a compound of formula (I) for use in a method of treating a disease or disorder associated with a mutant form of IDH, wherein the compound of formula (I) is prepared for administration with another therapeutic agent. The invention also provides another therapeutic agent for use in a method of treating a disease or disorder associated with a mutant form of IDH, wherein the other therapeutic agent is prepared for administration with a compound of formula (I). The invention also provides a compound of formula (I) for use in a method of treating a disease or disorder associated with a mutant form of IDH, wherein the compound of formula (I) is administered with another therapeutic agent. The invention also provides another therapeutic agent for use in a method of treating a disease or disorder associated with a mutant form of IDH, wherein the other therapeutic agent is administered with a compound of formula (I).

The invention also provides the use of a compound of formula (I) for treating a disease or disorder associated with a mutant form of IDH, wherein the patient has previously (e.g. within 24 hours) been treated with another therapeutic agent. The invention also provides the use of another therapeutic agent for treating a disease or disorder associated with a mutant form of IDH, wherein the patient has previously (e.g. within 24 hours) been treated with a compound of formula (I).

In one embodiment, the other therapeutic agent is selected from: vascular endothelial growth factor (VEGF) receptor inhibitors, topoisomerase II inhibitors, smoothen inhibitors, alkylating agents, anti-tumor antibiotics, anti-metabolites, retinoids, and other cytotoxic agents.

Examples of vascular endothelial growth factor (VEGF) receptor inhibitors include, but are not limited to, bevacizumab (sold under the trademark Avastin® by Genentech/Roche), axitinib, (N-methyl-2-[[3-[(E)-2-pyridin-2-ylethenyl]-1H-indazol-6-yl]sulfanyl]benzamide, also known as AG013736, and described in PCT Publication No. WO 01/002369), Brivanib Alaninate ((S)—((R)-1-(4-(4-Fluoro-2-methyl-1H-indol-5-yloxy)-5-methylpyrrolo[2,1-f][1,2,4]triazin-6-yloxy)propan-2-yl)2-aminopropanoate, also known as BMS-582664), motesanib (N-(2,3-dihydro-3,3-dimethyl-1H-indol-6-yl)-2-[(4-pyridinylmethyl)amino]-3-pyridinecarboxamide, and described in PCT Publication No. WO 02/066470), pasireotide (also known as SOM230, and described in PCT Publication No. WO 02/010192), and sorafenib (sold under the tradename Nexavar®).

Examples of topoisomerase II inhibitors, include but are not limited to, etoposide (also known as VP-16 and Etoposide phosphate, sold under the tradenames Toposar®, VePesid® and Etopophos®), and teniposide (also known as VM-26, sold under the tradename Vumon®).

Examples of alkylating agents, include but are not limited to, temozolomide (sold under the tradenames Temodar® and Temodal® by Schering-Plough/Merck), dactinomycin (also known as actinomycin-D and sold under the tradename Cosmegen®), melphalan (also known as L-PAM, L-sarcolysin, and phenylalanine mustard, sold under the tradename Alkeran®), altretamine (also known as hexamethylmelamine (HMM), sold under the tradename Hexalen®), carmustine (sold under the tradename BiCNU®), bendamustine (sold under the tradename Treanda®), busulfan (sold under the tradenames Busulfex® and Myleran®), carboplatin (sold under the tradename Paraplatin®), lomustine (also known as CCNU, sold under the tradename CeeNU®), cisplatin (also known as CDDP, sold under the tradenames Platinol® and Platinol®-AQ), chlorambucil (sold under the tradename Leukeran®), cyclophosphamide (sold under the tradenames Cytoxan® and Neosar®), dacarbazine (also known as DTIC, DIC and imidazole carboxamide, sold under the tradename DTIC-Dome®), altretamine (also known as hexamethylmelamine (HMM) sold under the tradename Hexalen®), ifosfamide (sold under the tradename Ifex®), procarbazine (sold under the tradename Matulane®), mechlorethamine (also known as nitrogen mustard, mustine and mechloroethamine hydrochloride, sold under the tradename Mustargen®), streptozocin (sold under the tradename Zanosar®), thiotepa (also known as thiophosphoamide, TESPA and TSPA, and sold under the tradename Thioplex®.

Examples of anti-tumor antibiotics include, but are not limited to, doxorubicin (sold under the tradenames Adriamycin® and Rubex®), bleomycin (sold under the tradename Lenoxane®), daunorubicin (also known as dauorubicin hydrochloride, daunomycin, and rubidomycin hydrochloride, sold under the tradename Cerubidine®), daunorubicin liposomal (daunorubicin citrate liposome, sold under the tradename DaunoXome®), mitoxantrone (also known as DHAD, sold under the tradename Novantrone®), epirubicin (sold under the tradename Ellence™), idarubicin (sold under the tradenames Idamycin®, Idamycin PFS®), and mitomycin C (sold under the tradename Mutamycin®).

Examples of anti-metabolites include, but are not limited to, claribine (2-chlorodeoxyadenosine, sold under the tradename Leustatin®), 5-fluorouracil (sold under the tradename Adrucil®), 6-thioguanine (sold under the tradename Purinethol®), pemetrexed (sold under the tradename Alimta®), cytarabine (also known as arabinosylcytosine (Ara-C), sold under the tradename Cytosar-U®), cytarabine liposomal (also known as Liposomal Ara-C, sold under the tradename DepoCyt™), decitabine (sold under the tradename Dacogen®), hydroxyurea (sold under the tradenames Hydrea®, Droxia™ and Mylocel™), fludarabine (sold under the tradename Fludara®), floxuridine (sold under the tradename FUDR®), cladribine (also known as 2-chlorodeoxyadenosine (2-CdA) sold under the tradename Leustatin™), methotrexate (also known as amethopterin, methotrexate sodim (MTX), sold under the tradenames Rheumatrex® and Trexall™), and pentostatin (sold under the tradename Nipent®).

Examples of retinoids include, but are not limited to, alitretinoin (sold under the tradename Panretin®), tretinoin (all-trans retinoic acid, also known as ATRA, sold under the tradename Vesanoid®), Isotretinoin (13-cis-retinoic acid, sold under the tradenames Accutane®, Amnesteem®, Claravis®, Clarus®, Decutan®, Isotane®, Izotech®, Oratane®, Isotret®, and Sotret®), and bexarotene (sold under the tradename Targretin®).

Examples of other cytotoxic agents include, but are not limited to, arsenic trioxide (sold under the tradename Trisenox®), asparaginase (also known as L-asparaginase, and *Erwinia* L-asparaginase, sold under the tradenames Elspar® and Kidrolase®).

INTERMEDIATES AND EXAMPLES

The following examples are intended to be illustrative only and not limiting in any way. Unless otherwise noted, the following Intermediates and Examples were purified vial silica gel column chromatograph using RediSep® Rf columns from Teledyne Isco, Inc. Abbreviations used are those conventional in the art or the following:
ACN acetonitrial
BSA bovine serum albumin
C Celsius
CDI 1,1'-carbonyldiimidazole
d doublet
dd doublet of doublets
DAST diethylaminosulfur trifluoride
DEAD diethyl azodicarboxylate
DIPEA NN-diisopropylethylamine
DMF N,N-dimethylformamide
DMSO dimethylsulfoxide
DTT dithiothreitol
EtOAc ethyl acetate
EtOH ethanol
g gram
h hour(s) HATU 2-(1H-7-azabenzotriazol-1-yl)-1,1,3,3-tetramethyluronium hexafluorophosphate
HEPES 4-(2-hydroxyethyl)-1-piperazineethylanesulfonic acid
HPLC high pressure liquid chromatography
Hunig's Base NN-diisopropylethylamine
kg kilogram
L liter
LC liquid chromatographyLCMS liquid chromatography and mass spectrometry
MeOH methanol
MS mass spectrometry
m multiplet
min minutes
mL milliliter(s)
µM micromolar
m/z mass to charge ratio
nm nanometer
nM nanomolar
N normal
NADPH nicotinamide adenine dinucleotide phosphate
NMP N-methylpyrrolidone
NMR nuclear magnetic resonance
PdCl$_2$(dppf).CH$_2$Cl$_2$ 1,1'-bis(diphenylphosphino)ferrocene-palladium(II)dichloride dichloromethane complex
pTsOH p-toluenesulfonic acid
rac racemic
Rt retention time
s singlet
sat. saturated
t triplet
TBTU O-(Benzotriazol-1-yl)-N,N,N',N'-tetramethyluronium tetrafluoroborate
TCEP tris(2-carboxyethyl)phosphine
TEA triethylamine
TFA trifluoroacetic acid
THF tetrahydrofuran
TLC thin layer chromatography
TMS-CN trimethylsilyl cyanide
Instrumentation
LCMS:

LCMS data (also reported herein as simply MS) were recorded using a Waters System (Acuity UPLC and a Micromass ZQ mass spectrometer; Column: Acuity HSS C18 1.8-micron, 2.1×50 mm; gradient: 5-95% acetonitrile in water with 0.05% TFA over a 1.8 min period; flow rate 1.2 mL/min; molecular weight range 200-1500; cone Voltage 20 V; column temperature 50° C.). All masses reported are those of the protonated parent ions unless recorded otherwise.
High Resolution Mass Spectrometry (HRMS):

HRMS Method A: ESI-MS data were recorded using a Synapt G2HDMS (TOF mass spectrometer, Waters) with electrospray ionization source. The resolution of the MS system was approximately 15000. Leucine Enkephalin was used as lock mass (internal standards) infused from lockspary probe. The compound was infused into the mass spectrometer by UPLC (Acquity, Waters) from sample probe. The separation was performed on Acquity UPLC BEH C18 1×50 mm column at 0.2 mL/min flow rate with the gradient from 5% to 95% in 3 min. Solvent A was Water with 0.1% Formic Acid and solvent B was Acetonitrile with 0.1% Formic Acid. The mass accuracy of the system has been found to be <5 ppm with lock mass.

HRMS Method B: LC-MS/ESI-MS data were recorded on an Acquity G2 Xevo QTof—Rs(FWHM)>20000 Accuracy<5 ppm. The separation was performed on Acquity CSH 1.7 µm 2.1×50 mm—50° C. column Eluent A: Water+3.75 mM ammonium acetate. Eluent B: Acetonitrile. Gradient: from 2 to 98% B in 4.4 min—flow 1.0 mL/min.

HRMS methods A and B are referred to throughout as HRMS(A) or HRMS(B), respectively.

INTERMEDIATES

Intermediate A (R)-4-isobutyloxazolidin-2-one

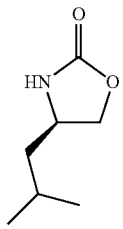

To a cooled (4° C.) solution of (R)-2-amino-4-methylpentan-1-ol (2.98 g, 25.4 mmol) and triethylamine (7.6 mL, 54 mmol, 2.1 equiv) in CH$_2$Cl$_2$ (80 mL) was added dropwise a solution of triphosgene (2.52 g, 8.49 mmol, 0.334 equiv) in 10 ml of CH$_2$Cl$_2$ over 30 min. The reaction mixture was stirred at 4° C. for 15 min, warmed up to room temperature and stirred for an additional 1 h. The mixture was treated with saturated NH$_4$Cl (25 mL), followed by CH$_2$Cl$_2$ (50 mL) and the resulting mixture was stirred for 20 min. The layers were separated and the organic layer was washed with water. The combined aqueous layers were extracted with CH$_2$Cl$_2$ (50 mL). The combined organic layers were dried over Na$_2$SO$_4$, filtered and concentrated to give (R)-4-isobutyloxazolidin-2-one (3.22 g) in 88% yield. The crude product was used for the next reaction without purification. $^1$H NMR (400 MHz, CD$_3$OD) δ 4.53-4.47 (m, 1H), 4.00-3.92 (m, 2H), 1.67 (ddq, J=13, 8.0, 6.5 Hz, 1H), 1.56-1.48 (m, 1H), 1.40-1.32 (m, 1H), 0.95 (d, J=6.1 Hz, 3H), 0.93 (d, J=6.1 Hz, 3H).

The Intermediates in Table 1 were prepared by a method similar to the one described for the preparation of Intermediate A.

TABLE 2

Chemical name, NMR chemical shifts and LCMS signal for each intermediate listed in Table 1.

| Intermediate: Name | $^1$H NMR (400 MHz) δ ppm | LCMS |
|---|---|---|
| B: (S)-4-isobutyloxazolidin-2-one | (CDCl$_3$) 6.59 (br s, 1 H), 4.53-4.48 (m, 1 H), 4.01-3.92 (m, 2 H), 1.71-1.54 (m, 2 H), 1.42-1.35 (m, 1 H), 0.94 (d, J = 6.5 Hz, 3 H), 0.93 (d, J = 6.5 Hz, 3 H). | no UV signal |
| C: (S)-4-tert-butyloxazolidin-2-one | (CD$_3$OD) 4.37 (t, J = 9.1 Hz, 1 H), 4.23 (dd, J = 9.1, 5.6 Hz, 1 H), 3.61 (dd, J = 9.1, 5.6 Hz, 1 H), 0.90 (s, 9 H) | no UV signal |
| D: (4S,5R)-5-methyl-4-phenyloxazolidin-2-one | (CD$_3$OD) δ 7.42-7.32 (m, 3 H), 7.27-7.24 (m, 2 H), 5.05 (dq, J = 8.0, 6.4 Hz, 1 H), 4.98 (d, J = 8.0 Hz, 1 H), 0.89 (d, J = 6.5 Hz, 3 H) | no UV signal |
| E: (S)-4-(pyridin-3-yl)oxazolidin-2-one | | MS m/z 165.1 (M + H)$^+$ |
| F: (S)-4-(pyridin-2-yl)oxazolidin-2-one | (CDCl$_3$) 8.62 (dt, J = 5.4, 1.1 Hz, 1 H), 7.80 (td, J = 7.8, 1.5 Hz, 1 H), 7.45 (d, J = 7.5 Hz, 1 H), 7.33-7.28 (m, 1 H), 6.40 (br s, 1 H), 5.12 (dd, J = 8.8, 5.8 Hz, 1 H), 4.86 (t, J = 9.0 Hz, 1 H), 4.43 (dd, J = 8.5, 5.5 Hz, 1 H) | HRMS(B) m/z 165.0663 (M + H)$^+$ |
| G: (S)-4-(pyridin-4-yl)oxazolidin-2-one | (CDCl$_3$) 8.67-8.66 (m, 2 H), 7.36-7.34 (m, 2 H), 6.50 (br s, 1 H), 5.04-5.00 (m, 1 H), 4.80 (t, J = 8.8 Hz, 1 H), 4.16 (dd, J = 8.5, 6.5 Hz, 1 H) | HRMS(B) m/z 165.0664 (M + H)$^+$ |
| H: (S)-4-methyl-4-phenyloxazolidin-2-one | (CDCl$_3$) 7.45-7.33 (m, 5 H), 6.10 (br s, 1 H), 4.39 (q, J = 8.4 Hz, 2 H), 1.79 (s, 3 H) | HRMS(B) m/z 178.0871 (M + H)$^+$ |
| I: 4,4-dimethyloxazolidin-2-one | (CDCl$_3$) 4.96 (br s, 1 H), 4.12 (s, 2 H), 1.40 (s, 6 H) | no UV signal |
| J: (S)-4-methyl-4-phenyloxazolidin-2-one | (CDCl$_3$) 7.33-7.19 (m, 5 H), 6.86 (br s, 1 H), 4.32-4.27 (m, 2 H), 1.67 (s, 3 H) | MS m/z 177.9 (M + H)$^+$ |
| K: (R)-4-(4-fluorophenyl)-4-methyloxazolidin-2-one | (CDCl$_3$) δ 7.41-7.36 (m, 2 H), 7.14-7.08 (m, 2 H), 6.06 (br s, 1 H), 4.39 (d, J = 8.3 Hz, 1 H), 4.33 (d, J = 8.3 Hz, 1 H), 1.78 (s, 3 H) | MS m/z 195.9 (M + H)+ |
| L: 3-oxa-1-azaspiro[4.4]nonan-2-one | (CDCl$_3$) δ 5.62 (br s, 1 H), 4.25 (s, 2 H), 1.90-1.65 (m, 8 H) | no UV signal |

Intermediate M 4-phenyl-1,8-dioxa-3-azaspiro[4.5]decan-2-one

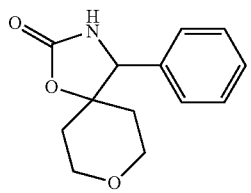 [SMILES: O=C1NC(c2ccccc2)C2(CCOCC2)O1]

Step 1: Preparation of 4-(amino(phenyl)methyl)tetrahydro-2H-pyran-4-ol

To dihydro-2H-pyran-4(3H)-one (1001 mg, 10 mmol) and triethylamine (0.279 mL, 2.00 mmol) was slowly added TMS-CN (1190 mg, 12.00 mmol) [Caution: exothermic reaction]. After stirring for 1 hour, the mixture was concentrated under reduced pressure. The residue, dissolved in diethyl ether (10 mL), was added dropwise to phenylmagnesium bromide (3M solution in diethyl ether, 4.33 mL, 13.00 mmol). Additional ~5 mL of diethyl ether was added and the suspension was stirred for ~4 hour. To the reaction mixture was added very slowly MeOH (3.0 mL), followed by the careful and slow additions of NaBH$_4$ (454 mg, 12.00 mmol) and MeOH (12 mL) in portions (gas development observed). The reaction mixture was stirred overnight and water (~6 mL) was added carefully, followed by 10% aqueous HCl solution (~20 mL). The mixture was vigorously stirred for 4 hour and diethyl ether was added. The separated organic layer was extracted with 10% aqueous HCl solution (1× ~20 mL). The combined aqueous layers were washed with diethylether (2×). The acidic layers were made basic by the addition of 6N aqueous NaOH solution. The milky white mixture was extracted with DCM (1×), ethyl acetate/THF (1:1; 1×) and ethyl acetate (2×). The organic layers (DCM and ethyl acetate solutions independently) were washed with saturated aqueous NaHCO$_3$ solution, dried over Na$_2$SO$_4$, filtered off and concentrated under reduced pressure providing crude 4-(amino(phenyl)methyl)tetrahydro-2H-pyran-4-ol, which was directly used in the next reaction without further purification.

Yellowish liquid. Yield: 451 mg. LCMS m/z 208.2 (M+H)$^+$, Rt 0.29 min.

Step 2: Preparation of 4-phenyl-1,8-dioxa-3-azaspiro[4.5]decan-2-one

To a mixture of CDI (388 mg, 2.394 mmol) in THF (1.5 mL) was added slowly a solution of 4-(amino(phenyl)methyl)tetrahydro-2H-pyran-4-ol (451 mg, 2.176 mmol) in THF (3 mL). The mixture was stirred under argon for ~5 hours. The mixture was diluted with saturated aqueous NaHCO₃ solution and DCM. The separated aqueous layer was extracted with DCM (2×) and the combined organic layers were washed with 0.5N aqueous HCl solution and brine, dried over sodium sulfate, filtered off and concentrated under reduced pressure. The residue was purified by column chromatography [SiO₂, 12 g, 0-100% heptane/ethyl acetate] providing 4-phenyl-1,8-dioxa-3-azaspiro[4.5]decan-2-one as a white solid. Yield: 330 mg. LCMS m/z 234.1 (M+H)⁺; Rt 0.52 min.

Intermediate N (S)-4-(biphenyl-4-yl)oxazolidin-2-one

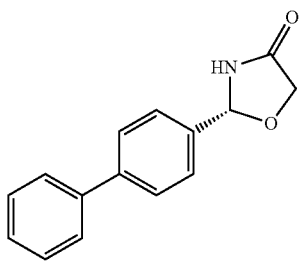 [SMILES: O=C1CO[C@H](c2ccc(-c3ccccc3)cc2)N1]

Step 1: Preparation of Vinylbiphenyl

To a suspension of methyltriphenylphosphonium bromide (5.10 g, 14.27 mmol) in THF (26 mL) was slowly added potassium tert-butoxide (1M solution in THF, 14.27 mL) over ~20 min at 0° C. The reaction mixture was allowed to warm up to room temperature and stirred for 10 min. The mixture was cooled to 0° C. and a solution of 4-biphenylcarbaldehyde (2.0 g, 10.98 mmol) in THF (9 mL) was added over 20 min. The reaction mixture was allowed to warm up to room temperature and stirred for ~19 hour. The mixture was filtered and the filtrate was concentrated under reduced pressure. The residue was dissolved/suspended in DCM and filtered through a silica pad and the filtrate was concentrated under reduced pressure. The residue was purified by column chromatography [SiO₂, 80 g, EtOAc/heptane] to provide vinylbiphenyl (1.845 g) as a white solid. LCMS Rt 0.79 min.

Step 2: Preparation of (S)-tert-butyl 1-(biphenyl-4-yl)-2-hydroxyethylcarbamate

To a solution of tert-butyl carbamate (2.82 g, 24.08 mmol) in 1-propanol (30 mL) was added aqueous NaOH solution (0.38M, 61.5 mL, 23.36 mmol). The mixture was stirred for 5 min and 1,3-dichloro-5,5-dimethylimidazolidine-2,4-dione (2.351 g, 11.93 mmol) was added. The mixture was stirred for 10 min and (DHQ)₂PHAL (0.303 g, 0.388 mmol), dissolved in 1-propanol (30 mL), was added followed by a solution of vinylbiphenyl (1.4 g, 7.77 mmol) in 1-propanol (60 mL). A suspension of potassium osmate dihydrate (0.114 g, 0.311 mmol) in aqueous NaOH solution, (0.38M, 0.613 mL, 0.233 mmol) was added and the mixture was stirred for ~16 hours. The reaction mixture was diluted with water (200 mL) and extracted with EtOAc (3×200 mL). The combined organic layers were washed with brine (2×400 mL), dried over sodium sulfate, filtered off and concentrated under reduced pressure. The residue was purified by column chromatography [SiO₂, 80 g, EtOAc/heptane] to provide (S)-tert-butyl 1-(biphenyl-4-yl)-2-hydroxyethylcarbamate (609 mg). LCMS m/z 258.2 (M+H; loss of t-Bu)⁺, Rt 0.97 min.

¹H NMR (400 MHz, CD₃OD) δ ppm 7.62-7.56 (m, 4H), 7.45-7.37 (m, 4H), 7.34-7.2 (m, 1H), 4.69 (t, J=5.8 Hz, 1H), 3.76-3.63 (m, 2H), 1.44 (br. s., 9H)

Step 3: Preparation of (S)-2-amino-2-(biphenyl-4-yl)ethanol

To a solution of (S)-tert-butyl 1-(biphenyl-4-yl)-2-hydroxyethylcarbamate (608 mg, 1.940 mmol) in MeOH (3 mL) was added HCl (4M in dioxane, 8 mL) at room temperature. The mixture was stirred for 1 hour and concentrated under reduced pressure. The residue was dissolved in DCM (10 mL)/water (1.0 mL) and stirred with NaHCO₃ for 1 hour. The mixture was filtered off and rinsed with DCM. The filtrate was dried over sodium sulfate, filtered off and concentrated under reduced pressure providing (S)-2-amino-2-(biphenyl-4-yl)ethanol (171 mg) as a white solid. LCMS m/z 214.2 (M+H)⁺, Rt 0.58 min.

Step 4: Preparation of (S)-4-(biphenyl-4-yl)oxazolidin-2-one

To a solution of (S)-2-amino-2-(biphenyl-4-yl)ethanol (171 mg, 0.802 mmol) in THF (12 mL) under argon atmosphere was added CDI (132 mg, 0.814 mmol). The solution was stirred at room temperature for 2 hours. The mixture was diluted with saturated aqueous NaHCO₃ solution (40 mL) and extracted with EtOAc (2×30 mL). The combined organic layers were washed with 0.5M aqueous HCl solution (30 mL), brine (40 mL), dried over sodium sulfate, filtered off and concentrated under reduced pressure. The residue was dissolved in DCM and concentrated under reduced pressure to provide crude (S)-4-(biphenyl-4-yl)oxazolidin-2-one (156 mg) as a beige solid, which was used without further purification. LCMS m/z 240.1 (M+H)⁺, Rt 0.80 min.

¹H NMR (400 MHz, CD₃OD) δ ppm 4.19 (dd, J=8.61, 6.50 Hz, 1H) 4.80 (t, J=8.73 Hz, 1H) 5.05 (dd, J=8.78, 6.48 Hz, 1H) 7.31-7.38 (m, 1H) 7.39-7.54 (m, 4H) 7.55-7.71 (m, 4H).

Intermediate P 4,4,5,5-tetramethyloxazolidin-2-one

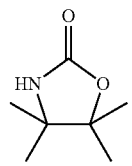

Step 1: Preparation of Methyl 2-(tert-butoxycarbonylamino)-2-methylpropanoate

To a solution of 2-(tert-butoxycarbonylamino)-2-methylpropanoic acid (10.03 g, 49.4 mmol) in MeOH/DCM (60 mL/140 mL) at room temperature was added drop wise (trimethylsilyl)diazomethane (37.0 mL, 74.0 mmol). The reaction mixture was stirred for 30 minutes. Acetic acid was added drop wise to quench (trimethylsilyl)diazomethane. The reaction mixture was concentrated under reduced pressure to afford the desired product as a white solid (10.56 g). LCMS m/z 240.2 (M+Na)⁺, Rt 0.71 min.

Step 2: Preparation of tert-butyl 3-hydroxy-2,3-dimethylbutan-2-ylcarbamate

To a solution of methyl 2-(tert-butoxycarbonylamino)-2-methylpropanoate (10.56 g, 48.6 mmol) in THF (300 mL) at 0° C. was added drop wise methylmagnesium bromide (64.8 mL, 194 mmol). Cold bath was removed after 1 hour. The reaction was stirred at 20° C. for 4 hours. The reaction was cooled back 0° C. and quenched with saturated NH$_4$Cl solution (10 mL). The reaction mixture was then allowed to warm to room temperature, and diluted with EtOAc (100 mL) and water (50 mL). The phases were separated and the aqueous layer was extracted with EtOAc (2×100 mL). The combined organics were then dried (Na$_2$SO$_4$) and concentrated. The residue was purified via silica gel flash chromatography (0-20% EtOAc-Hexanes) to afford the desired product as a white solid (9.02 g). LCMS m/z 240.1 (M+Na)$^+$, Rt 0.78 min.

Step 3: Preparation of 4,4,5,5-tetramethyloxazolidin-2-one

To tert-butyl 3-hydroxy-2,3-dimethylbutan-2-ylcarbamate (10.02 g, 46.1 mmol) in THF (300 ml) was added portion wise potassium 2-methylpropan-2-olate (7.24 g, 64.6 mmol). The reaction was stirred for five hours and quenched with HCl (1 M, 66 mL) to pH=2. The reaction mixture was then concentrated under vacuum to about one third of the volume, and diluted with water (50 mL). The aqueous layer was then extracted with DCM (3×100 mL). The combined organic was washed with brine (50 mL), dried (Na$_2$SO$_4$) and concentrated to give crude product as a light tan oil (6.25 g). LCMS m/z 144.1 (M+H)$^+$, Rt 0.42 min.

The Intermediates in Table 2b were prepared by a method similar to the one described for the preparation of Intermediate P.

TABLE 2b

| Intermediate: Name | Structure | LCMS |
|---|---|---|
| Q: (4S)-4-isopropyl-5-methyloxazolidin-2-one | 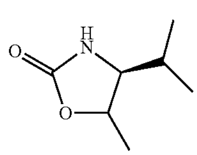 | MS m/z (M + H)$^+$ 144.4, Rt 0.47 min |
| R: 4,4,5-trimethyloxazolidin-2-one | 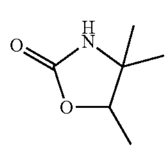 | MS m/z (M + H)$^+$ 130.4, Rt 0.36 min |
| S: 4,4-dimethyloxazolidin-2-one | 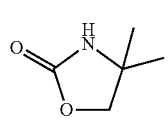 | MS m/z (M + H)+ 116.0, Rt 0.28 min |

Intermediate 1

(R)-3-(2-chloropyrimidin-4-yl)-4-phenyloxazolidin-2-one

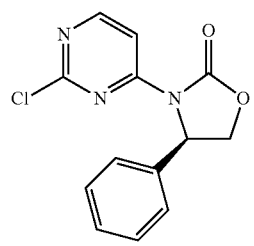 [SMILES: O=C1OC[C@@H](c2ccccc2)N1c1ccnc(Cl)n1]

A solution of (R)-4-phenyloxazolidin-2-one (2.9484 g, 18.07 mmol) and 2,4-dichloropyrimidine (3.1872 g, 21.39 mmol, 1.184 equiv) in DMF (30 mL) was treated with NaH (95%, 0.4773 g, 18.89 mmol, 1.046 equiv), then the resulting mixture (yellow to red cloudy) was stirred at room temperature for 3 h. The reaction mixture was diluted with EtOAc (200 mL), washed with sat. NH$_4$Cl (75 mL) and 4% aqueous NaCl (2×100 mL), dried over Na$_2$SO$_4$, filtered and concentrated. Silica gel column chromatography (EtOAc/Heptane 0 to 40%) provided (R)-3-(2-chloropyrimidin-4-yl)-4-phenyloxazolidin-2-one (2.7020 g, white sticky solid) in 46.9% yield. $^1$H NMR (400 MHz, CD$_3$OD) δ 8.47 (d, J=5.6 Hz, 1H), 8.18 (d, J=6.1 Hz, 1H), 7.38-7.30 (m, 5H), 5.81 (dd, J=8.6, 3.5 Hz, 1H), 4.88 (t, J=8.6 Hz, 1H), 4.37 (dd, J=8.6, 3.5 Hz, 1H); MS m/z 276.4 (M+H)$^+$.

The Intermediates in Table 3 were prepared by a method similar to the one described for the preparation of Intermediate 1.

TABLE 3

| | | |
|---|---|---|
| | | Intermediate 2 |
| | | Intermediate 3 |
| | | Intermediate 4 |

TABLE 3-continued
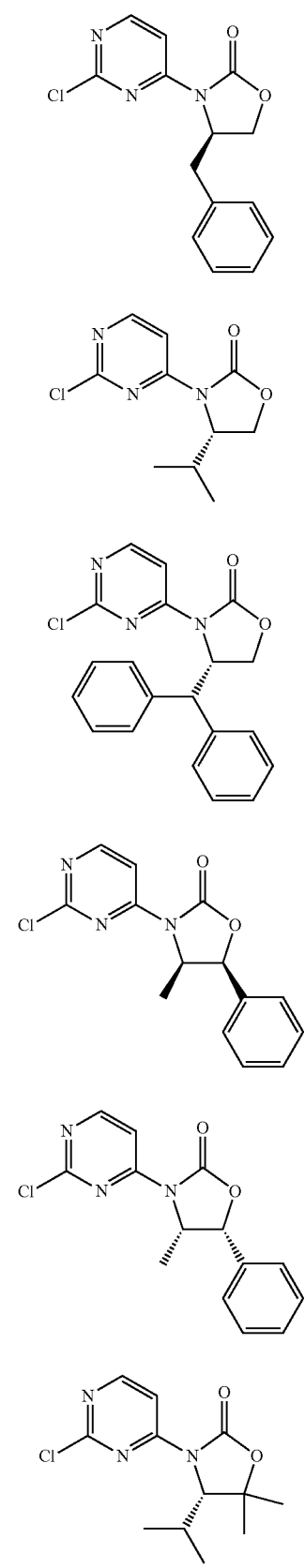
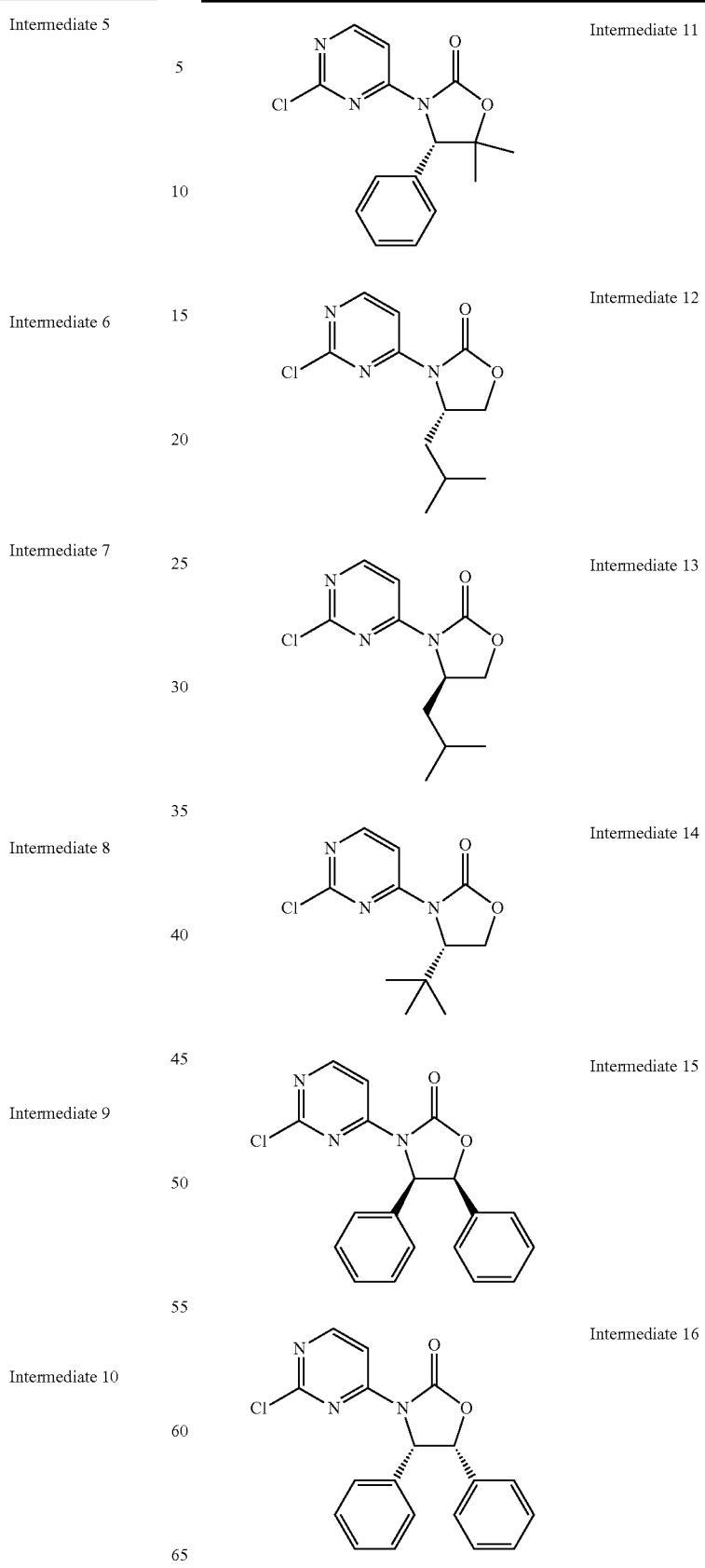

TABLE 3-continued
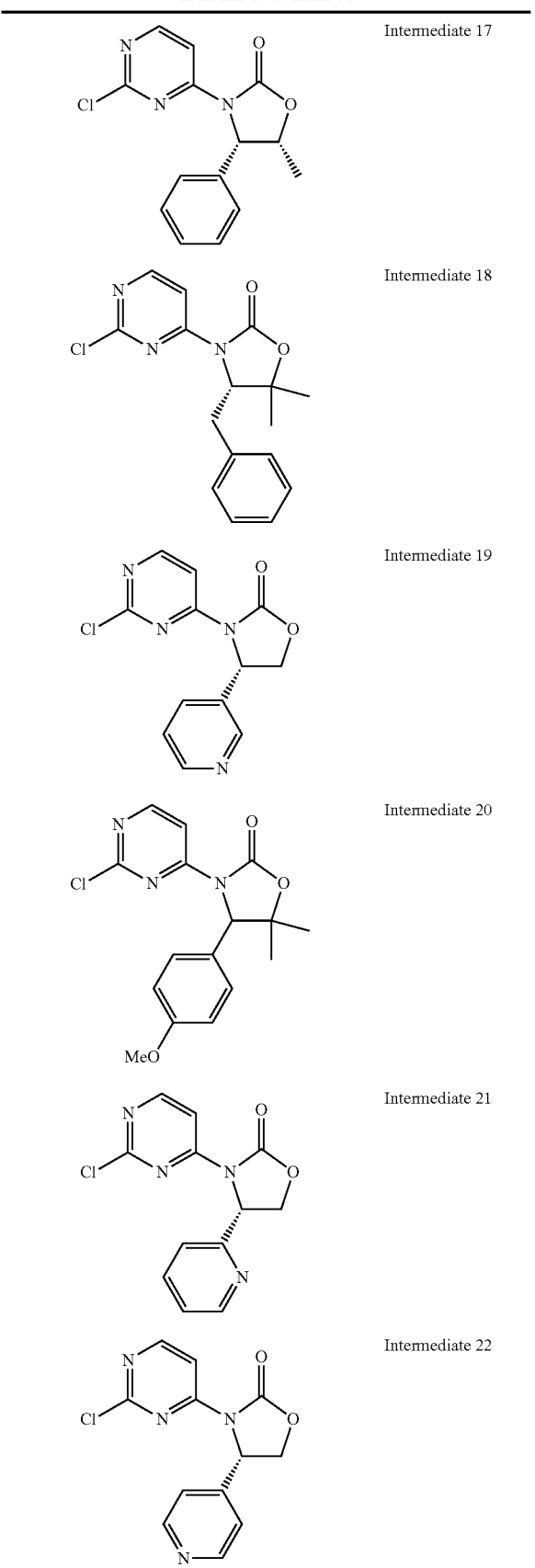
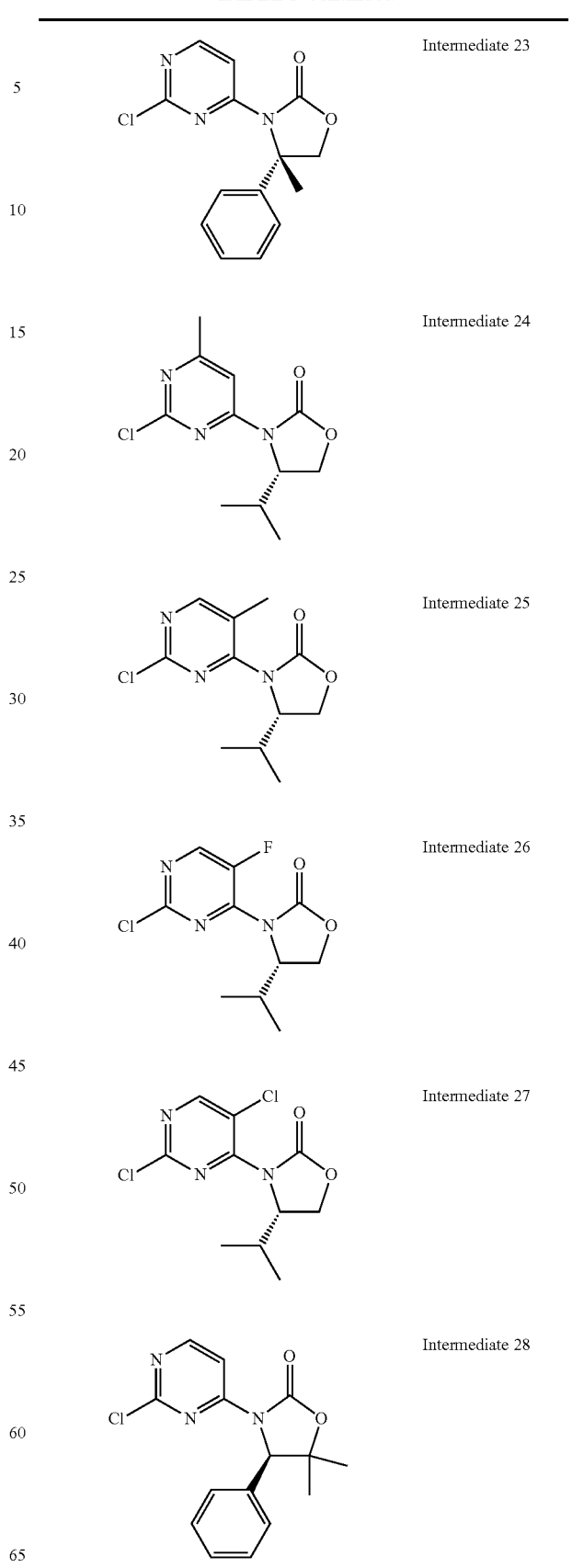

TABLE 3-continued

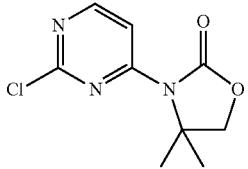

Intermediate 29

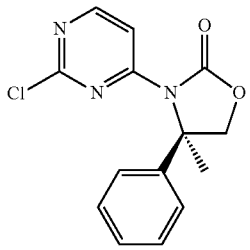 [SMILES: C[C@@]1(c2ccccc2)COC(=O)N1c1ccnc(Cl)n1]

Intermediate 30

TABLE 4

Chemical name, NMR chemical shifts and LCMS signal for each intermediate listed in Table 3.

| Intermediate: Name | $^1$H NMR (400 MHz) δ ppm | LCMS |
|---|---|---|
| 2: (S)-3-(2-chloropyrimidin-4-yl)-4-phenyloxazolidin-2-one | (CDCl$_3$) 8.47 (d, J = 6.1 Hz, 1 H), 8.18 (d, J = 5.7 Hz, 1 H), 7.39-7.29 (m, 5 H), 5.81 (dd, J = 8.6, 3.5 Hz, 1 H), 4.88 (t, J = 8.8 Hz, 1 H), 4.37 (dd, J = 8.8, 3.8 Hz, 1 H) | MS m/z 276.5 (M + H)$^+$ |
| 3: 3-(2-chloropyrimidin-4-yl)oxazolidin-2-one | (CD$_3$OD) 8.48 (d, J = 6.1 Hz, 1 H), 8.16 (d, J = 6.1 Hz, 1 H), 4.54 (t, J = 7.8 Hz, 2 H), 4.22 (t, J = 8.1 Hz, 2 H) | MS m/z 200.4 (M + H)$^+$ |
| 4: (S)-4-benzyl-3-(2-chloropyrimidin-4-yl)oxazolidin-2-one | (CD$_3$OD) 8.52 (d, J = 6.1 Hz, 1 H), 8.15 (d, J = 6.1 Hz, 1 H), 7.32-7.22 (m, 5 H), 5.07-5.02 (m, 1 H), 4.46-4.37 (m, 2 H), 3.30-3.27 (m, 1 H), 3.06 (dd, J = 13, 8.1 Hz, 1 H) | MS m/z 290.3 (M + H)$^+$ |
| 5: (R)-4-benzyl-3-(2-chloropyrimidin-4-yl)oxazolidin-2-one | (CD$_3$OD) 8.51 (d, J = 5.6 Hz, 1 H), 8.13 (d, J = 5.6 Hz, 1 H), 7.31-7.21 (m, 5 H), 5.06-4.98 (m, 1 H), 4.45-4.34 (m, 2 H), 3.30-3.25 (m, 1 H), 3.04 (dd, J = 14, 8.1 Hz, 1 H) | MS m/z 290.3 (M + H)$^+$ |
| 6: (S)-3-(2-chloropyrimidin-4-yl)-4-isopropyloxazolidin-2-one | (CD$_3$OD) 8.50 (d, J = 5.9 Hz, 1 H), 8.17 (d, J = 5.8 Hz, 1 H), 4.83-4.76 (m, 1 H), 4.48-4.43 (m, 2 H), 2.56 (dtd, J = 14, 7.0, 3.8 Hz, 1 H), 0.99 (d, J = 7.1 Hz, 3 H), 0.87 (d, J = 7.1 Hz, 3 H) | MS m/z 242.6 (M + H)$^+$ |
| 7: (S)-4-benzhydryl-3-(2-chloropyrimidin-4-yl)oxazolidin-2-one | (CD$_3$OD) 8.41 (d, J = 5.8 Hz, 1 H), 8.01 (d, J = 5.8 Hz, 1 H), 7.35-7.26 (m, 3 H), 7.24-7.12 (m, 7 H), 5.86-5.70 (m, 1 H), 4.74 (d, J = 7.1 Hz, 1 H), 4.64 (t, J = 8.5 Hz, 1 H), 4.45 (dd, J = 9.1, 2.0 Hz, 1 H) | MS m/z 366.1 (M + H)$^+$ |
| 8: (4R,5S)-3-(2-chloropyrimidin-4-yl)-4-methyl-5-phenyloxazolidin-2-one | (CD$_3$OD) 8.52 (d, J = 6.1 Hz, 1 H), 8.20 (d, J = 6.1 Hz, 1 H), 7.48-7.38 (m, 5 H), 5.92 (d, J = 7.6 Hz, 1 H), 5.15 (quin, J = 6.8 Hz, 1 H), 0.98 (d, J = 6.6 Hz, 3 H) | MS m/z 290.3 (M + H)$^+$ |
| 9: (4S,5R)-3-(2-chloropyrimidin-4-yl)-4-methyl-5-phenyloxazolidin-2-one | (CD$_3$OD) 8.52 (d, J = 6.1 Hz, 1 H), 8.20 (d, J = 6.1 Hz, 1 H), 7.48-7.38 (m, 5 H), 5.92 (d, J = 7.6 Hz, 1 H), 5.15 (quin, J = 6.7 Hz, 1 H), 0.98 (d, J = 6.6 Hz, 3 H) | MS m/z 290.3 (M + H)$^+$ |
| 10: (S)-3-(2-chloropyrimidin-4-yl)-4-isopropyl-5,5-dimethyloxazolidin-2-one | (CD$_3$OD) 8.48 (d, J = 5.8 Hz, 1 H), 8.20 (d, J = 5.8 Hz, 1 H), 4.63 (d, J = 3.1 Hz, 1 H), 2.29 (dtd, J = 14, 7.0, 3.1, 1 H), 1.60 (s, 3 H), 1.47 (s, 3 H), 1.05 (d, J = 7.1 Hz, 3 H), 0.99 (d, J = 7.1 Hz, 3 H) | MS m/z 270.1 (M + H)$^+$ |
| 11: (S)-3-(2-chloropyrimidin-4-yl)-5,5-dimethyl-4-phenyloxazolidin-2-one | (CD$_3$OD) 8.48 (d, J = 5.8 Hz, 1 H), 8.25 (d, J = 5.8 Hz, 1 H), 7.39-7.30 (m, 3 H), 7.22 (br s, 2 H), 1.67 (s, 3 H), 1.04 (s, 3 H) | MS m/z 304.3 (M + H)$^+$ |
| 12: (S)-3-(2-chloropyrimidin-4-yl)-4-isobutyloxazolidin-2-one | (CD$_3$OD) 8.49 (d, J = 5.9 Hz, 1 H), 8.13 (d, J = 5.9 Hz, 1 H), 4.83 (ddt, J = 10, 7.6, 2.9 Hz, 1 H), 4.58-4.54 (m, 1 H), 4.31 (dd, J = 8.8, 2.8 Hz, 1 H), 1.87-1.81 (m, 1 H), 1.75-1.65 (m, 1 H), 1.62-1.55 (m, 1 H), 1.05 (d, J = 6.5 Hz, 3 H), 0.99 (d, J = 6.5 Hz, 3 H) | MS m/z 256.3 (M + H)$^+$ |

TABLE 4-continued

Chemical name, NMR chemical shifts and LCMS signal for each intermediate listed in Table 3.

| Intermediate: Name | ¹H NMR (400 MHz) δ ppm | LCMS |
|---|---|---|
| 13: (R)-3-(2-chloropyrimidin-4-yl)-4-isobutyloxazolidin-2-one | (CD$_3$OD) 8.48 (d, J = 5.8 Hz, 1 H), 8.12 (d, J = 6.0 Hz, 1 H), 4.87-4.79 (m, 1 H), 4.57 (t, J = 8.6 Hz, 1 H), 4.31 (dd, J = 8.6, 2.5 Hz, 1 H), 1.87-1.81 (m, 1 H), 1.75-1.65 (m, 1 H), 1.62-1.56 (m, 1 H), 1.05 (d, J = 6.6 Hz, 3 H), 0.99 (d, J = 6.6 Hz, 3 H) | MS m/z 256.3 (M + H)⁺ |
| 14: (S)-4-tert-butyl-3-(2-chloropyrimidin-4-yl)oxazolidin-2-one | (CD$_3$OD) 8.50 (d, J = 5.9 Hz, 1 H), 8.12 (d, J = 5.9 Hz, 1 H), 4.94 (dd, J = 7.6, 1.5 Hz, 1 H), 4.54 (dd, J = 9.1, 1.5 Hz, 1 H), 4.46-4.42 (m, 1 H), 0.95 (s, 9 H) | MS m/z 256.4 (M + H)⁺ |
| 15: (4R,5S)-3-(2-chloropyrimidin-4-yl)-4,5-diphenyloxazolidin-2-one | (CD$_3$OD) 8.52 (d, J = 5.9 Hz, 1 H), 8.33 (d, J = 5.9 Hz, 1 H), 7.14-7.05 (m, 8 H), 6.93-6.91 (m, 2 H), 6.18-6.11 (m, 2 H) | MS m/z 352.4 (M + H)⁺ |
| 16: (4S,5R)-3-(2-chloropyrimidin-4-yl)-4,5-diphenyloxazolidin-2-one | (CD$_3$OD) 8.52 (d, J = 5.9 Hz, 1 H), 8.33 (d, J = 5.9 Hz, 1 H), 7.14-7.05 (m, 8 H), 6.93-6.91 (m, 2 H), 6.18-6.11 (m, 2 H) | MS m/z 352.3 (M + H)⁺ |
| 17: (4S,5R)-3-(2-chloropyrimidin-4-yl)-5-methyl-4-phenyloxazolidin-2-one | (CD$_3$OD) 8.47 (d, J = 5.9 Hz, 1 H), 8.25 (d, J = 5.9 Hz, 1 H), 7.40-7.31 (m, 3 H), 7.21 (d, J = 7.0 Hz, 2 H), 5.80 (d, J = 7.5 Hz, 1 H), 5.18-5.12 (m, 1 H), 1.02 (d, J = 6.5 Hz, 3 H); | MS m/z 290.4 (M + H)⁺ |
| 18: (S)-4-benzyl-3-(2-chloropyrimidin-4-yl)-5,5-dimethyloxazolidin-2-one | (CDCl$_3$) 8.45 (d, J = 5.8 Hz, 1 H), 8.16 (d, J = 5.8 Hz, 1 H), 7.37-7.28 (m, 4 H), 7.25-7.21 (m, 1 H), 4.87 (dd, J = 9.0, 4.5 Hz, 1 H), 3.24 (dd, J = 15, 4.5 Hz, 1 H), 2.97 (dd, J = 14, 9.0 Hz, 1 H), 1.51 (s, 3 H), 1.45 (s, 3 H) | MS m/z 318.1 (M + H)⁺ |
| 19: (S)-3-(2-chloropyrimidin-4-yl)-4-(pyridin-3-yl)oxazolidin-2-one | (CDCl$_3$) 8.76-8.75 (m, 1 H), 8.62 (d, J = 3.5 Hz, 1 H), 8.47 (d, J = 5.8 Hz, 1 H), 8.16 (d, J = 5.8 Hz, 1 H), 7.74 (dt, J = 8.0, 2.0 Hz, 1 H), 7.35 (dd, J = 7.8, 4.8 Hz, 1 H), 5.83 (dd, J = 8.8, 3.8 Hz, 1 H), 4.90 (t, J = 9.0 Hz, 1 H), 4.50 (dd, J = 9.0, 3.5 Hz, 1 H) | MS m/z 277.4 (M + H)⁺ |
| 20: 3-(2-chloropyrimidin-4-yl)-4-(4-methoxyphenyl)-5,5-dimethyloxazolidin-2-one | (CDCl$_3$) 8.44 (d, J = 5.8 Hz, 1 H), 8.25 (d, J = 5.8 Hz, 1 H), 7.13 (br d, J = 7.0 Hz, 2 H), 6.89 (d, J = 9.0 Hz, 2 H), 5.39 (s, 1 H), 3.82 (s, 3 H), 1.67 (s, 3 H), 1.11 (s, 3 H) | HRMS(B) m/z 334.0954 (M + H)⁺ |
| 21: (S)-3-(2-chloropyrimidin-4-yl)-4-(pyridin-2-yl)oxazolidin-2-one | (CDCl$_3$) 8.62-8.60 (m, 1 H), 8.45 (d, J = 5.8 Hz, 1 H), 8.22 (d, J = 5.8 Hz, 1 H), 7.73 (td, J = 7.7, 1.8 Hz, 1 H), 7.43 (d, J = 7.5 Hz, 1 H), 7.29-7.26 (m, 1 H), 5.85 (dd, J = 8.5, 3.5 Hz, 1 H), 4.82 (t, J = 8.8 Hz, 1 H), 4.64 (dd, J = 8.8, 3.8 Hz, 1 H) | MS m/z 277.0 (M + H)⁺ |
| 22: (S)-3-(2-chloropyrimidin-4-yl)-4-(pyridin-4-yl)oxazolidin-2-one | (CDCl$_3$) 8.72-8.70 (m, 1 H), 8.52 (d, J = 5.8 Hz, 1 H), 8.20 (d, J = 5.8 Hz, 1 H), 7.43-7.42 (m, 1 H), 5.81 (dd, J = 8.8, 3.8 Hz, 1 H), 4.91 (t, J = 9.0 Hz, 1 H), 4.44 (dd, J = 9.3, 3.8 Hz, 1 H) | MS m/z 276.9 (M + H)⁺ |
| 23: (S)-3-(2-chloropyrimidin-4-yl)-4-methyl-4-phenyloxazolidin-2-one | (CDCl$_3$) 8.44 (d, J = 5.8 Hz, 1 H), 8.13 (d, J = 5.8 Hz, 1 H), 7.41-7.28 (m, 5 H), 4.46 (d, J = 8.5 Hz, 1 H), 4.38 (d, J = 8.5 Hz, 1 H), 2.23 (s, 3 H) | MS m/z 289.9 (M + H)⁺ |
| 24: (S)-3-(2-chloro-6-methylpyrimidin-4-yl)-4-isopropyloxazolidin-2-one | (CDCl$_3$) 8.06 (s, 1 H), 4.83-4.77 (m, 1 H), 4.44-4.34 (m, 2 H), 2.65-2.55 (m, 1 H), 2.53 (s, 3 H), 1.00 (d, J = 8 Hz, 3 H), 0.88 (d, J = 8 Hz, 3 H) | MS m/z 255.8 (M + H)⁺ |
| 25: (S)-3-(2-chloro-5-methylpyrimidin-4-yl)-4-isopropyloxazolidin-2-one | (CDCl$_3$) 8.50 (s, 1 H), 5.01-4.96 (m, 1 H), 4.53 (t, J = 9.0 Hz, 1 H), 4.28 (t, J = 8.8 Hz, 1 H), 2.35 (s, 3 H), 2.16 (td, J = 7.0 Hz, J = 4.5 Hz, 1 H), 0.93 (d, J = 7.0 Hz, 3 H), 0.84 (d, J = 6.5 Hz, 3 H) | MS m/z 255.9 (M + H)⁺ |
| 26: (S)-3-(2-chloro-5-fluoropyrimidin-4-yl)-4-isopropyloxazolidin-2-one | (DMSO-d$_6$) 8.95 (d, J = 3.0 Hz, 1 H), 4.79-4.73 (m, 1 H), 4.58 (t, J = 9.0 Hz, 1 H), 4.41 (dd, J = 8.5 Hz, J = 6.5 Hz, 1 H), 2.24-2.16 (m, 1 H), 0.86 (d, J = 7.0 Hz, 3 H), 0.78 (d, J = 6.5 Hz, 3 H) | MS m/z 259.9 (M + H)⁺ |

TABLE 4-continued

Chemical name, NMR chemical shifts and LCMS signal for each intermediate listed in Table 3.

| Intermediate: Name | $^1$H NMR (400 MHz) δ ppm | LCMS |
|---|---|---|
| 27: (S)-3-(2,5-dichloropyrimidin-4-yl)-4-isopropyloxazolidin-2-one | (DMSO-d$_6$) 9.01 (s, 1 H), 4.81 (ddd, J = 9.1 Hz, J = 7.8 Hz, J = 4.3 Hz, 1 H), 4.59 (t, J = 8.8 Hz, 1 H), 4.38-4.33 (m, 1H), 2.06 (td, J = 7.0 Hz, J = 4.3 Hz, 1 H), 0.84 (d, J = 6.8 Hz, 3 H), 0.78 (d, J = 6.8 Hz, 3 H) | MS m/z 274.2 (M − H)$^−$ |
| 28: (R)-3-(2-chloropyrimidin-4-yl)-5,5-dimethyl-4-phenyloxazolidin-2-one | (CDCl$_3$) 8.20 (d, J = 5.8 Hz, 1 H), 8.01 (d, J = 5.8 Hz, 1 H), 7.16-7.07 (m, 3 H), 6.98-6.96 (m, 2 H), 5.19 (s, 1 H), 1.46 (s, 3 H), 0.87 (s, 3 H) | MS m/z 303.9 (M + H)$^+$ |
| 29: 3-(2-chloropyrimidin-4-yl)-4,4-dimethyloxazolidin-2-one | (CDCl$_3$) 8.47 (d, J = 5.8 Hz, 1 H), 8.06 (d, J = 5.8 Hz, 1 H), 4.17 (s, 2 H), 1.77 (s, 6 H) | MS m/z 228.3 (M + H)$^+$ |
| 30: (R)-3-(2-chloropyrimidin-4-yl)-4-methyl-4-phenyloxazolidin-2-one | (CDCl$_3$) 8.43 (d, J = 5.8 Hz, 1 H), 8.13 (d, J = 5.8 Hz, 1 H), 7.40-7.36 (m, 4 H), 7.35-7.28 (m, 1 H), 4.45 (d, J = 8.6 Hz, 1 H), 4.38 (d, J = 8.6 Hz, 1 H), 2.22 (s, 3 H) | MS m/z 289.9 (M + H)$^+$ |

Intermediate 31

(S)-3-(2-fluoropyrimidin-4-yl)-4-isopropyloxazolidin-2-one

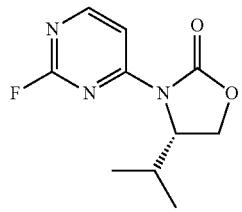 [SMILES: CC(C)[C@H]1COC(=O)N1c1ccnc(F)n1]

A solution of 2,4-difluoropyrimidine (3.5 mL, 41 mmol) and (S)-4-isopropyloxazolidin-2-one (5.3 g 41 mmol) in 30 mL DMF was cooled to 0° C. under N$_2$ atmosphere. NaH (2.1 g of 60% suspension, 53 mmol) was slowly added. Bubbling exotherm observed. Internal temp was kept below 5° C. After 5 minutes, cold bath was removed. Reaction mixture (a sandy suspension) was allowed to warm to room temp and stir 18 h. The reaction mixture was diluted with water (100 mL) and extracted with (3×75 mL) EtOAc. Organic layer was washed with 50 mL each water, and brine. Dried over Na$_2$SO$_4$, and concentrated on silica gel in vacuo. Column chromatography (EtOAc/heptane 10 to 100% gradient) gave 3.1 g (S)-3-(2-fluoropyrimidin-4-yl)-4-isopropyloxazolidin-2-one (IV) as a crystalline white solid (33%). $^1$H NMR (400 MHz, CDCl$_3$) δ 8.50 (dd, J=5.8, 2.2 Hz, 1H), 8.19 (dd, J=5.8, 3.8 Hz, 1H), 4.79 (dt, J=8.1, 3.5 Hz, 1H), 4.48-4.34 (m, 2H), 2.64 (heptd, J=7.0, 3.6 Hz, 1H), 1.01 (d, J=7.0 Hz, 3H), 0.90 (d, J=6.9 Hz, 3H). MS m/z 471.8 and 471.8 (M+H)+.

The Intermediates in Table 4b were prepared by a method similar to the one described for the preparation of Intermediate 1 and 31.

TABLE 4b

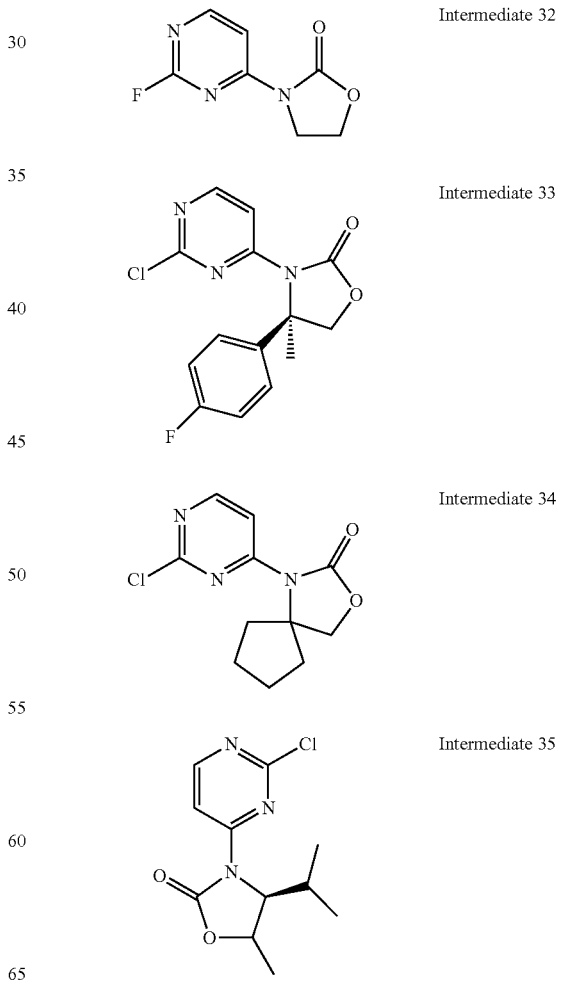

Intermediate 32

Intermediate 33

Intermediate 34

Intermediate 35

TABLE 4b-continued

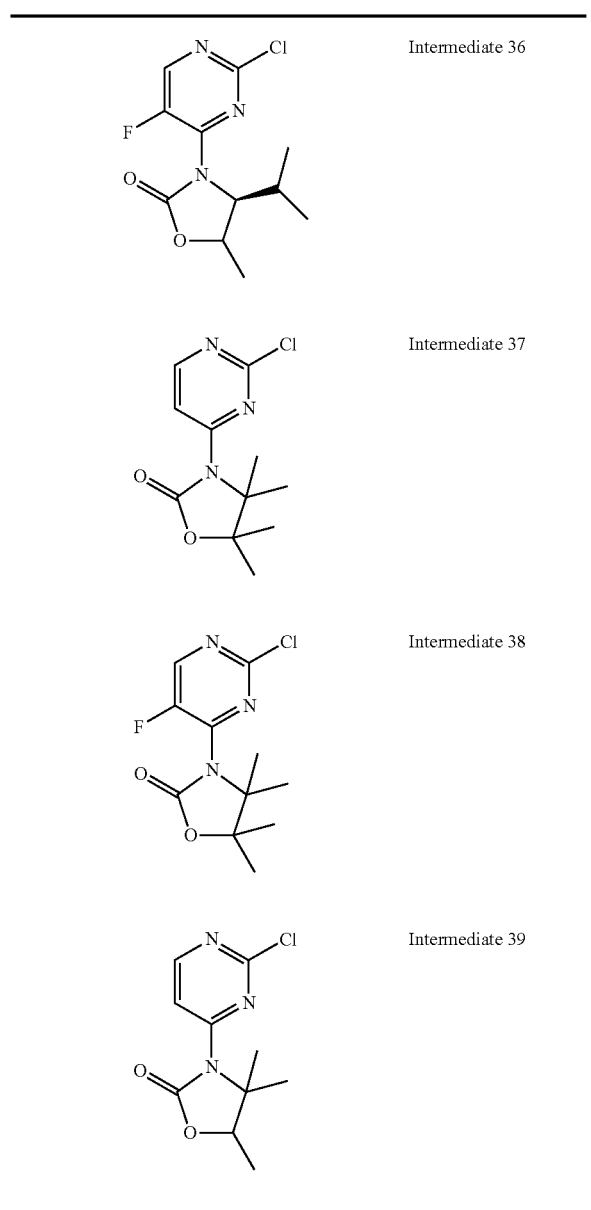
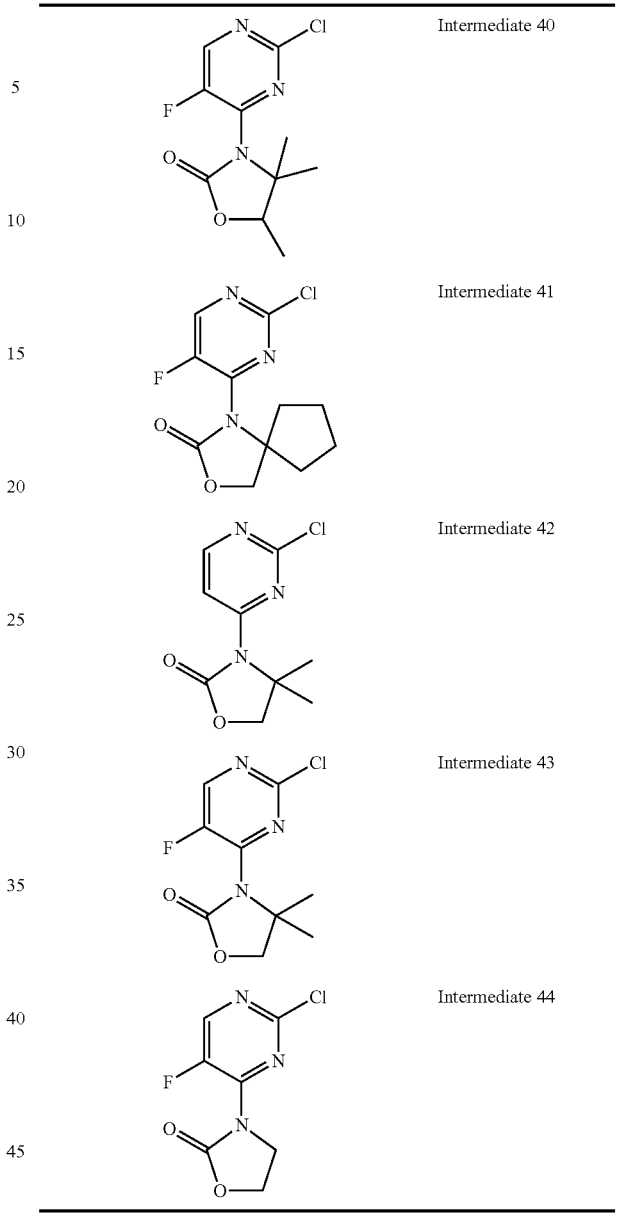

TABLE 4c

Chemical name, NMR chemical shifts and LCMS signal for each intermediate listed in Table 4b.

| Intermediate: Name | $^1$H NMR (400 MHz) δ ppm | LCMS |
|---|---|---|
| 32: 3-(2-fluoropyrimidin-4-yl)oxazolidin-2-one | (CDCl$_3$) 8.51 (dd, J = 5.8, 2.0 Hz, 1 H), 8.17 (dd, J = 5.8, 2.0 Hz, 1 H), 4.61-4.57 (m, 2 H), 4.31-4.27 (m, 2 H) | MS m/z 184.0 (M + H) |
| 33: (R)-3-(2-chloropyrimidin-4-yl)-4-(4-fluorophenyl)-4-methyloxazolidin-2-one | (CDCl$_3$) 8.45 (d, J = 5.8 Hz, 1 H), 8.12 (d, J = 5.8 Hz, 1 H), 7.40-7.35 (m, 2 H), 7.10-7.04 (m, 2 H), 4.40-4.37 (m, 2 H), 2.22 (s, 3 H) | MS m/z 308.0 (M + H)+ |
| 34: 1-(2-chloropyrimidin-4-yl)-3-oxa-1-azaspiro[4.4]nonan-2-one | (CDCl$_3$) 8.48 (d, J = 5.8 Hz, 1 H), 8.12 (d, J = 5.8 Hz, 1 H), 4.22 (s, 2 H), 2.66-2.59 (m, 2 H), 2.22-2.14 (m, 2 H), 1.75-1.62 (m, 4 H) | MS m/z 254.1 (M + H)+ |
| 35: (4S)-3-(2-chloropyrimidin-4-yl)-4-isopropyl-5-methyloxazolidin-2-one | | MS m/z (M + H)+ 256.2, Rt 0.87 min |

TABLE 4c-continued

Chemical name, NMR chemical shifts and LCMS signal for each intermediate listed in Table 4b.

| Intermediate: Name | $^1$H NMR (400 MHz) δ ppm | LCMS |
|---|---|---|
| 36: (4S)-3-(2-chloro-5-fluoropyrimidin-4-yl)-4-isopropyl-5-methyloxazolidin-2-one | | MS m/z (M + H)+ 274.1, Rt 0.82 min |
| 37: 3-(2-chloropyrimidin-4-yl)-4,4,5,5-tetramethyloxazolidin-2-one | | MS m/z (M + H)+ 256.1, Rt 0.85 min |
| 38: 3-(2-chloro-5-fluoropyrimidin-4-yl)-4,4,5,5-tetramethyloxazolidin-2-one | | MS m/z (M + H)+ 274.1, Rt 0.83 min |
| 39: 3-(2-chloropyrimidin-4-yl)-4,4,5-trimethyloxazolidin-2-one | | MS m/z (M + H)+ 242.1, Rt 0.81 min |
| 40: 3-(2-chloro-5-fluoropyrimidin-4-yl)-4,4,5-trimethyloxazolidin-2-one | | MS m/z (M + H)+ 260.1, Rt 0.77 min |
| 41: 1-(2-chloro-5-fluoropyrimidin-4-yl)-3-oxa-1-azaspiro[4.4]nonan-2-one | (CDCl$_3$) 8.47 (d, J = 2 Hz, 1 H), 4.28 (s, 2 H), 2.54-2.44 (m, 2 H), 2.11-1.99 (m, 2 H), 1.90-1.82 (m, 2 H), 1.72-1.61 (m, 42 H) | MS m/z (M + H)+ 272.4 |
| 42: 3-(2-chloropyrimidin-4-yl)-4,4-dimethyloxazolidin-2-one | | MS m/z (M + H)+ 228.0, Rt 0.73 min |
| 43: 3-(2-chloro-5-fluoropyrimidin-4-yl)-4,4-dimethyloxazolidin-2-one | | MS m/z (M + H)+ 246.0, Rt 0.70 min |
| 44: 3-(2-chloro-5-fluoropyrimidin-4-yl)oxazolidin-2-one | | MS m/z (M + H)+ 218.0, Rt 0.47 min |

Intermediate 46

(S)-4-(biphenyl-4-yl)-3-(2-chloropyrimidin-4-yl)oxazolidin-2-one

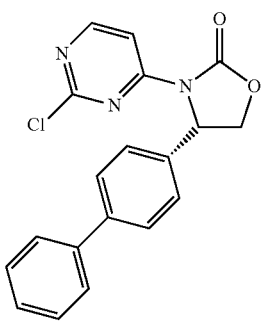

To a solution of 2,4-dichloropyrimidine (46.5 mg, 0.312 mmol) and (S)-4-(biphenyl-4-yl)oxazolidin-2-one (74.7 mg, 0.312 mmol) in DMF (700 μL) was added NaH (60% wt., 10.49 mg, 0.437 mmol) in two portions within ~5 min [Caution: exotherm; gas development] at room temperature (water bath). The reaction mixture was stirred for 1.5 hour. The mixture was diluted with EtOAc (25 mL), stirred for 5 min and then diluted slowly with diluted brine (10 mL; 1:1 brine/water). The mixture was poured into diluted brine (40 mL) and EtOAc (25 mL). The separated organic phase was washed with diluted brine (3×40 ml), dried over Na$_2$SO$_4$, filtered off and concentrated under reduced pressure. The residue was purified by column chromatography [SiO$_2$, 40 g, EtOAc/heptane] to provide (S)-4-(biphenyl-4-yl)-3-(2-chloropyrimidin-4-yl)oxazolidin-2-one (49.5 mg). LCMS m/z 352.2 (M+H)$^+$, Rt 1.06 min.

Intermediate 47

3-(2-chloropyrimidin-4-yl)-4-phenyl-1,8-dioxa-3-azaspiro[4.5]decan-2-one

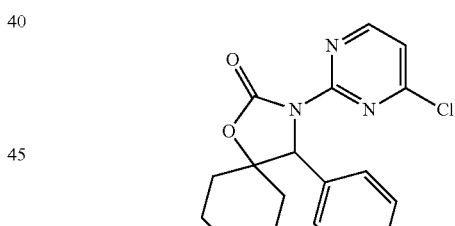

To a mixture of 4-phenyl-1,8-dioxa-3-azaspiro[4.5]decan-2-one (300 mg, 1.286 mmol) and 2,4-dichloropyrimidine (192 mg, 1.286 mmol) in DMF (7 mL) under argon was added NaH (60% wt., 67.9 mg, 2.83 mmol) in two portions. The mixture was stirred for ~1 hour. The reaction mixture was carefully poured into ice-coiled 0.25N aqueous HCl solution. DCM and aqueous NaHCO$_3$ solution were added. The separated aqueous layer was extracted with DCM (3×) and ethyl acetate (1×). The organic layers (DCM and ethyl acetate containing layers independently) were washed with brine, dried over Na$_2$SO$_4$ and filtered off. The organic layers were combined and concentrated under reduced pressure providing crude 3-(2-chloropyrimidin-4-yl)-4-phenyl-1,8-dioxa-3-azaspiro[4.5]decan-2-one (330 mg) as a yellowish liquid, which was directly used in the next reaction without further purification. LCMS m/z 346.1 (M+H)$^+$, Rt 0.83 min.

Intermediate 48

7-(2-chloropyrimidin-4-yl)-8-phenyl-2,5-dioxa-7-azaspiro[3.4]octan-6-one

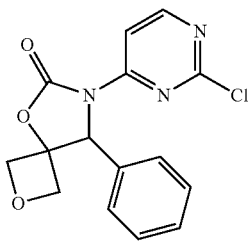 [SMILES: O=C1OC2(COC2)C(c2ccccc2)N1c1ccnc(Cl)n1]

Prepared using similar methods as described above for 3-(2-chloropyrimidin-4-yl)-4-phenyl-1,8-dioxa-3-azaspiro[4.5]decan-2-one, but starting with oxetan-3-one. LCMS m/z 318.1 (M+H)$^+$, Rt 0.78 min.

Intermediate 50

3-(2-chloro-5-fluoropyrimidin-4-yl)-5,5-dimethyloxazolidin-2-one

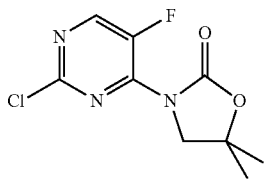 [SMILES: CC1(C)CN(c2nc(Cl)ncc2F)C(=O)O1]

Step 1

A solution of 2,4-dichloro-5-fluoropyrimidine (2 g, 11.98 mmol) in acetonitrile (10 mL) was cooled to −40° C., avoiding freezing. To this solution was added diisopropylamine (3.82 mL, 21.88 mmol) followed by 1-amino-2-methylpropan-2-ol (1.5 g, 16.83 mmol). The reaction mixture was removed from the cooling bath, warmed to room temperature and allowed to stir overnight (~18 hours). Solvents were removed in vacuo and the residue was taken up in a minimum of dichloromethane (~1.5-2 mL) and diluted with heptane until slightly cloudy. This mixture was loaded onto a 40 gram BioRad silica gel cartridge. Purification by flash chromatography (Analogix System, 20 min gradient, 0-25% methanol/dichloromethane, 40 mL/min.) provided 1-(2-chloro-5-fluoropyrimidin-4-ylamino)-2-methylpropan-2-ol as a white solid. LCMS m/z 220.1, 221.8 (M+H)$^+$, Rt 0.49 min.

Step 2

To a suspension of 1-(2-chloro-5-fluoropyrimidin-4-ylamino)-2-methylpropan-2-ol (400 mg, 1.82) in DCM/ethylacetate (5 mL) was added 2,6-lutidine (1 mL, 8.59 mmol). The reaction was cooled to −78° C. and triphosgene (292 mg, 0.983 mmol) was added in a single portion. The reaction was removed from the cooling bath and allowed to warm to room temperature. The reaction had a pinkish coloration at this time. LCMS indicated consumption of starting material and conversion the intermediate acyl chloroformate adduct of 1-(2-chloro-5-fluoropyrimidin-4-ylamino)-2-methylpropan-2-ol. The reaction was sealed and stirred overnight. The reaction was stirred at room temperature overnight to provide only partial closure of the intermediate acyl formate to the cyclic carbamate. The reaction (sealed) was then heated at 60° C. for ~4 hours until intermediate acyl chloroformate was consumed. Reaction was cooled to room temperature, diluted with DCM (~50 mL) and washed with water (1×50 mL) and sat. NaHCO$_3$ (1×50 mL). Aqueous layers were back extracted with DCM (~50 mL). The combined organics were dried over MgSO$_4$, filtered and concentrated in vacuo. The solid was dissolved in DCM (~15 mL) and celite (~4 gram) was added. The mixture was concentrated and dried in vacuo to provide a solid pre-load for subsequent purification. Purification by flash chromatography (Analogix System, 80 gram silica gel column, 25 min. gradient, 0-25% methanol/dichloromethane, 40 mL/min) provided 3-(2-chloro-5-fluoropyrimidin-4-yl)-5,5-dimethyloxazolidin-2-one as a white solid. $^1$H NMR (400 MHz, METHANOL-d4) δ ppm 1.58 (s, 8H) 4.02 (s, 2H) 8.59 (d, J=3.13 Hz, 1H): LCMS m/z (M+H)$^+$ 246.1, 247.8.0, Rt 0.61 min The Intermediates in Table 4d were prepared by methods similar to the one described for the preparation of Intermediate 50.

TABLE 4d

| Structure | Name |
|---|---|
| 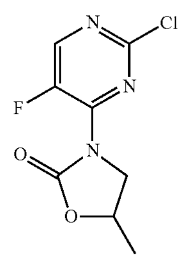 | Intermediate 51 |
| 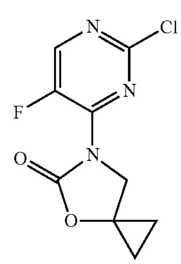 [SMILES: O=C1OC2(CC2)CN1c1nc(Cl)ncc1F] | Intermediate 52 |

TABLE 4e

Chemical name, NMR chemical shifts and LCMS signal for each intermediate listed in Table 4d.

| Intermediate: Name | $^1$H NMR (400 MHz, METHANOL-d4) δ ppm | LCMS |
|---|---|---|
| 51: 3-(2-chloro-5-fluoropyrimidin-4-yl)-5-methyloxazolidin-2-one | 1.52 (d, J = 6.26 Hz, 3 H) 3.89 (dd, J = 9.78, 7.43 Hz, 1 H) 4.26 (dd, J = 9.78, 7.43 Hz, 1 H) 4.90-4.98 (m, 1 H) 8.58 (d, J = 2.74 Hz, 1 H) | MS m/z (M + H)$^+$ 232.0, 233.9, Rt 0.52 min |
| 52: 6-(2-chloro-5-fluoropyrimidin-4-yl)-4-oxa-6-azaspiro[2.4]heptan-5-one | 0.90-1.08 (m, 2 H) 1.18-1.37 (m, 2 H) 4.31 (s, 2 H) 8.61 (d, J = 3.13 Hz, 1 H) | MS m/z (M + H)$^+$ 244.0, 245.8, Rt 0.61 min |

Intermediate 53

3-(2,6-dichloropyrimidin-4-yl)-4,4-dimethyloxazolidin-2-one

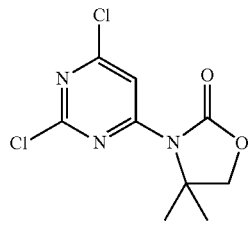 [SMILES: CC1(C)COC(=O)N1c1cc(Cl)nc(Cl)n1]

A solution of 4,4-dimethyloxazolidin-2-one (0.103 g, 0.895 mmol) and 2,4,6-trichloropyrimidine (0.181 g, 0.984 mmol, 1.10 equiv) in DMF (3 mL) was treated with NaH (60%, 0.0429 g, 1.07 mmol, 1.2 equiv), then the resulting mixture (yellow) was stirred at room temperature for 1 h. The reaction mixture was diluted with EtOAc (20 mL), washed with saturated aqueous NaCl (2×20 mL), dried over Na$_2$SO$_4$, filtered and concentrated. Silica gel column chromatography (EtOAc/Heptane 0 to 40%) provided 3-(2,6-dichloropyrimidin-4-yl)-4,4-dimethyloxazolidin-2-one (0.146 g, white solid) in 62.3% yield. $^1$H NMR (300 MHz, CDCl$_3$) δ 8.14 (s, 1H), 4.16 (s, 2H), 1.74 (s, 9H); LCMS m/z 261.9 (M+H)$^+$, Rt 0.91 min.

The Intermediates in Table 4f were prepared by a method similar to the one described for the preparation of Intermediate 53.

TABLE 4f

| Structure | |
|---|---|
| Cl-pyrimidine-oxazolidinone | Intermediate 54 |
| F-pyrimidine-dimethyloxazolidinone | Intermediate 55 |

TABLE 4g

Chemical name, NMR chemical shifts and LCMS signal for each intermediate listed in Table 4f.

| Intermediate: Name | $^1$H NMR (400 MHz) δ ppm | LCMS |
|---|---|---|
| 54: 3-(2,6-dichloropyrimidin-4-yl)oxazolidin-2-one | (CDCl$_3$) 8.20 (s, 1 H), 4.59 (t, J = 8.0 Hz, 2 H), 4.29 (t J = 8.0 Hz, 2 H) | MS m/z 234.0 (M + H)$^+$, Rt 0.67 min |
| 55: 3-(2,6-difluoropyrimidin-4-yl)-4,4-dimethyloxazolidin-2-one | (CDCl$_3$) 7.68 (d, J = 2.0 Hz, 1 H), 4.16 (s, 2 H), 1.74 (s, 6 H) | MS m/z 230.1 (M + H)$^+$, Rt 0.79 min |

Intermediate 56

(S)-methyl 4-(1-(tert-butoxycarbonylamino)ethyl)benzoate

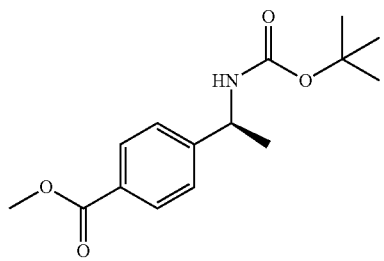 [SMILES: COC(=O)c1ccc([C@H](C)NC(=O)OC(C)(C)C)cc1]

To a solution of (S)-methyl 4-(1-aminoethyl)benzoate (4.9 g, 22.7 mmol) in DCM (114 mL) was added di-tert-butyl dicarbonate (5.95 g, 27.3 mmol) and triethylamine (6.97 mL, 50 mmol). The solution was stirred for 16 h at room temperature then washed with water and brine. The organic layer was dried over $Na_2SO_4$, filtered and concentrated. Silica gel column chromatography (EtOAc/heptane 0 to 80%) provided (S)-methyl 4-(1-(tert-butoxycarbonylamino)ethyl)benzoate as a white solid (6.35 g, 100% yield).

$^1$H NMR (400 MHz, $CDCl_3$) δ 8.04-7.96 (m, 2H), 7.40-7.33 (m, 2H), 4.83 (s, 1H), 3.91 (s, 3H), 1.43-1.23 (m, 12H); MS m/z 224.0 (M−56+H).

Intermediate 57

(S)-tert-butyl 1-(4-(hydroxymethyl)phenyl)ethylcarbamate

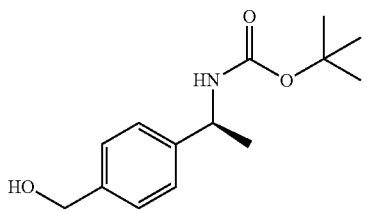 [SMILES: C[C@H](NC(=O)OC(C)(C)C)c1ccc(CO)cc1]

To a cooled (0° C.) solution of (S)-methyl 4-(1-(tert-butoxycarbonylamino)ethyl)benzoate (6.35 g, 22.7 mmol) in THF (114 mL) was added a solution of LAH in THF (2.0 M, 13.64 mL, 27.3 mmol) and the resulting mixture was stirred at room temperature for 40 min. The reaction mixture was quenched by addition of a 1N NaOH solution until gas evolution ceased. The reaction mixture was filtered, washed with EtOAc. After separation, the aqueous phase was washed with EtOAc (2×150 mL). Combined organics were dried over $Na_2SO_4$, filtered and concentrated. Silica gel column chromatography (EtOAc/heptane 0 to 100%) provided (S)-tert-butyl 1-(4-(hydroxymethyl)phenyl)ethylcarbamate as a white solid (5.01 g, 84% yield).

$^1$H NMR (400 MHz, $CDCl_3$) δ 7.35-7.23 (m, 4H), 4.80-4.71 (m, 1H), 4.67 (s, 2H), 2.04 (bs, 1H), 1.47-1.37 (m, 12H); MS m/z 196.0 (M−56+H).

Intermediate 58

(S)-tert-butyl 1-(4-(chloromethyl)phenyl)ethylcarbamate

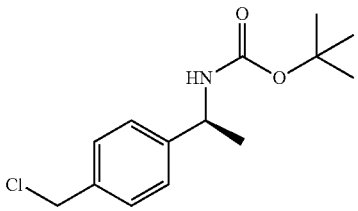 [SMILES: C[C@H](NC(=O)OC(C)(C)C)c1ccc(CCl)cc1]

To a solution of (S)-tert-butyl 1-(4-(hydroxymethyl)phenyl)ethylcarbamate (503 mg, 2 mmol) in DCM (10 mL) was added methanesulfonyl chloride (275 mg, 2.4 mmol) and triethylamine (0.56 mL, 4 mmol). The solution was stirred for 16 h at room temperature then washed with water and brine. After separation, the organic phase was dried over $Na_2SO_4$, filtered and concentrated. Silica gel column chromatography (EtOAc/heptane 0 to 80%) provided (S)-tert-butyl 1-(4-(chloromethyl)phenyl)ethylcarbamate as a white solid (254 g, 47.1% yield).

$^1$H NMR (400 MHz, $CDCl_3$) δ 7.40-7.24 (m, 4H), 4.79 (s, 1H), 4.58 (s, 2H), 1.50-1.30 (br m, 12H); MS m/z 214.0 (M−56+H).

Intermediate 59

(S)-tert-butyl 1-(4-((5,6-dihydro-[1,2,4]triazolo[4,3-a]pyrazin-7(8H)-yl)methyl)phenyl)ethylcarbamate

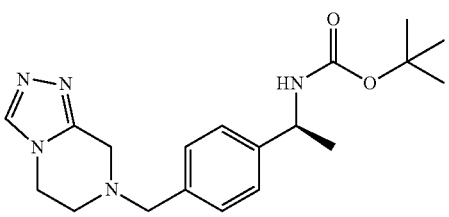 [SMILES: C[C@H](NC(=O)OC(C)(C)C)c1ccc(CN2CCn3cnnc3C2)cc1]

A solution of (S)-tert-butyl 1-(4-(chloromethyl)phenyl)ethylcarbamate (127 mg, 0.47 mmol), 5,6,7,8-tetrahydro-[1,2,4]triazolo[4,3-a]pyrazine (91 mg, 0.56 mmol) and DIPEA (183 mg, 1.41 mmol) in DMSO (2.3 mL) was heated at 80° C. for 16 h. The reaction mixture was diluted with EtOAc (20 mL) and washed with water (20 mL). After separation, the aqueous phase was washed with EtOAc (2×15 mL). Combined organics were dried over $Na_2SO_4$, filtered and concentrated. The crude product was used to next step without further purification.

MS m/z 358.3 (M+H)

Intermediate 60

(S)-1-(4-((5,6-dihydro-[1,2,4]triazolo[4,3-a]pyrazin-7(8H)-yl)methyl)phenyl)ethanamine

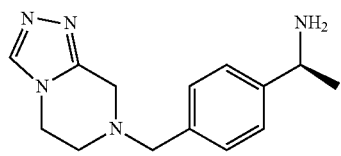 [SMILES: C[C@H](N)c1ccc(CN2CCn3cnnc3C2)cc1]

To a solution of (S)-tert-butyl 1-(4-((5,6-dihydro-[1,2,4]triazolo[4,3-a]pyrazin-7(8H)-yl)methyl)phenyl)ethylcarbamate (168 mg, 0.47 mmol) in DCM (2 mL) was added TFA (2 mL, 26 mmol) slowly at −78° C. The reaction was stirred at room temperature for 1 h then concentrated and diluted with DCM (10 mL). The solution was stirred with 3 eq. of MP-carbonate resin (3.28 mmol/g, Biotage) for 1 hour at room temperature. The resin was removed by filtration and washed (2×5 mL) with DCM. The filtrate was concentrated and the crude residue was used to next step without further purification.

MS m/z 258.2 (M+H).

Intermediate 61

(S)-4-(1-(tert-butoxycarbonylamino)ethyl)-2-fluorobenzoic acid

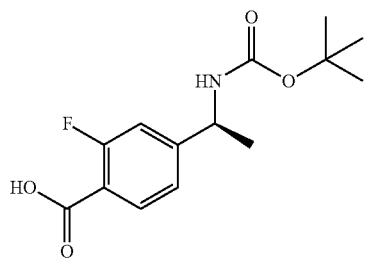 [SMILES: C[C@H](NC(=O)OC(C)(C)C)c1ccc(C(=O)O)c(F)c1]

To a solution of (S)-4-(1-aminoethyl)-2-fluorobenzoic acid (5 g, 22.76 mmol) in water (66 mL) and THF (66 mL) was added di-tert-butyl dicarbonate (6.95 g, 31.9 mmol) and sodium carbonate (5.74 g, 68.3 mmol). The solution was stirred for 16 h at room temperature then THF was removed under reduced pressure. The aqueous solution was acidified with 1N HCl to pH 3-4 and extracted with EtOAc (3×60 mL). Combined organics were dried over $Na_2SO_4$, filtered and concentrated to give a white solid (1.94 g, 30.1% yield). The crude product was used to next step without further purification.

$^1$H NMR (400 MHz, MeOD) δ 7.89 (t, J=7.8 Hz, 1H), 7.20 (dd, J=8.2, 1.7 Hz, 1H), 7.13 (dd, J=12.0, 1.6 Hz, 1H), 4.70 (d, J=7.1 Hz, 1H), 1.47-1.35 (m, 12H); MS m/z 282.0 (M−H).

Intermediate 62

(S)-tert-butyl 1-(3-fluoro-4-(methoxy(methyl)carbamoyl)phenyl)ethylcarbamate

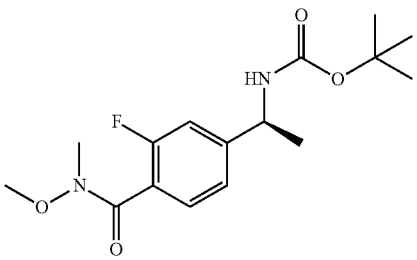 [SMILES: CON(C)C(=O)c1ccc([C@H](C)NC(=O)OC(C)(C)C)cc1F]

A solution of (S)-4-(1-(tert-butoxycarbonylamino)ethyl)-2-fluorobenzoic acid (1.416 g, 5 mmol), N,O-dimethylhydroxylamine hydrochloride (732 mg, 7.5 mmol), HATU (2.85 g, 7.5 mmol) and DIPEA (3.49 mL, 20 mmol) in DMF (25 mL) was stirred at room temperature for 16 h. The reaction mixture was diluted with EtOAc and washed with water. After separation, the aqueous phase was washed with EtOAc (2×75 mL). Combined organics were dried over $Na_2SO_4$, filtered and concentrated. Silica gel column chromatography (EtOAc/heptane 12 to 100%) provided (S)-tert-butyl 1-(3-fluoro-4-(methoxy(methyl)carbamoyl)phenyl)ethylcarbamate as a white solid (1.5 g, 92% yield).

$^1$H NMR (400 MHz, $CDCl_3$) δ 7.40 (t, J=7.4 Hz, 1H), 7.13 (dd, J=7.8, 1.6 Hz, 1H), 7.04 (dd, J=10.7, 1.6 Hz, 1H), 4.80 (br s, 1H), 3.56 (s, 3H), 3.34 (s, 3H), 1.50-1.29 (m, 12H); MS m/z 327.1 (M+H).

Intermediate 63

(S)-tert-butyl 1-(3-fluoro-4-formylphenyl)ethylcarbamate

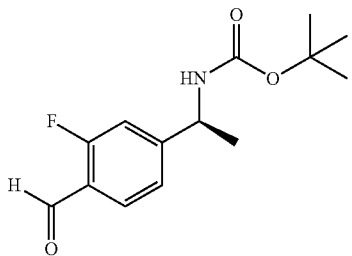 [SMILES: C[C@H](NC(=O)OC(C)(C)C)c1ccc(C=O)c(F)c1]

Procedure 1: To a cooled (0° C.) solution of (S)-tert-butyl 1-(3-fluoro-4-(methoxy(methyl)carbamoyl)phenyl)ethylcarbamate (1.175 g, 3.6 mmol) in THF (36 mL) was added a solution of LAH in THF (1.0 M, 18 mL, 18 mmol) and the resulting mixture was stirred at 0° C. for 20 min. The reaction mixture was quenched by addition of a saturated $Na_2SO_4$ solution until gas evolution ceased. The reaction mixture was extracted with EtOAc (2×100 mL). Combined organics were dried over $Na_2SO_4$, filtered and concentrated. Silica gel column chromatography (EtOAc/heptane 12 to 100%) provided (S)-tert-butyl 1-(3-fluoro-4-formylphenyl)ethylcarbamate as a white solid (760 mg, 79% yield).

Procedure 2: A solution of (S)-tert-butyl 1-(4-bromo-3-fluorophenyl)ethylcarbamate (318 mg, 1 mmol) in dry THF (5 mL) was cooled to −78° C. BuLi (2.5 M, 840 µL, 2.1 mmol) was added dropwise and the resulting solution was stirred at −78° C. for 1 h. Then DMF (232 µL, 3.00 mmol) was added in one portion. The reaction was stirred for another 30 min at −78° C. then quenched with sat. NH4Cl solution. The reaction was stirred at room temperature for another 30 min then diluted with EtOAc, washed with water and brine. The separated organic was dried over $Na_2SO_4$, filtered and concentrated. Silica gel column chromatography (EtOAc/heptane 0 to 80%) provided (S)-tert-butyl 1-(3-fluoro-4-formylphenyl)ethylcarbamate as a white solid (70 mg, 26.2% yield).

$^1$H NMR (400 MHz, $CDCl_3$) δ 10.31 (s, 1H), 7.87-7.80 (m, 1H), 7.20 (dd, J=8.2, 1.3 Hz, 1H), 7.11 (dd, J=11.5, 1.4 Hz, 1H), 4.80 (br s, 1H), 1.45 (br s, 12H); MS m/z 212.1 (M−56+H).

Intermediate 64

(S)-tert-butyl 1-(3-fluoro-4-((3,3,4-trimethylpiperazin-1-yl)methyl)phenyl)ethylcarbamate

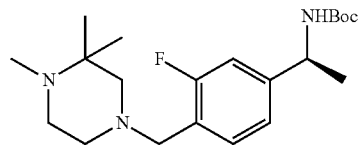 [SMILES: C[C@H](NC(=O)OC(C)(C)C)c1ccc(CN2CCN(C)C(C)(C)C2)c(F)c1]

(General Procedure A for Reductive Amination)

A solution of (S)-tert-butyl 1-(3-fluoro-4-formylphenyl)ethylcarbamate (267 mg, 1 mmol) and 1,2,2-trimethylpiperazine dihydrochloride (402 mg, 2 mmol) in THF (5 mL) was stirred at room temperature for 1 h and treated with sodium triacetoxyborohydride (848 mg, 4 mmol). The resulting mixture was stirred at room temperature for 16 h. The reaction mixture was quenched with saturated aqueous solution of $NaHCO_3$ (15 mL) and extracted with EtOAc (3×25 mL). Combined organics were dried over $Na_2SO_4$, filtered and concentrated. Silica gel column chromatography (MeOH/$CH_2Cl_2$ 0 to 10%) provided (S)-tert-butyl 1-(3-fluoro-4-((3,3,4-trimethylpiperazin-1-yl)methyl)phenyl)ethylcarbamate as a white solid (186 mg, 49% yield).

$^1$H NMR (400 MHz, $CDCl_3$) δ 7.35 (t, J=7.7 Hz, 1H), 7.03 (dd, J=7.9, 1.9 Hz, 1H), 6.95 (dd, J=11.1, 1.8 Hz, 1H), 4.77 (s, 1H), 3.49 (s, 2H), 2.56 (br s, 4H), 2.24 (br s, 5H), 1.42 (br s, 12H), 1.04 (s, 6H); MS m/z 380.4 (M+H).

Intermediate 65 tert-butyl (1S)-1-(4-((3,4-dimethylpiperazin-1-yl)methyl)phenyl)ethylcarbamate

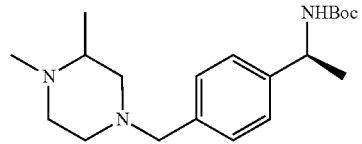 [SMILES: CC1CN(Cc2ccc([C@H](C)NC(=O)OC(C)(C)C)cc2)CCN1C]

A solution of (S)-tert-butyl 1-(4-formylphenyl)ethylcarbamate (84.1 mg, 0.337 mmol) [obtained from (S)-1-(4-bromophenyl)ethanamine following the procedure of Hashihayata, Takashi PCT Int. Appl., 2008081910, 10 Jul. 2008] and 1,2-dimethylpiperazine (86.3 mg, 0.756 mmol, 2.24 equiv) in THF (1.5 mL) was stirred at room temperature for 65 min and treated with sodium triacetoxyborohydride (277.2 mg, 1.308 mmol, 3.88 equiv). The resulting mixture was stirred at room temperature for 16 hours. The reaction mixture was quenched with saturated aqueous solution of $NaHCO_3$ (15 mL) and extracted with EtOAc (5×15 mL). Combined organics were dried over $Na_2SO_4$, filtered and concentrated. Silica gel column chromatography (MeOH/$CH_2Cl_2$ 0 to 20%) provided tert-butyl (1S)-1-(4-((3,4-dimethylpiperazin-1-yl)methyl)phenyl)ethyl carbamate (90.7 mg) in 34.5% yield.

$^1$H NMR (400 MHz, $CD_3OD$) δ 7.29 (s, 4H), 4.68 (br s, 1H), 3.54-3.47 (m, 2H), 3.37 (s, 1H), 2.84-2.74 (m, 3H), 2.38 (td, J=12, 2.5 Hz, 1H), 2.31 (s, 3H), 2.28-2.22 (m, 2H), 1.94-1.89 (m, 1H), 1.40 (br s, 9H), 1.38 (d, J=6.9 Hz, 3H), 1.06 (d, J=6.3 Hz, 3H); MS m/z 348.2 (M+H)

Intermediate 66

(R,E)-2-methyl-N-((3-methyl-1H-pyrazol-4-yl)methylene)propane-2-sulfinamide

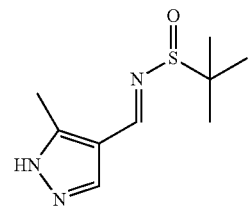

3-methyl-1H-pyrazole-4-carbaldehyde (2.03 g, 18.44 mmol) was dissolved in THF (30 ml) and (R)-2-methylpropane-2-sulfinamide (2.35, 19.39 mmol) was added followed by Ti(OEt)4 (8.41 mmol, 36.90 mmol). The resulting reaction mixture was stirred at 80° C. for 18 h. LCMS shows mostly product. The reaction mixture was diluted with EtOAc (300 mL), washed with 4% aqueous NaCl (2×150, 2×50 mL). The combined aq. layers were back extracted with EtOAc (100 ml). The combined organic layers were washed with brine (100 ml), dried over $Na_2SO_4$, filtered and concentrated. Purified by column chromatography (REDI 80 g, EtOAc/heptane 20-100% over 33 min 100% for 7 min.) to give title compound (2.25 g, 10.55 mmol).

$^1$H NMR (400 MHz, MeOD) δ 8.55 (s, 1H), 2.53 (s, 3H), 1.25 (s, 9H). MS 214.2 m/z (M+H)

Intermediate 67

(R)-2-methyl-N—((S)-1-(3-methyl-1H-pyrazol-4-yl)ethyl)propane-2-sulfinamide

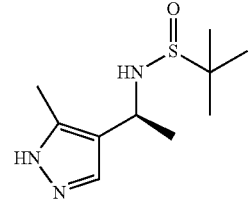

(R,E)-2-methyl-N-((3-methyl-1H-pyrazol-4-yl)methylene)propane-2-sulfinamide (2.25 g, 10.55 mmol) was dissolved in THF and cooled to 0 C. Methylmagnesium bromide (3M, 12.5 ml, 37.5 mmol) was added dropwise and the resulting solution was stirred for 1 h. Ice bath was removed and the reaction was stirred for another 15 h. Another 2.5 eq. of methylmagnesium bromide MeMgBr was added (at 0° C.). Not a lot of change by LCMS.

The reaction mixture was quenched with sat NH4Cl and the aq. layer was washed with THF (2×). Combined organic layers washed with brine, dried over Na$_2$SO$_4$, filtered and concentrated to give title compound (1.79 g, 7.80 mmol)

$^1$H NMR (400 MHz, MeOD) δ 7.48 (s, 1H), 4.49 (qd, J=6.7, 4.7 Hz, 1H), 2.26 (s, 3H), 1.57 (dd, J=6.5, 1.3 Hz, 3H), 1.23 (s, 9H). MS 230.2 m/z (M+H)

Intermediate 68

(R)—N—((S)-1-(1-benzyl-3-methyl-1H-pyrazol-4-yl)ethyl)-2-methylpropane-2-sulfinamide

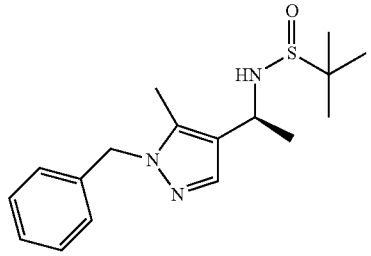 [SMILES: Cc1c([C@H](C)NS(=O)C(C)(C)C)cnn1Cc1ccccc1]

(R)-2-methyl-N—((S)-1-(3-methyl-1H-pyrazol-4-yl)ethyl)propane-2-sulfinamide (290 mg, 1.26 mmol) was dissolved in DMF (5 ml) and added dropwise to a solution of Cs2CO3 (458 mg, 1.41 mmol) in DMF (4 ml). The resulting reaction mixture was stirred at room temperature for 15 min. benzylbromide (216 mg, 1.26 mmol) was added and the reaction was stirred at room temperature for 2 h. LCMS shows mostly product with some starting pyrazole. Added another 0.1 ml of BnBr and 135 mg of Cs$_2$CO$_3$. Stirred another 24H at 50° C. The reaction mixture was diluted with EtOAc (300 mL), washed with 4% aqueous NaCl (2×150, 2×50 mL). The combined aq. layers were back extracted with EtOAc (100 ml). The combined organic layers were washed with brine (100 ml), dried over Na$_2$SO$_4$, filtered and concentrated. Silica gel chromatography, EtOAc/heptane 20-80% to give title compound (mix of regioisomers, 150 mg, 0.470 mmol).

$^1$H NMR (400 MHz, MeOD) δ 7.54 (s, 0.6H), 7.46 (s, 0.4H), 7.36-6.99 (m, 5H), 5.31 (s, 0.8H), 5.21 (s, 1.2H), 4.44 (t, J=6.9 Hz, 1H), 2.21 (2s, 3H), 1.54 (2 dt, 3H), 1.17 (s, 9H). MS 320.2 m/z (M+H)

Intermediate 69

(S)-1-(1-benzyl-3-methyl-1H-pyrazol-4-yl)ethanamine hydrochloride

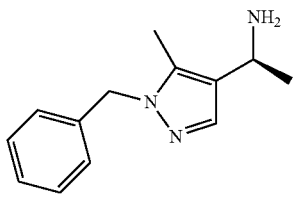 [SMILES: Cc1c([C@H](C)N)cnn1Cc1ccccc1]

(R)—N—((S)-1-(1-benzyl-3-methyl-1H-pyrazol-4-yl)ethyl)-2-methylpropane-2-sulfinamide was dissolved in dioxane (5 ml) and 4N HCl in dioxane (1.2 ml, 10 eq.) was added. Stirred 1H at room temperature. The solvents were removed and co-yapped twice with CH$_2$Cl$_2$. Some t-butyl observed by NMR. Resubmitted to reaction conditions and work-up to give title compound.

$^1$H NMR mixture of regioisomers (400 MHz, MeOD) δ 8.00 (s, 0.7H), 7.80 (s, 0.3H), 7.52-6.96 (m, 5H), 5.40 (s, 0.6H), 5.36 (s, 1.4H), 4.47 (q, J=6.9 Hz, 1H), 2.34 (s, 2.1H), 2.32 (s, 0.9H), 1.62 (2d, J=6.9 Hz, 3H).

MS 216.3 m/z (M+H)

The Intermediates in Table 4h were prepared by methods substantially similar to those described for the preparation of Intermediates 56 through 69.

TABLE 4h

| | |
|---|---|
| 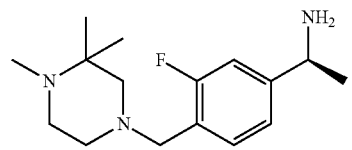 [SMILES: C[C@H](N)c1ccc(CN2CCN(C)C(C)(C)C2)c(F)c1] | Intermediate 70 |
| 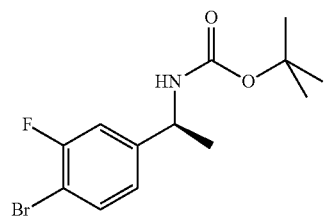 [SMILES: C[C@H](NC(=O)OC(C)(C)C)c1ccc(Br)c(F)c1] | Intermediate 71 |

TABLE 4h-continued
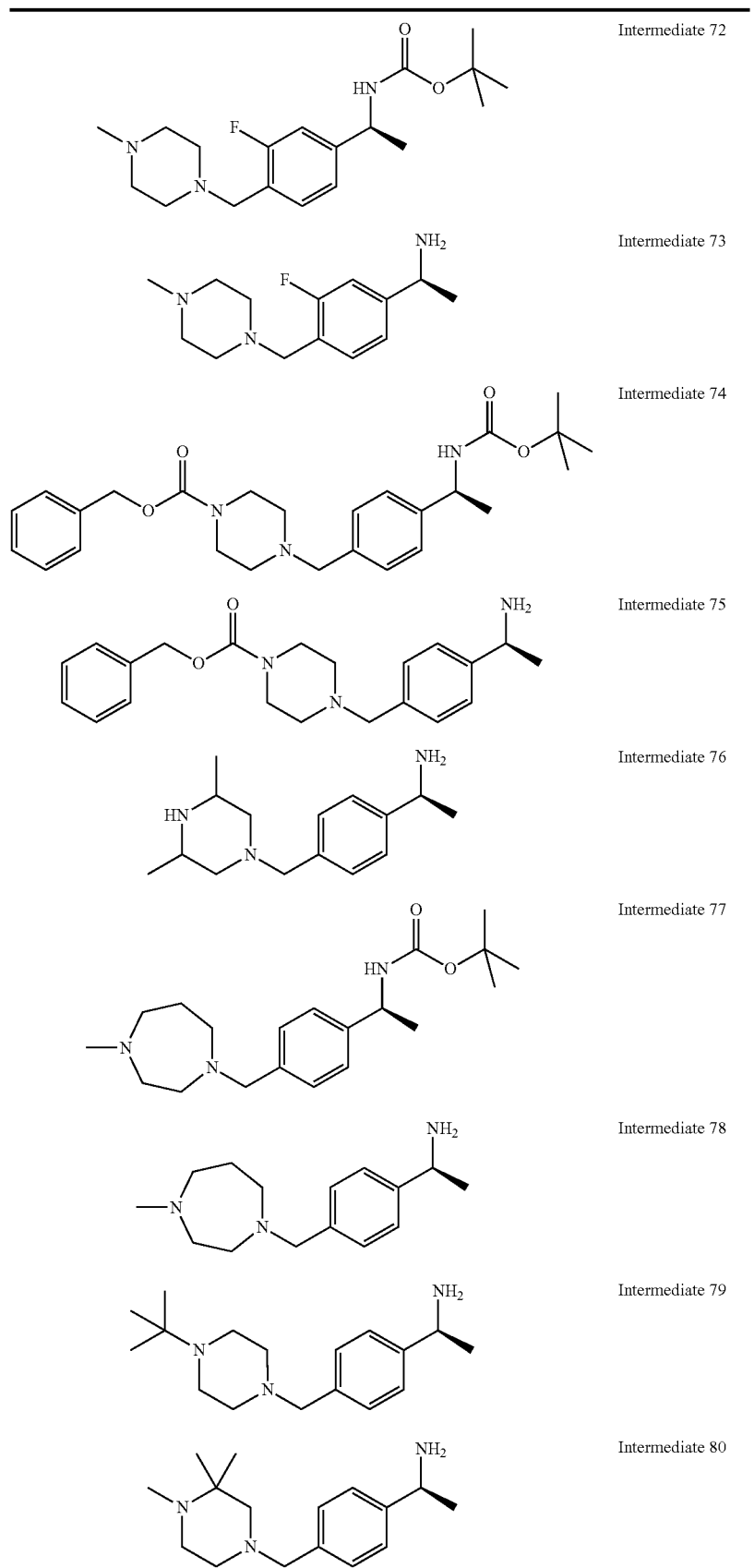
| | |
|---|---|
| | Intermediate 72 |
| | Intermediate 73 |
| | Intermediate 74 |
| | Intermediate 75 |
| | Intermediate 76 |
| | Intermediate 77 |
| | Intermediate 78 |
| | Intermediate 79 |
| | Intermediate 80 |

TABLE 4h-continued
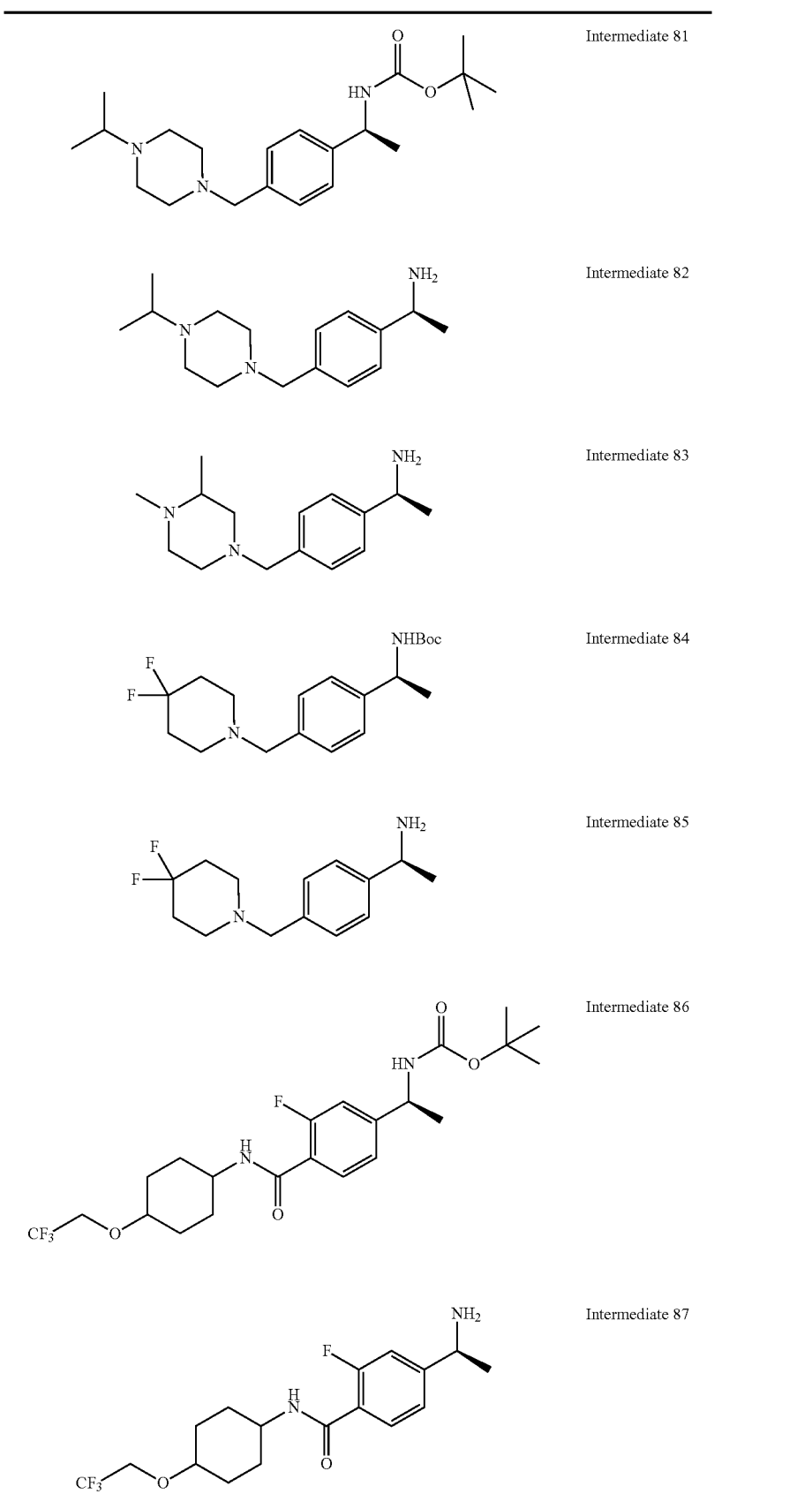

TABLE 4h-continued
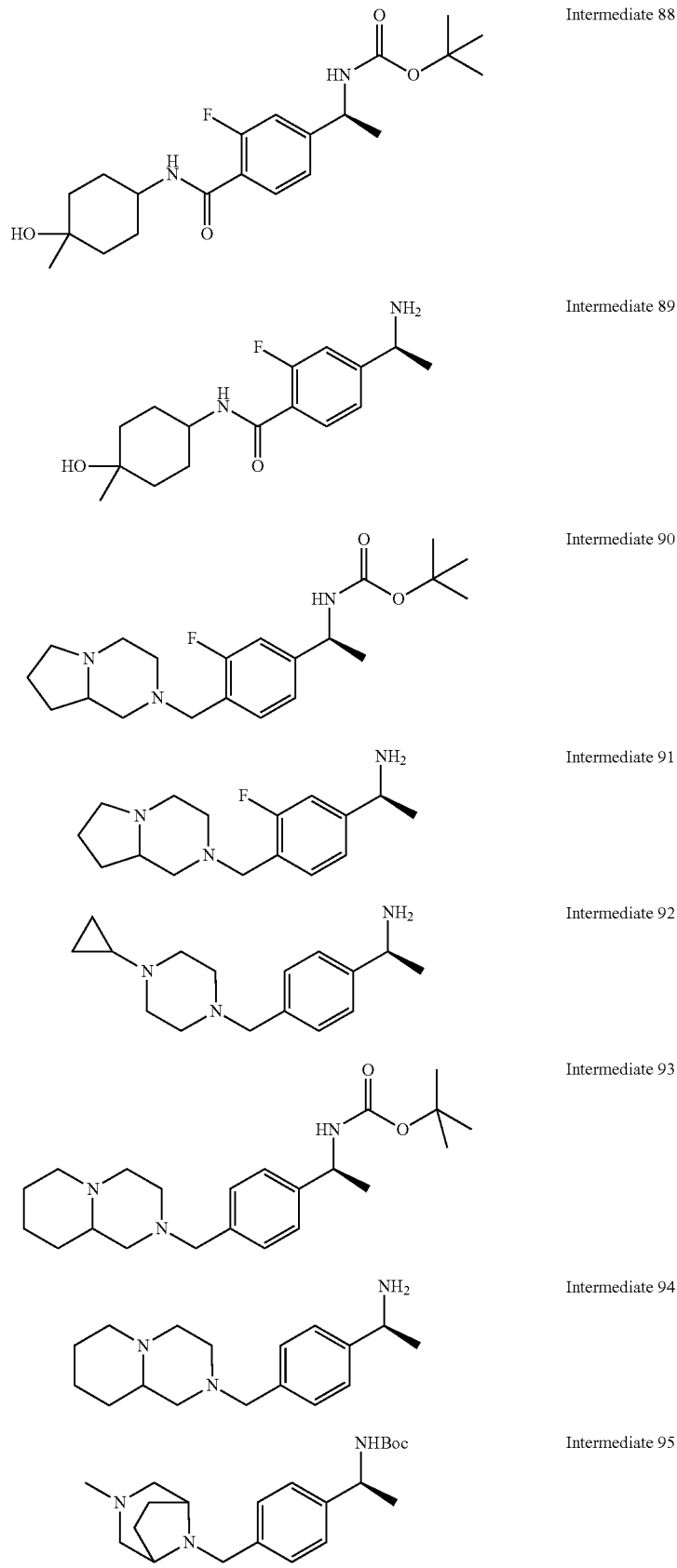

TABLE 4h-continued
| | |
|---|---|
| 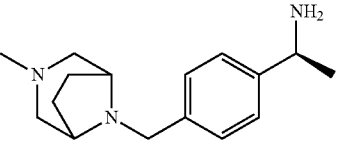 [SMILES: C[C@H](N)c1ccc(CN2C3CCC2CN(C)C3)cc1] | Intermediate 96 |
| 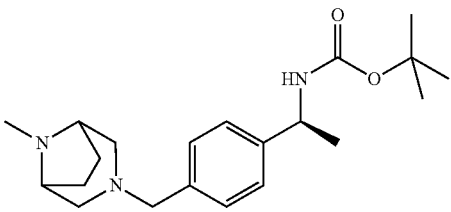 [SMILES: C[C@H](NC(=O)OC(C)(C)C)c1ccc(CN2CC3CCC(C2)N3C)cc1] | Intermediate 97 |
| 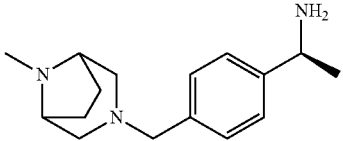 [SMILES: C[C@H](N)c1ccc(CN2CC3CCC(C2)N3C)cc1] | Intermediate 98 |
| 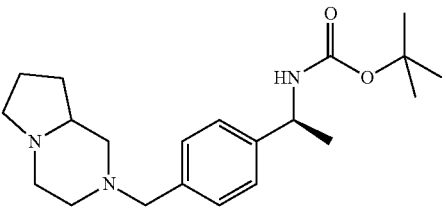 [SMILES: C[C@H](NC(=O)OC(C)(C)C)c1ccc(CN2CCN3CCCC3C2)cc1] | Intermediate 99 |
| 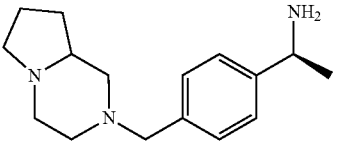 [SMILES: C[C@H](N)c1ccc(CN2CCN3CCCC3C2)cc1] | Intermediate 100 |
| 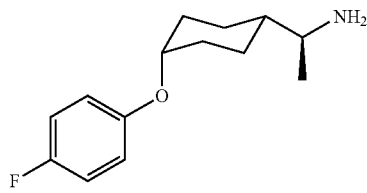 [SMILES: C[C@H](N)C1CCC(Oc2ccc(F)cc2)CC1] | Intermediate 101 |
| 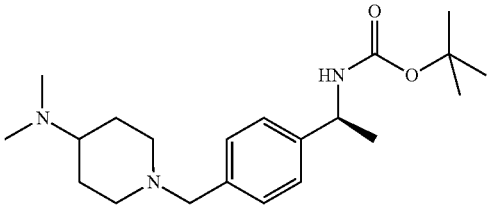 [SMILES: C[C@H](NC(=O)OC(C)(C)C)c1ccc(CN2CCC(N(C)C)CC2)cc1] | Intermediate 102 |
| 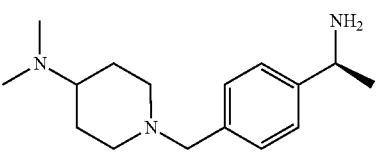 [SMILES: C[C@H](N)c1ccc(CN2CCC(N(C)C)CC2)cc1] | Intermediate 103 |
| 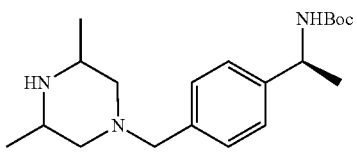 [SMILES: CC1CN(Cc2ccc([C@H](C)NC(=O)OC(C)(C)C)cc2)CC(C)N1] | Intermediate 104 |

TABLE 4h-continued
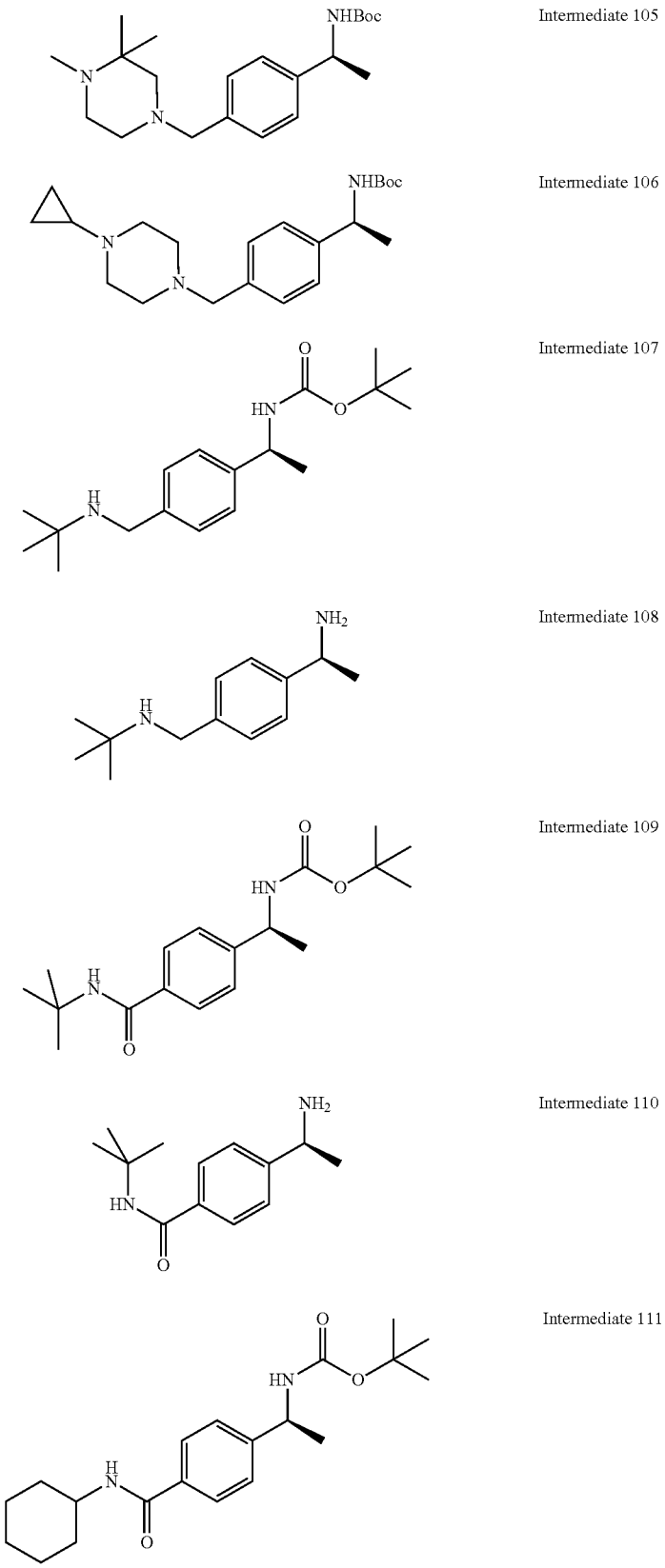
Intermediate 105
Intermediate 106
Intermediate 107
Intermediate 108
Intermediate 109
Intermediate 110
Intermediate 111

TABLE 4h-continued

| Structure | Name |
|---|---|
| (cyclohexyl-NH-C(O)-C6H4-CH(NH2)CH3) | Intermediate 112 |
| (PhNH-C(O)-C6H4-CH(NHBoc)CH3) | Intermediate 113 |
| (PhNH-C(O)-C6H4-CH(NH2)CH3) | Intermediate 114 |
| (piperidin-1-yl-C(O)-C6H4-CH(NHBoc)CH3) | Intermediate 115 |
| (piperidin-1-yl-C(O)-C6H4-CH(NH2)CH3) | Intermediate 116 |
| (4-methylpiperazin-1-yl-C(O)-C6H4-CH(NHBoc)CH3) | Intermediate 117 |
| (4-methylpiperazin-1-yl-C(O)-C6H4-CH(NH2)CH3) | Intermediate 118 |

TABLE 4h-continued

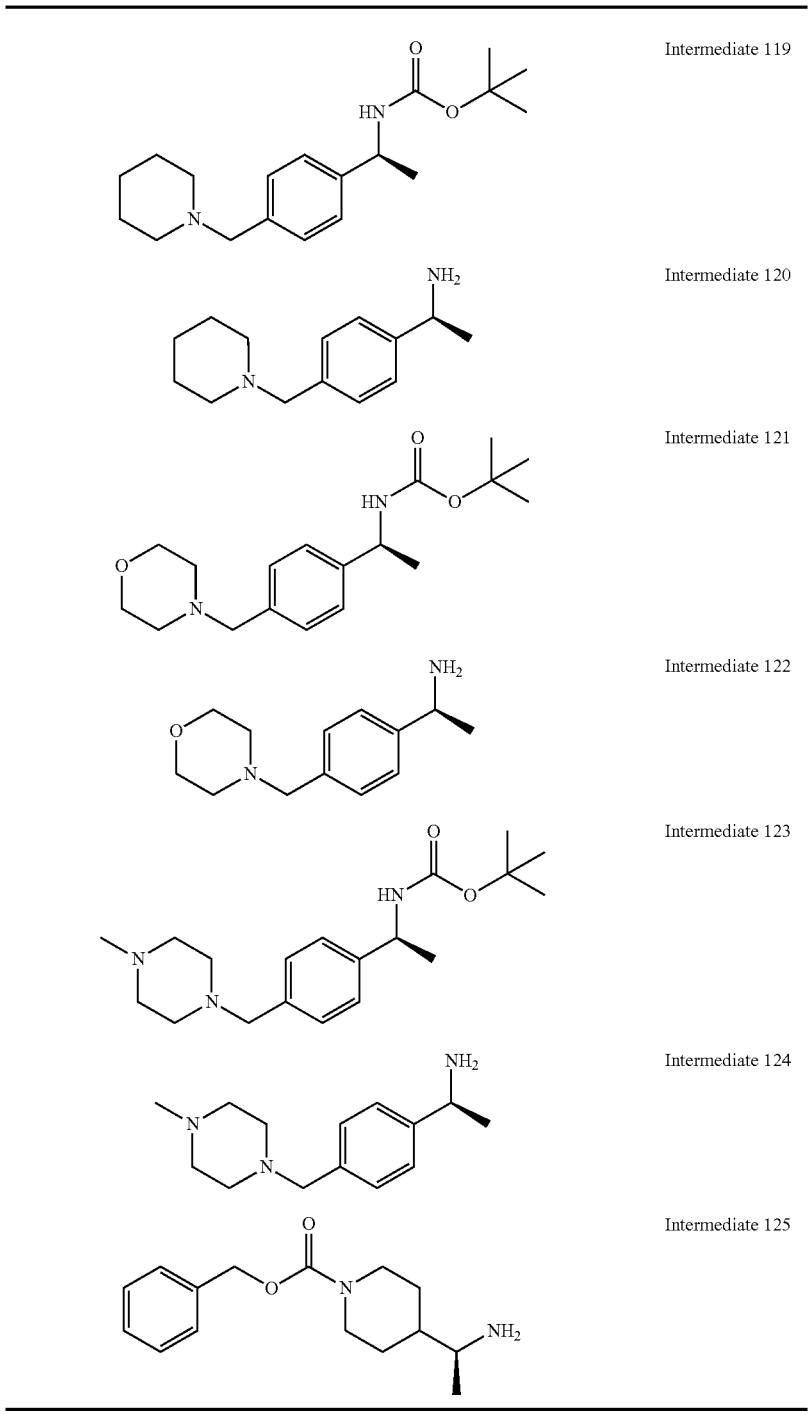

Intermediate 119

Intermediate 120

Intermediate 121

Intermediate 122

Intermediate 123

Intermediate 124

Intermediate 125

TABLE 4i

Chemical name, NMR chemical shifts and LCMS signal for each intermediate listed in Table 4h.

| Intermediate: Name | $^1$H NMR (400 MHz) δ ppm | LCMS |
|---|---|---|
| 70: (S)-1-(3-fluoro-4-((3,3,4-trimethylpiperazin-1-yl)methyl)phenyl)ethanamine | | MS m/z 280.2 (M + H). |
| 71: (S)-tert-butyl 1-(4-bromo-3-fluorophenyl)ethylcarbamate | (CDCl$_3$) 7.51-7.45 (m, 1H), 7.07 (dd, J = 9.8, 2.0 Hz, 1H), | MS m/z 317.9 (M + H). |

TABLE 4i-continued

Chemical name, NMR chemical shifts and LCMS signal for each intermediate listed in Table 4h.

| Intermediate: Name | $^1$H NMR (400 MHz) δ ppm | LCMS |
|---|---|---|
| 72: (S)-tert-butyl 1-(3-fluoro-4-((4-methylpiperazin-1-yl)methyl)phenyl)ethylcarbamate | (CDCl$_3$) 7.28 (t, J = 7.7 Hz, 1H), 7.01 (dd, J = 7.7, 1.8 Hz, 1H), 6.94 (dd, J = 10.8, 1.9 Hz, 1H), 6.98 (dd, J = 8.4, 2.1 Hz, 1H), 4.86 (br s, 1H), 4.74 (br s, 1H), 4.67 (br s, 1H),, 1.41(br s, 12H), 3.54 (s, 2H), 2.67-2.29 (m, 8H), 2.25 (s, 3H), 1.51-1.26 (m, 12H) | MS m/z 353.2 (M + H) |
| 73: (S)-1-(3-fluoro-4-((4-methylpiperazin-1-yl)methyl)phenyl)ethanamine | | MS m/z 252.1 (M + H) |
| 74: (S)-benzyl 4-(4-(1-(tert-butoxycarbonylamino)ethyl)benzyl)piperazine-1-carboxylate | (CDCl$_3$) 7.43-7.19 (m, 9H), 5.12 (s, 2H), 4.78 (br s, 2H), 3.95-3.20 (m, 6H), 2.43 (br s, 4H), 1.43 (br s, 12H) | MS m/z 454.3 (M + H) |
| 75: (S)-benzyl 4-(4-(1-aminoethyl)benzyl)piperazine-1-carboxylate | | MS m/z 354.3 (M + H) |
| 76: (1S)-1-(4-((3,5-dimethylpiperazin-1-yl)methyl)phenyl)ethanamine | | MS m/z 248.2 (M + H) |
| 77: (S)-tert-butyl 1-(4-((4-methyl-1,4-diazepan-1-yl)methyl)phenyl)ethylcarbamate | (CDCl$_3$) 7.31-7.20 (m, 4H), 4.78 (s, 1H), 3.61 (s, 2H), 2.81-2.69 (m, 8H), 2.44 (s, 3H), 1.94-1.85 (m, 2H), 1.43 (br s, 12H) | MS m/z 349.4 (M + H) |
| 78: (S)-1-(4-((4-methyl-1,4-diazepan-1-yl)methyl)phenyl)ethanamine | | MS m/z 248.1 (M + H) |
| 79: (S)-1-(4-((4-tert-butylpiperazin-1-yl)methyl)phenyl)ethanamine | | MS m/z 276.2 (M + H) |
| 80: (S)-1-(4-((3,3,4-trimethylpiperazin-1-yl)methyl)phenyl)ethanamine | | MS m/z 262.2 (M + H) |
| 81: (S)-tert-butyl 1-(4-((4-isopropylpiperazin-1-yl)methyl)phenyl)ethylcarbamate | (CDCl$_3$) 7.28-7.22 (m, 4H), 4.78 (s, 1H), 3.49 (s, 2H), 2.88-2.22 (m, 9H), 1.42 (br s, 12H), 1.05 (d, J = 6.5 Hz, 6H) | MS m/z 363.4 (M + H) |
| 82: (S)-1-(4-((4-isopropylpiperazin-1-yl)methyl)phenyl)ethanamine | | MS m/z 262.2 (M + H) |
| 83: (1S)-1-(4-((3,4-dimethylpiperazin-1-yl)methyl)phenyl)ethanamine | | MS m/z 248.2 (M + H) |
| 84: (S)-tert-butyl 1-(4-((4,4-difluoropiperidin-1-yl)methyl)phenyl)ethylcarbamate | | MS m/z 356.2 (M + H) |
| 85: (S)-1-(4-((4,4-difluoropiperidin-1-yl)methyl)phenyl)ethanamine | | MS m/z 255.2 (M + H) |
| 86: (S)-tert-butyl 1-(3-fluoro-4-(4-(2,2,2-trifluoroethoxy)cyclohexylcarbamoyl)phenyl)ethylcarbamate | (CDCl$_3$) 8.01 (t, J = 8.1 Hz, 1H), 7.16 (d, J = 7.9, 1H), 7.04 (d, J = 13.2, 1H), 6.67-6.63(m, 1H), 4.96 (br s, 1H), 4.76 (br s, 1H), 4.06 (br s, 1H), 3.85-3.77 (m, 2H), 3.64 (br s, 1H), 1.92-1.74 (m, 4H), 1.73-1.59 (m, 4H), 1.40 (br s, 12H) | MS m/z 463.3 (M + H) |
| 87: (S)-4-(1-aminoethyl)-2-fluoro-N-(4-(2,2,2-trifluoroethoxy)cyclohexyl)benzamide | | MS m/z 363.2 (M + H) |
| 88: (S)-tert-butyl 1-(3-fluoro-4-(4-hydroxy-4-methylcyclohexylcarbamoyl)phenyl)ethylcarbamate | (CDCl$_3$) 8.04 (t, J = 8.1 Hz, 1H), 7.19 (d, J = 8.3, 1H), 7.05 (dd, J = 13.2, 1.7 Hz, 1H), 6.65 (br dd, J = 12.1, 6.6 Hz, 2H), 4.84 (br s, 1H), 4.77 (br s, 1H), 4.17-4.06 (m, 1H), 2.09-2.00 (m, 2H), 1.61-1.59 (m, 4H), 1.55-1.47 (m, 2H), 1.42 (br s, 12H), 1.30 (s, 3H) | MS m/z 395.1 (M + H) |
| 89: (S)-4-(1-aminoethyl)-2-fluoro-N-(4-hydroxy-4-methylcyclohexyl)benzamide | | MS m/z 295.2 (M + H) |
| 90: tert-butyl (1S)-1-(3-fluoro-4-((hexahydropyrrolo[1,2-a]pyrazin-2(1H)-yl)methyl)phenyl)ethylcarbamate | | MS m/z 376.1 (M − H) |

TABLE 4i-continued

Chemical name, NMR chemical shifts and LCMS signal for each intermediate listed in Table 4h.

| Intermediate: Name | $^1$H NMR (400 MHz) δ ppm | LCMS |
|---|---|---|
| 91: (1S)-1-(3-fluoro-4-((hexahydropyrrolo[1,2-a]pyrazin-2(1H)-yl)methyl)phenyl)ethanamine | | MS m/z 278.1 (M + H) |
| 92: (S)-1-(4-((4-cyclopropylpiperazin-1-yl)methyl)phenyl)ethanamine | | MS m/z 260.2 (M + H) |
| 93: tert-butyl (1S)-1-(4-((dihydro-1H-pyrido[1,2-a]pyrazin-2(6H,7H,8H,9H,9aH)-yl)methyl)phenyl)ethylcarbamate | (CDCl$_3$) 7.30-7.20 (m, 4H), 4.78 (s, 2H), 3.46 (s, 2H), 2.89-2.61 (m, 4H), 2.39-2.21 (m, 2H), 2.10-1.93 (m, 2H), 1.86 (t, J = 10.7 Hz, 1H), 1.79-1.68 (m, 1H), 1.62 (br s, 2H), 1.43 (br s, 13H), 1.32-1.19 (m, 2H) | MS m/z 372.4 (M − H) |
| 94: (1S)-1-(4-((dihydro-1H-pyrido[1,2-a]pyrazin-2(6H,7H,8H,9H,9aH)-yl)methyl)phenyl)ethanamine | | MS m/z 274.2 (M + H) |
| 95: tert-butyl (1S)-1-(4-((3-methyl-3,8-diazabicyclo[3.2.1]octan-8-yl)methyl)phenyl)ethylcarbamate | | MS m/z 361.3 (M + H) |
| 96: (1S)-1-(4-((3-methyl-3,8-diazabicyclo[3.2.1]octan-8-yl)methyl)phenyl)ethanamine | | MS m/z 260.2 (M + H) |
| 97: tert-butyl (1S)-1-(4-((8-methyl-3,8-diazabicyclo[3.2.1]octan-3-yl)methyl)phenyl)ethylcarbamate | (CDCl$_3$) 7.28-7.19 (m, 4H), 4.77 (br s, 2H), 3.44 (s, 2H), 3.03 (br s, 2H), 2.55 (dd, J = 10.8, 2.9 Hz, 2H), 2.29 (d, J = 10.3 Hz, 2H), 2.25 (s, 3H), 1.93-1.78 (m, 4H), 1.64 (br s, 1H), 1.43 (br s, 12H) | MS m/z 360.6 (M + H) |
| 98: (1S)-1-(4-((8-methyl-3,8-diazabicyclo[3.2.1]octan-3-yl)methyl)phenyl)ethanamine | | MS m/z 260.2 (M + H). |
| 99: tert-butyl (1S)-1-(4-((hexahydropyrrolo[1,2-a]pyrazin-2(1H)-yl)methyl)phenyl)ethylcarbamate | (CDCl$_3$) 7.30-7.21 (m, 4H), 4.78 (br s, 1H), 3.61-3.44 (m, 2H), 3.05 (td, J = 8.6, 1.9 Hz, 1H), 3.00-2.93 (m, 2H), 2.86-2.76 (m, 1H), 2.33-2.19 (m, 2H), 2.17-2.00 (m, 2H), 1.87-1.65 (m, 4H), 1.43 (br s, 12H) | MS m/z 361.3 (M + H) |
| 100: (1S)-1-(4-((hexahydropyrrolo[1,2-a]pyrazin-2(1H)-yl)methyl)phenyl)ethanamine | | MS m/z 260.2 (M + H) |
| 101: (S)-1-[4-(4-Fluoro-phenoxy)-cyclohexyl]-ethylamine | | LC-MS m/z 237.4 (M + H)+; RT.: 1.08 min. |
| 102: (S)-tert-butyl 1-(4-((4-(dimethylamino)piperidin-1-yl)methyl)phenyl)ethylcarbamate | (CDCl$_3$) 7.28-7.20 (m, 4H), 4.79 (br s, 2H), 3.46 (s, 2H), 2.91 (br d, J = 12.1 Hz, 2H), 2.26 (s, 6H), 2.17-2.09 (m, 1H), 1.94 (td, J = 11.8, 2.4 Hz, 2H), 1.85 (br s, 1H), 1.81-1.71 (m, 2H), 1.53 (td, J = 12.1, 3.7 Hz, 2H), 1.44-1.42 (m, 12H) | MS m/z 361.8 (M + H) |
| 103: (S)-1-(4-(1-aminoethyl)benzyl)-N,N-dimethylpiperidin-4-amine | | MS m/z 262.1 (M + H) |
| 104: tert-butyl (1S)-1-(4-((3,5-dimethylpiperazin-1-yl)methyl)phenyl)ethylcarbamate | (CD$_3$OD) 7.29 (s, 4 H), 4.68 (br s, 1 H), 3.52 (s, 2 H), 2.96-2.88 (m, 2H), 2.82-2.79 (m, 2 H), 1.69 (t, J = 11 Hz, 2 H), 1.44 (br s, 9 H), 1.40 (d, J = 7.1 Hz, 3 H), 1.06 (d, J = 6.5 Hz, 6 H); | MS m/z 348.3 (M + H) |
| 105: (S)-tert-butyl 1-(4-((3,3,4-trimethylpiperazin-1-yl)methyl)phenyl)ethylcarbamate | (CD$_3$OD) δ 7.35-7.25 (m, 4 H), 4.67 (br s, 1 H), 4.59 (s, 1 H), 3.45 (s, 2 H), 3.31 (s, 1 H), 2.62 (br s, 2 H), 2.51 (br s, 1 H), 2.24 (s, 3 H), 2.18 (br s, 1 H), 1.43 (br s, 9 H), 1.40 (d, J = 7.1 Hz, 3 H), 1.07 (s, 6 H); | MS m/z 362.3 (M + H) |
| 106: ((S)-tert-butyl 1-(4-((4-cyclopropylpiperazin-1-yl)methyl)phenyl)ethylcarbamate | (CDCl$_3$) δ 7.21-7.16 (m, 4 H), 5.23 (s, 1 H), 4.72 (br s, 1 H), 3.42 (s, 2 H), 2.58 (br s, 4 H), 2.38 (br s, 4 H), 1.57-1.51 (m, 1 H), 1.41-1.30 (br m, 12 H), 0.39-0.33 (m, 4 H); | MS m/z 359.8 (M + H) |

TABLE 4i-continued

Chemical name, NMR chemical shifts and LCMS signal for each intermediate listed in Table 4h.

| Intermediate: Name | ¹H NMR (400 MHz) δ ppm | LCMS |
|---|---|---|
| 107: (S)-tert-butyl 1-(4-((tert-butylamino)methyl)phenyl)ethylcarbamate | (CDCl$_3$) 7.32 (d, J = 8.0 Hz, 1H), 7.25 (d, J = 8.2 Hz, 1H), 4.77 (s, 1H), 3.72 (s, 1H), 1.43 (d, J = 5.4 Hz, 6H), 1.18 (s, 4H) | MS m/z 308.2 (M + H)+ |
| 108: (S)-N-(4-(1-aminoethyl)benzyl)-2-methylpropan-2-amine | | MS m/z 207.2 (M + H)+ |
| 109: (S)-tert-butyl 1-(4-(tert-butylcarbamoyl)phenyl)ethyl carbamate | (CDCl$_3$) 7.71-7.62 (m, 2H), 7.33 (d, J = 8.1 Hz, 2H), 5.90 (s, 1H), 4.80 (br s, 2H), 1.46-1.41 (m, 21H) | MS m/z 321.2 (M + H)+ |
| 110: (S)-4-(1-aminoethyl)-N-tert-butylbenzamide hydrochloride | | MS m/z 221.3 (M + H)+ |
| 111: (S)-tert-butyl 1-(4-(cyclohexylcarbamoyl)phenyl)ethyl carbamate | (CDCl$_3$) 7.71 (dd, J = 8.3, 1.8 Hz, 2H), 7.35 (d, J = 7.8 Hz, 2H), 5.91 (d, J = 8.3 Hz, 1H), 4.94-4.59 (m, 2H), 3.97 (ddt, J = 10.8, 6.5, 2.9 Hz, 1H), 2.02 (dt, J = 12.6, 3.7 Hz, 2H), 1.75 (dp, J = 11.8, 3.9 Hz, 2H), 1.66-1.56 (m, 3H), 1.49-1.30 (m, 12H), 1.23 (m, 3H) | MS m/z 347.2 (M + H)+ |
| 112: (S)-4-(1-aminoethyl)-N-cyclohexylbenzamide hydrochloride | | MS m/z 247.3 (M + H)+ |
| 113: (S)-tert-butyl 1-(4-(phenylcarbamoyl)phenyl)ethyl carbamate | (CDCl$_3$) 7.90-7.83 (m, 2H), 7.81-7.62 (m, 3H), 7.49-7.36 (m, 4H), 7.18 (td, J = 7.4, 1.2 Hz, 1H), 4.87 (br s, 2H), 1.58 (s, 3H), 1.46 (m, 9H) | MS m/z 340.6 (M + H)+ |
| 114: (S)-4-(1-aminoethyl)-N-phenylbenzamide hydrochloride | | MS m/z 241.2 (M + H)+ |
| 115: (S)-tert-butyl 1-(4-(piperidine-1-carbonyl)phenyl)ethylcarbamate | (CDCl$_3$) 7.33 (q, J = 8.3 Hz, 4H), 4.80 (br s, 2H), 3.70 (br s, 2H), 3.47-3.22 (m, 2H), 1.70-1.63 (m, 4H), 1.53-1.26 (m, 14H) | MS m/z 333.2 (M + H)+ |
| 116: (S)-(4-(1-aminoethyl)phenyl)(piperidin-1-yl)methanone hydrochloride | | MS m/z 233.2 (M + H)+ |
| 117: (S)-tert-butyl 1-(4-(4-methylpiperazine-1-carbonyl)phenyl)ethylcarbamate | (CDCl$_3$) 7.35 (q, J = 8.2 Hz, 4H), 4.81 (br s, 1H), 3.79 (brs, 2H), 3.45 (br s, 2H), 2.50-2.32 (m, 7H), 1.61 (s, 1H), 1.51-1.29 (m, 12H) | MS m/z 348.2 (M + H)+ |
| 118: (S)-(4-(1-aminoethyl)phenyl)(4-methylpiperazin-1-yl)methanone hydrochloride | | MS m/z 248.2 (M + H)+ |
| 119: (S)-tert-butyl 1-(4-(piperidin-1-ylmethyl)phenyl)ethylcarbamate | (CDCl$_3$) 7.27 (q, J = 7.9 Hz, 4H), 4.80 (br s, 2H), 3.49 (s, 2H), 2.60-2.28 (m, 4H), 1.60 (p, J = 5.5 Hz, 4H), 1.52-1.31 (m, 15H) | MS m/z 319.0 (M + H)+ |
| 120: (S)-1-(4-(piperidin-1-ylmethyl)phenyl)ethanamine | | MS m/z 219.1 (M + H)+ |
| 121: (S)-tert-butyl 1-(4-(morpholinomethyl)phenyl)ethyl carbamate | (CDCl$_3$) 7.48-7.10 (m, 4H), 4.82 (d, J = 25.7 Hz, 2H), 3.80-3.62 (m, 3H), 3.48 (s, 2H), 2.61-2.24 (m, 3H), 1.44 (m, 13H) | MS m/z 321.2 (M + H)+ |
| 122: (S)-1-(4-(morpholinomethyl)phenyl)ethanamine | | MS m/z 220.9 M + H)+ |
| 123: (S)-tert-butyl 1-(4-((4-methylpiperazin-1-yl)methyl)phenyl)ethylcarbamate | (CDCl$_3$) 7.39-7.15 (m, 7H), 4.79 (br s, 2H), 3.51 (s, 2H), 2.41 (m, 9H), 1.46 (m, 11H) | MS m/z 321.2 (M + H)+ |
| 124: (S)-1-(4-((4-methylpiperazin-1-yl)methyl)phenyl)ethanamine | | MS m/z 234.2 (M + H)+ |
| 125: 4-((S)-1-Amino-ethyl)-piperidine-1-carboxylic acid benzyl ester | | LC-MS (M + H) = 263.1 RT.: 0.91 min. |

Intermediate 126

(S)-(4-(1-aminoethyl)-3-fluorophenyl)methanol

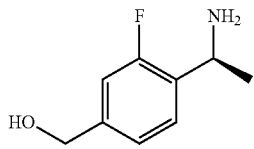

To a cooled (0° C.) suspension of (S)-methyl 4-(1-aminoethyl)-3-fluorobenzoate hydrochloride (0.109 g, 0.468 mmol) in THF (15 mL) was added a solution of LAH in THF (2.0 M, 1.05 mL, 2.10 mmol, 4.49 equiv) and the resulting mixture was stirred at 0° C. for 2 h 20 min and at room temperature for 2½ h. The reaction mixture was quenched by addition of a mixture of Na$_2$SO$_4$ decahydrate and Celite (1:1 by weight) until gas evolution ceased. The reaction mixture was filtered, washed with EtOAc. The filtrate was concentrated and used for the next reaction without purification.

$^1$H NMR (400 MHz, CD$_3$OD) δ 7.43 (t, J=7.7 Hz, 1H), 7.15 (d, J=8.1 Hz, 1H), 7.08 (d, J=12 Hz, 1H), 4.60 (s, 2H), 4.32 (q, J=6.6 Hz, 1H), 1.42-1.40 (m, 3H).

Intermediate 127

4-((S)-1-(4-((S)-4-isopropyl-2-oxooxazolidin-3-yl)pyrimidin-2-ylamino)ethyl)benzaldehyde

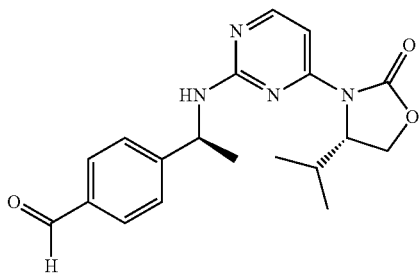 [SMILES: CC(C)[C@H]1COC(=O)N1c1ccnc(N[C@@H](C)c2ccc(C=O)cc2)n1]

A solution of (S)-3-(2-((S)-1-(4-(hydroxymethyl)phenyl)ethylamino)pyrimidin-4-yl)-4-isopropyloxazolidin-2-one (285 mg, 0.8 mmol) and manganese dioxide (2.78 g, 32 mmol, 40 equiv) in DCM (16 mL) was stirred at room temperature for 30 min. The solution was filtered through a pad of celite and washed with DCM. The filtrated was concentrated and used to next step without further purification.

Intermediate 128 tert-butyl 4-(4-((S)-1-(4-((S)-4-isopropyl-2-oxooxazolidin-3-yl)pyrimidin-2-ylamino)ethyl)benzyl)-2,2-dimethylpiperazine-1-carboxylate

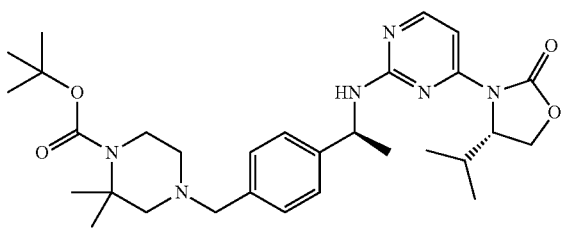 [SMILES: CC(C)[C@H]1COC(=O)N1c1ccnc(N[C@@H](C)c2ccc(CN3CCN(C(=O)OC(C)(C)C)C(C)(C)C3)cc2)n1]

A solution of 4-((S)-1-(4-((S)-4-isopropyl-2-oxooxazolidin-3-yl)pyrimidin-2-ylamino)ethyl)benzaldehyde (71 mg, 0.2 mmol) and tert-butyl 2,2-dimethylpiperazine-1-carboxylate (47.1 mg, 0.22 mmol) in MeOH (4 mL) was added acetic acid (14.4 mg, 0.24 mmol) and 5-Ethyl-2-methylpyridine borane complex (27 mg, 0.2 mmol, sigma aldrich). The solution was stirred at 50° C. for 4 h then 5 drops of water was added. The solution was stirred at room temperature for another 2 h then diluted with EtOAc (10 mL) and washed with water (10 mL). After separation, the aqueous phase was extracted with EtOAc (3×10 mL). Combined organics were dried over Na$_2$SO$_4$, filtered and concentrated. The crude material was purified through Silica gel column chromatography (MeOH/EtOAc 0 to 10%) to give tert-butyl 4-(4-((S)-1-(4-((S)-4-isopropyl-2-oxooxazolidin-3-yl)pyrimidin-2-ylamino)ethyl)benzyl)-2,2-dimethylpiperazine-1-carboxylate as a white solid (80 mg, 72.4% yield).

$^1$H NMR (400 MHz, CDCl$_3$) δ 8.18 (br s, 1H), 7.44 (d, J=5.7 Hz, 1H), 7.24-7.29 (m, 4H), 5.46 (br s, 1H), 5.03 (br s, 1H), 4.59-4.63 (m, 1H), 4.29 (t, J=8.7 Hz, 1H), 4.22 (dd, J=9.1, 3.1 Hz, 1H), 3.44 (br s, 4H), 2.40 (s, 2H), 2.16 (s, 2H), 1.54 (d, J=6.9 Hz, 3H), 1.45 (s, 9H), 1.36 (s, 6H), 0.80-0.57 (m, 6H); MS m/z 252.1 (M+H).

Intermediate 129 tert-butyl 1-(4-((S)-1-(4-((S)-4-isopropyl-2-oxooxazolidin-3-yl)pyrimidin-2-ylamino)ethyl)benzyl)-4-methylpiperidin-4-ylcarbamate

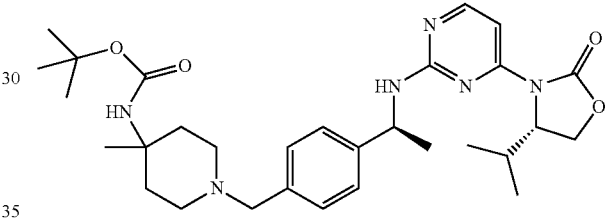

Prepared by a method similar to that described for the preparation of Intermediate 128.

$^1$H NMR (400 MHz, CDCl$_3$) 8.17 (d, J=5.7 Hz, 1H), 7.43 (d, J=5.7 Hz, 1H), 7.26 (br s, 4H), 5.40 (br s, 1H), 5.02 (br s, 1H), 4.60 (dt, J=8.2, 3.1 Hz, 1H), 4.34-4.19 (m, 3H), 3.47 (br s, 2H), 2.54 (br s, 2H), 2.26 (br s, 2H), 1.95 (br s, 3H), 1.60 (br s, 2H), 1.53 (d, J=6.9 Hz, 3H), 1.43 (s, 9H), 1.33 (s, 3H), 0.69 (br s, 3H), 0.63 (br s, 3H). MS m/z 553.6 (M+H).

Intermediate 130 tert-butyl (S)-1-(4-bromophenyl)ethyl(4-((S)-4-isopropyl-2-oxooxazolidin-3-yl)pyrimidin-2-yl)carbamate

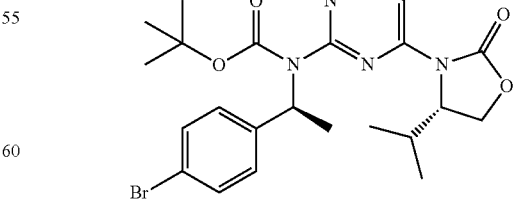

To a solution of (S)-3-(2-((S)-1-(4-bromophenyl)ethylamino)pyrimidin-4-yl)-4-isopropyloxazolidin-2-one (1.62 g, 4 mmol) in THF (20 mL) was added di-tert-butyl dicarbonate (1.31 g, 6 mmol), DMAP (49 mg, 0.4 mmol) and DIPEA (1.40 mL, 8 mmol). The solution was stirred at 50° C. for 7 days then concentrated under reduced pressure. The residue was diluted with EtOAc (40 mL) and washed with water and brine. The organic layer was dried over Na₂SO₄, filtered and concentrated. Silica gel column chromatography (EtOAc/heptane 0 to 80%) provided tert-butyl (S)-1-(4-bromophenyl)ethyl(4-((S)-4-isopropyl-2-oxooxazolidin-3-yl)pyrimidin-2-yl)carbamate as a white solid (1.03 g, 50.9% yield).

¹H NMR (400 MHz, CDCl₃) δ 8.57 (d, J=5.8 Hz, 1H), 7.99 (d, J=5.8 Hz, 1H), 7.44-7.39 (m, 2H), 7.33-7.28 (m, 2H), 5.63 (q, J=7.2 Hz, 1H), 4.63 (dt, J=8.0, 3.3 Hz, 1H), 4.39-4.26 (m, 2H), 2.47-2.39 (m, 1H), 1.66 (d, J=7.1 Hz, 3H), 1.30 (s, 9H), 0.84 (d, J=7.0, 3H), 0.83 (d, J=7.0, 3H); MS m/z 507.0 (M+H).

Intermediate 131 tert-butyl 4-((S)-4-isopropyl-2-oxooxazolidin-3-yl)pyrimidin-2-yl((S)-1-(4-(1-methyl-1H-pyrazol-4-yl)phenyl)ethyl)carbamate

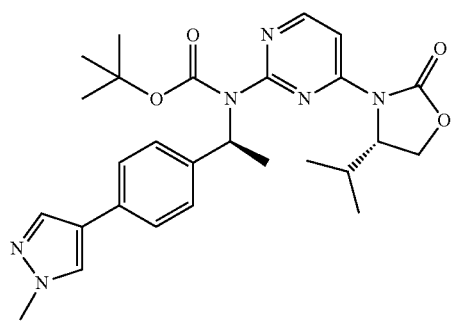 [SMILES: CC(C)[C@H]1COC(=O)N1c1ccnc(N(C(=O)OC(C)(C)C)[C@@H](C)c2ccc(-c3cnn(C)c3)cc2)n1]

In a 5 mL microwave vial a solution of tert-butyl (S)-1-(4-bromophenyl)ethyl(4-((S)-4-isopropyl-2-oxooxazolidin-3-yl)pyrimidin-2-yl)carbamate (101 mg, 0.2 mmol), 1-methyl-4-(4,4,5,5-tetramethyl-1,3,2-dioxaborolan-2-yl)-1H-pyrazole (50 mg, 0.24 mmol), Sodium bicarbonate (0.2 mL, 0.4 mmol, 2 M aqueous solution) in Dioxane (2 mL) was bubbled N2 for 3 min then Cl₂Pd(dppf)CH₂Cl₂ (16 mg, 0.02 mmol) was added. The capped tube was heated to 100° C. for 16 h. After cooling the reaction mixture was diluted with EtOAc (10 mL) and washed with water (10 mL). After separation, the aqueous phase was extracted with EtOAc (3×10 mL). Combined organics were dried over Na₂SO₄, filtered and concentrated. The crude material was purified through silica gel column chromatography (EtOAc in Heptane 12 to 100%) to give a white solid (50 mg, 49.3% yield).

¹H NMR (400 MHz, CDCl₃) δ 8.57 (d, J=5.7 Hz, 1H), 7.97 (d, J=5.8 Hz, 1H), 7.74 (s, 1H), 7.59 (s, 1H), 7.39 (s, 4H), 5.71 (q, J=7.0 Hz, 1H), 4.65 (dt, J=8.1, 3.2 Hz, 1H), 4.36-4.24 (m, 2H), 3.94 (s, 3H), 2.50-2.42 (m, 1H), 1.71 (d, J=7.0 Hz, 3H), 1.29 (s, 9H), 0.82 (d, J=7.0 Hz, 3H), 0.80 (d, J=7.0 Hz, 3H); MS m/z 507.1 (M+H).

Intermediate 132 tert-butyl (S)-1-(4-(cyclohexanecarboxamido)phenyl)ethyl(4-((S)-4-isopropyl-2-oxooxazolidin-3-yl)pyrimidin-2-yl)carbamate

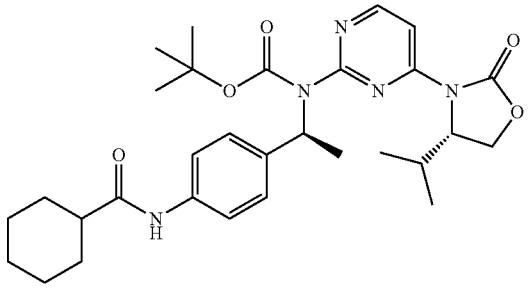 [SMILES: CC(C)[C@H]1COC(=O)N1c1ccnc(N(C(=O)OC(C)(C)C)[C@@H](C)c2ccc(NC(=O)C3CCCCC3)cc2)n1]

In a 5 ml microwave reaction vial was added tert-butyl (S)-1-(4-bromophenyl)ethyl(4-((S)-4-isopropyl-2-oxooxazolidin-3-yl)pyrimidin-2-yl)carbamate (101 mg, 0.2 mmol), cyclohexanecarboxamide (30 mg, 0.24 mol), cesium carbonate (91 mg, 0.28 mmol), XANTPHOS (7 mg, 0.012 mmol, strem chemicals), and Pd₂(dba)₃ (4 mg, 0.02 mmol). The vial was sealed, evacuated and purged with dry nitrogen three times before adding dioxane (1.6 mL). The reaction mixture was heated to 100° C. for 16 hours in an oil bath. After cooling the reaction was diluted with EtOAc (10 mL) and washed with water (10 mL). After separation, the aqueous phase was extracted with EtOAc (3×10 mL). Combined organics were dried over Na₂SO₄, filtered and concentrated. The crude material was purified through silica gel column chromatography (EtOAc in Heptane 12 to 100%) to give a white solid (65 mg, 58.9% yield).

¹H NMR (400 MHz, CDCl₃) δ 8.55 (d, J=5.8 Hz, 1H), 7.95 (d, J=5.8 Hz, 1H), 7.48-7.43 (m, 2H), 7.38-7.32 (m, 2H), 7.13 (br s, 1H), 5.66 (q, J=7.1 Hz, 1H), 4.64 (dt, J=8.2, 3.2 Hz, 1H), 4.38-4.26 (m, 2H), 2.51-2.43 (m, 1H), 2.20 (tt, J=11.8, 3.5 Hz, 1H), 1.95 (d, J=13.2, 2H), 1.87-1.81 (m, 2H), 1.71-1.68 (m, 4H), 1.60-1.47 (m, 2H), 1.33-1.25 (m, 12H), 0.85 (d, J=6.9 Hz, 3H), 0.82 (d, J=6.9 Hz, 3H); MS m/z 552.1 (M+H).

Intermediate 133

(S)-methyl 2-((4-((S)-4-isopropyl-2-oxooxazolidin-3-yl)pyrimidin-2-yl)amino)propanoate

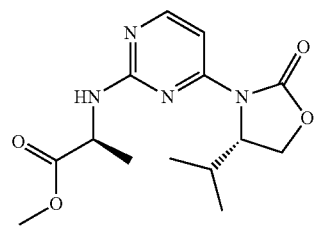 [SMILES: COC(=O)[C@H](C)Nc1nccc(N2C(=O)OC[C@@H]2C(C)C)n1]

To a solution of (S)-methyl 2-aminopropanoate (270 mg, 2.0 mmol, 1.2 equv. in 10 ml of DMSO) and (S)-3-(2-chloropyrimidin-4-yl)-4-isopropyloxazolidin-2-one (430 mg, 1.8 mmol, 1.0 equv.) was added DIPEA (805 mg, 6.23 mmol, 3.5 equiv), and the reaction mixture was heated at 110° C. for 120 min. The reaction mixture was poured into water (40 ml) and extracted with EtOAc (2×30 mL) and washed with water (30 mL). After separation, the aqueous phase was extracted with EtOAc (3×8 mL). Combined organics were dried over Na₂SO₄, filtered and concentrated. Silica gel column chromatography (ethyl acetate in heptane 10 to 80%) to provide (S)-methyl 2-((4-((S)-4-isopropyl-2-oxooxazolidin-3-yl)pyrimidin-2-yl)amino)propanoate (260 mg, white solid) in 47.4% yield. LCMS m/z 309.1 (M+H)⁺ RT=1.53 min.

Intermediate 134

(S)-2-((4-((S)-4-isopropyl-2-oxooxazolidin-3-yl)pyrimidin-2-yl)amino)propanehydrazide

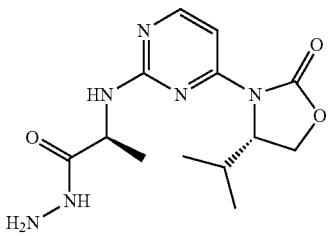 [SMILES: CC(C)[C@H]1COC(=O)N1c1ccnc(N[C@@H](C)C(=O)NN)n1]

To a solution of (S)-methyl 2-((4-((S)-4-isopropyl-2-oxooxazolidin-3-yl)pyrimidin-2-yl)amino)propanoate (120 mg, 0.39 mmol in 5 ml of MeOH) was added 99% hydrazine hydrate, the reaction solution was stirred at room temperature overnight (24 hours), the solvent was removed to yield the desired product (99 mg) in 78% yield, and was used for next step without purification. LCMS m/z 309.1 (M+H)⁺ RT=1.25 min.

Intermediate 135

(S)-tert-butyl (1-hydrazinyl-1-oxopropan-2-yl)carbamate

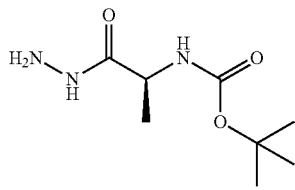

A solution of hydrazine (234 mg, 7.31 mmol, 1.5 equv. in 8 ml of THF) was added to (S)-methyl 2-(tert-butoxycarbonylamino)propanoate (1000 mg, 4.88 mmol, 1.0 equv.), it was stirred in a sealed tube and refluxed (72° C.) overnight (18 hours), the solvent was removed to yield the desired product (880 mg, white solid) in 84% yield.

Intermediate 136

(S)-tert-butyl (1-(2-benzoylhydrazinyl)-1-oxopropan-2-yl)carbamate

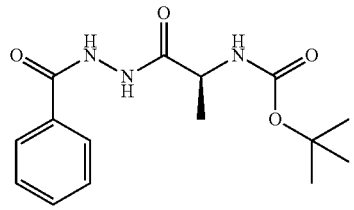 [SMILES: C[C@H](NC(=O)OC(C)(C)C)C(=O)NNC(=O)c1ccccc1]

To a solution of (S)-tert-butyl (1-hydrazinyl-1-oxopropan-2-yl)carbamate (293 mg, 1.44 mmol, 1.0 equv. in 3 ml of DCM) was added benzoyl fluoride (179 mg, 1.44 mmol in 2 ml of DCM), the reaction solution was stirred at room temperature for 50 min., the solvent was removed to yield the desired product. ¹H NMR (400 MHz, CDCl₃) δ 7.89-7.78 (m, 2H), 7.54 (t, J=7.4 Hz, 1H), 7.43 (t, J=7.6 Hz, 2H), 5.32 (b, 1H), 4.45 (b, 1H), 1.46 (s, 9H).

Intermediate 137

(S)-tert-butyl (1-(5-phenyl-1,3,4-thiadiazol-2-yl)ethyl)carbamate

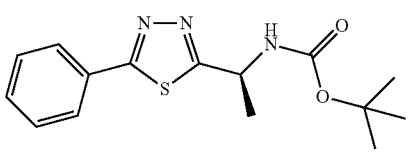 [SMILES: C[C@H](NC(=O)OC(C)(C)C)c1nnc(-c2ccccc2)s1]

To a solution of (S)-tert-butyl (1-(2-benzoylhydrazinyl)-1-oxopropan-2-yl)carbamate (155 mg, 0.5 mmol, 1.0 equv. in 5 ml of THF) was added Lawesson's reagent (36.4 mg, 0.5 mmol, 1.0 equv.) the reaction mixture was stirred at reflux for 3 hours, the reaction mixture was filtered and the solvent was removed to yield the crude product. Silica gel column chromatography (ethyl acetate in heptane 10 to 50%) to provide (S)-tert-butyl (1-(5-phenyl-1,3,4-thiadiazol-2-yl)ethyl)carbamate (114.6 mg, white solid) in 70.7% yield. ¹H NMR (400 MHz, CD₂Cl₂) δ 7.94-7.72 (m, 2H), 7.52-7.26 (m, 3H), 5.59 (b, 1H), 5.11 (b, 1H), 1.57 (d, J=7.0 Hz, 3H), 1.34 (s, 9H).

Intermediate 138

(S)-1-(5-phenyl-1,3,4-thiadiazol-2-yl)ethanamine

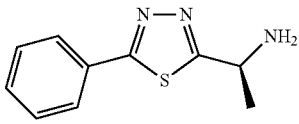

To a solution of (S)-tert-butyl (1-(5-phenyl-1,3,4-thiadiazol-2-yl)ethyl)carbamate (110 mg, 0.4 mmol, in 5 ml of DCM) was added 1 ml of TFA, the reaction mixture was stirred at room temperature for 3 hours, the solvent was removed to yield the desired product (52 mg) in 66.8% yield. LCMS m/z 206.0 (M+H)⁺ RT=0.97 min.

Intermediate 139

1-(5-(3-(trifluoromethyl)phenyl)pyrimidin-2-yl)ethanone

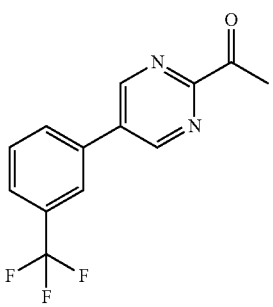 [SMILES: CC(=O)c1ncc(-c2cccc(C(F)(F)F)c2)cn1]

A cloudy solution of 1-(5-bromopyrimidin-2-yl)ethanone (300 mg, 1.49 mmol), 3-(trifluoromethyl)phenylboronic acid (567 mg, 2.98 mmol), K₃PO₄ (950 mg, 4.48 mmol), DavePhos ligand [2-dicyclohexylphosphino-2'-(N,N-dimethylamino)biphenyl] (59 mg, 0.15 mmol), and Pd(OAc)₂ (17 mg, 0.075 mmol) in 6 mL toluene was heated at 100° C. for 1 h. The mixture was cooled to room temperature, and filtered through Celite. Filter cake was rinsed with 30 mL EtOAc. The filtrate was poured into 20 mL water. Layers were separated, and the aqueous was further extracted with EtOAc (20 mL). Combined organics were washed with water (20 mL) and brine (20 mL), dried over Na₂SO₄, filtered and concentrated directly onto silica gel. Column chromatography (10-100% EtOAc/heptane) gave 0.26 g 1-(5-(3-(trifluoromethyl)phenyl)pyrimidin-2-yl)ethanone (V) as tan solid. MS m/z 267.1 (M+H)+. $^1$H NMR (400 MHz, CDCl₃) δ 9.16 (s, 2H), 7.93-7.69 (m, 4H), 2.87 (s, 3H).

The Following intermediates were prepared using a method similar to that described for the preparation of Intermediate 139. Using Anal. RP-HPLC Column=Inertsil C8 Column, 3.0 μm, 3.0×30 mm. Column Temperature=50° C. Eluents=A: Water (5 mM Ammonium formate, 2% ACN); B: ACN. Flow Rate=2 mL/min. Gradient=0 min 5% B; 5% to 95% B in 1.70 min; 0.3 min 95% B; 2.1 min 1% B.)

Intermediate 140

1-(5-(3,4-dichlorophenyl)pyrimidin-2-yl)ethanone

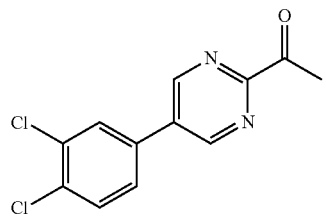 [SMILES: CC(=O)c1ncc(-c2ccc(Cl)c(Cl)c2)cn1]

Anal. RP-HPLC tR=1.17 min. MS m/z 266.9 (M+H)+.

Intermediate 141

1-(5-(3-fluoro-2-methylphenyl)pyrimidin-2-yl)ethanone

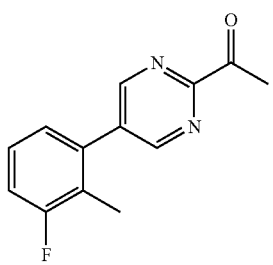 [SMILES: CC(=O)c1ncc(-c2cccc(F)c2C)cn1]

Anal. RP-HPLC tR=1.07 min. MS m/z 231.1 (M+H)+.

Intermediate 142

1-(5-(4-fluoro-2-methylphenyl)pyrimidin-2-yl)ethanone

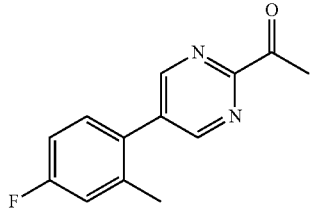 [SMILES: CC(=O)c1ncc(-c2ccc(F)cc2C)cn1]

Anal. RP-HPLC tR=1.18 min. MS m/z 231.1 (M+H)+.

Intermediate 143

1-(5-(5-fluoro-2-methylphenyl)pyrimidin-2-yl)ethanone

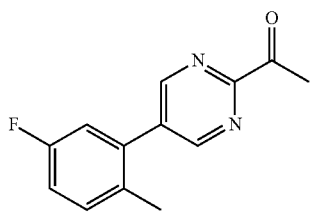 [SMILES: CC(=O)c1ncc(-c2cc(F)ccc2C)cn1]

Anal. RP-HPLC tR=1.16 min. MS m/z 231.2 (M+H)+.

Intermediate 144

1-(5-(4-fluoro-3-methylphenyl)pyrimidin-2-yl)ethanone

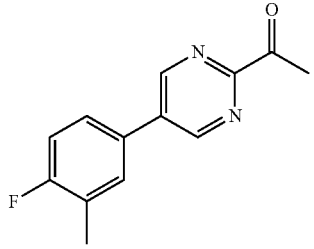 [SMILES: CC(=O)c1ncc(-c2ccc(F)c(C)c2)cn1]

$^1$H NMR (400 MHz, CDCl₃) δ 9.09 (s, 2H), 7.52-7.41 (m, 2H), 7.24-7.16 (m, 1H), 2.85 (s, 3H), 2.41 (d, J=2.0 Hz, 3H). Anal. RP-HPLC tR=1.20 min. MS m/z 231.0 (M+H)+.

Intermediate 145

1-(5-(2,3-dichlorophenyl)pyrimidin-2-yl)ethanone

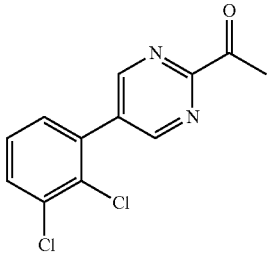 [SMILES: CC(=O)c1ncc(-c2cccc(Cl)c2Cl)cn1]

Anal. RP-HPLC tR=1.15 min. MS m/z 267.9 (M+H)+.

Intermediate 146

1-(5-(4-fluoro-3-methylphenyl)pyridin-2-yl)ethanone

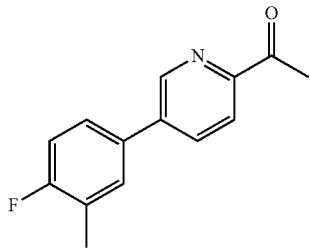 [SMILES: CC(=O)c1ccc(-c2ccc(F)c(C)c2)cn1]

$^1$H NMR (400 MHz, CDCl$_3$) δ 8.88 (dd, J=2.3, 0.8 Hz, 1H), 8.13 (dd, J=8.1, 0.8 Hz, 1H), 7.98 (dd, J=8.1, 2.3 Hz, 1H), 7.50-7.39 (m, 2H), 7.21-7.12 (m, 1H), 2.78 (s, 3H), 2.42-2.36 (m, 3H). Anal. RP-HPLC tR=1.40 min. MS m/z 230.8 (M+H)+.

Intermediate 147

1-(5-(3-(trifluoromethyl)phenyl)pyrimidin-2-yl)ethanamine

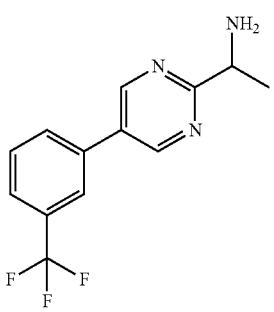 [SMILES: CC(N)c1ncc(-c2cccc(C(F)(F)F)c2)cn1]

1-(5-(3-(Trifluoromethyl)phenyl)pyrimidin-2-yl)ethanone (260 mg, 0.977 mmol), NH4OAc (1.13 g, 14.6 mmol), and NaBH3CN (245 mg, 3.91 mmol) were taken up in 8 mL 200 proof EtOH, and heated at 120° C. for 5 minutes in a microwave apparatus. The mixture was concentrated to remove the EtOH. Crude was taken up in 30 ml water+25 mL EtOAc. 6N NaOH was added until aqueous pH was ~10. Separated layers, and extracted aqueous with EtOAc (25 ml). The combined organic layer was washed with 25 mL brine and dried with Na$_2$SO$_4$. Filtered and concentrated with reduced pressure to give 262 mg crude yellow oil, which was carried forward without further purification. Anal. RP-HPLC tR=0.90 min. (Column=Inertsil C8 Column, 3.0 μm, 3.0×30 mm. Column Temperature=50° C. Eluents=A: Water (5 mM Ammonium formate, 2% ACN); B: ACN. Flow Rate=2 mL/min. Gradient=0 min 5% B; 5% to 95% B in 1.70 min; 0.3 min 95% B; 2.1 min 1% B.) MS m/z 268.1 (M+H)+.

The Following intermediates were prepared using a method similar to that described for the preparation of Intermediate 147.

Intermediate 148

1-(5-(3,4-dichlorophenyl)pyrimidin-2-yl)ethanamine

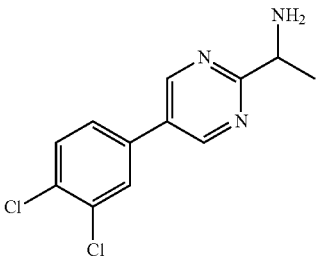 [SMILES: CC(N)c1ncc(-c2ccc(Cl)c(Cl)c2)cn1]

Anal. RP-HPLC tR=1.09 min (Gradient: 2 to 98% B in 1.7 min—flow 1 mL/min. Eluent A: Water+3.75 mM NH4Ac+2% ACN. Column: Acquity CSH 1.7 μm 2.1×50 mm—50° C.) MS m/z 268.4 (M+H)+.

Intermediate 149

1-(5-(3-fluoro-2-methylphenyl)pyrimidin-2-yl)ethanamine

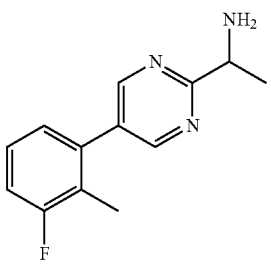 [SMILES: Cc1c(F)cccc1-c1cnc(C(C)N)nc1]

Anal. RP-HPLC tR=0.99 min. (Gradient: 2 to 98% B in 1.7 min—flow 1 mL/min. Eluent A: Water+3.75 mM NH4Ac+2% ACN. Column: Acquity CSH 1.7 μm 2.1×50 mm—50° C.) MS m/z 232.4 (M+H)+.

Intermediate 150

1-(5-(4-fluoro-2-methylphenyl)pyrimidin-2-yl)ethanamine

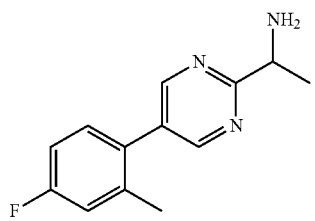 [SMILES: Cc1cc(F)ccc1-c1cnc(C(C)N)nc1]

Anal. RP-HPLC tR=0.87 min. (Column=Inertsil C8 Column, 3.0 μm, 3.0×30 mm. Column Temperature=50° C. Eluents=A: Water (5 mM Ammonium formate, 2% ACN); B:

ACN. Flow Rate=2 mL/min. Gradient=0 min 5% B; 5% to 95% B in 1.70 min; 0.3 min 95% B; 2.1 min 1% B.) MS m/z 231.0 (M)−.

Intermediate 151

1-(5-(5-fluoro-2-methylphenyl)pyrimidin-2-yl)ethanamine

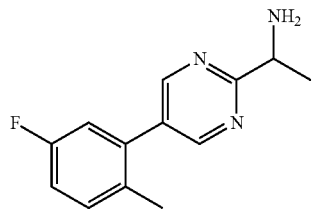 [SMILES: Cc1ccc(F)cc1-c1cnc(C(C)N)nc1]

Anal. RP-HPLC tR=0.79 min. (Column=Inertsil C8 Column, 3.0 μm, 3.0×30 mm. Column Temperature=50° C. Eluents=A: Water (5 mM Ammonium formate, 2% ACN); B: ACN. Flow Rate=2 mL/min. Gradient=0 min 5% B; 5% to 95% B in 1.70 min; 0.3 min 95% B; 2.1 min 1% B.) MS m/z 232.0 (M+H)+.

Intermediate 152

1-(5-(4-fluoro-3-methylphenyl)pyrimidin-2-yl)ethanamine

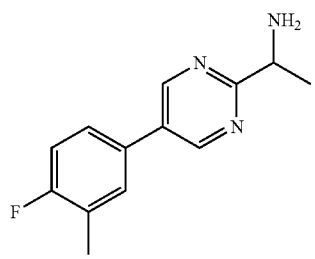 [SMILES: Cc1cc(-c2cnc(C(C)N)nc2)ccc1F]

Anal. RP-HPLC tR=0.81 min. (Column=Inertsil C8 Column, 3.0 μm, 3.0×30 mm. Column Temperature=50° C. Eluents=A: Water (5 mM Ammonium formate, 2% ACN); B: ACN. Flow Rate=2 mL/min. Gradient=0 min 5% B; 5% to 95% B in 1.70 min; 0.3 min 95% B; 2.1 min 1% B.) MS m/z 231.9 (M+H)+.

Intermediate 153

1-(5-(2,3-dichlorophenyl)pyrimidin-2-yl)ethanamine

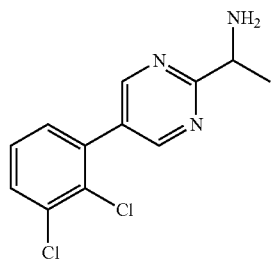 [SMILES: CC(N)c1ncc(-c2cccc(Cl)c2Cl)cn1]

Anal. RP-HPLC tR=1.01 min. (Column=Inertsil C8 Column, 3.0 μm, 3.0×30 mm. Column Temperature=50° C. Eluents=A: Water (5 mM Ammonium formate, 2% ACN); B: ACN. Flow Rate=2 mL/min. Gradient=0 min 5% B; 5% to 95% B in 1.70 min; 0.3 min 95% B; 2.1 min 1% B.) MS m/z 269.0 (M+H)+.

Intermediate 154

1-(5-(4-fluoro-3-methylphenyl)pyridin-2-yl)ethanamine

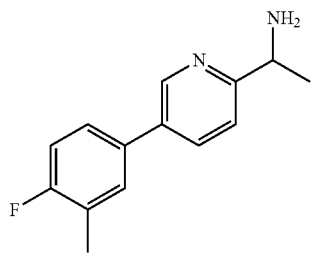 [SMILES: Cc1cc(-c2ccc(C(C)N)nc2)ccc1F]

Anal. RP-HPLC tR=0.92 min. (Column=Inertsil C8 Column, 3.0 μm, 3.0×30 mm. Column Temperature=50° C. Eluents=A: Water (5 mM Ammonium formate, 2% ACN); B: ACN. Flow Rate=2 mL/min. Gradient=0 min 5% B; 5% to 95% B in 1.70 min; 0.3 min 95% B; 2.1 min 1% B.) MS m/z 230.9 (M+H)+.

Intermediate 155

1-(5-(4-fluorophenoxy)pyrimidin-2-yl)ethanamine

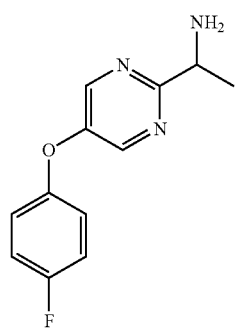 [SMILES: CC(N)c1ncc(Oc2ccc(F)cc2)cn1]

Step 1: A solution of 1-(5-fluoropyrimidin-2-yl)ethanone (700 mg, 5.0 mmol) and 4-fluorophenol (616 mg, 5.50 mmol) in 6 mL DMF was treated with potassium carbonate (829 mg 6.0 mmol) and heated to 50° C. for 3.5 h. The reaction mixture was poured into 20 mL water, and extracted with EtOAc (2×20 mL). Organics were washed with 20 mL each water, brine, and dried over $Na_2SO_4$. Mixture was filtered and concentrated on silica gel. Column chromatography (10-100% EtOAc/hept) gave 295 mg (25%) 1-(5-(4-fluorophenoxy)pyrimidin-2-yl)ethanone as a white solid used directly in the following step. MS m/z 233.2 (M+H)+. $^1$H NMR (400 MHz, $CDCl_3$) δ 8.55 (s, 2H), 7.23-7.07 (m, 4H), 2.78 (s, 3H).

Step 2: 1-(5-(4-fluorophenoxy)pyrimidin-2-yl)ethanone (290 mg, 1.25 mmol), NH4OAc (1.9 g, 24.6 mmol), and $NaBH_3CN$ (314 mg, 5.00 mmol) were taken up in 20 mL 200 proof EtOH, and heated at 130 C for 3 minutes in a microwave apparatus. The mixture was concentrated to remove the EtOH. Crude was taken up in 30 ml water+25 mL EtOAc. 6N NaOH was added until aqueous pH was ~10. Separated layers, and extracted aqueous with EtOAc (25 ml). The combined organic layer was washed with 25 mL brine and dried with Na$_2$SO$_4$. Filtered and concentrated with reduced pressure to give 275 mg crude tan oil, which was carried forward without further purification. Major product Anal. RP-HPLC tR=1.26 min. (Column=Inertsil C8 Column, 3.0 μm, 3.0×30 mm. Column Temperature=50° C. Eluents=A: Water (5 mM Ammonium formate, 2% ACN); B: ACN. Flow Rate=2 mL/min. Gradient=0 min 5% B; 5% to 95% B in 1.70 min; 0.3 min 95% B; 2.1 min 1% B.) MS m/z 234.1 (M+H)+.

The Following intermediates were prepared using methods similar to those described for the preparation of Intermediate 155.

Intermediate 156

1-(5-(2,4-difluorophenoxy)pyrimidin-2-yl)ethanamine

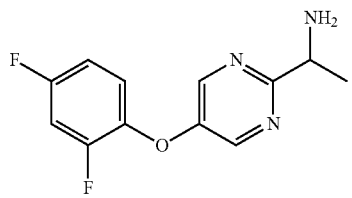 [SMILES: CC(N)c1ncc(Oc2ccc(F)cc2F)cn1]

Anal. RP-HPLC tR=0.81 min. (Column=Inertsil C8 Column, 3.0 μm, 3.0×30 mm. Column Temperature=50° C. Eluents=A: Water (5 mM Ammonium formate, 2% ACN); B: ACN. Flow Rate=2 mL/min. Gradient=0 min 5% B; 5% to 95% B in 1.70 min; 0.3 min 95% B; 2.1 min 1% B.) MS m/z 252.1 (M+H)+.

Intermediate 157

1-(5-(5-bromopyridin-3-yloxy)pyrimidin-2-yl)ethanamine

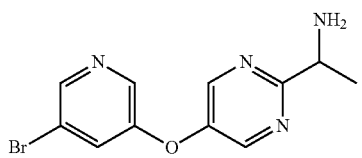 [SMILES: CC(N)c1ncc(Oc2cncc(Br)c2)cn1]

Anal. RP-HPLC tR=1.29 min. (Column=Inertsil C8 Column, 3.0 μm, 3.0×30 mm. Column Temperature=50° C. Eluents=A: Water (5 mM Ammonium formate, 2% ACN); B: ACN. Flow Rate=2 mL/min. Gradient=0 min 5% B; 5% to 95% B in 1.70 min; 0.3 min 95% B; 2.1 min 1% B.) MS m/z 297.3 (M+H)+.

Intermediate 158

1-(5-(3-chloro-4-fluorophenoxy)pyrimidin-2-yl)ethanamine

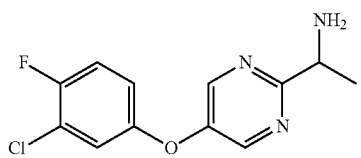 [SMILES: CC(N)c1ncc(Oc2ccc(F)c(Cl)c2)cn1]

Anal. RP-HPLC tR=1.40 min. (Column=Inertsil C8 Column, 3.0 μm, 3.0×30 mm. Column Temperature=50° C. Eluents=A: Water (5 mM Ammonium formate, 2% ACN); B: ACN. Flow Rate=2 mL/min. Gradient=0 min 5% B; 5% to 95% B in 1.70 min; 0.3 min 95% B; 2.1 min 1% B.) MS m/z 268.0 (M+H)+.

Intermediate 159

1-(5-(pyridin-3-yloxy)pyrimidin-2-yl)ethanamine

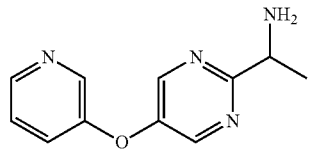 [SMILES: CC(N)c1ncc(Oc2cccnc2)cn1]

Anal. RP-HPLC tR=1.21 min. (Column=Inertsil C8 Column, 3.0 μm, 3.0×30 mm. Column Temperature=50° C. Eluents=A: Water (5 mM Ammonium formate, 2% ACN); B: ACN. Flow Rate=2 mL/min. Gradient=0 min 5% B; 5% to 95% B in 1.70 min; 0.3 min 95% B; 2.1 min 1% B.) MS m/z 218.4 (M+H)+.

Intermediate 160

1-(5-(5-(trifluoromethyl)pyridin-2-yloxy)pyrimidin-2-yl)ethanamine

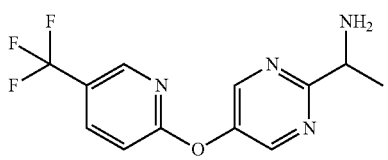 [SMILES: CC(N)c1ncc(Oc2ccc(C(F)(F)F)cn2)cn1]

Anal. RP-HPLC tR=1.16 min. (Column=Inertsil C8 Column, 3.0 μm, 3.0×30 mm. Column Temperature=50° C. Eluents=A: Water (5 mM Ammonium formate, 2% ACN); B: ACN. Flow Rate=2 mL/min. Gradient=0 min 5% B; 5% to 95% B in 1.70 min; 0.3 min 95% B; 2.1 min 1% B.) MS m/z 285.4 (M+H)+.

Intermediate 161

4-(4-fluorophenoxy)pyrimidine-2-carbonitrile

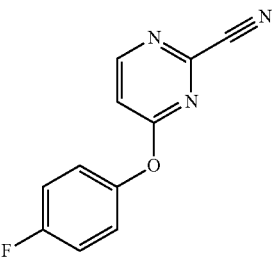 [SMILES: N#Cc1nccc(Oc2ccc(F)cc2)n1]

A solution of 4-chloropyrimidine-2-carbonitrile (0.63 g, 4.51 mmol) and 4-fluorophenol (0.51 g, 4.51 mmol) in 5 mL DMF was cooled to 0° C. under N2 atmosphere. NaH (0.217 g of 60% suspension, 5.42 mmol) was slowly added. Bubbling exotherm observed.

Internal temp was kept below 5° C. After 15 minutes, cold bath was removed. The reaction mixture was allowed to warm to room temp and stir 1 h. The reaction mixture was diluted with water (40 mL) and extracted with (3×25 mL) EtOAc. The organic layer was washed with 40 mL each water, and brine. Dried over Na$_2$SO$_4$, and concentrated on silica gel in vacuo. Column chromatography (EtOAc/heptane 10 to 100% gradient) gave 0.72 g (74%) of (4-fluorophenoxy)pyrimidine-2-carbonitrile as a crystalline white solid. Anal. RP-HPLC tR=1.38 min, Gradient: 2 to 98% B in 1.7 min—flow 1 mL/min. Eluent A: Water+3.75 mM NH4Ac+2% ACN. Column: Acquity CSH 1.7 μm 2.1×50 mm—50° C. MS m/z 216.1 (M+H)+.

Intermediate 162

1-(4-(4-fluorophenoxy)pyrimidin-2-yl)ethanone

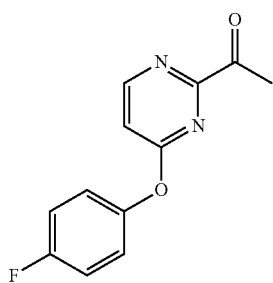 [SMILES: CC(=O)c1nccc(Oc2ccc(F)cc2)n1]

4-(4-fluorophenoxy)pyrimidine-2-carbonitrile (450 mg, 2.09 mmol) was suspended in 12 mL anhydrous ether under N2 atmosphere. Vessel was cooled to 0° C. MeMgBr (3.1 mL of 1.0 M solution in butyl ether, 3.10 mmol) was added over 5 min. The yellow-green suspension was stirred 30 minutes, then quenched with 50 mL sat'd NH4Cl solution. Adjusted pH to ~6 with conc. HCl. The mixture was extracted with (2×40 mL) EtOAc. Washed organics with 30 mL brine, and dried over Na$_2$SO$_4$. Filtered and concentrated on silica gel. Column chromatography (10-100% EtOAc in hept) gave 157 mg (32%) 1-(4-(4-fluorophenoxy)pyrimidin-2-yl)ethanone as a yellow oil. Anal. RP-HPLC tR=1.44 min. (Column=Inertsil C8 Column, 3.0 μm, 3.0×30 mm. Column Temperature=50° C. Eluents=A: Water (5 mM Ammonium formate, 2% ACN); B: ACN. Flow Rate=2 mL/min. Gradient=0 min 5% B; 5% to 95% B in 1.70 min; 0.3 min 95% B; 2.1 min 1% B.) MS m/z 233.2 (M+H)+.

Intermediate 163

1-(4-(4-fluorophenoxy)pyrimidin-2-yl)ethanol

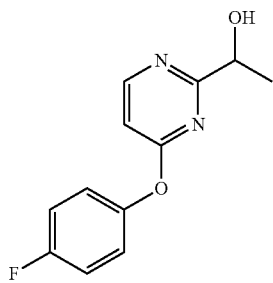 [SMILES: CC(O)c1nccc(Oc2ccc(F)cc2)n1]

1-(4-(4-fluorophenoxy)pyrimidin-2-yl)ethanone (0.150 g 0.646 mmol) was taken up in 2.5 mL 4:1 MeOH:DCM, and cooled to 0° C. NaBH$_4$ (49 mg 1.30 mmol) was added. Fizzing was observed. After 10 min, cold bath was removed, and the reaction was stirred 1 h. Solvent was removed in vacuo. White residue was taken up in 10 mL water, and extracted with (2×10 mL) EtOAc. Washed organics with 10 mL brine. Dried over Na$_2$SO$_4$. Filtered and concentrated to give 143 mg (95%) 1-(4-(4-fluorophenoxy)pyrimidin-2-yl)ethanol as a colorless oil. Anal. RP-HPLC tR=1.38 min. (Column=Inertsil C8 Column, 3.0 μm, 3.0×30 mm. Column Temperature=50° C. Eluents=A: Water (5 mM Ammonium formate, 2% ACN); B: ACN. Flow Rate=2 mL/min. Gradient=0 min 5% B; 5% to 95% B in 1.70 min; 0.3 min 95% B; 2.1 min 1% B.) MS m/z 235.1 (M+H)+.

Intermediate 164

2-(1-azidoethyl)-4-(4-fluorophenoxy)pyrimidine

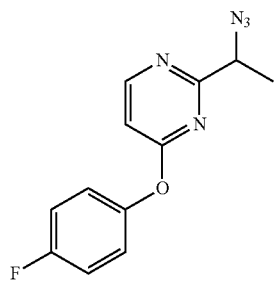

Under N$_2$ atmosphere, 1-(4-(4-fluorophenoxy)pyrimidin-2-yl)ethanol (140 mg, 0.598 mmol) was dissolved in 3 mL anhydrous DCM. Triethylamine (0.175 mL, 1.26 mmol) was added, and the mixture was cooled to 0° C. MsCl (0.070 mL, 0.897 mmol) was added, and the mixture was stirred 15 minutes. Maintaining 0° C., DCM solvent was removed under N$_2$ stream. Residue was taken up in 2 mL dry DMF. NaN$_3$ (78 mg, 1.19 mmol) added, and the reaction was stirred at rt for 24 h. Mixture was poured into 20 mL water, and extracted with 20 mL EtOAc. Organic layer was washed with 20 mL brine and dried over Na$_2$SO$_4$. Filtered and concentrated to give 120 mg (77%) 2-(1-azidoethyl)-4-(4-fluorophenoxy)pyrimidine as a yellow oil. $^1$H NMR (400 MHz, CDCl$_3$) δ 8.49 (d, J=5.7 Hz, 1H), 7.16-6.90 (m, 4H), 6.70 (d, J=5.7 Hz, 1H), 4.34 (q, J=6.9 Hz, 1H), 1.55-1.46 (m, 3H).

Intermediate 165

1-(4-(4-fluorophenoxy)pyrimidin-2-yl)ethanamine

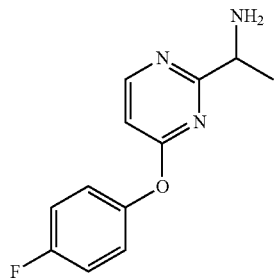 [SMILES: CC(N)c1nccc(Oc2ccc(F)cc2)n1]

2-(1-azidoethyl)-4-(4-fluorophenoxy)pyrimidine (120 mg, 0.463 mmol) was dissolved in 2 mL neat EtOH. 24.6 mg (0.023 mmol) of 10% Palladium on carbon catalyst was added. With vigorous stirring, the reaction vial was evacuated and purged 3 times with $H_2$. The reaction vessel was fitted with an $H_2$ balloon and stirred for 2 h. The mixture was filtered through Celite and concentrated in vacuo to give 75 mg (69%) 1-(4-(4-fluorophenoxy)pyrimidin-2-yl)ethanamine as a brown oil. $^1$H NMR (400 MHz, CDCl$_3$) δ 8.45 (d, J=5.7 Hz, 1H), 7.13-6.92 (m, 4H), 6.59 (d, J=5.7 Hz, 1H), 4.00 (q, J=6.8 Hz, 1H), 1.34-1.30 (m, 3H). Anal. RP-HPLC tR=1.18 min. (Column=Inertsil C8 Column, 3.0 μm, 3.0×30 mm. Column Temperature=50° C. Eluents=A: Water (5 mM Ammonium formate, 2% ACN); B: ACN. Flow Rate=2 mL/min. Gradient=0 min 5% B; 5% to 95% B in 1.70 min; 0.3 min 95% B; 2.1 min 1% B.) MS m/z 234.2 (M+H)+.

The Following intermediates were prepared using methods similar to those described for the preparation of Intermediates 161 to 165.

Intermediate 166

1-(5-(4-fluorophenoxy)pyridin-2-yl)ethanamine

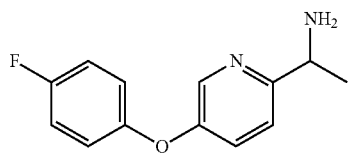

Anal. RP-HPLC tR=0.91 min. (Column=Inertsil C8 Column, 3.0 μm, 3.0×30 mm. Column Temperature=50° C. Eluents=A: Water (5 mM Ammonium formate, 2% ACN); B: ACN. Flow Rate=2 mL/min. Gradient=0 min 5% B; 5% to 95% B in 1.70 min; 0.3 min 95% B; 2.1 min 1% B.) MS m/z 233.1 (M+H)+.

Intermediate 167

1-(5-(4-fluorophenoxy)pyrazin-2-yl)ethanamine

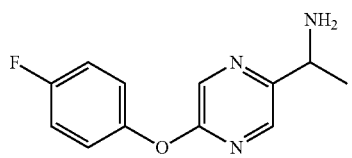 [SMILES: CC(N)c1cnc(Oc2ccc(F)cc2)cn1]

Anal. RP-HPLC tR=1.39 min. (Column=Inertsil C8 Column, 3.0 μm, 3.0×30 mm. Column Temperature=50° C. Eluents=A: Water (5 mM Ammonium formate, 2% ACN); B: ACN. Flow Rate=2 mL/min. Gradient=0 min 5% B; 5% to 95% B in 1.70 min; 0.3 min 95% B; 2.1 min 1% B.) MS m/z 217.1 (Major fragment+H)+.

Intermediate 168

1-(2-(4-fluorophenoxy)pyrimidin-5-yl)ethanamine

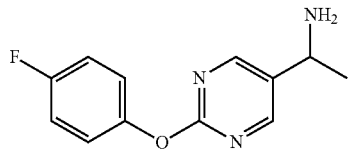 [SMILES: CC(N)c1cnc(Oc2ccc(F)cc2)nc1]

Anal. RP-HPLC tR=1.20 min. (Column=Inertsil C8 Column, 3.0 μm, 3.0×30 mm. Column Temperature=50° C. Eluents=A: Water (5 mM Ammonium formate, 2% ACN); B: ACN. Flow Rate=2 mL/min. Gradient=0 min 5% B; 5% to 95% B in 1.70 min; 0.3 min 95% B; 2.1 min 1% B.) MS m/z 233.9 (M+H)+.

Intermediate 169

(S)-4-Isopropyl-3-[2-((S)-1-methyl-prop-2-ynylamino)-pyrimidin-4-yl]-oxazolidin-2-one

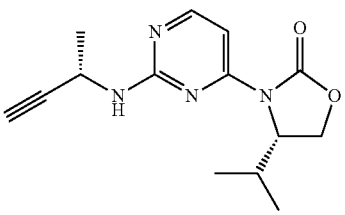 [SMILES: C#C[C@H](C)Nc1nccc(N2C(=O)OC[C@@H]2C(C)C)n1]

To a solution of compound (S)-3-(2-Chloro-pyrimidin-4-yl)-4-isopropyl-oxazolidin-2-one (1.03 g, 4.3 mmol) in DMSO (12 mL) was added methyl-prop-2-ynylamine HCl salt (450 mg, 4.3 mmol) and diisopropylethylamine (2.2 mL, 12.6 mmol). The reaction was heated to 110 C for 18 hours. The reaction mixture was diluted with EtOAc (50 mL) and washed with water (25 mL) and brine (25 mL). The organic layer was dried over Na$_2$SO$_4$, filtered and concentrated. The crude material was purified on silica gel column chromatography (EtOAc/Heptane 0 to 75%) provided (S)-4-Isopropyl-3-[2-((S)-1-methyl-prop-2-ynylamino)-pyrimidin-4-yl]-oxazolidin-2-one (360 mg) in 31% yield. LC-MS m/z: 275.1 (M−Boc)+; RT.: 1.33 min.

Intermediate 170

(S)-4,6-difluoro-N-(1-phenylethyl)pyrimidin-2-amine

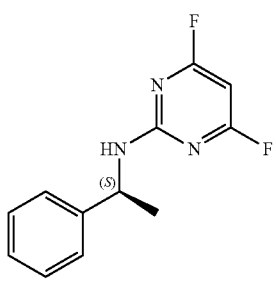

A solution of 2,4,6-trifluoropyrimidine (128.4 mg, 0.96 mmol) and isopropylethylamine (0.50 mL, 2.9 mmol, 3 equiv) in dioxane (5 mL) was cooled to 0° C. with an ice bath. After 30 min, the ice bath was removed, and the reaction was allowed to warm to room temperature. After stirring overnight, the reaction was concentrated to a light brown oil and purified by silica gel column chromatography (EtOAc/Heptane 0 to 100%) to provide (S)-4,6-difluoro-N-(1-phenylethyl)pyrimidin-2-amine (151.2 mg, white solid) in 45% yield. $^1$H NMR (400 MHz, CD$_3$OD) δ 7.35-7.40 (m, 2H), 7.29-7.34 (m, 2H), 7.20-7.26 (m, 1H), 5.84 (s, 1H), 5.08 (q, J=6.91 Hz, 1H), 1.52 (d, J=7.04 Hz, 3H); LCMS m/z 236.1 (M+H)$^+$, R$_t$ 0.95 min.

Intermediate 171

(S)-4,6-difluoro-N-(1-(2-fluoro-4-(trifluoromethyl)phenyl)ethyl) pyrimidin-2-amine

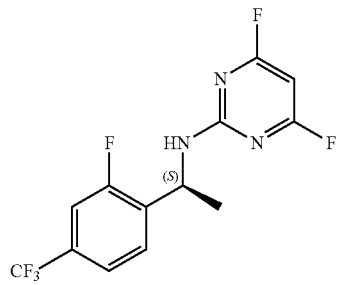

Intermediate 171 was prepared by a method similar to the one described for the preparation of Intermediate 170. ¹H NMR (400 MHz, CD$_3$OD) 7.58 (t, J=7.63 Hz, 1H), 7.34-7.48 (m, 2H), 5.84 (br. s., 1H), 5.35 (q, J=6.91 Hz, 1H), 1.54 (d, J=7.04 Hz, 3H). MS m/z 321.9 (M+H)+, Rt 1.11 min.

Intermediate 172 tert-butyl 3-hydroxy-2-methylbutan-2-ylcarbamate

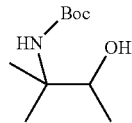

Step 1: Preparation of tert-butyl 1-(methoxy(methyl)amino)-2-methyl-1-oxopropan-2-ylcarbamate 2-(tert-butoxycarbonylamino)-2-methylpropanoic acid (6.62 g, 32.6 mmol), O,N-dimethylhydroxylamine hydrochloride (3.50 g, 35.8 mmol), and HATU (14.86 g, 39.1 mmol) were combined in DMF (100 mL). To this solution was added Hunig's Base (17.07 mL, 98 mmol). The reaction was stirred for overnight (17 hours). The reaction was then concentrated under vacuum and the residue was diluted with EtOAc (300 mL) and washed with water (2×80 mL). The organic layer was washed with brine, dried (Na$_2$SO$_4$), and concentrated under reduced pressure. The residue was purified via silica gel flash chromatography (10-50 percent EtOAc-Hexanes) to afford the desired product as a white solid (6.36 g). LCMS m/z 247.2 (M+H)$^+$, Rt 0.61 min.

Step 2: Preparation of tert-butyl 2-methyl-3-oxobutan-2-ylcarbamate

To a solution of tert-butyl 1-(methoxy(methyl)amino)-2-methyl-1-oxopropan-2-ylcarbamate (4.26 g, 17.30 mmol) in THF (100 mL) at −70° C. was added drop wise methyl lithium (32.4 mL, 51.9 mmol). Cold bath was replaced with −40° C. bath and the reaction was stirred for 4 hours. Saturated NH$_4$Cl solution (10 mL) was then added cautiously to quench the reaction. The reaction mixture was then allowed to warm to room temperature, and diluted with EtOAc (100 mL) and water (50 mL). The phases were separated and the aqueous layer was extracted with EtOAc (2×100 mL). The combined organics were then dried (Na$_2$SO$_4$) and concentrated under reduced pressure. The residue was purified via silica gel flash chromatography (10-50% EtOAc-Hexanes) to afford the desired product as a white solid (2.36 g). LCMS m/z 224.2 (M+Na)$^+$, Rt 0.7 min.

Step 3: Preparation of tert-butyl 3-hydroxy-2-methylbutan-2-ylcarbamate

To a solution of tert-butyl 2-methyl-3-oxobutan-2-ylcarbamate (2.36 g, 11.73 mmol) in MeOH (30 mL) at 0° C. was added portion wise NaBH$_4$ (0.887 g, 23.45 mmol). Cold bath was removed and the reaction was stirred for 1 hour. HCl solution (1 M, 0.2 mL) was then added cautiously to quench the reaction. The reaction mixture was then concentrated and diluted with EtOAc (50 mL) and water (10 mL). The phases were separated and the aqueous layer was extracted with EtOAc (2×20 mL). The combined organics were then dried (Na$_2$SO$_4$) and concentrated under reduced pressure. The residue was purified via silica gel flash chromatography (10-50% EtOAc-Hexanes) to afford the desired product as a white solid (2.12 g). LCMS m/z 204.1 (M+H)$^+$, Rt 0.69 min.

Intermediate 173 tert-butyl ((3S)-2-hydroxy-4-methylpentan-3-yl) carbamate

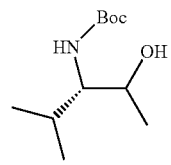

Step 1: Preparation of tert-butyl 1-(methoxy(methyl)amino)-2-methyl-1-oxopropan-2-ylcarbamate To a solution of (S)-2-(tert-butoxycarbonylamino)-3-methylbutanoic acid (5.86 g, 27.0 mmol) in DCM (100 mL) at 0° C. was added portion wise di(1H-imidazol-1-yl)methanone (4.81 g, 29.7 mmol). Cold bath was removed and the reaction was stirred at 20° C. for 30 minutes. O,N-dimethylhydroxylamine hydrochloride (3.16 g, 32.4 mmol) was then added and followed by slow addition of triethylamine (3.28 g, 32.4 mmol). The reaction mixture was stirred at 20° C. for overnight (18 hr), and diluted with DCM (200 mL) and washed with HCl (1 M, 2×50 mL) and saturated NaHCO$_3$ solution (2×50 mL), H2O (50 mL) and brine (50 mL). The organic was then dried (Na$_2$SO$_4$) and concentrated under reduced pressure to give crude product (6.61 g). LCMS m/z 261.2 (M+H)$^+$, Rt 0.77 min.

Step 2: Preparation of (S)-tert-butyl 2-methyl-4-oxopentan-3-ylcarbamate

To a solution of (S)-tert-butyl 1-(methoxy(methyl)amino)-3-methyl-1-oxobutan-2-ylcarbamate (4.23 g, 16.25 mmol) in THF (100 mL) at −70° C. was added drop wise methyl lithium (1.071 g, 48.7 mmol). Cold bath was replaced with −40° C. bath (MeCN in dry ice) removed and the reaction was stirred for 4 hours. Saturated NH$_4$Cl solution (10 mL) was then added cautiously to quench the reaction. The reaction mixture was then allowed to warm to room temperature, and diluted with EtOAc (100 mL) and water (50 mL). The phases were separated and the aqueous layer was extracted with EtOAc (2×100 mL). The combined organics were then dried (Na$_2$SO$_4$) and concentrated under reduced pressure. The residue was purified via silica gel flash chromatography (10-50% EtOAc-Hexanes) to afford the desired product as a white solid (3.01 g). LCMS m/z 238.2 (M+Na)$^+$, Rt 0.78 min.

Step 3: Preparation of tert-butyl 3-hydroxy-2-methylbutan-2-ylcarbamate

To a solution of (S)-tert-butyl 2-methyl-4-oxopentan-3-ylcarbamate (2.65 g, 12.31 mmol) in MeOH (30 mL) at 0° C. was added portion wise NaBH$_4$ (0.931 g, 24.62 mmol). Cold bath was removed and the reaction was stirred for 1 hour. HCl solution (1 M, 0.3 mL) was then added cautiously to quench the reaction. The reaction mixture was then concentrated and diluted with EtOAc (50 mL) and water (10 mL). The phases were separated and the aqueous layer was extracted with EtOAc (2×20 mL). The combined organics were then dried (Na$_2$SO$_4$) and concentrated. The residue was purified via silica gel flash chromatography (10-50% EtOAc-Hexanes) to afford the desired product as a white solid (2.05 g). LCMS m/z 240.2 (M+Na)$^+$, Rt 0.69 min.

Intermediate 174

(S)-tert-butyl (1-cyclopropyl-2-hydroxyethyl)carbamate

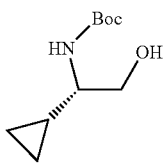 [SMILES: CC(C)(C)OC(=O)N[C@H](CO)C1CC1]

Step 1: Preparation of tert-butyl 1-(methoxy(methyl)amino)-2-methyl-1-oxopropan-2-ylcarbamate To (S)-2-(tert-butoxycarbonylamino)-2-cyclopropylacetic acid (5.01 g, 23.28 mmol) in MeOH (50 mL) was added drop wise trimethylsilyldiazomethane (18.62 ml, 37.2 mmol) until no bubbles. The reaction was stirred for 30 minutes and quenched with drops of HOAc (0.1 mL). The reaction mixture was then concentrated under reduced pressure to give crude product as a light tan oil (5.35 g). LCMS m/z 252.1 (M+Na)$^+$, Rt 0.77 min.

Step 2: Preparation of (S)-tert-butyl (1-cyclopropyl-2-hydroxyethyl)carbamate

To a solution of (S)-methyl 2-(tert-butoxycarbonylamino)-2-cyclopropylacetate (5.35 g, 23.33 mmol) in Et$_2$O (100 ml) was added LiBH$_4$ (0.762 g, 35.0 mmol), followed by drop wise addition of methanol (1.420 ml, 35.0 mmol). The reaction was refluxed at 40° C. for one hour. The reaction mixture was then cooled to 0° C., and quenched with HCl (1M) until pH=2 for aqueous layer. The phases were separated and the aqueous layer was extracted with DCM (3×100 mL). The organic was then dried (Na$_2$SO$_4$) and concentrated under reduced pressure to give final crude product (4.16 g). LCMS m/z 224.1 (M+Na)$^+$, Rt 0.62 min.

Intermediate 175

(R)—N—((S)-1-(2-fluoro-4-(1-methylcyclopropyl)phenyl)ethyl)-2-methylpropane-2-sulfinamide

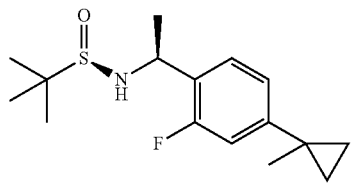 [SMILES: C[C@H](N[S@](=O)C(C)(C)C)c1ccc(C2(C)CC2)cc1F]

Step 1

To an oven dried round bottom flask with stir bar was added 4-bromo-2-fluorobenzaldehyde (5 g, 24.6 mmol), (R)-2-methylpropane-2-sulfinamide (3.28 g, 27.1 mmol) and DCE (49 mL). To this mixture was then added copper (II) sulfate (5.90 g, 36.9 mmol). Reaction mixture was heated in a preheated oil bath to 55° C. for 18 hours. Reaction mixture was filtered through a pad celite, washing the solids with CH$_2$Cl$_2$. The filtrate was concentrated to afford a viscous yellow oil of (R,E)-N-(4-bromo-2-fluorobenzylidene)-2-methylpropane-2-sulfinamide (7.73 g, 25.2 mmol, 103% yield). $^1$H NMR (400 MHz, CDCL$_3$) δ 1.27 (s, 9H) 7.31-7.42 (m, 2H) 7.87 (t, J=7.87 Hz, 1H) 8.83 (s, 1H). LCMS m/z 307.9 (M+H)$^+$, Rt 1.01 min.

Step 2

To a solution of (R,E)-N-(4-bromo-2-fluorobenzylidene)-2-methylpropane-2-sulfinamide (7.73 g, 25.2 mmol) in CH$_2$Cl$_2$ (252 mL), cooled to 0° C. (water/ice bath) under nitrogen, was added 3M methyl magnesium bromide (33.7 mL, 101 mmol) in Et$_2$O. Reaction mixture allowed to stir for 30 min at 0° C., then gradually allowed to warm to room temperature and stirred for 1 hour at room temperature. Reaction mixture was cooled to 0° C. then quenched with the slow addition of a saturated solution of NH$_4$Cl. Aqueous mixture extracted with EtOAc. Organic phases combined, washed with water, brine, dried (Na$_2$SO$_4$), filtered and concentrated onto silica gel. Silica gel column chromatography (EtOAc/Heptane 40 to 100%) provided (R)—N—((S)-1-(4-bromo-2-fluorophenyl)ethyl)-2-methylpropane-2-sulfinamide (4.93 g, 15.3 mmol, 60% yield) as a white crystalline solid. $^1$H NMR (400 MHz, CDCL$_3$) δ 1.20 (s, 9H) 1.56 (d, J=6.70 Hz, 3H) 3.34 (br. s., 1H) 4.77-4.87 (m, 1H) 7.19-7.31 (m, 3H). LCMS m/z 324.0 (M+H)$^+$, Rt 0.90 min.

Step 3

To a microwave vial with stir bar was added (R)—N—((S)-1-(4-bromo-2-fluorophenyl)ethyl)-2-methylpropane-2- (1 g, 3.10 mmol), isopropenyl boronic acid pinacol ester (1.51 ml, 8.07 mmol), DME (8 ml), sodium carbonate (7.76 ml, 15.5 mmol) (2.0 M aq) and PdCl$_2$(dppf).CH$_2$Cl$_2$ adduct (0.127 g, 0.155 mmol). Vessel was capped and heated by microwave irradiation for 20 min at 100° C. Reaction mixture was diluted with a saturated solution of NH$_4$Cl. The aqueous mixture was extracted with EtOAc. Organic phases combined, washed with water, brine, dried (Na$_2$SO$_4$), filtered and concentrated onto silica gel. Silica gel column chromatography (EtOAc/

Heptane 50 to 100%) provided (R)—N—((S)-1-(2-fluoro-4-(prop-1-en-2-yl)phenyl)ethyl)-2-methylpropane-2-sulfinamide (830 mg, 2.93 mmol, 94% yield) as a pale brown crystalline. $^1$H NMR (400 MHz, DMSO) δ 1.08-1.11 (m, 9H) 1.47 (d, J=6.80 Hz, 3H) 2.09 (d, J=0.54 Hz, 3H) 4.61-4.71 (m, 1H) 5.14 (t, J=1.32 Hz, 1H) 5.43 (d, J=5.58 Hz, 1H) 5.49 (s, 1H) 7.24-7.30 (m, 1H) 7.31-7.36 (m, 1H) 7.41-7.47 (m, 1H). LCMS m/z 284.0 (M+H)$^+$, Rt 0.93 min.

Step 4

To a round bottom flask containing (R)—N—((S)-1-(2-fluoro-4-(prop-1-en-2-yl)phenyl)ethyl)-2-methylpropane-2-(0.37 g, 1.31 mmol) in DCE (13 mL) at 0° C. was added under argon diethylzinc (1.0M in hexanes) (13.1 mL, 13.1 mmol) followed by the dropwise addition of chloroiodomethane (0.95 mL, 13.1 mmol). Reaction mixture allowed to warm to room temperature and stirred for 1 hour. Reaction mixture was cooled to 0° C. whereupon a second addition of diethylzinc (1.0M in hexanes) (13.1 mL, 13.1 mmol) took place followed by the addition of chloroiodomethane (0.95 mL, 13.1 mmol). Reaction mixture allowed to warm to room temperature and stirred 18 hours under argon. Reaction mixture was cooled to 0° C. in a ice bath and to the cold reaction mixture was slowly added a saturated solution of NH$_4$Cl. The aqueous mixture was extracted with EtOAc. Organic phases combined, washed with water, brine, dried (Na$_2$SO$_4$), filtered and concentrated onto silica gel. Silica gel column chromatography (EtOAc/Heptane 20 to 100%) provided a white crystalline of (R)—N—((S)-1-(2-fluoro-4-(1-methylcyclopropyl)phenyl)ethyl)-2-methylpropane-2-sulfinamide (89 mg, 0.299 mmol, 22.92% yield). $^1$H NMR (400 MHz, CDCL$_3$) δ 0.75-0.79 (m, 2H) 0.85-0.90 (m, 2H) 1.20 (s, 9H) 1.55 (s, 3H) 1.57 (d, J=6.80 Hz, 1H) 3.34 (d, J=5.23 Hz, 1H) 4.75-4.85 (m, 1H) 6.90 (dd, J=12.30, 1.74 Hz, 1H) 6.97 (dd, J=8.05, 1.78 Hz, 1H) 7.22 (t, J=7.97 Hz, 1H). LCMS m/z 298.1 (M+H)$^+$, Rt 1.01 min.

The Intermediates in Table 4k were prepared by a method similar to the one described for the preparation of Intermediate 175.

TABLE 4k

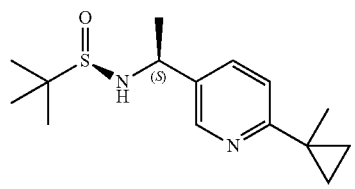

Intermediate 176

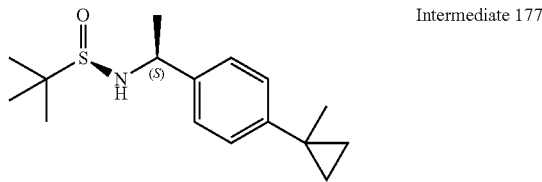

Intermediate 177

TABLE 4m

Chemical name, NMR chemical shifts and LCMS signal for each intermediate listed in Table 4k.

| Intermediate: Name | $^1$H NMR (400 MHz) δ ppm | LCMS |
|---|---|---|
| 176: (R)-2-methyl-N-((S)-1-(6-(1-methylcyclopropyl)pyridin-3-yl)ethyl) propane-2-sulfinamide | | MS m/z 282.1 (M + H)$^+$, Rt 0.48 min. |
| 177: (R)-2-methyl-N-((S)-1-(4-(1-methylcyclopropyl)phenyl)ethyl) propane-2-sulfinamide | (CDCl$_3$) 0.71-0.76 (m, 2 H) 0.85-0.89 (m, 2 H) 1.20-1.22 (m, 9 H) 1.41 (s, 3 H) 1.53 (d, J = 6.65 Hz, 3 H) 3.29 (d, J = 3.57 Hz, 1 H) 4.50-4.57 (m, 1 H) 7.21 (s, 2 H) 7.23 (s, 2 H) | MS m/z 280.1 (M + H)$^+$, Rt 0.98 min. |

Intermediate 178

(R)—N—((S)-1-(4-(1-ethoxycyclopropyl)-2-fluorophenyl)ethyl)-2-methylpropane-2-sulfinamide

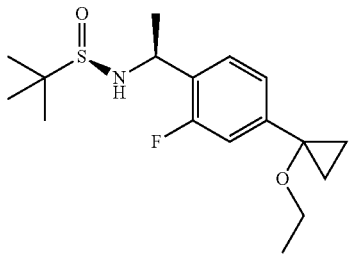 [SMILES: CCOC1(c2ccc([C@H](C)N[S@](=O)C(C)(C)C)c(F)c2)CC1]

Step 1

To a microwave vial with stir bar was added (R)—N—((S)-1-(4-bromo-2-fluorophenyl)ethyl)-2-methylpropane-2-sulfinamide (500 mg, 1.55 mmol) followed by the addition of tributyl(1-ethoxyvinyl)stannane (1.12 g, 3.10 mmol), triethylamine (0.65 ml, 4.65 mmol) and PdCl$_2$(dppf). CH$_2$Cl$_2$ adduct (63 mg, 0.078 mmol). To the solids was added toluene (10 ml). Vial capped and heated in a preheated sand bath at 100° C. for 1 hour. Reaction mixture was loaded onto silica gel column. Silica gel column chromatography (MeOH/CH$_2$Cl$_2$ 0 to 10% with 1% NH$_4$OH buffer) provided (R)—N—((S)-1-(4-(1-ethoxyvinyl)-2-fluorophenyl)ethyl)-2-methylpropane-2-sulfinamide (498 mg, 1.59 mmol, 102% yield) as a brown viscous oil which crystallizes upon standing. $^1$H NMR (400 MHz, CDCL$_3$) δ 1.20 (s, 9H) 1.43 (t, J=6.97 Hz, 3H) 1.58 (d, J=6.75 Hz, 3H) 3.35 (d, J=4.74 Hz, 1H) 3.92 (q, J=6.96 Hz, 2H) 4.23 (d, J=2.79 Hz, 1H) 4.65 (d, J=2.79 Hz, 1H) 4.79-4.89 (m, 1H) 7.16-7.20 (m, 1H) 7.29-7.34 (m, 1H) 7.39 (dd, J=8.07, 1.66 Hz, 1H).

Step 2

To a round bottom flask containing (R)—N—((S)-1-(4-(1-ethoxyvinyl)-2-fluorophenyl)ethyl)-2-methylpropane-2-sulfinamide (0.49 g, 1.56 mmol) and chloroiodomethane (1.14 mL, 15.6 mmol) in toluene (15 mL) at 0° C. under argon was added diethylzinc (1.0M in hexanes) (15.6 mL, 15.6 mmol). Reaction mixture allowed to warm to room temperature and stirred for 1 hour. Reaction mixture was cooled to 0° C. in an ice bath and to the cold reaction mixture was slowly added a saturated solution of NH$_4$Cl. The aqueous mixture was extracted with EtOAc. Organic phases combined, washed with water, brine, dried (Na$_2$SO$_4$), filtered and concentrated onto silica gel. Silica gel column chromatography (MeOH/CH$_2$Cl$_2$ 0 to 10%) provided (R)—N—((S)-1-(4-(1-ethoxycyclopropyl)-2-fluorophenyl)ethyl)-2-methylpropane-2-sulfinamide (145 mg, 0.44 mmol, 28% yield) as a viscous brown oil. $^1$H NMR (300 MHz, CDCL$_3$) δ 0.93-0.99 (m, 2H) 1.14-1.20 (m, 3H) 1.21 (s, 9H) 1.22-1.27 (m, 2H) 1.57-1.61 (m, 4H) 3.35 (d, J=4.98 Hz, 1H) 3.45 (q, J=7.07 Hz, 2H) 4.77-4.87 (m, 1H) 6.98 (dd, J=7.58, 1.43 Hz, 3H) 7.00-7.03 (m, 4H) 7.28-7.32 (m, 1H). LCMS m/z 328.1 (M+H)$^+$, Rt 0.95 min.

The Intermediate in Table 4n were prepared by a method similar to the one described for the preparation of Intermediate 178.

TABLE 4n

| | |
|---|---|
| 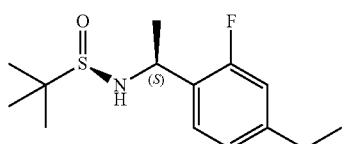 | Intermediate 179 |
| 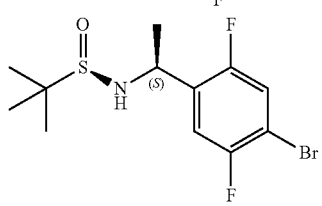 | Intermediate 180 |
| 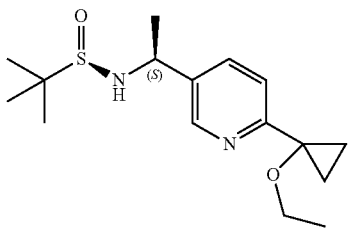 | Intermediate 181 |

TABLE 4p

Chemical name, NMR chemical shifts and LCMS signal for each intermediate listed in Table 4n.

| Intermediate: Name | $^1$H NMR (400 MHz) δ ppm | LCMS |
|---|---|---|
| 179: (R)-N-((S)-1-(2,5-difluoro-4-isopropylphenyl)ethyl)-2-methylpropane-2-sulfinamid | | MS m/z 304.2 (M + H)$^+$, Rt 1.04 min. |
| 180: (R)-N-((S)-1-(4-bromo-2,5-difluorophenyl)ethyl)-2-methylpropane-2-sulfinamide | | MS m/z 340.1, 342.1 (M + H)$^+$, Rt 0.96 min. |
| 181: (R)-N-((S)-1-(6-(1-ethoxycyclopropyl)pyridin-3-yl)ethyl)-2-methylpropane-2-sulfinamide | | MS m/z 311.1 (M + H)$^+$, Rt 0.52 min. |

Intermediate 182

(R)—N—((S)-1-(4-(1-cyanocyclopropyl)-2-fluorophenyl)ethyl)-2-methylpropane-2-sulfinamide

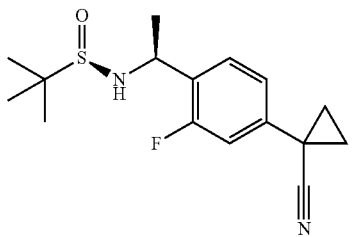 [SMILES: C[C@H](N[S@](=O)C(C)(C)C)c1ccc(C2(C#N)CC2)cc1F]

Step 1

To a microwave vial with a stir bar was added (R)—N—((S)-1-(4-bromo-2-fluorophenyl)ethyl)-2-methylpropane-2-sulfinamide (300 mg, 0.93 mmol), 4-isoxazoleboronic acid pinacol ester (218 mg, 1.12 mmol), PdCl$_2$(dppf).CH$_2$Cl$_2$ adduct (76 mg, 0.09 mmol), potassium fluoride (2.7 mL, 1.0 M in water, 2.79 mmol) and finally DMSO (9 mL). The reaction mixture was degassed with bubbling nitrogen (3 min) and the vial capped and heated in a preheated oil bath at 130° C. for 18 hours. The reaction mixture was diluted with a saturated solution of NH$_4$Cl and extracted with EtOAc. Organic phases combined, washed with water, brine, dried (Na$_2$SO$_4$), filtered and concentrated onto silica gel. Silica gel column chromatography (EtOAc/Heptanes 40 to 100%) provided (R)—N—((S)-1-(4-(cyanomethyl)-2-fluorophenyl)

ethyl)-2-methylpropane-2-sulfinamide (136 mg, 0.48 mmol, 52% yield) as a viscous brown oil. $^1$H NMR (400 MHz, CDCL$_3$) δ 1.19 (s, 9H) 1.57 (d, J=6.80 Hz, 3H) 3.39 (d, J=4.35 Hz, 1H) 3.74 (s, 2H) 4.81-4.88 (m, 1H) 7.04 (d, J=10.66 Hz, 1H) 7.11 (d, J=7.97 Hz, 1H) 7.38 (t, J=7.73 Hz, 1H). LCMS m/z 283.0 (M+H)$^+$, Rt 0.72 min.

Step 2

To a scintillation vial containing (R)—N—((S)-1-(4-(cyanomethyl)-2-fluorophenyl)ethyl)-2-methylpropane-2- (86 mg, 0.31 mmol) and a stir bar was added toluene (2 mL). To this mixture was then added tetrabutylammonium bromide (19 mg, 0.06 mmol) followed by the addition of NaOH (1.52 ml, 1.0 M (aq), 1.52 mmol) and 1,2-dibromoethane (0.11 ml, 1.22 mmol). Vial capped and reaction mixture was stirred vigorously at room temperature for 18 hours. Whereupon, 1,2-dibromoethane (0.11 ml, 1.22 mmol) and tetrabutylammonium bromide (19 mg, 0.06 mmol) were added and reaction mixture allowed to stir an additional 18 hours. A third addition of 1,2-dibromoethane (0.11 ml, 1.22 mmol) was added and the reaction mixture heated to 50° C. for an additional 18 hours in a preheated aluminum tray. The reaction mixture was quenched with a saturated solution of NH$_4$Cl and the aqueous mixture extracted with EtOAc. Organics combined and washed twice with water, brine, dried (Na$_2$SO$_4$), filtered and concentrated. Crude material was passed through a small plug of silica gel using 10% MeOH:90% DCM to elute product. The solution was concentrated to afford a viscous orange oil of (R)—N—((S)-1-(4-(1-cyanocyclopropyl)-2-fluorophenyl)ethyl)-2-methylpropane-2-sulfinamide (23 mg, 0.08 mmol, 24% yield). $^1$H NMR (400 MHz, CDCL$_3$) δ 1.20 (s, 9H) 1.38-1.44 (m, 2H) 1.56 (d, J=6.75 Hz, 3H) 1.73-1.79 (m, 2H) 3.37 (d, J=4.45 Hz, 1H) 4.78-4.88 (m, 1H) 6.94 (dd, J=11.35, 1.91 Hz, 1H) 7.09 (dd, J=8.07, 1.91 Hz, 1H) 7.34 (t, J=7.90 Hz, 1H). LCMS m/z 309.2 (M+H)$^+$, Rt 0.83 min.

Intermediate 183

(R)—N—((S)-1-(2-fluoro-4-isopropylphenyl)ethyl)-2-methylpropane-2-sulfinamide

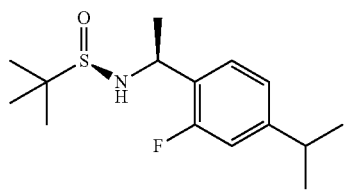 [SMILES: CC(C)c1ccc([C@H](C)N[S@](=O)C(C)(C)C)c(F)c1]

To a round bottom flask containing (R)—N—((S)-1-(2-fluoro-4-(prop-1-en-2-yl)phenyl)ethyl)-2-methylpropane-2-sulfinamide (204 mg, 0.72 mmol) and a stir bar was added MeOH (7.2 mL). To this solution was added palladium on carbon (77 mg, 10%, 0.07 mmol) in MeOH (1 mL). A hydrogen atmosphere was inserted and the resulting reaction mixture stirred at room temperature for 18 hours, at which time more palladium on carbon was added (300 mg) in MeOH (5 mL). A hydrogen atmosphere was inserted again and the reaction mixture allowed to stir an additional 18 hours at room temperature. The reaction mixture was filtered through a syringe filter and concentrated to afford a light brown viscous oil of (R)—N—((S)-1-(2-fluoro-4-isopropylphenyl)ethyl)-2-methylpropane-2-sulfinamide (149 mg, 0.52 mmol, 73% yield) which crystallizes upon standing. $^1$H NMR (400 MHz, CDCl$_3$) δ 1.20 (s, 9H) 1.24 (d, J=5.87 Hz, 6H) 1.58 (d, J=6.70 Hz, 3H) 2.89 (dt, J=13.79, 6.90 Hz, 1H) 3.35 (d, J=5.04 Hz, 1H) 4.76-4.85 (m, 1H) 6.90 (dd, J=12.03, 1.52 Hz, 1H) 6.98 (dd, J=7.90, 1.54 Hz, 1H) 7.24 (t, J=7.97 Hz, 1H). LCMS m/z 286.3 (M+H)$^+$, Rt 1.01 min.

Intermediate 184

(R)—N—((S)-1-(4-cyclopropyl-2-fluorophenyl)ethyl)-2-methylpropane-2-sulfinamide

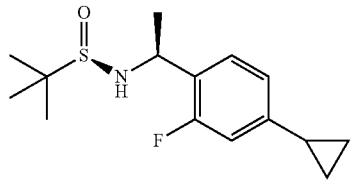 [SMILES: C[C@H](N[S@](=O)C(C)(C)C)c1ccc(C2CC2)cc1F]

To a microwave vial containing a stir bar was added (R)—N—((S)-1-(4-bromo-2-fluorophenyl)ethyl)-2-methylpropane-2-sulfinamide (100 mg, 0.31 mmol) followed by the addition of potassium cyclopropyltrifluoroborate (459 mg, 3.10 mmol), cesium carbonate (506 mg, 1.55 mmol) and Pd(OAc)$_2$ (7 mg, 0.03 mmol) and di(1-adamantyl)-n-butylphosphine (22 mg, 0.06 mmol), toluene (2.6 mL) and finally water (0.5 mL). The vial capped and heated by microwave irradiation for 20 min at 100° C., followed by thermal heating at 100° C. in a preheated aluminum tray for 18 hours. The reaction mixture was diluted with a saturated solution of NH$_4$Cl. The aqueous mixture extracted with EtOAc. Organic phases combined, washed with water, brine, dried (Na$_2$SO$_4$), filtered and concentrated to afford a yellow crystalline of (R)—N—((S)-1-(4-cyclopropyl-2-fluorophenyl)ethyl)-2-methylpropane-2-sulfinamide (116 mg, 0.33 mmol, 106% yield). LCMS m/z 284.0 (M+H)$^+$, Rt 0.90 min.

Intermediate 185

(R)—N—((S)-1-(6-cyclopropylpyridin-3-yl)ethyl)-2-methylpropane-2-sulfinamide

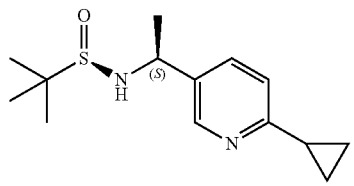

(R)—N—((S)-1-(6-cyclopropylpyridin-3-yl)ethyl)-2-methylpropane-2-sulfinamide is prepared with a method similar to that used to access Intermediate 184. MS m/z 267.1 (M+H)+, Rt 0.44 min.

Intermediate 186

(R)—N—((S)-1-(2-fluoro-4-(1-methyl-1H-pyrazol-4-yl)phenyl)ethyl)-2-methylpropane-2-sulfinamide

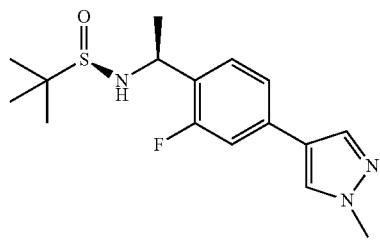 [SMILES: C[C@H](N[S@](=O)C(C)(C)C)c1ccc(-c2cnn(C)c2)cc1F]

To a two microwave vials with stir bars were added (R)—N—((S)-1-(4-bromo-2-fluorophenyl)ethyl)-2-methylpropane-2-sulfinamide (1.5 g, 4.65 mmol), 1-methyl-4-1H-pyrazoleboronic acid pinacol ester (2.91 g, 13.9 mmol), DME (20 mL), sodium carbonate (11.6 mL, 23.3 mmol, 2.0 M aq) and $PdCl_2(dppf).CH_2Cl_2$ adduct (190 mg, 0.23 mmol) divided between the two vials. The vials were capped and heated by microwave irradiation for 20 min at 100° C. respectively. The reaction mixtures combined, diluted with a saturated solution of $NH_4Cl$ and EtOAc. The phases were partitioned and the aqueous phase extracted with EtOAc. Organic phases combined, washed with water, brine, dried ($Na_2SO_4$), filtered and concentrated onto silica gel. Silica gel column chromatography (EtOAc/Heptane 40 to 100%) provided a orange crystalline of (R)—N—((S)-1-(2-fluoro-4-(1-methyl-1H-pyrazol-4-yl)phenyl)ethyl)-2-methylpropane-2-sulfinamide (1.07 g, 3.31 mmol, 71% yield. $^1$H NMR (400 MHz, $CDCL_3$) δ ppm 1.21 (s, 9H) 1.60 (d, J=6.80 Hz, 3H) 3.36 (d, J=4.25 Hz, 1H) 3.96 (s, 3H) 4.79-4.91 (m, 1H) 7.13 (dd, J=11.69, 1.61 Hz, 1H) 7.23 (dd, J=8.00, 1.64 Hz, 1H) 7.30-7.37 (m, 1H) 7.60 (s, 1H) 7.74 (s, 1H). LCMS m/z 324.0 (M+H)$^+$, Rt 0.74 min.

The Intermediates in Table 4q were prepared by a method similar to the one described for the preparation of Intermediate 186.

TABLE 4q

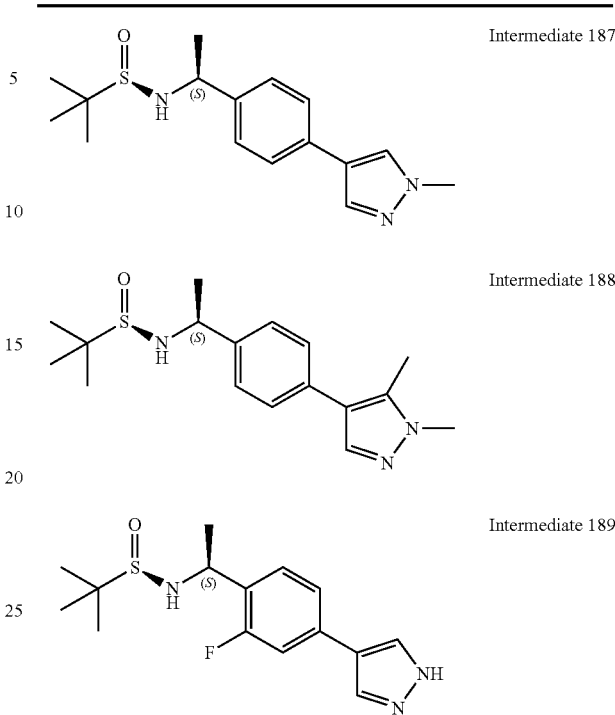

TABLE 4r

Chemical name, NMR chemical shifts and LCMS signal for each intermediate listed in Table 4q.

| Intermediate: Name | $^1$H NMR (400 MHz) δ ppm | LCMS |
|---|---|---|
| 187: (R)-2-methyl-N-((S)-1-(4-(1-methyl-1H-pyrazol-4-yl)phenyl)ethyl)propane-2-sulfinamide | | MS m/z 306.0 (M + H)$^+$, Rt 0.71 min. |
| 188: (R)-N-((S)-1-(4-(1,5-dimethyl-1H-pyrazol-4-yl)phenyl)ethyl)-2-methylpropane-2-sulfinamide | | MS m/z 320.0 (M + H)$^+$, Rt 0.72 min. |
| 189: (R)-N-((S)-1-(2-fluoro-4-(1H-pyrazol-4-yl)phenyl)ethyl)-2-methylpropane-2-sulfinamide | (DMSO) 1.10 (s, 9 H) 1.47 (d, J = 6.75 Hz, 3 H) 4.60-4.70 (m, 1 H) 5.41 (d, J = 5.48 Hz, 1 H) 7.38-7.44 (m, 3 H) 7.96 (br. s., 1 H) 8.23 (br. s., 1 H) 12.97 (br. s., 1 H) | MS m/z 310.0 (M + H)$^+$, Rt 0.67 min. |

Intermediate 190

(R)—N—((S)-1-(2-fluoro-4-(trifluoromethyl)phenyl)ethyl)-2-methylpropane-2-sulfinamide

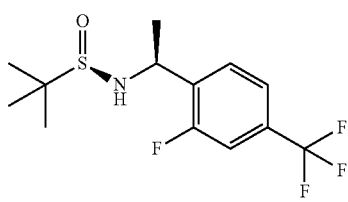 [SMILES: C[C@H](N[S@](=O)C(C)(C)C)c1ccc(C(F)(F)F)cc1F]

Step 1

To a oven dried round bottom flask with stir bar was added 2-fluoro-4-(trifluoromethyl)benzaldehyde (5 g, 26.0 mmol), (R)-2-methylpropane-2-sulfinamide (3.47 g, 28.6 mmol) and DCE (52 mL). To this mixture was then added copper (II) sulfate (6.23 g, 39.0 mmol). The reaction mixture was heated in a preheated oil bath at 55° C. for 18 hours. The reaction mixture was filtered through a pad celite, washing the solids with DCE. The filtrate was concentrated to afford a viscous green oil of (R,E)-N-(2-fluoro-4-(trifluoromethyl)benzylidene)-2-methyl propane-2-sulfinamide (7.3 g, 24.7 mmol, 95% yield). Material was taken onto next step without further purification. $^1$H NMR (400 MHz, CDCl$_3$) δ ppm 1.29 (s, 9H) 7.44 (d, J=10.08 Hz, 1H) 7.51 (d, J=8.27 Hz, 1H) 8.13 (t, J=7.46 Hz, 1H) 8.92 (s, 1H). LCMS m/z 296.0 (M+H)$^+$, Rt 1.02 min.

Step 2

To a solution of (R,E)-N-(2-fluoro-4-(trifluoromethyl)benzylidene)-2-methylpropane-2-sulfinamide (7.3 g, 24.7 mmol) in CH$_2$Cl$_2$ (247 mL) cooled to 0° C. (water/ice bath) under nitrogen, was added 3M methyl magnesium bromide (33 mL, 99 mmol) in Et$_2$O. Reaction mixture allowed to stir for 30 min at 0° C., then gradually allowed to warm to room temperature and stirred for 1 hour at room temperature. Reaction mixture was cooled to 0° C. then quenched with the slow addition of a saturated solution of NH$_4$Cl. Aqueous mixture extracted with EtOAc. Organic phases combined, washed with water, brine, dried (Na$_2$SO$_4$), filtered and concentrated onto silica gel. Silica gel column chromatography (EtOAc/Heptane 40 to 100%) provided (R)—N—((S)-1-(2-fluoro-4-(trifluoromethyl)phenyl)ethyl)-2-methylpropane-2-sulfinamide (4.68 g, 15.0 mmol, 61% yield) as a white crystalline solid. $^1$H NMR (400 MHz, CDCL$_3$) δ 1.22 (s, 9H) 1.60 (d, J=6.80 Hz, 3H) 3.38 (d, J=4.01 Hz, 1H) 4.87-4.97 (m, 1H) 7.33 (d, J=10.32 Hz, 1H) 7.39-7.45 (m, 1H) 7.49-7.55 (m, 1H). LCMS m/z 312.0 (M+H)$^+$, Rt 0.92 min.

Intermediate 191

(R)—N—((S)-1-(6-tert-butylpyridin-3-yl)ethyl)-2-methylpropane-2-sulfinamide

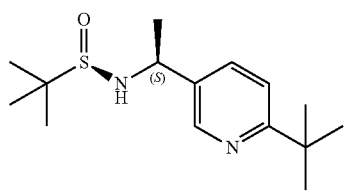

(R)—N—((S)-1-(6-tert-butylpyridin-3-yl)ethyl)-2-methylpropane-2-sulfinamide is prepared with methods similar to those used to prepare Intermediate 190. $^1$H NMR (400 MHz, CDCl$_3$) δ 1.22 (s, 9H) 1.37 (s, 9H) 1.57 (d, J=6.75 Hz, 3H) 3.31 (d, J=3.37 Hz, 1H) 4.56-4.65 (m, 1H) 7.32 (d, J=8.22 Hz, 1H) 7.57 (dd, J=8.24, 2.23 Hz, 1H) 8.54 (d, J=2.05 Hz, 1H). MS m/z 283.1 (M+H)+, Rt 0.51 min.

Intermediate 192

(S)-tert-butyl 1-(3-chloro-4-(cyclopentylcarbamoyl)phenyl)ethyl carbamate

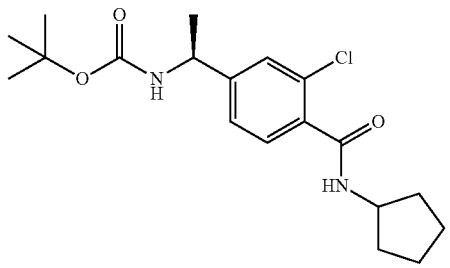 [SMILES: C[C@H](NC(=O)OC(C)(C)C)c1ccc(C(=O)NC2CCCC2)c(Cl)c1]

Step 1

To a round bottom flask with stir bar was added 4-((S)-1 aminoethyl-2-chlorobenzoic acid HCl salt (1.05 g, 4.45 mmol) followed by the addition of THF (40 mL). To this solution was added DIEA (1.86 ml, 10.7 mmol). The reaction mixture becomes cloudy white followed by the addition of di-tert-butyl dicarbonate (1.07 g, 4.89 mmol). Resulting reaction mixture allowed to stir for 18 hours at room temperature. At which time the reaction mixture was then heated to 60° C. for 2 hours in a oil bath. Di-tert-butyl dicarbonate (1.07 g, 4.89 mmol) and NMP (20 ml) were then added and the resulting reaction mixture allowed to stir for 2 hours at 60° C. Volatiles were removed. The resulting oil was diluted with a saturated solution of NH$_4$Cl and the aqueous mixture extracted with EtOAc. The organic phases combined, washed twice with water, brine, dried (Na$_2$SO$_4$), filtered and concentrated to a viscous yellow oil of (S)-4-(1-(tert-butoxycarbonylamino)ethyl)-2-chlorobenzoic acid (2.32 g, 6.19 mmol, 139% yield) which contains some excess di-tert-butyl dicarbonate and NMP. LCMS m/z 284.9 (M+H)$^+$ (carboxylic acid fragment+CH$_3$CN adduct), Rt 0.75 min.

Step 2

To a round bottom flask with stir bar was added (S)-4-(1-(tert-butoxycarbonylamino)ethyl)-2-chlorobenzoic acid (450 mg, 1.20 mmol), cyclopentylamine (355 μL, 3.60 mmol), EDC HCl (460 mg, 2.40 mmol), 1-hydroxy-7-azabenzotriazole (229 mg, 1.68 mmol) and DMF (6 mL). To this mixture was then added DIEA (629 μL, 3.60 mmol). Reaction mixture was allowed to stir at room temperature for 18 hours. The reaction mixture was diluted with water and extracted with EtOAc. The organic phases were combined, washed with twice with water, brine, dried (Na$_2$SO$_4$), filtered and concentrated to a brown crystalline of (S)-tert-butyl 1-(3-chloro-4-(cyclopentylcarbamoyl)phenyl)ethylcarbamate (476 mg, 1.17 mmol, 97% yield). LCMS m/z 367.0 (M+H)$^+$, Rt 0.90 min.

The Intermediates in Table 4s were prepared by a method similar to the one described for the preparation of Intermediate 192.

TABLE 4s

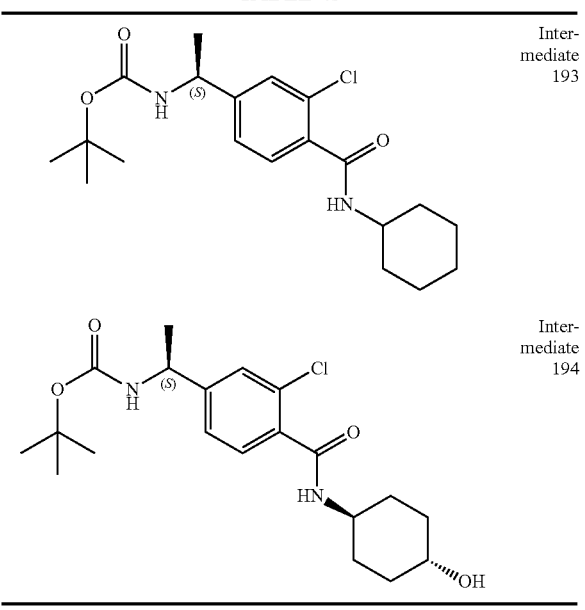

| | |
|---|---|
| | Intermediate 193 |
| | Intermediate 194 |

TABLE 4t

Chemical name and LCMS signal for each intermediate listed in Table 4s.

| Intermediate: Name | LCMS |
|---|---|
| 193: (S)-tert-butyl 1-(3-chloro-4-(cyclohexyl carbamoyl) phenyl) ethylcarbamate | MS m/z 381.1 (M + H)$^+$, Rt 0.96 min. |
| 194: tert-butyl (S)-1-(3-chloro-4-((1r,4S)-4-hydroxycyclohexyl carbamoyl)phenyl)ethylcarbamate | MS m/z 391.1 (M + H)$^+$, Rt 0.71 min. |

Intermediate 195

(S)-tert-butyl 1-(3-hydroxyphenyl)ethylcarbamate

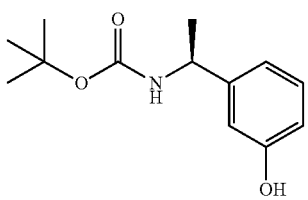 [SMILES: C[C@H](NC(=O)OC(C)(C)C)c1cccc(O)c1]

A slurry of (S)-3-(1-aminoethyl)phenol (1.188 g, 6.84 mmol) and Boc$_2$O (1.747 mL, 7.53 mmol) in DCM (17.10 mL) was stirred at room temperature under N$_2$ while slowly adding DIEA (1.434 mL, 8.21 mmol). The initially insoluble starting materials slowly dissolve. The solution was stirred at room temperature for 16 hours and then concentrated. The oily residue was re-dissolved in EtOAc and washed with Na$_2$CO$_3$ saturated, followed by brine. The original aqueous layer was re-extracted with EtOAc, which was then washed with brine and combined with the previous EtOAc batch. The combined organics were dried over Na$_2$SO$_4$, filtered and concentrated to 2.4 g crude clear yellowish oil which was purified by silica gel column chromatography (EtOAc/Heptane 0 to 30%), yielding (S)-tert-butyl 1-(3-hydroxyphenyl)ethylcarbamate as a clear colourless oil, which solidifies upon sitting (1.79 g, 7.55 mmol, 110% yield). $^1$H NMR (400 MHz, CDCL$_3$) δ 1.44 (br. s., 12H) 4.08-4.18 (m, 1H) 4.76 (br. s., 1H) 6.72 (dd, J=7.46, 1.83 Hz, 1H) 6.78 (br. s., 1H) 6.88 (br. s., 1H) 7.16-7.24 (m, 1H). LCMS m/z 223.0/182.0 (the parent not observed, just the Boc fragments) (M+H)$^+$, Rt 0.71 min.

Intermediate 196

(S)-1-(3-(cyclopentyloxy)phenyl)ethanamine hydrochloride

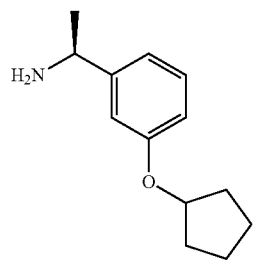

Step 1: Mitsunobu A

To a solution of (S)-tert-butyl 1-(3-hydroxyphenyl)ethylcarbamate (107.5 mg, 0.453 mmol), PPh$_3$ (238 mg, 0.906 mmol) and cyclopentanol (0.164 ml, 1.812 mmol) in THF (2 ml) at room temperature was added DEAD (0.143 ml, 0.906 mmol) dropwise under N$_2$. The resulting yellow solution was stirred for 4 hours and then concentrated. The viscous yellow oil was re-dissolved in DMSO and purified by reverse phase HPLC. The combined product fractions were desalted by addition of equal amount of EtOAc and about 250 mg Na$_2$CO$_3$ in a separatory funnel. The phases were separated and the organic washed with brine, dried over MgSO$_4$, filtered and concentrated in vacuo to yield (S)-tert-butyl 1-(3-(cyclopentyloxy)phenyl)ethylcarbamate (75.1 mg, 0.246 mmol, 54.3% yield) as a white solid film. LCMS m/z 291.1/250.0 (the parent not observed, just the Boc fragments) (M+H)$^+$, Rt 1.07 min.

Step 2

(S)-tert-butyl 1-(3-(cyclopentyloxy)phenyl)ethylcarbamate (75.1 mg, 0.246 mmol) was dissolved in 4M HCl in dioxane (1 ml, 4.00 mmol) and the resulting mixture was allowed to sit for 1 hour, then concentrated to yield (S)-1-(3-(cyclopentyloxy)phenyl)ethanamine as an HCl salt (yield assumed quantitative). LCMS m/z 206.1 (M+H)$^+$, Rt 0.61 min.

Intermediate 197

(S)-1-(3-(cyclohexyloxy)phenyl)ethanamine hydrochloride

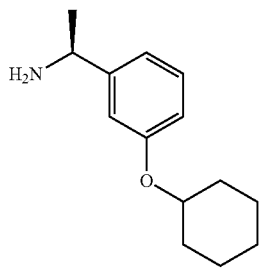 [SMILES: C[C@H](N)c1cccc(OC2CCCCC2)c1]

Step 1: Mitsunobu B

To a solution of (S)-tert-butyl 1-(3-hydroxyphenyl)ethylcarbamate (100 mg, 0.421 mmol), cyclohexanol (0.180 ml, 1.686 mmol) and PPh$_3$ (221 mg, 0.843 mmol) in THF (2 ml), was added DEAD (0.133 ml, 0.843 mmol) dropwise, under N$_2$, at room temperature. The resulting yellow solution was stirred for 3 hours, at which point another batch of cyclohexanol (0.180 ml, 1.686 mmol), PPh$_3$ (221 mg, 0.843 mmol), and 10 min later DEAD (0.133 ml, 0.843 mmol), was added at room temperature. The reaction mixture was stirred for 16 hours and then concentrated. The crude clear oil was re-dissolved in DMSO and purified by reverse phase HPLC. The combined product fractions were desalted by addition of equal amount of EtOAc and about 250 mg Na$_2$CO$_3$ in a separatory funnel. The phases were separated and the organic washed with brine, dried over MgSO$_4$, filtered and concentrated in vacuo to yield (S)-tert-butyl 1-(3-(cyclohexyloxy)phenyl)ethylcarbamate (74.1 mg, 0.232 mmol, 55.0% yield) as a clear colourless film. LCMS m/z 305.0/264.0 (the parent not observed, just the Boc fragments) (M+H)$^+$, Rt 1.12 min.

Step 2

(S)-tert-butyl 1-(3-(cyclohexyloxy)phenyl)ethylcarbamate (74.1 mg, 0.232 mmol) was dissolved in 4M HCl in dioxane (1 ml, 4.00 mmol) and the resulting mixture was allowed to sit for 1 hour, then concentrated to yield (S)-1-(3-(cyclohexyloxy)phenyl)ethanamine as an HCl salt (yield assumed quantitative). LCMS m/z 220.1 (M+H)$^+$, Rt 0.66 min.

The Intermediates in Table 4v were prepared using either the method described for the preparation of Intermediate 196 or Intermediate 197.

TABLE 4v

| Intermediate: Name | Structure | LCMS |
| --- | --- | --- |
| 198: (S)-1-(3-(cyclopentyloxy)phenyl)ethanamine | 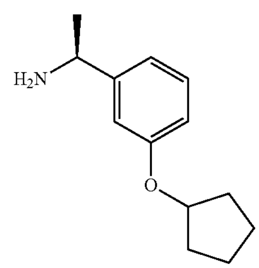 | MS m/z 206.1 (M + H)$^+$, Rt 0.61 min. |
| 199: (S)-1-(3-(cyclohexyloxy)phenyl)ethanamine | 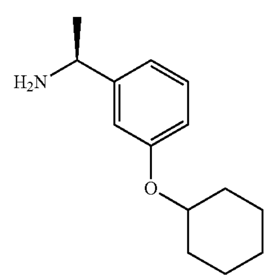 [SMILES: C[C@H](N)c1cccc(OC2CCCCC2)c1] | MS m/z 220.1 (M + H)$^+$, Rt 0.66 min. |
| 200: (S)-1-(3-(cycloheptyloxy)phenyl)ethanamine | 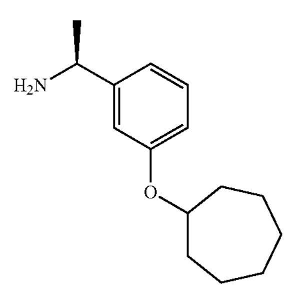 [SMILES: C[C@H](N)c1cccc(OC2CCCCCC2)c1] | MS m/z 234.1 (M + H)$^+$, Rt 0.73 min. |

TABLE 4v-continued

| Intermediate: Name | Structure | LCMS |
|---|---|---|
| 201: (S)-1-(3-isopropoxyphenyl)ethanamine | 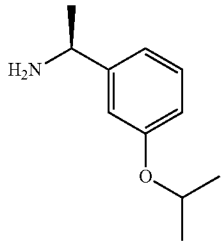 | MS m/z 180.1 (M + H)+, Rt 0.50 min. |
| 202: (S)-1-(3-isobutoxyphenyl)ethanamine | 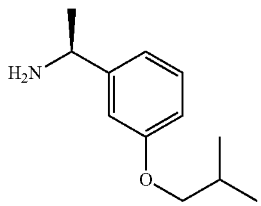 | MS m/z 194.1 (M + H)+, Rt 0.61 min. |
| 203: (S)-1-(3-((S)-tetrahydrofuran-3-yloxy)phenyl)ethanamine | 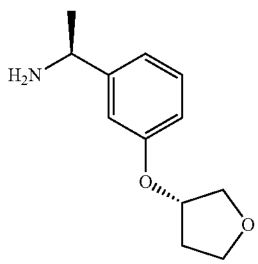 | MS m/z 208.1 (M + H)+, Rt 0.41 min. |
| 204: (1S)-1-(3-(tetrahydro-2H-pyran-3-yloxy)phenyl)ethanamine | 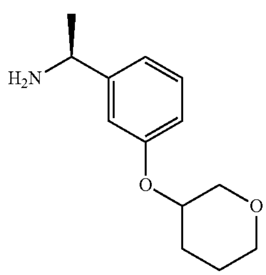 [SMILES: C[C@H](N)c1cccc(OC2CCCOC2)c1] | MS m/z 222.1 (M + H)+, Rt 0.46 min. |

Intermediate 205

(S)-1-(3-phenoxyphenyl)ethanamine

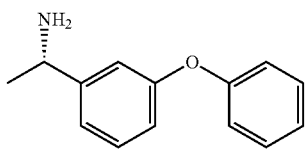 [SMILES: C[C@H](N)c1cccc(Oc2ccccc2)c1]

Into a 20 ml microwave vial was weighted 1-(pyridin-2-yl)propan-2-one ligand (90 mg, 0.665 mmol), phenol (407 mg, 4.32 mmol), CuBr (47.7 mg, 0.332 mmol) and Cs₂CO₃ (2166 mg, 6.65 mmol). To the mixture was added DMSO (5 ml) and (S)-1-(3-bromophenyl)ethanamine (0.5 ml, 3.32 mmol). The tube was flushed with N₂, capped, and the black mixture heated in the oil bath at 90° C. for 18 hours. The heterogenous mixture was diluted with EtOAc and filtered through a glass-fritted funnel, eluting with EtOAc and another 5 mls of DMSO. The volatiles were then removed in vacuo and the crude brown liquid was filtered through 1 μm PTFE filter and purified by reverse phase HPLC. The combined product fractions were desalted by addition of equal amount of EtOAc and about 250 mg Na₂CO₃ in a separatory funnel. The phases were separated and the organic washed with brine, dried over MgSO₄, filtered and concentrated in vacuo to yield (S)-1-(3-phenoxyphenyl)ethanamine (361.5 mg, 1.678 mmol, 50.5% yield) as an amber oil. LCMS m/z 214.1 (M+H)+, Rt 0.61 min.

Intermediate 206

(S)-1-(2,3-difluorophenyl)ethanamine

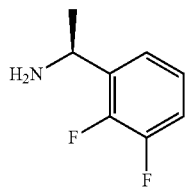

Step 1

To a oven dried round bottom flask with stir bar was added 2,3-difluorobenzaldehyde (0.5 g, 3.52 mmol), (R)-2-methylpropane-2-sulfinamide (0.469 g, 3.87 mmol) and DCE (7.04 mL). To this mixture was then added Copper (II) Sulfate (0.842 g, 5.28 mmol). Reaction mixture heated in a preheated oil bath to 55° C. for 24 hours. The reaction mixture was filtered through a celite pad washing solids with DCE. Combined filtrate was concentrated to afford a viscous yellow oil of (R,E)-N-(2,3-difluorobenzylidene)-2-methylpropane-2-sulfinamide (0.8007 g, 3.26 mmol, 93% yield). LCMS m/z 246.1 (M+H)+, Rt 0.91 min.

Step 2

To a solution of (R,E)-N-(2,3-difluorobenzylidene)-2-methylpropane-2-sulfinamide (0.800 g, 3.26 mmol) in DCM (32.6 mL), cooled to 0° C. (water/icebath) under N2, was added 3M MeMgBr (4.35 mL, 13.05 mmol) in diethyl ether. Reaction mixture allowed to stir for 30 min at 0° C. Then gradually allowed to warm to room temperature and stirred for 30 min at room temperature. Reaction mixture was cooled to 0° C. then quenched with the slow addition of a saturated solution of NH4Cl and diluted with EtOAc. Phases partitioned aqueous phase extracted with EtOAc and the organic layers combined washed with water, brine, dried with MgSO4, filtered and concentrated to afford (R)—N—((S)-1-(2,3-difluorophenyl)ethyl)-2-methylpropane-2-sulfinamide (0.7868 g, 3.01 mmol, 92% yield) as yellow solid. LCMS m/z 262.0 (M+H)+, Rt 0.70 min.

Step 3

To a round bottom flask containing (R)—N—((S)-1-(2,3-difluorophenyl)ethyl)-2-methylpropane-2-sulfinamide (786.8 mg, 3.01 mmol) was added Dioxane (10.000 mL). To this solution was added HCl in dioxane 4.0M (1.505 mL, 6.02 mmol) and the solution was allowed to stir 15 min at room temperature. The reaction mixture was concentrated, dissolved in Et2O 10 ml, and concentrated again. Et2O was again added and resulting mixture sonnicated and a solid material was filtered and dried to afford (S)-1-(2,3-difluorophenyl)ethanamine (0.4213 g, 2.176 mmol, 72.3% yield) as a white crystalline HCl salt. $^1$H NMR (400 MHz, D2O) d ppm 1.55 (d, J=6.99 Hz, 3H) 4.71 (q, J=6.96 Hz, 1H) 7.10-7.26 (m, 3H); LCMS m/z 158.0 (M+H)+, Rt 0.37 min.

Intermediate 207

(S)-1-(4-(difluoromethyl)-2-fluorophenyl)ethanamine

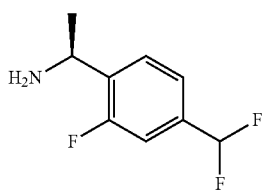

Step 1: Preparation of 1-bromo-4-(difluoromethyl)-2-fluorobenzene

A mixture of 4-bromo-3-fluorobenzaldehyde (2.03 g, 10 mmol) and (diethylamino)sulfur trifluoride (DAST; 1.32 mL, 10 mmol) is heated carefully until exothermic reaction occurs, then heated at 60° C. for 15 min, and allowed to cool to room temperature. The mixture was diluted with DCM (20 mL) and poured into ice/water (30 mL). The mixture was neutralized with NaHCO3 to ~pH 8. The separated aqueous layer was extracted with DCM (20 mL). The combined organic layers were dried over Na2SO4, filtered off, and concentrated under reduced pressure. The residue was purified by column chromatography [SiO2, 40 g, heptane/ethyl acetate], providing 1-bromo-4-(difluoromethyl)-2-fluorobenzene (0.845 g) as a clear colorless oil.

Step 2: Preparation of 4-(difluoromethyl)-2-fluorobenzaldehyde

To a solution of 1-bromo-4-(difluoromethyl)-2-fluorobenzene (311 mg, 1.382 mmol) in THF (2.99 mL) was added butyllithium (1.6M solution in hexanes; 0.881 mL, 1.410 mmol) over ~5 min at −78° C. The reaction mixture was stirred for 30 min at −78° C. then DMF (0.161 mL, 2.073 mmol) was added dropwise over ~1 min. Stirring was continued for 20 min. The reaction mixture was quenched with aqueous 1M HCl solution/MeOH (2:1, 3 mL) and allowed to warm to room temperature. The mixture was diluted with 5 mL of water. The separated aqueous layer was with ether (5 mL). The combined organic layers were washed with 1M aqueous NaOH solution (10 mL) and saturated brine (10 mL), dried over MgSO4, filtered off and concentrated under reduced pressure. Repeated reaction with 420 mg of 1-bromo-4-(difluoromethyl)-2-fluorobenzene and combined crude materials for purification. The crude material was purified by column chromatography [SiO2, 24 g, heptane/ethyl acetate], providing 4-(difluoromethyl)-2-fluorobenzaldehyde (162.8 mg) as a yellow oil.

Step 3: Preparation of (R,E)-N-(4-(difluoromethyl)-2-fluorobenzylidene)-2-methylpropane-2-sulfinamide To a mixture of 4-(difluoromethyl)-2-fluorobenzaldehyde (162 mg, 0.930 mmol) and (R)-2-methylpropane-2-sulfinamide (124 mg, 1.023 mmol) in DCE (3 mL) was added copper sulfate (223 mg, 1.396 mmol). Reaction mixture was heated in a preheated oil bath to 55° C. for 38 hours. The mixture was allowed to cool to room temperature, filtered through a pad of celites and washed with DCE. Combined filtrates were concentrated under reduced pressure to afford (R,E)-N-(4-(difluoromethyl)-2-fluorobenzylidene)-2-methylpropane-2-sulfinamide (266 mg) as a yellow oil, which was used without further purification. LCMS m/z 278.1 (M+H)+, Rt 0.98 min.

Step 4: Preparation of (R)—N—((S)-1-(4-(difluoromethyl)-2-fluorophenyl)ethyl)-2-methylpropane-2-sulfinamide To a solution of (R,E)-N-(4-(difluoromethyl)-2-fluorobenzylidene)-2-methylpropane-2-sulfinamide (266 mg, 0.959 mmol) in DCM (9.6 mL) was added methylmagnesium bromide (3M in diethylether; 1.20 mL) at 0° C. The reaction mixture was allowed to stir for 30 min at 0° C., gradually allowed to warm to room temperature and stirred for 1 hour at room temperature. The mixture was cooled to 0° C., and carefully quenched with saturated aqueous NH4Cl solution (3 mL). The separated aqueous phase was extracted with DCM. The combined organic layers were washed with brine, dried over sodium sulfate, filtered off and concentrated under reduced pressure. The crude material was purified by column chromatography [SiO$_2$, 40 g, heptane/ethyl acetate], providing (R)—N—((S)-1-(4-(difluoromethyl)-2-fluorophenyl)ethyl)-2-methylpropane-2-sulfinamide (160.5 mg) as a white solid. LCMS m/z 294.5 (M+H)$^+$, Rt 0.85 min.

Step 5: Preparation of (5)-1-(4-(difluoromethyl)-2-fluorophenyl)ethanamine

To (R)—N—((S)-1-(4-(difluoromethyl)-2-fluorophenyl)ethyl)-2-methylpropane-2-sulfinamide (160 mg, 0.545 mmol) was added 4M HCl in dioxane (409 μL) to give a yellow solution. The resulting mixture was stirred at room temperature for ~1 hour. To the mixture was added slowly diethylether (~20 mL). The solids were filtered off, suspended in diethylether, filtered off and rinsed with diethylether, dried under reduced pressure providing (S)-1-(4-(difluoromethyl)-2-fluorophenyl)ethanamine (103 mg) as an off-white solid, which was used without further purification. LCMS m/z 190.1 (M+H)$^+$, Rt 0.42 min.

Intermediate 208

(S)-1-(4-(pyrimidin-5-yloxy)phenyl)ethanamine

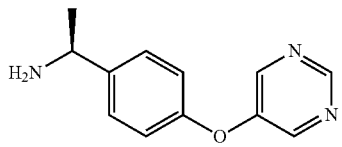 [SMILES: C[C@H](N)c1ccc(Oc2cncnc2)cc1]

Step 1: Preparation of 4-(pyrimidin-5-yloxy)benzaldehyde

To a solution of pyrimidin-5-ol (500 mg, 5.20 mmol) in DMF (5.20 mL) under argon was added 4-fluorobenzaldehyde (0.558 mL, 5.20 mmol), sodium methanesulfinate (133 mg, 1.30 mmol), and potassium carbonate (1.079 g, 7.81 mmol). The reaction mixture was heated at 120° C. for 3 hour. The mixture was allowed to cool to room temperature and was diluted with water (25 mL). The mixture was extracted with EtOAc (2×25 mL). The combined organic layers were washed with brine (2×50 mL), dried over sodium sulfate, filtered off and concentrated under reduced pressure. The residue was purified by column chromatography [SiO$_2$, 24 g, heptane/ethyl acetate], providing 4-(pyrimidin-5-yloxy)benzaldehyde (666 mg) as a yellow solid. LCMS m/z 201.0 (M+H)$^+$, Rt 0.52 min.

Step 2: Preparation of (R,E)-2-methyl-N-(4-(pyrimidin-5-yloxy)benzylidene)propane-2-sulfinamide A mixture of 4-(pyrimidin-5-yloxy)benzaldehyde (666 mg, 3.33 mmol), (R)-(+)-tert-butanesulfinamide (450 mg, 3.71 mmol) and copper sulfate (796 mg, 4.99 mmol) in anhydrous in dichloroethane (7.648 mL) and under argon was heated at 55° C. for ~21 hours. The reaction mixture was allowed to cool to room temperature. The slurry was filtered through a celite pad, eluted with DCM (5×10 mL). The combined filtrates were concentrated under reduced pressure and the resulting yellowish oil was purified by column chromatography [SiO$_2$, 24 g, heptane/ethyl acetate] providing (R,E)-2-methyl-N-(4-(pyrimidin-5-yloxy)benzylidene)propane-2-sulfinamide (836 mg) as a pale viscous oil. LCMS m/z 304.0 (M+H)$^+$, Rt 0.79 min.

Step 3: Preparation of 2-methyl-N—((S)-1-(4-(pyrimidin-5-yloxy)phenyl)ethyl)propane-2-sulfinamide A solution of (R,E)-2-methyl-N-(4-(pyrimidin-5-yloxy)benzylidene)propane-2-sulfinamide (830 mg, 2.74 mmol) in DCM (6.72 mL) was cooled to −40° C. To the solution was added methylmagnesium bromide (3M in diethylether; 1.81 mL) dropwise over 10 min. Additional DCM (5 mL) were added to retain stirring. The yellow suspension was stirred at −40° C. for ~30 min while warming to −20° C. The mixture was cooled to −40° C. and additional methylmagnesium bromide (3M in diethylether; 1.8 mL) was added. The suspension was stirred for ~3 hour while slowly warming to −20° C. The mixture was cooled to ~−40° C., and additional methylmagnesium bromide (3M in diethylether; 0.4 mL) was added. The suspension was stirred for 30 min and allowed to warm to −10° C. The mixture was quenched slowly over 10 min with saturated aqueous NH$_4$Cl solution (10 mL). The mixture was diluted with saturated aqueous NH$_4$Cl solution (30 mL) and water (15 mL). The separated aqueous phase was extract with DCM (2×75 mL). The combined organic layers were washed with brine (50 mL), dried over Na$_2$SO$_4$, filtered off and concentrated under reduced pressure. The residue was purified by column chouromatography [SiO$_2$, 40 g, heptane/ethyl acetate followed by 5% MeOH in EtOAc] providing 2-methyl-N—((S)-1-(4-(pyrimidin-5-yloxy)phenyl)ethyl)propane-2-sulfinamide (55 mg; purity ~87%) as an off-white solid. LCMS m/z 320.0 (M+H)$^+$, Rt 0.69 min.

Step 4: Preparation of (5)-1-(4-(pyrimidin-5-yloxy)phenyl)ethanamine

To 2-methyl-N—((S)-1-(4-(pyrimidin-5-yloxy)phenyl)ethyl)propane-2-sulfinamide (55 mg, 0.172 mmol) was added 4M HCl in dioxane (800 μL, 3.20 mmol) to give a white suspension. This resulting mixture was stirred at room temperature for ~35 min and concentrated under reduced pressure to provide crude (S)-1-(4-(pyrimidin-5-yloxy)phenyl)ethanamine (44 mg) as its HCl salt, which was used without further purification. LCMS m/z 217.1 (M+H)$^+$, Rt 0.37 min.

Intermediate 209

5-chloro-6-(1,1-difluoroethyl)nicotinaldehyde

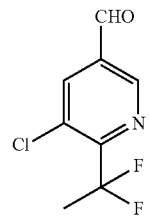

Step 1: Preparation of ethyl 5,6-dichloronicotinate

To a solution of 5,6-dichloronicotinic acid (20.01 g, 104 mmol) in EtOH (500 mL) at 20° C. was added chlorotrimethylsilane (132 mL, 1042 mmol). The reaction was stirred for 72 hours. The reaction mixture was then concentrated and diluted with EtOAc (500 mL), and washed with saturated NaHCO₃ (2×100 mL) and brine (100 mL). The organic was then dried (Na₂SO₄) and concentrated under reduced pressure to give final crude product (21.25 g). LCMS m/z 220.1 (M+H)⁺, Rt 0.94 min.

Step 2: Preparation of ethyl 6-acetyl-5-chloronicotinate

To a suspension of ethyl 5,6-dichloronicotinate (5.26 g, 23.90 mmol) and tetraethylammonium-chloride (11.88 g, 71.7 mmol) in MeCN (50 mL) was added tributyl(1-ethoxyvinyl)stannane (9.50 g, 26.3 mmol) and PdCl₂(PPh₃)₂ (0.671 g, 0.956 mmol). The reaction was sealed, heated at 80° C. for 5 hours. A dark color clear solution resulted. The reaction mixture was then cooled to 20° C., concentrated and diluted with EtOAc (200 mL), and washed with water (50 mL) and brine (50 mL). The organic was then dried (Na₂SO₄) and concentrated to give crude ethyl 5-chloro-6-(1-ethoxyvinyl)nicotinate. The residue was then dissolved in THF (100 mL) and HCl (20 mL, 3M in H₂O) was added. The reaction mixture was stirred at 20° C. for 5 hours, and saturated NaHCO₃ solution was added until pH=8. The mixture was then diluted with EtOAc (200 mL) and water (50 mL). The phases were separated and the aqueous layer was extracted with EtOAc (2×50 mL). The combined organics was washed with brine (20 mL), dried (Na₂SO₄) and concentrated to afford the desired product (3.56 g). LCMS m/z 228.5 (M+H)⁺, Rt 0.83 min.

Step 3: Preparation of ethyl 5-chloro-6-(1,1-difluoroethyl)nicotinate

To a solution of ethyl 6-acetyl-5-chloronicotinate (3.01 g, 13.22 mmol) in CHCl3 (7 mL) was added DAST (5.20 mL, 39.7 mmol) and ethanol (0.061 g, 1.32 mmol). The reaction was sealed, heated at 60° C. for 24 hours. A dark color clear solution resulted. The reaction mixture was then cooled to 20° C., and added cautiously with cold concentrated NaHCO₃ aqueous solution (50 mL). The aqueous layer was extracted with DCM (2×100 mL). The combined organic was then dried (Na₂SO₄) and concentrated. The residue was purified via silica gel flash chromatography (0-20percent EtOAc-Hexanes) to afford the desired product as yellow oil (2.88 g). LCMS m/z 250.1 (M+H)⁺, Rt 0.99 min.

Step 4: Preparation of (5-chloro-6-(1,1-difluoroethyl)pyridin-3-yl)methanol

To a solution of ethyl 5-chloro-6-(1,1-difluoroethyl)nicotinate (2.68 g, 10.74 mmol) in Et₂O (40 mL) was added LiBH₄ (0.351 g, 16.10 mmol), followed by dropwise addition of methanol (0.653 mL, 16.10 mmol). The reaction was refluxed at 40° C. for one hour. The reaction mixture was then cooled to 0° C., and quenched with HCl (1M) until pH=2 for aqueous layer. The phases were separated and the aqueous layer was extracted with DCM (3×50 mL). The organic was then dried (Na₂SO₄) and concentrated under reduced pressure to give final crude product (2.12 g). LCMS m/z 208.0 (M+H)⁺, Rt 0.63 min.

Step 5: Preparation of 5-chloro-6-(1,1-difluoroethyl)nicotinaldehyde

To a solution of (5-chloro-6-(1,1-difluoroethyl)pyridin-3-yl)methanol (2.12 g, 10.21 mmol) in DCM (100 ml) was added PCC (3.30 g, 15.32 mmol). The reaction was stirred at 20° C. for 3 hours. A dark color suspension resulted. LCMS showed clean conversion to the product. The reaction mixture was then filtered through a pad of celite, and washed with DCM (200 mL). The filtrate was then concentrated to give crude product (1.78 g). LCMS m/z 224.0 (M+H2O+H)⁺, Rt 0.72 min.

Intermediate 210

5-chloro-6-(2,2,2-trifluoroethoxy)nicotinaldehyde

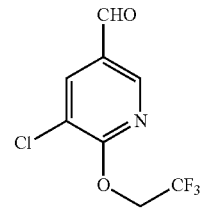 [SMILES: O=Cc1cnc(OCC(F)(F)F)c(Cl)c1]

Step 1: Preparation of ethyl 5-chloro-6-(2,2,2-trifluoroethoxy)nicotinate

To a solution of ethyl 5,6-dichloronicotinate (6.28 g, 28.5 mmol) and 2,2,2-trifluoroethanol (2.71 ml, 37.1 mmol) in THF (90 ml) at −73° C. was added NaHMDS (37.1 ml, 37.1 mmol). The reaction was stirred at −73° C. for 30 minutes, then at 0° C. for 5 hours. The reaction was quenched with 30 mL saturated NH₄Cl solution. The reaction mixture was then poured into 50 mL brine and phases were separated. The aqueous layer was extracted with DCM (2×100 mL). The combined organics were dried (Na₂SO₄) and concentrated. Silica gel chromatography with 100% heptane to 30% EtOAc in heptane provided final product (7.51 g). LCMS m/z 284.1 (M+H)⁺, Rt 1.07 min.

Step 2: Preparation of (5-chloro-6-(2,2,2-trifluoroethoxy)pyridin-3-yl)methanol

To a solution of ethyl 5-chloro-6-(2,2,2-trifluoroethoxy)nicotinate (7.51 g, 26.5 mmol) in Et2O (200 mL) was added LiBH₄ (0.865 g, 39.7 mmol), followed by drop wise addition of methanol (1.611 ml, 39.7 mmol). The reaction was refluxed at 40° C. for one hour. The reaction mixture was then cooled to 0° C., and quenched with HCl (1M) until pH=2 for aqueous layer. The phases were separated and the aqueous layer was extracted with DCM (3×200 mL). The organic was then dried (Na₂SO₄) and concentrated under reduced pressure to give final crude product (6.31 g). LCMS m/z 242.1 (M+H)⁺, Rt 0.77 min.

Step 3: Preparation of 5-chloro-6-(2,2,2-trifluoroethoxy)nicotinaldehyde

To a solution of (5-chloro-6-(2,2,2-trifluoroethoxy)pyridin-3-yl)methanol (4.00 g, 16.56 mmol) in EtOAc (15 mL) was added manganese(IV) oxide (16.93 g, 166 mmol). The reaction was heated with microwave at 120° C. for 30 minutes. The mixture was then filtered through a pad of celite, and rinsed with EtOAc. The filtrated was concentrated to give crude product (3.38 g).

The intermediates in Table 4w were prepared with procedures similar to those used to prepare Intermediate 210 and 192.

TABLE 4w

| Intermediate: Name | Structure | LCMS |
|---|---|---|
| 211: (R)-N-((S)-1-(5-chloro-6-(1,1-difluoroethyl)pyridin-3-yl)ethyl)-2-methylpropane-2-sulfinamide | 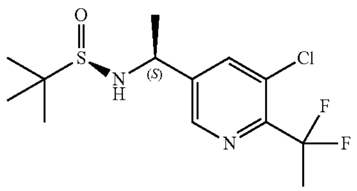 | MS m/z 325.2 (M + H)+, Rt 0.85 min. |
| 212: (R)-N-((S)-1-(5-chloro-6-(2,2,2-trifluoroethoxy)pyridin-3-yl)ethyl)-2-methylpropane-2-sulfinamide | 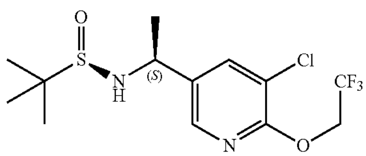 | MS m/z 359.1 (M + H)+, Rt 0.95 min. |

Intermediate 213

(S)-3-(2-((S)-1-(4-(chloromethyl)phenyl)ethylamino)pyrimidin-4-yl)-4-isopropyloxazolidin-2-one

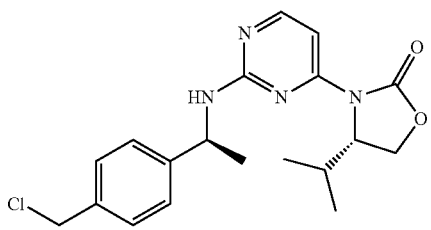 [SMILES: CC(C)[C@H]1COC(=O)N1c1ccnc(N[C@@H](C)c2ccc(CCl)cc2)n1]

To a solution of (S)-3-(2-((S)-1-(4-(hydroxymethyl)phenyl)ethylamino)pyrimidin-4-yl)-4-isopropyloxazolidin-2-one (71 mg, 0.2 mmol) in DCM (2 mL) was added methanesulfonyl chloride (27 mg, 0.24 mmol) and DIPEA (0.070 mL, 0.4 mmol). The solution was stirred for 16 h at room temperature then washed with water and brine. After separation, the organic phase was dried over Na₂SO₄, filtered and concentrated. The crude product was used to next step without further purification.
MS m/z 373.4 (M−H).

Intermediate 214 tert-butyl 3-(4-((S)-1-(4-((S)-4-isopropyl-2-oxooxazolidin-3-yl)pyrimidin-2-ylamino)ethyl)benzyl)-3,8-diazabicyclo[4.2.0]octane-8-carboxylate

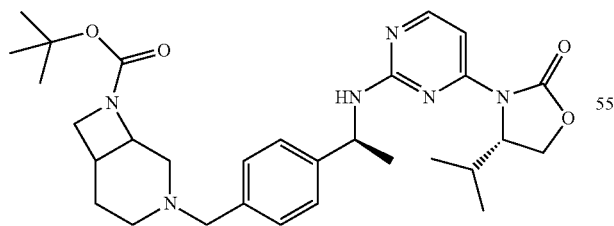

Title compound was prepared as a white solid (64 mg, 58.1% yield), with procedures similar to those used to prepare Intermediate 128, but utilizing 4-((S)-1-(4-((S)-4-isopropyl-2-oxooxazolidin-3-yl)pyrimidin-2-ylamino)ethyl)benzaldehyde and tert-butyl 3,8-diazabicyclo[4.2.0]octane-8-carboxylate.

¹H NMR (400 MHz, CDCl3) δ 8.17 (dd, J=5.9, 0.9 Hz, 1H), 7.42 (d, J=5.7 Hz, 1H), 7.28-7.23 (m, 4H), 5.39 (br s, 1H), 5.02 (br s, 1H), 4.62-4.59 (m, 1H), 4.28 (t, J=8.7 Hz, 1H), 4.21 (dd, J=9.0, 3.2 Hz, 2H), 3.89 (td, J=7.7, 1.9 Hz, 1H), 3.54-3.50 (m, 2H), 3.03 (d, J=12.2 Hz, 1H), 2.65-2.60 (m, 1H), 2.54-2.40 (m, 2H), 2.10 (br s, 1H), 1.99-1.88 (m, 1H), 1.79-1.72 (m, 1H), 1.65 (br s, 1H), 1.52 (dd, J=6.8, 1.9 Hz, 3H), 1.38 (t, J=7.7 Hz, 9H), 0.71 (br s, 3H), 0.66 (br s, 3H). MS m/z 569.1 (M+H).

Intermediate 215 tert-butyl 1-(4-((S)-1-(4-((S)-4-isopropyl-2-oxooxazolidin-3-yl)pyrimidin-2-ylamino)ethyl)benzyl)piperidin-4-ylcarbamate

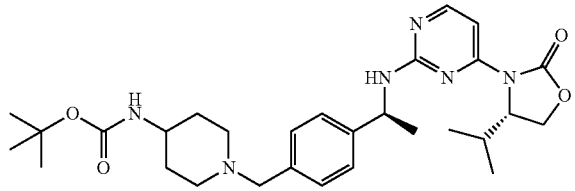 [SMILES: CC(C)[C@H]1COC(=O)N1c1ccnc(N[C@@H](C)c2ccc(CN3CCC(NC(=O)OC(C)(C)C)CC3)cc2)n1]

Title compound was prepared as a white solid (32 mg, 59% yield), with procedures similar to those used to prepare Intermediate 128, but utilizing 4-((S)-1-(4-((S)-4-isopropyl-2-oxooxazolidin-3-yl)pyrimidin-2-ylamino)ethyl)benzaldehyde and tert-butyl piperidin-4-ylcarbamate. MS m/z 539.4 (M+H).

EXAMPLES

Example 1

(S)-5,5-dimethyl-4-phenyl-3-(2-((S)-1-phenylethylamino)pyrimidin-4-yl)oxazolidin-2-one

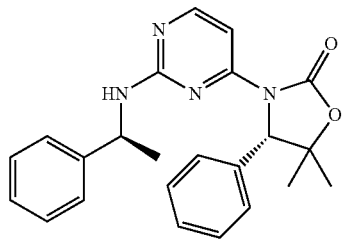 [SMILES: C[C@H](Nc1nccc(N2C(=O)OC(C)(C)[C@@H]2c2ccccc2)n1)c1ccccc1]

A solution of (S)-3-(2-chloropyrimidin-4-yl)-5,5-dimethyl-4-phenyloxazolidin-2-one (33.9 mg, 0.112 mmol) and (S)-(−)-1-phenylethanamine (0.15 mL, 1.2 mmol, 10 equiv) in DMSO (1 mL) was heated at 110° C. for 140 min. The reaction mixture was diluted with EtOAc (8 mL) and washed with water (30 mL). After separation, the aqueous phase was extracted with EtOAc (3×8 mL). Combined organics were dried over Na$_2$SO$_4$, filtered and concentrated. Silica gel column chromatography (EtOAc/Heptane 10 to 50%) provided (S)-5,5-dimethyl-4-phenyl-3-(2-((S)-1-phenylethylamino)pyrimidin-4-yl) oxazolidin-2-one (37.0 mg, white solid) in 85% yield. $^1$H NMR (400 MHz, CD$_3$OD) δ 8.06 (d, J=5.8 Hz, 1H), 7.43 (d, J=5.8 Hz, 1H), 7.31-7.24 (m, 3H), 7.19-7.11 (m, 5H), 7.01 (br s 2H), 5.48 (s, 1H), 4.86-4.80 (m, 1H), 1.65 (s, 3H), 1.43 (d, J=7.0 Hz, 3H), 0.98 (s, 3H); HRMS(B) m/z 389.1987 (M+H)$^+$.

Alternative Procedure

Example 113

(S)-3-(2-((S)-1-(4-hydroxyphenyl)ethylamino)pyrimidin-4-yl)-4-isopropyloxazolidin-2-one

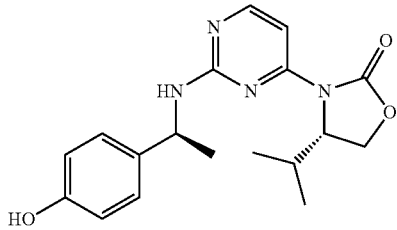

A solution of (S)-3-(2-chloropyrimidin-4-yl)-4-isopropyloxazolidin-2-one (42 mg, 0.17 mmol), (S)-4-(1-aminoethyl)phenol hydrochloride (107 mg, 0.616 mmol, 3.5 equiv) and iPr$_2$Net (0.121 mL, 0.695 mmol, 4.0 equiv) in DMSO (1 mL) was heated at 110° C. for 3 h and at 130° C. for additional 2 h. The reaction mixture was diluted with EtOAc (8 mL) and washed with water (30 mL). After separation, the aqueous phase was extracted with EtOAc (3×8 mL). Combined organics were dried over Na$_2$SO$_4$, filtered and concentrated. Silica gel column chromatography (EtOAc/Heptane 10 to 80%) provided (S)-3-(2-((S)-1-(4-hydroxyphenyl)ethylamino)pyrimidin-4-yl)-4-isopropyloxazolidin-2-one (3 mg) in 5% yield. $^1$H NMR (400 MHz, CD$_3$OD) δ 8.11 (d, J=5.8 Hz, 1H), 7.33 (d, J=5.8 Hz, 1H), 7.12 (d, J 8.1 Hz, 2H), 6.72-6.68 (m, 2H), 4.95 (q, J=6.9 Hz, 1H), 4.69-4.65 (m, 1H), 4.35-4.28 (m, 2H), 1.47 (d, J=7.1 Hz, 3H), 0.75 (br s, 3H), 0.62 (br s, 3H); HRMS(B) m/z 343.1776 (M+H)$^+$.

The compounds in Table 5 were prepared using methods similar to those described for the preparation of Examples 1 and 113.

TABLE 5

| | |
|---|---|
| 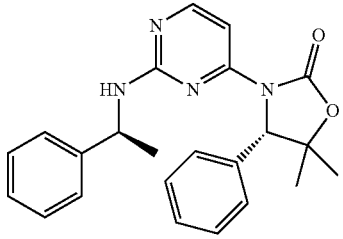 [SMILES: C[C@H](Nc1nccc(N2C(=O)OC(C)(C)[C@@H]2c2ccccc2)n1)c1ccccc1] | 1 |
| 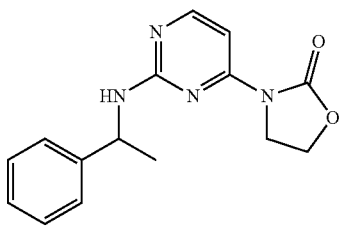 [SMILES: CC(Nc1nccc(N2CCOC2=O)n1)c1ccccc1] | 2 |
| 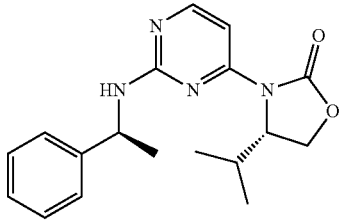 [SMILES: CC(C)[C@H]1COC(=O)N1c1ccnc(N[C@@H](C)c2ccccc2)n1] | 3 |
| 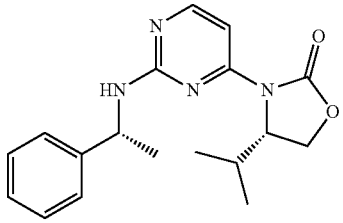 [SMILES: CC(C)[C@H]1COC(=O)N1c1ccnc(N[C@H](C)c2ccccc2)n1] | 4 |
| 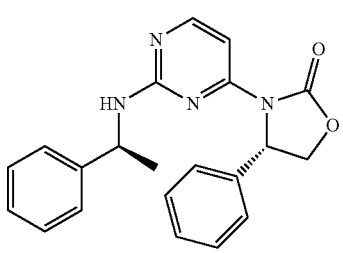 | 5 |
| 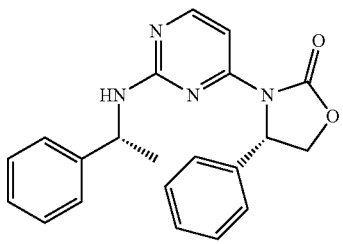 [SMILES: C[C@@H](Nc1nccc(N2C(=O)OC[C@@H]2c2ccccc2)n1)c1ccccc1] | 6 |

TABLE 5-continued
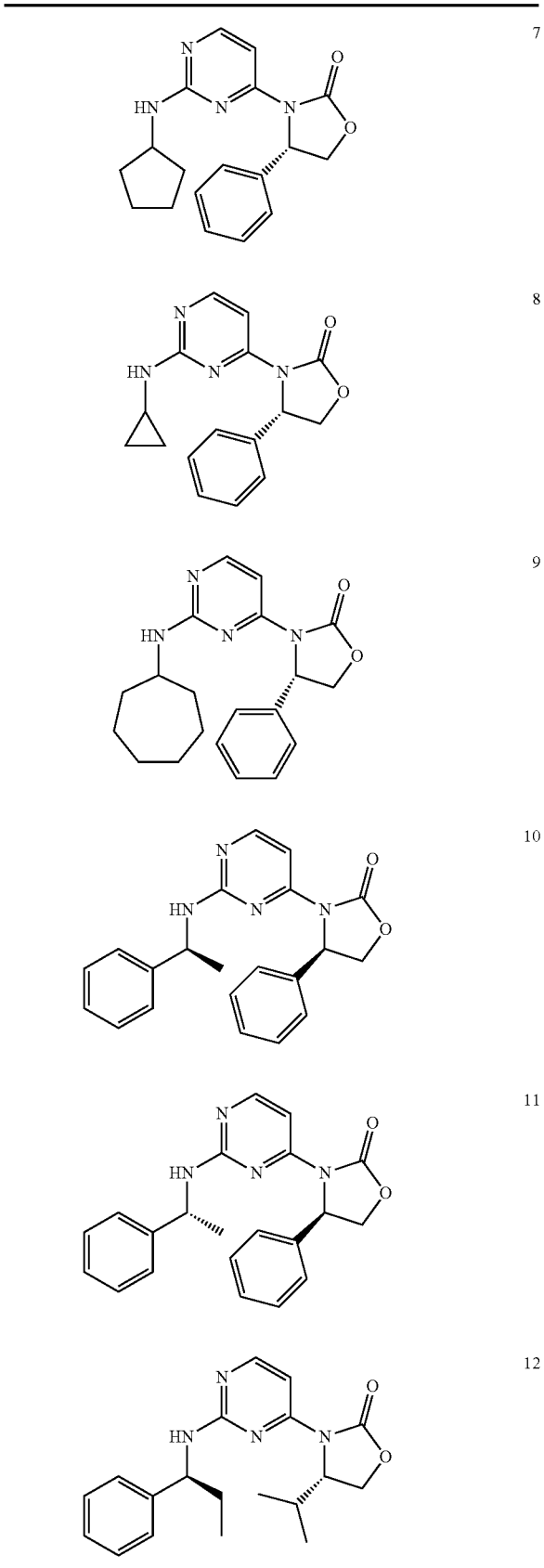
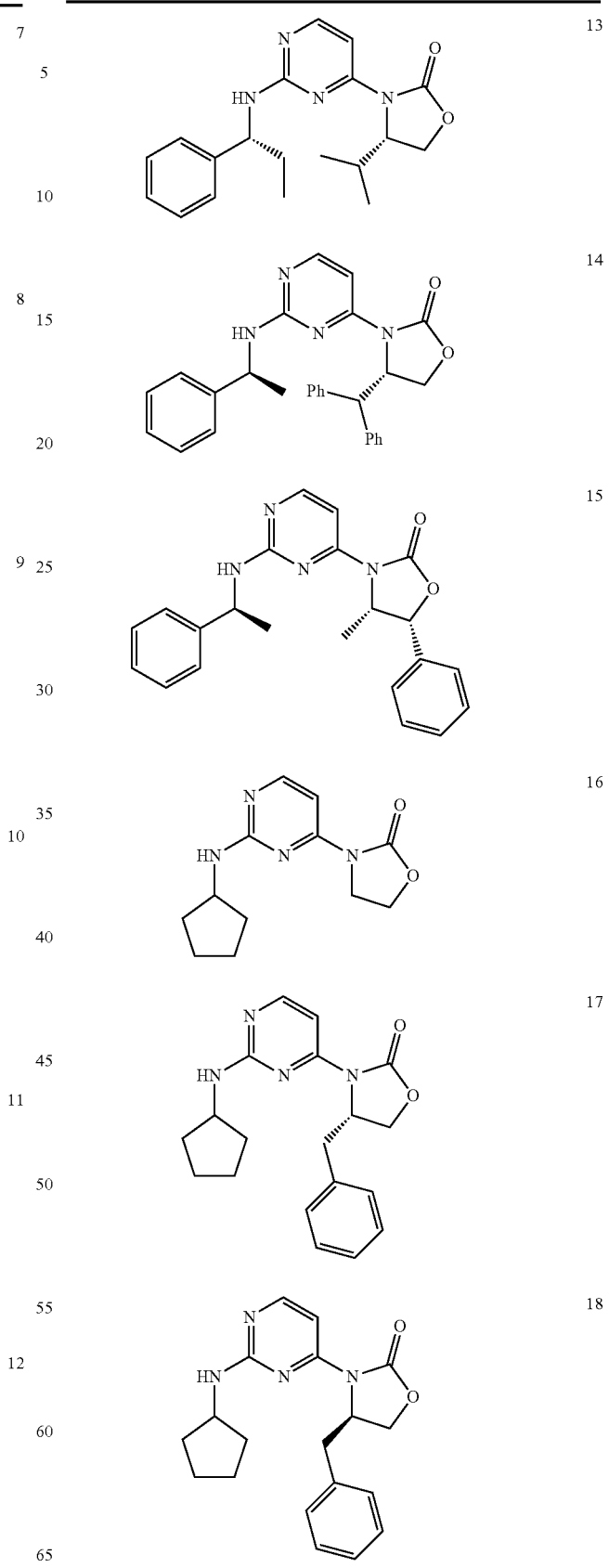

TABLE 5-continued
| | |
|---|---|
| 19 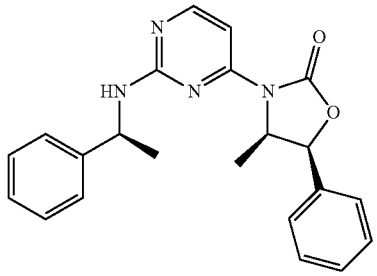 [SMILES: C[C@H](Nc1nccc(N2C(=O)O[C@@H](c3ccccc3)[C@H]2C)n1)c1ccccc1] | 25 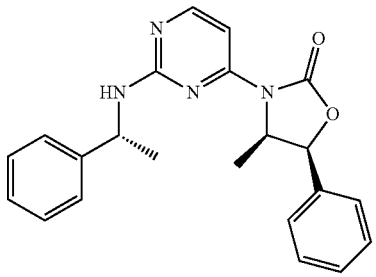 |
| 20 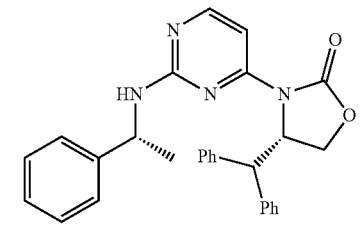 [SMILES: C[C@@H](Nc1nccc(N2C(=O)OC[C@@H]2C(c2ccccc2)c2ccccc2)n1)c1ccccc1] | 26 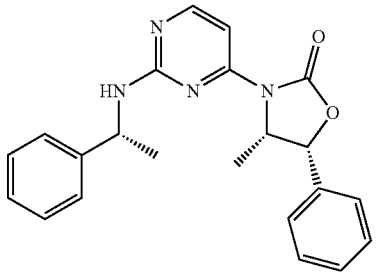 |
| 21 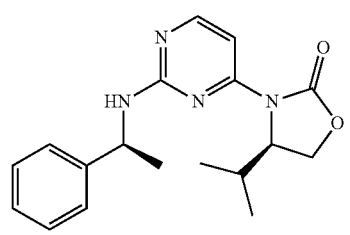 [SMILES: CC(C)[C@@H]1COC(=O)N1c1ccnc(N[C@@H](C)c2ccccc2)n1] | 27 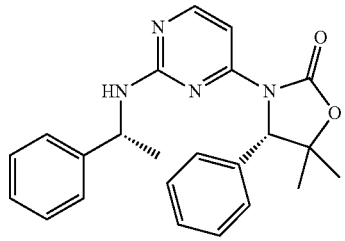 |
| 22 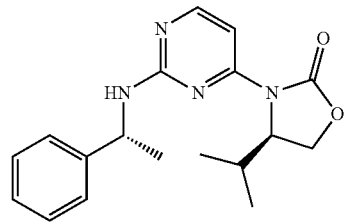 [SMILES: CC(C)[C@@H]1COC(=O)N1c1ccnc(N[C@H](C)c2ccccc2)n1] | 28 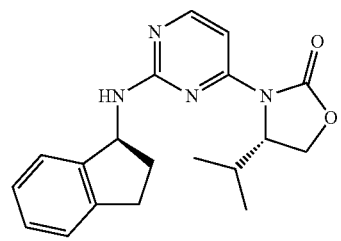 |
| 23 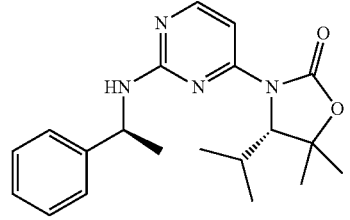 [SMILES: CC(C)[C@@H]1N(c2ccnc(N[C@@H](C)c3ccccc3)n2)C(=O)OC1(C)C] | 29 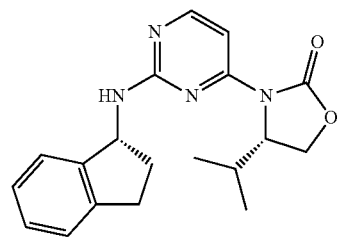 |
| 24 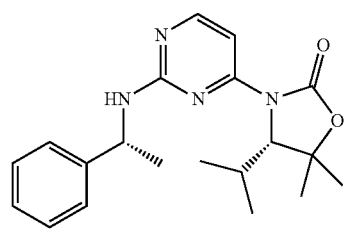 [SMILES: CC(C)[C@@H]1N(c2ccnc(N[C@H](C)c3ccccc3)n2)C(=O)OC1(C)C] | 30 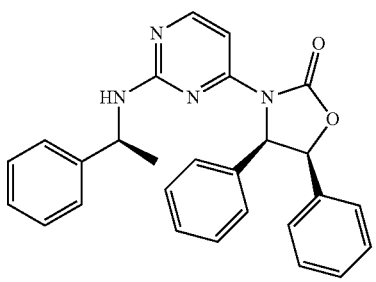 [SMILES: C[C@H](Nc1nccc(N2C(=O)O[C@@H](c3ccccc3)[C@H]2c2ccccc2)n1)c1ccccc1] |

TABLE 5-continued
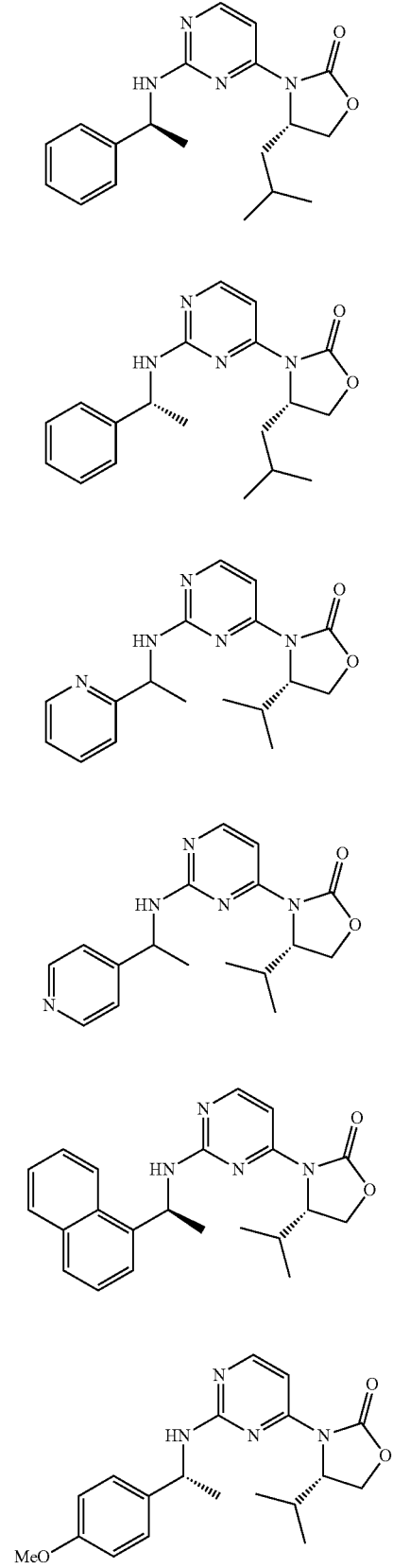
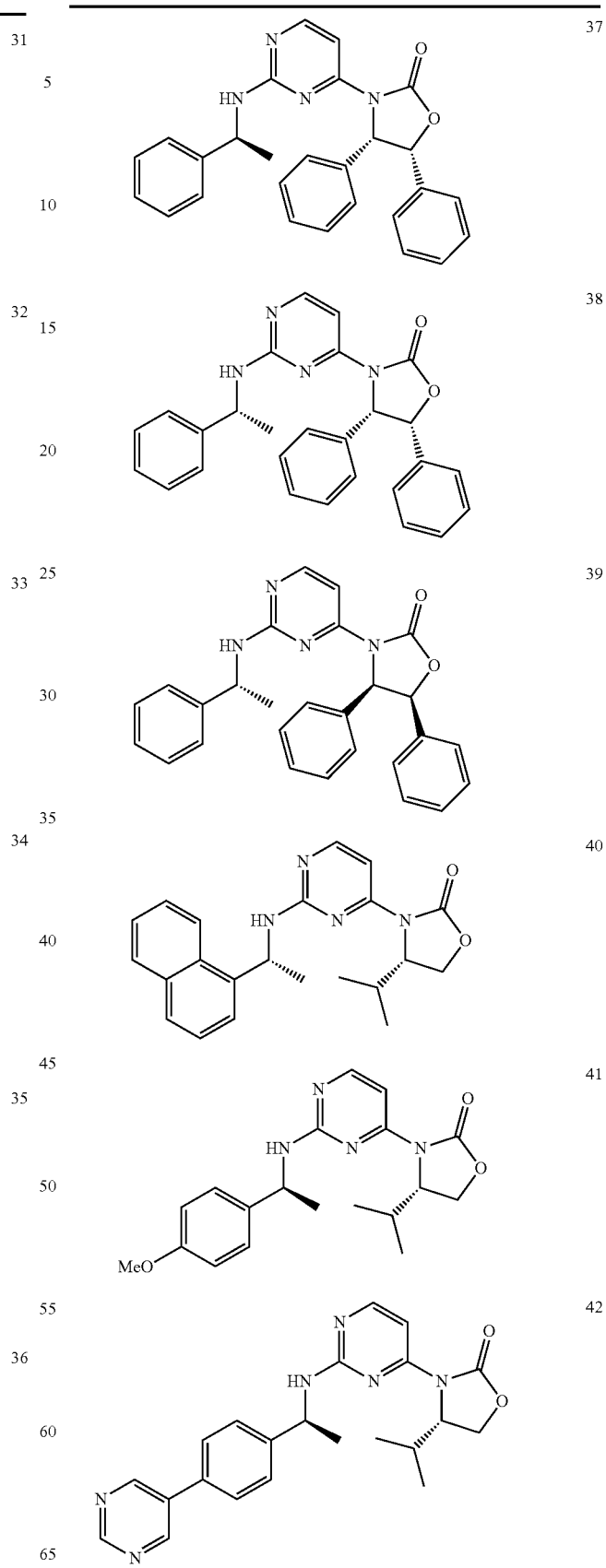

TABLE 5-continued
43 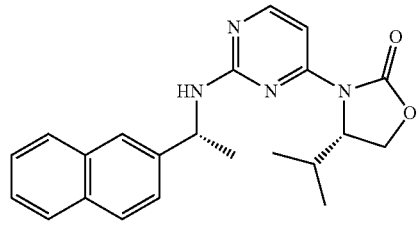 [SMILES: CC(C)[C@H]1COC(=O)N1c1ccnc(N[C@H](C)c2ccc3ccccc3c2)n1]
44 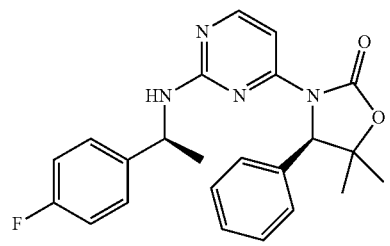 [SMILES: C[C@H](Nc1nccc(N2C(=O)OC(C)(C)[C@H]2c2ccccc2)n1)c1ccc(F)cc1]
45 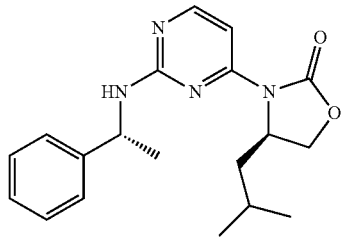 [SMILES: CC(C)C[C@@H]1COC(=O)N1c1ccnc(N[C@H](C)c2ccccc2)n1]
46 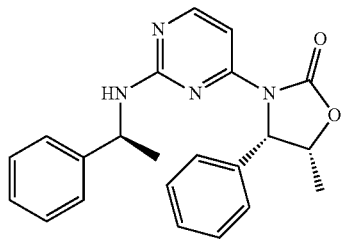 [SMILES: C[C@H](Nc1nccc(N2C(=O)O[C@H](C)[C@@H]2c2ccccc2)n1)c1ccccc1]
47 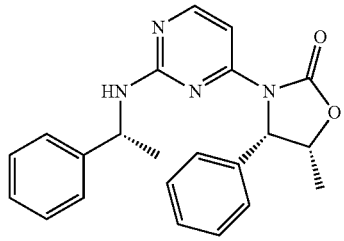 [SMILES: C[C@@H](Nc1nccc(N2C(=O)O[C@H](C)[C@@H]2c2ccccc2)n1)c1ccccc1]
48 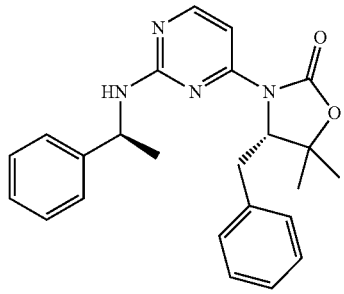 [SMILES: C[C@H](Nc1nccc(N2C(=O)OC(C)(C)[C@@H]2Cc2ccccc2)n1)c1ccccc1]
TABLE 5-continued
49 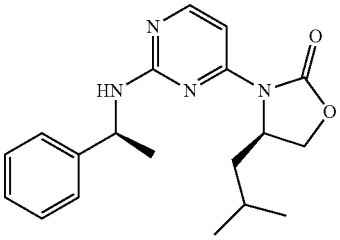 [SMILES: CC(C)C[C@@H]1COC(=O)N1c1ccnc(N[C@@H](C)c2ccccc2)n1]
50 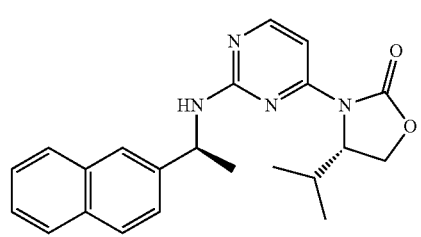 [SMILES: CC(C)[C@H]1COC(=O)N1c1ccnc(N[C@@H](C)c2ccc3ccccc3c2)n1]
51 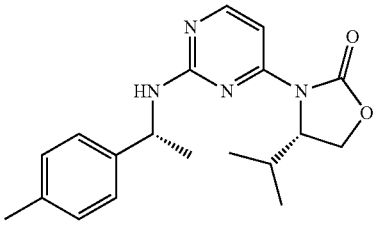 [SMILES: Cc1ccc([C@@H](C)Nc2nccc(N3C(=O)OC[C@@H]3C(C)C)n2)cc1]
52 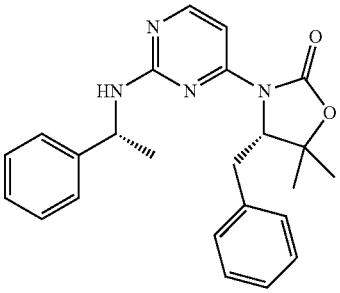 [SMILES: C[C@@H](Nc1nccc(N2C(=O)OC(C)(C)[C@@H]2Cc2ccccc2)n1)c1ccccc1]
53 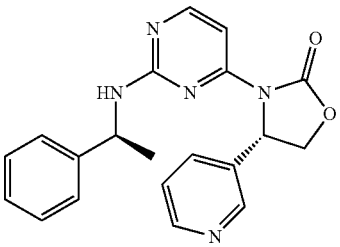 [SMILES: C[C@H](Nc1nccc(N2C(=O)OC[C@@H]2c2cccnc2)n1)c1ccccc1]
54 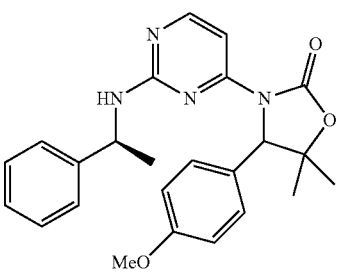 [SMILES: COc1ccc(C2N(c3ccnc(N[C@@H](C)c4ccccc4)n3)C(=O)OC2(C)C)cc1]

TABLE 5-continued
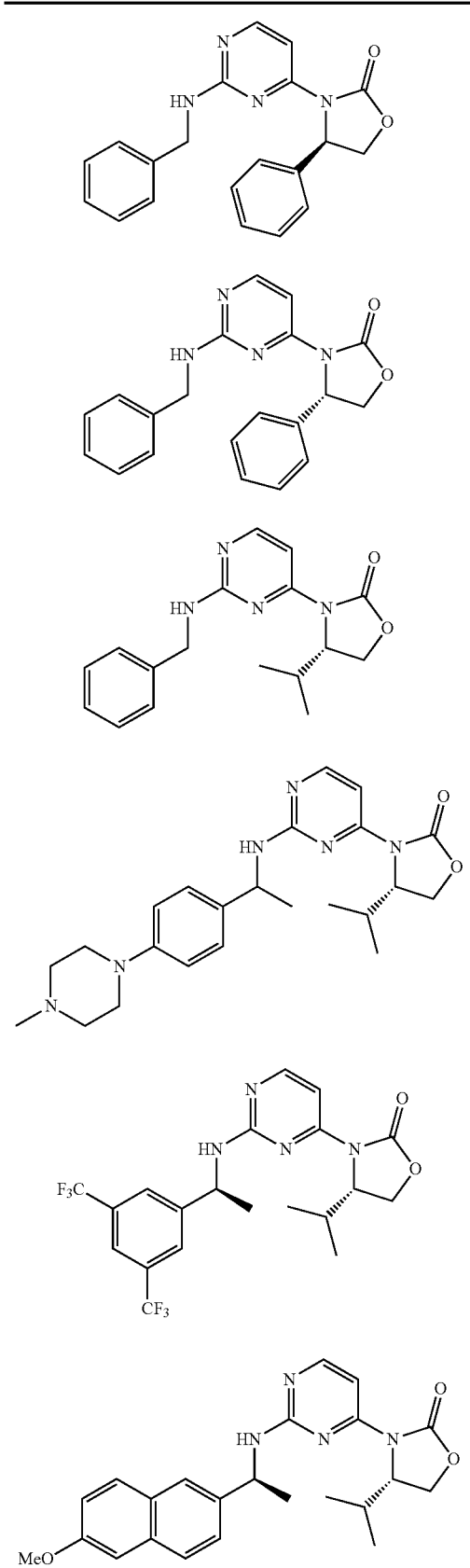
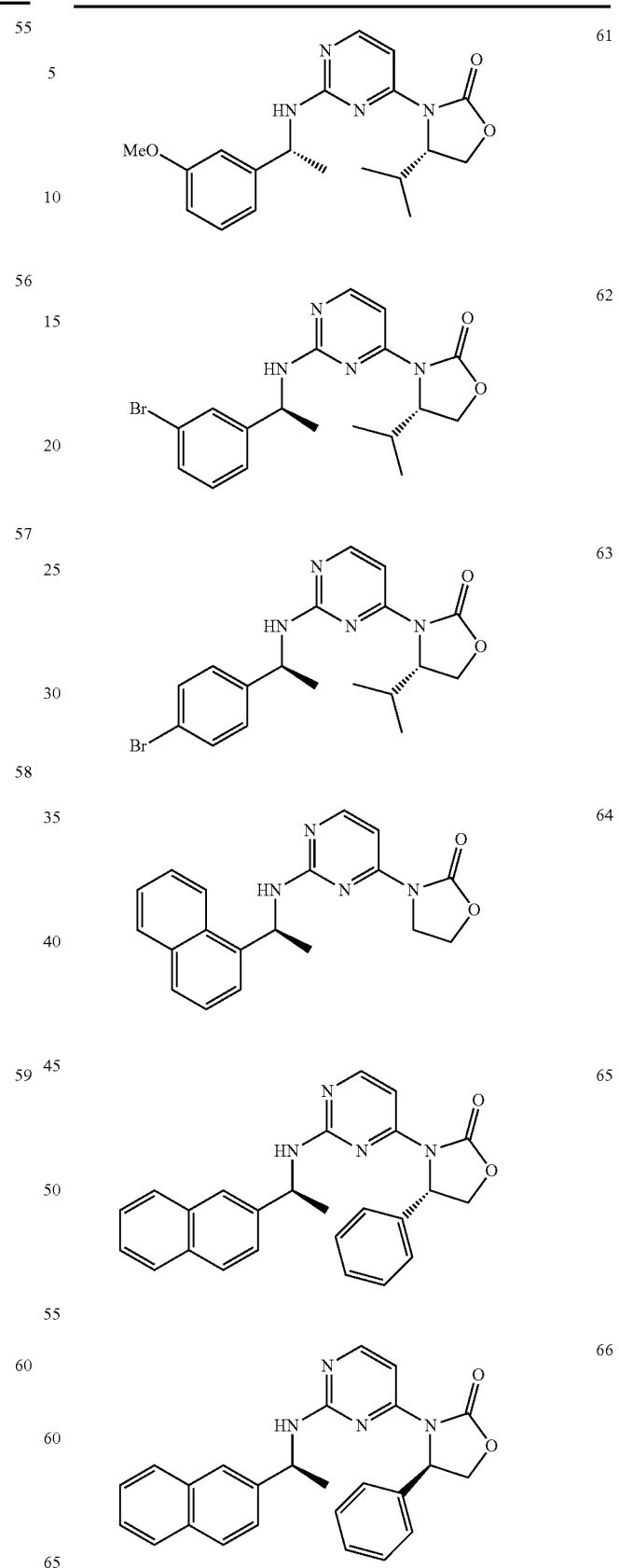

TABLE 5-continued
| | |
|---|---|
| 67 | 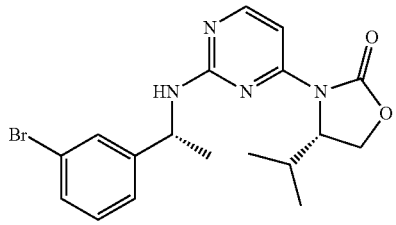 [SMILES: CC(C)[C@H]1COC(=O)N1c1ccnc(N[C@H](C)c2cccc(Br)c2)n1] |
| 68 | 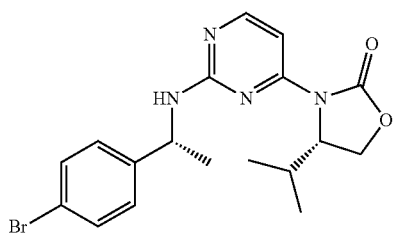 |
| 69 | 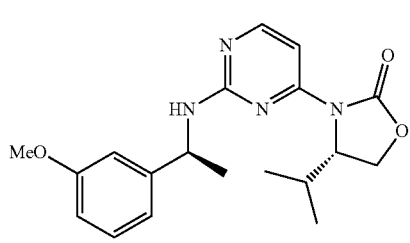 [SMILES: COc1cccc([C@H](C)Nc2nccc(N3C(=O)OC[C@@H]3C(C)C)n2)c1] |
| 70 | 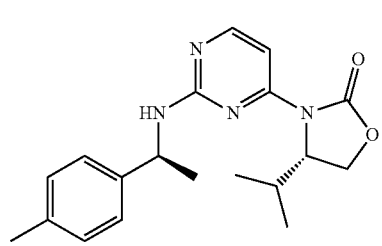 [SMILES: Cc1ccc([C@H](C)Nc2nccc(N3C(=O)OC[C@@H]3C(C)C)n2)cc1] |
| 71 | 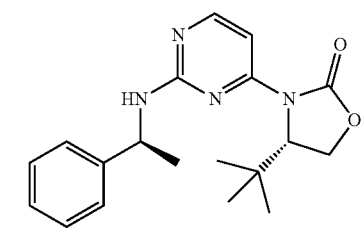 [SMILES: C[C@H](Nc1nccc(N2C(=O)OC[C@@H]2C(C)(C)C)n1)c1ccccc1] |
| 72 | 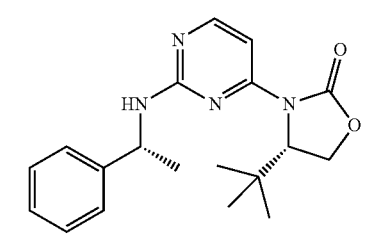 [SMILES: C[C@@H](Nc1nccc(N2C(=O)OC[C@@H]2C(C)(C)C)n1)c1ccccc1] |
TABLE 5-continued
| | |
|---|---|
| 73 | 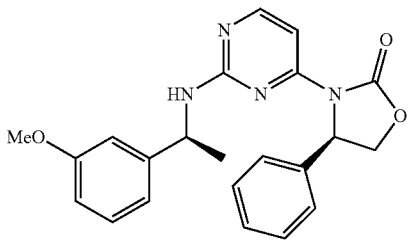 [SMILES: COc1cccc([C@H](C)Nc2nccc(N3C(=O)OC[C@H]3c3ccccc3)n2)c1] |
| 74 | 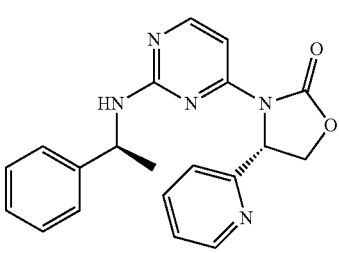 [SMILES: C[C@H](Nc1nccc(N2C(=O)OC[C@@H]2c2ccccn2)n1)c1ccccc1] |
| 75 | 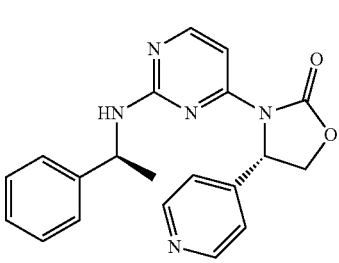 [SMILES: C[C@H](Nc1nccc(N2C(=O)OC[C@@H]2c2ccncc2)n1)c1ccccc1] |
| 76 | 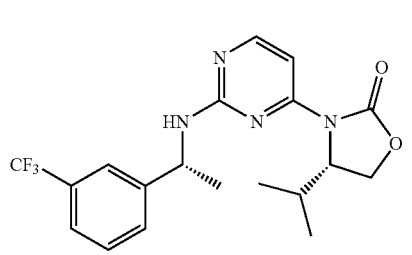 [SMILES: CC(C)[C@H]1COC(=O)N1c1ccnc(N[C@H](C)c2cccc(C(F)(F)F)c2)n1] |
| 77 | 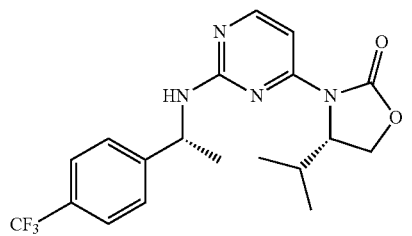 [SMILES: CC(C)[C@H]1COC(=O)N1c1ccnc(N[C@H](C)c2ccc(C(F)(F)F)cc2)n1] |
| 78 | 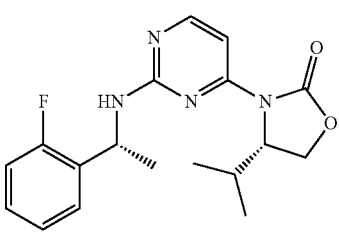 [SMILES: CC(C)[C@H]1COC(=O)N1c1ccnc(N[C@H](C)c2ccccc2F)n1] |

TABLE 5-continued
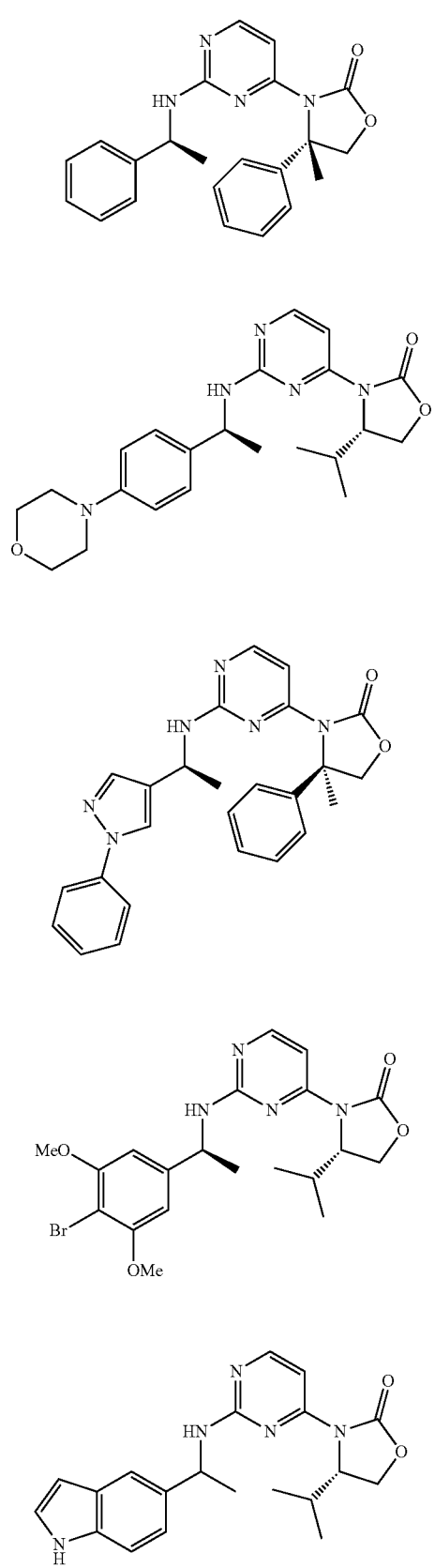
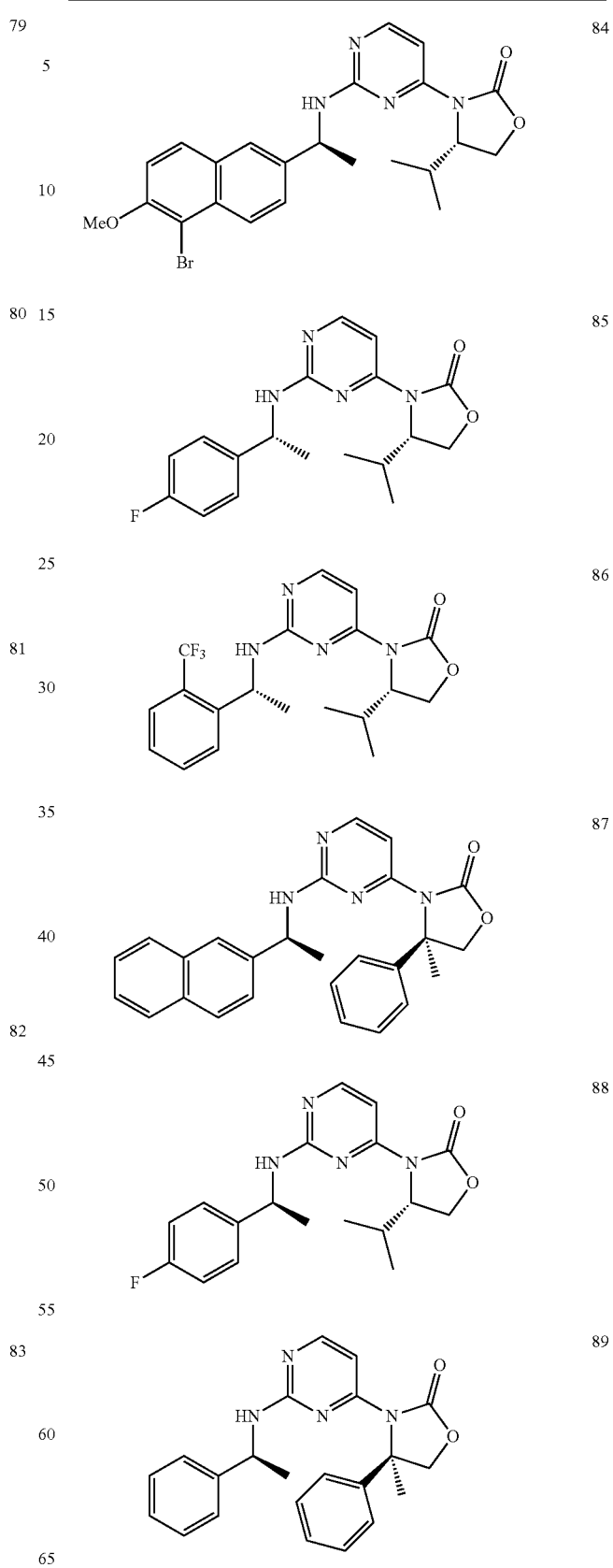

TABLE 5-continued
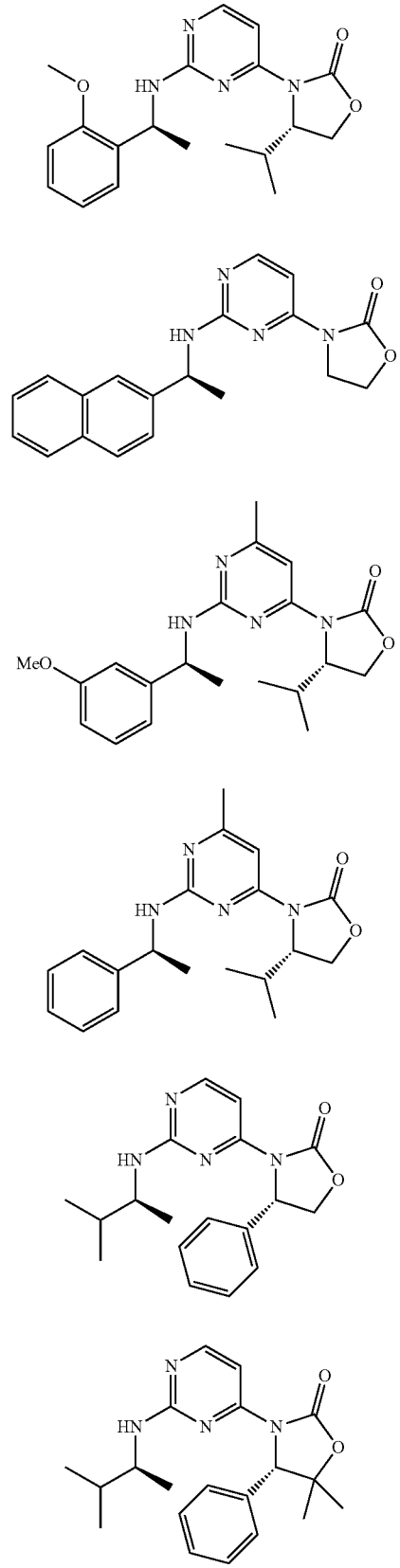
TABLE 5-continued
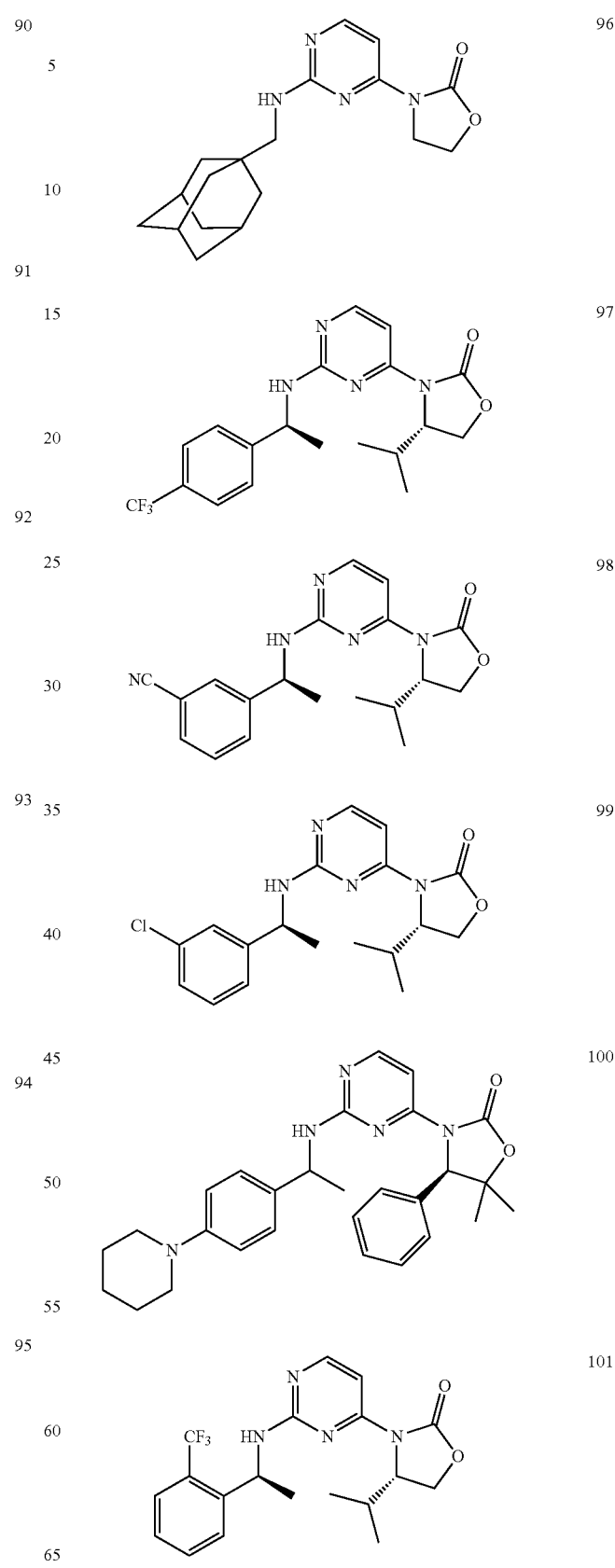

TABLE 5-continued
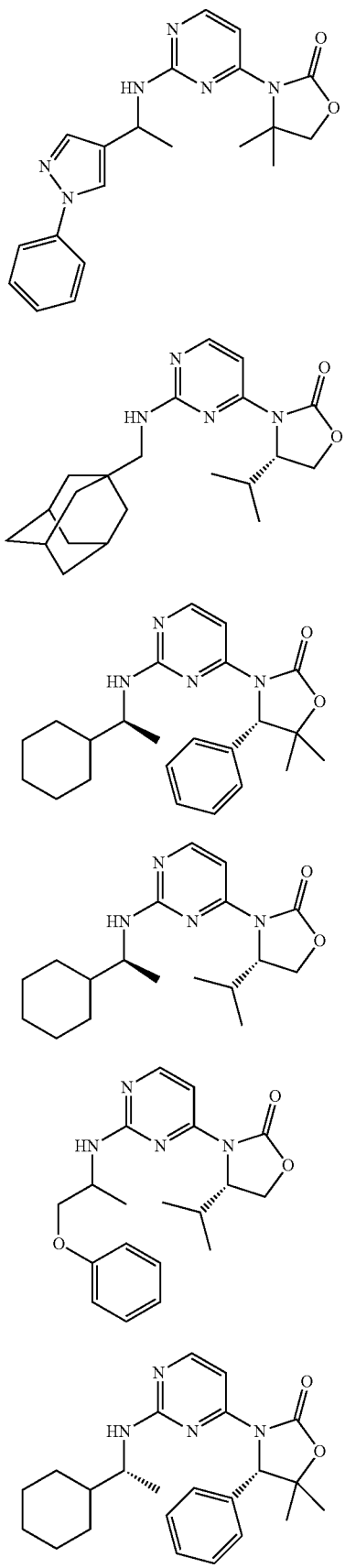
TABLE 5-continued
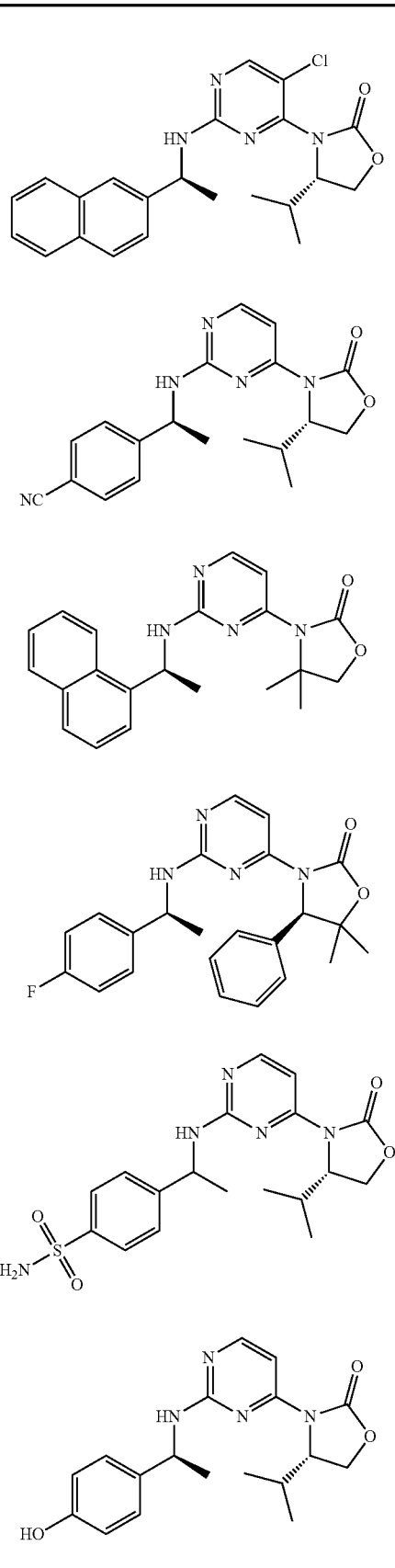

TABLE 5-continued
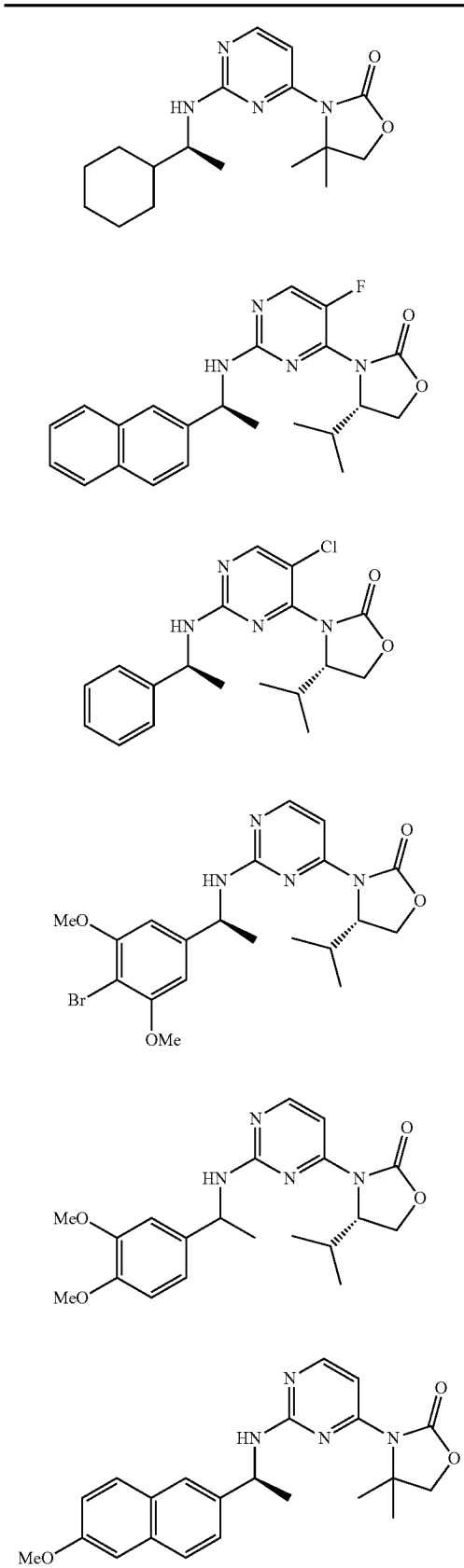
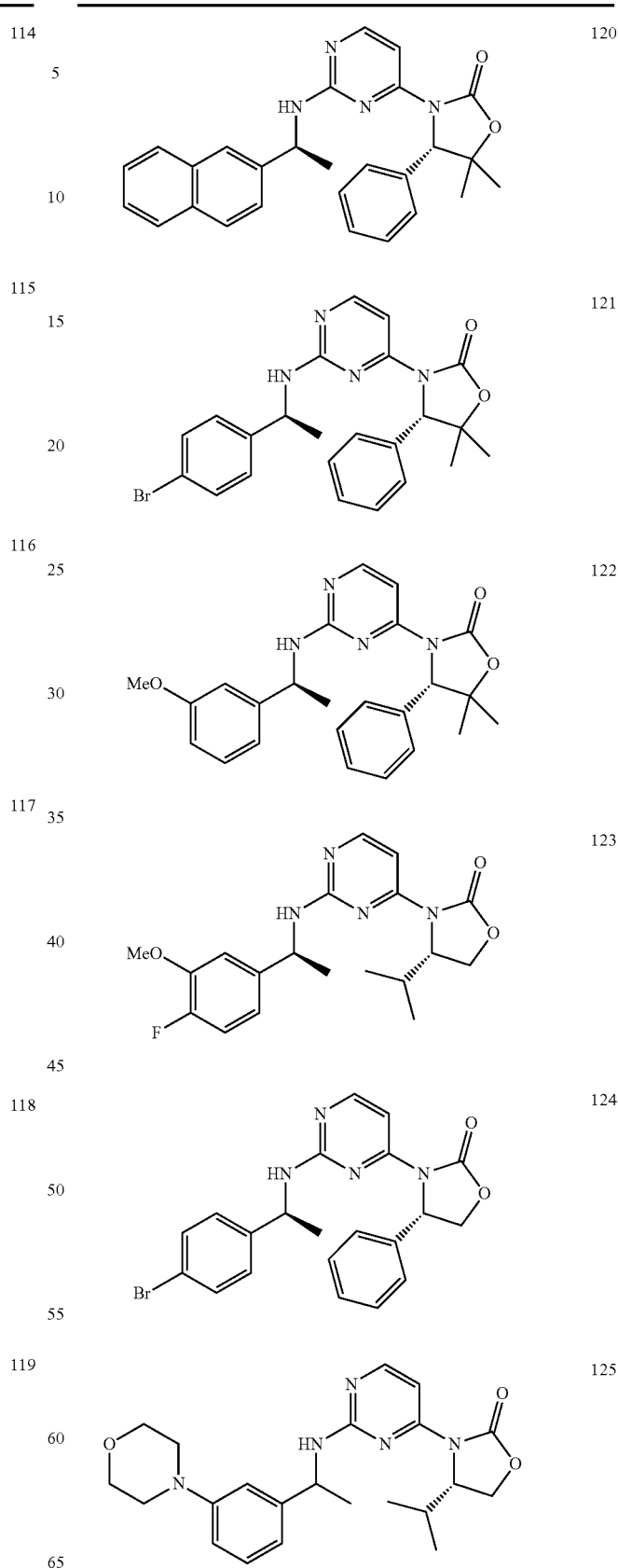

TABLE 5-continued
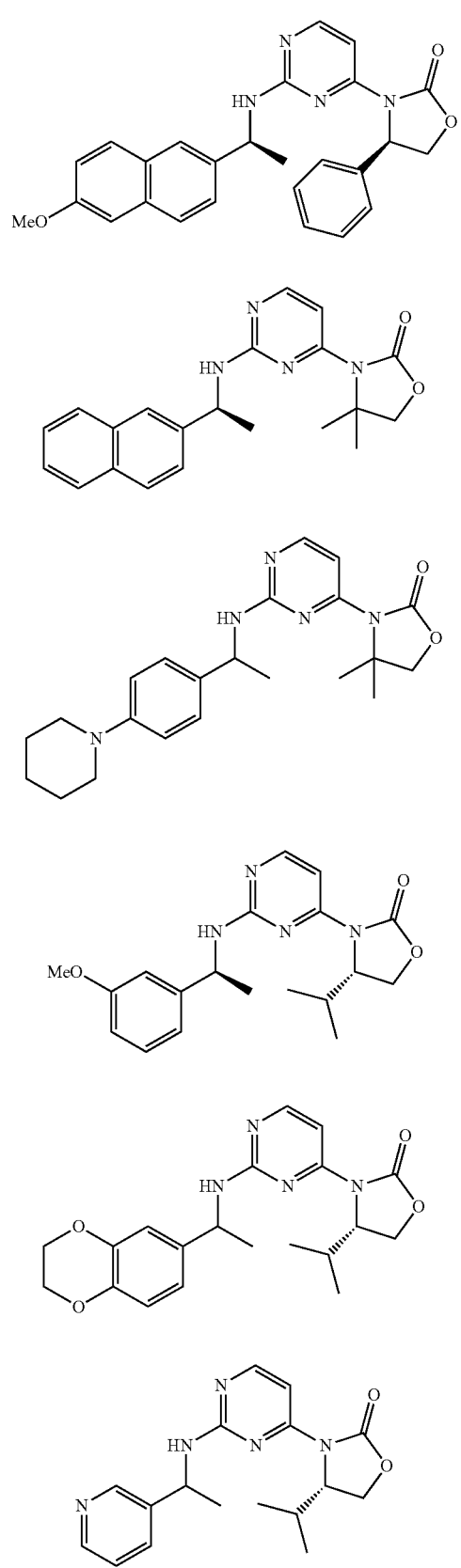
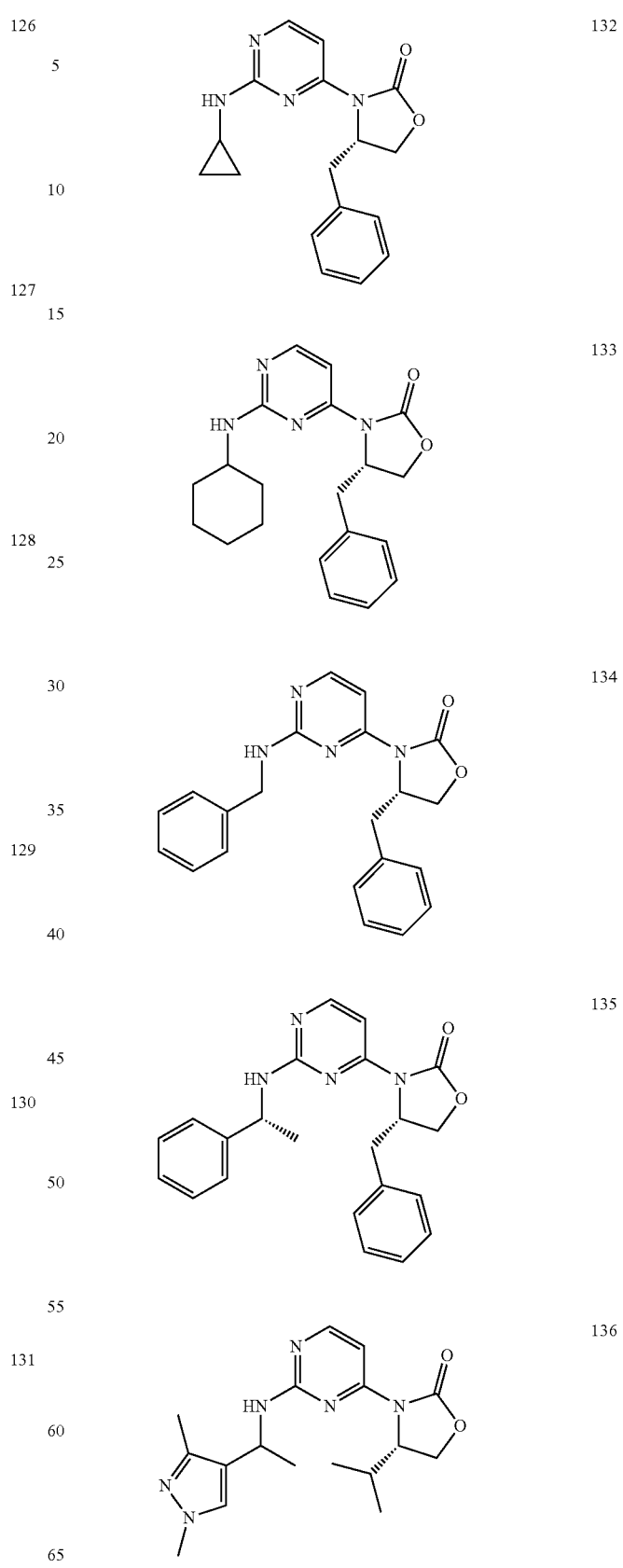

TABLE 5-continued
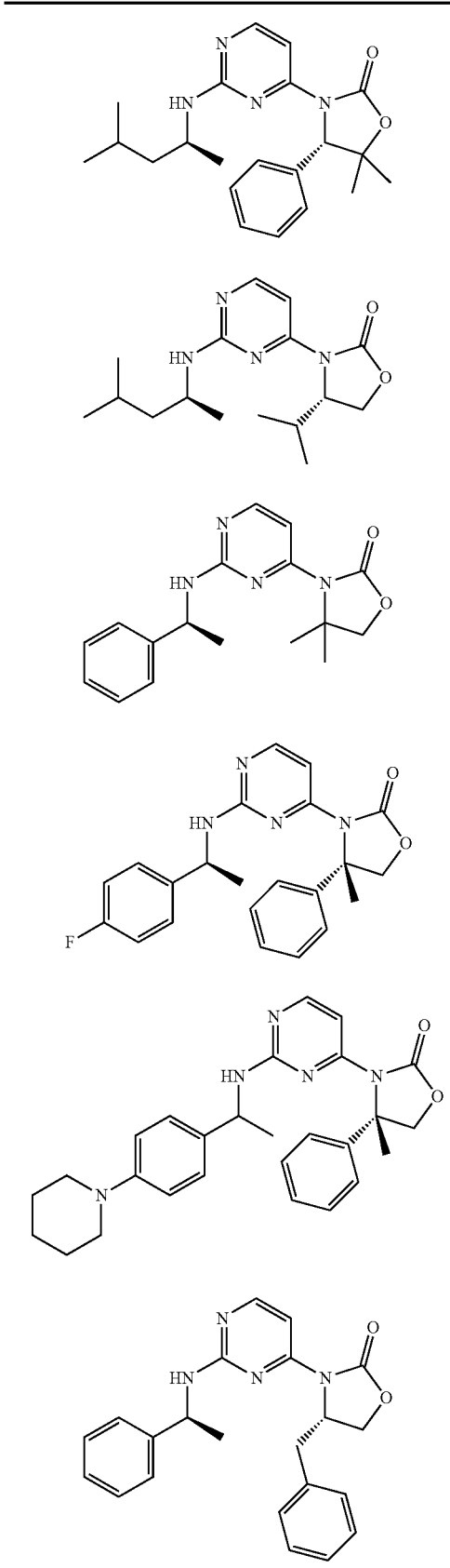
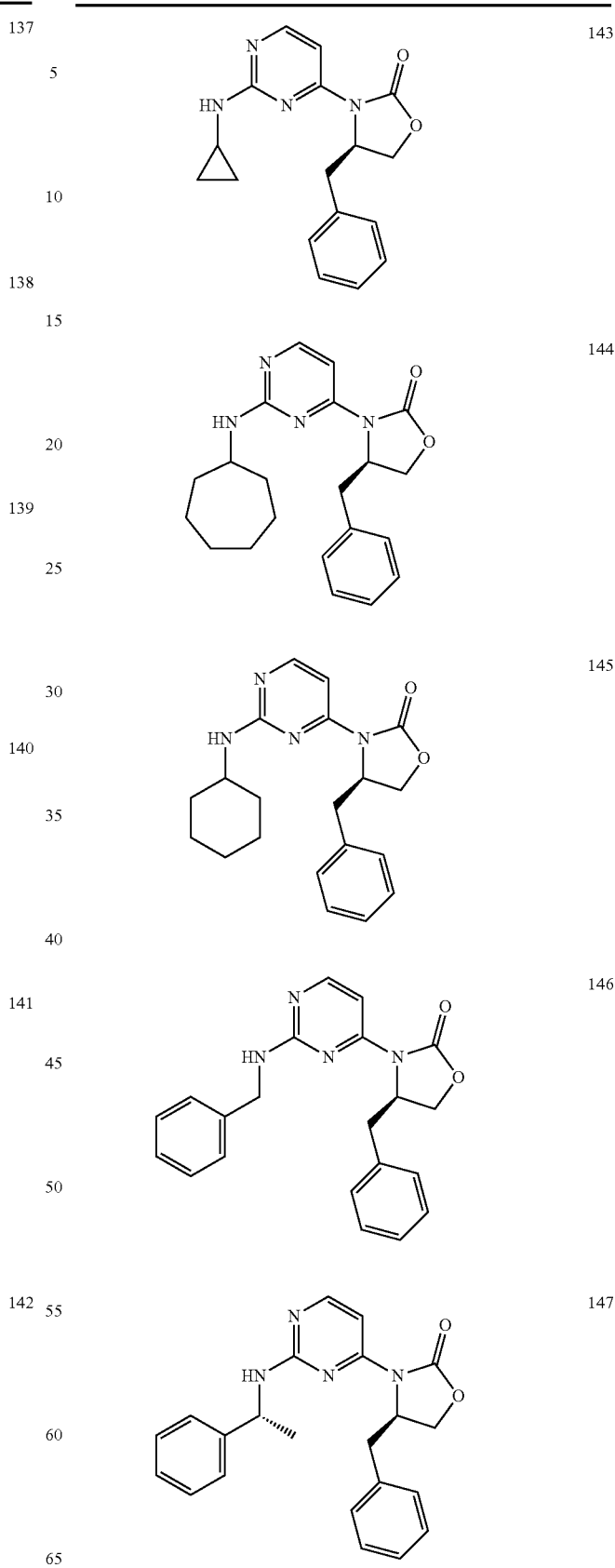

TABLE 5-continued
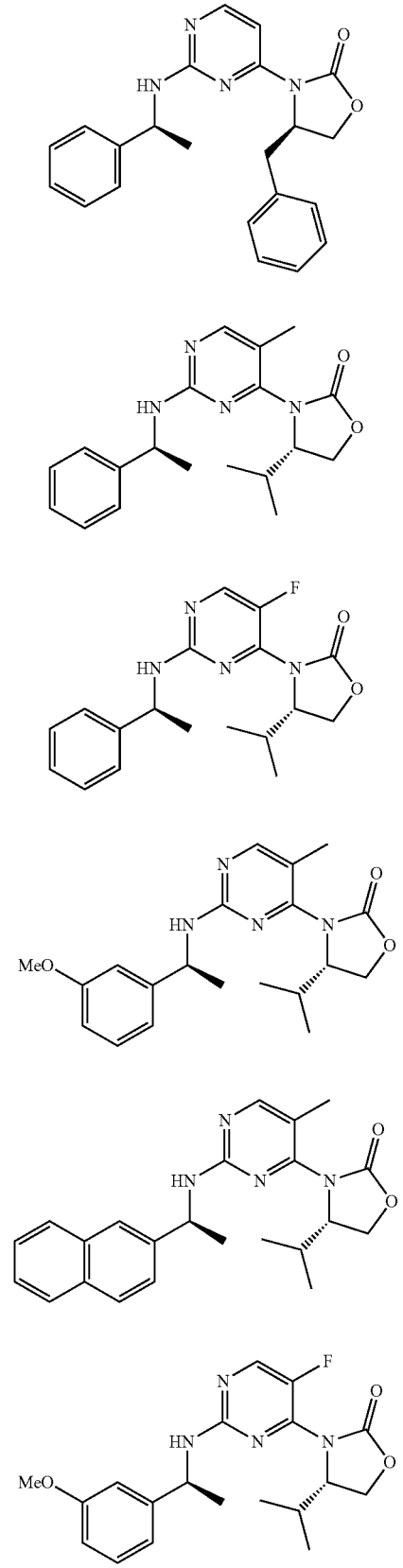
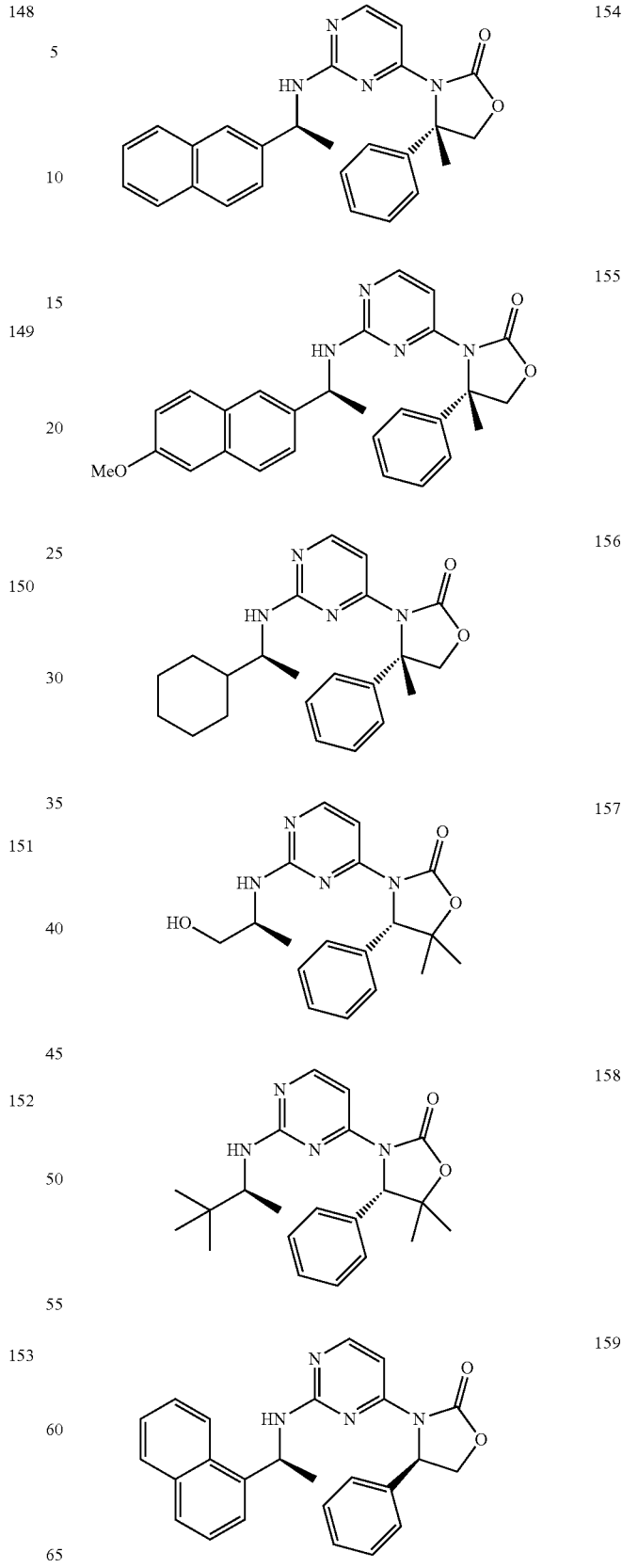

TABLE 5-continued

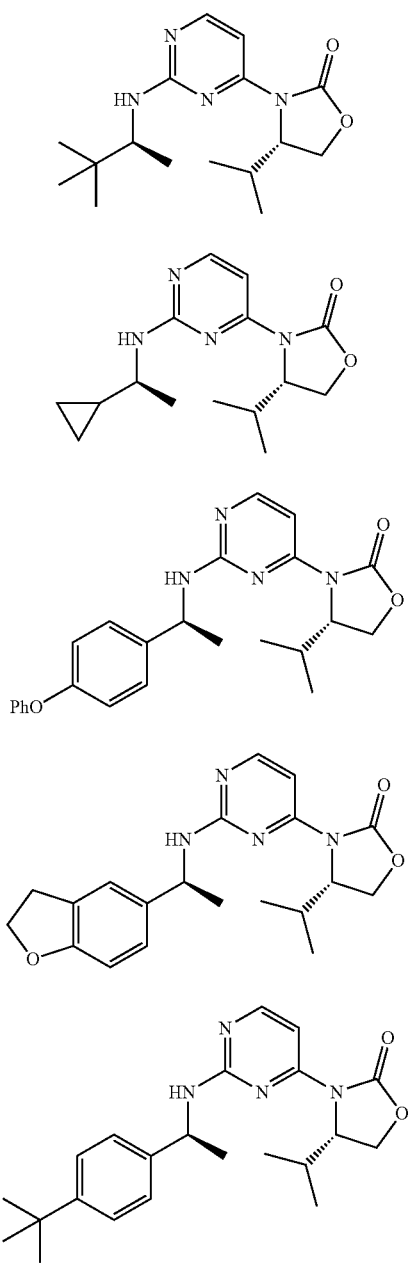

TABLE 5-continued

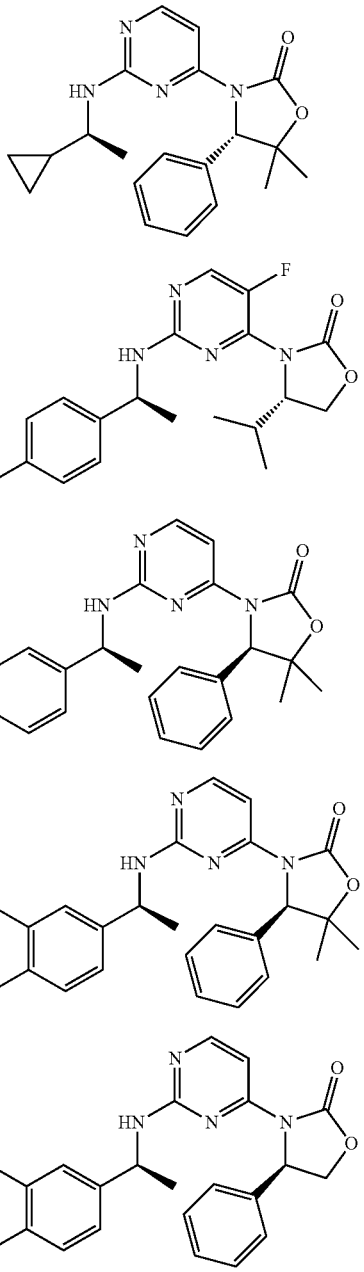

TABLE 6

Chemical name, NMR chemical shifts and LCMS signal for each compound listed in Table 5.

| Example: Name | $^1$H NMR (400 MHz, CD$_3$OD) δ ppm (other solvents described) | LCMS |
|---|---|---|
| 1: (S)-5,5-dimethyl-4-phenyl-3-(2-((S)-1-phenylethylamino)pyrimidin-4-yl)oxazolidin-2-one | 8.06 (d, J = 5.8 Hz, 1 H), 7.43 (d, J = 5.8 Hz, 1 H), 7.31-7.24 (m, 3 H), 7.19-7.11 (m, 5 H), 7.01 (br s 2 H), 5.48 (s, 1 H), 4.86-4.80 (m, 1 H), 1.65 (s, 3 H), 1.43 (d, J = 7.0 Hz, 3 H), 0.98 (s, 3 H) | HRMS(B) m/z 389.1987 (M + H)$^+$ |
| 2: 3-(2-(1-phenylethylamino)pyrimidin-4-yl)oxazolidin-2-one | 8.06 (d, J = 6.1 Hz, 1 H), 7.37-7.26 (m, 5 H), 7.22-7.15 (m, 1 H), 5.04 (q, J = 6.9 Hz, 1 H), 4.43 (sxt, J = 8.2 Hz, 2 H), 4.17 | HRMS(B) m/z 284.1275 |

TABLE 6-continued

Chemical name, NMR chemical shifts and LCMS
signal for each compound listed in Table 5.

| Example: Name | $^1$H NMR (400 MHz, CD$_3$OD) δ ppm (other solvents described) | LCMS |
|---|---|---|
|  | (td, J = 9.8, 7.1 Hz, 1 H), 3.92 (br s, 1 H), 1.50 (d, J = 7.1 Hz, 3 H) | M$^+$ |
| 3: (S)-4-isopropyl-3-(2-((S)-1-phenylethylamino)pyrimidin-4-yl)oxazolidin-2-one | 8.12 (d, J = 5.6 Hz, 1 H), 7.34-7.26 (m, 5 H), 7.22-7.13 (m, 1 H), 5.04 (q, J = 7.1 Hz, 1 H), 4.64 (br s, 1 H), 4.34-4.26 (m, 2 H), 1.85 (br s, 1 H), 1.50 (d, J = 7.1 Hz, 3 H), 0.70 (br s, 3 H), 0.57 (br s, 3 H) | HRMS(B) m/z 326.1745 M$^+$ |
| 4: (S)-4-isopropyl-3-(2-((R)-1-phenylethylamino)pyrimidin-4-yl)oxazolidin-2-one | 8.10 (d, J = 5.8 Hz, 1 H), 7.35-7.27 (m, 5 H), 7.23-7.15 (m, 1 H), 4.96 (q, J = 6.9 Hz, 1 H), 4.44 (br s, 1 H), 4.34-4.23 (m, 2 H), 2.72-2.58 (m, 1 H), 1.51 (d, J = 6.6 Hz, 3 H), 0.99 (d, J = 7.1 Hz, 3 H), 0.85 (d, J = 7.1 Hz, 3 H) | HRMS(B) m/z 326.1746 M$^+$ |
| 5: (S)-4-phenyl-3-(2-((S)-1-phenylethylamino)pyrimidin-4-yl)oxazolidin-2-one | 8.07 (d, J = 5.6 Hz, 1 H), 7.38 (d, J = 5.6 Hz, 1 H), 7.28-7.05 (m, 10 H), 5.84 (dd, J = 8.6, 3.5 Hz, 2 H), 4.88 (q, J = 6.8 Hz, 1 H), 4.83-4.79 (m, 1 H), 4.24 (dd, J = 8.6, 3.5 Hz, 1 H), 1.44 (d, J = 6.8 Hz, 3 H) | HRMS(B) m/z 361.1666 (M + H)$^+$ |
| 6: (S)-4-phenyl-3-(2-((R)-1-phenylethylamino)pyrimidin-4-yl)oxazolidin-2-one | 8.08 (d, J = 5.8 Hz, 1 H), 7.43-7.18 (m, 11 H), 5.55 (br s, 1H), 4.74 (t, J = 8.6 Hz, 1 H), 4.63 (br s, 1 H), 4.18 (dd, J = 8.3, 3.8 Hz, 1 H), 1.19 (d, J = 6.7 Hz, 3 H) | HRMS(B) m/z 360.1591 M$^+$ |
| 7: (S)-3-(2-(cyclopentylamino)pyrimidin-4-yl)-4-phenyloxazolidin-2-one | 8.06 (d, J = 6.1 Hz, 1 H), 7.39-7.28 (m, 6 H), 5.80 (dd, J = 8.8, 3.8 Hz, 1 H), 4.83-4.80 (m, 1 H), 4.20 (dd, J = 8.6, 4.0 Hz, 1 H), 3.79 (br m, 1 H), 1.90-1.99 (m, 1 H), 1.72-1.53 (m, 4 H), 1.49-1.35 (m, 3 H) | HRMS(B) m/z 325.1671 (M + H)$^+$ |
| 8: (S)-3-(2-(cyclopropylamino)pyrimidin-4-yl)-4-phenyloxazolidin-2-one | 8.10 (d, J = 5.6 Hz, 1 H), 7.44 (d, J = 5.6 Hz, 1 H), 7.36-7.26 (m, 5 H), 5.86 (dd, J = 8.6, 3.5 Hz, 1 H), 4.83-4.80 (m, 1 H), 4.26 (dd, J = 8.6, 3.5 Hz, 1 H), 2.40 (br s, 1 H), 0.64-0.71 (m, 1 H), 0.54 (br s, 1 H), 0.44-0.37 (m, 1 H), 0.25 (br s, 1 H) | HRMS(B) m/z 297.1356 (M + H)$^+$ |
| 9: (S)-3-(2-(cycloheptylamino)pyrimidin-4-yl)-4-phenyloxazolidin-2-one | 8.06 (d, J = 6.1 Hz, 1 H), 7.38-7.27 (m, 6 H), 5.82 (dd, J = 8.6, 3.5 Hz, 1 H), 4.83-4.80 (m, 1 H), 4.21 (dd, J = 8.6, 3.5 Hz, 1 H), 3.57 (br s, 1 H), 1.90 (br s, 1 H), 1.69-1.42 (m, 8 H), 1.32-1.18 (m, 3 H) | HRMS(B) m/z 353.1961 (M + H)$^+$ |
| 10: (R)-4-phenyl-3-(2-((S)-1-phenylethylamino)pyrimidin-4-yl)oxazolidin-2-one | 8.08 (d, J = 5.8 Hz, 1 H), 7.43-7.18 (m, 11 H), 5.54 (br s, 1H), 4.74 (t, J = 8.6 Hz, 1 H), 4.62 (br s, 1 H), 4.18 (dd, J = 8.8, 3.8 Hz, 1 H), 1.19 (d, J = 6.6 Hz, 3 H) | HRMS(B) m/z 361.1712 (M + H)$^+$ |
| 11: (R)-4-phenyl-3-(2-((R)-1-phenylethylamino)pyrimidin-4-yl)oxazolidin-2-one | 8.07 (d, J = 5.8 Hz, 1 H), 7.38 (d, J = 5.8 Hz, 1 H), 7.28-7.05 (m, 10 H), 5.84 (dd, J = 8.3, 3.3 Hz, 1 H), 4.88 (q, J = 6.9 Hz, 1 H), 4.82-4.78 (m, 1 H), 4.24 (dd, J = 8.6, 3.5 Hz, 1 H), 1.44 (d, J = 6.9 Hz, 3 H) | HRMS(B) m/z 361.1661 (M + H)$^+$ |
| 12: (S)-4-isopropyl-3-(2-((S)-1-phenylpropylamino)pyrimidin-4-yl)oxazolidin-2-one | 8.11 (d, J = 5.6 Hz, 1 H), 7.33-7.26 (m, 5 H), 7.22-7.15 (m, 1 H), 4.83-4.79 (m, 1 H), 4.68 (br s, 1 H), 4.36-4.28 (m, 2 H), 1.84 (quin, J = 7.3 Hz, 2 H), 0.99 (t, J = 7.3 Hz, 3 H), 0.76 (br s, 3 H), 0.59 (br s, 3 H) | HRMS(B) m/z 341.1974 (M + H)$^+$ |
| 13: (S)-4-isopropyl-3-(2-((R)-1-phenylpropylamino)pyrimidin-4-yl)oxazolidin-2-one | 8.09 (d, J = 5.8 Hz, 1 H), 7.34-7.27 (m, 5 H), 7.24-7.16 (m, 1 H), 4.74 (t, J = 6.8 Hz, 1 H), 4.52 (br s, 1 H), 4.36-4.26 (m, 2 H), 2.66 (td, J = 6.9, 3.8 Hz, 1 H), 1.95-1.75 (m, 2 H), 1.02 (d, J = 7.1 Hz, 3 H), 0.96 (t, J = 7.3 Hz, 3 H), 0.86 (d, J = 7.1 Hz, 3 H) | HRMS(B) m/z 341.1976 (M + H)$^+$ |
| 14: provided (S)-4-benzhydryl-3-(2-((S)-1-phenylethylamino)pyrimidin-4-yl)oxazolidin-2-one | 8.09 (d, J = 5.8 Hz, 1 H), 7.32-7.23 (m, 3 H), 7.20-7.16 (br m, 6 H), 7.00 (br s, 5 H), 6.72 (br s, 2 H), 5.76-5.68 (m, 1 H), 5.04 (q, J = 7.1 Hz, 1 H), 4.59 (t, J = 8.8 Hz, 1 H), 4.50 (br s, 1H), 4.47 (dd, J = 9.1, 2.5 1H), 1.44 (d, J = 7.1 Hz, 3 H) | HRMS(B) m/z 451.2126 (M + H)$^+$ |
| 15: (4S,5R)-4-methyl-5-phenyl-3-(2-((S)-1-phenylethylamino)pyrimidin-4-yl)oxazolidin-2-one | 8.12 (d, J = 5.8 Hz, 1 H), 7.45-7.30 (m, 8 H), 7.20 (t, J = 7.6 Hz, 2 H), 7.10-7.07 (m, 1 H), 5.80 (t, J = 7.1 Hz, 1 H), 5.10-4.92 (m, 2 H), 1.49 (d, J = 7.0 Hz, 3 H), 0.37 (br s, 3 H) | HRMS(B) m/z 375.1823 (M + H)$^+$ |
| 16: 3-(2-(cyclopentylamino)pyrimidin-4-yl)oxazolidin-2-one | 8.07 (d, J = 5.7 Hz, 1 H), 7.32 (d, J = 5.8 Hz, 1 H), 4.48 (t, J = 8.1 Hz, 2 H), 4.22-4.16 (m, 3 H), 2.02 (dq, J = 12, 6.1 Hz, 2 | HRMS(B) m/z 248.1275 |

TABLE 6-continued

Chemical name, NMR chemical shifts and LCMS
signal for each compound listed in Table 5.

| Example: Name | ¹H NMR (400 MHz, CD₃OD) δ ppm (other solvents described) | LCMS |
|---|---|---|
| | H), 1.70-1.80 (m, 2 H), 1.67-1.47 (m, 4 H) | M⁺ |
| 17: (S)-4-benzyl-3-(2-(cyclopentylamino)pyrimidin-4-yl)oxazolidin-2-one | 8.13 (d, J = 5.8 Hz, 1 H), 7.35-7.21 (m, 6 H), 5.14-5.04 (m, 1 H), 4.36 (t, J = 8.4 Hz, 1 H), 4.33-4.24 (m, 2 H), 3.37-3.33 (m, 1 H), 3.06 (dd, J = 13, 8.3 Hz, 1 H), 2.11-1.98 (m, 2 H), 1.86-1.71 (m, 2 H), 1.70-1.53 (m, 4H) | HRMS(B) m/z 338.1749 M⁺ |
| 18: (R)-4-benzyl-3-(2-(cyclopentylamino)pyrimidin-4-yl)oxazolidin-2-one | 8.13 (d, J = 5.6 Hz, 1 H), 7.35-7.21 (m, 6 H), 5.14-5.05 (m, 1 H), 4.36 (t, J = 8.5 Hz, 1 H), 4.32-4.26 (m, 2 H), 3.37-3.33 (m, 1 H), 3.06 (dd, J = 13, 8.3 Hz, 1 H), 2.13-1.99 (m, 2 H), 1.85-1.71 (m, 2 H), 1.70-1.51 (m, 4 H) | HRMS(B) m/z 338.1748 M⁺ |
| 19: (4R,5S)-4-methyl-5-phenyl-3-(2-((S)-1-phenylethylamino)pyrimidin-4-yl)oxazolidin-2-one | 8.11 (d, J = 5.8 Hz, 1 H), 7.48-7.28 (m, 10 H), 7.24-7.21 (m, 1 H), 5.70 (d, J = 6.8 Hz, 1 H), 4.96-4.90 (m, 1 H), 4.65 (br s, 1 H)1.49 (d, J = 7.1 Hz, 3 H), 0.97 (d, J = 6.6 Hz, 3 H) | HRMS(B) m/z 375.1824 (M + H)⁺ |
| 20: (S)-4-benzhydryl-3-(2-((R)-1-phenylethylamino)pyrimidin-4-yl)oxazolidin-2-one | 8.13 (d, J = 5.8 Hz, 1 H), 7.47-7.40 (m, 2 H), 7.35-7.22 (m, 5 H), 7.19-7.10 (m, 5 H), 7.01-6.99 (m, 2 H), 6.89 (br s, 2 H), 5.26 (br s, 1 H), 5.09 (br s, 1 H), 4.76 (br s, 1 H), 4.54-4.44 (m, 2 H), 1.37 (d, J = 7.1 Hz, 3 H) | HRMS(B) m/z 451.2134 (M + H)⁺ |
| 21: (R)-4-isopropyl-3-(2-((S)-1-phenylethylamino)pyrimidin-4-yl)oxazolidin-2-one | 8.10 (d, J = 5.8 Hz, 1 H), 7.35-7.27 (m, 5 H), 7.20-7.17 (m, 1 H), 4.96 (q, J = 6.7 Hz, 1 H), 4.44 (br s, 1 H), 4.32 (dd, J = 9.1, 2.5 Hz, 1 H), 4.25 (t, J = 8.6 Hz, 1 H), 2.65 (dtd, J = 14, 7.0, 3.5 Hz, 1 H), 1.51 (d, J = 7.1 Hz, 3 H), 0.99 (d, J = 7.1 Hz, 3 H), 0.85 (d, J = 7.1 Hz, 3 H) | HRMS(B) m/z 327.1824 (M + H)⁺ |
| 22: (R)-4-isopropyl-3-(2-((R)-1-phenylethylamino)pyrimidin-4-yl)oxazolidin-2-one | 8.12 (d, J = 5.8 Hz, 1 H), 7.37-7.25 (m, 5 H), 7.19-7.16 (m, 1H), 5.04 (q, J = 6.9 Hz, 1 H), 4.64 (br s, 1 H), 4.35-4.26 (m, 2 H), 1.88 (br s, 1 H), 1.50 (d, J = 6.6 Hz, 3 H), 0.70 (br s, 3 H), 0.57 (br s, 3 H) | HRMS(B) m/z 327.1821 (M + H)⁺ |
| 23: (S)-4-isopropyl-5,5-dimethyl-3-(2-((S)-1-phenylethylamino)pyrimidin-4-yl)oxazolidin-2-one | 8.13 (d, J = 5.8 Hz, 1 H), 7.35-7.26 (m, 5 H), 7.19-7.16 (m, 1H), 5.08-5.03 (m, 1 H), 4.45 (br s, 1 H), 1.99 (br s, 1 H), 1.52 (s, 3 H), 1.50 (d, J = 7.1 Hz, 3 H), 1.41 (s, 3 H), 0.73 (br s, 3 H), 0.58 (br s, 3 H) | HRMS(B) m/z 355.2132 (M + H)⁺ |
| 24: (S)-4-isopropyl-5,5-dimethyl-3-(2-((R)-1-phenylethylamino)pyrimidin-4-yl)oxazolidin-2-one | 8.10 (d, J = 5.8 Hz, 1 H), 7.34-7.25 (m, 5 H), 7.18-7.15 (m, 1 H), 4.93 (br s, 1 H), 4.32 (br s, 1 H), 2.25 (td, J = 6.8, 3.5 Hz, 1 H), 1.50 (d, J = 7.1 Hz, 3 H), 1.49 (s, 3 H), 1.09 (br s, 3 H), 1.03 (d, J = 7.1 Hz, 3 H), 0.95 (d, J = 7.1 Hz, 3 H) | HRMS(B) m/z 355.2128 (M + H)⁺ |
| 25: (4R,5S)-4-methyl-5-phenyl-3-(2-((R)-1-phenylethylamino)pyrimidin-4-yl)oxazolidin-2-one | 8.12 (d, J = 5.8 Hz, 1 H), 7.45-7.30 (m, 8 H), 7.20 (t, J = 7.3 Hz, 2 H), 7.10-7.06 (m, 1 H), 5.80 (d, J = 7.0 Hz, 1 H), 5.01-4.94 (m, 2 H), 1.49 (d, J 7.0 Hz, 3 H), 0.30 (br s, 3H) | HRMS(B) m/z 375.1823 (M + H)⁺ |
| 26: (4S,5R)-4-methyl-5-phenyl-3-(2-((R)-1-phenylethylamino)pyrimidin-4-yl)oxazolidin-2-one | 8.10 (d, J = 5.8 Hz, 1 H), 7.48-7.28 (m, 10 H), 7.24-7.20 (m, 1 H), 5.69 (br s, 1 H), 5.01-4.93 (m, 1 H), 4.59 (br s, 1 H)1.49 (d, J = 7.1 Hz, 3 H), 0.96 (d, J = 6.5 Hz, 3 H) | HRMS(B) m/z 375.1819 (M + H)⁺ |
| 27: (S)-5,5-dimethyl-4-phenyl-3-(2-((R)-1-phenylethylamino)pyrimidin-4-yl)oxazolidin-2-one | δ 8.08 (d, J = 5.9 Hz, 1 H), 7.44-7.39 (m, 3 H), 7.36-7.29 (m, 5 H), 7.22-7.17 (m, 3 H), 5.16 (br s, 1 H), 4.55 (br s, 1 H), 1.49 (s, 3 H), 1.18 (d, J = 6.8 Hz, 3 H), 0.96 (s, 3 H) | HRMS(B) m/z 389.1974 (M + H)⁺ |
| 28: (S)-3-(2-((S)-2,3-dihydro-1H-inden-1-ylamino)pyrimidin-4-yl)-4-isopropyloxazolidin-2-one | 8.16 (d, J = 5.8 Hz, 1 H), 7.41 (d, J = 5.9 Hz, 1 H), 7.25-7.13 (m, 4 H), 5.48 (t, J = 7.8 Hz, 1 H), 4.79-4.68 (m, 1 H), 4.36 (d, J = 6.1 Hz, 2 H), 3.01 (ddd, J = 16, 8.6, 3.0 Hz, 1 H), 2.94-2.81 (m, 1 H), 2.66-2.54 (m, 2 H), 2.01-1.92 (m, 1 H), 0.86 (d, J = 6.9 Hz, 3 H), 0.85 (d, J = 6.9 Hz, 3 H) | HRMS(B) m/z 339.1825 (M + H)⁺ |
| 29: (S)-3-(2-((R)-2,3-dihydro-1H-inden-1-ylamino)pyrimidin-4-yl)-4-isopropyloxazolidin-2-one | 8.15 (d, J = 5.8 Hz, 1 H), 7.41 (d, J = 5.8 Hz, 1 H), 7.29-7.15 (m, 4 H), 5.48 (t, J = 7.6 Hz, 1 H), 4.83-4.79 (m, 1 H), 4.41-4.36 (m, 2 H), 3.03 (ddd, J = 16, 8.8, 3.3 | HRMS(B) m/z 339.1830 (M + H)⁺ |

TABLE 6-continued

Chemical name, NMR chemical shifts and LCMS
signal for each compound listed in Table 5.

| Example: Name | $^1$H NMR (400 MHz, CD$_3$OD) δ ppm (other solvents described) | LCMS |
|---|---|---|
| | Hz, 1 H), 2.86 (dt, J = 16, 8.0 Hz, 1 H), 2.64-2.50 (m, 2 H), 2.00-1.91 (m, 1 H), 0.93 (d, J = 7.1 Hz, 3 H), 0.87 (d, J = 7.1 Hz, 3 H) | |
| 30: (4R,5S)-4,5-diphenyl-3-(2-((S)-1-phenylethylamino)pyrimidin-4-yl)oxazolidin-2-one | 8.12 (d, J = 5.8 Hz, 1 H), 7.48 (d, J = 5.8 Hz, 1 H), 7.33-7.20 (m, 5 H), 7.13-7.08 (m, 6 H), 7.03-7.00 (m, 2 H), 6.88-6.86 (m, 2 H), 5.99 (d, J = 8.0 Hz, 1 H), 5.76 (br s, 1 H), 4.53 (br s, 1 H), 1.11 (br s, 3 H) | HRMS(B) m/z 437.1982 (M + H)$^+$ |
| 31: (S)-4-isobutyl-3-(2-((S)-1-phenylethylamino)pyrimidin-4-yl)oxazolidin-2-one | 8.11 (d, J = 5.8 Hz, 1 H), 7.36-7.28 (m, 5 H), 7.21-7.18 (m, 1 H), 5.18 (q, J = 6.9 Hz, 1 H), 4.83-4.79 (m, 1 H), 4.46 (t, J = 8.5 Hz, 1 H), 4.23 (dd, J = 9.0, 3.0 Hz, 1 H), 1.57 (br s, 2 H), 1.53 (d, J = 7.0 Hz, 3 H), 1.33 (br s, 1 H), 0.82 (br s, 3 H), 0.73 (br s, 3 H) | HRMS(B) m/z 341.1974 (M + H)$^+$ |
| 32: (S)-4-isobutyl-3-(2-((R)-1-phenylethylamino)pyrimidin-4-yl)oxazolidin-2-one | 8.09 (d, J = 5.8 Hz, 1 H), 7.36-7.27 (m, 5 H), 7.21-7.18 (m, 1 H), 5.16 (q, J = 7.0 Hz, 1 H), 4.69 (br s, 1 H), 4.42 (t, J = 8.3 Hz, 1 H), 4.24 (dd, J = 8.8, 2.8 Hz, 1 H), 1.92-1.86 (m, 1 H), 1.80-1.70 (m, 1 H), 1.58 (ddd, J = 13, 10, 4.8 Hz, 1 H), 1.52 (d, J = 7.0 Hz, 3 H), 1.07 (d, J = 6.5 Hz, 3 H), 0.98 (d, J = 6.5 Hz, 3 H) | HRMS(B) m/z 341.1972 (M + H)$^+$ |
| 33: (4S)-4-isopropyl-3-(2-(1-(pyridin-2-yl)ethylamino)pyrimidin-4-yl)oxazolidin-2-one | 8.49-8.48 (m, 1 H), 8.13 (dd, J = 10, 5.8 Hz, 1 H), 7.75 (td, J = 7.7, 1.8 Hz, 1 H), 7.43-7.36 (m, 2 H), 7.29-7.23 (m, 1 H), 5.08-4.99 (m, 1 H), 4.60 (br s, 0.5 H), 4.34-4.22 (m, 2.5 H), 2.63-2.56 (m, 0.5 H), 1.55 (d, J = 7.0 Hz, 1.5 H), 1.54 (d, J = 7.0 Hz, 1.5 H), 1.53 (br s, 0.5 H), 0.97 (d, J = 7.1 Hz, 1.5 H), 0.83 (d, J = 7.1 Hz, 1.5 H), 0.65 (br s, 1.5 H), 0.55 (br s, 1.5 H) | HRMS(B) m/z 328.1762 (M + H)$^+$ |
| 34: (4S)-4-isopropyl-3-(2-(1-(pyridin-4-yl)ethylamino)pyrimidin-4-yl)oxazolidin-2-one | 8.45-8.43 (m, 2 H), 8.14 (dd, J = 12, 5.6 Hz, 1 H), 7.43-7.37 (m, 2 H), 5.05 (q, J = 7.1 Hz, 0.5 H), 4.99-4.95 (br m, 0.5 H), 4.59 (br s, 0.5 H), 4.33-4.26 (m, 2.5 H), 2.64-2.59 (m, 0.5 H), 1.53 (d, J = 7.1 Hz, 3.5 H), 0.97 (d, J = 7.1 Hz, 1.5 H), 0.84 (d, J = 7.1 Hz, 1.5 H), 0.62 (br s, 1.5 H), 0.57 (br s, 1.5 H) | HRMS(B) m/z 328.1772 (M + H)$^+$ |
| 35: (S)-4-isopropyl-3-(2-((S)-1-(naphthalen-1-yl)ethylamino)pyrimidin-4-yl)oxazolidin-2-one | 8.19-8.16 (m, 2 H), 7.88 (d, J = 8.1 Hz, 1 H), 7.72 (d, J = 8.1 Hz, 1 H), 7.56-7.45 (m, 3 H), 7.40-7.32 (m, 2 H), 5.80 (q, J = 6.6 Hz, 1 H), 4.32 (br s, 1 H), 4.17-4.13 (m, 1 H), 4.05 (br s, 1 H), 1.64 (d, J = 7.1 Hz, 3 H), 1.15 (br s, 1 H), 0.23 (br s, 3 H), −0.31 (br s, 3 H) | HRMS(B) m/z 377.1969 (M + H)$^+$ |
| 36: (S)-4-isopropyl-3-(2-((R)-1-(4-methoxyphenyl)ethylamino)pyrimidin-4-yl)oxazolidin-2-one | 8.09 (d, J = 5.6 Hz, 1 H), 7.33 (d, J = 6.1 Hz, 1 H), 7.28-7.24 (m, 2 H), 6.87-6.83 (m, 2 H), 4.93 (q, J = 6.9 Hz, 1 H), 4.52 (br s, 1 H), 4.35-4.26 (m, 2 H), 3.75 (s, 3 H), 2.65 (ddt, J = 10, 6.9, 3.5, 1 H), 1.48 (d, J = 7.1 Hz, 3 H), 0.99 (d, J = 7.1 Hz, 3 H), 0.83 (d, J = 6.8 Hz, 3 H) | HRMS(B) m/z 357.1928 (M + H)$^+$ |
| 37: (4S,5R)-4,5-diphenyl-3-(2-((S)-1-phenylethylamino)pyrimidin-4-yl)oxazolidin-2-one | 8.10 (d, J = 5.8 Hz, 1 H), 7.50 (d, J = 5.8 Hz, 1 H), 7.12-7.09 (m, 6 H), 7.06-7.03 (m, 2 H), 7.01-6.97 (m, 5 H), 6.83-6.81 (m, 2 H), 6.10 (s, 2 H), 4.86-4.81 (br m, 1 H), 1.42 (d, J = 6.5 Hz, 3 H) | HRMS(B) m/z 437.1984 (M + H)$^+$ |
| 38: (4S,5R)-4,5-diphenyl-3-(2-((R)-1-phenylethylamino)pyrimidin-4-yl)oxazolidin-2-one | 8.11-8.09 (m, 1 H), 7.47 (d, J = 5.8 Hz, 1 H), 7.32-7.20 (m, 5 H), 7.12-7.07 (m, 6 H), 7.02-6.99 (m, 2 H), 6.86 (d, J = 6.5 Hz, 2 H), 5.98-5.93 (br m, 1 H), 5.75 (br s, 1 H), 4.53 (br s, 1 H), 1.11 (br s, 3 H) | HRMS(B) m/z 437.1970 (M + H)$^+$ |
| 39: (4R,5S)-4,5-diphenyl-3-(2-((R)-1-phenylethylamino)pyrimidin-4-yl)oxazolidin-2-one | 8.09 (d, J = 5.9 Hz, 1 H), 7.50 (d, J = 5.8 Hz, 1 H), 7.11-7.09 (m, 6 H), 7.05-7.03 (m, 2 H), 7.00-6.95 (m, 5 H), 6.82-6.80 (m, 2 H), 6.09 (s, 2 H), 4.87-4.81 (br m, 1 H), 1.41 (d, J = 7.0 Hz, 3 H) | HRMS(B) m/z 437.1975 (M + H)$^+$ |
| 40: (S)-4-isopropyl-3-(2-((R)-1-(naphthalen-1-yl)ethylamino)pyrimidin-4-yl)oxazolidin-2-one | 8.16 (d, J = 8.4 Hz, 1 H), 8.12 (d, J = 5.8 Hz, 1 H), 7.73 (d, J = 8.2 Hz, 1 H), 7.56-7.45 (m, 3 H), 7.42-7.38 (m, 1 H), 7.33 (d, J = 5.8 Hz, 1 H), 5.81 (q, J = 6.6 Hz, 1 | HRMS(B) m/z 377.1981 (M + H)$^+$ |

TABLE 6-continued

Chemical name, NMR chemical shifts and LCMS signal for each compound listed in Table 5.

| Example: Name | ¹H NMR (400 MHz, CD₃OD) δ ppm (other solvents described) | LCMS |
|---|---|---|
| | H), 4.15 (br s, 1 H), 4.03 (br s, 1 H), 2.56 (td, J = 7.1, 3.5 Hz, 1 H), 1.65 (d, J = 7.1 Hz, 3 H), 0.78 (d, J = 6.6 Hz, 3 H), 0.74 (br s, 3 H) | |
| 41: (S)-4-isopropyl-3-(2-((S)-1-(4-methoxyphenyl)ethylamino)pyrimidin-4-yl)oxazolidin-2-one | 8.11 (d, J = 5.8 Hz, 1 H), 7.33 (d, J = 5.9 Hz, 1 H), 7.22 (d, J = 8.6 Hz, 2 H), 6.85-6.82 (m, 2 H), 4.98 (q, J = 6.9 Hz, 1 H), 4.67-4.63 (m, 1 H), 4.34-4.27 (m, 2 H), 3.75 (s, 3 H), 1.94 (br s, 1 H), 1.48 (d, J = 7.1 Hz, 3 H), 0.73 (br s, 3 H), 0.61 (br s, 3 H) | HRMS(B) m/z 357.1922 (M + H)⁺ |
| 42: (S)-4-isopropyl-3-(2-((S)-1-(4-(pyrimidin-5-yl)phenyl)ethylamino)pyrimidin-4-yl)oxazolidin-2-one | 9.11 (s, 1 H), 9.03 (s, 2 H), 8.14 (d, J = 5.8 Hz, 1 H), 7.69-7.66 (m, 2 H), 7.52 (d, J = 8.1 Hz, 2 H), 7.35 (d, J = 5.8 Hz, 1 H), 5.11 (q, J = 6.9 Hz, 1 H), 4.65 (br s, 1 H), 4.35-4.26 (m, 2 H), 1.80 (br s, 1 H), 1.55 (d, J = 7.1 Hz, 3 H), 0.66 (br s, 3 H), 0.55 (br s, 3 H) | HRMS(B) m/z 405.2035 (M + H)⁺ |
| 43: (S)-4-isopropyl-3-(2-((R)-1-(naphthalen-2-yl)ethylamino)pyrimidin-4-yl)oxazolidin-2-one | 8.10 (d, J = 5.9 Hz, 1 H), 7.80-7.75 (m, 4 H), 7.51-7.48 (m, 1 H), 7.43-7.36 (m, 2 H), 7.32 (d, J = 5.8 Hz, 1 H), 5.15-5.07 (m, 1 H), 4.36 (br s, 1 H), 4.24 (dd, J = 9.1, 2.5 Hz, 1 H), 4.14-4.06 (br m, 1 H), 2.67 (dtd, J = 14, 6.9, 3.5 Hz, 1 H), 1.60 (d, J = 7.1 Hz, 3 H), 0.99 (d, J = 7.1 Hz, 3 H), 0.83 (d, J = 7.1 Hz, 3 H) | HRMS(B) m/z 377.1984 (M + H)⁺ |
| 44: (R)-3-(2-((S)-1-(4-fluorophenyl)ethylamino)pyrimidin-4-yl)-5,5-dimethyl-4-phenyloxazolidin-2-one | 8.09-8.07 (m, 1 H), 7.41-7.18 (m, 8 H), 7.12-7.07 (m, 2 H), 5.21 (s, 1 H), 4.99-4.93 (m, 1 H), 1.50 (s, 3 H), 1.24 (d, J = 7.1 Hz, 3 H), 0.98 (s, 3 H) | HRMS(B) m/z 407.188 (M + H)⁺ |
| 45: (R)-4-isobutyl-3-(2-((R)-1-phenylethylamino)pyrimidin-4-yl)oxazolidin-2-one | 8.10 (d, J = 5.8 Hz, 1 H), 7.36-7.27 (m, 5 H), 7.22-7.17 (m, 1 H), 5.18 (q, J = 6.9 Hz, 1 H), 4.82-4.78 (m, 1 H), 4.46 (t, J = 8.6 Hz, 1 H), 4.22 (dd, J = 8.6, 3.0 Hz, 1 H), 1.62-1.54 (m, 2 H), 1.53 (d, J = 7.0 Hz, 3 H), 1.36-1.30 (m, 1 H), 0.82 (br s, 3 H), 0.73 (br s, 3 H) | HRMS(B) m/z 341.1967 (M + H)⁺ |
| 46: (4S,5R)-5-methyl-4-phenyl-3-(2-((S)-1-phenylethylamino)pyrimidin-4-yl)oxazolidin-2-one | 8.05 (d, J = 5.8 Hz, 1 H), 7.42 (d, J = 5.8 Hz, 1 H), 7.31-7.26 (m, 3 H), 7.19-7.15 (m, 5 H), 7.02 (br s, 2 H), 5.80 (d, J = 7.5 Hz, 1 H), 5.11-5.04 (m, 1 H), 4.85 (q, J = 6.7 Hz, 1 H), 1.44 (d, J = 7.0 Hz, 3 H), 0.97 (d, J = 6.5 Hz, 3 H) | HRMS(B) m/z 375.1828 (M + H)⁺ |
| 47: (4S,5R)-5-methyl-4-phenyl-3-(2-((R)-1-phenylethylamino)pyrimidin-4-yl)oxazolidin-2-one | 8.06 (d, J = 5.8 Hz, 1 H), 7.43-7.40 (m, 3 H), 7.37-7.30 (m, 5 H), 7.23-7.17 (m, 3 H), 5.51 (br d, J = 7.1 Hz, 1 H), 4.99 (quin, J = 6.8 Hz, 1 H), 4.63 (br s, 1 H), 1.16 (br d, J = 6.3 Hz, 3 H), 0.95 (d, J = 6.5 Hz, 3 H) | HRMS(B) m/z 375.1819 (M + H)⁺ |
| 48: (S)-4-benzyl-5,5-dimethyl-3-(2-((S)-1-phenylethylamino)pyrimidin-4-yl)oxazolidin-2-one | (CDCl₃) 8.18 (d, J = 5.7 Hz, 1 H), 7.43 (d, J = 5.7 Hz, 1 H), 7.31-7.17 (m, 10 H), 5.34 (br s, 1 H), 5.14 (quin, J = 7.0 Hz, 1 H), 4.85 (dd, J = 10, 3.5 Hz, 1 H), 3.22 (br d, J = 14 Hz, 1 H), 2.72 (br s, 1 H), 1.57 (d, J = 6.5 Hz, 3 H), 1.42 (s, 3 H), 1.33 (s, 3 H) | HRMS(B) m/z 403.2133 (M + H)⁺ |
| 49: (R)-4-isobutyl-3-(2-((S)-1-phenylethylamino)pyrimidin-4-yl)oxazolidin-2-one | 8.09 (d, J = 6.1 Hz, 1 H), 7.36-7.27 (m, 5 H), 7.21-7.17 (m, 1 H), 5.16 (q, J = 7.1 Hz, 1 H), 4.69 (t, J = 8.6 Hz, 1 H), 4.41 (t, J = 8.3 Hz, 1 H), 4.23 (dd, J = 8.6, 3.0 Hz, 1 H), 1.92-1.86 (m, 1 H), 1.79-1.69 (m, 1 H), 1.57 (ddd, J = 13, 10, 4.8 Hz, 1 H), 1.52 (d, J = 7.1 Hz, 3 H), 1.07 (d, J = 6.6 Hz, 3 H), 0.98 (d, J = 6.6 Hz, 3 H) | HRMS(B) m/z 341.1973 (M + H)⁺ |
| 50: (S)-4-isopropyl-3-(2-((S)-1-(naphthalen-2-yl)ethylamino)pyrimidin-4-yl)oxazolidin-2-one | 8.15 (d, J = 5.7 Hz, 1 H), 7.81-7.73 (m, 4 H), 7.49-7.38 (m, 3 H), 7.33 (d, J = 5.8 Hz, 1 H), 5.18 (q, J = 7.1 Hz, 1 H), 4.57 (br s, 1 H), 4.30-4.25 (m, 1 H), 4.20 (br s, 1 H), 1.60 (d, J = 7.1 Hz, 3 H), 1.59 (br s, 1 H), 0.34 (br s, 6 H) | HRMS(B) m/z 377.1979 (M + H)⁺ |
| 51: (S)-4-isopropyl-3-(2-((R)-1-p-tolylethylamino)pyrimidin-4-yl)oxazolidin-2-one | 8.08 (d, J = 5.6 Hz, 1 H), 7.32 (d, J = 5.6 Hz, 1 H), 7.22 (d, J = 8.1 Hz, 2 H), 7.10 (d, J = 8.1 Hz, 2 H), 4.95-4.90 (m, 1 H), 4.48 (br s, 1 H), 4.32 (dd, J 9.1, 3.0 Hz, 1 H), | HRMS(B) m/z 341.1972 (M + H)⁺ |

TABLE 6-continued

Chemical name, NMR chemical shifts and LCMS signal for each compound listed in Table 5.

| Example: Name | ¹H NMR (400 MHz, CD₃OD) δ ppm (other solvents described) | LCMS |
|---|---|---|
| | 4.25 (t, J = 8.8 Hz, 1 H), 2.65 (dtd, J = 14, 7.1, 3.5 Hz, 1 H), 2.28 (s, 3 H), 1.48 (d, J = 7.1 Hz, 3 H), 0.99 (d, J = 7.1 Hz, 3 H), 0.84 (d, J = 7.1 Hz, 3 H) | |
| 52: (S)-4-benzyl-5,5-dimethyl-3-(2-((R)-1-phenylethylamino)pyrimidin-4-yl)oxazolidin-2-one | (CDCl₃) 8.17 (d, J = 5.7 Hz, 1 H), 7.44 (d, J = 5.7 Hz, 1 H), 7.38-7.21 (m, 10 H), 5.32 (br s, 1 H), 5.02 (br s, 1 H), 4.69-4.68 (br m, 1 H), 3.34 (dd, J = 15, 4.0 Hz, 1 H), 2.93 (dd, J = 15, 9.5 Hz, 1 H), 1.51 (d, J = 6.9 Hz, 3 H), 1.35 (s, 3 H), 1.29 (s, 3 H) | HRMS(B) m/z 403.2133 (M + H)⁺ |
| 53: (S)-3-(2-((S)-1-phenylethylamino)pyrimidin-4-yl)-4-(pyridin-3-yl)oxazolidin-2-one | (CDCl₃) 8.56-8.53 (br m, 2 H), 8.18 (d, J = 5.7 Hz, 1 H), 7.48 (d, J = 5.7 Hz, 1 H), 7.45-7.34 (m, 1 H), 7.30-7.16 (m, 6 H), 5.77 (dd, J = 8.8, 3.8 Hz, 1 H), 5.26 (br s, 1 H), 4.83 (br s, 1 H), 4.81 (t, J = 8.8 Hz, 1 H), 4.31 (dd, J = 8.8, 3.8 Hz, 1 H), 1.51 (d, J = 6.8 Hz, 3 H) | HRMS(B) m/z 362.1620 (M + H)⁺ |
| 54: 4-(4-methoxyphenyl)-5,5-dimethyl-3-(2-((S)-1-phenylethylamino)pyrimidin-4-yl)oxazolidin-2-one | (CDCl₃) 8.06 (d, J = 5.7 Hz, 1 H), 7.55-7.52 (m, 1 H), 7.37-7.20 (m, 4 H), 7.13-6.99 (m, 3 H), 6.91 (d, J = 8.0 Hz, 1 H), 6.78 (d, J = 8.0 Hz, 1 H), 5.87 (br s, 0.5 H), 5.67 (br s, 0.5 H), 5.01 (br s, 0.5 H), 4.82 (br s, 0.5 H), 4.64 (br s, 0.5 H), 3.83 (s, 1.5 H), 3.78 (s, 1.5 H), 3.36 (br s, 0.5 H), 1.66 (s, 1.5 H), 1.51 (d, J = 6.9 Hz, 1.5 H), 1.49 (s, 1.5 H), 1.29-1.27 (m, 1.5 H), 1.04 (s, 1.5 H), 1.00 (s, 1.5 H) | HRMS(B) m/z 419.2093 (M + H)⁺ |
| 55: (R)-3-(2-(benzylamino)pyrimidin-4-yl)-4-phenyloxazolidin-2-one | 8.08 (d, J = 5.8 Hz, 1 H), 7.41 (d, J = 5.8 Hz, 1 H), 7.30-7.17 (m, 8 H), 7.09 (br d, J = 7.1 Hz, 2 H), 5.69 (br dd, J = 8.1, 3.0 Hz, 1 H), 4.76 (t, J = 8.8 Hz, 1 H), 4.28 (dd, J = 44, 15 Hz, 2 H), 4.19 (dd, J = 8.8, 3.8 Hz, 1 H) | HRMS(B) m/z 347.1512 (M + H)⁺ |
| 56: (S)-3-(2-(benzylamino)pyrimidin-4-yl)-4-phenyloxazolidin-2-one | 8.10 (d, J = 5.7 Hz, 1 H), 7.42 (d, J = 5.9 Hz, 1 H), 7.31-7.16 (m, 8 H), 7.09 (br d, J = 7.1 Hz, 2 H), 5.71 (br m, 1 H), 4.78 (t, J = 8.8 Hz, 1 H), 4.28 (dd, J = 45, 15 Hz, 2 H), 4.21 (dd, J = 8.6, 3.5 Hz, 1 H) | HRMS(B) m/z 347.1499 (M + H)⁺ |
| 57: (S)-3-(2-(benzylamino)pyrimidin-4-yl)-4-isopropyloxazolidin-2-one | 8.13 (d, J = 5.8 Hz, 1 H), 7.37 (d, J = 5.8 Hz, 1 H), 7.28 (d, J = 4.6 Hz, 4 H), 7.20 (dq, J = 8.5, 4.2 Hz, 1 H), 4.64 (br s, 1 H), 4.56 (dd, J = 51, 16 Hz, 2 H), 4.35-4.29 (m, 2 H), 2.31 (br s, 1 H), 0.77 (br s, 3 H), 0.72 (br d, J = 6.6 Hz, 3 H) | HRMS(B) m/z 312.1584 M⁺ |
| 58: (4S)-4-isopropyl-3-(2-(1-(4-(4-methylpiperazin-1-yl)phenyl)ethylamino)pyrimidin-4-yl)oxazolidin-2-one | 8.23 (d, J = 5.8 Hz, 1 H), 7.40 (d, J = 5.8 Hz, 1 H), 7.28-7.24 (m, 2 H), 7.01-6.98 (m, 2 H), 4.85-4.82 (m, 1 H), 4.44-4.39 (m, 2 H), 4.03-3.98 (m, 1 H), 3.93-3.90 (m, 4 H), 3.30 (s, 3 H), 3.21-3.18 (m, 4 H), 2.60 (dtt, J = 10, 6.9, 3.5 Hz, 1 H), 1.37 (d, J = 7.1 Hz, 3 H), 1.00 (d, J = 7.1 Hz, 3 H), 0.87 (d, J = 6.9 Hz, 3 H) | HRMS(B) m/z 425.2651 (M + H)⁺ |
| 59: (S)-3-(2-((S)-1-(3,5-bis(trifluoromethyl)phenyl)ethylamino)pyrimidin-4-yl)-4-isopropyloxazolidin-2-one | 8.17 (br d, J = 5.0 Hz, 1 H), 7.93 (s, 2 H), 7.82 (s, 1 H), 7.40 (d, J = 5.9 Hz, 1 H), 5.21 (q, J = 7.1 Hz, 1 H), 4.59 (br s, 1 H), 4.33-4.25 (m, 2 H), 1.69 (br s, 1 H), 1.57 (d, J = 7.1 Hz, 3 H), 0.57 (br s, 6 H) | HRMS(B) m/z 463.1564 (M + H)⁺ |
| 60: (S)-4-isopropyl-3-(2-((S)-1-(6-methoxynaphthalen-2-yl)ethylamino)pyrimidin-4-yl)oxazolidin-2-one | 8.14 (d, J = 5.8 Hz, 1 H), 7.71 (d, J = 8.6 Hz, 1 H), 7.67-7.64 (m, 2 H), 7.42 (dd, J = 8.3, 1.8 Hz, 1 H), 7.33 (d, J = 5.8 Hz, 1 H), 7.19 (d, J = 2.5 Hz, 1 H), 7.08 (dd, J = 9.1, 2.5 Hz, 1 H), 5.15 (q, J = 7.1 Hz, 1 H), 4.59 (br s, 1 H), 4.29 (t, J = 8.8 Hz, 1 H), 4.24-4.19 (br m, 1 H), 3.88 (s, 3 H), 1.74 (br s, 1 H), 1.58 (d, J = 7.1 Hz, 3 H), 0.39 (br s, 6 H) | HRMS(B) m/z 407.2084 (M + H)⁺ |
| 61: (S)-4-isopropyl-3-(2-((R)-1-(3-methoxyphenyl)ethylamino)pyrimidin-4-yl)oxazolidin-2-one | 8.09 (d, J = 5.8 Hz, 1 H), 7.33 (d, J = 5.9 Hz, 1 H), 7.20 (t, J = 7.8 Hz, 1 H), 6.92-6.90 (m, 2 H), 6.75 (ddd, J = 8.1, 2.5, 1.0 Hz, 1 H), 4.94-4.89 (m, 1 H), 4.46 (br s, 1 H), 4.34-4.23 (m, 2 H), 3.75 (s, 3 H), 2.65 (dtd, J = 14, 6.9, 3.5 Hz, 1 H), 1.49 (d, J = 7.1 Hz, 3 H), 0.99 (d, J = 7.1 Hz, 3 H), 0.85 (d, J = 6.9 Hz, 3 H) | HRMS(B) m/z 357.1927 (M + H)⁺ |

TABLE 6-continued

Chemical name, NMR chemical shifts and LCMS
signal for each compound listed in Table 5.

| Example: Name | $^1$H NMR (400 MHz, CD$_3$OD) δ ppm (other solvents described) | LCMS |
|---|---|---|
| 62: (S)-3-(2-((S)-1-(3-bromophenyl)ethylamino)pyrimidin-4-yl)-4-isopropyloxazolidin-2-one | 8.14 (d, J 5.8 Hz, 1 H), 7.48 (s, 1 H), 7.37-7.28 (m, 3 H), 7.20 (t, J = 7.1 Hz, 1 H), 5.01 (q, J = 7.1 Hz, 1 H), 4.62 (br s, 1 H), 4.34-4.26 (m, 2 H), 1.83 (br s, 1 H), 1.50 (d, J = 7.1 Hz, 3 H), 0.71 (br s, 3 H), 0.59 (br s, 3 H) | HRMS(B) m/z 405.0937 (M + H)$^+$ |
| 63: (S)-3-(2-((S)-1-(4-bromophenyl)ethylamino)pyrimidin-4-yl)-4-isopropyloxazolidin-2-one | 8.13 (d, J 5.8 Hz, 1 H), 7.44-7.41 (m, 2 H), 7.35 (d, J = 5.8 Hz, 1 H), 7.26-7.22 (m, 2 H), 4.98 (q, J = 7.1 Hz, 1 H), 4.60 (br s, 1 H), 4.33-4.26 (m, 2 H), 1.73 (br s, 1 H), 1.49 (d, J = 7.1 Hz, 3 H), 0.68 (br s, 3 H), 0.58 (br s, 3 H) | HRMS(B) m/z 405.0912 (M + H)$^+$ |
| 64: (S)-3-(2-(1-(naphthalen-1-yl)ethylamino)pyrimidin-4-yl)oxazolidin-2-one | 8.23 (d, J = 8.1 Hz, 1 H), 8.07 (d, J = 5.8 Hz, 1 H), 7.88-7.86 (m, 1 H), 7.73 (d, J = 8.1 Hz, 1 H), 7.58 (d, J = 7.1 Hz, 1 H), 7.54-7.45 (m, 2 H), 7.42-7.39 (m, 1 H), 7.29 (d, J = 5.8 Hz, 1 H), 5.90 (q, J = 6.7 Hz, 1 H), 4.32 (br s, 1 H), 4.22 (br s, 1 H), 3.98 (br s, 1 H), 3.37 (br s, 1 H), 1.65 (d, J = 6.9 Hz, 3 H) | HRMS(B) m/z 335.1500 (M + H)$^+$ |
| 65: (S)-3-(2-((S)-1-(naphthalen-2-yl)ethylamino)pyrimidin-4-yl)-4-phenyloxazolidin-2-one | 8.11 (d, J = 5.8 Hz, 1 H), 7.80-7.77 (m, 1 H), 7.73-7.68 (m, 2 H), 7.56 (s, 1 H), 7.45-7.40 (m, 2 H), 7.37 (d, J = 5.8 Hz, 1 H), 7.23 (dd, J = 8.6, 1.5 Hz, 1 H), 7.08-7.00 (m, 5 H), 5.80 (dd, J = 8.8, 3.8 Hz, 1 H), 5.07 (q, J = 6.9 Hz, 1 H), 4.79 (t, J = 8.7 Hz, 1 H), 4.20 (dd, J = 8.6, 3.5 Hz, 1 H), 1.55 (d, J = 6.9 Hz, 3 H) | HRMS(B) m/z 411.1820 (M + H)$^+$ |
| 66: (R)-3-(2-((S)-1-(naphthalen-2-yl)ethylamino)pyrimidin-4-yl)-4-phenyloxazolidin-2-one | 8.10 (d, J = 5.8 Hz, 1 H), 7.82-7.78 (m, 3 H), 7.69 (s, 1 H), 7.47-7.40 (m, 5 H), 7.38-7.29 (m, 4 H), 5.53 (dd, J = 8.8, 3.8 Hz, 1 H), 4.82 (q, J = 6.9 Hz, 1 H), 4.68 (t, J = 8.6 Hz, 1 H), 4.15 (dd, J = 8.6, 4.0 Hz, 1 H), 1.31 (d, J = 6.9 Hz, 3 H) | HRMS(B) m/z 411.1821 (M + H)$^+$ |
| 67: (S)-3-(2-((R)-1-(3-bromophenyl)ethylamino)pyrimidin-4-yl)-4-isopropyloxazolidin-2-one | 8.10 (d, J 5.8 Hz, 1 H), 7.53-7.50 (m, 1 H), 7.36-7.31 (m, 3 H), 7.21 (t, J = 7.8 Hz, 1 H), 4.94-4.86 (m, 1 H), 4.42 (br s, 1 H), 4.33 (dd, J = 9.1, 2.5, 1 H), 4.26 (t, J = 8.8 Hz, 1 H), 2.65 (dtd, J = 14, 7.0, 3.8 Hz, 1 H), 1.50 (d, J = 7.1 Hz, 3 H), 1.00 (d, J = 7.1 Hz, 3 H), 0.85 (d, J = 7.1 Hz, 3 H) | HRMS(B) m/z 405.0930 (M + H)$^+$ |
| 68: (S)-3-(2-((R)-1-(4-bromophenyl)ethylamino)pyrimidin-4-yl)-4-isopropyloxazolidin-2-one | 8.10 (d, J 5.8 Hz, 1 H), 7.45-7.42 (m, 2 H), 7.35 (d, J = 5.9 Hz, 1 H), 7.29-7.25 (m, 2 H), 4.95-4.90 (m, 1 H), 4.44 (br s, 1 H), 4.34-4.25 (m, 2 H), 2.63 (dtd, J = 14, 6.9, 3.5 Hz, 1 H), 1.49 (d, J = 7.1 Hz, 3 H), 0.98 (d, J = 7.1 Hz, 3 H), 0.84 (d, J = 7.1 Hz, 3 H) | HRMS(B) m/z 405.0934 (M + H)$^+$ |
| 69: (S)-4-isopropyl-3-(2-((S)-1-(3-methoxyphenyl)ethylamino)pyrimidin-4-yl)oxazolidin-2-one | 8.12 (d, J = 5.8 Hz, 1 H), 7.34 (d, J = 6.0 Hz, 1 H), 7.20-7.16 (m, 1 H), 6.89-6.87 (m, 2 H), 6.75-6.73 (m, 1 H), 4.99 (q, J = 6.7 Hz, 1 H), 4.63 (br s, 1 H), 4.34-4.25 (m, 2 H), 3.74 (s, 3 H), 1.84 (br s, 1 H), 1.49 (d, J = 7.1 Hz, 3 H), 0.68 (br s, 3 H), 0.57 (br s, 3 H) | HRMS(B) m/z 357.1918 (M + H)$^+$ |
| 70: (S)-4-isopropyl-3-(2-((S)-1-p-tolylethylamino)pyrimidin-4-yl)oxazolidin-2-one | 8.11 (d, J = 5.8 Hz, 1 H), 7.33 (d, J = 5.9 Hz, 1 H), 7.18 (d, J = 8.1 Hz, 2 H), 7.08 (d, J = 8.1 Hz, 2 H), 4.99 (q, J = 7.1 Hz, 1 H), 4.63 (br s, 1 H), 4.34-4.26 (m, 2 H), 2.28 (s, 3 H), 1.86 (br s, 1 H), 1.48 (d, J = 7.1 Hz, 3 H), 0.69 (br s, 3 H), 0.58 (br s, 3 H) | HRMS(B) m/z 341.1977 (M + H)$^+$ |
| 71: (S)-4-tert-butyl-3-(2-((S)-1-phenylethylamino)pyrimidin-4-yl)oxazolidin-2-one | 8.14 (d, J = 5.7 Hz, 1 H), 7.37-7.34 (m, 2 H), 7.30-7.26 (m, 2 H), 7.19-7.15 (m, 2 H), 5.00 (q, J = 6.9 Hz, 1 H), 4.76 (br s, 1 H), 4.41-4.33 (m, 2 H), 1.48 (d, J = 7.1 Hz. 3 H), 0.55 (br s, 9 H) | HRMS(B) m/z 341.1979 (M + H)$^+$ |
| 72: (S)-4-tert-butyl-3-(2-((R)-1-phenylethylamino)pyrimidin-4-yl)oxazolidin-2-one | 8.09 (d, J = 5.7 Hz, 1 H), 7.35-7.32 (m, 2 H), 7.29-7.24 (m, 3 H), 7.19-7.15 (m, 1 H), 5.01-4.96 (m, 1 H), 4.68 (br s, 1 H), 4.39 (d, H = 9.2 Hz, 1 H), 4.15 (br s, 1 H), 1.50 (d, J = 7.0 Hz. 3 H), 0.94 (s, 9 H) | HRMS(B) m/z 341.1974 (M + H)$^+$ |
| 73: (R)-3-(2-((S)-1-(3-methoxyphenyl)ethylami- | 8.09 (d, J = 5.8 Hz, 1 H), 7.42-7.37 (m, 3 H), 7.34-7.28 (m, 3 H), 7.21 (t, J = 7.8 | HRMS(B) m/z |

TABLE 6-continued

Chemical name, NMR chemical shifts and LCMS signal for each compound listed in Table 5.

| Example: Name | $^1$H NMR (400 MHz, CD$_3$OD) δ ppm (other solvents described) | LCMS |
|---|---|---|
| no)pyrimidin-4-yl)-4-phenyloxazolidin-2-one | Hz, 1 H), 6.86-6.83 (m, 2 H), 6.78-6.76 (m, 1 H), 5.58 (dd, J = 8.6, 4.0 Hz, 1 H), 4.74 (t, J = 8.7 Hz, 1 H), 4.66-4.61 (m, 1 H), 4.18 (dd, J = 8.6, 4.0 Hz, 1 H), 3.77 (s, 3 H), 1.20 (d, J = 6.9 Hz, 3 H) | 391.1768 (M + H)$^+$ |
| 74: (S)-3-(2-((S)-1-phenylethylamino)pyrimidin-4-yl)-4-(pyridin-2-yl)oxazolidin-2-one | 8.55 (d, J = 4.5 Hz, 1 H), 8.10 (d, J = 6.0 Hz, 1 H), 7.64 (d, J = 6.0 Hz, 1 H), 7.43 (br s, 1 H), 7.26-7.15 (m, 4 H), 7.06 (br s, 2 H), 6.92 (br s, 1 H), 5.84 (dd, J = 8.7, 3.2 Hz, 1 H), 4.94 (br s, 1 H), 4.88-4.78 (m, 2 H), 4.48 (dd, J = 8.7, 3.2 Hz, 1 H), 1.51 (d, J = 6.9 Hz, 3 H) | HRMS(B) m/z 362.1624 (M + H)$^+$ |
| 75: (S)-3-(2-((S)-1-phenylethylamino)pyrimidin-4-yl)-4-(pyridin-4-yl)oxazolidin-2-one | 8.43 (br s, 2 H), 8.16 (br d, J = 5.0 Hz, 1 H), 7.65 (br s, 1 H), 7.36-7.09 (br m, 6 H), 6.90 (br s, 1 H), 5.88 (br s, 1 H), 4.83 (t, J = 8.8 Hz, 1 H), 4.78 (br s, 1 H), 4.23 (br s, 1 H), 1.34 (d, J = 7.0 Hz, 3 H) | HRMS(B) m/z 362.1623 (M + H)$^+$ |
| 76: (S)-4-isopropyl-3-(2-((R)-1-(3-(trifluoromethyl)phenyl)ethylamino)pyrimidin-4-yl)oxazolidin-2-one | 8.11 (d, J = 5.8 Hz, 1 H), 7.66 (s, 1 H), 7.64-7.61 (m, 1 H), 7.53-7.49 (m, 2 H), 7.36 (d, J = 5.9 Hz, 1 H), 5.05-4.99 (m, 1 H), 4.42 (br s, 1 H), 4.33 (dd, J = 9.1, 3.0 Hz, 1 H), 4.24 (t, J = 8.6 Hz, 1 H), 2.68-2.60 (m, 1 H), 1.54 (d, J = 7.1 Hz, 3 H), 0.99 (d, J = 7.1 Hz, 3 H), 0.85 (d, J = 7.0 Hz, 3 H) | HRMS(B) m/z 395.1686 (M + H)$^+$ |
| 77: (S)-4-isopropyl-3-(2-((R)-1-(4-(trifluoromethyl)phenyl)ethylamino)pyrimidin-4-yl)oxazolidin-2-one | 8.11 (d, J = 5.8 Hz, 1 H), 7.60 (d, J = 8.3 Hz, 2 H), 7.54 (d, J = 8.3 Hz, 2 H), 7.36 (d, J = 5.8 Hz, 1 H), 5.07-5.00 (m, 1 H), 4.39 (br s, 1 H), 4.33-4.30 (m, 1 H), 4.27-4.23 (m, 1 H), 2.63 (dtd, J = 14, 7.1, 3.5 Hz, 1 H), 1.54 (d, J = 7.0 Hz, 3 H), 0.98 (d, J = 7.1 Hz, 3 H), 0.84 (d, J = 7.1 Hz, 3 H) | HRMS(B) m/z 395.1698 (M + H)$^+$ |
| 78: (S)-3-(2-((R)-1-(2-fluorophenyl)ethylamino)pyrimidin-4-yl)-4-isopropyloxazolidin-2-one | 8.10 (d, J = 5.8 Hz, 1 H), 7.40-7.34 (m, 2 H), 7.24-7.18 (m, 1 H), 7.10-7.02 (m, 2 H), 5.28 (q, J = 7.1 Hz, 1 H), 4.42 (br s, 1 H), 4.32 (dd, J = 9.1, 2.5 Hz, 1 H), 4.24 (t, J = 8.8 Hz, 1 H), 2.64 (dtd, J = 14, 7.0, 3.8 Hz, 1 H), 1.50 (d, J = 7.1 Hz, 3 H), 0.98 (d, J = 7.1 Hz, 3 H), 0.84 (d, J = 7.1 Hz, 3 H) | HRMS(B) m/z 345.1727 (M + H)$^+$ |
| 79: (S)-4-methyl-4-phenyl-3-(2-((S)-1-phenylethylamino)pyrimidin-4-yl)oxazolidin-2-one | 8.15 (d, J = 5.8 Hz, 1 H), 7.44-7.38 (m, 3 H), 7.36-7.21 (m, 6 H), 7.15-7.13 (m, 2 H), 5.40 (br s, 1 H), 4.22-4.17 (m, 2 H), 4.15 (br s, 1 H), 1.63 (br s, 3 H), 1.15 (d, J 6.6 Hz, 3 H) | HRMS(B) m/z 375.1809 (M + H)$^+$ |
| 80: (S)-4-isopropyl-3-(2-((S)-1-(4-morpholinophenyl)ethylamino)pyrimidin-4-yl)oxazolidin-2-one | 8.11 (d, J = 5.8 Hz, 1 H), 7.33 (d, J = 5.8 Hz, 1 H), 7.22-7.19 (m, 2 H), 6.92-6.89 (m, 2 H), 5.00-4.95 (m, 1 H), 4.66 (br s, 1 H), 4.58 (br s, 1 H), 4.35-4.27 (m, 2 H), 3.82-3.80 (m, 4 H), 3.09-3.07 (m, 4 H), 1.48 (d, J = 7.1 Hz, 3 H), 0.73 (br s, 3 H), 0.60 (br s, 3 H) | HRMS(B) m/z 412.2359 (M + H)$^+$ |
| 81: (4R)-4-methyl-4-phenyl-3-(2-((1-(1-phenyl-1H-pyrazol-4-yl)ethyl)amino)pyrimidin-4-yl)oxazolidin-2-one | | HRMS(B) m/z 441.2049 (M + H)$^+$ |
| 82: (S)-3-(2-((S)-1-(4-bromo-3,5-dimethoxyphenyl)ethylamino)pyrimidin-4-yl)-4-isopropyloxazolidin-2-one | 8.16 (d, J = 5.8 Hz, 1 H), 7.36 (d, J = 5.8 Hz, 1 H), 6.64 (s, 2 H), 5.00-4.95 (m, 1 H), 4.58 (br s, 1 H), 4.33-4.23 (m, 2 H), 3.79 (s, 6 H), 1.54 (d, J = 7.0 Hz, 3 H), 0.55 (br s, 6 H) | HRMS(B) m/z 465.1134 (M + H)$^+$ |
| 83: (4S)-3-(2-(1-(1H-indol-5-yl)ethylamino)pyrimidin-4-yl)-4-isopropyloxazolidin-2-one | 8.11 (d, J = 5.8 Hz, 0.5 H), 8.09 (d, J = 5.8 Hz, 0.5 H), 7.52 (s, 0.5 H), 7.46 (s, 0.5 H), 7.32-7.29 (m, 2 H), 7.19-7.18 (m, 1 H), 7.10 (ddd, J = 14, 8.6, 1.5 Hz, 1 H), 6.36 (dt, J = 4.0, 3.0 Hz, 1 H), 5.11 (q, J = 6.9 Hz, 0.5 H), 5.05 (q, J = 6.8 Hz, 0.5 H), 4.64 (br s, 0.5 H), 4.50 (br s, 0.5 H), 4.33-4.19 (m, 2 H), 2.74-2.64 (m, 0.5 H), 1.86 (br s, 0.5 H), 1.55 (d, J = 7.1 Hz, 3 H), 1.02 (d, J = 7.1 Hz, 1.5 H), 0.86 (d, J = 7.1 Hz, 1.5 H), 0.57 (br s, 1.5 H), 0.46 (br s, 1.5 H) | HRMS(B) m/z 366.1928 (M + H)$^+$ |
| 84: (S)-3-(2-((S)-1-(5-bromo-6- | δ 8.16-8.12 (m, 2 H), 7.80 (d, J = 9.1 Hz, 1 H), 7.72 (s, 1 H), 7.56 (dd, J = 8.8, 1.8 | HRMS(B) m/z |

TABLE 6-continued

Chemical name, NMR chemical shifts and LCMS signal for each compound listed in Table 5.

| Example: Name | $^1$H NMR (400 MHz, CD$_3$OD) δ ppm (other solvents described) | LCMS |
|---|---|---|
| methoxynaphthalen-2-yl)ethylamino)pyrimidin-4-yl)-4-isopropyloxazolidin-2-one | Hz, 1 H), 7.37 (d, J = 9.1 Hz, 1 H), 7.32 (d, J = 5.7 Hz, 1 H), 5.18 (q, J = 6.7 Hz, 1 H), 4.60-4.54 (m, 1 H), 4.28 (t, J = 8.8 Hz, 1 H), 4.19 (dd, J = 9.1, 3.0 Hz, 1 H), 3.99 (s, 3 H), 1.72 (br s, 1 H), 1.61 (d, J = 7.1 Hz, 3 H), 0.39 (br d, J = 6.6 Hz, 3 H), 0.43 (br d, J = 6.1 Hz, 3 H) | 485.1184 (M + H)$^+$ |
| 85: (S)-3-(2-((R)-1-(4-fluorophenyl)ethylamino)pyrimidin-4-yl)-4-isopropyloxazolidin-2-one | 8.09 (d, J = 5.9 Hz, 1 H), 7.38-7.33 (m, 3 H), 7.04-6.98 (m, 2 H), 4.96 (q, J = 6.7 Hz, 1 H), 4.48 (br s, 1 H), 4.35-4.25 (m, 2 H), 2.64 (dtd, J = 14, 7.1, 3.5 Hz, 1 H), 1.50 (d, J = 6.6 Hz, 3 H), 0.98 (d, J = 7.1 Hz, 3 H), 0.85 (d, J = 7.0 Hz, 3 H) | HRMS(B) m/z 345.1725 (M + H)$^+$ |
| 86: (S)-4-isopropyl-3-(2-((R)-1-(2-(trifluoromethyl)phenyl)ethylamino)pyrimidin-4-yl)oxazolidin-2-one | 8.12 (d, J = 5.8 Hz, 1 H), 7.77 (d, J = 8.1 Hz, 1 H), 7.66 (d, J = 8.1 Hz, 1 H), 7.60 (t, J = 7.6 Hz, 1 H), 7.42-7.36 (m, 2 H), 5.58 (q, J = 6.7 Hz, 1 H), 4.70 (dt, J = 7.8, 3.7 Hz, 1 H), 4.38-4.31 (m, 2 H), 2.58 (dtd, J = 14, 7.0, 3.8 Hz, 1 H), 1.50 (d, J = 6.9 Hz, 3 H), 0.98 (d, J = 7.0 Hz, 3 H), 0.85 (d, J = 6.9 Hz, 3 H) | HRMS(B) m/z 395.1706 (M + H)$^+$ |
| 87: (R)-4-methyl-3-(2-((S)-1-(naphthalen-2-yl)ethylamino)pyrimidin-4-yl)-4-phenyloxazolidin-2-one | | HRMS(B) m/z 425.1967 (M + H)$^+$ |
| 88: (S)-3-(2-((S)-1-(4-fluorophenyl)ethylamino)pyrimidin-4-yl)-4-isopropyloxazolidin-2-one | 8.12 (d, J = 5.8 Hz, 1 H), 7.35-7.31 (m, 3 H), 7.03-6.97 (m, 2 H), 5.03 (q, J = 7.1 Hz, 1 H), 4.66-4.63 (br m, 1 H), 4.35-4.27 (m, 2 H), 1.85 (br s, 1 H), 1.49 (d, J = 7.0 Hz, 3 H), 0.71 (br s, 3 H), 0.60 (br s, 3 H) | HRMS(B) m/z 345.1724 (M + H)$^+$ |
| 89: (R)-4-methyl-4-phenyl-3-(2-((S)-1-phenylethylamino)pyrimidin-4-yl)oxazolidin-2-one | (CDCl$_3$) 8.12 (d, J = 5.8 Hz, 1 H), 7.43 (d, J = 5.8 Hz, 1 H) 7.32-7.20 (m, 8 H), 6.99 (br s, 2 H), 5.20 (br s, 1 H), 4.33 (br s, 1 H), 4.32-4.27 (m, 2 H), 2.20 (s, 3 H), 1.41 (d, J = 6.8 Hz, 3 H) | HRMS(B) m/z 375.1822 (M + H)$^+$ |
| 90: (S)-4-isopropyl-3-(2-((S)-1-(2-methoxyphenyl)ethylamino)pyrimidin-4-yl)oxazolidin-2-one | 8.11 (d, J = 5.8 Hz, 1 H), 7.33 (d, J = 5.8 Hz, 3 H), 7.20-7.16 (m, 2 H), 6.95 (d, J = 8.1 Hz, 1 H), 6.86-6.82 (m, 1 H), 5.28 (q, J = 7.1 Hz, 1 H), 4.63 (br s, 1 H), 4.35-4.26 (m, 2 H), 3.87 (s, 3 H), 1.86 (br s, 1 H), 1.46 (d, J = 6.9 Hz, 3 H), 0.69 (br s, 3 H), 0.56 (br s, 3 H) | HRMS(B) m/z 357.1924 (M + H)$^+$ |
| 91: (S)-3-(2-(1-(naphthalen-2-yl)ethylamino)pyrimidin-4-yl)oxazolidin-2-one | 8.08 (d, J = 5.8 Hz, 1 H), 7.82-7.78 (m, 4 H), 7.52 (dd, J = 8.6, 1.5 Hz, 1 H), 7.45-7.38 (m, 2 H), 7.29 (d, J = 5.8 Hz, 1 H), 5.23 (q, J = 6.9 Hz, 1 H), 4.46-4.33 (m, 2 H), 4.21-4.15 (m, 1 H), 3.93-3.86 (m, 1 H), 1.61 (d, J = 7.1 Hz, 3 H) | HRMS(B) m/z 335.1509 (M + H)$^+$ |
| 92: (S)-4-isopropyl-3-(2-((S)-1-(3-methoxyphenyl)ethylamino)-6-methylpyrimidin-4-yl)oxazolidin-2-one hydrochloride | (CDCl$_3$) 15.12 (br s, 1 H), 9.23 (br s, 1 H), 7.67-7.56 (m, 1 H), 7.24 (dd, J = 8, 8 Hz, 1 H), 6.92-6.72 (m, 3 H), 5.04-4.86 (m, 1 H), 4.72-4.51 (m, 1 H), 4.42-4.25 (m, 2 H), 3.81 (s, 3 H), 2.56 (s, 3 H), 1.90-1.76 (m, 1 H), 1.64 (br s, 3 H), 0.73 (d, J = 8 Hz, 3 H), 0.64 (d, J = 8 Hz, 3 H) | HRMS(B) m/z 371.2082 (M + H)$^+$ |
| 93: (S)-4-isopropyl-3-(6-methyl-2-((S)-1-phenylethylamino)pyrimidin-4-yl)oxazolidin-2-one | (CDCl$_3$) 7.57-7.19 (m, 6 H), 5.05-4.86 (m, 1 H), 4.63-4.09 (m, 3 H), 2.561/2.49 (2 x s, 3 H), 1.91-1.70 (m, 1 H), 1.62/ 1.54 (2 x d, 3 H), 0.75-0.45 (m, 6 H) | HRMS(B) m/z 341.1982 (M + H)$^+$ |
| 94: (S)-3-(2-(((S)-3-methylbutan-2-yl)amino)pyrimidin-4-yl)-4-phenyloxazolidin-2-one | (DMSO-d$_6$) 8.11 (d, J = 5.5 Hz, 1 H), 7.39-7.32 (m, 2 H), 7.31-7.19 (m, 4 H), 6.95-6.82 (m, 1 H), 5.83-5.73 (m, 1 H), 4.82 (t, J = 8.5 Hz, 1 H), 4.15 (br s., 1 H), 1.37-1.21 (m, 1 H), 0.97 (d, J = 7.0 Hz, 3 H), 0.58 (br s., 3 H), 0.47 (br s., 3 H) | HRMS(B) m/z 327.1822 (M + H)$^+$ |
| 95: (S)-5,5-dimethyl-3-(2-(((S)-3-methylbutan-2-yl)amino)pyrimidin-4-yl)-4-phenyloxazolidin-2-one | (DMSO-d$_6$) 8.10 (d, J = 5.5 Hz, 1 H), 7.39-7.32 (m, 2 H), 7.31-7.23 (m, 2 H), 7.18 (br. s, 1 H), 6.93-6.79 (m, 1 H), 5.43 (s, 1 H), 1.62 (s, 3 H), 1.30-1.14 (m, 1 H), 0.96 (d, J = 6.5 Hz, 3 H), 0.90 (s, 3 H), 0.54 (d, J = 5.0 Hz, 3 H), 0.43 (d, J = 5.0 Hz, 3 H) | HRMS(B) m/z 355.2123 (M + H)$^+$ |

TABLE 6-continued

Chemical name, NMR chemical shifts and LCMS
signal for each compound listed in Table 5.

| Example: Name | $^1$H NMR (400 MHz, CD$_3$OD) δ ppm (other solvents described) | LCMS |
|---|---|---|
| 96: 3-(2-(((3r,5r,7r)-adamantan-1-ylmethyl)amino)pyrimidin-4-yl)oxazolidin-2-one | (DMSO-d$_6$) 8.11 (br s, 1 H), 7.15 (br s, 1 H), 4.52-4.36 (m, 2 H), 4.09 (br s, 2 H), 3.03 (br s, 2 H), 1.92 (br s, 3 H), 1.74-1.31 (m, 12 H) | HRMS(B) m/z 329.1971 (M + H)$^+$ |
| 97: (S)-4-isopropyl-3-(2-((S)-1-(4-(trifluoromethyl)phenyl)ethylamino)pyrimidin-4-yl)oxazolidin-2-one | 8.14 (d, J = 5.8 Hz, 1 H), 7.59 (d, J = 8.1 Hz, 2 H), 7.51 (d, J = 8.1 Hz, 2 H), 7.36 (d, J = 5.8 Hz, 1 H), 5.08 (q, J = 6.9 Hz, 1 H), 4.59 (br s, 1 H), 4.33-4.25 (m, 2 H), 1.57 (br s, 1 H), 1.54 (d, J = 7.1 Hz, 3 H), 0.60 (br s, 3 H), 0.53 (br s, 3 H) | HRMS(B) m/z 395.1686 (M + H)$^+$ |
| 98: 3-((S)-1-(4-((S)-4-isopropyl-2-oxooxazolidin-3-yl)pyrimidin-2-ylamino)ethyl)benzonitrile | 8.14 (d, J = 5.8 Hz, 1 H), 7.69-7.65 (m, 2 H), 7.58-7.56 (m, 1 H), 7.48 (t, J = 7.7 Hz, 1 H), 7.37 (d, J = 5.8 Hz, 1 H), 5.09 (q, J = 7.1 Hz, 1 H), 4.64 (br s, 1 H), 4.35-4.27 (m, 2 H), 1.74 (br s, 1 H), 1.52 (d, J = 7.1 Hz, 3 H), 0.71 (br s, 3 H), 0.60 (br s, 3 H) | HRMS(B) m/z 352.1764 (M + H)$^+$ |
| 99: (S)-3-(2-((S)-1-(3-chlorophenyl)ethylamino)pyrimidin-4-yl)-4-isopropyloxazolidin-2-one | 8.14 (d, J = 5.8 Hz, 1 H), 7.36 (d, J = 5.8 Hz, 1 H), 7.32 (br s, 1 H), 7.29-7.23 (m, 2 H), 7.20-7.17 (m, 1 H), 5.02 (q, J = 6.9 Hz, 1 H), 4.63 (br s, 1 H), 4.34-4.27 (m, 2 H), 1.82 (br s, 1 H), 1.50 (d, J = 7.1 Hz, 3 H), 0.70 (br s, 3 H), 0.59 (br s, 3 H) | HRMS(B) m/z 361.1424 (M + H)$^+$ |
| 100: (4R)-5,5-dimethyl-4-phenyl-3-(2-(1-(4-(piperidin-1-yl)phenyl)ethylamino)pyrimidin-4-yl)oxazolidin-2-one | 8.07 (d, J = 5.8 Hz, 0.5 H), 8.06 (d, J = 5.8 Hz, 0.5 H), 7.41-7.37 (m, 2 H), 7.34-7.26 (m, 2 H), 7.19-7.14 (m, 3 H), 6.95-6.89 (m, 2 H), 6.81-6.78 (m, 1 H), 5.46 (s, 0.5 H), 5.25 (s, 0.5 H), 4.73-4.68 (m, 0.5 H), 4.60-4.55 (m, 0.5 H), 3.12-3.07 (m, 4 H), 1.73-1.68 (m, 4 H), 1.65 (s, 1.5 H), 1.61-1.57 (m, 2 H), 1.54 (s, 1.5 H), 1.41 (d, J = 6.9 Hz, 1.5 H), 1.14 (d, J = 6.9 Hz, 1.5 H), 0.99 (d, J = 4.7 Hz, 3 H) | HRMS(B) m/z 472.2715 (M + H)$^+$ |
| 101: (S)-4-isopropyl-3-(2-((S)-1-(2-(trifluoromethyl)phenyl)ethylamino)pyrimidin-4-yl)oxazolidin-2-one | 8.15 (d, J = 5.8 Hz, 1 H), 7.74 (d, J = 8.1 Hz, 1 H), 7.69 (d, J = 8.1 Hz, 1 H), 7.58 (t, J = 7.6 Hz, 1 H), 7.42-7.35 (m, 2 H), 5.35 (q, J = 6.6 Hz, 1 H), 4.65 (dt, J = 8.0, 3.8 Hz, 1 H), 4.35-4.26 (m, 2 H), 1.76 (br s, 1 H), 1.52 (d, J = 6.6 Hz, 3 H), 0.64 (br d, J = 5.5 Hz, 3 H), 0.58 (br d, J = 6.3 Hz, 3 H) | HRMS(B) m/z 395.1682 (M + H)$^+$ |
| 102: 4,4-dimethyl-3-(2-(1-(1-phenyl-1H-pyrazol-4-yl)ethylamino)pyrimidin-4-yl)oxazolidin-2-one | (CDCl$_3$) 8.22 (d, J = 5.8 Hz, 1 H), 7.87 (s, 1 H), 7.69-7.65 (m, 3 H), 7.48-7.43 (m, 2 H), 7.35-7.28 (m, 2 H), 5.34 (br s, 1 H), 5.24-5.17 (m, 1 H), 4.09-4.05 (m, 2 H), 1.74 (s, 3 H), 1.64 (d, J = 7.1 Hz, 3 H), 1.58 (s, 3 H) | HRMS(B) m/z 379.1890 (M + H)$^+$ |
| 103: (S)-3-(2-(((3S,5S,7S)-adamantan-1-ylmethyl)amino)pyrimidin-4-yl)-4-isopropyloxazolidin-2-one | (DMSO-d$_6$) 8.13 (d, J = 5.5 Hz, 1 H), 7.20 (br s., 1 H), 7.17 (d, J = 5.5 Hz, 1 H), 4.69-4.63 (m, 1 H), 4.44-4.33 (m, 2 H), 3.11-2.85 (m, 2 H), 2.54 (br s, 1 H), 1.92 (br s., 3 H), 1.70-1.53 (m, 6 H), 1.47 (br s., 6 H), 0.93 (d, J = 7.0 Hz, 3 H), 0.78 (d, J = 6.5 Hz, 3 H) | HRMS(B) m/z 371.2448 (M + H)$^+$ |
| 104: (S)-3-(2-(((S)-1-cyclohexylethyl)amino)pyrimidin-4-yl)-5,5-dimethyl-4-phenyloxazolidin-2-one | (DMSO-d$_6$) 8.09 (d, J = 5.5 Hz, 1 H), 7.40-7.32 (m, 2 H), 7.32-7.23 (m, 3 H), 6.83 (d, J = 9.0 Hz, 1 H), 5.42 (s, 1 H), 3.36 (br s, 1 H), 1.72-1.23 (m, 9 H), 1.02-0.82 (m, 10 H), 0.62 (s, 1 H), 0.20-0.04 (m, 1 H) | HRMS(B) m/z 395.2446 (M + H)$^+$ |
| 105: (S)-3-(2-(((S)-1-cyclohexylethyl)amino)pyrimidin-4-yl)-4-isopropyloxazolidin-2-one | (DMSO-d$_6$) 8.13 (d, J = 5.8 Hz, 1 H), 7.19-7.09 (m, 2 H), 4.68 (br s, 1 H), 4.41-4.33 (m, 2 H), 3.77 (br s, 1 H), 2.47 (br s, 1 H), 1.76-1.58 (m, 5 H), 1.43-1.35 (m, 1 H), 1.15-1.04 (m, 6 H), 0.97-0.88 (m, 5 H), 0.77 (d, J = 6.8 Hz, 3 H); | HRMS(B) m/z 333.2288 (M + H)$^+$ |
| 106: (4S)-4-isopropyl-3-(2-((1-phenoxypropan-2-yl)amino)pyrimidin-4-yl)oxazolidin-2-one | (DMSO-d$_6$) 8.19 (d, J = 5.6 Hz, 1 H), 7.30-7.24 (m, 3 H), 7.18 (br s, 1 H), 6.96-6.85 (m, 3 H), 4.70-4.52 (m, 1 H), 4.39-4.19 (m, 3 H), 4.12-4.00 (m, 1 H), 3.92-3.78 (m, 1 H), 2.46 (br s, 1 H), 1.29-1.21 (m, 3 H), 0.93-0.58 (m, 6 H) | HRMS(B) m/z 357.1921 (M + H)$^+$ |
| 107: (S)-3-(2-(((R)-1-cyclohexylethyl)amino)pyrimidin-4-yl)-5,5- | (DMSO-d$_6$) 8.09 (d, J = 5.6 Hz, 1 H), 7.38-7.12 (m, 6 H), 6.71 (br s, 1 H), 5.36 (s, 1 H), 1.77-1.56 (m, 9 H), 1.31-1.05 (m, 4 | HRMS(B) m/z 395.2440 |

TABLE 6-continued

Chemical name, NMR chemical shifts and LCMS
signal for each compound listed in Table 5.

| Example: Name | ¹H NMR (400 MHz, CD₃OD) δ ppm (other solvents described) | LCMS |
|---|---|---|
| dimethyl-4-phenyloxazolidin-2-one | H), 0.92 (s, 6 H), 0.48 (br s., 2 H) | (M + H)⁺ |
| 108: (S)-3-(5-chloro-2-((S)-1-(naphthalen-2-yl)ethylamino)pyrimidin-4-yl)-4-isopropyloxazolidin-2-one | (CDCl₃) 8.29 (s, 1 H), 7.84-7.74 (m, 4 H), 7.49-7.43 (m, 3 H), 5.76 (br s, 1 H), 5.17-5.10 (m, 1 H), 4.39-4.30 (m, 1 H), 4.31 (t, J = 8.1 Hz, 1 H), 4.09-4.05 (m, 1 H), 1.66 (d, J = 7.0 Hz, 3 H), 1.40-1.30 (m, 1 H), 0.52 (d, J = 6.1 Hz, 3 H), 0.27 (br s, 3 H) | HRMS(B) m/z 411.1588 (M + H)⁺ |
| 109: 4-((S)-1-(4-((S)-4-isopropyl-2-oxooxazolidin-3-yl)pyrimidin-2-ylamino)ethyl)benzonitrile | 8.14 (d, J = 5.8 Hz, 1 H), 7.68-7.66 (m, 2 H), 7.52 (d, J = 8.1 Hz, 3 H), 7.36 (d, J = 5.9 Hz, 1 H), 5.08 (q, J = 7.1 Hz, 1 H), 4.61 (br s, 1 H), 4.34-4.26 (m, 2 H), 1.60 (br s, 1 H), 1.52 (d, J = 7.1 Hz, 3 H), 0.65 (br s, 3 H), 0.58 (br s, 3 H) | HRMS(B) m/z 352.1775 (M + H)⁺ |
| 110: (S)-4,4-dimethyl-3-(2-(1-(naphthalen-1-yl)ethylamino)pyrimidin-4-yl)oxazolidin-2-one | (CDCl₃) 8.10 (d, J = 5.8 Hz, 1 H), 8.01 (d, J = 8.6 Hz, 1 H), 7.81-7.78 (m, 1 H), 7.66 (d, J = 8.1 Hz, 1 H), 7.52 (d, J = 6.6 Hz, 1 H), 7.48-7.39 (m, 2 H), 7.36-7.32 (m, 1 H), 7.19-7.18 (m, 1 H), 5.66 (br s, 2 H), 3.78-3.69 (m, 2 H), 1.65 (s, 3 H), 1.64 (s, 3H), 1.35 (br s, 3 H) | HRMS(B) m/z 363.1822 (M + H)⁺ |
| 111: (R)-3-(2-((S)-1-(4-fluorophenyl)ethylamino)pyrimidin-4-yl)-5,5-dimethyl-4-phenyloxazolidin-2-one | 8.09 (d, J = 5.7 Hz, 1 H), 7.41-7.07 (m, 10 H), 5.21 (s, 3 H), 4.96 (q, J = 7.1 Hz, 1 H), 1.50 (s, 3 H), 1.24 (d, J = 7.1 Hz, 3 H), 0.98 (s, 3 H) | HRMS(B) m/z 407.188 (M + H)⁺ |
| 112: 4-(1-(4-((S)-4-isopropyl-2-oxooxazolidin-3-yl)pyrimidin-2-ylamino)ethyl)benzenesulfonamide | 8.13 (d, J = 5.8 Hz, 0.5 H), 8.11 (d, J = 5.8 Hz, 0.5 H), 7.85-7.80 (m, 2 H), 7.51 (d, J = 8.6 Hz, 1 H), 7.49 (d, J = 8.6 Hz, 1 H), 7.36 (d, J = 5.7 Hz, 0.5 H), 7.35 (d, J = 5.7 Hz, 0.5 H), 5.09 (q, J = 6.9 Hz, 0.5 H), 5.03-4.97 (br m, 0.5 H), 4.61 (br s, 0.5 H), 4.33-4.24 (m, 2.5 H), 2.66-2.58 (m, 0.5 H), 1.62 (br s, 0.5 H), 1.532 (d, J = 7.1 Hz, 1.5 H), 1.527 (d, J = 7.1 Hz, 1.5 H), 0.98 (d, J = 7.0 Hz, 1.5 H), 0.84 (d, J = 7.0 Hz, 1.5 H), 0.67 (br s, 1.5 H), 0.56 (br s, 1.5 H) | HRMS(B) m/z 406.1553 (M + H)⁺ |
| 113: (S)-3-(2-((S)-1-(4-hydroxyphenyl)ethylamino)pyrimidin-4-yl)-4-isopropyloxazolidin-2-one | 8.11 (d, J = 5.8 Hz, 1 H), 7.33 (d, J = 5.8 Hz, 1 H), 7.12 (d, J 8.1 Hz, 2 H), 6.72-6.68 (m, 2 H), 4.95 (q, J = 6.9 Hz, 1 H), 4.69-4.65 (m, 1 H), 4.35-4.28 (m, 2 H), 1.47 (d, J = 7.1 Hz, 3 H), 0.75 (br s, 3 H), 0.62 (br s, 3 H) | HRMS(B) m/z 343.1776 (M + H)⁺ |
| 114: (S)-3-(2-(1-cyclohexylethylamino)pyrimidin-4-yl)-4,4-dimethyloxazolidin-2-one | (CDCl₃) 8.14 (d, J = 5.8 Hz, 1 H), 7.24 (d, J = 5.8 Hz, 1 H), 5.08 (br s, 1 H), 4.10 (s, 2 H), 3.87 (q, J = 7.0 Hz, 1 H), 1.83-1.68 (m, 6 H), 1.75 (s, 3 H), 1.74 (s, 3 H), 1.48 (dddd, J = 12, 8.7, 5.7, 2.8 Hz, 1 H), 1.28-1.03 (m, 4 H), 1.17 (d, J = 6.8 Hz, 3 H) | HRMS(B) m/z 319.2132 (M + H)⁺ |
| 115: (S)-3-(5-fluoro-2-((S)-1-(naphthalen-2-yl)ethylamino)pyrimidin-4-yl)-4-isopropyloxazolidin-2-one | (CDCl₃) 8.15 (d, J = 3.5 Hz, 1 H), 7.83-7.72 (m, 4 H), 7.49-7.42 (m, 3 H), 5.06-5.03 (m, 1 H), 4.35-4.28 (m, 2 H), 4.10-4.08 (m, 1 H), 1.65 (d, J = 7.0 Hz, 3 H), 1.33-1.26 (m, 1 H), 0.38 (br s, 3 H), 0.14 (br s, 3 H) | HRMS(B) m/z 395.1884 (M + H)⁺ |
| 116: (S)-3-(5-chloro-2-((S)-1-phenylethylamino)pyrimidin-4-yl)-4-isopropyloxazolidin-2-one | (DMSO-d₆) 8.39-8.31 (m, 2 H), 7.35-7.32 (m, 2 H), 7.28 (t, J = 7.8 Hz, 2 H), 7.17 (t, J = 7.8 Hz, 1 H), 4.89-4.82 (m, 1 H), 4.49-4.45 (m, 2 H), 4.16 (br s, 1 H), 1.42 (d, J = 7.0 Hz, 3 H), 1.24 (br s, 1 H), 0.86-0.78 (m, 3 H), 0.48 (br s, 3 H) | HRMS(B) m/z 361.1431 (M + H)⁺ |
| 117: (S)-3-(2-((S)-1-(4-bromo-3,5-dimethoxyphenyl)ethylamino)pyrimidin-4-yl)-4-isopropyloxazolidin-2-one | 8.16 (d, J = 5.8 Hz, 1 H), 7.36 (d, J = 5.8 Hz, 1 H), 6.64 (s, 2 H), 5.00-4.95 (m, 1 H), 4.58 (br s, 1 H), 4.33-4.23 (m, 2 H), 3.79 (s, 6 H), 1.54 (d, J = 7.0 Hz, 3 H), 0.55 (br s, 6 H) | HRMS(B) m/z 465.1134 (M + H)⁺ |
| 118: (4S)-3-(2-(1-(3,4-dimethoxyphenyl)ethylamino)pyrimidin-4-yl)-4-isopropyloxazolidin-2-one | 8.12 (d, J = 5.8 Hz, 0.5 H), 8.10 (d, J = 5.8 Hz, 0.5 H), 7.35-7.32 (m, 1 H), 6.97-6.85 (m, 3 H), 5.00-4.91 (m, 1 H), 4.65 (br s, 0.5 H), 4.55 (br s, 0.5 H), 4.36-4.27 (m, 2 H), 3.80-3.79 (m, 6 H), 2.69-2.61 (m, 0.5 H), 1.87 (br s, 0.5 H), 1.50 (d, J = 7.1 Hz, 3 H), 1.00 (d, J = 7.1 Hz, 1.5 H), | HRMS(B) m/z 387.2035 (M + H)⁺ |

TABLE 6-continued

Chemical name, NMR chemical shifts and LCMS
signal for each compound listed in Table 5.

| Example: Name | ¹H NMR (400 MHz, CD₃OD) δ ppm (other solvents described) | LCMS |
|---|---|---|
| | 0.86 (d, J = 7.0 Hz, 1.5 H), 0.69 (br s, 1.5 H), 0.60 (br s, 1.5 H) | |
| 119: (S)-3-(2-(1-(6-methoxynaphthalen-2-yl)ethylamino)pyrimidin-4-yl)-4,4-dimethyloxazolidin-2-one | (CDCl₃) 8.09 (d, J = 5.8 Hz, 1 H), 7.64-7.59 (m, 3 H), 7.36 (dd, J = 8.3, 1.8 Hz, 1 H), 7.20-7.18 (m, 1 H), 7.07-7.03 (m, 2 H), 5.56 (br s, 1 H), 5.07-5.03 (br m, 1 H), 3.91-3.82 (m, 5 H), 1.61 (s, 3 H), 1.56 (d, J = 6.8 Hz, 3 H), 0.97 (br s, 3 H) | HRMS(B) m/z 393.1925 (M + H)⁺ |
| 120: (S)-5,5-dimethyl-3-(2-((S)-1-(naphthalen-2-yl)ethylamino)pyrimidin-4-yl)-4-phenyloxazolidin-2-one | 8.09 (d, J = 5.8 Hz, 1 H), 7.81-7.79 (m, 1 H), 7.74-7.68 (m, 2 H), 7.52 (br s, 1 H), 7.46-7.41 (m, 3 H), 7.18 (br s, 1 H), 7.02 (br s, 2 H), 6.99 (s, 3 H), 5.43 (s, 1 H), 5.02 (q, 6.6 Hz, 1 H), 1.62 (s, 3 H), 1.53 (d, J = 6.6 Hz, 3 H), 0.93 (s, 3 H) | HRMS(B) m/z 439.2131 (M + H)⁺ |
| 121: (S)-3-(2-((S)-1-(4-bromophenyl)ethylamino)pyrimidin-4-yl)-5,5-dimethyl-4-phenyloxazolidin-2-one | 8.08 (d, J = 5.8 Hz, 1 H), 7.44 (d, J = 5.8 Hz, 1 H), 7.29-7.24 (m, 5 H), 7.06 (br s, 2 H), 6.92 (br s, 2 H), 5.44 (s, 1 H), 4.88-4.84 (m, 1 H), 1.63 (s, 3 H), 1.42 (d, J = 7.1 Hz, 3 H), 0.95 (s, 3 H) | HRMS(B) m/z 467.1088 (M + H)⁺ |
| 122: (S)-3-(2-((S)-1-(3-methoxyphenyl)ethylamino)pyrimidin-4-yl)-5,5-dimethyl-4-phenyloxazolidin-2-one | 8.07 (d, J = 5.8 Hz, 1 H), 7.42 (d, J = 5.8 Hz, 1 H), 7.28-7.21 (m, 3 H), 7.11-7.08 (m, 3 H), 6.72 (dd, J = 8.3, 1.8 Hz, 1 H), 6.66 (br s, 1 H), 6.62 (br s, 1 H), 5.46 (s, 1 H), 4.80-4.74 (m, 1 H), 3.73 (s, 3 H), 1.64 (s, 3 H), 1.42 (d, J = 7.1 Hz, 3 H), 0.98 (s, 3 H) | HRMS(B) m/z 419.2067 (M + H)⁺ |
| 123: (S)-3-(2-((S)-1-(4-fluoro-3-methoxyphenyl)ethylamino)pyrimidin-4-yl)-4-isopropyloxazolidin-2-one | 8.14 (d, J = 6.6 Hz, 1 H), 7.57 (d, J = 6.6 Hz, 1 H), 7.08-6.99 (m, 2 H), 6.88 (ddd, J = 8.5, 4.2, 2.0 Hz, 1 H), 5.07 (q, J = 7.1 Hz, 1 H), 4.68 (dt, J = 7.8, 3.7 Hz, 1 H), 4.40-4.32 (m, 2 H), 3.86 (s, 3 H), 1.99 (br s, 1 H), 1.57 (d, J = 7.1 Hz, 3 H), 0.75 (d, J = 7.1 Hz, 3 H), 0.66 (d, J = 7.1 Hz, 3 H) | HRMS(B) m/z 375.1824 (M + H)⁺ |
| 124: (S)-3-(2-((S)-1-(4-bromophenyl)ethylamino)pyrimidin-4-yl)-4-phenyloxazolidin-2-one | 8.10 (d, J = 5.8 Hz, 1 H), 7.39 (d, J = 5.8 Hz, 1 H), 7.29-7.26 (m, 2 H), 7.25-7.21 (m, 3 H), 7.12 (dd, J = 6.3, 2.8 Hz, 2 H), 6.96 (d, J = 8.6 Hz, 2 H), 5.80 (dd, J = 8.6, 3.5 Hz, 1 H), 4.87 (q, J = 7.1 Hz, 1 H), 4.79 (t, J = 8.6 Hz, 1 H), 4.20 (dd, J = 8.6, 3.5 Hz, 1 H), 1.43 (d, J = 7.1 Hz, 3 H) | HRMS(B) m/z 439.0763 (M + H)⁺ |
| 125: (4S)-4-isopropyl-3-(2-((1-(3-morpholinophenyl)ethyl)amino)pyrimidin-4-yl)oxazolidin-2-one | 8.215 (d, J = 6.1 Hz, 0.5 H), 8.212 (d, J = 6.1 Hz, 0.5 H), 7.52 (t, J = 7.1 Hz, 2 H), 7.46 (dd, J = 5.8, 3.8 Hz, 1 H), 7.43-7.34 (m, 3 H), 5.86 (qd, J = 8.2, 4.0 Hz, 1 H), 4.83-4.75 (m, 1 H), 4.42-4.33 (m, 2 H), 2.62 (dtd, J = 14, 7.0, 3.8 Hz, 0.5 H), 2.28 (br s, 0.5 H), 1.02 (d, J = 7.1 Hz, 1.5 H), 0.91 (d, J = 7.1 Hz, 1.5 H), 0.88 (d, J = 7.11 Hz, 1.5 H), 0.73 (d, J = 7.1 Hz, 1.5 H) | HRMS(B) m/z 412.2342 (M + H)⁺ |
| 126: (R)-3-(2-((S)-1-(6-methoxynaphthalen-2-yl)ethylamino)pyrimidin-4-yl)-4-phenyloxazolidin-2-one | 8.10 (d, J = 5.6 Hz, 1 H), 7.69 (d, J = 9.1 Hz, 1 H), 7.72 (d, J = 8.6 Hz, 1 H), 7.62 (s, 1 H), 7.44-7.29 (m, 7 H), 7.20 (d, J = 2.5 Hz, 1 H), 7.11 (dd, J = 9.1, 2.5 Hz, 1 H), 5.55 (dd, J = 8.8, 3.8 Hz, 1 H), 4.80 (q, J = 7.1 Hz, 1 H), 4.69 (t, J = 8.6 Hz, 1 H), 4.16 (dd, J = 8.6, 4.0 Hz, 1 H), 3.90 (s, 3 H), 1.28 (d, J = 7.1 Hz, 3 H) | HRMS(B) m/z 441.1929 (M + H)⁺ |
| 127: (S)-4,4-dimethyl-3-(2-(1-(naphthalen-2-yl)ethylamino)pyrimidin-4-yl)oxazolidin-2-one | (CDCl₃) 8.20 (d, J = 5.8 Hz, 1 H), 7.84-7.79 (m, 4 H), 7.51-7.43 (m, 3 H), 7.29 (d, J = 5.8 Hz, 1 H), 5.65 (br s, 1 H), 5.19-5.16 (br m, 1 H), 3.98 (d, J = 8.1 Hz, 1 H), 3.91 (d, J = 8.1 Hz, 1 H), 1.70 (s, 3 H), 1.66 (d, J = 6.9 Hz, 3 H), 1.02 (br s, 3 H) | HRMS(B) m/z 363.1819 (M + H)⁺ |
| 128: 4,4-dimethyl-3-(2-(1-(4-(piperidin-1-yl)phenyl)ethylamino)pyrimidin-4-yl)oxazolidin-2-one | (CDCl₃) 8.17 (d, J = 5.8 Hz, 1 H), 7.26-7.22 (m, 3 H), 6.91 (d, J = 8.6 Hz, 2 H), 5.39 (br s, 1 H), 5.01-4.94 (m, 1 H), 4.04-3.99 (m, 2 H), 3.14-3.12 (m, 4 H), 1.75-1.69 (m, 8 H), 1.61-1.57 (m, 2 H), 1.55 (d, J = 7.1 Hz, 3 H), 1.34-1.29 (br m, 2 H) | HRMS(B) m/z 396.2396 (M + H)⁺ |
| 129: (S)-3-(2-((S)-1-(3-methoxyphenyl)ethylamino)pyrimidin-4-yl)-4-phenyloxazolidin-2-one | 8.09 (d, J = 5.8 Hz, 1 H), 7.36 (d, J = 5.8 Hz, 1 H), 7.26-7.16 (m, 5 H), 7.11 (t, J = 7.8 Hz, 3 H), 6.74-6.66 (m, 3 H), 5.81 (dd, J = 8.6, 3.5 Hz, 1 H), 4.86-4.79 (m, 2 | HRMS(B) m/z 391.1771 (M + H)⁺ |

TABLE 6-continued

Chemical name, NMR chemical shifts and LCMS
signal for each compound listed in Table 5.

| Example: Name | $^1$H NMR (400 MHz, CD$_3$OD) δ ppm (other solvents described) | LCMS |
|---|---|---|
| | H), 4.23 (dd, J = 8.8, 3.8 Hz, 1 H), 3.73 (s, 3 H), 1.44 (d, J 7.1 Hz, 3 H) | |
| 130: (4S)-3-(2-(1-(2,3-dihydrobenzo[b][1,4]dioxin-6-yl)ethylamino)pyrimidin-4-yl)-4-isopropyloxazolidin-2-one | 8.11 (d, J = 5.8 Hz, 0.5 H), 8.09 (d, J = 5.8 Hz, 0.5 H), 7.34-7.33 (m, 1 H), 6.81-6.71 (m, 3 H), 4.93-4.88 (m, 1 H), 4.65 (br s, 0.5 H), 4.52 (br s, 0.5 H), 4.36-4.27 (m, 2 H), 4.20-4.17 (m, 4 H), 2.66 (dtd, J = 14, 6.9, 3.5 Hz, 0.5 H), 1.99 (br s, 0.5 H), 1.456 (d, J = 7.1 Hz, 1.5 H), 1.454 (d, J = 7.1 Hz, 1.5 H), 1.00 (d, J = 7.1 Hz, 1.5 H), 0.85 (d, J = 7.1 Hz, 1.5 H), 0.75 (br s, 1.5 H), 0.63 (br s, 1.5 H) | HRMS(B) m/z 385.1854 (M + H)$^+$ |
| 131: (4S)-4-isopropyl-3-(2-(1-(pyridin-3-yl)ethylamino)pyrimidin-4-yl)oxazolidin-2-one | 8.545 (d, J = 6.1 Hz, 0.5 H), 8.540 (d, J = 6.1 Hz, 0.5 H), 8.39 (dt, J = 4.9, 1.6 Hz, 1 H), 8.13 (dd, J = 11, 5.7 Hz, 1 H), 7.86-7.80 (m, 1 H), 7.40-7.36 (m, 2 H), 5.12 (q, J = 7.1 Hz, 0.5 H), 5.02 (m, 0.5 H), 4.65 (br s, 0.5 H), 4.42 (br s, 0.5 H), 4.35-4.25 (m, 2 H), 2.67-2.62 (m, 0.5 H), 1.76 (br s, 0.5 H), 1.56 (d, J = 7.1 Hz, 1.5 H), 1.55 (d, J = 7.1 Hz, 1.5 H), 0.99 (d, J = 7.1 Hz, 1.5 H), 0.85 (d, J = 7.1 Hz, 1.5 H), 0.70 (br s, 1.5 H), 0.60 (br s, 1.5 H) | HRMS(B) m/z 328.1771 (M + H)$^+$ |
| 132: (S)-4-benzyl-3-(2-(cyclopropylamino)pyrimidin-4-yl)oxazolidin-2-one | 8.17 (d, J = 5.5 Hz, 1 H), 7.46 (d, J = 6.0 Hz, 1 H), 7.32-7.18 (m, 4 H), 7.15 (d, J = 7.0 Hz, 2 H), 5.04-4.91 (m, 1 H) 5.39 (br s, 1 H), 4.25-4.11 (m, 2 H), 3.51 (d, J = 13.0 Hz, 1 H), 2.80 (dd, J = 13.3, 9.79 Hz, 1 H), 2.76-2.69 (m, 1 H), 0.84-0.71 (m, 2 H), 0.60-0.47 (m, 2 H) | HRMS(B) m/z 311.1515 (M + H)$^+$ |
| 133: (S)-4-benzyl-3-(2-(cyclohexylamino)pyrimidin-4-yl)oxazolidin-2-one | (CDCl$_3$) 8.18 (d, J = 5.5 Hz, 1 H), 7.48 (d, J = 6.0 Hz, 1 H), 7.42-7.31 (m, 3 H), 7.26 (d, J = 7.0 Hz, 2 H), 5.56 (br s, 1 H), 5.02 (ddd, J = 9.9, 3.6, 3.5 Hz, 1 H), 4.33-4.22 (m, 2 H), 3.96-3.83 (m, 1 H), 3.53 (d, J = 12.6 Hz, 1 H), 2.85 (dd, J = 13.3, 9.8 Hz, 1 H), 1.89-1.75 (m, 2 H), 2.16-2.05 (m, 2 H), 1.73-1.63 (m, 1 H), 1.52-1.26 (m, 7 H) | HRMS(B) m/z 353.1979 (M + H)$^+$ |
| 134: (S)-4-benzyl-3-(2-(benzylamino)pyrimidin-4-yl)oxazolidin-2-one | 8.17 (d, J = 5.8 Hz, 1 H), 7.38 (d, J = 5.8 Hz, 1 H), 7.36-7.30 (m, 2 H), 7.30-7.11 (m, 6 H), 7.02 (br s, 2 H), 4.95 (br s, 1 H), 4.76-4.65 (m, 1 H), 4.65-4.55 (m, 1 H), 4.30 (t, J = 8.4 Hz, 1 H), 4.26-4.18 (m, 1 H), 3.05 (br s, 1 H), 2.84 (br s, 1 H) | HRMS(B) m/z 361.1669 (M + H)$^+$ |
| 135: (S)-4-benzyl-3-(2-(((R)-1-phenylethyl)amino)pyrimidin-4-yl)oxazolidin-2-one | (CDCl$_3$) 8.22 (d, J = 5.5 Hz, 1 H), 7.48 (d, J = 5.5 Hz, 1 H), 7.42-7.29 (m, 8 H), 7.19 (d, J = 7.0 Hz, 2 H), 5.62 (br s, 1 H), 5.15 (t, J = 6.8 Hz, 1 H), 4.77 (br s, 1 H), 4.25-4.16 (m, 2 H), 3.45 (dd, J = 13.8, 3.3 Hz, 1 H), 2.94 (dd, J = 13.6, 9.0 Hz, 1 H), 1.61 (d, J = 7.0 Hz, 3 H) | HRMS(B) m/z 375.1817 (M + H)$^+$ |
| 136: (4S)-3-(2-(1-(1,3-dimethyl-1H-pyrazol-4-yl)ethylamino)pyrimidin-4-yl)-4-isopropyloxazolidin-2-one | 8.14 (d, J = 5.8 Hz, 0.5 H), 8.13 (d, J = 5.8 Hz, 0.5 H), 7.42 (s, 0.5 H), 7.35 (s, 0.5 H), 7.35 (d, J = 5.7 Hz, 0.5 H), 7.34 (d, J = 5.8 Hz, 0.5 H), 5.10-5.00 (m, 1 H), 4.75 (dq, J = 7.8, 4.0 Hz, 1 H), 4.41-4.32 (m, 2 H), 3.76 (s, 1.5 H), 3.74 (s, 1.5 H), 2.64-2.57 (m, 0.5 H), 2.41-2.32 (m, 0.5 H), 2.18 (s, 3 H), 1.493 (d, J = 7.1 Hz, 1.5 H), 1.488 (d, J = 7.1 Hz, 1.5 H), 0.97 (d, J = 7.1 Hz, 1.5 H), 0.88 (d, J = 7.1 Hz, 3 H), 0.78 (d, J = 7.1 Hz, 1.5 H) | HRMS(B) m/z 345.2038 (M + H)$^+$ |
| 137: (S)-3-[2-((S)-1,3-dimethyl-butylamino)-pyrimidin-4-yl]-5,5-dimethyl-4-phenyl-oxazolidin-2-one | (DMSO-d$_6$) 8.10 (m, 1 H), 7.34 (m, 2 H), 7.26 (m, 3 H), 7.17 (br s, 1 H), 6.83 (s, 1 H), 5.39 (s, 1 H), 1.61 (s, 3 H), 1.39 (s, 1 H), 1.26 (s, 1 H), 1.02 (m, 4 H), 0.90 (s, 3 H), 0.81 (s, 1 H), 0.71 (s, 3 H), 0.41 (s, 3 H) | HRMS(B) m/z 369.2297 (M + H)$^+$ |
| 138: (S)-3-[2-((S)-2-hydroxy-1-methyl-ethylamino)-pyrimidin-4-yl]-5,5-dimethyl-4-phenyl-oxazolidin-2-one | (DMSO-d$_6$) 8.14 (d, J = 5.8 Hz, 1 H), 7.17 (d, J = 5.8 Hz, 1 H), 7.03 (br s, 1 H), 4.67 (br s, 1 H), 4.42-4.34 (m, 2 H), 3.96 (br s, 1 H), 2.46 (m, 1 H), 1.63 (m, 1 H), 1.47 (m, 1 H), 1.21 (m, 1 H), 1.09 (d, J = 6.3 Hz, 3 | HRMS(B) m/z 307.2141 (M + H)$^+$ |

TABLE 6-continued

Chemical name, NMR chemical shifts and LCMS
signal for each compound listed in Table 5.

| Example: Name | $^1$H NMR (400 MHz, CD$_3$OD) δ ppm (other solvents described) | LCMS |
|---|---|---|
| | H), 0.89 (d, J = 7.3 Hz, 3 H), 0.87 (d, J = 6.5 Hz, 3 H), 0.84 (d, J = 6.5 Hz, 3 H), 0.77 (d, J = 6.8 Hz, 3 H) | |
| 139: (S)-4,4-dimethyl-3-(2-(1-phenylethylamino)pyrimidin-4-yl)oxazolidin-2-one | (CDCl$_3$) 8.08 (d, J = 5.8 Hz, 1 H), 7.27-7.20 (m, 4 H), 7.17 (d, J = 5.6 Hz, 1 H), 7.15-7.11 (m, 1 H), 5.42 (br s, 1 H), 4.94-4.87 (m, 1 H), 3.92-3.86 (m, 2 H), 1.58 (s, 3 H), 1.47 (d, J = 6.9 Hz, 3 H), 1.06 (br s, 3 H) | HRMS(B) m/z 313.1668 (M + H)$^+$ |
| 140: (S)-3-(2-((S)-1-(4-fluorophenyl)ethylamino)pyrimidin-4-yl)-4-methyl-4-phenyloxazolidin-2-one | (CDCl$_3$) 8.17 (d, J = 5.8 Hz, 1 H), 7.45-7.31 (m, 4 H), 7.28-7.24 (m, 2 H), 7.09-7.06 (m, 2 H), 7.01-6.95 (m, 2 H), 5.21 (br s, 1 H), 4.20 (s, 2 H), 4.13 (br s, 1 H), 1.65 (br s, 3 H), 1.13 (d, J = 6.8 Hz, 3 H) | HRMS(B) m/z 393.1729 (M + H)$^+$ |
| 141: (4S)-4-methyl-4-phenyl-3-(2-(1-(4-(piperidin-1-yl)phenyl)ethylamino)pyrimidin-4-yl)oxazolidin-2-one | (CDCl$_3$) 8.14 (d, J = 5.8 Hz, 0.35 H), 8.12 (d, J = 5.8 Hz, 0.65 H), 7.42-7.27 (m, 6 H), 7.04 (d, J = 8.6 Hz, 0.65 H), 6.91-6.82 (m, 3.35 H), 5.16 (br s, 0.35 H), 5.02 (br s, 0.65 H), 4.30 (s, 1.3 H), 4.22 (s, 0.7 H), 4.19 (br s, 1 H), 3.16-3.13 (m, 4 H), 2.20 (s, 1.95 H), 1.79-1.70 (br m, 5.05 H), 1.62-1.56 (m, 2 H), 1.37 (d, J = 6.8 Hz, 1.95 H), 1.06 (d, J = 6.3 Hz, 1.05 H) | HRMS(B) m/z 458.2551 (M + H)$^+$ |
| 142: (S)-4-benzyl-3-(2-(((S)-1-phenylethyl)amino)pyrimidin-4-yl)oxazolidin-2-one | 8.15 (d, J = 5.77 Hz, 1 H), 7.40-7.30 (m, 3 H), 7.25-7.13 (m, 5 H), 7.07 (t, J = 7.0 Hz, 1 H), 6.91 (br s, 2 H), 5.13 (q, J = 7.0 Hz, 1 H), 5.01 (t, J = 7.4 Hz, 1 H), 4.34 (t, J = 8.5 Hz, 1 H), 4.20 (dd, J = 8.9, 2.4 Hz, 1 H), 2.64 (br s, 1 H), 2.47 (br s, 1 H), 1.54 (d, J = 7.3 Hz, 3 H) | HRMS(B) m/z 375.1817 (M + H)$^+$ |
| 143: (R)-4-benzyl-3-(2-(cyclopropylamino)pyrimidin-4-yl)oxazolidin-2-one | (CDCl$_3$) 8.19 (d, J = 5.0 Hz, 1 H), 7.62 (d, J = 6.0 Hz, 1 H), 7.41-7.29 (m, 4 H), 7.26-7.19 (m, 2 H), 6.42 (br s, 1 H), 5.07 (t, J = 8.3 Hz, 1 H), 4.30-4.24 (m, 2 H), 3.60 (d, J = 12.6 Hz, 1 H), 2.97-2.79 (m, 2 H), 0.95-0.81 (m, 2 H), 0.75-0.62 (m, 2 H) | HRMS(B) m/z 311.1516 (M + H)$^+$ |
| 144: (R)-4-benzyl-3-(2-(cycloheptylamino)pyrimidin-4-yl)oxazolidin-2-one | 8.12 (d, J = 6.0 Hz, 1 H), 7.36-7.28 (m, 3 H), 7.28-7.19 (m, 3 H), 5.15-5.05 (m, 1 H), 4.37 (t, J = 8.5 Hz, 1 H), 4.30-4.24 (m, 1 H), 4.04 (br s., 1 H), 3.09 (dd, J = 13.6, 8.0 Hz, 1 H), 2.11-1.94 (m, 2 H), 1.78-1.48 (m, 11 H) | HRMS(B) m/z 367.2134 (M + H)$^+$ |
| 145: (R)-4-benzyl-3-(2-(cyclohexylamino)pyrimidin-4-yl)oxazolidin-2-one | (CDCl$_3$) 8.18 (d, J = 5.0 Hz, 1 H), 7.48 (d, J = 6.0 Hz, 1 H), 7.42-7.29 (m, 3 H), 7.26 (d, J = 7.0 Hz, 2 H), 5.55 (br s, 1 H), 5.10-4.94 (m, 1 H), 4.33-4.22 (m, 2 H), 3.96-3.82 (m, 1 H), 3.53 (d, J = 12.1 Hz, 1 H), 2.85 (dd, J = 13.3, 9.8 Hz, 1 H), 2.22-2.01 (m, 2 H), 1.81 (td, J = 13.6, 4.0 Hz, 2 H), 1.68 (dd, J = 9.0, 3.5 Hz, 1 H), 1.51-1.22 (m, 6 H) | HRMS(B) m/z 353.1981 (M + H)$^+$ |
| 146: (R)-4-benzyl-3-(2-(benzylamino)pyrimidin-4-yl)oxazolidin-2-one | 8.17 (d, J = 5.8 Hz, 1 H), 7.38 (d, J = 6.0 Hz, 1 H), 7.35-7.30 (m, 2 H), 7.29-7.18 (m, 5 H), 7.15 (t, J = 7.3 Hz, 1 H), 7.02 (br s, 2 H), 4.95 (br s, 1 H), 4.75-4.65 (m, 1 H), 4.65-4.56 (m, 1 H), 4.30 (t, J = 8.5 Hz, 1 H), 4.27-4.20 (m, 1 H), 3.05 (br s, 1 H), 2.82 (br s, 1 H) | HRMS(B) m/z 361.1659 (M + H)$^+$ |
| 147: (R)-4-benzyl-3-(2-(((R)-1-phenylethyl)amino)pyrimidin-4-yl)oxazolidin-2-one | (CDCl$_3$) 8.21 (d, J = 5.5 Hz, 1 H), 7.50 (d, J = 6.0 Hz, 1 H), 7.43-7.29 (m, 5 H), 7.28-7.12 (m, 4 H), 7.00 (br s., 2 H), 5.97 (br s, 1 H), 5.17 (t, J = 6.8 Hz, 1 H), 5.03-4.89 (m, 1 H), 4.28 (t, J = 8.5 Hz, 1 H), 4.19 (dd, J = 9.0, 3.0 Hz, 1 H), 2.97 (br s, 1 H), 2.53 (br s, 1 H), 1.63 (d, J = 7.0 Hz, 3 H) | HRMS(B) m/z 375.1822 (M + H)$^+$ |
| 148: (R)-4-benzyl-3-(2-(((S)-1-phenylethyl)amino)pyrimidin-4-yl)oxazolidin-2-one | (CDCl$_3$) 8.21 (d, J = 6.0 Hz, 1 H), 7.49 (d, J = 5.5 Hz, 1 H), 7.44-7.29 (m, 8 H), 7.19 (d, J = 6.5 Hz, 2 H), 5.69 (br s, 1 H),, 5.15 (t, J = 7.0 Hz, 1 H), 4.76 (br s, 1 H), 4.24-4.16 (m, 2 H), 3.45 (dd, J = 13.8, 3.3 Hz, 1 H), 2.94 (dd, J = 13.6, 9.5 Hz, 1 H), 1.61 (d, J = 7.0 Hz, 3 H) | HRMS(B) m/z 375.1816 (M + H)$^+$ |
| 149: (S)-4-isopropyl-3-(5-methyl-2-((S)-1- | (CDCl$_3$) 8.13 (s, 1 H), 7.35-7.28 (m, 4 H), 7.24-7.20 (m, 1 H), 5.73 (br s, 1 H), 5.00- | HRMS(B) m/z |

TABLE 6-continued

Chemical name, NMR chemical shifts and LCMS signal for each compound listed in Table 5.

| Example: Name | $^1$H NMR (400 MHz, CD$_3$OD) δ ppm (other solvents described) | LCMS |
|---|---|---|
| phenylethylamino)pyrimidin-4-yl)oxazolidin-2-one | 4.92 (m, 1 H), 4.59-4.51 (m, 1 H), 4.38 (t, J = 8.8 Hz, 1 H), 4.12 (t, J = 8.8 Hz, 1 H), 2.14 (s, 3 H), 1.55 (d, J = 6.5 Hz, 3 H), 1.44 (br s, 1 H), 0.59 (d, J = 6.5 Hz, 3 H), 0.53 (d, J = 5.0 Hz, 3 H) | 341.1974 (M + H)$^+$ |
| 150: (S)-3-(5-fluoro-2-((S)-1-phenylethylamino)pyrimidin-4-yl)-4-isopropyloxazolidin-2-one | (CDCl$_3$) 8.18 (d, J = 3.0 Hz, 1 H), 7.32-7.28 (m, 4 H), 7.25-7.20 (m, 1 H), 5.64 (br s, 1 H), 4.92-4.87 (m, 1 H), 4.47-4.40 (m, 1 H), 4.39 (t, J = 8.5 Hz, 1 H), 4.17 (t, J = 8.6 Hz, 1 H), 1.86 (br s, 1 H), 1.54 (d, J = 7.0 Hz, 3 H), 0.68-0.56 (m, 6 H) | HRMS(B) m/z 345.1724 (M + H)$^+$ |
| 151: (S)-4-isopropyl-3-(2-((S)-1-(3-methoxyphenyl)ethylamino)-5-methylpyrimidin-4-yl)oxazolidin-2-one | (CDCl$_3$) 8.11 (s, 1 H), 7.24-7.20 (m, 1 H), 6.94-6.89 (m, 2H), 6.76 (dd, J = 7.6 Hz, J = 2.5 Hz, 1 H), 5.99 (br s, 1 H), 4.97 (quin, J = 6.8 Hz, 1 H), 4.58 (td, J = 8.8 Hz, J = 5.1 Hz, 1 H), 4.39 (t, J = 8.8 Hz, 1 H), 4.13 (t, J = 8.6 Hz, 1 H), 3.80 (s, 3 H), 2.16 (s, 3 H), 1.62-1.56 (m, 1 H), 1.57 (d, J = 6.5 Hz, 3 H), 0.64 (d, J = 7.1 Hz, 3 H), 0.59 (d, J = 7.1 Hz, 3 H) | HRMS(B) m/z 371.2083 (M + H)$^+$ |
| 152: (S)-4-isopropyl-3-(5-methyl-2-((S)-1-(naphthalen-2-yl)ethylamino)pyrimidin-4-yl)oxazolidin-2-one | (CDCl$_3$) 8.13 (s, 1 H), 7.81-7.74 (m, 4 H), 7.48-7.40 (m, 3 H), 5.87 (br s, 1 H), 5.17-5.10 (m, 1 H), 4.42 (td, J = 8.7 Hz, J = 4.8 Hz, 1 H), 4.29 (t, J = 8.8 Hz, 1 H), 4.02 (t, J = 8.6 Hz, 1 H), 2.13 (s, 3 H), 1.64 (d, J = 7.0 Hz, 3 H), 1.35-1.28 (m, 1 H), 0.42 (d, J = 7.1 Hz, 3 H), 0.17 (d, J = 7.0 Hz, 3 H) | HRMS(B) m/z 391.2135 (M + H)$^+$ |
| 153: (S)-3-(5-fluoro-2-((S)-1-(3-methoxyphenyl)ethylamino)pyrimidin-4-yl)-4-isopropyloxazolidin-2-one | (CDCl$_3$) 8.16 (d, J = 2.5 Hz, 1 H), 7.23 (t, J = 7.8 Hz, 1 H), 6.91-6.83 (m, 2 H), 6.78-6.74 (m, 1 H), 6.05 (br s, 1 H), 4.86 (br s, 1 H), 4.49-4.38 (m, 2 H), 4.19 (t, J = 7.8 Hz, 1 H), 3.79 (s, 3 H), 1.54 (d, J = 8.0 Hz, 3 H), 1.32-1.25 (m, 1 H), 0.66-0.58 (m, 6 H) | HR-MS m/z (M + H)$^+$ |
| 154: (S)-4-methyl-3-(2-((S)-1-(naphthalen-2-yl)ethylamino)pyrimidin-4-yl)-4-phenyloxazolidin-2-one | (CDCl$_3$) 8.17 (d, J = 5.8 Hz, 1 H), 7.84-7.78 (m, 3 H), 7.55 (s, 1 H), 7.51-7.43 (m, 5 H), 7.39-7.36 (m, 1 H), 7.29-7.25 (m, 3 H), 5.54 (br s, 1 H), 4.31 (br s, 1 H), 4.19-4.12 (m, 2 H), 1.84 (br s, 1 H), 1.24 (d, J = 6.8 Hz, 3 H) | HRMS(B) m/z 425.1972 (M + H)$^+$ |
| 155: (S)-3-(2-((S)-1-(6-methoxynaphthalen-2-yl)ethylamino)pyrimidin-4-yl)-4-methyl-4-phenyloxazolidin-2-one | (CDCl$_3$) 8.18 (d, J = 5.8 Hz, 1 H), 7.69 (t, J = 7.8 Hz, 2 H), 7.47-7.41 (m, 4 H), 7.38-7.34 (m, 1 H), 7.28-7.23 (m, 3 H), 7.17-7.13 (m, 2 H), 5.31 (br s, 1 H), 4.31 (br s, 1 H), 4.19-4.13 (m, 2 H), 3.94 (s, 3 H), 1.56 (br s, 3 H), 1.20 (d, J = 6.6 Hz, 3 H) | HRMS(B) m/z 455.2081 (M + H)$^+$ |
| 156: (S)-3-(2-((S)-1-cyclohexylethylamino)pyrimidin-4-yl)-4-methyl-4-phenyloxazolidin-2-one | (CDCl$_3$) 8.11 (d, J = 5.8 Hz, 1 H), 7.38-7.32 (m, 5 H), 7.29-7.25 (m, 1 H), 4.81 (br s, 1 H), 4.31-4.26 (m, 2 H), 3.16 (br s, 1 H), 2.17 (s, 3 H), 1.77-1.57 (m, 6 H), 1.28-1.09 (m, 4 H), 0.99-0.85 (m, 2 H), 0.55 (br s, 2 H) | HRMS(B) m/z 381.2280 (M + H)$^+$ |
| 157: (S)-3-[2-((S)-2-hydroxy-1-methyl-ethylamino)-pyrimidin-4-yl]-5,5-dimethyl-4-phenyl-oxazolidin-2-one | (DMSO-d$_6$) 8.13 (m, 1 H), 7.36 (m, 2 H), 7.29 (m, 3 H), 7.19 (br s, 1 H), 6.65 (s, 1 H), 5.44 (s, 1 H), 4.30 (br s, 1 H), 2.95 (br s, 1 H), 2.77 (br s, 3 H), 1.61 (s, 3 H), 1.25 (s, 1 H), 1.04 (m, 3 H), 0.92 (s, 3 H) | HRMS(B) m/z 343.1778 (M + H)$^+$ |
| 158: (S)-5,5-dimethyl-4-phenyl-3-[2-((S)-1,2,2-trimethyl-propylamino)-pyrimidin-4-yl]-oxazolidin-2-one | (DMSO-d$_6$) 8.10 (d, J = 5.5 Hz, 1 H), 7.37-7.33 (m, 2 H), 7.29-7.25 (m, 3 H), 7.20 (br s, 1 H), 6.75 (d, J = 10 Hz, 1 H), 5.42 (s, 1 H), 3.47 (m, 1 H), 1.62 (s, 3 H), 0.96 (d, J = 6.8 Hz, 3 H), 0.88 (s, 3 H), 0.46 (s, 9 H) | HRMS(B) m/z 369.2277 (M + H)$^+$ |
| 159: (R)-3-(2-((S)-1-(naphthalen-1-yl)ethylamino)pyrimidin-4-yl)-4-phenyloxazolidin-2-one | 8.11 (d, J = 6.1 Hz, 1 H), 8.04 (d, J = 8.6 Hz, 1 H), 7.89 (d, J = 8.1 Hz, 1 H), 7.74 (d, J = 8.1 Hz, 1 H), 7.60-7.56 (m, 1 H), 7.53-7.49 (m, 1 H), 7.46-7.44 (m, 1 H), 7.42-7.31 (m, 5 H), 7.21-7.18 (m, 2 H), 5.52 (q, J = 6.9 Hz, 1 H), 5.44 (dd, J = 8.8, 3.8 Hz, 1 H), 4.63 (t, J = 8.7 Hz, 1 H), 4.10 (dd, J = 8.6, 4.0 Hz, 1 H), 1.33 (d, J = 7.1 Hz, 3 H) | HRMS(B) m/z 411.1823 (M + H)$^+$ |

TABLE 6-continued

Chemical name, NMR chemical shifts and LCMS
signal for each compound listed in Table 5.

| Example: Name | $^1$H NMR (400 MHz, CD$_3$OD) δ ppm (other solvents described) | LCMS |
|---|---|---|
| 160: (S)-4-isopropyl-3-[2-((S;-1,2,2-trimethyl-propylamino)-pyrimidin-4-yl]-oxazolidin-2-one | (DMSO-d$_6$) 8.14 (d, J = 5.5 Hz, 1 H), 7.16 (d, J = 5.5 Hz, 1 H), 7.00 (br. s, 1 H), 4.73-4.66 (m, 1 H), 4.41-4.34 (m, 2 H), 3.92 (br s, 1 H), 2.46 (br s, 1 H), 1.05 (d, J = 6.8 Hz, 3 H), 0.91 (d, J = 7.3 Hz, 3 H), 0.87 (s, 9 H), 0.77 (d, J = 6.8 Hz, 3 H) | HRMS(B) m/z 307.2130 (M + H)$^+$ |
| 161: (S)-3-[2-((S)-1-cyclopropyl-ethylamino)-pyrimidin-4-yl]-4-isopropyl-oxazolidin-2-one | (DMSO-d$_6$) 8.13 (d, J = 5.5 Hz, 1 H), 7.17 (d, J = 5.5 Hz, 1 H), 7.09 (br s, 1 H), 4.67-4.63 (m, 1 H), 4.37 (m, 2 H), 3.52-3.43 (m, 1 H), 2.46 (br s, 1 H), 1.19 (d, J = 6.8 Hz, 3 H), 1.01-0.93 (m, 1 H), 0.89 (d, J = 7.0 Hz, 3 H), 0.77 (d, J = 6.8 Hz, 3 H), 0.41 (m, 1 H), 0.33 (m, 1 H), 0.22 (br s, 1 H), 0.10 (br s, 1 H) | HRMS(B) m/z 291.1812 (M + H)$^+$ |
| 162: (S)-4-isopropyl-3-(2-((S)-1-(4-phenoxyphenyl)ethylamino)pyrimidin-4-yl)oxazolidin-2-one | 8.13 (d, J = 5.8 Hz, 1 H), 7.34-7.28 (m, 5 H), 7.09-7.05 (m, 1 H), 6.96-6.90 (m, 4 H), 5.06 (q, J = 7.1 Hz, 1 H), 4.71-4.67 (m, 1 H), 4.37-4.28 (m, 2 H), 2.08 (br s, 1 H), 1.52 (d, J = 7.1 Hz, 3 H), 0.76 (d, J = 7.1 Hz, 3 H), 0.67 (d, J = 7.1 Hz, 3 H) | HRMS(B) m/z 419.2081 (M + H)$^+$ |
| 163: (S)-3-(2-((S)-1-(2,3-dihydrobenzofuran-5-yl)ethylamino)pyrimidin-4-yl)-4-isopropyloxazolidin-2-one | 8.12 (d, J = 5.6 Hz, 1 H), 7.32 (d, J = 5.6 Hz, 1 H), 7.17 (s, 1 H), 7.04-7.02 (m, 1 H), 6.63 (d, J = 8.1 Hz, 1 H), 4.98 (q, J = 7.1 Hz, 1 H), 4.69-4.65 (m, 1 H), 4.51-4.47 (m, 2 H), 4.36-4.27 (m, 2 H), 3.16-3.12 (m, 2 H), 2.09 (br s, 1 H), 1.48 (d, J = 7.0 Hz, 3 H), 0.75 (d, J = 7.0 Hz, 3 H), 0.65 (d, J = 7.1 Hz, 3 H) | HRMS(B) m/z 369.1915 (M + H)$^+$ |
| 164: (S)-3-(2-((S)-1-(4-tert-butylphenyl)ethylamino)pyrimidin-4-yl)-4-isopropyloxazolidin-2-one | 8.12 (d, J = 5.8 Hz, 1 H), 7.34-7.31 (m, 3 H), 7.24-7.21 (m, 2 H), 5.02 (q, J = 7.1 Hz, 1 H), 4.66-4.63 (m, 1 H), 4.35-4.25 (m, 2 H), 1.95 (br s, 1 H), 1.50 (d, J = 7.0 Hz, 3 H), 1.29 (s, 9 H), 0.69 (d, J = 7.0 Hz, 3 H), 0.58 (d, J = 6.9 Hz, 3 H) | HRMS(B) m/z 383.2449 (M + H)$^+$ |
| 165: (S)-3-[2-((S)-1-cyclopropyl-ethylamino)-pyrimidin-4-yl]-5,5-dimethyl-4-phenyl-oxazolidin-2-one | (DMSO-d$_6$) 8.10 (d, J = 5.5 Hz, 1 H), 7.37-7.33 (m, 2 H), 7.30-7.24 (m, 3 H), 7.15 (br s, 1 H), 7.00 (br s, 1 H), 5.37 (s, 1 H), 2.82 (br s, 1 H), 1.61 (s, 3 H), 1.07 (d, J = 6.5 Hz, 3 H), 0.89 (s, 3 H), 0.65 (br s, 1 H), 0.17 (br s, 1 H), 0.00 (br s, 1 H), −0.23 (br s, 1 H), −0.65 (br s, 1 H) | HRMS(B) m/z 353.1974 (M + H)$^+$ |
| 166: (S)-3-(5-fluoro-2-((S)-1-(4-methoxyphenyl)ethylamino)pyrimidin-4-yl)-4-isopropyloxazolidin-2-one | (DMSO-d$_6$) 8.36 (br s, 1 H), 7.95 (br s, 1 H), 7.24 (d, J = 8.5 Hz, 2 H), 6.82 (d, J = 9.0 Hz, 2 H), 6.05 (br s, 1 H), 4.77 (br s, 1 H), 4.54-4.45 (m, 2 H), 4.24 (br s, 1 H), 3.70 (s, 3 H), 1.38 (d, J = 7.0 Hz, 3 H), 1.26-1.22 (m, 1 H), 0.66-0.47 (m, 6 H) | HRMS(B) m/z 375.1815 (M + H)$^+$ |
| 167: (R)-5,5-dimethyl-4-phenyl-3-(2-((S)-1-phenylethylamino)pyrimidin-4-yl)oxazolidin-2-one | 8.08 (d, J = 5.8 Hz, 1 H), 7.42-7.38 (m, 3 H), 7.35-7.27 (m, 5 H), 7.22-7.17 (m, 3 H), 5.18 (s, 1 H), 4.62-4.57 (m, 1 H), 1.51 (s, 3 H), 1.19 (d, J = 7.0 Hz, 3 H), 0.98 (s, 3 H) | HRMS(B) m/z 389.1975 (M + H)$^+$ |
| 168: (R)-5,5-dimethyl-3-(2-((S)-1-(naphthalen-2-yl)ethylamino)pyrimidin-4-yl)-4-phenyloxazolidin-2-one | 8.10 (d, J = 5.8 Hz, 1 H), 7.82 (d, J = 8.1 Hz, 3 H), 7.73 (s, 1 H), 7.48-7.33 (m, 7 H), 7.19 (d, J = 7.1 Hz, 2 H), 5.07 (s, 1 H), 4.74 (q, J = 6.6 Hz, 1 H), 1.32 (d, J = 6.9 Hz, 3 H), 1.29 (s, 3 H), 0.92 (s, 3 H) | HRMS(B) m/z 439.2132 (M + H)$^+$ |
| 169: (R)-3-(2-((S)-1-(4-fluoro-3-methoxyphenyl)ethylamino)pyrimidin-4-yl)-4-phenyloxazolidin-2-one | δ 8.10 (d, J = 5.8 Hz, 1 H), 7.41-7.28 (m, 6 H), 7.02-6.97 (m, 2 H), 6.82 (ddd, J = 8.2, 4.4, 2.0 Hz, 1 H), 5.61 (dd, J = 8.6, 4.0 Hz, 1 H), 4.77 (t, J = 8.6 Hz, 1 H), 4.65 (q, J = 7.1 Hz, 1 H), 4.19 (dd, J = 9.1, 4.0 Hz, 1 H), 3.83 (s, 3 H), 1.20 (d, J = 7.9 Hz, 3 H) | HRMS(B) m/z 409.1677 (M + H)$^+$ |

Example 170

(4S)-4-isopropyl-3-(2-(2,2,2-trifluoro-1-phenylethylamino)pyrimidin-4-yl)oxazolidin-2-one

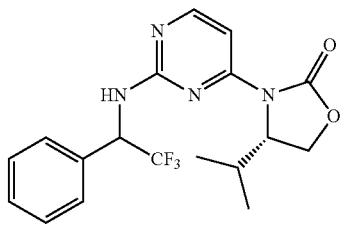 [SMILES: CC(C)[C@H]1COC(=O)N1c1ccnc(NC(c2ccccc2)C(F)(F)F)n1]

A solution of (S)-3-(2-chloropyrimidin-4-yl)-4-isopropyloxazolidin-2-one (163 mg, 0.674 mmol), 2,2,2-trifluoro-1-phenylethanamine (624 mg, 3.56 mmol, 5.3 equiv) and p-toluenesulfonic acid monohydrate (321 mg, 1.69 mmol, 2.5 equiv) in n-BuOH (3 mL) was heated at 110° C. for 2 h and treated with additional p-toluenesulfonic acid monohydrate (321 mg, 1.69 mmol, 2.5 equiv), then heated at 110° C. for 1½ h. After cooling, the solid reaction mixture was treated with MeCN, sonicated and filtered. The filtrated was concentrated and purified by silica gel column chromatography (EtOAc/Heptane 0 to 30%) to give (4S)-4-isopropyl-3-(2-(2,2,2-trifluoro-1-phenylethylamino)pyrimidin-4-yl)oxazolidin-2-one (65 mg) in 25% yield. $^1$H NMR (400 MHz, CD$_3$OD) δ 8.215 (d, J=6.1 Hz, 0.5H), 8.212 (d, J=6.1 Hz, 0.5H), 7.52 (t, J=7.1 Hz, 2H), 7.46 (dd, J=5.8, 3.8 Hz, 1H), 7.43-7.34 (m, 3H), 5.86 (qd, J=8.2, 4.0 Hz, 1H), 4.83-4.75 (m, 1H), 4.42-4.33 (m, 2H), 2.62 (dtd, J=14, 7.0, 3.8 Hz, 0.5H), 2.28 (br s, 0.5H), 1.02 (d, J=7.1 Hz, 1.5H), 0.91 (d, J=7.1 Hz, 1.5H), 0.88 (d, J=7.11 Hz, 1.5H), 0.73 (d, J=7.1 Hz, 1.5H); HRMS(B) m/z 381.1545 (M+H)$^+$.

Examples 171 and 172

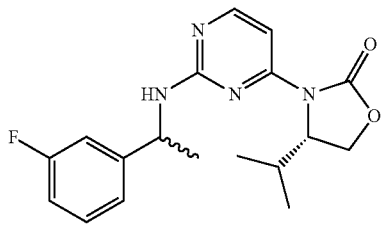 [SMILES: CC(Nc1nccc(N2C(=O)OC[C@@H]2C(C)C)n1)c1cccc(F)c1]

A solution of (S)-3-(2-chloropyrimidin-4-yl)-4-isopropyloxazolidin-2-one (106 mg, 0.439 mmol) and 1-(3-fluorophenyl)ethanamine (196 mg, 1.41 mmol, 3.21 equiv) in DMSO (1 mL) was heated at 110° C. for 1½ h. The reaction mixture was diluted with EtOAc (8 mL) and washed with water (30 mL). After separation, the aqueous phase was extracted with EtOAc (3×8 mL). Combined organics were dried over Na$_2$SO$_4$, filtered and concentrated. Silica gel column chromatography (EtOAc/Heptane 10 to 50%) provided (S)-3-(2-((R)-1-(3-fluorophenyl)ethylamino)pyrimidin-4-yl)-4-isopropyloxazolidin-2-one and (S)-3-(2-((S)-1-(3-fluorophenyl)ethylamino)pyrimidin-4-yl)-4-isopropyloxazolidin-2-one.

Example 171 first eluted product (28 mg) $^1$H NMR (400 MHz, CD$_3$OD) δ 8.11 (d, J=5.8 Hz, 1H), 7.36-7.27 (m, 2H), 7.16 (d, J=7.6 Hz, 1H), 7.07 (dt, J=10, 2.0 Hz, 1H), 6.92-6.88 (m, 1H), 4.98-4.93 (m, 1H), 4.42 (br s, 1H), 4.32 (dd, J=9.1, 2.8 Hz, 1H), 4.26 (t, J=8.7 Hz, 1H), 2.64 (dtd, J=14, 7.1, 3.5 Hz, 1H), 1.50 (d, J=7.0 Hz, 3H), 0.98 (d, J=7.1 Hz, 3H), 0.85 (d, J=7.0 Hz, 3H); HRMS(B) m/z 345.1729 (M+H)$^+$.

Example 172 second eluted product (22 mg) $^1$H NMR (400 MHz, CD$_3$OD) δ 8.13 (d, J=5.7 Hz, 1H), 7.36 (d, J=5.8 Hz, 1H), 7.29 (td, J=8.1, 6.1 Hz, 1H), 7.13 (d, J=7.6 Hz, 1H), 7.06-7.04 (m, 1H), 6.94-6.87 (m, 1H), 5.03 (q, J=7.1 Hz, 1H), 4.64 (br s, 1H), 4.34-4.26 (m, 2H), 1.79 (br s, 1H), 1.50 (d, J=7.1 Hz, 3H), 0.70 (br s, 3H), 0.58 (br s, 3H); HRMS(B) m/z 345.1727 (M+H)$^+$.

Examples 173 and 174

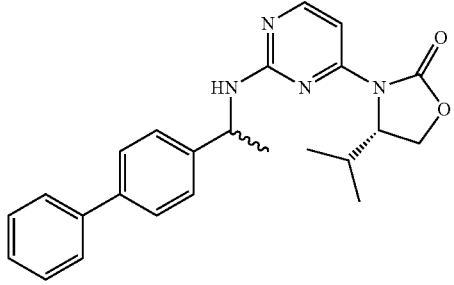 [SMILES: CC(Nc1nccc(N2C(=O)OC[C@@H]2C(C)C)n1)c1ccc(-c2ccccc2)cc1]

A solution of (S)-3-(2-chloropyrimidin-4-yl)-4-isopropyloxazolidin-2-one (90 mg, 0.37 mmol), iPr$_2$NEt (0.455 mL, 2.61 mmol, 7.0 equiv) and 1-(biphenyl-4-yl)ethanamine hydrochloride (87 mg, 0.37 mmol) in DMSO (1 mL) was heated at 110° C. for 2 h. The reaction mixture was diluted with EtOAc (8 mL) and washed with water (30 mL). After separation, the aqueous phase was extracted with EtOAc (3×8 mL). Combined organics were dried over Na$_2$SO$_4$, filtered and concentrated. Silica gel column chromatography (EtOAc/Heptane 10 to 50%) provided (S)-3-(2-((R)-1-(biphenyl-4-yl)ethylamino)pyrimidin-4-yl)-4-isopropyloxazolidin-2-one and (S)-3-(2-((S)-1-(biphenyl-4-yl)ethylamino)pyrimidin-4-yl)-4-isopropyloxazolidin-2-one.

Example 173 first eluted product (17 mg) $^1$H NMR (400 MHz, CD$_3$OD) δ 8.11 (d, J=5.8 Hz, 1H), 7.59-7.54 (m, 4H), 7.43-7.28 (m, 6H), 5.01 (q, J=6.8 Hz, 1H), 4.49 (br s, 1H), 4.32 (dd, J=9.1, 3.0 Hz, 1H), 4.26 (t, J=8.6 Hz, 1H), 2.67 (dtd, J=14, 7.0, 3.5 Hz, 1H), 1.55 (d, J=7.1 Hz, 3H), 1.01 (d, J=7.1 Hz, 3H), 0.86 (d, J=7.0 Hz, 3H); HRMS(B) m/z 403.2141 (M+H)$^+$.

Example 174 second eluted product (21 mg) $^1$H NMR (400 MHz, CD$_3$OD) δ 8.14 (d, J=5.8 Hz, 1H), 7.58-7.52 (m, 4H), 7.42-7.28 (m, 6H), 5.06 (q, J=7.1 Hz, 1H), 4.63 (br s, 1H), 4.34-4.25 (m, 2H), 1.79 (br s, 1H), 1.55 (d, J=7.1 Hz, 3H), 0.65 (br s, 3H), 0.53 (br s, 3H); HRMS(B) m/z 403.2139 (M+H)$^+$.

Examples 175 and 176

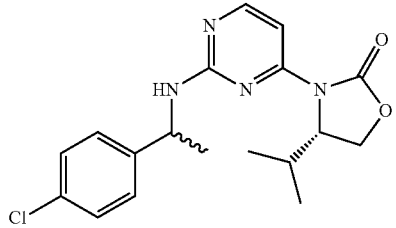 [SMILES: CC(Nc1nccc(N2C(=O)OC[C@@H]2C(C)C)n1)c1ccc(Cl)cc1]

A solution of (S)-3-(2-chloropyrimidin-4-yl)-4-isopropyloxazolidin-2-one (96 mg, 0.40 mmol) and 1-(4-chlorophenyl)ethanamine (204 mg, 1.31 mmol, 3.3 equiv) in DMSO (1 mL) was heated at 110° C. for 3 h. The reaction mixture was diluted with EtOAc (8 mL) and washed with water (30 mL). After separation, the aqueous phase was extracted with EtOAc (3×8 mL). Combined organics were dried over Na$_2$SO$_4$, filtered and concentrated. Silica gel column chromatography (EtOAc/Heptane 10 to 50%) provided (S)-3-(2-((R)-1-(4-chlorophenyl)ethylamino)pyrimidin-4-yl)-4-isopropyloxazolidin-2-one and (S)-3-(2-((S)-1-(4-chlorophenyl)ethylamino)pyrimidin-4-yl)-4-isopropyloxazolidin-2-one.

Example 175 first eluted product (32 mg) $^1$H NMR (400 MHz, CD$_3$OD) δ 8.10 (d, J=5.8 Hz, 1H), 7.36-7.28 (m, 5H), 4.95 (q, J=6.7 Hz, 1H), 4.45 (br s, 1H), 4.35-4.26 (m, 2H), 2.64 (dtt, J=11, 7.0, 3.4 Hz, 1H), 1.50 (d, J=7.1 Hz, 3H), 0.98 (d, J=7.1 Hz, 3H), 0.85 (d, J=7.1 Hz, 3H); HRMS(B) m/z 361.1430 (M+H)$^+$.

Example 176 second eluted product (40 mg) $^1$H NMR (400 MHz, CD$_3$OD) δ 8.13 (d, J=5.7 Hz, 1H), 7.36-7.26 (m, 5H), 5.00 (q, J=7.1 Hz, 1H), 4.62 (br s, 1H), 4.34-4.26 (m, 2H), 1.77 (br s, 1H), 1.50 (d, J=7.1 Hz, 3H), 0.68 (br s, 3H), 0.59 (br s, 3H); HRMS(B) m/z 361.1431 (M+H)$^+$.

Examples 177 and 178

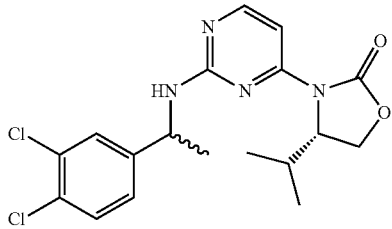 [SMILES: CC(Nc1nccc(N2C(=O)OC[C@@H]2C(C)C)n1)c1ccc(Cl)c(Cl)c1]

A solution of (S)-3-(2-chloropyrimidin-4-yl)-4-isopropyloxazolidin-2-one (93 mg, 0.38 mmol) and 1-(3,4-dichlorophenyl)ethanamine (73.1 mg, 0.385 mmol, 1.0 equiv) in DMSO (1 mL) was heated at 110° C. for 1½ h. The reaction mixture was diluted with EtOAc (8 mL) and washed with water (30 mL). After separation, the aqueous phase was extracted with EtOAc (3×8 mL). Combined organics were dried over Na$_2$SO$_4$, filtered and concentrated. Silica gel column chromatography (EtOAc/Heptane 10 to 50%) provided (S)-3-(2-((R)-1-(3,4-dichlorophenyl)ethylamino)pyrimidin-4-yl)-4-isopropyloxazolidin-2-one and (S)-3-(2-((S)-1-(3,4-dichlorophenyl)ethylamino)pyrimidin-4-yl)-4-isopropyloxazolidin-2-one.

Example 177 first eluted product (21 mg) $^1$H NMR (400 MHz, CD$_3$OD) δ 8.12 (d, J=5.8 Hz, 1H), 7.50 (d, J=2.0 Hz, 1H), 7.44 (d, J=8.2 Hz, 1H), 7.37 (d, J=5.8 Hz, 1H), 7.28 (dd, J=8.6, 2.0 Hz, 1H), 4.94-4.88 (m, 1H), 4.43 (br s, 1H), 4.35-4.26 (m, 2H), 2.68-2.60 (m, 1H), 1.50 (d, J=7.1 Hz, 3H), 0.99 (d, J=7.1 Hz, 3H), 0.85 (d, J=7.1 Hz, 3H); HRMS(B) m/z 395.1035 (M+H)$^+$.

Example 178 second eluted product (28 mg) $^1$H NMR (400 MHz, CD$_3$OD) δ 8.15 (d, J=5.8 Hz, 1H), 7.47-7.42 (m, 2H), 7.37 (d, J=5.8 Hz, 1H), 7.25 (dd, J=8.1, 2.0 Hz, 1H), 5.01-4.96 (m, 1H), 4.61 (br s, 1H), 4.34-4.26 (m, 2H), 1.72 (br s, 1H), 1.50 (d, J=7.1 Hz, 3H), 0.67 (br s, 3H), 0.60 (br s, 3H); HRMS(B) m/z 395.1044 (M+H)$^+$.

Examples 179 and 180

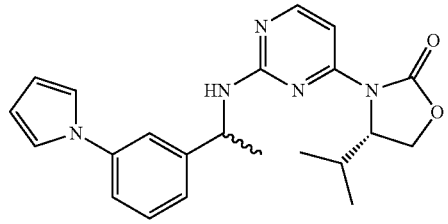 [SMILES: CC(Nc1nccc(N2C(=O)OC[C@@H]2C(C)C)n1)c1cccc(-n2cccc2)c1]

A solution of (S)-3-(2-chloropyrimidin-4-yl)-4-isopropyloxazolidin-2-one (86 mg, 0.36 mmol) and 1-(3-(1H-pyrrol-1-yl)phenyl)ethanamine (100 mg, 0.537 mmol, 1.5 equiv) in DMSO (1 mL) was heated at 110° C. for 1½ h. The reaction mixture was diluted with EtOAc (8 mL) and washed with water (30 mL). After separation, the aqueous phase was extracted with EtOAc (3×8 mL). Combined organics were dried over Na$_2$SO$_4$, filtered and concentrated. Silica gel column chromatography (EtOAc/Heptane 10 to 50%) provided (S)-3-(2-((R)-1-(3-(1H-pyrrol-1-yl)phenyl)ethylamino)pyrimidin-4-yl)-4-isopropyloxazolidin-2-one and (S)-3-(2-((S)-1-(3-(1H-pyrrol-1-yl)phenyl)ethylamino)pyrimidin-4-yl)-4-isopropyloxazolidin-2-one.

Example 179 first eluted product (14 mg) $^1$H NMR (400 MHz, CD$_3$OD) δ 8.11 (d, J=5.8 Hz, 1H), 7.45 (t, J=1.8 Hz, 1H), 7.39-7.29 (m, 3H), 7.23 (d, J=7.6 Hz, 1H), 7.13 (t, J=2.0 Hz, 2H), 6.25 (t, J=2.1 Hz, 2H), 5.03-4.97 (m, 1H), 4.46 (br s, 1H), 4.31-4.20 (m, 2H), 2.64 (dtd, J=14, 7.0, 3.8 Hz, 1H), 1.56 (d, J=7.1 Hz, 3H), 0.95 (d, J=7.1 Hz, 3H), 0.84 (d, J=7.0 Hz, 3H); HRMS(B) m/z 392.2092 (M+H)$^+$.

Example 180 second eluted product (10 mg) $^1$H NMR (400 MHz, CD$_3$OD) δ 8.14 (d, J=5.7 Hz, 1H), 7.42 (br s, 1H), 7.38-7.28 (m, 3H), 7.20 (d, J=7.6 Hz, 1H), 7.12 (t, J=2.3 Hz, 2H), 6.25 (t, J=2.0 Hz, 2H), 5.09 (q, J=6.9 Hz, 1H), 4.64 (br s, 1H), 4.32-4.23 (m, 2H), 1.84 (br s, 1H), 1.55 (d, J=7.1 Hz, 3H), 0.54 (br s, 6H); HRMS(B) m/z 392.2090 (M+H)$^+$.

Examples 181 and 182

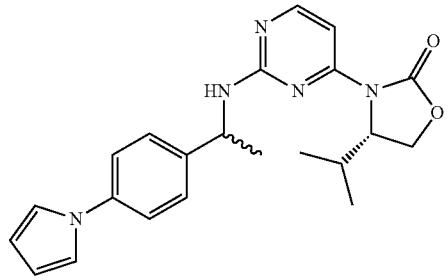 [SMILES: CC(Nc1nccc(N2C(=O)OC[C@@H]2C(C)C)n1)c1ccc(-n2cccc2)cc1]

A solution of (S)-3-(2-chloropyrimidin-4-yl)-4-isopropyloxazolidin-2-one (44 mg, 0.18 mmol) and 1-(4-(1H-pyrrol-1-yl)phenyl)ethanamine (33.9 mg, 0.182 mmol, 1 equiv) in DMSO (1 mL) was heated at 110° C. for 2 h. The reaction mixture was diluted with EtOAc (8 mL) and washed with water (30 mL). After separation, the aqueous phase was extracted with EtOAc (3×8 mL). Combined organics were dried over Na$_2$SO$_4$, filtered and concentrated. Silica gel column chromatography (EtOAc/Heptane 10 to 50%) provided (S)-3-(2-((R)-1-(4-(1H-pyrrol-1-yl)phenyl)ethylamino)pyrimidin-4-yl)-4-isopropyloxazolidin-2-one and (S)-3-(2-((S)-1-(4-(1H-pyrrol-1-yl)phenyl)ethylamino)pyrimidin-4-yl)-4-isopropyloxazolidin-2-one.

Example 181 first eluted product (18 mg) ¹H NMR (400 MHz, CD₃OD) δ 8.11 (d, J=5.8 Hz, 1H), 7.44-7.39 (m, 4H), 7.35 (d, J=5.9 Hz, 1H), 7.13 (t, J=2.2 Hz, 2H), 6.24 (t, J=2.0 Hz, 2H), 5.02-4.96 (m, 1H), 4.49 (br s, 1H), 4.34-4.25 (m, 2H), 2.66 (dtd, J=14, 7.0, 3.3 Hz, 1H), 1.53 (d, J=7.1 Hz, 3H), 1.00 (d, J=7.1 Hz, 3H), 0.86 (d, J=7.1 Hz, 3H); HRMS(B) m/z 392.2089 (M+H)⁺.

Example 182 second eluted product (9 mg) ¹H NMR (400 MHz, CD₃OD) δ 8.14 (d, J=5.8 Hz, 1H), 7.39 (s, 4H), 7.35 (d, J=5.9 Hz, 1H), 7.12 (t, J=2.2 Hz, 2H), 6.25 (t, J=2.0 Hz, 2H), 5.05 (q, J=7.1 Hz, 1H), 4.64 (br s, 1H), 4.34-4.26 (m, 2H), 1.87 (br s, 1H), 1.53 (d, J=7.1 Hz, 3H), 0.68 (br s, 3H), 0.57 (br s, 3H); HRMS(B) m/z 392.2082 (M+H)⁺.

Examples 183 and 184

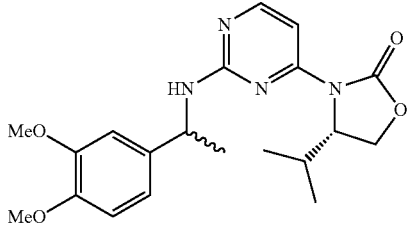 [SMILES: COc1ccc(C(C)Nc2nccc(N3C(=O)OC[C@@H]3C(C)C)n2)cc1OC]

A mixture of (4S)-3-(2-((1-(3,4-dimethoxyphenyl)ethyl)amino)pyrimidin-4-yl)-4-isopropyloxazolidin-2-one (example 118) was resolved on a column (AS-H 4.6×100 mm) using 30% iPrOH in CO₂ to give (S)-3-(2-((R)-1-(3,4-dimethoxyphenyl)ethylamino)pyrimidin-4-yl)-4-isopropyloxazolidin-2-one and (S)-3-(2-((S)-1-(3,4-dimethoxyphenyl)ethylamino)pyrimidin-4-yl)-4-isopropyloxazolidin-2-one.

Example 183 first eluted product (13 mg) ¹H NMR (400 MHz, CD₃OD) δ 8.11 (d, J=5.8 Hz, 1H), 7.33 (d, J=5.8 Hz, 1H), 6.97 (br d, J=1.5 Hz, 1H), 6.92-6.88 (m, 2H), 4.96 (q, J=6.7 Hz, 1H), 4.61-4.55 (m, 1H), 4.35-4.28 (m, 2H), 3.803 (s, 3H), 3.800 (s, 3H), 2.63 (dtd, J=14, 7.0, 3.5 Hz, 1H), 1.51 (d, J=7.1 Hz, 3H), 0.99 (d, J=7.1 Hz, 3H), 0.86 (d, J=7.1 Hz, 3H); HRMS(B) m/z 387.2031 (M+H)⁺.

Example 184 second eluted product (10 mg) ¹H NMR (400 MHz, CD₃OD) δ 8.13 (d, J=5.8 Hz, 1H), 7.32 (d, J=5.7 Hz, 1H), 6.94 (br d, J=1.1 Hz, 1H), 6.89-6.84 (m, 2H), 4.99 (q, J=7.1 Hz, 1H), 4.67-4.63 (m, 1H), 4.36-4.26 (m, 2H), 3.79 (s, 6H), 2.01 (br s, 1H), 1.51 (d, J=7.1 Hz, 3H), 0.71 (d, J=7.1 Hz, 3H), 0.63 (d, J=7.0 Hz, 3H); HRMS(B) m/z 387.2029 (M+H)⁺.

Examples 185 and 186

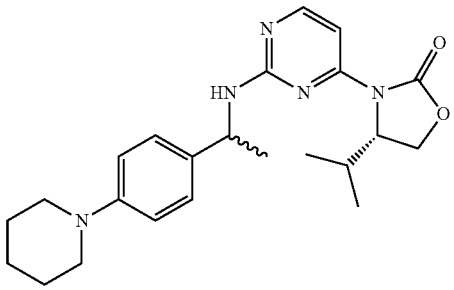 [SMILES: CC(Nc1nccc(N2C(=O)OC[C@@H]2C(C)C)n1)c1ccc(N2CCCCC2)cc1]

A solution of (S)-3-(2-chloropyrimidin-4-yl)-4-isopropyloxazolidin-2-one (93 mg, 0.38 mmol) and 1-(4-(piperidin-1-yl)phenyl)ethanamine (410 mg, 2.01 mmol, 5.2 equiv) in DMSO (1 mL) was heated at 110° C. for 2 h. The reaction mixture was diluted with EtOAc (8 mL) and washed with water (30 mL). After separation, the aqueous phase was extracted with EtOAc (3×8 mL). Combined organics were dried over Na₂SO₄, filtered and concentrated. Silica gel column chromatography (EtOAc/Heptane 10 to 100%) provided (4S)-4-isopropyl-3-(2-((1-(4-(piperidin-1-yl)phenyl)ethyl)amino)pyrimidin-4-yl)oxazolidin-2-one (57 mg) in 36% yield. A mixture of (4S)-4-isopropyl-3-(2-(1-(4-(piperidin-1-yl)phenyl)ethylamino)pyrimidin-4-yl)oxazolidin-2-one was resolved on a column (AD-H 4.6×100 mm) using 5 to 55% MeOH with 0.2% Et₂NH in CO₂ to give (S)-4-isopropyl-3-(2-((R)-1-(4-(piperidin-1-yl)phenyl)ethylamino)pyrimidin-4-yl)oxazolidin-2-one and (S)-4-isopropyl-3-(2-((S)-1-(4-(piperidin-1-yl)phenyl)ethylamino)pyrimidin-4-yl)oxazolidin-2-one.

Example 185 first eluted product (16 mg) ¹H NMR (400 MHz, CD₃OD) δ 8.10 (d, J=5.8 Hz, 1H), 7.31 (d, J=5.8 Hz, 1H), 7.24-7.20 (m, 2H), 6.94-6.91 (m, 2H), 4.93 (q, J=7.1 Hz, 1H), 4.58-4.54 (m, 1H), 4.34-4.27 (m, 2H), 3.11-3.08 (m, 4H), 2.63 (dtd, J=14, 7.1, 3.5 Hz, 1H), 1.73-1.67 (m, 4H), 1.60-1.54 (m, 2H), 1.49 (d, J=7.1 Hz, 3H), 0.98 (d, J=7.1 Hz, 3H), 0.86 (d, J=7.1 Hz, 3H); HRMS(B) m/z 410.2555 (M+H)⁺.

Example 186 second eluted product (16 mg) ¹H NMR (400 MHz, CD₃OD) δ 8.11 (d, J=5.8 Hz, 1H), 7.31 (d, J=5.8 Hz, 1H), 7.20-7.16 (m, 2H), 6.93-6.89 (m, 2H), 4.98 (q, J=6.9 Hz, 1H), 4.69-4.65 (m, 1H), 4.36-4.26 (m, 2H), 3.10-3.07 (m, 4H), 2.07 (br s, 1H), 1.73-1.67 (m, J=4H), 1.60-1.54 (m, 2H), 1.48 (d, J=7.1 Hz, 3H), 0.75 (d, J=7.0 Hz, 3H), 0.63 (d, J=7.1 Hz, 3H); HRMS(B) m/z 410.2556 (M+H)⁺.

Examples 187 and 188

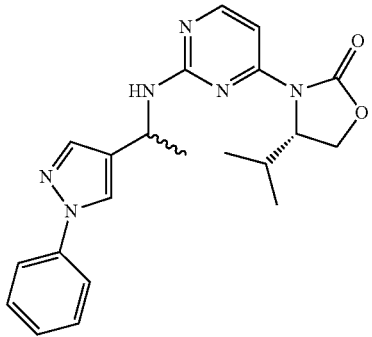 [SMILES: CC(Nc1nccc(N2C(=O)OC[C@@H]2C(C)C)n1)c1cnn(-c2ccccc2)c1]

A solution of (S)-3-(2-chloropyrimidin-4-yl)-4-isopropyloxazolidin-2-one (96 mg, 0.40 mmol) and 1-(1-phenyl-1H-pyrazol-4-yl)ethanamine (387 mg, 2.97 mmol, 5.2 equiv) in DMSO (1.5 mL) was heated at 110° C. for 1½ h. The reaction mixture was diluted with EtOAc (8 mL) and washed with water (30 mL). After separation, the aqueous phase was extracted with EtOAc (3×8 mL). Combined organics were dried over Na₂SO₄, filtered and concentrated. Silica gel column chromatography (EtOAc/Heptane 20 to 80%) provided (S)-4-isopropyl-3-(2-((R)-1-(1-phenyl-1H-pyrazol-4-yl)ethylamino)pyrimidin-4-yl)oxazolidin-2-one and (S)-4-isopropyl-3-(2-((S)-1-(1-phenyl-1H-pyrazol-4-yl)ethylamino)pyrimidin-4-yl)oxazolidin-2-one.

Example 187 first eluted product (13 mg) ¹H NMR (400 MHz, CD₃OD) δ 8.16 (d, J=5.8 Hz, 1H), 8.10 (s, 1H), 7.70-7.66 (m, 3H), 7.48-7.43 (m, 2H), 7.37 (d, J=5.7 Hz, 1H), 7.32-7.28 (m, 1H), 5.20 (q, J=6.6 Hz, 1H), 4.75 (dt, J=7.7, 4.0 Hz, 1H), 4.40-4.33 (m, 2H), 2.61 (dtt, J=11, 7.0, 3.6 Hz, 1H), 1.60 (d, J=6.9 Hz, 3H), 0.96 (d, J=7.1 Hz, 3H), 0.87 (d, J=6.9 Hz, 3H); HRMS(B) m/z 393.2029 (M+H)⁺.

Example 188 second eluted product (11 mg) ¹H NMR (400 MHz, CD₃OD) δ 8.17 (d, J=5.8 Hz, 1H), 8.03 (s, 1H), 7.68-7.62 (m, 3H), 7.48-7.43 (m, 2H), 7.37 (d, J=5.8 Hz, 1H), 7.32-7.27 (m, 1H), 5.19 (q, J=7.1 Hz, 1H), 4.74 (dt, J=8.5, 3.6 Hz, 1H), 4.38-4.29 (m, 2H), 2.37-2.33 (m, 1H), 1.60 (d, J=7.1 Hz, 3H), 0.79 (d, J=7.1 Hz, 3H), 0.73 (s, J=7.1 Hz, 3H); HRMS(B) m/z 393.2039 (M+H)⁺.

Examples 189 and 190

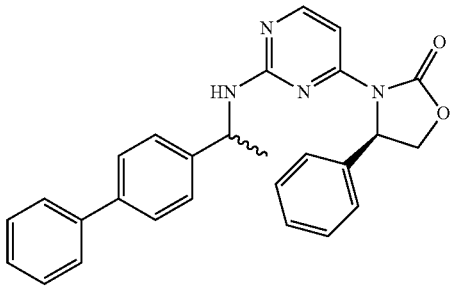 [SMILES: CC(Nc1nccc(N2C(=O)OC[C@H]2c2ccccc2)n1)c1ccc(-c2ccccc2)cc1]

A solution of (R)-3-(2-chloropyrimidin-4-yl)-4-phenyloxazolidin-2-one (97 mg, 0.35 mmol), 1-(biphenyl-4-yl)ethanamine hydrochloride (304 mg, 1.30 mmol, 3.7 equiv) and iPr₂NEt (0.307 mL, 1.76 mmol, 5.0 equiv) in DMSO (1 mL) was heated at 110° C. for 1½ h and at 130° C. for 20 h. The reaction mixture was diluted with EtOAc (8 mL) and washed with water (30 mL). After separation, the aqueous phase was extracted with EtOAc (3×8 mL). Combined organics were dried over Na₂SO₄, filtered and concentrated. Silica gel column chromatography (EtOAc/Heptane 10 to 50%) provided (R)-3-(2-((R)-1-(biphenyl-4-yl)ethylamino)pyrimidin-4-yl)-4-phenyloxazolidin-2-one and (R)-3-(2-((S)-1-(biphenyl-4-yl)ethylamino)pyrimidin-4-yl)-4-phenyloxazolidin-2-one.

Example 189 first eluted product (12 mg) ¹H NMR (400 MHz, CD₃OD) δ 8.10 (d, J=5.8 Hz, 1H), 7.58-7.55 (m, 2H), 7.44-7.37 (m, 6H), 7.33-7.28 (m, 1H), 7.24-7.14 (m, 6H), 5.84 (dd, J=8.6, 3.5 Hz, 1H), 4.94 (q, J=6.7 Hz, 1H), 4.81 (t, J=8.6 Hz, 1H), 4.22 (dd, J=8.8, 3.8 Hz, 1H), 1.49 (d, J=7.1 Hz, 3H); HRMS(B) m/z 437.1981 (M+H)⁺.

Example 190 second eluted product (11 mg) ¹H NMR (400 MHz, CD₃OD) δ 8.10 (d, J=5.8 Hz, 1H), 7.60-7.54 (m, 4H), 7.44-7.28 (m, 11H), 5.60 (dd, J=8.6, 4.0 Hz, 1H), 4.77-4.69 (m, 2H), 4.19 (dd, J=8.6, 4.0 Hz, 1H), 1.25 (d, J=7.0 Hz, 3H); HRMS(B) m/z 437.1971 (M+H)⁺.

Examples 191 and 192

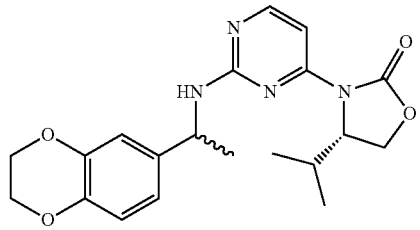 [SMILES: CC(Nc1nccc(N2C(=O)OC[C@@H]2C(C)C)n1)c1ccc2c(c1)OCCO2]

(4S)-3-(2-(1-(2,3-dihydrobenzo[b][1,4]dioxin-6-yl)ethylamino)pyrimidin-4-yl)-4-isopropyloxazolidin-2-one (example 130, 52 mg) was resolved on a column (IA 4.6×100 mm) using 40% iPrOH in CO₂ to give (S)-3-(2-((R)-1-(2,3-dihydrobenzo[b][1,4]dioxin-6-yl)ethylamino)pyrimidin-4-yl)-4-isopropyloxazolidin-2-one and (S)-3-(2-((S)-1-(2,3-dihydrobenzo[b][1,4]dioxin-6-yl)ethylamino)pyrimidin-4-yl)-4-isopropyloxazolidin-2-one.

Example 191 first eluted product (7 mg) ¹H NMR (400 MHz, CD₃OD) δ 8.10 (d, J=5.6 Hz, 1H), 7.33-7.31 (m, 1H), 6.82-6.74 (m, 3H), 4.88 (q, J=7.1 Hz, 1H), 4.58-4.53 (m, 1H), 4.34-4.28 (m, 2H), 4.21-4.18 (m, 4H), 2.63 (td, J=7.1, 3.5 Hz, 1H), 1.47 (d, J=7.1 Hz, 3H), 0.99 (d, J=7.1 Hz, 3H), 0.86 (d, J=7.1 Hz, 3H); HRMS(B) m/z 385.1875 (M+H)⁺.

Example 192 second eluted product (19 mg) ¹H NMR (400 MHz, CD₃OD) δ 8.12 (d, J=5.8 Hz, 1H), 7.33-7.31 (m, 1H), 6.78-6.72 (m, 3H), 4.93 (q, J=6.7 Hz, 1H), 4.68-4.64 (m, 1H), 4.36-4.27 (m, 2H), 2.08 (br s, 1H), 1.47 (d, J=7.1 Hz, 3H), 0.76 (d, J=7.1 Hz, 3H), 0.65 (d, J=7.1 Hz, 3H); HRMS(B) m/z 385.1873 (M+H)⁺.

Examples 193 and 194

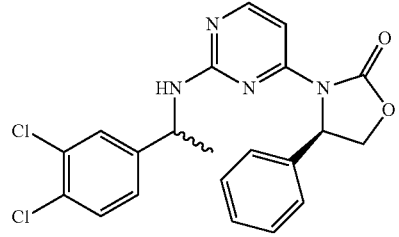 [SMILES: CC(Nc1nccc(N2C(=O)OC[C@H]2c2ccccc2)n1)c1ccc(Cl)c(Cl)c1]

A solution of (R)-3-(2-chloropyrimidin-4-yl)-4-phenyloxazolidin-2-one (83 mg, 0.30 mmol) and 1-(3,4-dichlorophenyl)ethanamine (260 mg, 1.37 mmol, 4.5 equiv) in DMSO (1.5 mL) was heated at 110° C. for 1½ h. The reaction mixture was diluted with EtOAc (8 mL) and washed with water (30 mL). After separation, the aqueous phase was extracted with EtOAc (3×8 mL). Combined organics were dried over Na₂SO₄, filtered and concentrated. Silica gel column chromatography (EtOAc/Heptane 0 to 40%) provided (R)-3-(2-((R)-1-(3,4-dichlorophenyl)ethylamino)pyrimidin-4-yl)-4-phenyloxazolidin-2-one and (R)-3-(2-((S)-1-(3,4-dichlorophenyl)ethylamino)pyrimidin-4-yl)-4-phenyloxazolidin-2-one.

Example 193 first eluted product (13 mg) ¹H NMR (400 MHz, CD₃OD) δ 8.11 (d, J=5.6 Hz, 1H), 7.44-7.38 (m, 5H), 7.35-7.31 (m, 1H), 7.27-7.25 (m, 2H), 7.18 (dd, J=8.3, 2.3 Hz, 1H), 5.53 (dd, J=8.8, 3.8 Hz, 1H), 4.76 (t, J=8.8 Hz, 1H), 4.59-4.53 (m, 1H), 4.18 (dd, J=8.8, 4.3 Hz, 1H), 1.22 (d, J=7.1 Hz, 3H); HRMS(B) m/z 429.0899 (M+H)⁺.

Example 194 second eluted product (26 mg) ¹H NMR (400 MHz, CD₃OD) δ 8.13 (d, J=5.6 Hz, 1H), 7.41 (d, J=6.1 Hz, 1H), 7.25-7.18 (m, 5H), 7.09-7.06 (m, 2H), 6.95-6.93 (m, 1H), 5.78 (dd, J=8.6, 3.5 Hz, 1H), 4.89 (q, J=6.7 Hz, 1H), 4.79 (t, J=8.6 Hz, 1H), 4.18 (dd, J=8.8, 3.8 Hz, 1H), 1.42 (d. J=7.1 Hz, 3H); HRMS(B) m/z 429.0887 (M+H)⁺.

Examples 195 and 196

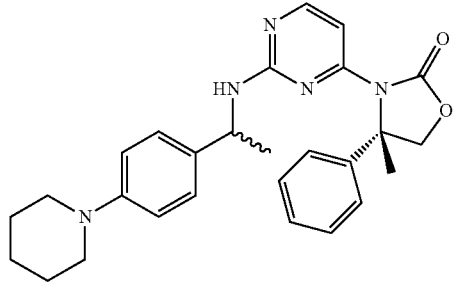 [SMILES: CC(Nc1nccc(N2C(=O)OC[C@]2(C)c2ccccc2)n1)c1ccc(N2CCCCC2)cc1]

(4S)-4-methyl-4-phenyl-3-(2-(1-(4-(piperidin-1-yl)phenyl)ethylamino)pyrimidin-4-yl)oxazolidin-2-one (example 141, 51 mg) was resolved on a column (IA 4.6×100 mm) using 45% MeOH in CO$_2$ to give (S)-4-methyl-4-phenyl-3-(2-((S)-1-(4-(piperidin-1-yl)phenyl)ethylamino)pyrimidin-4-yl)oxazolidin-2-one and (S)-4-methyl-4-phenyl-3-(2-((R)-1-(4-(piperidin-1-yl)phenyl)ethylamino)pyrimidin-4-yl)oxazolidin-2-one.

Example 195 first eluted product (21.6 mg) $^1$H NMR (400 MHz, CDCl$_3$) δ 8.13 (d, J=5.8 Hz, 1H), 7.41 (d, J=5.8 Hz, 1H), 7.36-7.33 (m, 4H), 7.32-7.26 (m, 1H), 6.88-6.82 (br m, 4H), 5.01 (br s, 1H), 4.30 (s, 2H), 3.16-3.13 (m, 4H), 2.20 (s, 3H), 1.76-1.57 (br m, 6H), 1.37 (d, J=6.7 Hz, 3H); HRMS(B) m/z 458.2558 (M+H)$^+$.

Example 196 second eluted product (20.6 mg) $^1$H NMR (400 MHz, CDCl$_3$) δ 8.14 (d, J=5.8 Hz, 1H), 7.50-7.27 (m, 6H), 7.05 (d, J=8.6 Hz, 2H), 6.96-6.92 (br m, 2H), 5.27 (br s, 1H), 4.22 (s, 2H), 3.21-3.13 (m, 4H), 1.78-1.76 (br m, 7H), 1.63-1.57 (br m, 2H), 1.07 (d, J=6.1 Hz, 3H); HRMS(B) m/z 458.2559 (M+H)$^+$.

Examples 197 and 198

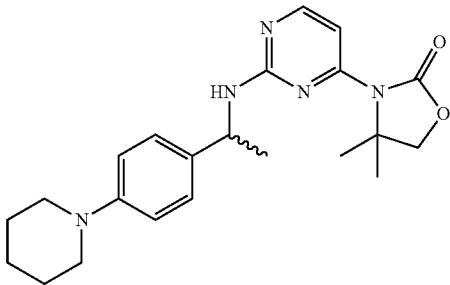 [SMILES: CC(Nc1nccc(N2C(=O)OCC2(C)C)n1)c1ccc(N2CCCCC2)cc1]

4,4-dimethyl-3-(2-(1-(4-(piperidin-1-yl)phenyl)ethylamino)pyrimidin-4-yl)oxazolidin-2-one (example 183, 70 mg) was resolved on a column (IA 4.6×100 mm) using 40% MeOH in CO$_2$ to give (S)-4,4-dimethyl-3-(2-(1-(4-(piperidin-1-yl)phenyl)ethylamino)pyrimidin-4-yl)oxazolidin-2-one and (R)-4,4-dimethyl-3-(2-(1-(4-(piperidin-1-yl)phenyl)ethylamino)pyrimidin-4-yl)oxazolidin-2-one.

Example 197 first eluted product (23.8 mg) $^1$H NMR (400 MHz, CDCl$_3$) δ 8.17 (br d, J=5.8 Hz, 1H), 7.28-7.23 (m, 3H), 6.93 (br d, J=7.7 Hz, 2H), 5.44 (br s, 1H), 4.97 (br s, 1H), 4.05-3.99 (m, 2H), 3.15-3.12 (m, 4H), 1.77-1.70 (m, 8H), 1.61-1.54 (m, 5H), 1.32 (br s, 2H); HRMS(B) m/z 396.2413 (M+H)$^+$.

Example 198 second eluted product (22.3 mg) $^1$H NMR (400 MHz, CDCl$_3$) δ 8.17 (br d, J=5.5 Hz, 1H), 7.28-7.23 (m, 3H), 6.94 (br d, J=7.5 Hz, 2H), 5.48 (br s, 1H), 4.97 (br s, 1H), 4.05-3.99 (m, 2H), 3.15-3.12 (m, 4H), 1.77-1.70 (m, 8H), 1.61-1.54 (m, 5H), 1.31 (br s, 2H); HRMS(B) m/z 396.2410 (M+H)$^+$.

Examples 199 and 200

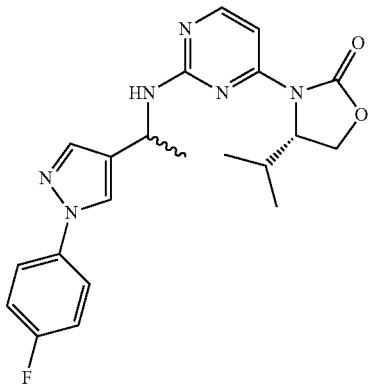 [SMILES: CC(Nc1nccc(N2C(=O)OC[C@@H]2C(C)C)n1)c1cnn(-c2ccc(F)cc2)c1]

A solution of (S)-3-(2-chloropyrimidin-4-yl)-4-isopropyloxazolidin-2-one (98 mg, 0.41 mmol), 1-(1-(4-fluorophenyl)-1H-pyrazol-4-yl)ethanamine hydrochloride (502 mg, 2.08 mmol, 5.1 equiv) and iPr$_2$NEt (0.637 mL, 3.65 mmol, 9.0 equiv) in DMSO (1.5 mL) was heated at 110° C. for 16 h. The reaction mixture was diluted with EtOAc (8 mL) and washed with water (30 mL). After separation, the aqueous phase was extracted with EtOAc (3×8 mL). Combined organics were dried over Na$_2$SO$_4$, filtered and concentrated. Silica gel column chromatography (EtOAc/Heptane 20 to 80%) provided (S)-3-(2-((R)-1-(1-(4-fluorophenyl)-1H-pyrazol-4-yl)ethylamino)pyrimidin-4-yl)-4-isopropyloxazolidin-2-one and (S)-3-(2-((S)-1-(1-(4-fluorophenyl)-1H-pyrazol-4-yl)ethylamino)pyrimidin-4-yl)-4-isopropyloxazolidin-2-one.

Example 199 first eluted product (49 mg) $^1$H NMR (400 MHz, CD$_3$OD) δ 8.16 (d, J=5.8 Hz, 1H), 8.06 (s, 1H), 7.71-7.67 (m, 3H), 7.37 (d, J=5.9 Hz, 1H), 7.22-7.16 (m, 2H), 5.20 (q, J=6.6 Hz, 1H), 4.74 (dt, J=7.6, 3.8 Hz, 1H), 4.40-4.34 (m, 2H), 2.60 (dtd, J=14, 7.0, 3.5 Hz, 1H), 1.59 (d, J=6.9 Hz, 3H), 0.96 (d, J=7.1 Hz, 3H), 0.87 (d, J=7.1 Hz, 3H); HRMS(B) m/z 411.1943 (M+H)$^+$.

Example 200 second eluted product (27 mg) $^1$H NMR (400 MHz, CD$_3$OD) δ 8.17 (d, J=5.8 Hz, 1H), 8.00 (s, 1H), 7.69-7.66 (m, 2H), 7.61 (s, 1H), 7.37 (d, J=5.9 Hz, 1H), 7.22-7.16 (m, 2H), 5.19 (q, J=6.7 Hz, 1H), 4.73 (dt, J=8.1, 3.5 Hz, 1H), 4.39-4.30 (m, 2H), 2.38-2.31 (m, 1H), 1.59 (d, J=6.8 Hz, 3H), 0.79 (d, J=7.1 Hz, 3H), 0.73 (d, J=7.0 Hz, 3H); HRMS(B) m/z 411.1937 (M+H)$^+$.

Examples 201 and 202

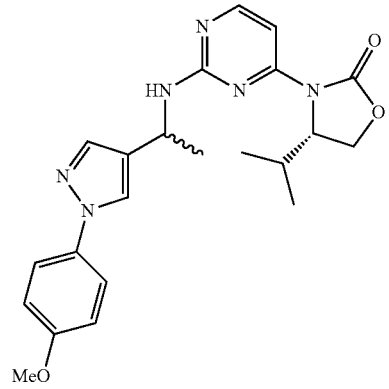 [SMILES: COc1ccc(-n2cc(C(C)Nc3nccc(N4C(=O)OC[C@@H]4C(C)C)n3)cn2)cc1]

A solution of (S)-3-(2-chloropyrimidin-4-yl)-4-isopropyloxazolidin-2-one (93 mg, 0.38 mmol), 1-(1-(4-methoxyphenyl)-1H-pyrazol-4-yl)ethanamine hydrochloride (514 mg, 2.03 mmol, 5.3 equiv) and iPr$_2$NEt (0.605 mL, 3.46 mmol, 9.0 equiv) in DMSO (1.5 mL) was heated at 110° C. for 16 h. The reaction mixture was diluted with EtOAc (8 mL) and washed with water (30 mL). After separation, the aqueous phase was extracted with EtOAc (3×8 mL). Combined organics were dried over Na$_2$SO$_4$, filtered and concentrated. Silica gel column chromatography (EtOAc/Heptane 10 to 70%) provided (S)-4-isopropyl-3-(2-((R)-1-(1-(4-methoxyphenyl)-1H-pyrazol-4-yl)ethylamino)pyrimidin-4-yl)oxazolidin-2-one and (S)-4-isopropyl-3-(2-((S)-1-(1-(4-methoxyphenyl)-1H-pyrazol-4-yl)ethylamino)pyrimidin-4-yl)oxazolidin-2-one.

Example 201 first eluted product (17 mg) $^1$H NMR (400 MHz, CD$_3$OD) δ 8.15 (d, J=5.8 Hz, 1H), 7.98 (s, 1H), 7.63 (s, 1H), 7.58-7.54 (m, 2H), 7.37 (d, J=5.8 Hz, 1H), 7.03-6.99 (m, 2H), 5.19 (q, J=7.1 Hz, 1H), 4.75 (dt, J=7.7, 4.0 Hz, 1H), 4.40-4.33 (m, 2H), 3.83 (s, 3H), 2.61 (dtd, J=14, 7.1, 3.5 Hz, 1H), 1.59 (d, J=7.1 Hz, 3H), 0.96 (d, J=7.1 Hz, 3H), 0.87 (d, J=7.1 Hz, 3H); HRMS(B) m/z 423.2138 (M+H)+.

Example 202 second eluted product (18 mg) $^1$H NMR (400 MHz, CD$_3$OD) δ 8.16 (d, J=5.8 Hz, 1H), 7.91 (s, 1H), 7.58-7.53 (m, 3H), 7.37 (d, J=5.9 Hz, 1H), 7.03-6.99 (m, 2H), 5.18 (q, J=6.7 Hz, 1H), 4.76-4.72 (m, 1H), 4.39-4.30 (m, 2H), 3.83 (s, 3H), 2.31 (br s, 1H), 1.59 (d, J=7.1 Hz, 3H), 0.80 (d, J=7.1 Hz, 3H), 0.73 (d, J=7.1 Hz, 3H); HRMS(B) m/z 423.214 (M+H)+.

Examples 203 and 204

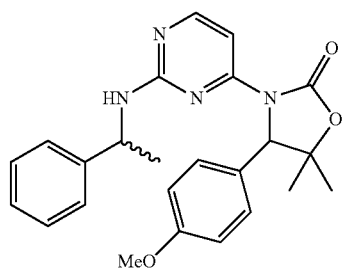 [SMILES: COc1ccc(C2N(c3ccnc(NC(C)c4ccccc4)n3)C(=O)OC2(C)C)cc1]

4-(4-methoxyphenyl)-5,5-dimethyl-3-(2-((S)-1-phenylethylamino)pyrimidin-4-yl)oxazolidin-2-one (example 54, 62 mg) was resolved in on a column (AD-H 4.6×100 mm) with 30% MeOH modified with 0.2% Et$_2$NH in CO$_2$ to give (S)-4-(4-methoxyphenyl)-5,5-dimethyl-3-(2-((S)-1-phenylethylamino)pyrimidin-4-yl)oxazolidin-2-one and (R)-4-(4-methoxyphenyl)-5,5-dimethyl-3-(2-((S)-1-phenylethylamino)pyrimidin-4-yl)oxazolidin-2-one.

Example 203 first eluted product (22 mg) $^1$H NMR (400 MHz, CDCl$_3$) δ 8.12 (br d, J=5.6 Hz, 1H), 7.53 (d, J=5.7 Hz, 1H), 7.37-7.24 (m, 5H), 7.08-7.05 (m, 2H), 6.92-6.89 (m, 2H), 5.47 (br s, 1H), 5.02 (br s, 1H), 4.66 (br s, 1H), 3.83 (s, 3H), 1.50 (s, 3H), 1.28 (br d, J=6.6 Hz, 3H), 1.01 (s, 3H); HRMS(B) m/z 419.208 (M+H)+.

Example 204 second eluted product (22.2 mg) $^1$H NMR (400 MHz, CDCl$_3$) δ 8.11 (br d, J=6.1 Hz, 1H), 7.55 (d, J=5.8 Hz, 1H), 7.28-7.22 (m, 3H), 7.08 (br s, 2H), 7.01 (d, J=8.6 Hz, 2H), 6.79 (d, J=8.6 Hz, 2H), 5.40 (br s, 1H), 5.30 (s, 1H), 4.83 (br s, 1H), 3.78 (s, 3H), 1.66 (s, 3H), 1.51 (d, J=6.8 Hz, 3H), 1.04 (s, 2H); HRMS(B) m/z 419.2083 (M+H)+.

Example 205

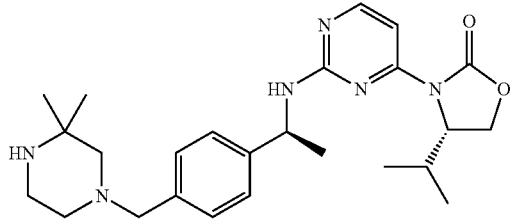 [SMILES: CC(C)[C@H]1COC(=O)N1c1ccnc(N[C@@H](C)c2ccc(CN3CCNC(C)(C)C3)cc2)n1]

To a solution of tert-butyl 4-(4-((S)-1-(4-((S)-4-isopropyl-2-oxooxazolidin-3-yl)pyrimidin-2-ylamino)ethyl)benzyl)-2,2-dimethylpiperazine-1-carboxylate (78 mg, 0.14 mmol) in DCM (1 mL) was added TFA (1 mL, 12 mmol) slowly at −78° C. The reaction was stirred at room temperature for 1 h then was concentrated and diluted with DCM (10 mL). The solution was stirred with 3 eq. of MP-carbonate resin (3.28 mmol/g, Biotage) for 1 h at room temperature. The resin was removed by filtration and washed (2×5 mL) with DCM. The filtrate was concentrated and purified through HPLC to give (S)-3-(2-(((S)-1-(4-((3,3-dimethylpiperazin-1-yl)methyl)phenyl)ethyl)amino)pyrimidin-4-yl)-4-isopropyloxazolidin-2-one as a white solid (23 mg, 36% yield).

$^1$H NMR (400 MHz, MeOD) δ 8.07 (d, J=5.8 Hz, 1H), 7.30 (d, J=5.8 Hz, 1H), 7.26-7.18 (m, 4H), 5.00 (q, J=6.9 Hz, 1H), 4.62 (br s, 1H), 4.36-4.16 (m, 2H), 3.36 (s, 2H), 2.81 (br t, J=5.1 Hz, 2H), 2.30 (br s, 2H), 2.10 (br s, 2H), 1.82 (br s, 1H), 1.45 (d, J=7.0 Hz, 3H), 1.08 (s, 6H), 0.67 (br s, 3H), 0.52 (br s, 3H); HRMS(B) m/z 453.2969 (M+H)+.

Example 206

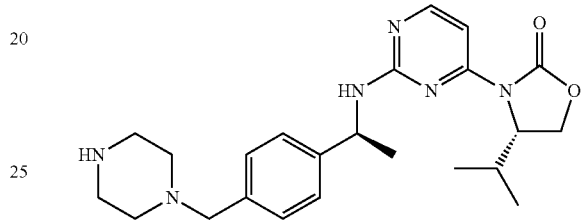

A mixture of benzyl 4-(4-((S)-1-(4-((S)-4-isopropyl-2-oxooxazolidin-3-yl)pyrimidin-2-ylamino)ethyl)benzyl)piperazine-1-carboxylate (190 mg, 0.34 mmol) and 10% Pd—C (40 mg, 0.038 mmol) in ethanol (3.4 ml) is stirred under 1 atmosphere pressure of hydrogen for 3 h. The mixture is filtered and concentrated to give (S)-4-isopropyl-3-(2-(((S)-1-(4-(piperazin-1-ylmethyl)phenyl)ethyl)amino)pyrimidin-4-yl)oxazolidin-2-one as a white solid (97 mg, 67.2% yield).

$^1$H NMR (400 MHz, MeOD) δ 8.08 (d, J=5.8 Hz, 1H), 7.30 (d, J=5.8 Hz, 1H), 7.28-7.19 (m, 4H), 5.01 (q, J=7.0 Hz, 1H), 4.63 (br s, 1H), 4.37-4.14 (m, 2H), 3.44 (s, 2H), 2.78 (t, J=5.0 Hz, 4H), 2.39 (br s, 4H), 1.89 (br s, 1H), 1.45 (d, J=7.0 Hz, 3H), 0.68 (br s, 3H), 0.52 (br s, 3H); HRMS(B) m/z 425.2662 (M+H)+.

Example 207

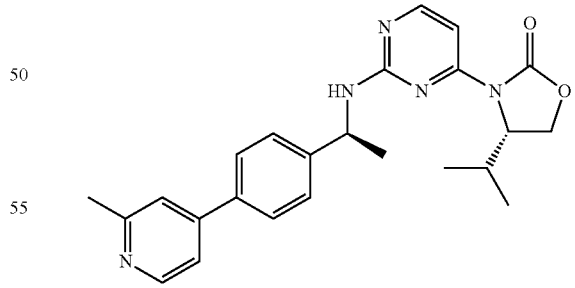

In a 5 mL microwave vial a solution of (S)-3-(2-((S)-1-(4-bromophenyl)ethylamino)pyrimidin-4-yl)-4-isopropyloxazolidin-2-one (86 mg, 0.21 mmol), pyridin-4-ylboronic acid (26 mg, 0.21 mmol), Sodium bicarbonate (0.21 mL, 0.42 mmol, 2 M solution) in Dioxane (1 mL) was bubbled N2 for 3 min then Cl2Pd(dppf).CH$_2$Cl$_2$ (17 mg, 0.021 mmol) was added. The capped tube was heated to 100° C. for 16 h. After cooling the reaction mixture was diluted with EtOAc (10 mL)

and washed with water (10 mL). After separation, the aqueous phase was extracted with EtOAc (3×10 mL). Combined organics were dried over Na$_2$SO$_4$, filtered and concentrated. The crude material was purified through silica gel column chromatography (EtOAc in Heptane 12 to 100%) to yield (S)-4-isopropy-3-(2-(((S)-1-(4-(2-yl)phenyl)ethyl)amino)pyrimidin-4-yl)oxazolidin-2-one as a white solid (27 mg, 30.5% yield).

$^1$H NMR (400 MHz, MeOD) δ 8.35 (d, J=5.4 Hz, 1H), 8.08 (d, J=5.9 Hz, 1H), 7.64-7.60 (m, 2H), 7.49 (br d, J=1.8 Hz, 1H), 7.43-7.39 (m, 3H), 7.30 (d, J=5.8 Hz, 1H), 5.02 (q, J=6.8 Hz, 1H), 4.55 (br s, 1H), 4.27-4.18 (m, 2H), 2.52 (s, 3H), 1.65 (br s, 1H), 1.49 (d, J=7.1 Hz, 3H), 0.55 (br s, 3H), 0.43 (br s, 3H); HRMS(B) m/z 418.2227 (M+H)+.

Example 208

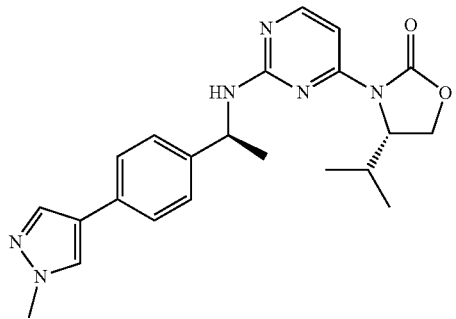 [SMILES: CC(C)[C@H]1COC(=O)N1c1ccnc(N[C@@H](C)c2ccc(-c3cnn(C)c3)cc2)n1]

To a solution of tert-butyl 4-((S)-4-isopropyl-2-oxooxazolidin-3-yl)pyrimidin-2-yl((S)-1-(4-(1-methyl-1H-pyrazol-4-yl)phenyl)ethyl)carbamate (45 mg, 0.09 mmol) in DCM (1 mL) was added TFA (1 mL, 12 mmol) slowly at −78° C. The reaction was stirred at room temperature for 1 h then was concentrated and diluted with DCM (10 mL). The solution was washed with saturated NaHCO$_3$ solution and brine. After separation, the aqueous phase was extracted with DCM (3×10 mL). Combined organics were dried over Na$_2$SO$_4$, filtered and concentrated to give (S)-4-isopropyl-3-(2-(((S)-1-(4-(1-methyl-1H-pyrazol-4-yl)phenyl)ethyl)amino)pyrimidin-4-yl)oxazolidin-2-one as a white solid (35 mg, 97% yield).

$^1$H NMR (400 MHz, MeOD) δ 8.09 (d, J=5.9 Hz, 1H), 7.86 (s, 1H), 7.72 (d, J=0.8 Hz, 1H), 7.45-7.41 (m, 2H), 7.30 (d, J=5.8 Hz, 1H), 7.25 (d, J=7.9 Hz, 2H), 4.97 (q, J=7.0 Hz, 1H), 4.58 (br s, 1H), 4.30-4.21 (m, 2H), 3.86 (s, 3H), 1.66 (br s, 1H), 1.48 (d, J=7.0 Hz, 3H), 0.60 (br s, 3H), 0.48 (br s, 3H); HRMS(B) m/z 407.2179 (M+H)+.

Example 209

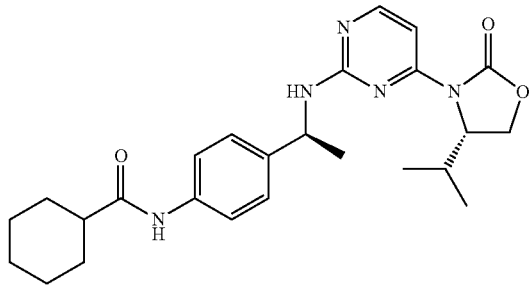 [SMILES: CC(C)[C@H]1COC(=O)N1c1ccnc(N[C@@H](C)c2ccc(NC(=O)C3CCCCC3)cc2)n1]

Following the above procedure for Example 208, N-(4-((S)-1-(4-((S)-4-isopropyl-2-oxooxazolidin-3-yl)pyrimidin-2-ylamino)ethyl)phenyl)cyclohexanecarboxamide was prepared as a white solid (45 mg, 92% yield) from tert-butyl (S)-1-(4-(cyclohexanecarboxamido)phenyl)ethyl(4-((S)-4-isopropyl-2-oxooxazolidin-3-yl)pyrimidin-2-yl)carbamate.

$^1$H NMR (400 MHz, MeOD) δ 8.08 (d, J=5.9 Hz, 1H), 7.47-7.41 (m, 2H), 7.30 (d, J=5.8 Hz, 1H), 7.23-7.16 (m, 2H), 4.95 (q, J=7.0 Hz, 1H), 4.60 (br s, 1H), 4.32-4.19 (m, 2H), 2.30 (tt, J=11.8, 3.3 Hz, 1H), 1.89-1.72 (m, 4H), 1.72-1.63 (m, 1H), 1.54-1.39 (m, 5H), 1.39-1.14 (m, 4H), 0.67 (br s, 3H), 0.54 (br s, 3H); HRMS(B) m/z 452.2636 (M+H)+.

Example 210

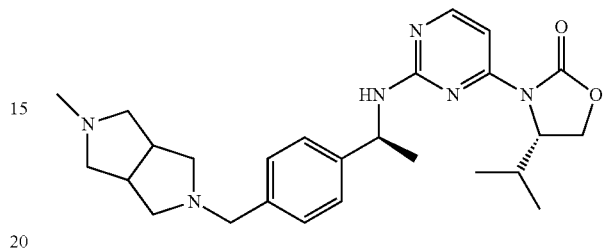

A solution of 4-((S)-1-(4-((S)-4-isopropyl-2-oxooxazolidin-3-yl)pyrimidin-2-ylamino)ethyl)benzaldehyde (35 mg, 0.1 mmol) and 2-methyloctahydropyrrolo[3,4-c]pyrrole (14 mg, 0.11 mmol) in MeOH (2 mL) was added acetic acid (7.2 mg, 0.12 mmol) and 5-Ethyl-2-methylpyridine borane complex (14 mg, 0.1 mmol, sigmaaldrich). The solution was stirred at 50° C. for 4 h then 5 drops of water was added. The solution was stirred at room temperature for another 2 h then diluted with EtOAc (10 mL) and washed with water (10 mL). After separation, the aqueous phase was extracted with EtOAc (3×10 mL). Combined organics were dried over Na$_2$SO$_4$, filtered and concentrated. The crude material was purified through HPLC to give (4S)-4-isopropyl-3-(2-(((1)-1-(4-((5-methylhexahydropyrrolo[3,4-c]pyrrol-2(1H)-yl)methyl)phenyl)ethyl)amino)pyrimidin-4-yl)oxazolidin-2-one as a white solid (10 mg, 21.7% yield).

$^1$H NMR (400 MHz, MeOD) δ 8.07 (d, J=5.8 Hz, 1H), 7.29 (d, J=5.8 Hz, 1H), 7.25-7.20 (m, 4H), 5.00 (q, J=7.0 Hz, 1H), 4.63 (br s, 1H), 4.31-4.23 (m, 2H), 3.55-3.48 (m, 2H), 2.68 (dh, J=13.6, 4.3, 3.7 Hz, 2H), 2.64-2.48 (m, 4H), 2.36-2.29 (m, 4H), 2.28 (s, 4H), 1.84 (br s, 1H), 1.45 (d, J=7.0 Hz, 3H), 0.68 (br s, 3H), 0.52 (br s, 3H); HRMS(B) m/z 465.2975 (M+H)+.

Example 211

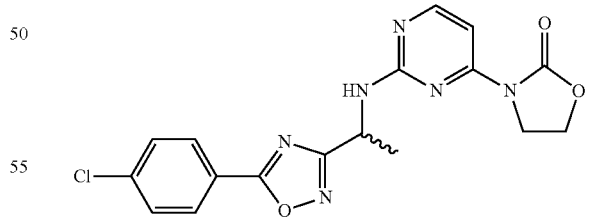

A solution of 3-(2-fluoropyrimidin-4-yl)oxazolidin-2-one (89.1 mg, 0.487 mmol), 1-(3-(4-chlorophenyl)-1,2,4-oxadiazol-5-yl)ethanamine (115.9 mg, 0.518 mmol, 1.06 equiv), and DIPEA (0.20 mL, 1.1 mmol, 2.4 equiv) in DMSO (1.5 mL) was heated at 110° C. for 100 min. The reaction mixture was diluted with EtOAc (8 mL) and washed with water (30 mL). After separation, the aqueous phase was extracted with EtOAc (3×8 mL). Combined organics were dried over Na$_2$SO$_4$, filtered and concentrated. Silica gel column chromatography (MeOH in CH$_2$Cl$_2$ 0 to 5%) provided 3-(2-(1-(3-(4-chlorophenyl)-1,2,4-oxadiazol-5-yl)ethylamino)pyrimidin-4-yl)oxazolidin-2-one (18.2 mg, white solid) in 10.3% yield.

$^1$H NMR (400 MHz, DMSO-d$_6$) 8.21 (br s, 1H), 8.00-7.97 (m, 2H), 7.65-7.61 (m, 2H), 7.30 (br s, 1H), 5.28 (br s, 1H), 4.44-4.38 (br m, 2H), 4.14-4.08 (m, 1H), 3.99 (br s, 0.5H), 3.75 (br s, 0.5H), 1.64 (d, J=7.0 Hz, 3H); HRMS(B) m/z 387.0962 (M+H)$^+$

Example 212

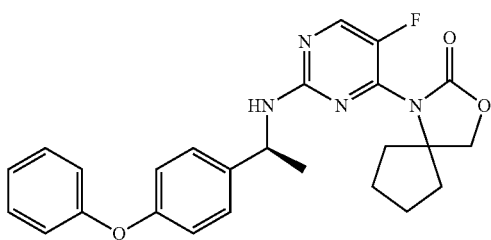 [SMILES: C[C@H](Nc1ncc(F)c(N2C(=O)OCC23CCCC3)n1)c1ccc(Oc2ccccc2)cc1]

A solution of (S)-1-(4-phenoxyphenyl)ethanamine hydrochloride (281 mg, 1.125 mmol), 3-(2-chloro-5-fluoropyrimidin-4-yl)oxazolidin-2-one (103 mg, 0.379 mmol) and DIPEA (0.331 ml, 1.896 mmol) in DMSO was heated to 110° C. for 1 h. LCMS showed little product. Heated for an additional 16 h. LCMS still showed starting material. Added an additional 5 equivalents of DIPEA and 1 equivalent of KF. Heated to 110° C. for 2 h. LCMS shows product. The reaction mixture was diluted with EtOAc (8 mL) and washed with water (30 mL). After separation, the aqueous phase was extracted with EtOAc (3×8 mL). Combined organics were dried over Na$_2$SO$_4$, filtered and concentrated. Purified by column chromatography (10% to 50% EtOAc/Heptane) to give (S)-1-(5-fluoro-2-(1-(4-phenoxyphenyl)ethylamino) pyrimidin-4-yl)-3-oxa-1-azaspiro[4.4]nonan-2-one (62 mg, 0.138 mmol).

$^1$H NMR (400 MHz, MeOD) δ 8.25 (d, J=2.8 Hz, 1H), 7.34 (ddd, J=8.7, 4.9, 2.3 Hz, 4H), 7.16-7.04 (m, 1H), 7.02-6.90 (m, 4H), 4.96 (q, J=7.0 Hz, 1H), 4.30-4.25 (m, 2H), 2.38 (dt, J=13.1, 8.4 Hz, 1H), 2.02 (br s, 1H), 1.80 (ddd, J=12.7, 7.3, 4.2 Hz, 1H), 1.71-1.63 (br m, 2H), 1.61-1.49 (m, 3H), 1.53 (d, J=7.0 Hz, 3H). HRMS(B) (M+H) 449.1984 Calc'd (M+H) 449.1989

The compounds in Table 7 were prepared using methods substantially similar to those described for the preparation of Examples 1, 113, 211 and 212.

TABLE 7

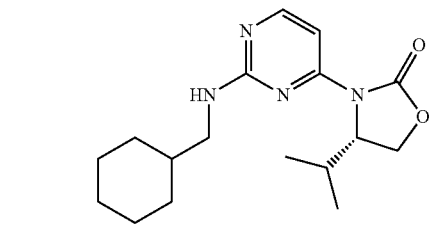 [SMILES: CC(C)[C@H]1COC(=O)N1c1ccnc(NCC2CCCCC2)n1]

213

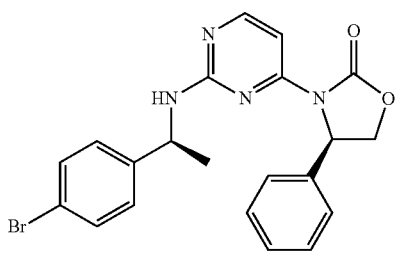 [SMILES: C[C@H](Nc1nccc(N2C(=O)OC[C@H]2c2ccccc2)n1)c1ccc(Br)cc1]

214

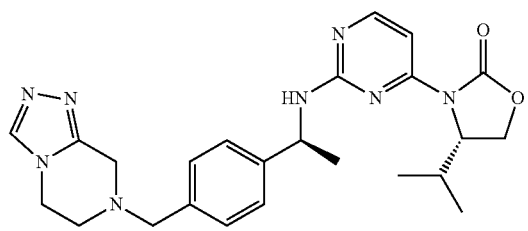 [SMILES: CC(C)[C@H]1COC(=O)N1c1ccnc(N[C@@H](C)c2ccc(CN3CCn4cnnc4C3)cc2)n1]

215

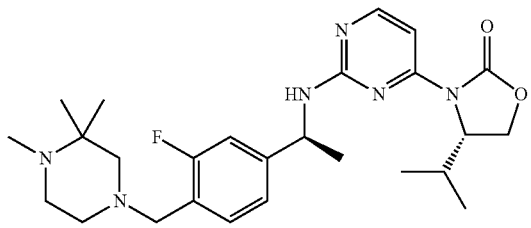 [SMILES: CC(C)[C@H]1COC(=O)N1c1ccnc(N[C@@H](C)c2ccc(CN3CCN(C)C(C)(C)C3)c(F)c2)n1]

216

US 8,957,068 B2
TABLE 7-continued
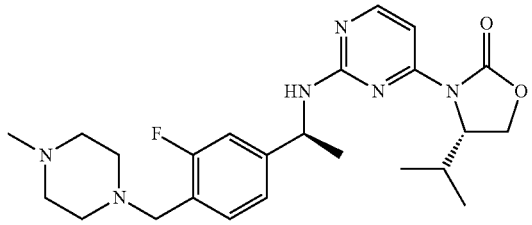 [SMILES: CC(C)[C@H]1COC(=O)N1c1ccnc(N[C@@H](C)c2ccc(CN3CCN(C)CC3)c(F)c2)n1] 217
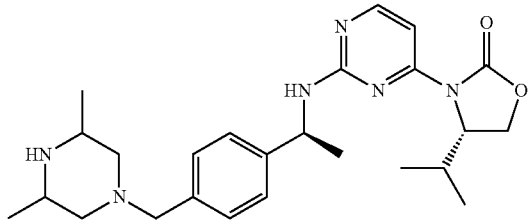 [SMILES: CC1CN(Cc2ccc([C@H](C)Nc3nccc(N4C(=O)OC[C@@H]4C(C)C)n3)cc2)CC(C)N1] 218
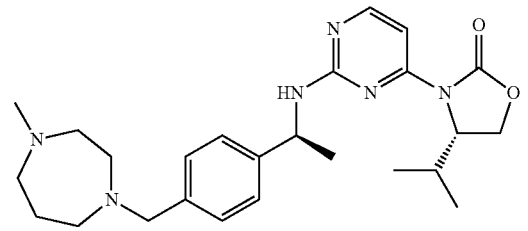 [SMILES: CC(C)[C@H]1COC(=O)N1c1ccnc(N[C@@H](C)c2ccc(CN3CCCN(C)CC3)cc2)n1] 219
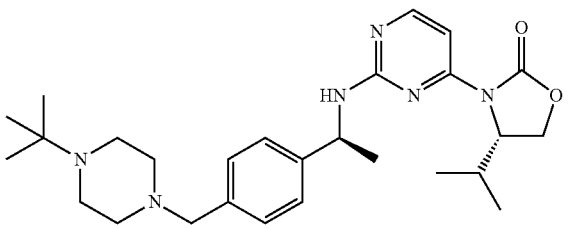 [SMILES: CC(C)[C@H]1COC(=O)N1c1ccnc(N[C@@H](C)c2ccc(CN3CCN(C(C)(C)C)CC3)cc2)n1] 220
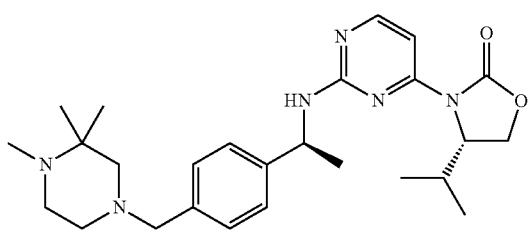 [SMILES: CC(C)[C@H]1COC(=O)N1c1ccnc(N[C@@H](C)c2ccc(CN3CCN(C)C(C)(C)C3)cc2)n1] 221
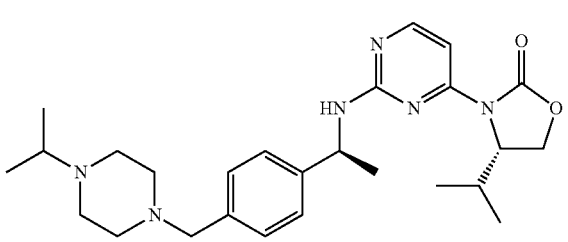 [SMILES: CC(C)[C@H]1COC(=O)N1c1ccnc(N[C@@H](C)c2ccc(CN3CCN(C(C)C)CC3)cc2)n1] 222
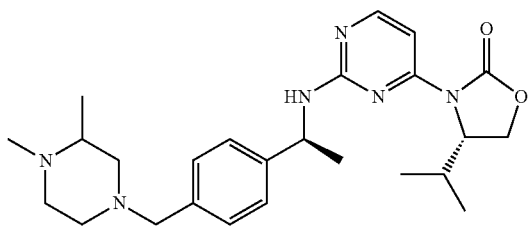 [SMILES: CC(C)[C@H]1COC(=O)N1c1ccnc(N[C@@H](C)c2ccc(CN3CCN(C)C(C)C3)cc2)n1] 223

TABLE 7-continued
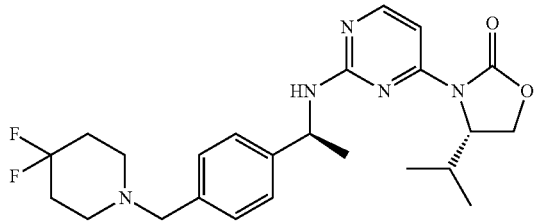 [SMILES: CC(C)[C@H]1COC(=O)N1c1ccnc(N[C@@H](C)c2ccc(CN3CCC(F)(F)CC3)cc2)n1]
224
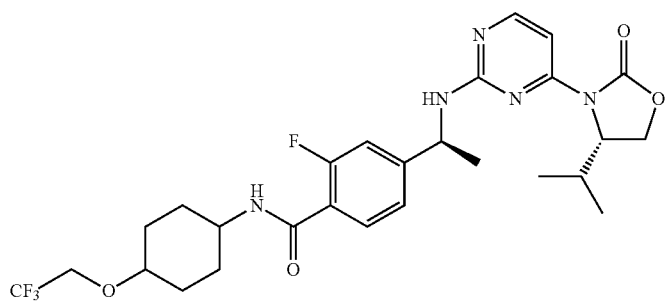 [SMILES: CC(C)[C@H]1COC(=O)N1c1ccnc(N[C@@H](C)c2ccc(C(=O)NC3CCC(OCC(F)(F)F)CC3)c(F)c2)n1]
225
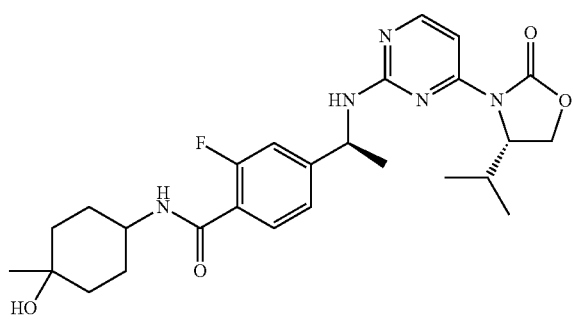 [SMILES: CC(C)[C@H]1COC(=O)N1c1ccnc(N[C@@H](C)c2ccc(C(=O)NC3CCC(C)(O)CC3)c(F)c2)n1]
226
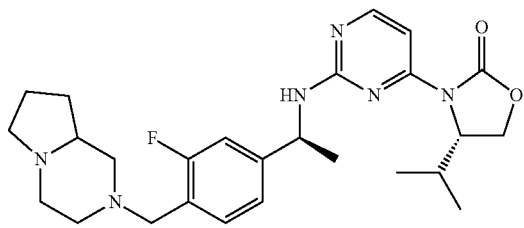 [SMILES: CC(C)[C@H]1COC(=O)N1c1ccnc(N[C@@H](C)c2ccc(CN3CCN4CCCC4C3)c(F)c2)n1]
227
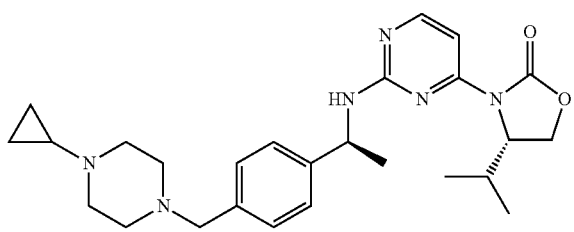 [SMILES: CC(C)[C@H]1COC(=O)N1c1ccnc(N[C@@H](C)c2ccc(CN3CCN(C4CC4)CC3)cc2)n1]
228
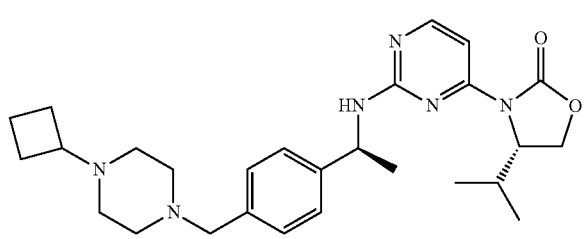 [SMILES: CC(C)[C@H]1COC(=O)N1c1ccnc(N[C@@H](C)c2ccc(CN3CCN(C4CCC4)CC3)cc2)n1]
229

TABLE 7-continued
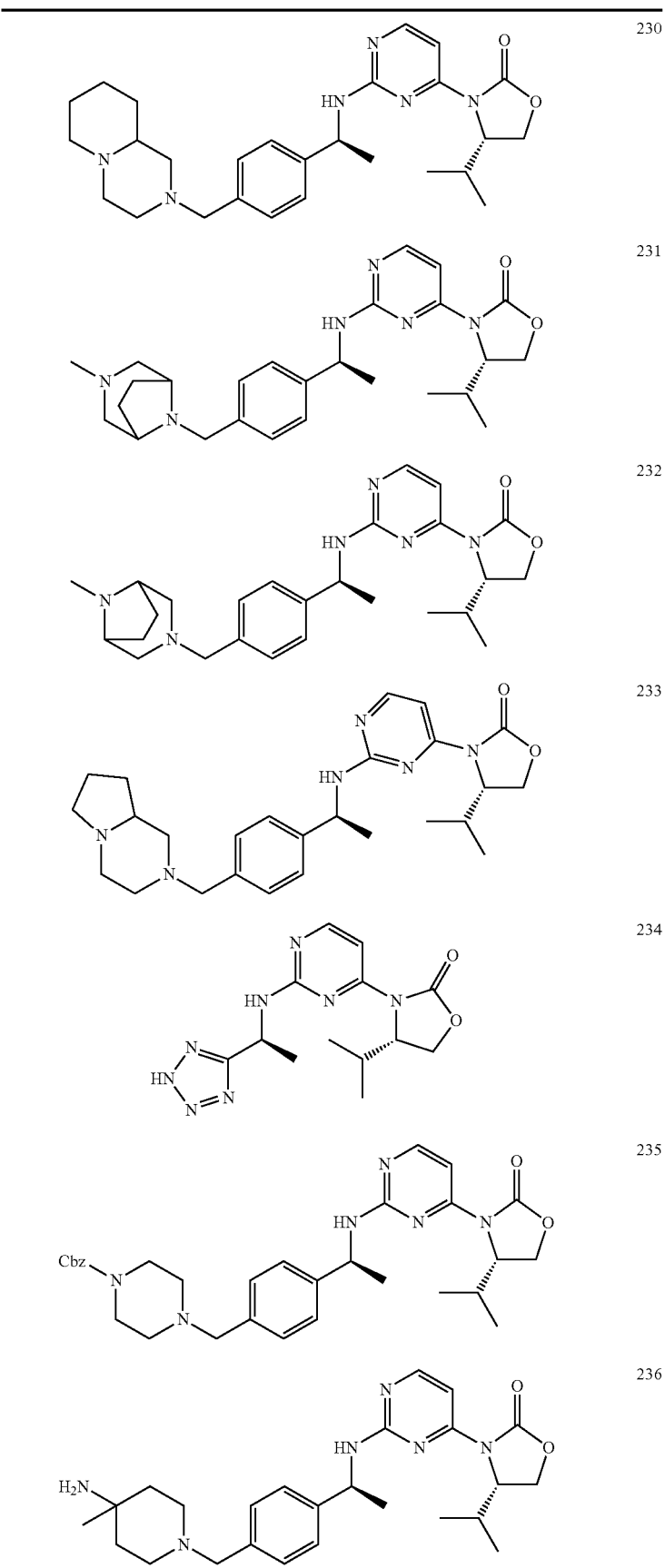

TABLE 7-continued
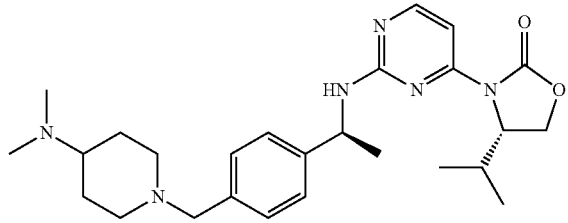 [SMILES: CC(C)[C@H]1COC(=O)N1c1ccnc(N[C@@H](C)c2ccc(CN3CCC(N(C)C)CC3)cc2)n1]
237
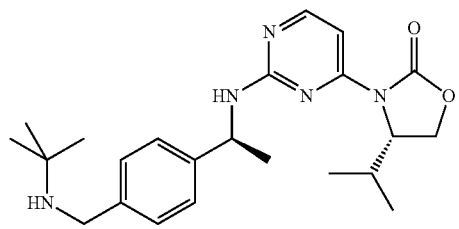 [SMILES: CC(C)[C@H]1COC(=O)N1c1ccnc(N[C@@H](C)c2ccc(CNC(C)(C)C)cc2)n1]
238
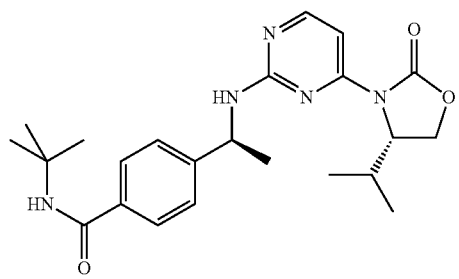 [SMILES: CC(C)[C@H]1COC(=O)N1c1ccnc(N[C@@H](C)c2ccc(C(=O)NC(C)(C)C)cc2)n1]
239
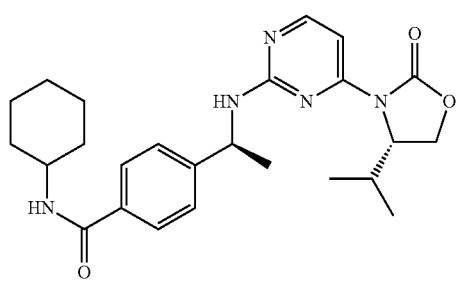 [SMILES: CC(C)[C@H]1COC(=O)N1c1ccnc(N[C@@H](C)c2ccc(C(=O)NC3CCCCC3)cc2)n1]
240
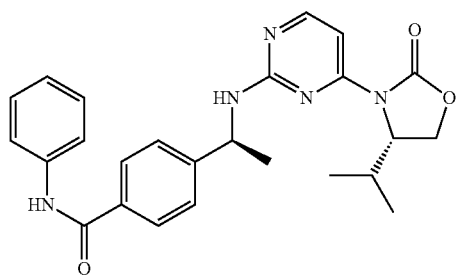 [SMILES: CC(C)[C@H]1COC(=O)N1c1ccnc(N[C@@H](C)c2ccc(C(=O)Nc3ccccc3)cc2)n1]
241
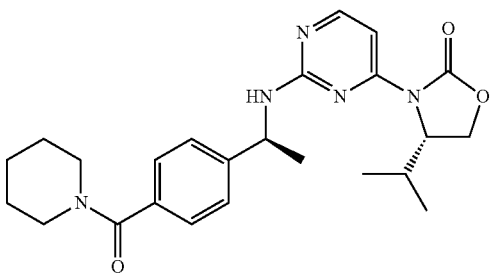 [SMILES: CC(C)[C@H]1COC(=O)N1c1ccnc(N[C@@H](C)c2ccc(C(=O)N3CCCCC3)cc2)n1]
242

TABLE 7-continued
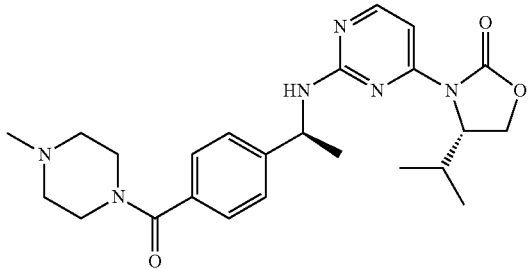 [SMILES: CC(C)[C@H]1COC(=O)N1c1ccnc(N[C@@H](C)c2ccc(C(=O)N3CCN(C)CC3)cc2)n1]
243
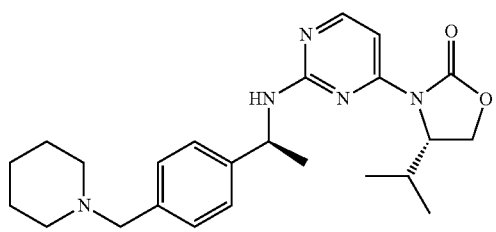 [SMILES: CC(C)[C@H]1COC(=O)N1c1ccnc(N[C@@H](C)c2ccc(CN3CCCCC3)cc2)n1]
244
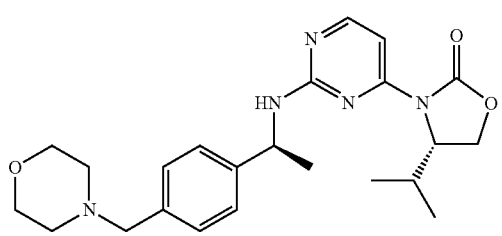 [SMILES: CC(C)[C@H]1COC(=O)N1c1ccnc(N[C@@H](C)c2ccc(CN3CCOCC3)cc2)n1]
245
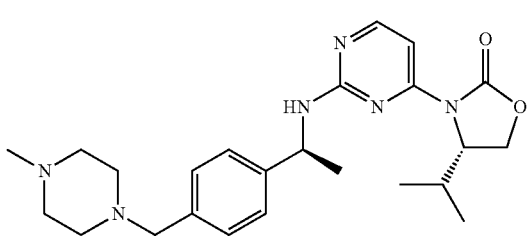 [SMILES: CC(C)[C@H]1COC(=O)N1c1ccnc(N[C@@H](C)c2ccc(CN3CCN(C)CC3)cc2)n1]
246
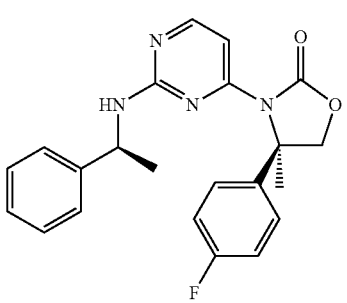 [SMILES: C[C@H](Nc1nccc(N2C(=O)OC[C@@]2(C)c2ccc(F)cc2)n1)c1ccccc1]
247
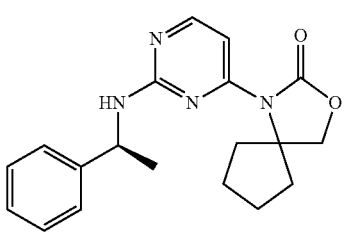 [SMILES: C[C@H](Nc1nccc(N2C(=O)OCC23CCCC3)n1)c1ccccc1]
248

TABLE 7-continued
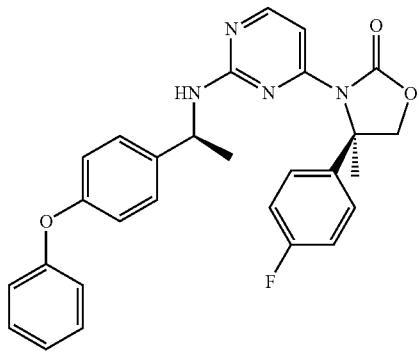 [SMILES: C[C@H](Nc1nccc(N2C(=O)OC[C@@]2(C)c2ccc(F)cc2)n1)c1ccc(Oc2ccccc2)cc1]
249
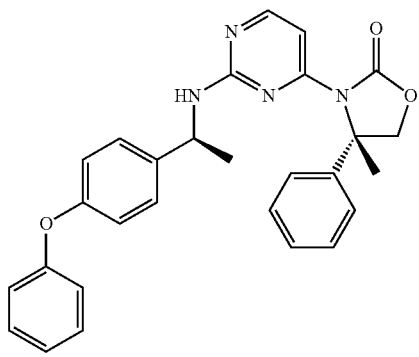 [SMILES: C[C@H](Nc1nccc(N2C(=O)OC[C@]2(C)c2ccccc2)n1)c1ccc(Oc2ccccc2)cc1]
250
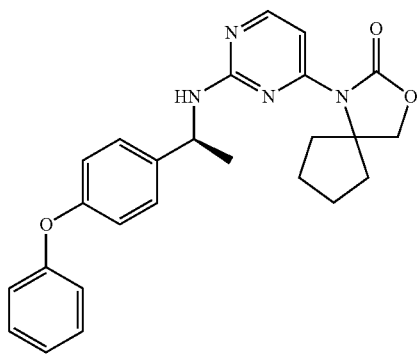 [SMILES: C[C@H](Nc1nccc(N2C(=O)OCC23CCCC3)n1)c1ccc(Oc2ccccc2)cc1]
251
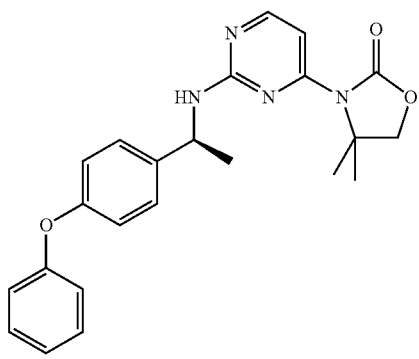 [SMILES: C[C@H](Nc1nccc(N2C(=O)OCC2(C)C)n1)c1ccc(Oc2ccccc2)cc1]
252

TABLE 7-continued
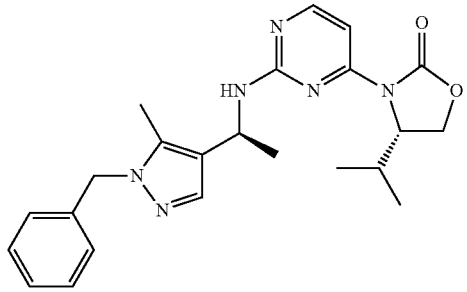 [SMILES: Cc1c([C@H](C)Nc2nccc(N3C(=O)OC[C@@H]3C(C)C)n2)cnn1Cc1ccccc1]
253
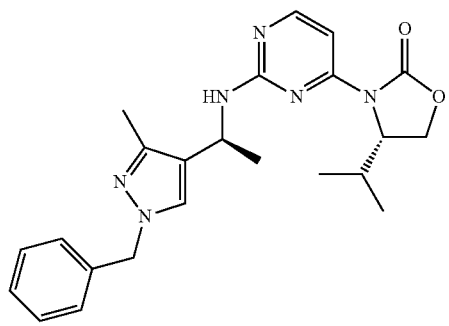 [SMILES: Cc1nn(Cc2ccccc2)cc1[C@H](C)Nc1nccc(N2C(=O)OC[C@@H]2C(C)C)n1]
254
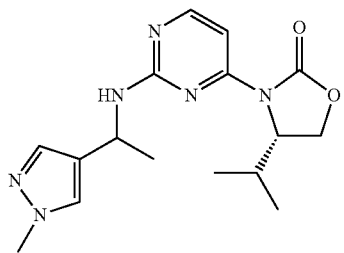 [SMILES: CC(Nc1nccc(N2C(=O)OC[C@@H]2C(C)C)n1)c1cnn(C)c1]
255
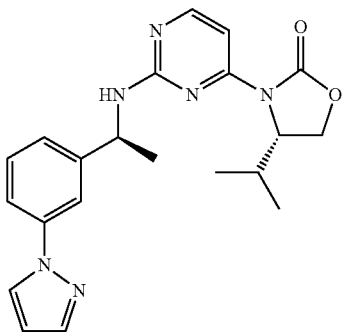 [SMILES: CC(C)[C@H]1COC(=O)N1c1ccnc(N[C@@H](C)c2cccc(-n3cccn3)c2)n1]
256
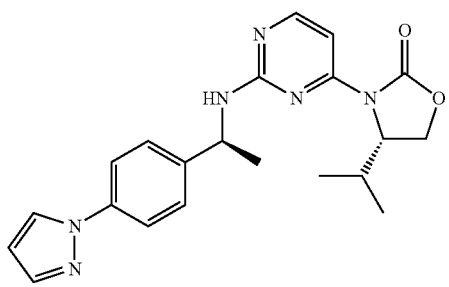 [SMILES: CC(C)[C@H]1COC(=O)N1c1ccnc(N[C@@H](C)c2ccc(-n3cccn3)cc2)n1]
257

TABLE 7-continued
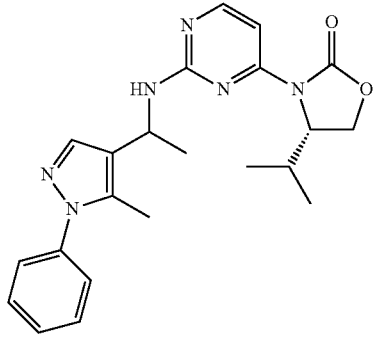 [SMILES: Cc1c(C(C)Nc2nccc(N3C(=O)OC[C@@H]3C(C)C)n2)cnn1-c1ccccc1] 258
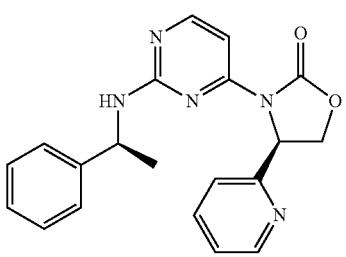 [SMILES: C[C@H](Nc1nccc(N2C(=O)OC[C@H]2c2ccccn2)n1)c1ccccc1] 259
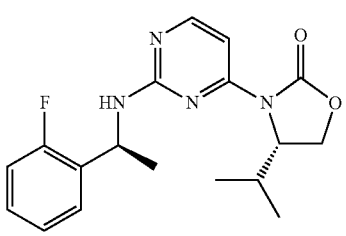 [SMILES: CC(C)[C@H]1COC(=O)N1c1ccnc(N[C@@H](C)c2ccccc2F)n1] 260
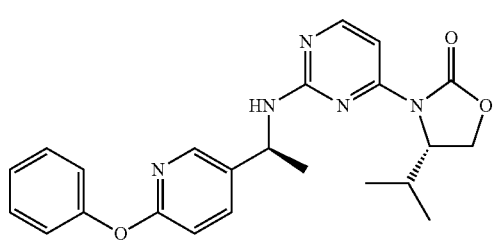 [SMILES: CC(C)[C@H]1COC(=O)N1c1ccnc(N[C@@H](C)c2ccc(Oc3ccccc3)nc2)n1] 261
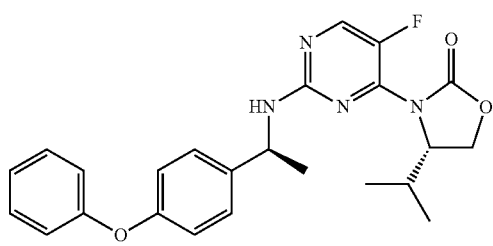 [SMILES: CC(C)[C@H]1COC(=O)N1c1nc(N[C@@H](C)c2ccc(Oc3ccccc3)cc2)ncc1F] 262
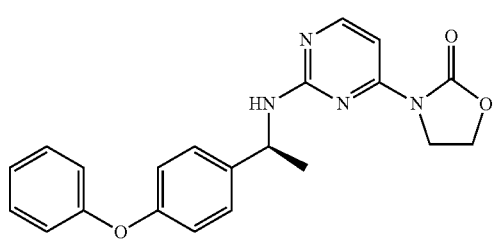 [SMILES: C[C@H](Nc1nccc(N2CCOC2=O)n1)c1ccc(Oc2ccccc2)cc1] 263

TABLE 7-continued
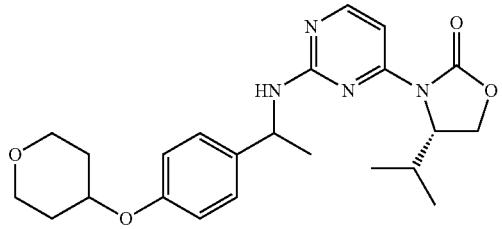 [SMILES: CC(Nc1nccc(N2C(=O)OC[C@@H]2C(C)C)n1)c1ccc(OC2CCOCC2)cc1]
264
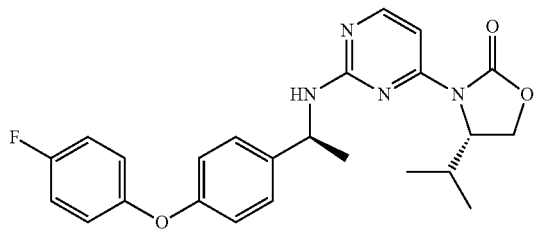 [SMILES: CC(C)[C@H]1COC(=O)N1c1ccnc(N[C@@H](C)c2ccc(Oc3ccc(F)cc3)cc2)n1]
265
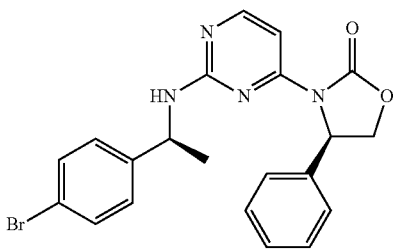 [SMILES: C[C@H](Nc1nccc(N2C(=O)OC[C@H]2c2ccccc2)n1)c1ccc(Br)cc1]
266
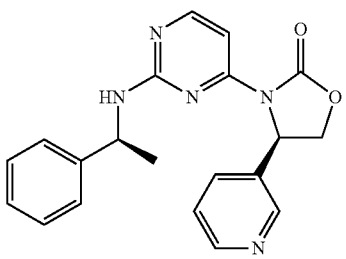
267
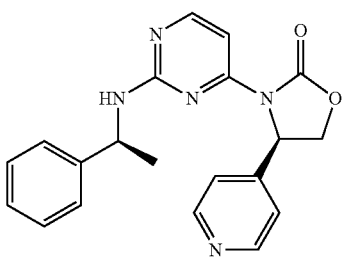 [SMILES: C[C@H](Nc1nccc(N2C(=O)OC[C@H]2c2ccncc2)n1)c1ccccc1]
268
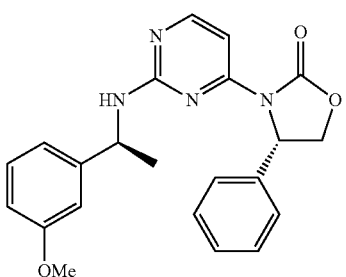 [SMILES: COc1cccc([C@H](C)Nc2nccc(N3C(=O)OC[C@@H]3c3ccccc3)n2)c1]
269

TABLE 7-continued
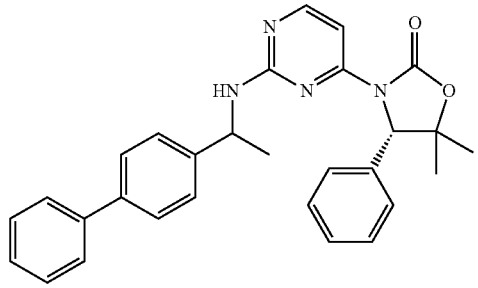 [SMILES: CC(Nc1nccc(N2C(=O)OC(C)(C)[C@@H]2c2ccccc2)n1)c1ccc(-c2ccccc2)cc1]
270
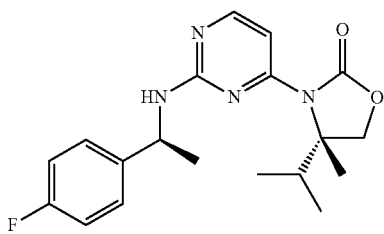 [SMILES: CC(C)[C@@]1(C)COC(=O)N1c1ccnc(N[C@@H](C)c2ccc(F)cc2)n1]
271
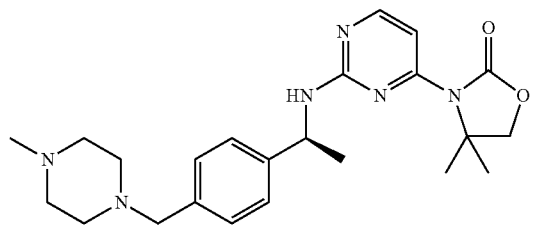 [SMILES: C[C@H](Nc1nccc(N2C(=O)OCC2(C)C)n1)c1ccc(CN2CCN(C)CC2)cc1]
272
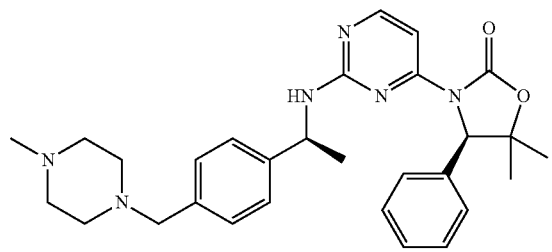
273
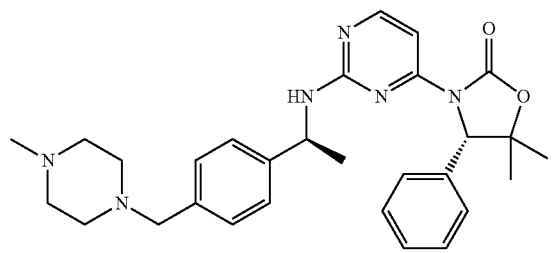
274
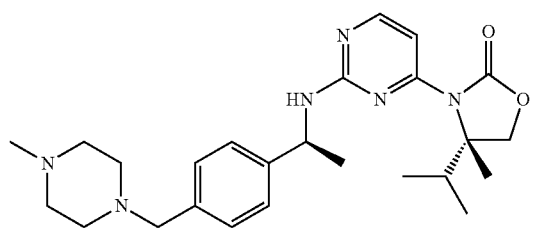 [SMILES: CC(C)[C@@]1(C)COC(=O)N1c1ccnc(N[C@@H](C)c2ccc(CN3CCN(C)CC3)cc2)n1]
275

TABLE 7-continued
| | |
|---|---|
| 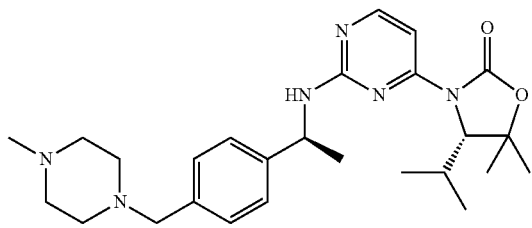 | 276 |
| 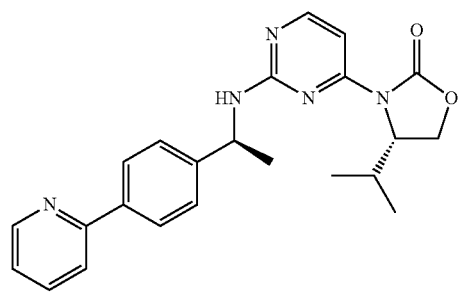 [SMILES: CC(C)[C@H]1COC(=O)N1c1ccnc(N[C@@H](C)c2ccc(-c3ccccn3)cc2)n1] | 277 |
| 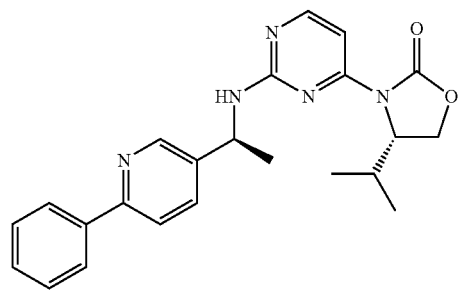 [SMILES: CC(C)[C@H]1COC(=O)N1c1ccnc(N[C@@H](C)c2ccc(-c3ccccc3)nc2)n1] | 278 |
| 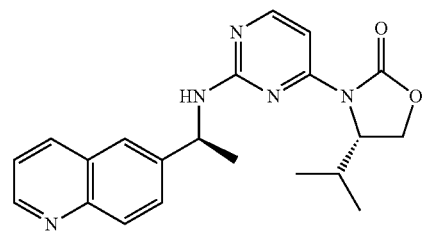 [SMILES: CC(C)[C@H]1COC(=O)N1c1ccnc(N[C@@H](C)c2ccc3ncccc3c2)n1] | 279 |
| 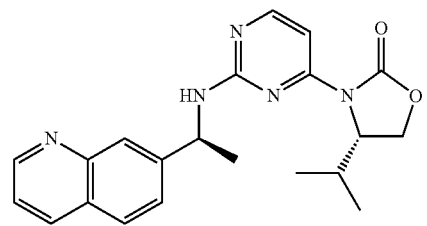 [SMILES: CC(C)[C@H]1COC(=O)N1c1ccnc(N[C@@H](C)c2ccc3cccnc3c2)n1] | 280 |
| 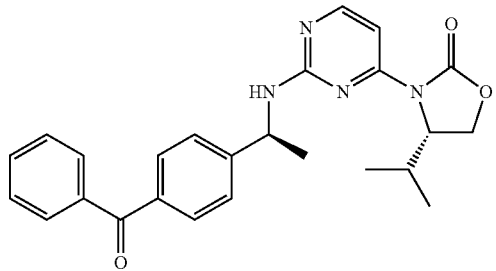 [SMILES: CC(C)[C@H]1COC(=O)N1c1ccnc(N[C@@H](C)c2ccc(C(=O)c3ccccc3)cc2)n1] | 281 |

TABLE 7-continued
| | |
|---|---|
| 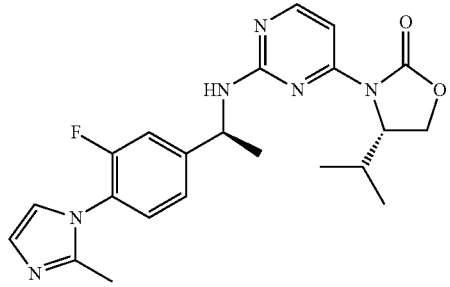 [SMILES: Cc1nccn1-c1ccc([C@H](C)Nc2nccc(N3C(=O)OC[C@@H]3C(C)C)n2)cc1F] | 282 |
| 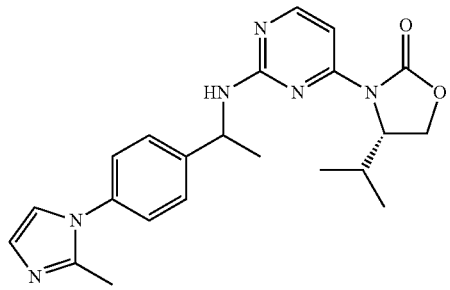 [SMILES: Cc1nccn1-c1ccc(C(C)Nc2nccc(N3C(=O)OC[C@@H]3C(C)C)n2)cc1] | 283 |
| 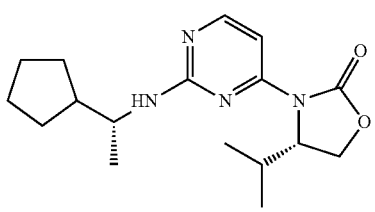 [SMILES: CC(C)[C@H]1COC(=O)N1c1ccnc(N[C@H](C)C2CCCC2)n1] | 284 |
| 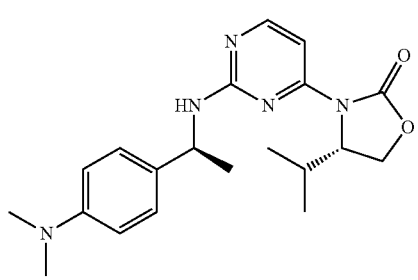 [SMILES: CC(C)[C@H]1COC(=O)N1c1ccnc(N[C@@H](C)c2ccc(N(C)C)cc2)n1] | 285 |
| 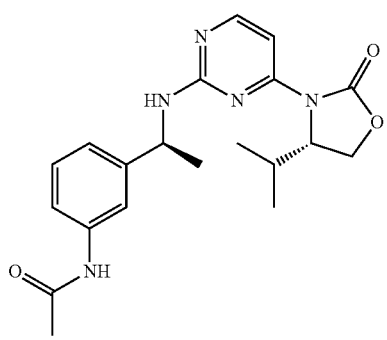 [SMILES: CC(=O)Nc1cccc([C@H](C)Nc2nccc(N3C(=O)OC[C@@H]3C(C)C)n2)c1] | 286 |
| 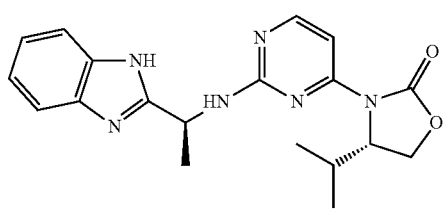 [SMILES: CC(C)[C@H]1COC(=O)N1c1ccnc(N[C@@H](C)c2nc3ccccc3[nH]2)n1] | 287 |

TABLE 7-continued
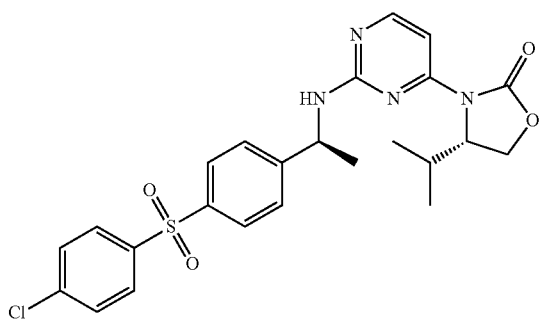 [SMILES: CC(C)[C@H]1COC(=O)N1c1ccnc(N[C@@H](C)c2ccc(S(=O)(=O)c3ccc(Cl)cc3)cc2)n1]
288
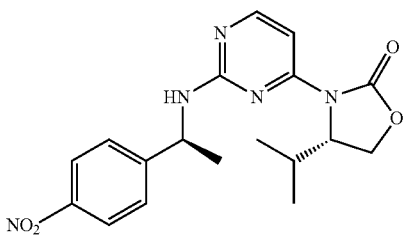 [SMILES: CC(C)[C@H]1COC(=O)N1c1ccnc(N[C@@H](C)c2ccc([N+](=O)[O-])cc2)n1]
289
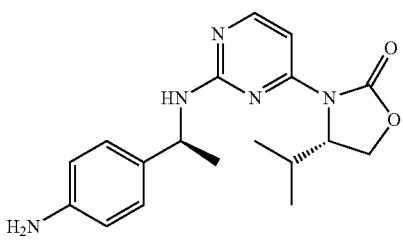 [SMILES: CC(C)[C@H]1COC(=O)N1c1ccnc(N[C@@H](C)c2ccc(N)cc2)n1]
290
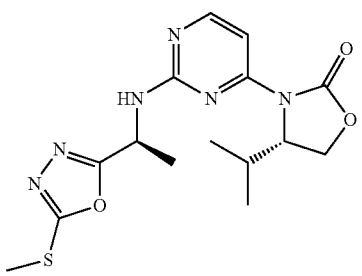 [SMILES: CSc1nnc([C@H](C)Nc2nccc(N3C(=O)OC[C@@H]3C(C)C)n2)o1]
291
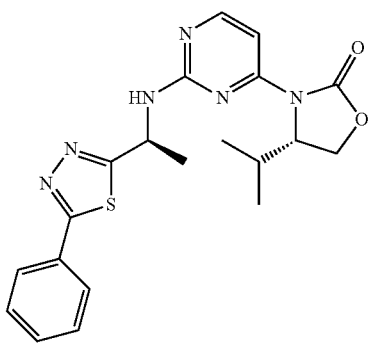 [SMILES: CC(C)[C@H]1COC(=O)N1c1ccnc(N[C@@H](C)c2nnc(-c3ccccc3)s2)n1]
292
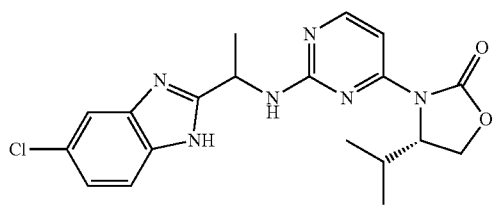 [SMILES: CC(Nc1nccc(N2C(=O)OC[C@@H]2C(C)C)n1)c1nc2cc(Cl)ccc2[nH]1]
293

TABLE 7-continued
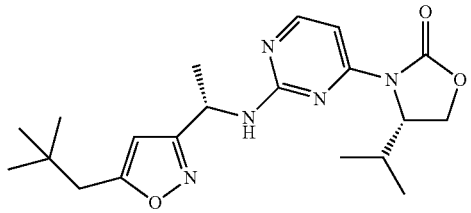 [SMILES: CC(C)[C@H]1COC(=O)N1c1ccnc(N[C@@H](C)c2cc(CC(C)(C)C)on2)n1]
294
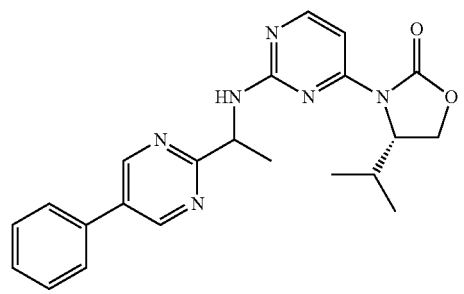 [SMILES: CC(Nc1nccc(N2C(=O)OC[C@@H]2C(C)C)n1)c1ncc(-c2ccccc2)cn1]
295
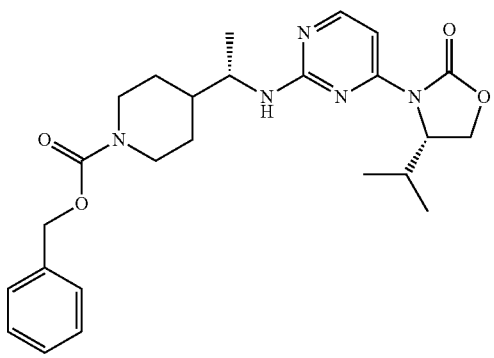 [SMILES: CC(C)[C@H]1COC(=O)N1c1ccnc(N[C@@H](C)C2CCN(C(=O)OCc3ccccc3)CC2)n1]
296
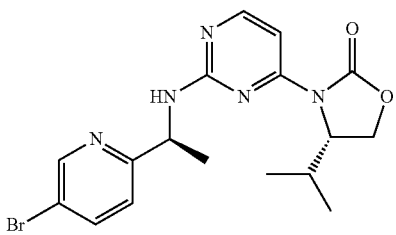
297
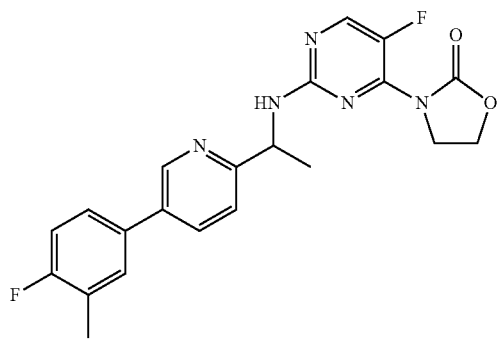 [SMILES: Cc1cc(-c2ccc(C(C)Nc3ncc(F)c(N4CCOC4=O)n3)nc2)ccc1F]
298

TABLE 7-continued
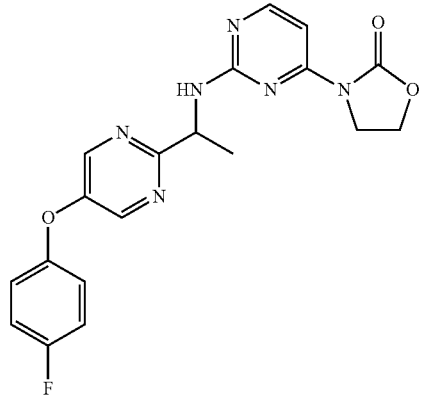 [SMILES: CC(Nc1nccc(N2CCOC2=O)n1)c1ncc(Oc2ccc(F)cc2)cn1]
299
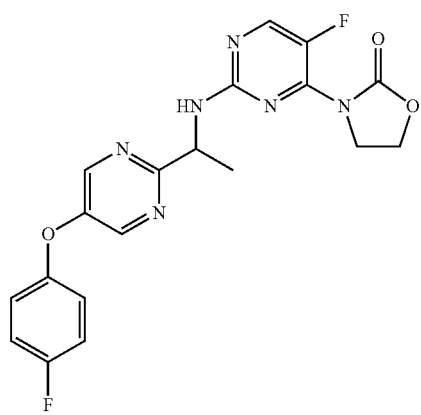 [SMILES: CC(Nc1ncc(F)c(N2CCOC2=O)n1)c1ncc(Oc2ccc(F)cc2)cn1]
300
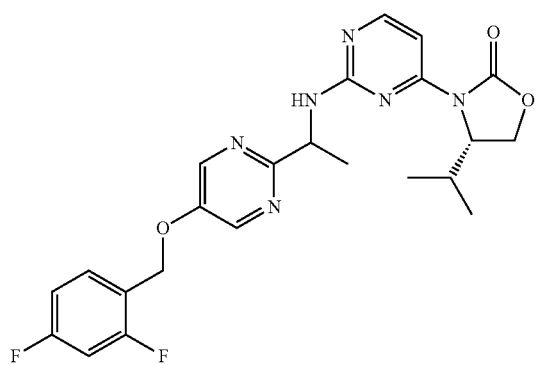 [SMILES: CC(Nc1nccc(N2C(=O)OC[C@@H]2C(C)C)n1)c1ncc(OCc2ccc(F)cc2F)cn1]
301
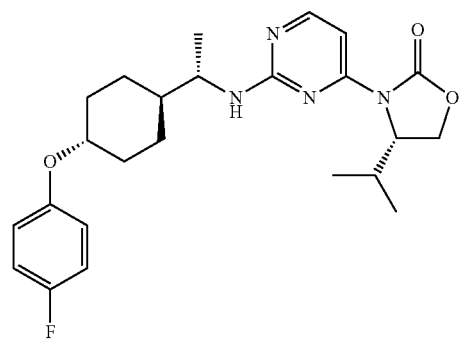 [SMILES: CC(C)[C@H]1COC(=O)N1c1ccnc(N[C@@H](C)[C@H]2CC[C@H](Oc3ccc(F)cc3)CC2)n1]
302

TABLE 7-continued
| | |
|---|---|
| 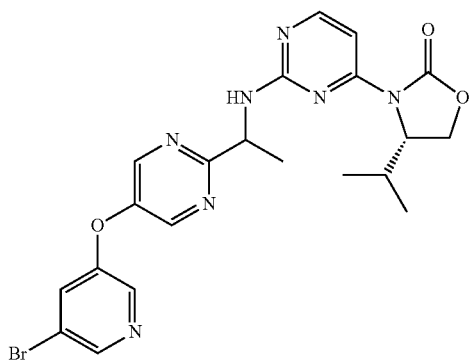 [SMILES: CC(Nc1nccc(N2C(=O)OC[C@@H]2C(C)C)n1)c1ncc(Oc2cncc(Br)c2)cn1] | 303 |
| 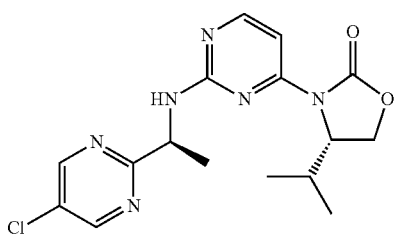 | 304 |
| 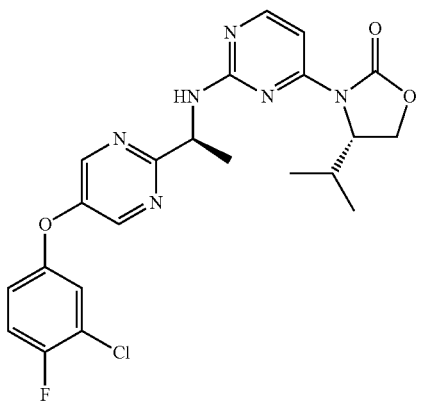 [SMILES: CC(C)[C@H]1COC(=O)N1c1ccnc(N[C@@H](C)c2ncc(Oc3ccc(F)c(Cl)c3)cn2)n1] | 305 |
| 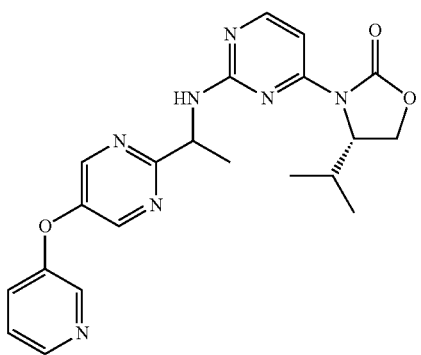 [SMILES: CC(Nc1nccc(N2C(=O)OC[C@@H]2C(C)C)n1)c1ncc(Oc2cccnc2)cn1] | 306 |

TABLE 7-continued
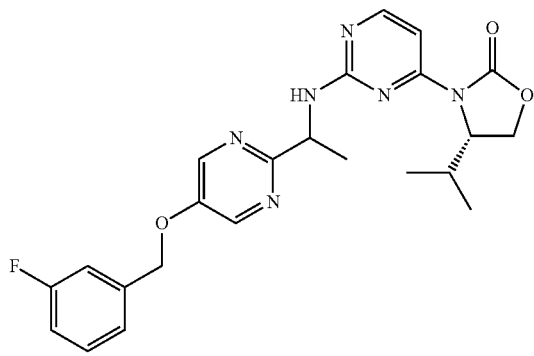 [SMILES: CC(Nc1nccc(N2C(=O)OC[C@@H]2C(C)C)n1)c1ncc(OCc2cccc(F)c2)cn1]
307
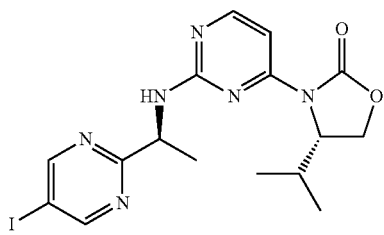 [SMILES: CC(C)[C@H]1COC(=O)N1c1ccnc(N[C@@H](C)c2ncc(I)cn2)n1]
308
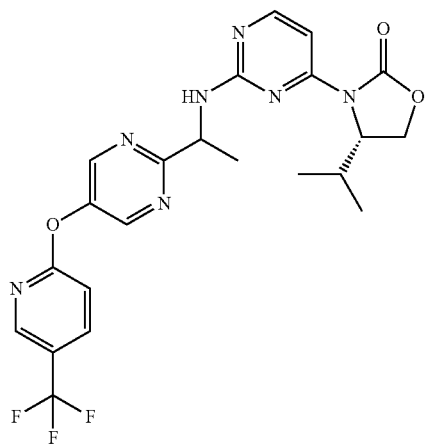 [SMILES: CC(Nc1nccc(N2C(=O)OC[C@@H]2C(C)C)n1)c1ncc(Oc2ccc(C(F)(F)F)cn2)cn1]
309
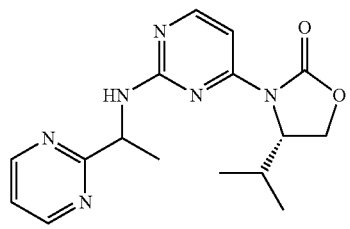 [SMILES: CC(Nc1nccc(N2C(=O)OC[C@@H]2C(C)C)n1)c1ncccn1]
310
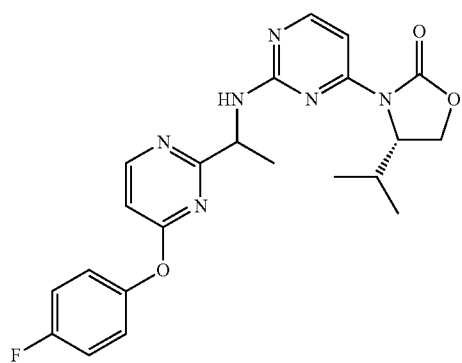 [SMILES: CC(Nc1nccc(N2C(=O)OC[C@@H]2C(C)C)n1)c1nccc(Oc2ccc(F)cc2)n1]
311

TABLE 7-continued

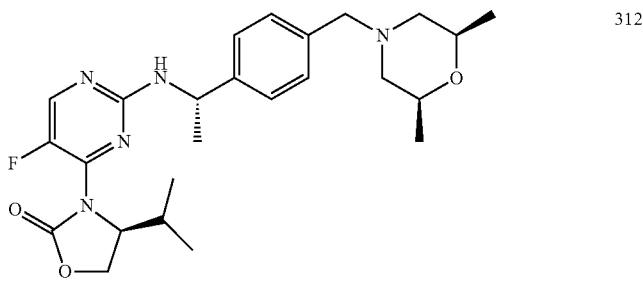

312

TABLE 8

Chemical name, NMR chemical shifts and LCMS signal for each compound listed in Table 7.

| Example: Name | $^1$H NMR (400 MHz, CD$_3$OD) δ ppm (other solvents described) | LCMS |
|---|---|---|
| 213: (S)-3-(2-((cyclohexylmethyl)amino)pyrimidin-4-yl)-4-isopropyloxazolidin-2-one | 8.08 (d, J = 5.8 Hz, 1 H), 7.33 (d, J = 5.8 Hz, 1 H), 4.80-4.76 (m, 1 H), 4.42-4.37 (m, 2 H), 3.24 (dd, J = 13, 6.3 Hz, 1 H), 3.10 (dt, J = 13, 6.8 Hz, 1 H), 2.68-2.60 (m, 1 H), 1.82-1.56 (m, 7 H), 1.31-1.18 (m, 4 H), 0.98 (d, J = 7.1 Hz, 3 H), 0.87 (d, J = 7.0 Hz, 3 H); | HRMS(B) m/z 319.2132 (M + H)+ |
| 214: (R)-3-(2-(((S)-1-(4-bromophenyl)ethyl)amino)pyrimidin-4-yl)-4-phenyloxazolidin-2-one | 8.46 (d, J = 5.8 Hz, 1H), 7.85-7.73 (m, 5H), 7.73-7.67 (m, 1H), 7.64 (dd, J = 7.1, 1.8 Hz, 2H), 7.58-7.52 (m, 2H), 5.92 (dd, J = 8.6, 4.0 Hz, 1H), 5.13 (t, J = 8.7 Hz, 1H), 4.98 (d, J = 7.0 Hz, 1H), 4.55 (dd, J = 8.7, 4.0 Hz, 1H), 1.58 (d, J = 7.0 Hz, 3H); | HRMS(B) m/z 439.0762 M+ |
| 215: (S)-3-(2-(((S)-1-(4-((5,6-dihydro-[1,2,4]triazolo[4,3-a]pyrazin-7(8H)-yl)methyl)phenyl)ethyl)amino)pyrimidin-4-yl)-4-isopropyloxazolidin-2-one | 8.38 (s, 1H), 8.07 (d, J = 5.9 Hz, 1H), 7.30 (d, J = 6.0 Hz, 1H), 7.28 (s, 4H), 5.03 (q, J = 7.0 Hz, 1H), 4.63 (br s, 1H), 4.31-4.23 (m, 2H), 4.08 (t, J = 5.5 Hz, 2H), 3.78-3.69 (m, 4H), 2.89 (td, J = 5.4, 2.1 Hz, 2H), 1.80 (br s, 1H), 1.46 (d, J = 7.0 Hz, 3H), 0.68 (br s, 3H), 0.53 (br s, 3H) | HRMS(B) m/z 463.2567 (M + H)+ |
| 216: (S)-3-(2-(((S)-1-(3-fluoro-4-((3,3,4-trimethylpiperazin-1-yl)methyl)phenyl)ethyl)amino)pyrimidin-4-yl)-4-isopropyloxazolidin-2-one | 8.04 (d, J = 5.9 Hz, 1H), 7.36-7.15 (m, 2H), 7.02 (dd, J = 7.9, 1.8 Hz, 1H), 6.94 (dd, J = 11.0, 1.8 Hz, 1H), 4.95 (q, J = 7.0 Hz, 1H), 4.58 (br s, 1H), 4.32-4.11 (m, 2H), 3.38 (br s, 2H), 2.46 (br t, J = 4.9 Hz, 2H), 2.32 (br s, 2H), 2.14 (br s, 2 H), 2.10 (s, 3H), 1.73 (br s, 1H), 1.40 (d, J = 7.1 Hz, 3H), 0.95 (s, 3H), 0.95 (s, 3H), 0.63 (br s, 3H), 0.49 (br s, 3H) | HRMS(B) m/z 485.3107 (M + H)+ |
| 217: (S)-3-(2-(((S)-1-(3-fluoro-4-((4-methylpiperazin-1-yl)methyl)phenyl)ethyl)amino)pyrimidin-4-yl)-4-isopropyloxazolidin-2-one | 8.09 (d, J = 6.0 Hz, 1H), 7.41-7.20 (m, 2H), 7.11 (dd, J = 7.8, 1.7 Hz, 1H), 7.04 (dd, J = 11.0, 1.8 Hz, 1H), 5.01 (q, J = 7.0 Hz, 1H), 4.63 (br s, 1H), 4.36-4.16 (m, 2H), 3.57 (br s, 2H), 2.82 (br s, 4H), 2.60 (br s, 4H), 2.51 (s, 3H), 1.83 (br s, 1H), 1.45 (d, J = 7.1 Hz, 3H), 0.69 (s, 3H), 0.54 (s, 3H) | HRMS(B) m/z 457.2699 (M + H)+. |
| 218: (4S)-3-(2-(((1S)-1-(4-((3,5-dimethylpiperazin-1-yl)methyl)phenyl)ethyl)amino)pyrimidin-4-yl)-4-isopropyloxazolidin-2-one | 8.07 (d, J = 5.8 Hz, 1H), 7.30 (d, J = 5.8 Hz, 1H), 7.28-7.19 (m, 4H), 5.01 (q, J = 7.0 Hz, 1H), 4.63 (br s, 1H), 4.34-4.18 (m, 2H), 3.46-3.39 (m, 2H), 2.89-2.76 (m, 2H), 2.76-2.67 (m, 2H), 1.82 (br s, 1H), 1.59 (t, J = 10.9 Hz, 2H), 1.45 (d, J = 7.0 Hz, 3H), 0.98 (s, 3H), 0.96 (s, 3H), 0.68 (br s, 3H), 0.52 (br s, 3H) | HRMS(B) m/z 453.2971 (M + H)+ |
| 219: (S)-4-isopropyl-3-(2-(((S)-1-(4-((4-methyl-1,4-diazepan-1-yl)methyl)phenyl)ethyl)amino)pyrimidin-4-yl)oxazolidin-2-one | 8.07 (d, J = 5.8 Hz, 1H), 7.30 (d, J = 5.9 Hz, 1H), 7.28-7.24 (m, 4H), 5.02 (q, J = 7.0 Hz, 1H), 4.63 (br s, 1H), 4.35-4.22 (m, 2H), 3.67-3.59 (m, 2H), 3.09-3.07 (m, 2H), 2.99 (dd, J = 6.2, 3.5 Hz, 2H), 2.79-2.77 (m, 2H), 2.72 (t, J = 6.0 Hz, 2H), 2.63 (s, 3H), 1.93-1.87 (m, 3H), 1.80 (br s, 1H), 1.45 (d, J = 7.0 Hz, 3H), 0.69 (br s, 3H), 0.54 (br s, 3H) | HRMS(B) m/z 453.2968 (M + H)+ |

TABLE 8-continued

Chemical name, NMR chemical shifts and LCMS signal for each compound listed in Table 7.

| Example: Name | $^1$H NMR (400 MHz, CD$_3$OD) δ ppm (other solvents described) | LCMS |
|---|---|---|
| 220: (S)-3-(2-(((S)-1-(4-((4-(tert-butyl)piperazin-1-yl)methyl)phenyl)ethyl)amino)pyrimidin-4-yl)-4-isopropyloxazolidin-2-one | 8.07 (d, J = 5.9 Hz, 1H), 7.30 (d, J = 5.8 Hz, 1H), 7.24 (q, J = 8.2 Hz, 4H), 5.01 (q, J = 6.9 Hz, 1H), 4.63 (br s, 1H), 4.31-4.24 (m, 2H), 3.49-3.42 (m, 2H), 2.60 (br s, 4H), 2.46 (br s, 4H), 1.76 (br s, 1H), 1.45 (d, J = 7.0 Hz, 3H), 1.03 (s, 9H), 0.69 (s, 3H), 0.53 (s, 3H) | HRMS(B) m/z 481.3283 (M + H)+ |
| 221: (S)-4-isopropyl-3-(2-(((S)-1-(4-((3,3,4-trimethylpiperazin-1-yl)methyl)phenyl)ethyl)amino)pyrimidin-4-yl)oxazolidin-2-one | 8.08 (d, J = 5.8 Hz, 1H), 7.30 (d, J = 5.8 Hz, 1H), 7.26-7.18 (m, 4H), 5.01 (q, J = 7.0 Hz, 1H), 4.63 (br s, 1H), 4.31-4.24 (m, 2H), 3.37 (s, 2H), 2.54 (br t, J = 5.0 Hz, 2H), 2.38 (br s, 2H), 2.17 (s, 3H), 2.14 (br s, 2H), 1.85 (br s, 1H), 1.45 (d, J = 7.0 Hz, 3H), 1.01 (s, 6H), 0.68 (br s, 3H), 0.53 (br s, 3H) | HRMS(B) m/z 467.3127 (M + H)+ |
| 222: (S)-4-isopropyl-3-(2-(((S)-1-(4-((4-isopropylpiperazin-1-yl)methyl)phenyl)ethyl)amino)pyrimidin-4-yl)oxazolidin-2-one | 8.07 (d, J = 5.8 Hz, 1H), 7.30 (d, J = 5.8 Hz, 1H), 7.24 (q, J = 8.3 Hz, 4H), 5.01 (q, J = 7.0 Hz, 1H), 4.63 (br s, 1H), 4.31-4.24 (m, 2H), 3.46 (s, 2H), 2.63-2.44 (m, 9H), 1.84 (br s, 1H), 1.45 (d, J = 7.1 Hz, 3H), 1.02 (d, J = 6.5 Hz, 6H), 0.68 (br s, 3H), 0.53 (br s, 3H) | HRMS(B) m/z 467.3120 (M + H)+ |
| 223: (4S)-3-(2-(((1S)-1-(4-((3,4-dimethylpiperazin-1-yl)methyl)phenyl)ethyl)amino)pyrimidin-4-yl)-4-isopropyloxazolidin-2-one | 8.07 (d, J = 5.9 Hz, 1H), 7.30 (d, J = 5.8 Hz, 1H), 7.23 (q, J = 8.1 Hz, 4H), 5.01 (q, J = 7.0 Hz, 1H), 4.63 (br s, 1H), 4.35-4.20 (m, 2H), 3.51-3.35 (m, 2H), 2.82-2.61 (m, 3H), 2.36-2.24 (m, 1H), 2.23 (s, 3H), 2.20-2.08 (m, 2H), 1.89-1.80 (m, 2H), 1.45 (d, J = 7.0 Hz, 3H), 0.99 (d, J = 6.3 Hz, 3H), 0.68 (br s, 3H), 0.52 (br s, 3H) | HRMS(B) m/z 453.2960 (M + H)+ |
| 224: (S)-3-(2-(((S)-1-(4-((4,4-difluoropiperidin-1-yl)methyl)phenyl)ethyl)amino)pyrimidin-4-yl)-4-isopropyloxazolidin-2-one | 8.08 (d, J = 5.8 Hz, 1H), 7.31 (d, J = 5.8 Hz, 1H), 7.25 (q, J = 8.2 Hz, 4H), 5.02 (q, J = 7.0 Hz, 1H), 4.63 (br s, 1H), 4.32-4.24 (m, 2H), 3.51 (s, 2H), 2.52 (br t, J = 5.8 Hz, 4H), 1.98-1.87 (m, 4H), 1.81 (br s, 1H), 1.46 (d, J = 7.0 Hz, 3H), 0.68 (br s, 3H), 0.52 (br s, 3H) | HRMS(B) m/z 460.2514 (M + H)+ |
| 225: 2-fluoro-4-((S)-1-((4-((S)-4-isopropyl-2-oxooxazolidin-3-yl)pyrimidin-2-yl)amino)ethyl)-N-(4-(2,2,2-trifluoroethoxy)cyclohexyl)benzamide | 8.09 (d, J = 5.7 Hz, 1H), 7.58 (t, J = 7.7 Hz, 1H), 7.33 (d, J = 5.8 Hz, 1H), 7.20 (dd, J = 7.9, 1.6 Hz, 1H), 7.13 (dd, J = 12.1, 1.7 Hz, 1H), 5.03 (q, J = 7.0 Hz, 1H), 4.61 (br s, 1H), 4.31-4.24 (m, 2H), 3.97-3.80 (m, 3H), 3.65 (dt, J = 4.7, 2.3 Hz, 1H), 1.90 (dt, J = 12.5, 4.0 Hz, 2H), 1.72-1.58 (m, 6H), 1.47 (d, J = 7.0 Hz, 3H), 0.68 (br s, 3H), 0.56 (br s, 3H) | HRMS(B) m/z 568.2549 (M + H)+ |
| 226: 2-fluoro-N-(4-hydroxy-4-methylcyclohexyl)-4-((S)-1-((4-((S)-4-isopropyl-2-oxooxazolidin-3-yl)pyrimidin-2-yl)amino)ethyl)benzamide | 8.09 (d, J = 6.0 Hz, 1H), 7.58 (t, J = 7.7 Hz, 1H), 7.33 (d, J = 5.8 Hz, 1H), 7.20 (dd, J = 8.0, 1.6 Hz, 1H), 7.13 (dd, J = 12.0, 1.7 Hz, 1H), 5.03 (q, J = 7.0 Hz, 1H), 4.61 (br s, 1H), 4.31-4.25 (m, 2H), 3.89 (dt, J = 9.4, 4.7 Hz, 1H), 1.95-1.82 (m, 2H), 1.75-1.49 (m, 7H), 1.47 (d, J = 7.0 Hz, 3H), 1.21 (s, 3H), 0.68 (br s, 3H), 0.56 (br s, 3H) | HRMS(B) m/z 500.2589 (M + H)+ |
| 227: (4S)-3-(2-(((1S)-1-(3-fluoro-4-((hexahydropyrrolo[1,2-a]pyrazin-2(1H)-yl)methyl)phenyl)ethyl)amino)pyrimidin-4-yl)-4-isopropyloxazolidin-2-one | 8.09 (d, J = 5.8 Hz, 1H), 7.32 (d, J = 5.8 Hz, 1H), 7.29 (t, J = 7.7 Hz, 1H), 7.10 (dd, J = 7.9, 1.8 Hz, 1H), 7.03 (dd, J = 11.0, 1.8 Hz, 1H), 5.00 (q, J = 7.0 Hz, 1H), 4.63 (br s, 1H), 4.31-4.24 (m, 2H), 3.62-3.53 (m, 2H), 2.98-2.91 (m, 3H), 2.80-2.75 (m, 1H), 2.34-2.18 (m, 2H), 2.18-2.01 (m, 2H), 1.90 (t, J = 10.4 Hz, 1H), 1.83-1.65 (m, 4H), 1.45 (d, J = 7.0 Hz, 3H), 1.36-1.27 (m, 1H), 0.68 (br s, 3H), 0.54 (br s, 3H) | HRMS(B) m/z 483.2878 (M + H)+ |
| 228: (S)-3-(2-((S)-1-(4-((4-cyclopropylpiperazin-1-yl)methyl)phenyl)ethylamino)pyrimidin-4-yl)-4-isopropyloxazolidin-2-one | 8.07 (d, J = 5.9 Hz, 1H), 7.30 (d, J = 5.8 Hz, 1H), 7.23 (q, J = 8.0 Hz, 4H), 5.01 (q, J = 7.0 Hz, 1H), 4.62 (br s, 1H), 4.35-4.19 (m, 2H), 3.45 (s, 2H), 2.62 (br s, 4H), 2.41 (br s, 4H), 1.79 (br s, 1H), 1.65-1.56 (m, 1H), 1.45 (d, J = 7.0 Hz, 3H), 0.67 (br s, 3H), 0.52 (br s, 3H), 0.45-0.38 (m, 2H), 0.38-0.29 (m, 2H) | HRMS(B) m/z 465.2975 (M + H)+ |

TABLE 8-continued

Chemical name, NMR chemical shifts and LCMS
signal for each compound listed in Table 7.

| Example: Name | $^1$H NMR (400 MHz, CD$_3$OD) δ ppm (other solvents described) | LCMS |
|---|---|---|
| 229: (S)-3-(2-((S)-1-(4-((4-cyclobutylpiperazin-1-yl)methyl)phenyl)ethylamino)pyrimidin-4-yl)-4-isopropyloxazolidin-2-one | 8.08 (d, J = 7.2 Hz, 1H), 7.70 (d, J = 7.2 Hz, 1H), 7.47-7.24 (m, 4H), 5.28-5.06 (m, 1H), 4.66 (q, J = 4.8, 4.4 Hz, 1H), 4.34 (d, J = 5.7 Hz, 2H), 3.91 (s, 2H), 3.61 (p, J = 8.3 Hz, 1H), 3.20 (br s, 4H), 3.02 (br s, 4H), 2.32-2.04 (m, 4H), 1.90-1.66 (m, 3H), 1.52 (d, J = 7.0 Hz, 3H), 0.71 (d, J = 7.0 Hz, 3H), 0.54 (d, J = 6.7 Hz, 3H) | HRMS(B) m/z 479.3165 (M + H)+ |
| 230: (4S)-3-(2-((1S)-1-(4-((dihydro-1H-pyrido[1,2-a]pyrazin-2(6H,7H,8H,9H,9aH)-yl)methyl)phenyl)ethylamino)pyrimidin-4-yl)-4-isopropyloxazolidin-2-one | 8.07 (d, J = 5.8 Hz, 1H), 7.34-7.19 (m, 5H), 5.01 (q, J = 7.0 Hz, 1H), 4.63 (br s, 1H), 4.33-4.22 (m, 2H), 3.49-3.39 (m, 2H), 2.83-2.71 (m, 2H), 2.66 (dq, J = 11.0, 2.2 Hz, 2H), 2.32-2.14 (m, 2H), 2.09-1.94 (m, 2H), 1.82 (t, J = 10.8 Hz, 1H), 1.70 (dt, J = 12.4, 3.5 Hz, 1H), 1.64-1.50 (m, 2H), 1.48-1.39 (m, 5H), 1.35-1.21 (m, 1H), 1.14 (tdd, J = 13.0, 10.8, 3.6 Hz, 1H), 0.68 (br s, 3H), 0.52 (br s, 3H) | HRMS(B) m/z 479.3131 (M + H)+ |
| 231: (4S)-4-isopropyl-3-(2-((1S)-1-(4-((3-methyl-3,8-diazabicyclo[3.2.1]octan-8-yl)methyl)phenyl)ethylamino)pyrimidin-4-yl)oxazolidin-2-one | 8.07 (d, J = 5.9 Hz, 1H), 7.36-7.21 (m, 5H), 5.01 (q, J = 7.0 Hz, 1H), 4.62 (br s, 1H), 4.33-4.21 (m, 2H), 3.45 (s, 2H), 3.07 (qd, J = 4.6, 4.2, 1.9 Hz, 2H), 2.63-2.50 (m, 2H), 2.25 (ddd, J = 10.7, 4.4, 1.8 Hz, 2H), 2.15 (s, 3H), 2.04-1.93 (m, 2H), 1.83-1.72 (m, 3H), 1.45 (d, J = 7.0 Hz, 3H), 0.67 (br s, 3H), 0.51 (br s, 3H) | HRMS(B) m/z 465.2964 (M + H)+ |
| 232: (4S)-4-isopropyl-3-(2-((1S)-1-(4-((8-methyl-3,8-diazabicyclo[3.2.1]octan-3-yl)methyl)phenyl)ethylamino)pyrimidin-4-yl)oxazolidin-2-one | (CDCl$_3$) 8.17 (d, J = 5.7 Hz, 1H), 7.42 (d, J = 5.7 Hz, 1H), 7.23 (s, 4H), 5.46 (br s, 1H), 5.01 (br s, 1H), 4.60 (dt, J = 6.9, 3.3 Hz, 1H), 4.28 (t, J = 8.7 Hz, 1H), 4.21 (dd, J = 9.1, 3.1 Hz, 1H), 3.42 (d, J = 1.7 Hz, 2H), 3.10-2.96 (m, 2H), 2.58-2.48 (m, 2H), 2.33-2.18 (m, 5H), 2.06-1.84 (m, 3H), 1.81 (dd, J = 7.8, 4.4 Hz, 2H), 1.52 (d, J = 6.8 Hz, 3H), 0.71 (br s, 3H), 0.64 (br s, 3H) | HRMS(B) m/z 465.2963 (M + H)+ |
| 233: (4S)-3-(2-((1S)-1-(4-((hexahydropyrrolo[1,2-a]pyrazin-2(1H)-yl)methyl)phenyl)ethylamino)pyrimidin-4-yl)-4-isopropyloxazolidin-2-one | 8.12 (d, J = 5.8 Hz, 1H), 7.34 (d, J = 5.8 Hz, 1H), 7.33-7.24 (m, 4H), 5.05 (q, J = 7.0 Hz, 1H), 4.67 (br s, 1H), 4.38-4.26 (m, 2H), 3.64-3.49 (m, 2H), 3.11-3.00 (m, 2H), 2.96 (br d, J = 11.0 Hz, 1H), 2.83 (br d, J = 11.2 Hz, 1H), 2.45-2.34 (m, 1H), 2.32-2.25 (m, 3H), 1.94 (t, J = 10.5 Hz, 1H), 1.88-1.77 (m, 4H), 1.49 (d, J = 7.0 Hz, 3H), 1.47-1.35 (m, 1H), 0.72 br (s, 3H), 0.56 (br s, 3H) | HRMS(B) m/z 465.2972 (M + H)+ |
| 234: (S)-3-(2-(((S)-1-(2H-tetrazol-5-yl) ethyl) amino) pyrimidin-4-yl)-4-isopropyloxazolidin-2-one | | HRMS(B) m/z 319.1624 (M + H)+, RT = 1.33 min. |
| 235: benzyl 4-(4-((S)-1-(4-((S)-4-isopropyl-2-oxooxazolidin-3-yl)pyrimidin-2-ylamino)ethyl)benzyl)piperazine-1-carboxylate | 8.07 (d, J = 5.8 Hz, 1H), 7.34-7.18 (m, 10H), 5.05 (s, 2H), 5.01 (q, J = 6.9 Hz, 1H), 4.62 (br s, 1H), 4.32-4.18 (m, 2H), 3.49-3.34 (m, 4H), 3.46 (s, 2H), 2.36 (t, J = 5.1 Hz, 4H), 1.75 (br s, 1H), 1.45 (d, J = 7.0 Hz, 3H), 0.66 (br s, 3H), 0.50 (br s, 3H) | HRMS(B) m/z 559.3026 (M + H)+ |
| 236: (S)-3-(2-((1-(4-((4-amino-4-methylpiperidin-1-yl)methyl)phenyl)ethylamino)pyrimidin-4-yl)-4-isopropyloxazolidin-2-one | 8.07 (d, J = 5.8 Hz, 1H), 7.30 (d, J = 5.8 Hz, 1H), 7.27-7.21 (m, 4H), 5.01 (q, J = 7.0 Hz, 1H), 4.63 (br s, 1H), 4.34-4.18 (m, 2H), 3.53-3.40 (m, 2H), 2.59-2.21 (br m, 4H), 1.78 (br s, 1H), 1.52 (ddt, J = 11.8, 8.7, 5.2 Hz, 4H), 1.45 (d, J = 7.0 Hz, 3H), 1.07 (s, 3H), 0.67 (br s, 3H), 0.51 (br s, 3H) | HRMS(B) m/z 453.2972 (M + H)+ |
| 237: (S)-3-(2-((1S)-1-(4-((4-(dimethylamino)piperidin-1-yl)methyl)phenyl)ethylamino)pyrimidin-4-yl)-4-isopropyloxazolidin-2-one | (CDCl$_3$) 8.17 (d, J = 5.7 Hz, 1H), 7.42 (d, J = 5.7 Hz, 1H), 7.25 (d, J = 8.2 Hz, 4H), 5.43 (br s, 1H), 5.01 (br s, 1H), 4.60 (dt, J = 8.6, 3.3 Hz, 1H), 4.28 (t, J = 8.7 Hz, 1H), 4.21 (dd, J = 9.1, 3.2 Hz, 1H), 3.44 (s, 2H), 2.89 (dp, J = 11.5, 2.8 Hz, 2H), 2.26 (s, 6H), 2.11 (tt, J = 11.3, 3.6 Hz, 1H), 1.93 (td, J = 11.9, 2.4 Hz, 2H), 1.90 (br s, 1H), 1.75 (dq, J = 12.0, 2.8 Hz, 2H), 1.60-1.43 | HRMS(B) m/z 467.3121 (M + H)+ |

TABLE 8-continued

Chemical name, NMR chemical shifts and LCMS signal for each compound listed in Table 7.

| Example: Name | $^1$H NMR (400 MHz, CD$_3$OD) δ ppm (other solvents described) | LCMS |
|---|---|---|
| | (m, 2H), 1.53 (d, J = 6.8 Hz, 3H), 0.70 (br s, 3H), 0.63 (br s, 3H) | |
| 238: (S)-3-(2-((S)-1-(4-((tert-butylamino)methyl)phenyl)ethylamino)pyrimidin-4-yl)-4-isopropyloxazolidin-2-one | (CDCl$_3$) δ 8.18 (dd, J = 5.8, 1.3 Hz, 1H), 7.44 (dd, J = 5.7, 1.2 Hz, 1H), 7.37-7.22 (m, 5H), 5.52 (br s, 1H), 5.15-4.95 (m, 1H), 4.70-4.55 (m, 1H), 4.30 (td, J = 8.8, 2.1 Hz, 1H), 4.23 (dd, J = 9.1, 3.0 Hz, 1H), 3.71 (d, J = 2.0 Hz, 2H), 2.06 (s, 1H), 1.54 (dd, J = 7.1, 1.9 Hz, 3H), 1.18 (sm, 9H), 0.85-0.59 (m, 6H); | HRMS(B) m/z 412.2701 (M + H)+ |
| 239: N-tert-butyl-4-((S)-1-(4-((S)-4-isopropyl-2-oxooxazolidin-3-yl)pyrimidin-2-ylamino)ethyl)benzamide | (CDCl$_3$) δ 8.16 (dd, J = 5.8, 1.2 Hz, 1H), 7.66 (d, J = 8.3 Hz, 2H), 7.43 (dd, J = 5.8, 0.9 Hz, 1H), 7.35 (d, J = 7.9 Hz, 2H), 5.88 (s, 1H), 5.57 (br s, 1H), 5.04 (br s, 1H), 4.55 (br s, 1H), 4.26 (t, J = 8.7 Hz, 1H), 4.19 (dd, J = 9.2, 3.2 Hz, 1H), 1.53 (d, J = 6.9 Hz, 3H), 1.45 (s, 9H), 0.64 (m, 6H) | HRMS(B) m/z 426.2488 (M + H)+ |
| 240: N-cyclohexyl-4-((S)-1-(4-((S)-4-isopropyl-2-oxooxazolidin-3-yl)pyrimidin-2-ylamino)ethyl)benzamide | (CDCl$_3$) δ 8.17 (d, J = 5.7 Hz, 1H), 7.69 (d, J = 8.1 Hz, 2H), 7.44 (d, J = 5.8 Hz, 1H), 7.36 (d, J = 7.9 Hz, 2H), 5.91 (d, J = 8.3 Hz, 1H), 5.51 (br s, 1H), 5.04 (br s, 1H), 4.53 (br s, 1H), 4.26 (t, J = 8.7 Hz, 1H), 4.19 (dd, J = 9.1, 3.2 Hz, 1H), 4.04-3.89 (m, 1H), 2.07-1.95 (m, 2H), 1.74 (dp, J = 11.5, 3.8 Hz, 2H), 1.64 (tt, J = 7.4, 3.7 Hz, 2H), 1.54 (d, J = 6.9 Hz, 3H), 1.42 (qt, J = 12.4, 3.5 Hz, 2H), 1.30-1.17 (m, 3H), 0.64 (br s, 6H) | HRMS(B) m/z 452.2640 (M + H)+ |
| 241: 4-((S)-1-(4-((S)-4-isopropyl-2-oxooxazolidin-3-yl)pyrimidin-2-ylamino)ethyl)-N-phenylbenzamide | (CDCl$_3$) δ 8.19 (d, J = 5.8 Hz, 1H), 7.83 (d, J = 8.2 Hz, 2H), 7.77 (s, 1H), 7.68-7.59 (m, 2H), 7.48-7.41 (m, 3H), 7.37 (dd, J = 8.5, 7.3 Hz, 2H), 7.22-7.11 (m, 1H), 5.48 (br s, 1H), 5.08 (br s, 1H), 4.56 (br s, 1H), 4.27 (t, J = 8.7 Hz, 1H), 4.20 (dd, J = 9.2, 3.2 Hz, 1H), 1.57 (t, J = 5.6 Hz, 3H), 0.65 (br s, 6H); | HRMS(B) m/z 446.2170 (M + H)+ |
| 242: (S)-4-isopropyl-3-(2-((S)-1-(4-(piperidine-1-carbonyl)phenyl)ethylamino)pyrimidin-4-yl)oxazolidin-2-one | (CDCl$_3$) δ 8.18 (d, J = 5.7 Hz, 1H), 7.45 (d, J = 5.7 Hz, 1H), 7.33 (s, 4H), 5.45 (br s, 1H), 5.05 (br s, 1H), 4.59 (dt, J = 7.3, 2.9 Hz, 1H), 4.27 (t, J = 8.7 Hz, 1H), 4.21 (dd, J = 9.1, 3.2 Hz, 1H), 3.51 (d, J = 141.8 Hz, 4H), 1.60 (dd, J = 52.4, 5.9 Hz, 10H), 0.68 (d, J = 25.5 Hz, 6H); | HRMS(B) m/z 438.2492 (M + H)+ |
| 243: (S)-4-isopropyl-3-(2-((S)-1-(4-(4-methylpiperazine-1-carbonyl)phenyl)ethylamino)pyrimidin-4-yl)oxazolidin-2-one | (CDCl$_3$) δ 8.18 (d, J = 5.7 Hz, 1H), 7.45 (d, J = 5.7 Hz, 1H), 7.35 (s, 4H), 5.42 (br s, 1H), 5.05 (br s, 1H), 4.58 (br s, 1H), 4.28 (t, J = 8.8 Hz, 1H), 4.21 (dd, J = 9.2, 3.1 Hz, 1H), 3.78 (br s, 2H), 3.44 (br s, 2H), 2.53-2.39 (m, 2H), 2.32 (s, 4H), 1.65 (m, 2H), 1.53 (d, J = 6.9 Hz, 3H), 0.82-0.50 (m, 6H) | HRMS(B) m/z 453.2611 (M + H)+ |
| 244: (S)-4-isopropyl-3-(2-((S)-1-(4-(piperidin-1-ylmethyl)phenyl)ethylamino)pyrimidin-4-yl)oxazolidin-2-one | (CDCl$_3$) δ 8.16 (d, J = 5.7 Hz, 1H), 7.42 (d, J = 5.7 Hz, 1H), 7.24 (s, 4H), 5.58 (br s, 1H), 5.15-4.85 (m, 1H), 4.60 (dt, J = 8.4, 3.4 Hz, 1H), 4.27 (t, J = 8.7 Hz, 1H), 4.20 (dd, J = 9.1, 3.2 Hz, 1H), 3.43 (s, 2H), 2.54-2.22 (m, 4H), 1.99 (br s, 1H), 1.61-1.48 (m, 7H), 1.42 (q, J = 6.6, 6.0 Hz, 2H), 0.86-0.41 (m, 6H); | HRMS(B) m/z 424.2704 (M + H)+ |
| 245: (S)-4-isopropyl-3-(2-((S)-1-(4-(morpholinomethyl)phenyl)ethylamino)pyrimidin-4-yl)oxazolidin-2-one | (CDCl$_3$) δ 8.18 (d, J = 5.7 Hz, 1H), 7.45 (d, J = 5.7 Hz, 1H), 7.28 (s, 4H), 5.56 (br s, 1H), 5.16-4.94 (m, 1H), 4.63 (dt, J = 7.6, 3.5 Hz, 1H), 4.30 (t, J = 8.8 Hz, 1H), 4.23 (dd, J = 9.0, 3.1 Hz, 1H), 3.72 (t, J = 4.6 Hz, 4H), 3.49 (s, 2H), 2.45 (t, J = 4.6 Hz, 4H), 2.19-1.82 (m, 1H), 1.55 (d, J = 6.9 Hz, 3H), 0.90-0.46 (m, 6H); | HRMS(B) m/z 426.2487 (M + H)+ |
| 246: (S)-4-isopropyl-3-(2-((S)-1-(4-((4-methylpiperazin-1-yl)methyl)phenyl)ethylamino)pyrimidin-4-yl)oxazolidin-2-one | (CDCl$_3$) δ 8.17 (d, J = 5.8 Hz, 1H), 7.43 (d, J = 5.8 Hz, 1H), 7.27 (d, J = 6.2 Hz, 4H), 5.52 (br s, 1H), 5.03 (br s, 0H), 4.62 (dt, J = 8.5, 3.4 Hz, 1H), 4.29 (t, J = 8.7 Hz, 1H), 4.22 (dd, J = 9.1, 3.2 Hz, 1H), 3.48 (s, 2H), 2.46 (br s, 9H), 2.30 (s, 3H), 1.54 (d, J = 6.9 Hz, 3H), 0.97-0.57 (m, 6H); | HRMS(B) m/z 439.2801 (M + H)+ |

TABLE 8-continued

Chemical name, NMR chemical shifts and LCMS signal for each compound listed in Table 7.

| Example: Name | $^1$H NMR (400 MHz, CD$_3$OD) δ ppm (other solvents described) | LCMS |
|---|---|---|
| 247: (R)-4-(4-fluorophenyl)-4-methyl-3-(2-((S)-1-phenylethylamino)pyrimidin-4-yl)oxazolidin-2-one | (CDCl$_3$) δ 8.18 (d, J = 5.8 Hz, 1 H), 7.41 (d, J = 5.8 Hz, 1 H), 7.33-7.29 (m, 2 H), 7.25-7.20 (m, 3 H), 7.15-7.06 (m, 4 H), 5.17 (br s, 1 H), 4.21 (br s, 1 H), 4.20-4.15 (m, 2 H), 1.61 (s, 3 H), 1.21 (d, J = 7.1 Hz, 3 H) | HRMS(B) m/z 393.1726 (M + H)+. |
| 248: (S)-1-(2-(1-phenylethylamino)pyrimidin-4-yl)-3-oxa-1-azaspiro[4.4]nonan-2-one | (CDCl$_3$) δ 8.19 (d, J = 5.8 Hz, 1 H), 7.37-7.33 (m, 4 H), 7.29-7.24 (m, 2 H), 5.39 (br s, 1 H), 5.12-5.05 (m, 1 H), 4.09-4.05 (m, 2 H), 2.83-2.75 (m, 1 H), 2.35 (br s, 1 H), 1.95-1.86 (m, 1 H), 1.71 (br s, 1 H), 1.67-1.61 (m, 2 H), 1.58 (d, J = 7.0 Hz, 3 H), 1.45 (br s, 2 H) | HRMS(B) m/z 339.1805 (M + H)+ |
| 249: (R)-4-(4-fluorophenyl)-4-methyl-3-(2-((S)-1-(4-phenoxyphenyl)ethylamino)pyrimidin-4-yl)oxazolidin-2-one | (CDCl$_3$) δ 8.18 (d, J = 5.8 Hz, 1 H), 7.42 (d, J = 5.8 Hz, 1 H), 7.38-7.33 (m, 2 H), 7.26-7.22 (m, 2 H), 7.14-7.06 (m, 5 H), 7.00-6.94 (m, 4 H), 5.21 (br s, 1 H), 4.23-4.17 (m, 3 H), 1.71 (br s, 3 H), 1.20 (d, J = 6.8 Hz, 3 H) | HRMS(B) m/z 485.1979 (M + H)+ |
| 250: (S)-4-methyl-3-(2-((S)-1-(4-phenoxyphenyl)ethylamino)pyrimidin-4-yl)-4-phenyloxazolidin-2-one | (CDCl$_3$) δ 8.17 (dd, J = 5.9, 1.1 Hz, 1H), 7.47-7.23 (m, 8H), 7.16-7.05 (m, 3H), 7.02-6.91 (m, 4H), 5.10 (br s, 1H), 4.22 (s, 2H), 1.73 (s, 3H), 1.67-1.53 (m, 1H), 1.14 (d, J = 7.0 Hz, 3H); | HRMS(B) m/z 467.2065 (M + H)+ |
| 251: (S)-1-(2-(1-(4-phenoxyphenyl)ethylamino)pyrimidin-4-yl)-3-oxa-1-azaspiro[4.4]nonan-2-one | (CDCl$_3$) δ 8.19 (d, J = 5.8 Hz, 1 H), 7.37-7.28 (m, 5 H), 7.13-7.09 (m, 1 H), 7.01-6.96 (m, 4 H), 5.47 (br s, 1 H), 5.12-5.05 (m, 1 H), 4.11-4.07 (m, 2 H), 2.84-2.76 (m, 1 H), 2.42 (br s, 1 H), 1.97-1.88 (m, 1 H), 1.77 (br s, 1 H), 1.68-1.61 (m, 2 H), 1.58 (d, J = 6.9 Hz, 3 H), 1.54-1.46 (m, 2 H) | HRMS(B) m/z 431.2073 (M + H)+ |
| 252: (S)-4,4-dimethyl-3-(2-(1-(4-phenoxyphenyl)ethylamino)pyrimidin-4-yl)oxazolidin-2-one | (CDCl$_3$) δ 8.19 (d, J = 5.8 Hz, 1H), 7.38-7.26 (m, 5H), 7.11 (tt, J = 7.4, 1.1 Hz, 1H), 7.01-6.94 (m, 4H), 5.37 (br s, 1H), 5.01 (d, J = 9.1 Hz, 1H), 4.09-3.93 (m, 2H), 1.71 (s, 3H), 1.57 (d, J = 6.9 Hz, 3H), 1.28 (m, 3H); | MS m/z 405.1 (M + H)+ |
| 253: (S)-3-(2-(((S)-1-(1-benzyl-5-methyl-1H-pyrazol-4-yl)ethyl)amino)pyrimidin-4-yl)-4-isopropyloxazolidin-2-one | 8.49 (d, J = 5.7 Hz, 1H), 7.84-7.38 (m, 7H), 5.65 (s, 1.2H), 5.55 (s, 0.8H), 5.43 (dq, J = 8.9, 6.9 Hz, 1H), 5.11 (tt, J = 6.1, 3.6 Hz, 1H), 4.79-4.60 (m, 2H), 2.76 (dtt, J = 22.3, 7.2, 3.5 Hz, 1H), 2.56 (2s, 3H), 1.87 (2d, J = 6.9 Hz, 3H), 1.22 (2d, J = 7.1 Hz, 3H), 1.13 (dd, J = 6.9 Hz, 3H) | HRMS(B) (M + H) 421.2338 |
| 254: (S)-3-(2-(((S)-1-(1-benzyl-3-methyl-1H-pyrazol-4-yl)ethyl)amino)pyrimidin-4-yl)-4-isopropyloxazolidin-2-one | 8.14 (d, J = 5.8 Hz, 1H), 7.50 (s, 1H), 7.38 (d, J = 5.8 Hz, 1H), 7.36-7.25 (m, 3H), 7.24-7.17 (m, 2H), 5.21 (s, 2H), 5.06 (q, J = 6.9 Hz, 1H), 4.76 (dt, J = 7.5, 3.9 Hz, 1H), 4.42-4.32 (m, 2H), 2.38 (br s, 1H), 2.22 (s, 3H), 1.51 (d, J = 6.8 Hz, 3H), 0.86 (d, J = 7.0 Hz, 3H), 0.75 (d, J = 6.9 Hz, 3H). | HRMS(B) (M + H) 421.2340 |
| 255: (4S)-4-isopropyl-3-(2-(1-(1-methyl-1H-pyrazol-4-yl)ethylamino)pyrimidin-4-yl)oxazolidin-2-one | $^1$H NMR (400 MHz, MeOD) δ 8.16 (d, J = 5.8 Hz, 0.5H), 8.14 (d, J = 5.8 Hz, 0.5H), 7.54 (s, 0.5H), 7.48 (s, 0.5H), 7.44 (s, 0.5H), 7.40 (d, J = 2.0 Hz, 0.5H), 7.38 (d, J = 2.0 Hz, 0.5H), 7.38 (s, 0.5H), 5.11 (q, J = 6.9 Hz, 1H), 4.75 (dq, J = 9.4, 3.7 Hz, 1H), 4.46-4.29 (m, 2H), 3.85 (d, J = 5.5 Hz, 3H), 2.62 (ddq, J = 10.4, 7.0, 3.5 Hz, 0.5H), 2.40 (br s, 0.5H), 1.53 (d, J = 6.9 Hz, 3H), 0.98 (d, J = 7.1 Hz, 1.5H), 0.88 (d, J = 7.1 Hz, 1.5H), 0.86 (d, J = 7.0 Hz, 1.5H), 0.78 (d, J = 7.0 Hz, 1.5H). HRMS(B) (M + H) 421.2340 Calc'd (M + H) 421.2352 | HRMS(B) (M + H) 421.2340 |
| 256: (S)-3-(2-((S)-1-(3-(1H-pyrazol-1-yl)phenyl)ethylamino)pyrimidin-4-yl)-4-isopropyloxazolidin-2-one | 8.20 (d, J = 2.5 Hz, 1H), 8.16 (d, J = 5.8 Hz, 1H), 7.75 (t, J = 2.0 Hz, 1H), 7.72 (d, J = 1.8 Hz, 1H), 7.58 (ddd, J = 8.0, 2.2, 1.0 Hz, 1H), 7.43 (t, J = 7.8 Hz, 1H), 7.37 (d, J = 5.8 Hz, 1H), 7.32 (d, J = 7.6 Hz, 1H), 6.56-6.49 (m, 1H), 5.13 (q, J = 7.0 Hz, 1H), 4.66 (br s, 1H), 4.39-4.19 (m, 2H), | HRMS(B) (M + H) 393.2036 |

TABLE 8-continued

Chemical name, NMR chemical shifts and LCMS signal for each compound listed in Table 7.

| Example: Name | ¹H NMR (400 MHz, CD₃OD) δ ppm (other solvents described) | LCMS |
|---|---|---|
|  | 1.82 (br s, 1H), 1.58 (d, J = 7.0 Hz, 3H), 0.56 (br s, 6H). |  |
| 257: (S)-3-(2-((S)-1-(4-(1H-pyrazol-1-yl)phenyl)ethylamino)pyrimidin-4-yl)-4-isopropyloxazolidin-2-one | 8.18 (d, J = 2.5 Hz, 1H), 8.16 (d, J = 5.8 Hz, 1H), 7.72 (d, J = 1.8 Hz, 1H), 7.69 (d, J = 1.9 Hz, 1H), 7.67 (d, J = 2.0 Hz, 1H), 7.52-7.44 (m, 2H), 7.37 (d, J = 5.8 Hz, 1H), 6.56-6.49 (m, 1H), 5.11 (q, J = 7.1 Hz, 1H), 4.68 (s, 1H), 4.40-4.24 (m, 2H), 1.86 (s, 1H), 1.57 (d, J = 7.1 Hz, 3H), 0.71 (s, 3H), 0.59 (s, 3H). | HRMS(B) (M + H) 393.2050 |
| 258: (4S)-4-isopropyl-3-(2-(1-(5-methyl-1-phenyl-1H-pyrazol-4-yl)ethylamino)pyrimidin-4-yl)oxazolidin-2-one | 8.17 (dd, J = 5.8, 4.6 Hz, 1H), 7.67 (s, 0.5H), 7.61 (s, 0.5H), 7.55 (dd, J = 8.5, 6.7 Hz, 2H), 7.52-7.47 (m, 1H), 7.44 (ddd, J = 8.1, 3.3, 1.4 Hz, 2H), 7.40 (d, J = 5.8 Hz, 1H), 5.17 (dq, J = 10.4, 6.9 Hz, 1H), 4.83-4.77 (m, 1H), 4.45-4.34 (m, 2H), 2.66 (td, J = 7.0, 3.5 Hz, 0.5H), 2.45 (br s, 0.5H), 2.32 (s, 1.5H), 2.31 (s, 1.5H), 1.59 (dd, J = 6.8, 1.7 Hz, 3H), 1.01 (d, J = 7.0 Hz, 1.5H), 0.94-0.85 (m, 3H), 0.81 (d, J = 6.9 Hz, 1.5H). | HRMS(B) (M + H) 407.2202 |
| 259: (R)-3-(2-((S)-1-phenylethylamino)pyrimidin-4-yl)-4-(pyridin-2-yl)oxazolidin-2-one | 8.60 (ddd, J = 4.8, 1.7, 0.9 Hz, 1H), 8.10 (d, J = 5.7 Hz, 1H), 7.89 (td, J = 7.7, 1.8 Hz, 1H), 7.46-7.36 (m, 3H), 7.33-7.28 (m, 4H), 7.21 (ddd, J = 8.6, 5.5, 2.2 Hz, 1H), 5.66 (br s, 1H), 4.79 (t, J = 8.9 Hz, 1H), 4.60 (br s, 1H), 4.31 (dd, J = 8.9, 3.8 Hz, 1H), 1.22 (d, J = 6.6 Hz, 3H). | HRMS(B) (M + H) 362.1617 |
| 260: (S)-3-(2-((S)-1-(2-fluorophenyl)ethylamino)pyrimidin-4-yl)-4-isopropyloxazolidin-2-one | 8.51 (d, J = 5.7 Hz, 1H), 7.76-7.51 (m, 3H), 7.48-7.37 (m, 2H), 5.71 (q, J = 7.0 Hz, 1H), 5.06-5.02 (m, 1H), 4.75-4.61 (m, 2H), 2.30 (br s, 1H), 1.89 (d, J = 7.0, 3H), 1.10 (d, J = 7.1 Hz, 3H), 0.95 (d, J = 7.0 Hz, 3H). | HRMS(B) (M + H) 393.2026 |
| 261: (S)-4-isopropyl-3-(2-((S)-1-(6-phenoxypyridin-3-yl)ethylamino)pyrimidin-4-yl)oxazolidin-2-one | 8.25-8.05 (m, 2H), 7.83 (dd, J = 8.6, 2.5 Hz, 1H), 7.50-7.34 (m, 2H), 7.27-7.16 (m, 1H), 7.15-7.02 (m, 2H), 6.89 (d, J = 8.5 Hz, 1H), 5.10 (q, J = 7.1 Hz, 1H), 4.75-4.61 (m, 1H), 4.41-4.29 (m, 2H), 1.94 (br s, 1H), 1.56 (d, J = 7.1 Hz, 3H), 0.78 (br s, 3H), 0.70 (br s, 3H). | HRMS(B) (M + H) 420.2019 |
| 262: (S)-3-(5-fluoro-2-(1-(4-phenoxyphenyl)ethylamino)pyrimidin-4-yl)oxazolidin-2-one | 8.16 (d, J = 3.5 Hz, 1H), 7.45-7.28 (m, 4H), 7.09 (tt, J = 7.3, 1.1 Hz, 1H), 7.02-6.89 (m, 4H), 4.99 (q, J = 6.9 Hz, 1H), 4.58-4.48 (m, 2H), 4.18 (ddd, J = 9.7, 8.5, 7.2 Hz, 1H), 3.99 (br s, 1H), 1.52 (d, J = 6.9 Hz, 3H). | HRMS(B) (M + H) 395.1507 |
| 263: (S)-3-(2-(1-(4-phenoxyphenyl)ethylamino)pyrimidin-4-yl)oxazolidin-2-one | 8.09 (d, J = 5.8 Hz, 1H), 7.43-7.29 (m, 5H), 7.09 (tt, J = 7.3, 1.1 Hz, 1H), 7.00-6.90 (m, 4H), 5.07 (q, J = 7.0 Hz, 1H), 4.53-4.41 (m, 2H), 4.21 (ddd, J = 10.5, 9.2, 7.0 Hz, 1H), 4.01 (br s, 1H), 1.53 (d, J = 7.0 Hz, 3H). | HRMS(B) (M + H) 377.1600 |
| 264: (4S)-4-isopropyl-3-(2-((1-(4-((tetrahydro-2H-pyran-4-yl)oxy)phenyl)ethyl)amino)pyrimidin-4-yl)oxazolidin-2-one | 8.12 (dd, J = 8.5, 5.8 Hz, 1H), 7.35 (dd, J = 5.8, 1.0 Hz, 1H), 7.32-7.19 (m, 2H), 6.95-6.86 (m, 2H), 4.98 (dq, J = 25.6, 7.2 Hz, 1H), 4.68 (br s, 0.5H), 4.59-4.48 (m, 1.5H), 4.39-4.25 (m, 2H), 4.01-3.90 (m, 2H), 3.65-3.53 (m, 2H), 2.74-2.61 (m, 0.5H), 2.08-1.96 (m, 2H), 1.95 (br s, 0.5H), 1.78-1.64 (m, 2H), 1.50 (dd, J = 6.9, 1.6 Hz, 3H), 1.01 (d, J = 7.0 Hz, 1.5H), 0.88 (d, J = 6.9 Hz, 1.5H), 0.75 (br s, 1.5H), 0.62 (br s, 1.5H). | HRMS(B) (M + H) |
| 265: (S)-3-(2-((S)-1-(4-(4-fluorophenoxy)phenyl)ethylamino)pyrimidin-4-yl)-4-isopropyloxazolidin-2-one | 8.14 (d, J = 5.8 Hz, 1H), 7.37 (d, J = 5.8 Hz, 1H), 7.36-7.31 (m, 2H), 7.12-7.05 (m, 2H), 7.01-6.94 (m, 2H), 6.94-6.89 (m, 2H), 5.06 (q, J = 7.0 Hz, 1H), 4.71 (br s, 1H), 4.41-4.29 (m, 2H), 1.99 (br s, 1H), 1.52 (d, J = 7.0 Hz, 3H), 0.77 (br s, 3H), 0.67 (br s, 3H). | HRMS(B) (M + H) 437.1981 |
| 266: (R)-3-(2-((S)-1-(4-bromophenyl)ethylamino) | 8.46 (d, J = 5.8 Hz, 1H), 7.84-7.73 (m, 5H), 7.72-7.67 (m, 1H), 7.64 (dd, J = 7.1, | HRMS(B) (M + H) |

TABLE 8-continued

Chemical name, NMR chemical shifts and LCMS
signal for each compound listed in Table 7.

| Example: Name | ¹H NMR (400 MHz, CD₃OD) δ ppm (other solvents described) | LCMS |
|---|---|---|
| pyrimidin-4-yl)-4-phenyloxazolidin-2-one | 1.8 Hz, 2H), 7.59-7.53 (m, 2H) 5.92 (dd, J = 8.6, 4.0 Hz, 1H), 5.13 (t, J = 8.7 Hz, 1H), 4.98 (q, J = 8.4, 7.5 Hz, 1H), 4.55 (dd, J = 8.7, 4.0 Hz, 1H), 1.58 (d, J = 7.0 Hz, 3H). | 439.0762 |
| 267: (R)-3-(2-((S)-1-phenylethylamino)pyrimidin-4-yl)-4-(pyridin-3-yl)oxazolidin-2-one | 8.60 (d, J = 2.5 Hz, 1H), 8.55 (dd, J = 4.8, 1.5 Hz, 1H), 8.12 (d, J = 5.8 Hz, 1H), 7.81 (dt, J = 7.8, 2.0 Hz, 1H), 7.54-7.47 (m, 1H), 7.41 (d, J = 5.8 Hz, 1H), 7.36-7.25 (m, 4H), 7.25-7.17 (m, 1H), 5.60 (br s, 1H), 4.80 (t, J = 8.9 Hz, 1H), 4.61 (br s, 1H), 4.27 (dd, J = 9.0, 4.1 Hz, 1H), 1.25 (br d, J = 7.5 Hz, 3H). | HRMS(B) (M + H) 362.1615 |
| 268: (R)-3-(2-((S)-1-phenylethylamino)pyrimidin-4-yl)-4-(pyridin-4-yl)oxazolidin-2-one | 8.61-8.60 (m, 2H), 8.14 (d, J = 5.8 Hz, 1H), 7.43 (d, J = 5.8 Hz, 1H), 7.42-7.37 (m, 2H), 7.32 (t, J = 7.5 Hz, 2H), 7.28-7.17 (m, 3H), 5.57 (br s, 1H), 4.80 (t, J = 9.0 Hz, 1H), 4.55 (br s, 1H), 4.22 (dd, J = 9.0, 4.1 Hz, 1H), 1.20(br s, 3H). | HRMS(B) (M + H) 362.1610 |
| 269: (S)-3-(2-((S)-1-(3-methoxyphenyl)ethylamino)pyrimidin-4-yl)-4-phenyloxazolidin-2-one | 8.46 (d, J = 5.7 Hz, 1H), 7.73 (d, J = 5.8 Hz, 1H), 7.64-7.52 (m, 5H), 7.48 (t, J = 7.8 Hz, 1H), 7.11-7.03 (m, 3H), 6.18 (dd, J = 8.7, 3.7 Hz, 1H), 5.25-5.13 (m, 2H), 4.60 (dd, J = 8.7, 3.7 Hz, 1H), 4.10 (s, 3H), 1.81 (d, J = 7.0 Hz, 3H). | HRMS(B) (M + H) 391.1771 |
| 270: (4S)-3-(2-(1-(biphenyl-4-yl)ethylamino)pyrimidin-4-yl)-5,5-dimethyl-4-phenyloxazolidin-2-one | 8.50-8.45 (m, 1H), 7.95 (ddt, J = 7.6, 5.3, 2.3 Hz, 3H), 7.83-7.64 (m, 8H), 7.63-7.54 (m, 2H), 7.49 (dd, J = 4.9, 3.0 Hz, 2H), 5.83 (s, 0.5H), 5.57 (s, 0.5H), 5.29-5.24 (m, 0.5H), 5.04-4.99 (m, 0.5H), 2.02 (s, 1.5H), 1.85-1.84 (m, 3H), 1.62 (d, J = 7.0 Hz, 1.5H), 1.35 (d, J = 3.3 Hz, 3H). | HRMS(B) (M + H) 465.2284 |
| 271: (S)-3-(2-((S)-1-(4-fluorophenyl)ethylamino)pyrimidin-4-yl)-4-isopropyl-4-methyloxazolidin-2-one | 8.15 (d, J = 5.8 Hz, 1H), 7.41-7.29 (m, 2H), 7.25 (d, J = 5.8 Hz, 1H), 7.09-6.98 (m, 2H), 4.96 (q, J = 7.1 Hz, 1H), 4.29 (d, J = 9.0 Hz, 1H), 3.88 (d, J = 8.9 Hz, 1H), 2.17 (br s, 1H), 1.70 (s, 3H), 1.53 (d, J = 7.0 Hz, 3H), 0.70 (br s, 3H), 0.44 (br s, 3H). | HRMS(B) (M + H) 359.1889 |
| 272: (S)-4,4-dimethyl-3-(2-(1-(4-((4-methylpiperazin-1-yl)methyl)phenyl)ethylamino)pyrimidin-4-yl)oxazolidin-2-one | 8.12 (d, J = 5.8 Hz, 1H), 7.35-7.26i (m, 4H), 7.17 (d, J = 5.9 Hz, 1H), 5.02 (q, J = 6.9 Hz, 1H), 4.06 (q, J = 8.4 Hz, 2H), 3.51 (s, 2H), 2.49 (br s, 8H), 2.28 (s, 3H), 1.70 (s, 3H), 1.53 (d, J = 7.0 Hz, 3H), 1.15 (br s, 3H). | HRMS(B) (M + H) 425.2661 |
| 273: (R)-5,5-dimethyl-3-(2-((S)-1-(4-((4-methylpiperazin-1-yl)methyl)phenyl)ethylamino)pyrimidin-4-yl)-4-phenyloxazolidin-2-one | 8.09 (d, J = 5.8 Hz, 1H), 7.50-7.39 (m, 3H), 7.36 (tt, J = 7.1, 1.4 Hz, 1H), 7.30 (s, 4H), 7.21 (br s, 2H), 5.22 (br s, 1H), 4.58 (br s, 1H), 3.53 (s, 2H), 2.50 (br s, 8H), 2.28 (s, 3H), 1.52 (s, 3H), 1.19 (d, J = 6.8 Hz, 3H), 0.99 (s, 3H). | HRMS(B) (M + H) 501.2971 |
| 274: (S)-5,5-dimethyl-3-(2-((S)-1-(4-((4-methylpiperazin-1-yl)methyl)phenyl)ethylamino)pyrimidin-4-yl)-4-phenyloxazolidin-2-one | 8.08 (d, J = 5.8 Hz, 1H), 7.45 (d, J = 5.8 Hz, 1H), 7.38-7.23 (m, 3H), 7.1 6 (t, J = 7.5 Hz, 4H), 7.00 (br s, 2H), 5.51 (s, 1H), 4.89-4.83 (m, 1H), 3.49 (d, J = 2.3 Hz, 2H), 2.50 (br s, 8H), 2.29 (s, 3H), 1.67 (s, 3H), 1.44 (d, J = 6.9 Hz, 3H), 1.00 (s, 3H). | HRMS(B) (M + H) 501.2981 |
| 275: (S)-4-isopropyl-4-methyl-3-(2-((S)-1-(4-((4-methylpiperazin-1-yl)methyl)phenyl)ethylamino)pyrimidin-4-yl)oxazolidin-2-one | 8.14 (d, J = 5.9 Hz, 1H), 7.29 (s, 4H), 7.24 (d, J = 5.9 Hz, 1H), 4.97 (p, J = 7.0 Hz, 1H), 4.60 (br s, 1H), 4.29 (d, J = 8.8 Hz, 1H), 3.88 (d, J = 9.0 Hz, 1H), 3.51 (s, 2H), 2.59 (br s, 8H), 2.28 (s, 3H), 1.71 (s, 3H), 1.52 (d, J = 6.9 Hz, 3H), 0.70 (br s, 3H), 0.39 (br s, 3H). | |
| 276: (S)-4-isopropyl-5,5-dimethyl-3-(2-(((S)-1-(4-((4-methylpiperazin-1-yl)methyl)phenyl)ethyl)amino)pyrimidin-4-yl)oxazolidin-2-one | 8.14 (d, J = 5.8 Hz, 1H), 7.39-7.20 (m, 5H), 5.09 (q, J = 7.0 Hz, 1H), 4.49 (br s, 1H), 3.52 (s, 2H), 2.57 (br s, 8H), 2.32 (s, 3H), 2.03 (br s, 1H), 1.54 (s, 3H), 1.51 (d, J = 7.0 Hz, 3H), 1.42 (s, 3H), 0.75 (br s, 3H), 0.62 (br s, 3H). | HRMS(B) (M + H) 453.2975 |
| 277: (S)-4-isopropyl-3-(2-((S)-1-(4-(pyridin-2-yl)phenyl)ethylami- | 8.60 (ddd, J = 4.9, 1.8, 1.0 Hz, 1H), 8.16 (d, J = 5.8 Hz, 1H), 7.94-7.86 (m, 3H), 7.84 (dt, J = 7.9, 1.2 Hz, 1H), 7.51-7.43 | HRMS(B) (M + H) 404.2089 |

TABLE 8-continued

Chemical name, NMR chemical shifts and LCMS signal for each compound listed in Table 7.

| Example: Name | $^1$H NMR (400 MHz, CD$_3$OD) δ ppm (other solvents described) | LCMS |
|---|---|---|
| no)pyrimidin-4-yl)oxazolidin-2-one | (m, 2H), 7.41-7.32 (m, 2H), 5.12 (q, J = 7.0 Hz, 1H), 4.67 (br s, 1H), 4.40-4.18 (m, 2H), 1.83 (br s, 1H), 1.58 (d, J = 7.1 Hz, 3H), 0.68 (br s, 3H), 0.56 (br s, 3H). | |
| 278: (S)-4-isopropyl-3-(2-((S)-1-(6-phenylpyridin-3-yl)ethylamino)pyrimidin-4-yl)oxazolidin-2-one | 8.60 (d, J = 2.2 Hz, 1H), 8.18 (d, J = 5.8 Hz, 1H), 7.95-7.89 (m, 2H), 7.87 (dd, J = 8.2, 2.3 Hz, 1H), 7.81 (dd, J = 8.3, 0.8 Hz, 1H), 7.55-7.42 (m, 3H), 7.40 (d, J = 5.8 Hz, 1H), 5.16 (q, J = 7.1 Hz, 1H), 4.66 (br s, 1H), 4.40-4.22 (m, 2H), 1.74 (br s, 1H), 1.62 (d, J = 7.0 Hz, 3H), 0.67 (br s, 3H), 0.57 (br s, 3H). | HRMS(B) (M + H) 404.2079 |
| 279: (S)-4-isopropyl-3-(2-((S)-1-(quinolin-6-yl)ethylamino)pyrimidin-4-yl)oxazolidin-2-one | 8.81 (dd, J = 4.3, 1.6 Hz, 1H), 8.32 (dt, J = 8.2, 1.1 Hz, 1H), 8.18 (d, J = 5.8 Hz, 1H), 8.01 (d, J = 8.7 Hz, 1H), 7.89-7.76 (m, 2H), 7.53 (dd, J = 8.3, 4.4 Hz, 1H), 7.37 (d, J = 5.8 Hz, 1H), 5.24 (q, J = 7.1 Hz, 1H), 4.59 (br s, 1H), 4.30 (t, J = 8.7 Hz, 1H), 4.22 (br s, 1H), 1.64 (d, J = 7.1 Hz, 3H), 1.49 (br s, 1H), 0.35 (br s, 6H). | HRMS(B) (M + H) 378.1930 |
| 280: (S)-4-isopropyl-3-(2-((S)-1-(quinolin-7-yl)ethylamino)pyrimidin-4-yl)oxazolidin-2-one | 8.81 (dd, J = 4.3, 1.7 Hz, 1H), 8.34 (dt, J = 8.4, 1.2 Hz, 1H), 8.13 (d, J = 5.9 Hz, 1H), 8.00 (d, J = 1.6 Hz, 1H), 7.93 (d, J = 8.5 Hz, 1H), 7.68 (dd, J = 8.6, 1.8 Hz, 1H), 7.50 (dd, J = 8.3, 4.4 Hz, 1H), 7.36 (d, J = 5.8 Hz, 1H), 5.23-5.17 (m, 1H), 4.50 (br d, J = 84.2 Hz, 1H), 4.35-4.25 (m, 1H), 4.19 (br s, 1H), 2.68 (pd, J = 7.0, 3.5 Hz, 1H), 1.65 (d, J = 7.0 Hz, 3H), 1.01 (d, J = 7.0 Hz, 3H), 0.86 (d, J = 6.9 Hz, 3H). | HRMS(B) (M + H) 378.1941 |
| 281: (S)-3-(2-((S)-1-(4-benzoylphenyl)ethylamino)pyrimidin-4-yl)-4-isopropyloxazolidin-2-one | 8.17 (d, J = 5.8 Hz, 1H), 7.81-7.71 (m, 4H), 7.69-7.61 (m, 1H), 7.59-7.49 (m, 4H), 7.39 (d, J = 5.8 Hz, 1H), 5.15 (q, J = 7.1 Hz, 1H), 4.67 (br s, 1H), 4.41-4.23 (m, 2H), 1.75 (br s, 1H), 1.58 (d, J = 7.1 Hz, 3H), 0.69 (br s, 3H), 0.61 (br s, 3H). | HRMS(B) (M + H) 431.2072 |
| 282: (S)-3-(2-((S)-1-(3-fluoro-4-(2-methyl-1H-imidazol-1-yl)phenyl)ethylamino)pyrimidin-4-yl)-4-isopropyloxazolidin-2-one | 8.18 (d, J = 7.1 Hz, 1H), 7.75 (d, J = 7.3 Hz, 1H), 7.71-7.62 (m, 3H), 7.58 (dd, J = 10.9, 1.9 Hz, 1H), 7.51 (dd, J = 8.2, 1.8 Hz, 1H), 5.33 (br s, 1H), 4.81-4.73 (m, 1H), 4.46-4.36 (m, 2H), 2.54 (s, 3H), 2.03 (br s, 1H), 1.64 (d, J = 7.0 Hz, 3H), 0.84 (br d, J = 7.2 Hz, 3H), 0.70 (br d, J = 7.2 Hz, 3H). | HRMS(B) (M + H) 425.2093 |
| 283: (4S)-4-isopropyl-3-(2-(1-(4-(2-methyl-1H-imidazol-1-yl)phenyl)ethylamino)pyrimidin-4-yl)oxazolidin-2-one | 8.15 (dd, J = 8.9, 5.8 Hz, 1H), 7.60-7.50 (m, 2H), 7.42-7.32 (m, 3H), 7.14 (dd, J = 13.3, 1.5 Hz, 1H), 6.96 (dd, J = 3.5, 1.5 Hz, 1H), 5.17 (q, J = 7.1 Hz, 0.5H), 5.07 (d, J = 7.4 Hz, 0.5H), 4.71 (br s, 0.5H), 4.50 (br s, 0.5H), 4.40-4.24 (m, 2H), 2.67 (ddq, J = 10.6, 7.0, 3.6 Hz, 0.5H), 2.323 (s, 1.5H), 2.321 (s, 1.5H), 1.95 (br s, 0.5H), 1.58 (dd, J = 7.0, 2.3 Hz, 3H), 1.02 (d, J = 7.0 Hz, 1.5H), 0.88 (d, J = 6.9 Hz, 1.5H), 0.76 (br s, 1.5H), 0.64 (br s, 1.5H). | HRMS(B) (M+) 406.2217 |
| 284: (S)-3-(2-(((R)-1-cyclopentylethyl)amino)pyrimidin-4-yl)-4-isopropyloxazolidin-2-one | | HRMS(B) m/z 319.2133 (M + H)+, RT = 2.68 min. |
| 285: (S)-3-(2-(((S)-1-(4-(dimethylamino)phenyl)ethyl)amino)pyrimidin-4-yl)-4-isopropyloxazolidin-2-one | | HRMS(B) m/z 370.2227 (M + H)+, RT = 2.47 min. |
| 286: N-(3-((S)-1-((4-((S)-4-isopropyl-2-oxooxazolidin-3-yl)pyrimidin-2-yl)amino)Ethylphenyl)acetamide | | HRMS(B) m/z 384.2032 (M + H)+, RT = 1.97 min |
| 287: (S)-3-(2-(((S)-1-(1H-benzo[d]imidazol-2- | | HRMS(B) m/z |

TABLE 8-continued

Chemical name, NMR chemical shifts and LCMS signal for each compound listed in Table 7.

| Example: Name | ¹H NMR (400 MHz, CD₃OD) δ ppm (other solvents described) | LCMS |
|---|---|---|
| yl)ethyl)amino)pyrimidin-4-yl)-4-isopropyloxazolidin-2-one | | 367.1887 (M + H)+ RT = 2.39 min. |
| 288: (S)-3-(2-(((S)-1-(4-((4-chlorophenyl)sulfonyl)phenyl)ethyl)amino)pyrimidin-4-yl)-4-isopropyloxazolidin-2-one | | HRMS(B) m/z 501.1343, (M + H)+ RT = 2.68 min. |
| 289: (S)-4-isopropyl-3-(2-(((S)-1-(4-nitrophenyl)ethyl)amino)pyrimidin-4-yl)oxazolidin-2-one | | HRMS(B) m/z 372.1672, (M + H)+, RT = 2.59 min. |
| 290: (S)-3-(2-(((S)-1-(4-aminophenyl)ethyl)amino)pyrimidin-4-yl)-4-isopropyloxazolidin-2-one | | HRMS(B) m/z 342.1931, (M + H)+, RT = 2.17 min |
| 291: (S)-4-isopropyl-3-(2-(((S)-1-(5-(methylthio)-1,3,4-oxadiazol-2-yl)ethyl)amino)pyrimidin-4-yl)oxazolidin-2-one | | HRMS(B) m/z 365.1367, (M + H)+, RT = 1.88 min. |
| 292: (S)-4-isopropyl-3-(2-(((S)-1-(5-phenyl-1,3,4-thiadiazol-2-yl)ethyl)amino) pyrimidin-4-yl)oxazolidin-2-one | (CDCl₃) δ 8.15 (d, J = 5.9 Hz, 1H), 7.87-7.74 (m, 2H), 7.51 (d, J = 5.9 Hz, 1H), 7.46-7.28 (m, 3H), 6.39 (b, 1H), 5.43 (s, 1H), 4.58 (dt, J = 8.3, 3.3 Hz, 1H), 4.29-4.12 (m, 2H), 1.94-1.80 (b, 1H), 1.74 (d, J = 7.0 Hz, 3H), 0.69 (d, J = 6.8 Hz, 3H), 0.60 (d, J = 7.2 Hz, 3H) | HRMS(B) m/z 411.1596 (M + H)+, RT = 2.54 min. |
| 293: (S)-3-{2-[1-(5-Chloro-1H-benzoimidazol-2-yl)-ethylamino]-pyrimidin-4-yl}-4-isopropyl-oxazolidin-2-one | | HRMS(B) m/z 400.1414, RT = 2.04 min. |
| 294: (S)-3-(2-{(S)-1-[5-(2,2-Dimethyl-propyl)-isoxazol-3-yl]-ethylamino}-pyrimidin-4-yl)-4-isopropyl-oxazolidin-2-one | (CDCl₃) δ 8.22 (d, J = 5.7 Hz, 1.0 H), 7.52 (d, J = 5.8 Hz, 0.95 H), 5.92 (s, 0.96 H), 5.50 (d, J = 7.5 Hz, 0.97 H), 5.22 (s, 0.83H), 4.72 (d, J = 8.3 Hz, 1.0 H), 4.42-4.20 (m, 2.06 H), 3.51 (s, 0.27 H), 2.61 (s, 2.05 H), 1.62 (d, J = 7.0 Hz, 4.13 H), 0.97 (s, 8.95 H), 0.90 (d, J = 7.0 Hz, 2.56 H), 0.80 (d, J = 7.0 Hz, 2.93 H). | HRMS(B) m/z 387.2271 |
| 295: (4S)-4-isopropyl-3-(2-(1-(5-phenylpyrimidin-2-yl)ethylamino)pyrimidin-4-yl)oxazolidin-2-one | (CDCl₃) δ 8.93 (d, J = 5.9 Hz, 4H), 8.26-8.17 (m, 2H), 7.64-7.44 (m, 12H), 6.41 (br s, 1H), 5.31 (br s, 1H), 4.79-4.65 (m, 2H), 4.41-4.24 (m, 4H), 2.65 (dddd, J = 27.4, 14.1, 7.1, 3.5 Hz, 1H), 2.20 (br s, 1H), 1.75-1.64 (m, 4H), 1.07-0.85 (m, 9H), 0.78 (s, 3H). | HRMS(B) m/z 405.2024 and 405.2025 (M + H)+. |
| 296: 4-{(S)-1-[4-((S)-4-Isopropyl-2-oxo-oxazolidin-3-yl)-pyrimidin-2-ylamino]-ethyl}-piperidine-1-carboxylic acid benzyl ester | | HRMS(B) (M+) = 467.2533 RT.: 2.83 min. |
| 297: (S)-3-(2-((S)-1-(5-bromopyridin-2-yl)ethylamino)pyrimidin-4-yl)-4-isopropyloxazolidin-2-one. | | HRMS(B) m/z 406.0870 (M + H)+. RT.: 2.50 min. |
| 298: 3-(5-fluoro-2-((1-(5-(4-fluoro-3-methylphenyl)pyridin-2-yl)ethyl)amino)pyrimidin-4-yl)oxazolidin-2-one | | HRMS(B) m/z 412.1578 (M + H)+. RT.: 2.35 min. |

TABLE 8-continued

Chemical name, NMR chemical shifts and LCMS signal for each compound listed in Table 7.

| Example: Name | ¹H NMR (400 MHz, CD₃OD) δ ppm (other solvents described) | LCMS |
|---|---|---|
| 299: 3-(2-(1-(5-(4-fluoropnenoxy)pyrimidin-2-yl)ethylamino)pyrimidin-4-yl)oxazolidin-2-one. | | HRMS(B) m/z 411.1572 (M + H)+. RT.: 2.25 min. |
| 300: 3-(5-fluoro-2-(1-(5-(4-fluoropnenoxy)pyrimidin-2-yl)ethylamino)pyrimidin-4-yl)oxazolidin-2-one. | | HRMS(B) m/z 415.1320 (M + H)+. RT.: 2.26 min. |
| 301: (4S)-3-(2-(1-(5-(2,4-difluorobenzyloxy)pyrimidin-2-yl)ethylamino)pyrimidin-4-yl)-4-isopropyloxazolidin-2-one | (CDCl₃) δ 8.45 (d, J = 4.6 Hz, 4H), 8.21 (d, J = 5.8 Hz, 2H), 7.53-7.41 (m, 4H), 6.93 (ddddd, J = 19.9, 9.8, 8.7, 2.6, 1.2 Hz, 4H), 6.21 (s, 1H), 6.11 (s, 1H), 5.21 (br s, 2H), 5.18 (s, 2H), 5.16 (s, 2H), 4.74 (dt, J = 7.7, 3.3 Hz, 1H), 4.66 (d, J = 7.4 Hz, 1H), 4.38-4.24 (m, 4H), 2.65 (ddq, J = 10.5, 7.1, 3.5 Hz, 1H), 2.30 (br s, 1H), 1.65-1.59 (m, 6H), 1.01 (d, J = 7.0 Hz, 3H), 0.89 (dq, J = 7.6, 4.9, 4.4 Hz, 6H), 0.79 (d, J = 6.5 Hz, 3H). | MS m/z 471.8 (M + H)+. |
| 302: (S)-3-(2-{(S)-1-[4-(4-Fluoro-phenoxy)-cyclohexyl]-ethylamino}-pyrimidin-4-yl)-4-isopropyl-oxazolidin-2-one | | LC-MS m/z 442.53 (M + H)+; RT.: 1.77 min. |
| 303: (4S)-3-(2-(1-(5-(5-bromopyridin-3-yloxy)pyrimidin-2-yl)ethylamino)pyrimidin-4-yl)-4-isopropyloxazolidin-2-one | (CDCl₃) δ 8.62-8.49 (m, 6H), 8.44-8.36 (m, 2H), 8.22 (dd, J = 5.7, 0.6 Hz, 2H), 7.57-7.46 (m, 4H), 6.14 (br s, 2H), 5.33 (br s, 2H), 4.76 (dt, J = 8.2, 3.4 Hz, 1H), 4.67 (s, 1H), 4.40-4.26 (m, 4H), 2.67 (pd, J = 7.0, 3.4 Hz, 1H), 2.32 (br s, 1H), 1.69-1.61 (m, 6H), 1.02 (d, J = 7.0 Hz, 3H), 0.99-0.80 (m, 9H). | HRMS(B) m/z 500.1038 and 500.1034 (M + H)+. |
| 304: (S)-3-(2-((S)-1-(5-chloropyrimidin-2-yl)ethylamino)pyrimidin-4-yl)-4-isopropyloxazolidin-2-one. | (CDCl₃) δ 8.58 (s, 2H), 8.12 (d, J = 5.8 Hz, 1H), 7.40 (d, J = 5.8 Hz, 1H), 5.97 (br s, 1H), 5.17 (br s, 1H), 4.63 (dt, J = 8.0, 3.2 Hz, 1H), 4.29-4.15 (m, 2H), 2.10 (br s, 1H), 1.50-1.46 (m, 3H), 0.88-0.66 (m, 6H). | LC-MS m/z 363.1 (M + H)+; RT.: 1.39 min. |
| 305: (S)-3-(2-((S)-1-(5-(3-chloro-4-fluorophenoxy)pyrimidin-2-yl)ethylamino)pyrimidin-4-yl)-4-isopropyloxazolidin-2-one. | (CDCl₃) δ 8.36 (s, 2H), 8.13 (s, 1H), 7.41 (d, J = 5.4 Hz, 1H), 7.15-7.00 (m, 2H), 6.85 (ddd, J = 9.0, 3.7, 3.0 Hz, 1H), 6.08 (s, 1H), 5.21 (br s, 1H), 4.66 (dt, J = 8.3, 3.4 Hz, 1H), 4.30-4.16 (m, 2H), 2.25 (br s, 1H), 1.56-1.51 (m, 3H), 0.85-0.78 (m, 3H), 0.77-0.70 (m, 3H). | HRMS(B) m/z 473.1484 (M + H)+. |
| 306: (4S)-4-isopropyl-3-(2-(1-(5-(pyridin-3-yloxy)pyrimidin-2-yl)ethylamino)pyrimidin-4-yl)oxazolidin-2-one | | HRMS(B) m/z 422.1938, RT 1.91 min and 422.1944, RT 2.01 min (M + H)+. |
| 307: (4S)-3-(2-(1-(5-(3-fluorobenzyloxy)pyrimidin-2-yl)ethylamino)pyrimidin-4-yl)-4-isopropyloxazolidin-2-one | (CDCl₃) δ 8.43 (d, J = 4.9 Hz, 4H), 8.21 (d, J = 5.7 Hz, 2H), 7.49-7.34 (m, 4H), 7.26-7.02 (m, 6H), 6.20 (br s, 1H), 6.11 (br s, 1H), 5.22 (br s, 2H), 5.16 (s, 2H), 4.74 (dt, J = 7.7, 3.3 Hz, 1H), 4.66 (br s, 1H), 4.38-4.23 (m, 4H), 2.66 (heptd, J = 7.0, 3.5 Hz, 1H), 2.26 (br s, 1H), 1.64-1.58 (m, 6H), 1.00 (d, J = 7.0 Hz, 3H), 0.94-0.85 (m, 6H), 0.78 (br s, 3H). | HRMS(B) m/z 453.2048 and 453.2047 (M + H)+. |
| 308: (S)-3-(2-((S)-1-(5-iodopyrimidin-2-yl)ethylamino)pyrimidin-4-yl)-4-isopropyloxazolidin-2-one. | | HRMS(B) m/z 454.0614 (M+). RT 2.35 min |

TABLE 8-continued

Chemical name, NMR chemical shifts and LCMS signal for each compound listed in Table 7.

| Example: Name | $^1$H NMR (400 MHz, CD$_3$OD) δ ppm (other solvents described) | LCMS |
|---|---|---|
| 309: (4S)-4-isopropyl-3-(2-(1-(5-(5-(trifluoromethyl)pyridin-2-yloxy)pyrimidin-2-yl)ethylamino)pyrimidin-4-yl)oxazolidin-2-one | | HRMS(B) m/z 490.1800, RT 2.17 min and 490.1795, RT 2.23 min (M + H)+. |
| 310: (4S)-4-isopropyl-3-(2-(1-(pyrimidin-2-yl)ethylamino)pyrimidin-4-yl)oxazolidin-2-one | | HRMS(B) m/z 329.1728, RT 1.81 min and 329.1726, RT 1.93 min (M + H)+. |
| 311: (4S)-3-(2-(1-(4-(4-fluorophenoxy)pyrimidin-2-yl)ethylamino)pyrimidin-4-yl)-4-isopropyloxazolidin-2-one | (CDCl$_3$) δ 8.56 (dd, J = 5.7, 2.3 Hz, 2H), 8.20 (dd, J = 5.7, 4.0 Hz, 2H), 7.46 (dd, J = 5.7, 4.4 Hz, 2H), 7.20-7.00 (m, 8H), 6.71 (dd, J = 5.7, 2.0 Hz, 2H), 6.03 (br s, 1H), 5.87 (br s, 1H), 5.11 (br s, 2H), 4.72-4.61 (m, 2H), 4.40-4.23 (m, 4H), 2.59 (ddp, J = 10.5, 7.1, 3.5 Hz, 1H), 2.21 (br s, 1H), 1.59-1.55 (m, 6H), 1.00-0.85 (m, 9H), 0.80 (d, J = 6.3 Hz, 3H). | HRMS(B) m/z 439.1887 and 439.1887 (M + H)+. |
| 312: (S)-3-(2-((S)-1-(4-(((2S,6R)-2,6-dimethylmorpholino)methyl)phenyl)ethylamino)pyrimidin-4-yl)-4-isopropyloxazolidin-2-one | $^1$H NMR (400 MHz, CD$_3$OD) δ ppm 0.63 (br. s., 3 H) 0.79 (br. s., 3 H) 1.20 (dd, J = 6.26, 2.74 Hz, 6 H) 1.58 (d, J = 7.04 Hz, 3 H) 2.54-2.82 (m, 2H) 3.73-3.90 (m, 2 H) 4.32 (d, J = 3.52 Hz, 2 H) 4.39 (d, J = 5.87 Hz, 2 H) 4.68-4.78 (m, 1 H) 5.15-5.31 (m, 1 H) 7.51 (s, 4 H) 7.62-7.76 (m, 1 H) 8.08-8.22 (m, 1 H) | LCMS m/z 454.3 (M + H)+, Rt 0.57 min |

The compounds in Table 9 were prepared using methods substantially similar to those described for the preparation of Examples 1, 113, and 171 through 212, including chiral separation to isolate the two diastereomers.

TABLE 9

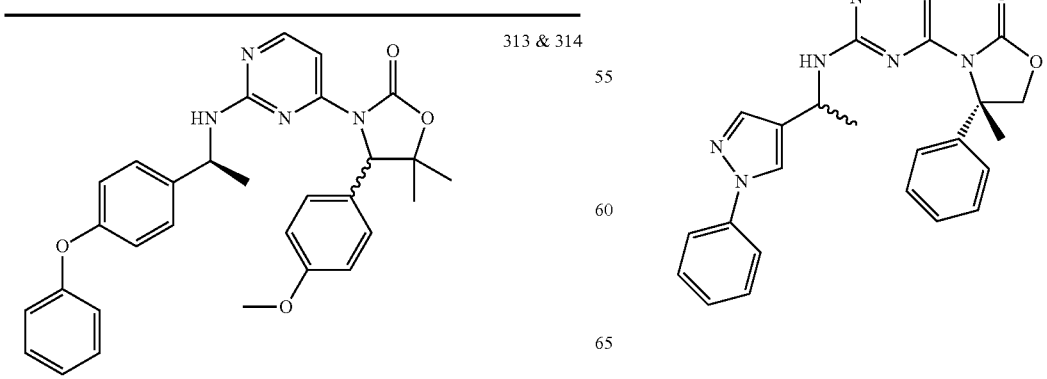

313 & 314

315 & 316

TABLE 9-continued
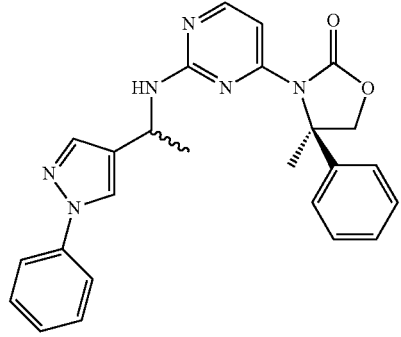 [SMILES: CC(Nc1nccc(N2C(=O)OC[C@@]2(C)c2ccccc2)n1)c1cnn(-c2ccccc2)c1] 317 & 318
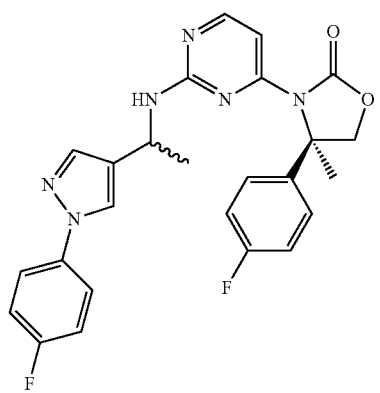 [SMILES: CC(Nc1nccc(N2C(=O)OC[C@@]2(C)c2ccc(F)cc2)n1)c1cnn(-c2ccc(F)cc2)c1] 319 & 320
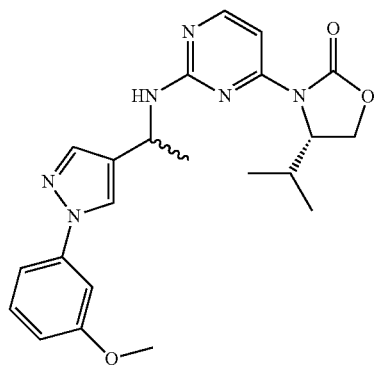 [SMILES: COc1cccc(-n2cc(C(C)Nc3nccc(N4C(=O)OC[C@@H]4C(C)C)n3)cn2)c1] 321 & 322
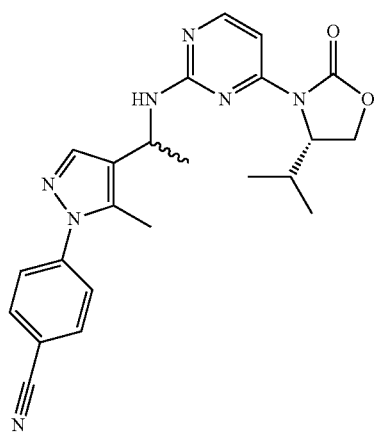 [SMILES: Cc1c(C(C)Nc2nccc(N3C(=O)OC[C@@H]3C(C)C)n2)cnn1-c1ccc(C#N)cc1] 323 & 324
TABLE 9-continued
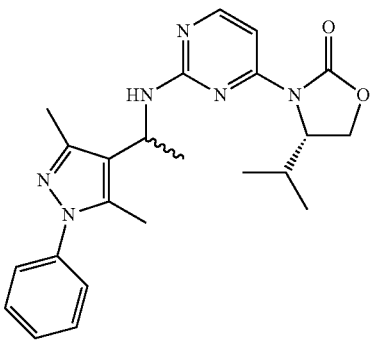 [SMILES: Cc1nn(-c2ccccc2)c(C)c1C(C)Nc1nccc(N2C(=O)OC[C@@H]2C(C)C)n1] 325 & 326
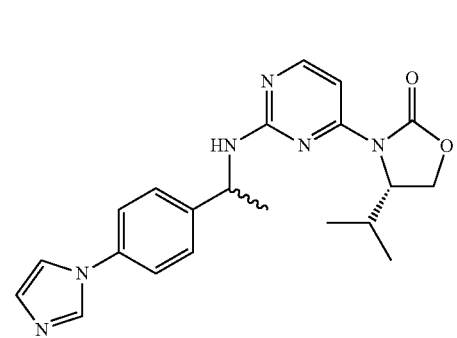 [SMILES: CC(Nc1nccc(N2C(=O)OC[C@@H]2C(C)C)n1)c1ccc(-n2ccnc2)cc1] 327 & 328
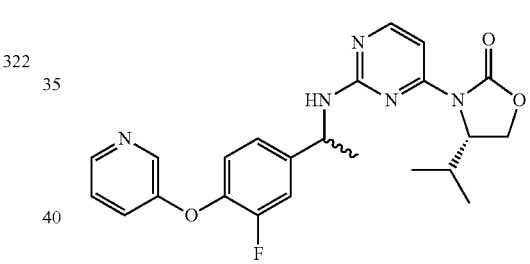 329 & 330
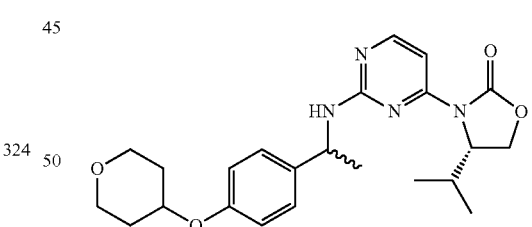 331 & 332
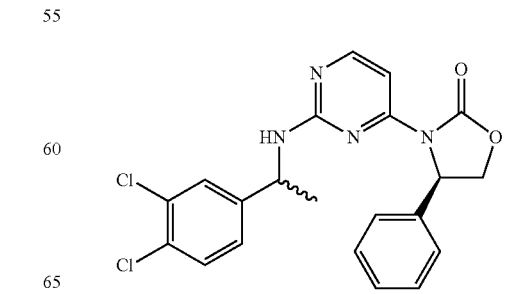 333 & 334

TABLE 9-continued
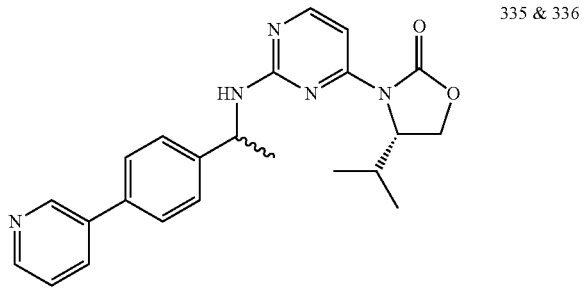
335 & 336
337 & 338
339 & 340
341 & 342
343 & 344
TABLE 9-continued
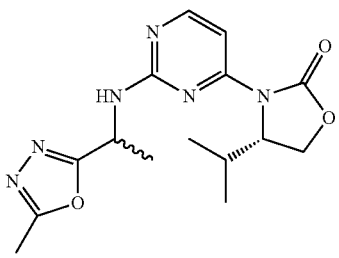 [SMILES: Cc1nnc(C(C)Nc2nccc(N3C(=O)OC[C@@H]3C(C)C)n2)o1]
345 & 346
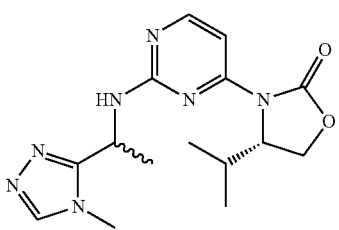 [SMILES: CC(Nc1nccc(N2C(=O)OC[C@@H]2C(C)C)n1)c1nncn1C]
347 & 348
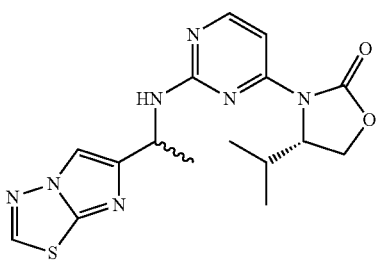 [SMILES: CC(Nc1nccc(N2C(=O)OC[C@@H]2C(C)C)n1)c1cn2ncsc2n1]
349 & 350
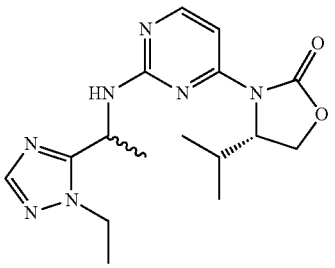 [SMILES: CCn1ncnc1C(C)Nc1nccc(N2C(=O)OC[C@@H]2C(C)C)n1]
351 & 352
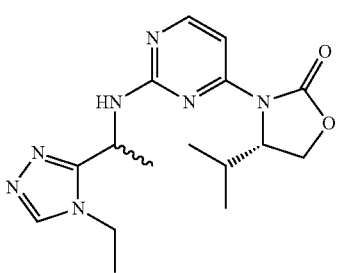 [SMILES: CCn1cnnc1C(C)Nc1nccc(N2C(=O)OC[C@@H]2C(C)C)n1]
353 & 354
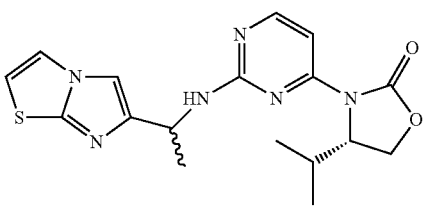 [SMILES: CC(Nc1nccc(N2C(=O)OC[C@@H]2C(C)C)n1)c1cn2ccsc2n1]
355 & 356

TABLE 9-continued
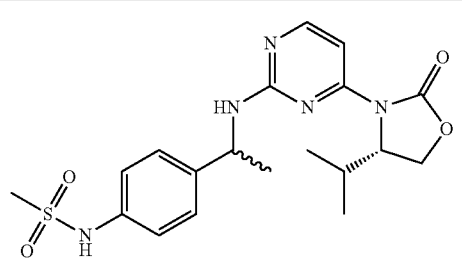 [SMILES: CC(Nc1nccc(N2C(=O)OC[C@@H]2C(C)C)n1)c1ccc(NS(C)(=O)=O)cc1]
357 & 358
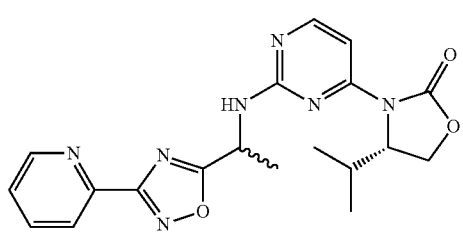 [SMILES: CC(Nc1nccc(N2C(=O)OC[C@@H]2C(C)C)n1)c1nc(-c2ccccn2)no1]
359 & 360
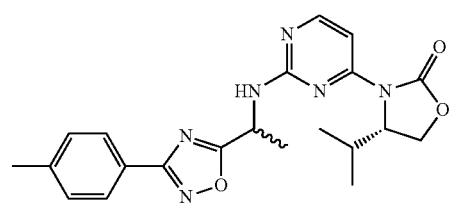 [SMILES: Cc1ccc(-c2noc(C(C)Nc3nccc(N4C(=O)OC[C@@H]4C(C)C)n3)n2)cc1]
361 & 362
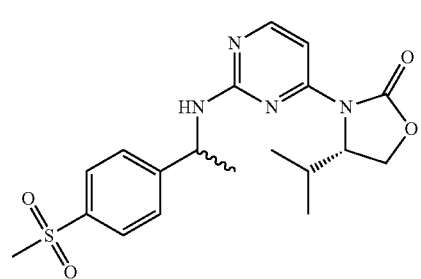 [SMILES: CC(Nc1nccc(N2C(=O)OC[C@@H]2C(C)C)n1)c1ccc(S(C)(=O)=O)cc1]
363 & 364
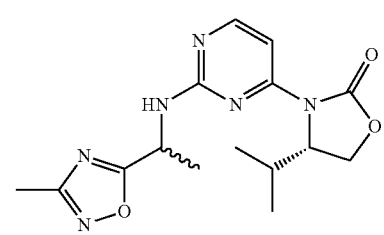 [SMILES: Cc1noc(C(C)Nc2nccc(N3C(=O)OC[C@@H]3C(C)C)n2)n1]
365 & 366
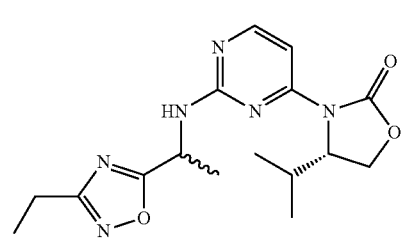 [SMILES: CCc1noc(C(C)Nc2nccc(N3C(=O)OC[C@@H]3C(C)C)n2)n1]
367 & 368
TABLE 9-continued
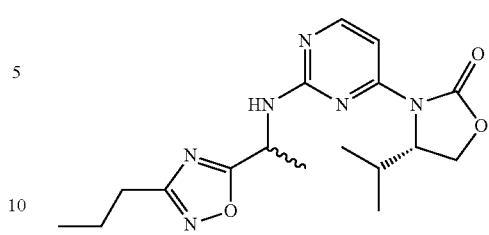
369 & 370
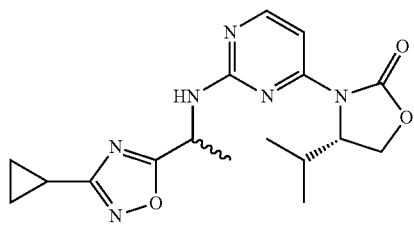 [SMILES: CC(Nc1nccc(N2C(=O)OC[C@@H]2C(C)C)n1)c1nc(C2CC2)no1]
371 & 372
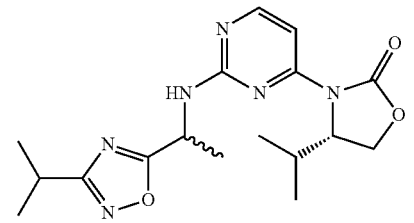 [SMILES: CC(C)c1noc(C(C)Nc2nccc(N3C(=O)OC[C@@H]3C(C)C)n2)n1]
373 & 374
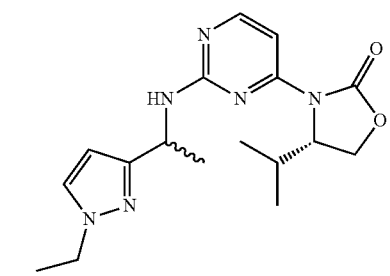 [SMILES: CCn1ccc(C(C)Nc2nccc(N3C(=O)OC[C@@H]3C(C)C)n2)n1]
375 & 376
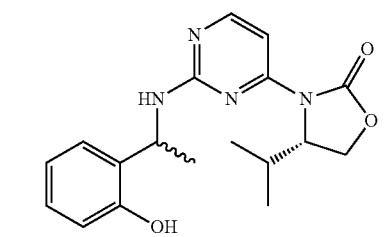 [SMILES: CC(Nc1nccc(N2C(=O)OC[C@@H]2C(C)C)n1)c1ccccc1O]
377 & 378
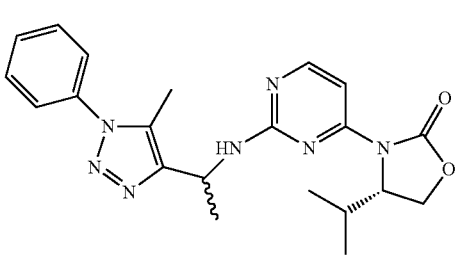 [SMILES: Cc1c(C(C)Nc2nccc(N3C(=O)OC[C@@H]3C(C)C)n2)nnn1-c1ccccc1]
379 & 380

TABLE 9-continued
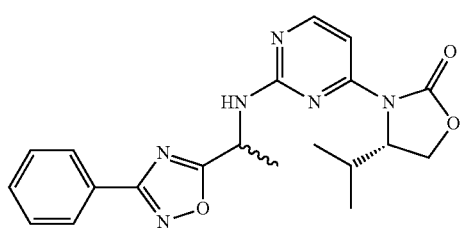 [SMILES: CC(Nc1nccc(N2C(=O)OC[C@@H]2C(C)C)n1)c1nc(-c2ccccc2)no1] 381 & 382
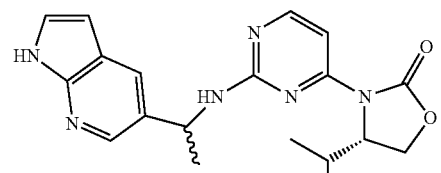 383 & 384
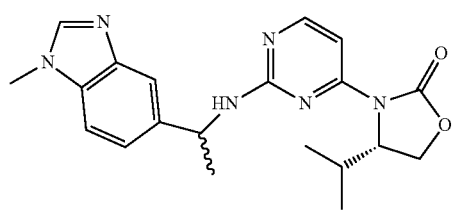 [SMILES: CC(Nc1nccc(N2C(=O)OC[C@@H]2C(C)C)n1)c1ccc2c(c1)ncn2C] 385 & 386
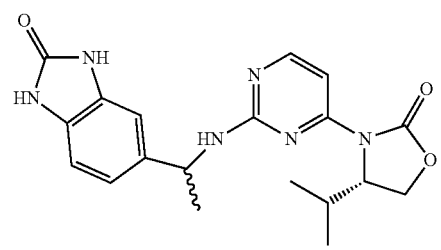 [SMILES: CC(Nc1nccc(N2C(=O)OC[C@@H]2C(C)C)n1)c1ccc2[nH]c(=O)[nH]c2c1] 387 & 388
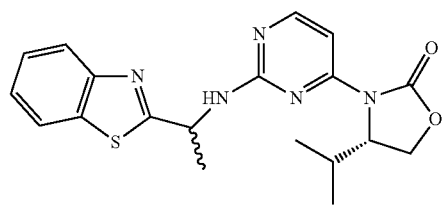 [SMILES: CC(Nc1nccc(N2C(=O)OC[C@@H]2C(C)C)n1)c1nc2ccccc2s1] 389 & 390
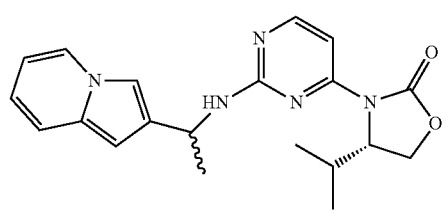 [SMILES: CC(Nc1nccc(N2C(=O)OC[C@@H]2C(C)C)n1)c1cc2ccccn2c1] 391 & 392
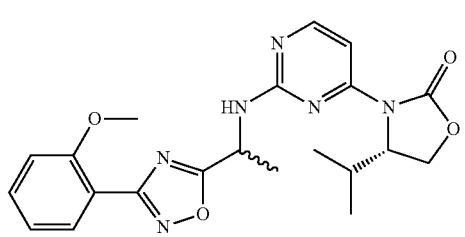 [SMILES: COc1ccccc1-c1noc(C(C)Nc2nccc(N3C(=O)OC[C@@H]3C(C)C)n2)n1] 393 & 394
TABLE 9-continued
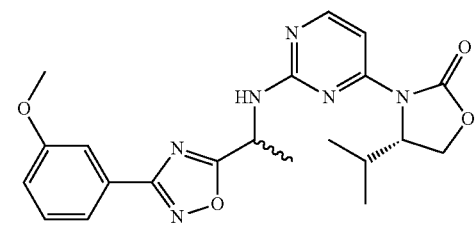 [SMILES: COc1cccc(-c2noc(C(C)Nc3nccc(N4C(=O)OC[C@@H]4C(C)C)n3)n2)c1] 395 & 396
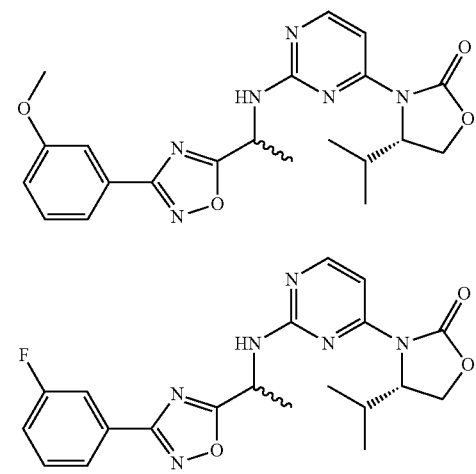 397 & 398
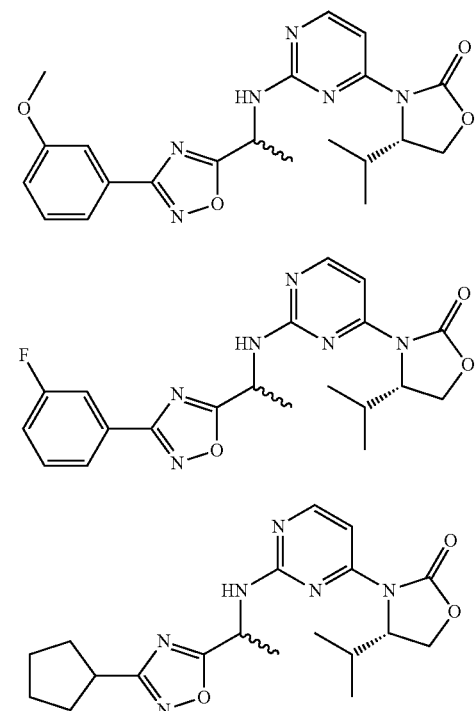 399 & 400
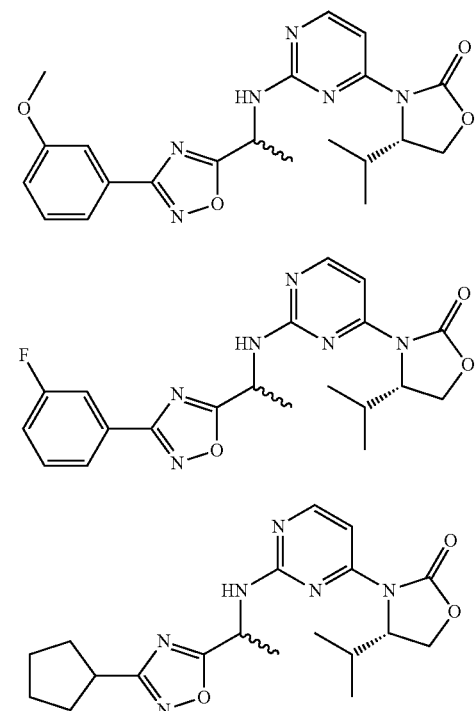 401 & 402
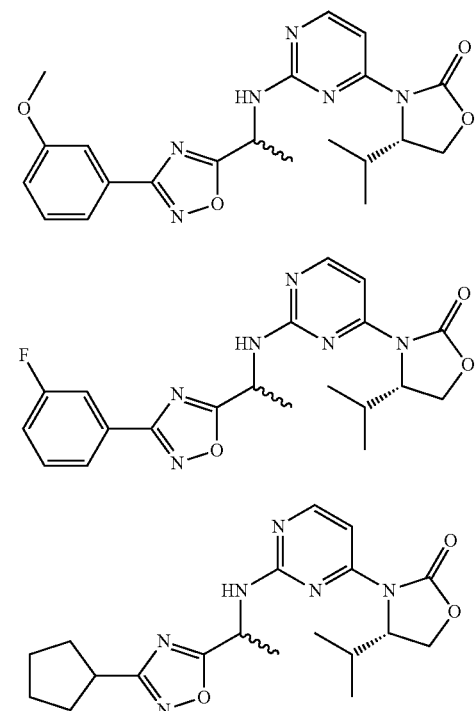 403 & 404
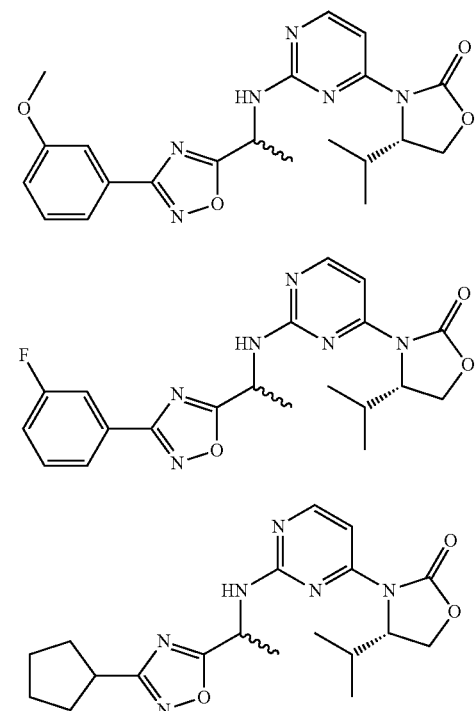 405 & 406
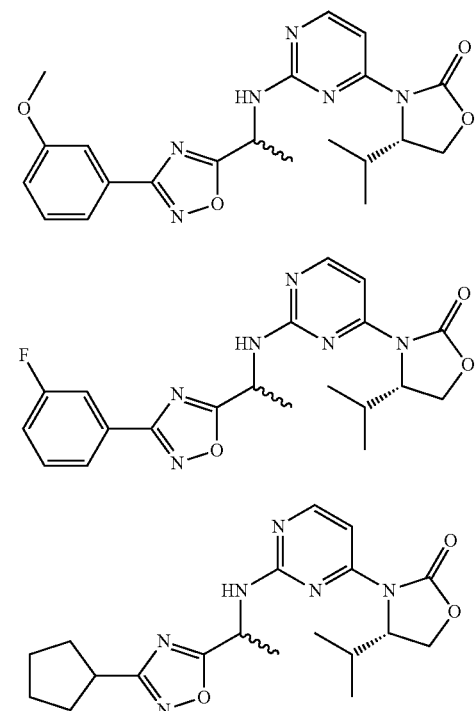 407 & 408

TABLE 9-continued
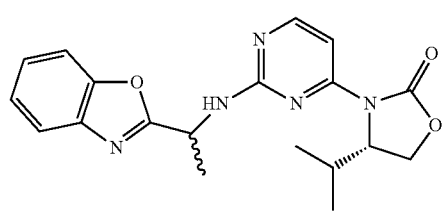 [SMILES: CC(Nc1nccc(N2C(=O)OC[C@@H]2C(C)C)n1)c1nc2ccccc2o1]
409 & 410
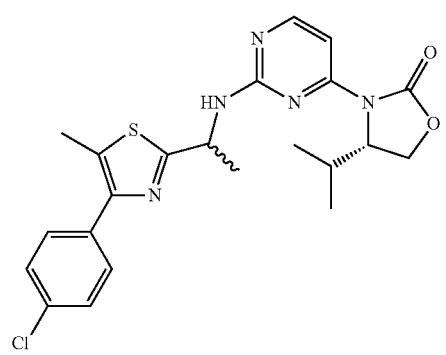 [SMILES: Cc1sc(C(C)Nc2nccc(N3C(=O)OC[C@@H]3C(C)C)n2)nc1-c1ccc(Cl)cc1]
411 & 412
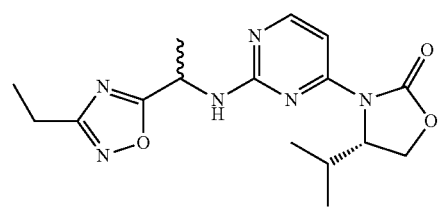 [SMILES: CCc1noc(C(C)Nc2nccc(N3C(=O)OC[C@@H]3C(C)C)n2)n1]
413 & 414
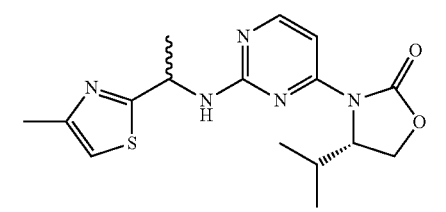 [SMILES: Cc1csc(C(C)Nc2nccc(N3C(=O)OC[C@@H]3C(C)C)n2)n1]
415 & 416
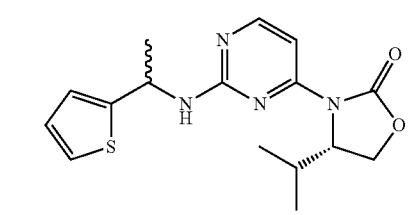 [SMILES: CC(Nc1nccc(N2C(=O)OC[C@@H]2C(C)C)n1)c1cccs1]
417 & 418
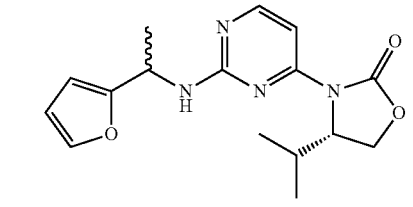 [SMILES: CC(Nc1nccc(N2C(=O)OC[C@@H]2C(C)C)n1)c1ccco1]
419 & 420
TABLE 9-continued
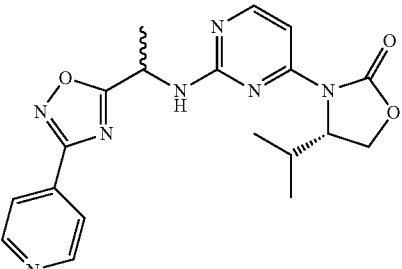
421 & 422
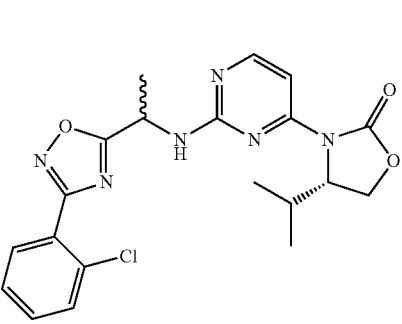 [SMILES: CC(Nc1nccc(N2C(=O)OC[C@@H]2C(C)C)n1)c1nc(-c2ccccc2Cl)no1]
423 & 424
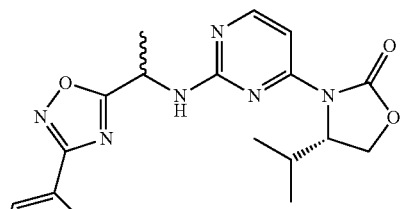
425 & 426
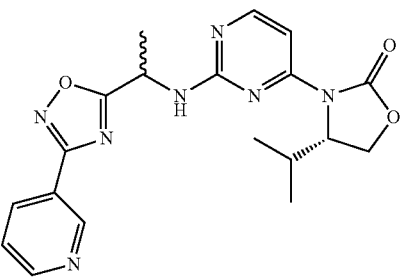 [SMILES: CC(Nc1nccc(N2C(=O)OC[C@@H]2C(C)C)n1)c1nc(-c2cccnc2)no1]
427
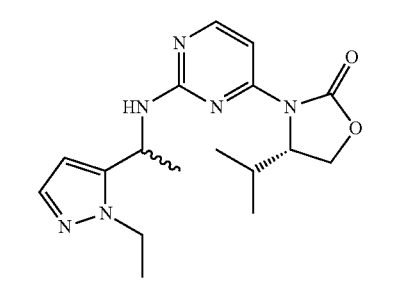
428 & 429

TABLE 9-continued
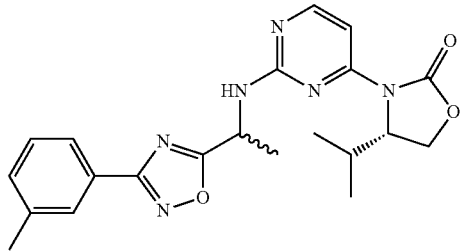 [SMILES: Cc1cccc(-c2noc(C(C)Nc3nccc(N4C(=O)OC[C@@H]4C(C)C)n3)n2)c1]
430
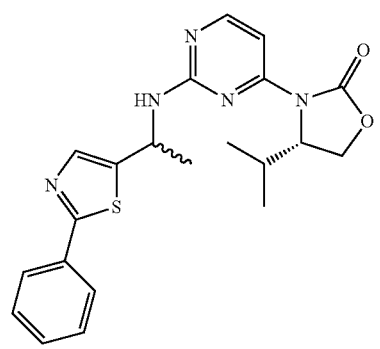 [SMILES: CC(Nc1nccc(N2C(=O)OC[C@@H]2C(C)C)n1)c1cnc(-c2ccccc2)s1]
431 & 432
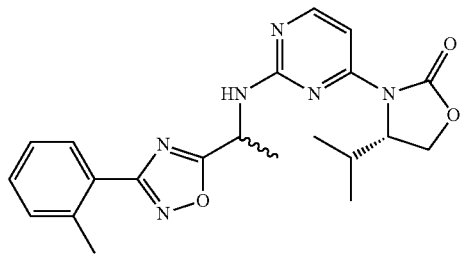 [SMILES: Cc1ccccc1-c1noc(C(C)Nc2nccc(N3C(=O)OC[C@@H]3C(C)C)n2)n1]
433 & 434
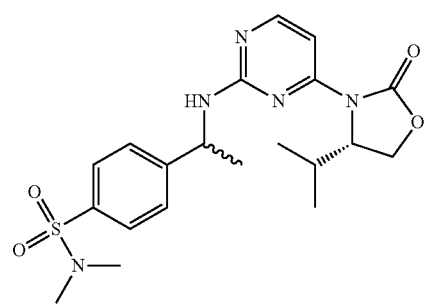 [SMILES: CC(Nc1nccc(N2C(=O)OC[C@@H]2C(C)C)n1)c1ccc(S(=O)(=O)N(C)C)cc1]
435 & 436
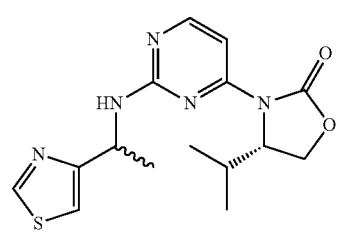 [SMILES: CC(Nc1nccc(N2C(=O)OC[C@@H]2C(C)C)n1)c1cscn1]
437 & 438
TABLE 9-continued
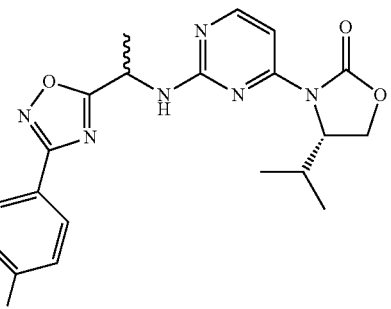
439 & 440
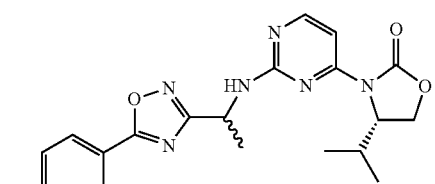
441 & 442
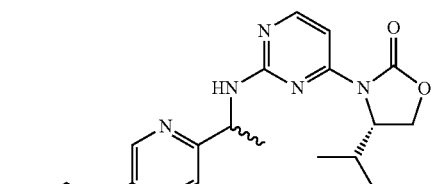
443
444 & 445
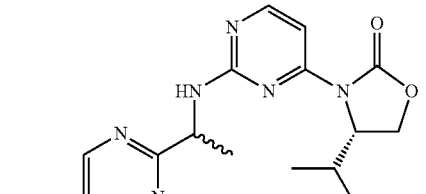
446 & 447
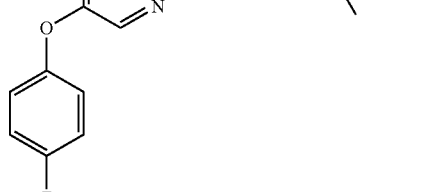

TABLE 9-continued
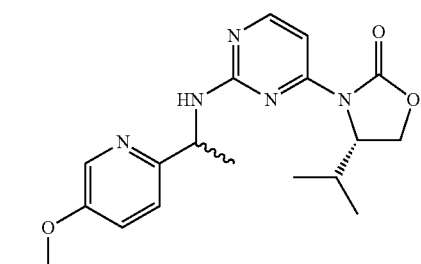 448 & 449
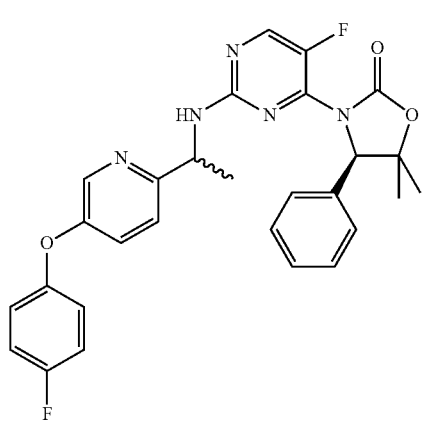 [SMILES: CC(Nc1ncc(F)c(N2C(=O)OC(C)(C)[C@H]2c2ccccc2)n1)c1ccc(Oc2ccc(F)cc2)cn1] 450 & 451
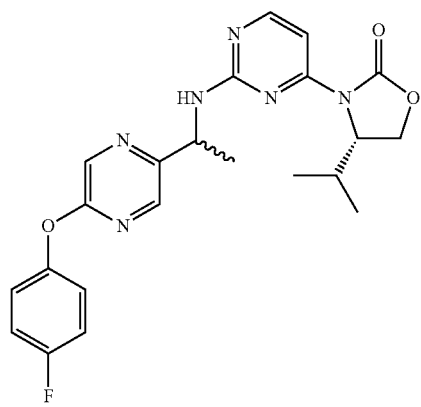 [SMILES: CC(Nc1nccc(N2C(=O)OC[C@@H]2C(C)C)n1)c1cnc(Oc2ccc(F)cc2)cn1] 452 & 453
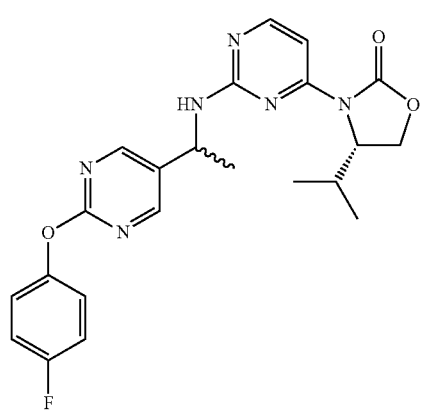 [SMILES: CC(Nc1nccc(N2C(=O)OC[C@@H]2C(C)C)n1)c1cnc(Oc2ccc(F)cc2)nc1] 454 & 455
TABLE 9-continued
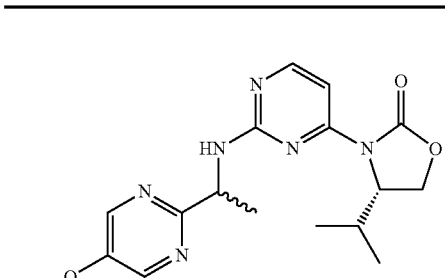 456
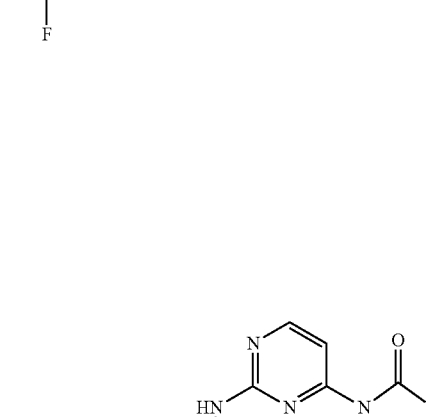 457
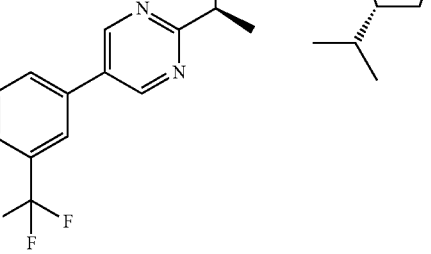 458

TABLE 10

Chemical name, NMR chemical shifts, chiral separation conditions and LCMS signal for each compound listed in Table 9.

| Example: Name | Chiral separation conditions, peak identification and analytical data |
|---|---|
| 331 & 314: 4-(4-methoxyphenyl)-5,5-dimethyl-3-(2-((S)-1-(4-phenoxyphenyl)ethylamino)pyrimidin-4-yl)oxazolidin-2-one | The chiral separation was carried out with SFC (IA-H, 5 μM, 20 × 50 mm) using 28% MeOH in CO2 to give (R)-4-(4-methoxyphenyl)-5,5-dimethyl-3-(2-(((S)-1-(4-phenoxyphenyl)ethyl)amino)pyrimidin-4-yl)oxazolidin-2-one and (S)-4-(4-methoxyphenyl)-5,5-dimethyl-3-(2-(((S)-1-(4-phenoxyphenyl)ethyl)amino)pyrimidin-4-yl)oxazolidin-2-one.<br>1$^{st}$ Peak 313: $^1$H NMR (400 MHz, CDCl$_3$) δ 8.03 (dd, J = 5.9, 1.6 Hz, 1H), 7.43 (d, J = 5.7 Hz, 1H), 7.30-7.22 (m, 2H), 7.20-7.14 (m, 2H), 7.06-7.00 (m, 1H), 6.98 (d, J = 8.2 Hz, 2H), 6.94-6.86 (m, 4H), 6.83-6.76 (m, 2H), 5.24 (br s, 1H), 5.01 (s, 1H), 4.57 (br s, 1H), 3.72 (s, 3H), 1.46 (s, 3H), 1.24-1.09 (m, 3H), 0.92 (s, 3H); HRMS(B) m/z 511.2326 (M + H)+.<br>2$^{nd}$ Peak 314: $^1$H NMR (400 MHz, CDCl$_3$) δ 8.11 (d, J = 5.7 Hz, 1H), 7.51 (d, J = 5.7 Hz, 1H), 7.38-7.29 (m, 2H), 7.10 (tt, J = 7.3, 1.2 Hz, 1H), 7.06-6.90 (m, 6H), 6.89-6.82 (m, 2H), 6.82-6.75 (m, 2H), 5.29 (s, 1H), 5.09 (br s, 1H), 4.80 (br s, 1H), 3.72 (s, 3H), 1.63 (s, 3H), 1.48 (d, J = 6.8 Hz, 3H), 1.01 (s, 3H); HRMS(B) m/z 511.2323 (M + H)+. |
| 315 & 316: (S)-4-methyl-4-phenyl-3-(2-(1-(1-phenyl-1H-pyrazol-4-yl)ethylamino)pyrimidin-4-yl)oxazolidin-2-one | The chiral separation was carried out with SFC (IA, 5 μm, 20 × 250 mm) using 45% iPrOH with 0.2% Et2NH in CO2 to give (S)-4-methyl-4-phenyl-3-(2-(((R)-1-(1-phenyl-1H-pyrazol-4-yl)ethyl)amino)pyrimidin-4-yl)oxazolidin-2-one and (S)-4-methyl-4-phenyl-3-(2-(((S)-1-(1-phenyl-1H-pyrazol-4-yl)ethyl)amino)pyrimidin-4-yl)oxazolidin-2-one.<br>1st Peak 315: $^1$H NMR (400 MHz, CDCl$_3$) δ 8.19 (d, J = 5.8 Hz, 1 H), 7.63-7.60 (m, 2 H), 7.49-7.44 (m, 4 H), 7.37-7.28 (m, 4 H), 7.26-7.22 (m, 2 H), 7.12-7.08 (m, 1 H), 4.94 (br s, 1 H), 4.45 (br s, 1 H), 4.31-4.27 (m, 2 H), 2.19 (s, 3 H), 1.44 (d, J = 6.8 Hz, 3 H); HRMS(B) m/z 441.2036 (M + H)+.<br>2nd Peak 316: $^1$H NMR (400 MHz, CDCl$_3$) δ 8.20 (d, J = 5.8 Hz, 1 H), 7.67-7.63 (m, 3 H), 7.53 (s, 1 H), 7.49-7.44 (m, 3 H), 7.40-7.37 (m, 2 H), 7.33-7.30 (m, 4 H), 4.99 (br s, 1 H), 4.38 (br s, 1 H), 4.26 (s, 2 H), 2.00 (s, 3 H), 1.07 (br s, 3 H); HRMS(B) m/z 441.2039 (M + H)+. |
| 317 & 318: (R)-4-methyl-4-phenyl-3-(2-(1-(1-phenyl-1H-pyrazol-4-yl)ethylamino)pyrimidin-4-yl)oxazolidin-2-one | The chiral separation was carried out with SFC (IA, 5 μm, 20 × 250 mm) with 45% iPrOH modified with 0.2% Et2NH in CO2 to give (R)-4-methyl-4-phenyl-3-(2-(((S)-1-(1-phenyl-1H-pyrazol-4-yl)ethyl)amino)pyrimidin-4-yl)oxazolidin-2-one and (S)-4-methyl-4-phenyl-3-(2-(((S)-1-(1-phenyl-1H-pyrazol-4-yl)ethyl)amino)pyrimidin-4-yl)oxazolidin-2-one.<br>1st peak 317: $^1$H NMR (400 MHz, CDCl$_3$) δ 8.20 (d, J = 5.8 Hz, 1 H), 7.68-7.63 (m, 3 H), 7.53 (s, 1 H), 7.49-7.44 (m, 3 H), 7.41-7.37 (m, 2 H), 7.33-7.30 (m, 4 H), 4.98 (br s, 1 H), 4.39 (br s, 1 H), 4.26 (s, 2 H), 2.00 (s, 3 H), 1.07 (br s, 3 H); HRMS(B) m/z 441.2037 (M + H)+.<br>2nd peak 318: $^1$H NMR (400 MHz, CDCl$_3$) δ 8.17 (d, J = 5.8 Hz, 1 H), 7.63-7.60 (m, 2 H), 7.49-7.44 (m, 4 H), 7.36-7.29 (m, 4 H), 7.26-7.22 (m, 2 H), 7.12-7.08 (m, 1 H), 5.02 (br s, 1 H), 4.45 (br s, 1 H), 4.31-4.26 (m, 2 H), 2.19 (s, 3 H), 1.44 (d, J = 6.8 Hz, 3 H); HRMS(B) m/z 441.2039 (M + H)+. |
| 319 & 320: (R)-4-(4-fluorophenyl)-3-(2-(1-(1-(4-fluorophenyl)-1H-pyrazol-4-yl)ethylamino)pyrimidin-4-yl)-4-methyloxazolidin-2-one | Separation was achieved on a normal phase silica gel column with 10 to 50% ethylacetate/heptane to give (R)-4-(4-fluorophenyl)-3-(2-(((R)-1-(1-(4-fluorophenyl)-1H-pyrazol-4-yl)ethyl)amino)pyrimidin-4-yl)-4-methyloxazolidin-2-one and (R)-4-(4-fluorophenyl)-3-(2-(((S)-1-(1-(4-fluorophenyl)-1H-pyrazol-4-yl)ethyl)amino)pyrimidin-4-yl)-4-methyloxazolidin-2-one.<br>1st peak 319: $^1$H NMR (400 MHz, CDCl$_3$) δ 8.10 (d, J = 5.8 Hz, 1 H), 7.53-7.48 (m, 3 H), 7.44 (s, 1 H), 7.36 (d, J = 5.8 Hz, 1 H), 7.22-7.17 (m, 2 H), 7.09-7.03 (m, 2 H), 7.01-6.95 (m, 2 H), 4.98 (br s, 1 H), 4.33 (br s, 1 H), 4.15 (q, J = 8.6 Hz, 2 H), 1.90 (s, 3 H), 1.04 (br s, 3 H); HRMS(B) m/z 477.1827 (M + H)+.<br>2nd peak 320: $^1$H NMR (400 MHz, CDCl$_3$) δ 8.18 (d, J = 5.8 Hz, 1 H), 7.62-7.56 (m, 2 H), 7.45-7.39 (m, 3 H), |

TABLE 10-continued

Chemical name, NMR chemical shifts, chiral separation conditions and LCMS signal for each compound listed in Table 9.

| Example: Name | Chiral separation conditions, peak identification and analytical data |
|---|---|
| | 7.31-7.26 (m, 2 H), 7.18-7.12 (m, 2 H), 6.93 (t, J = 8.6 Hz, 2 H), 5.01 (br s, 1 H), 4.50 (br s, 1 H), 4.30-4.23 (m, 2 H), 2.17 (s, 3 H), 1.45 (d, J = 6.8 Hz, 3 H); HRMS(B) m/z 477.1829 (M + H)+. |
| 321 & 322: (S)-4-isopropyl-3-(2-(1-(1-(3-methoxyphenyl)-1H-pyrazol-4-yl)ethylamino)pyrimidin-4-yl)oxazolidin-2-one | Separation was achieved on a normal phase silica gel column with 10 to 50% ethylacetate/heptane to give (S)-4-isopropyl-3-(2-(((R)-1-(1-(3-methoxyphenyl)-1H-pyrazol-4-yl)ethyl)amino)pyrimidin-4-yl)oxazolidin-2-one and (S)-4-isopropyl-3-(2-(((S)-1-(1-(3-methoxyphenyl)-1H-pyrazol-4-yl)ethyl)amino)pyrimidin-4-yl)oxazolidin-2-one.<br>1st peak 321: $^1$H NMR (400 MHz, MeOD) δ 8.18 (dd, J = 3.3, 2.5 Hz, 2H), 7.70 (s, 1H), 7.42 (d, J = 5.8 Hz, 1H), 7.38 (t, J = 8.1 Hz, 1H), 7.31 (t, J = 2.3 Hz, 1H), 7.27 (ddd, J = 8.0, 2.1, 0.9 Hz, 1H), 6.89 (ddd, J = 8.1, 2.5, 0.9 Hz, 1H), 5.21 (q, J = 6.8 Hz, 1H), 4.81-4.73 (m, 1H), 4.44-4.34 (m, 2H), 3.87 (s, 3H), 2.64 (pd, J = 7.0, 3.5 Hz, 1H), 1.61 (d, J = 6.9 Hz, 3H), 0.99 (d, J = 7.1 Hz, 3H), 0.88 (d, J = 6.9 Hz, 3H). HRMS(B) (M + H) 423.2141 Calc'd (M + H) 423.2145<br>2nd peak 322: $^1$H NMR (400 MHz, MeOD) δ 8.18 (d, J = 5.8 Hz, 1H), 8.10 (s, 1H), 7.63 (s, 1H), 7.41 (d, J = 5.8 Hz, 1H), 7.37 (t, J = 8.2 Hz, 1H), 7.28 (t, J = 2.3 Hz, 1H), 7.24 (ddd, J = 8.1, 2.1, 0.9 Hz, 1H), 6.88 (ddd, J = 8.3, 2.5, 0.9 Hz, 1H), 5.19 (q, J = 6.9 Hz, 1H), 4.74 (dt, J = 7.6, 3.5 Hz, 1H), 4.42-4.28 (m, 2H), 3.86 (s, 3H), 2.31 (br s, 1H), 1.61 (d, J = 6.9 Hz, 3H), 0.79 (br s, 3H), 0.75-0.64 (br m, 3H). HRMS(B) (M + H) 423.2139 Calc'd (M + H) 423.2145 |
| 323 & 324: 4-(4-(1-(4-((S)-4-isopropyl-2-oxooxazolidin-3-yl)pyrimidin-2-ylamino)ethyl)-5-methyl-1H-pyrazol-1-yl)benzonitrile | Chiral separation was achieved by SFC. (Column: Chiralpak-ID (Semi-Prep 20 mm × 250 mm) Isocratic: 65% CO2: 35% MeOH (5 mM NH4OH additive) to give (S)-4-isopropyl-3-(2-(((R)-1-(1-(3-methoxyphenyl)-1H-pyrazol-4-yl)ethyl)amino)pyrimidin-4-yl)oxazolidin-2-one and (S)-4-isopropyl-3-(2-(((S)-1-(1-(3-methoxyphenyl)-1H-pyrazol-4-yl)ethyl)amino)pyrimidin-4-yl)oxazolidin-2-one.<br>1st peak 323: $^1$H NMR (400 MHz, MeOD) δ 8.16 (d, J = 5.8 Hz, 1H), 7.95-7.88 (m, 2H), 7.75 (s, 1H), 7.73-7.67 (m, 2H), 7.40 (d, J = 5.8 Hz, 1H), 5.19 (q, J = 6.9 Hz, 1H), 4.79 (td, J = 5.7, 3.5 Hz, 1H), 4.40 (d, J = 5.7 Hz, 2H), 2.65 (pd, J = 7.0, 3.6 Hz, 1H), 2.41 (s, 3H), 1.59 (d, J = 6.8 Hz, 3H), 1.00 (d, J = 7.0 Hz, 3H), 0.89 (d, J = 6.9 Hz, 3H). HRMS(B) (M + H) 432.2138 Calc'd (M + H) 432.2148<br>2nd peak 324: $^1$H NMR (400 MHz, MeOD) δ 8.17 (d, J = 5.8 Hz, 1H), 7.97-7.84 (m, 2H), 7.77-7.63 (m, 3H), 7.40 (d, J = 5.8 Hz, 1H), 5.16 (q, J = 6.8 Hz, 1H), 4.79 (dt, J = 7.5, 3.8 Hz, 1H), 4.43-4.33 (m, 2H), 2.41 (s, 4H), 1.59 (d, J = 6.9 Hz, 3H), 0.87 (br d, J = 7.1 Hz, 3H), 0.80 (br d, J = 6.9 Hz, 3H). HRMS(B) (M + H) 432.2137 Calc'd (M + H) 432.2148 |
| 325 & 326: (S)-3-(2-(1-(3,5-dimethyl-1-phenyl-1H-pyrazol-4-yl)ethylamino)pyrimidin-4-yl)-4-isopropyloxazolidin-2-one | Chiral separation was achieved by chiral SFC column chromatography (Column AD-H 5 mM 20 × 250 mm column 15% MeOH + DEA) to give (S)-3-(2-(((R)-1-(3,5-dimethyl-1-phenyl-1H-pyrazol-4-yl)ethyl)amino)pyrimidin-4-yl)-4-isopropyloxazolidin-2-one and (S)-3-(2-(((S)-1-(3,5-dimethyl-1-phenyl-1H-pyrazol-4-yl)ethyl)amino)pyrimidin-4-yl)-4-isopropyloxazolidin-2-one.<br>1st peak 325: $^1$H NMR (400 MHz, MeOD) δ 8.16 (d, J = 5.8 Hz, 1H), 7.57-7.49 (m, 2H), 7.48-7.42 (m, 1H), 7.42-7.38 (m, 3H), 5.12 (q, J = 7.0 Hz, 1H), 4.78 (td, J = 5.6, 3.5 Hz, 1H), 4.44-4.36 (m, 2H), 2.63 (td, J = 7.0, 3.6 Hz, 1H), 2.34 (s, 3H), 2.32 (s, 3H), 1.59 (d, J = 7.1 Hz, 3H), 1.00 (d, J = 7.0 Hz, 3H), 0.88 (d, J = 7.0 Hz, 3H). HRMS(B) (M + H) 421.2348 Calc'd (M + H) 421.2352<br>2nd peak 326: $^1$H NMR (400 MHz, MeOD) δ 8.18 (d, J = 5.8 Hz, 1H), 7.56-7.49 (m, 2H), 7.48-7.41 (m, 1H), 7.40-7.35 (m, 3H), 5.07 (q, J = 7.1 Hz, 1H), 4.78 (dt, J = 7.8, 3.8 Hz, 1H), 4.44-4.32 (m, 2H), 2.33 (s, 3H), 2.31 (br s, 1H) 2.29 (s, 3H), 1.59 (d, J = 7.1 Hz, 3H), 0.85 (br d, J = 7.0 Hz, 3H), 0.77 (br d, J = 6.9 Hz, 3H). HRMS(B) (M + H) 421.2347 Calc'd (M + H) 421.2352 |

TABLE 10-continued

Chemical name, NMR chemical shifts, chiral separation conditions and LCMS signal for each compound listed in Table 9.

| Example: Name | Chiral separation conditions, peak identification and analytical data |
|---|---|
| 327 & 328: (S)-3-(2-(1-(4-(1H-imidazol-1-yl)phenyl)ethylamino)pyrimidin-4-yl)-4-isopropyloxazolidin-2-one | Separation was achieved by reverse HPLC (10-85% ACN/water 0.1% NH4OH modifier) to give (S)-3-(2-(((R)-1-(4-(1H-imidazol-1-yl)phenyl)ethyl)amino)pyrimidin-4-yl)-4-isopropyloxazolidin-2-one and (S)-3-(2-(((S)-1-(4-(1H-imidazol-1-yl)phenyl)ethyl)amino)pyrimidin-4-yl)-4-isopropyloxazolidin-2-one.<br>1st peak 327: $^1$H NMR (400 MHz, MeOD) δ 8.25-8.00 (m, 2H), 7.53 (d, J = 0.7 Hz, 5H), 7.38 (d, J = 5.9 Hz, 1H), 7.15 (s, 1H), 5.04 (q, J = 7.1 Hz, 1H), 4.50 (br s, 1H), 4.40-4.19 (m, 2H), 2.68 (pd, J = 7.0, 3.6 Hz, 1H), 1.57 (d, J = 7.0 Hz, 3H), 1.02 (d, J = 7.0 Hz, 3H), 0.87 (d, J = 7.0 Hz, 3H). HRMS(B) (M + H) 393.2042 Calc'd (M + H) 393.2039<br>2nd peak 328: $^1$H NMR (400 MHz, MeOD) δ 8.16 (d, J = 5.8 Hz, 1H), 8.10 (t, J = 1.2 Hz, 1H), 7.55 (t, J = 1.4 Hz, 1H), 7.52 (s, 4H), 7.38 (d, J = 5.8 Hz, 1H), 7.15 (t, J = 1.2 Hz, 1H), 5.12 (q, J = 7.0 Hz, 1H), 4.67 (br s, 1H), 4.44-4.23 (m, 2H), 1.84 (br s, 1H), 1.57 (d, J = 7.0 Hz, 3H), 0.71 (br s, 3H), 0.60 (br s, 3H). HRMS(B) (M + H) 393.2026 Calc'd (M + H) 393.2039 |
| 329 & 330: (S)-3-(2-(1-(3-fluoro-4-(pyridin-3-yloxy)phenyl)ethylamino)pyrimidin-4-yl)-4-isopropyloxazolidin-2-one | Chiral separation was achieved by chiral SFC column chromatography (Column AD-H 5 mM 20 × 250 mm column 15% MeOH + DEA) to give (S)-3-(2-(((R)-1-(3-fluoro-4-(pyridin-3-yloxy)phenyl)ethyl)amino)pyrimidin-4-yl)-4-isopropyloxazolidin-2-one and (S)-3-(2-(((S)-1-(3-fluoro-4-(pyridin-3-yloxy)phenyl)ethyl)amino)pyrimidin-4-yl)-4-isopropyloxazolidin-2-one.<br>1st peak 329: $^1$H NMR (400 MHz, MeOD) δ 8.32-8.23 (m, 2H), 8.15 (d, J = 5.8 Hz, 1H), 7.45-7.35 (m, 3H), 7.31 (dd, J = 11.8, 2.0 Hz, 1H), 7.26 (dd, J = 8.5, 2.0 Hz, 1H), 7.19 (t, J = 8.2 Hz, 1H), 5.15-4.95 (m, 1H), 4.51 (s, 1H), 4.41-4.26 (m, 2H), 2.68 (pd, J = 7.1, 3.6 Hz, 1H), 1.56 (d, J = 7.0 Hz, 3H), 1.01 (d, J = 7.1 Hz, 3H), 0.88 (d, J = 6.9 Hz, 3H). HRMS(B) (M + H) 438.1935 Calc'd (M + H) 438.1941<br>2nd peak 330: $^1$H NMR (400 MHz, MeOD) δ 8.28 (dd, J = 4.7, 1.4 Hz, 1H), 8.26 (d, J = 2.8 Hz, 1H), 8.17 (d, J = 5.8 Hz, 1H), 7.43-7.40 (m, 2H), 7.36 (ddd, J = 8.4, 2.9, 1.5 Hz, 1H), 7.30 (dd, J = 11.8, 2.0 Hz, 1H), 7.25 (dd, J = 8.4, 2.0 Hz, 1H), 7.19 (t, J = 8.2 Hz, 1H), 5.10 (q, J = 7.1 Hz, 1H), 4.72 (br s, 1H), 4.43-4.29 (m, 2H), 1.93 (br s, 1H), 1.55 (d, J = 7.0 Hz, 3H), 0.78 (br s, 3H), 0.69 (br s, 3H). HRMS(B) (M + H) 438.1928 Calc'd (M + H) 438.1941 |
| 331 & 332: (4S)-4-isopropyl-3-(2-((1-(4-((tetrahydro-2H-pyran-4-yl)oxy)phenyl)ethyl)amino)pyrimidin-4-yl)oxazolidin-2-one | Chiral separation was achieved by chiral SFC column chromatography (Column IA-H 5 mM 20 × 250 mm column 30% MeOH) to give (S)-4-isopropyl-3-(2-(((R)-1-(4-((tetrahydro-2H-pyran-4-yl)oxy)phenyl)ethyl)amino)pyrimidin-4-yl)oxazolidin-2-one and (S)-4-isopropyl-3-(2-(((S)-1-(4-((tetrahydro-2H-pyran-4-yl)oxy)phenyl)ethyl)amino)pyrimidin-4-yl)oxazolidin-2-one.<br>1st peak 331: HRMS(B) (M+) 426.2267, RT = 2.45 min<br>2nd peak 332: HRMS(B) (M+) 426.2267, RT = 2.37 min |
| 333 & 334: (R)-3-(2-(1-(3,4-dichlorophenyl)ethylamino)pyrimidin-4-yl)-4-phenyloxazolidin-2-one | Separation was achieved on a normal phase silica gel column with 10 to 40% ethylacetate/heptane to give (R)-3-(2-(((S)-1-(3,4-dichlorophenyl)ethyl)amino)pyrimidin-4-yl)-4-phenyloxazolidin-2-one and (R)-3-(2-(((R)-1-(3,4-dichlorophenyl)ethyl)amino)pyrimidin-4-yl)-4-phenyloxazolidin-2-one<br>1st peak 333: $^1$H NMR (400 MHz, MeOD) δ 8.49 (d, J = 5.7 Hz, 1H), 7.85-7.74 (m, 5H), 7.74-7.68 (m, 1H), 7.66-7.61 (m, 2H), 7.55 (dd, J = 8.3, 2.1 Hz, 1H), 5.90 (dd, J = 8.9, 4.0 Hz, 1H), 5.14 (t, J = 8.7 Hz, 1H), 4.97-4.89 (m, 1H), 4.56 (dd, J = 8.8, 4.1 Hz, 1H), 1.60 (d, J = 7.0 Hz, 3H). HRMS(B) (M + H) 429.0899 Calc'd (M + H) 429.0885<br>2nd peak 334: $^1$H NMR (400 MHz, MeOD) δ 8.50 (d, J = 5.7 Hz, 1H), 7.79 (d, J = 5.9 Hz, 1H), 7.61 (d, J = 8.4 Hz, 1H), 7.57 (dt, J = 4.6, 2.3 Hz, 3H), 7.45 (dd, J = 6.4, 2.9 Hz, 2H), 7.31 (dd, J = 8.3, 2.2 Hz, 1H), 6.16 (dd, J = 8.6, 3.5 Hz, 1H), 5.26 (q, J = 6.9 Hz, 1H), 5.16 (t, J = 8.6 |

TABLE 10-continued

Chemical name, NMR chemical shifts, chiral separation conditions and LCMS signal for each compound listed in Table 9.

| Example: Name | Chiral separation conditions, peak identification and analytical data |
|---|---|
| | Hz, 1H), 4.97-4.88 (m, 1H), 4.56 (dd, J = 8.8, 3.6 Hz, 1H), 1.80 (d, J = 7.0 Hz, 3H). HRMS(B) (M + H) 429.0887 Calc'd (M + H) 429.0885 |
| 335 & 336: (S)-4-isopropyl-3-(2-(1-(4-(pyridin-3-yl)phenyl)ethylamino)pyrimidin-4-yl)oxazolidin-2-one | Chiral separation was achieved by chiral SFC column chromatography (Column IA-H 5 mM 20 × 250 mm column 40% MeOH, 10 mM NH4OH) to give (S)-4-isopropyl-3-(2-(((R)-1-(4-(pyridin-3-yl)phenyl)ethyl)amino)pyrimidin-4-yl)oxazolidin-2-one and (S)-4-isopropyl-3-(2-(((S)-1-(4-(pyridin-3-yl)phenyl)ethyl)amino)pyrimidin-4-yl)oxazolidin-2-one. 1st peak 335: $^1$H NMR (400 MHz, MeOD) δ 8.81 (br s, 1H), 8.52 (br s, 1H), 8.14 (br s, 1H), 8.10 (dt, J = 8.2, 1.7 Hz, 1H), 7.71-7.59 (m, 2H), 7.58-7.46 (m, 3H), 7.37 (d, J = 5.8 Hz, 1H), 5.04 (dd, J = 11.2, 5.3 Hz, 1H), 4.50 (br s, 1H), 4.40-4.19 (m, 2H), 2.69 (ddd, J = 10.4, 7.0, 3.5 Hz, 1H), 1.58 (d, J = 7.0 Hz, 3H), 1.03 (d, J = 7.0 Hz, 3H), 0.88 (d, J = 7.0 Hz, 3H). HRMS(B) (M + H) 404.2085 Calc'd (M + H) 404.2086 2nd peak 336: $^1$H NMR (400 MHz, MeOD) δ 8.82 (br s, 1H), 8.55 (br s, 1H), 8.17 (br s, 1H), 8.09 (d, J = 8.0 Hz, 1H), 7.70-7.59 (m, 2H), 7.54 (br s, 1H), 7.51-7.45 (m, 2H), 7.38 (d, J = 5.7 Hz, 1H), 5.11 (q, J = 7.0 Hz, 1H), 4.66 (br s, 1H), 4.36-4.30 (m, 2H), 1.80 (br s, 1H), 1.58 (d, J = 7.0 Hz, 3H), 0.67 (br s, 3H), 0.56 (br s, 3H). HRMS(B) (M + H) 404.2079 Calc'd (M + H) 404.2086 |
| 337 & 338: (S)-4-isopropyl-3-(2-(1-(4-(pyridin-4-yl)phenyl)ethylamino)pyrimidin-4-yl)oxazolidin-2-one | Separation was achieved on a normal phase silica gel column with 20 to 100% ethylacetate/heptane to give (S)-4-isopropyl-3-(2-(((R)-1-(4-(pyridin-4-yl)phenyl)ethyl)amino)pyrimidin-4-yl)oxazolidin-2-one and (S)-4-isopropyl-3-(2-(((S)-1-(4-(pyridin-4-yl)phenyl)ethyl)amino)pyrimidin-4-yl)oxazolidin-2-one. 1st peak 337: $^1$H NMR (400 MHz, MeOD) δ 8.58 (br s, 2H), 8.14 (d, J = 5.9 Hz, 1H), 7.83-7.66 (m, 4H), 7.60-7.46 (m, 2H), 7.37 (d, J = 5.8 Hz, 1H), 5.15-4.96 (m, 1H), 4.48 (br s, 1H), 4.38-4.15 (m, 2H), 2.69 (ddp, J = 10.5, 7.0, 3.5 Hz, 1H), 1.58 (d, J = 7.0 Hz, 3H), 1.03 (d, J = 7.0 Hz, 3H), 0.88 (d, J = 6.9 Hz, 3H). HRMS(B) (M + H) 404.2068 Calc'd (M + H) 404.2086 2nd peak 338: $^1$H NMR (400 MHz, MeOD) δ 8.59 (br s, 2H), 8.17 (br s, 1H), 7.80-7.68 (m, 4H), 7.56-7.44 (m, 2H), 7.38 (d, J = 5.8 Hz, 1H), 5.11 (q, J = 7.0 Hz, 1H), 4.65 (br s, 1H), 4.31 (dt, J = 17.1, 9.0 Hz, 2H), 1.76 (br s, 1H), 1.58 (d, J = 7.1 Hz, 3H), 0.66 (br s, 3H), 0.55 (br s, 3H). HRMS(B) (M + H) 404.1939 Calc'd (M + H) 404.2086 |
| 339 & 340: (S)-4-isopropyl-3-(2-(1-(4-(methyl(phenyl)amino)phenyl)etnylamino)pyrimidin-4-yl)oxazolidin-2-one | Separation was achieved on a normal phase silica gel column with 40 to 100% ethylacetate/heptane to give (S)-4-isopropyl-3-(2-(((R)-1-(4-(methyl(phenyl)amino)phenyl)ethyl)amino)pyrimidin-4-yl)oxazolidin-2-one and (S)-4-isopropyl-3-(2-(((S)-1-(4-(methyl(phenyl)amino)phenyl)ethyl)amino)pyrimidin-4-yl)oxazolidin-2-one. 1st peak 339: $^1$H NMR (400 MHz, MeOD) δ 8.12 (d, J = 5.8 Hz, 1H), 7.37 (d, J = 5.8 Hz, 1H), 7.31-7.18 (m, 4H), 7.03-6.94 (m, 4H), 6.91 (tt, J = 7.4, 1.1 Hz, 1H), 4.99-4.93 (m, 1H), 4.57 (br s, 1H), 4.42-4.27 (m, 2H), 3.28 (s, 3H), 2.68 (ddq, J = 10.5, 6.9, 3.4 Hz, 1H), 1.53 (d, J = 6.9 Hz, 3H), 1.01 (d, J = 7.1 Hz, 3H), 0.88 (d, J = 7.0 Hz, 3H). HRMS(B) (M + H) 432.2390 Calc'd (M + H) 432.2400 2nd peak 340: $^1$H NMR (400 MHz, MeOD) 5 8.15 (d, J = 5.8 Hz, 1H), 7.37 (d, J = 5.8 Hz, 1H), 7.30-7.18 (m, 4H), 7.02-6.92 (m, 4H), 6.89 (tt, J = 7.3, 1.1 Hz, 1H), 5.04 (q, J = 7.0 Hz, 1H), 4.77-4.67 (m, 1H), 4.43-4.26 (m, 2H), 3.27 (s, 3H), 2.11 (br s, 1H), 1.52 (d, J = 7.0 Hz, 3H), 0.79 (br s, 3H), 0.68 (br s, 3H). HRMS(B) (M + H) 432.2386 Calc'd (M + H) 432.2400 |
| 341 & 342: S)-3-(2-(1-(3-fluoro-4-(4-methyl-1H-pyrazol-1-yl)phenyl)ethylamino)pyrimidin-4-yl)-4-isopropyloxazolidin-2-one | Chiral separation was achieved by chiral SFC column (IC 20 × 250 nm 45% IPA in CO2, 75 g/min Flow) to give (S)-3-(2-(((R)-1-(3-fluoro-4-(4-methyl-1H-pyrazol-1-yl)phenyl)ethyl)amino)pyrimidin-4-yl)-4-isopropyloxazolidin-2-one and (S)-3-(2-(((S)-1-(3-fluoro-4-(4-methyl-1H-pyrazol-1-yl)phenyl)ethyl)amino)pyrimidin-4-yl)-4- |

TABLE 10-continued

Chemical name, NMR chemical shifts, chiral separation conditions
and LCMS signal for each compound listed in Table 9.

| Example: Name | Chiral separation conditions, peak identification and analytical data |
|---|---|
| | isopropyloxazolidin-2-one.<br>1st peak 341: $^1$H NMR (400 MHz, MeOD) δ 8.15 (d, J = 5.8 Hz, 1H), 7.81 (dt, J = 2.9, 0.9 Hz, 1H), 7.66 (t, J = 8.3 Hz, 1H), 7.56 (s, 1H), 7.40 (d, J = 5.8 Hz, 1H), 7.36-7.25 (m, 2H), 5.01 (d, J = 7.5 Hz, 1H), 4.46 (br s, 1H), 4.38-4.25 (m, 2H), 2.68 (pd, J = 7.0, 3.5 Hz, 1H), 2.17 (d, J = 0.6 Hz, 3H), 1.56 (d, J = 7.0 Hz, 3H), 1.02 (d, J = 7.1 Hz, 3H), 0.87 (d, J = 6.9 Hz, 3H). HRMS(B) (M + H) 425.2089 Calc'd (M + H) 425.2101<br>2nd peak 342: $^1$H NMR (400 MHz, MeOD) δ 8.17 (d, J = 5.8 Hz, 1H), 7.80 (d, J = 2.6 Hz, 1H), 7.66 (t, J = 8.3 Hz, 1H), 7.56 (s, 1H), 7.40 (d, J = 5.8 Hz, 1H), 7.35-7.26 (m, 2H), 5.10 (q, J = 7.0 Hz, 1H), 4.69 (br s, 1H), 4.43-4.24 (m, 2H), 2.17 (s, 3H), 1.80 (br s,1H), 1.56 (d, J = 7.1 Hz, 3H), 0.73 (br s, 3H), 0.62 (br s, 3H). HRMS(B) (M + H) 425.2081 Calc'd (M + H) 424.2101 |
| 343 & 344: (S)-3-(2-(1-(4-(3,5-dimethyl-1H-pyrazol-1-yl)phenyl)ethylamino)pyrimidin-4-yl)-4-isopropyloxazolidin-2-one | Chiral separation was achieved by chiral SFC column chromatography (Column IA 20 × 250 mm column 25% MeOH, 0.2% DEA) to give (S)-3-(2-(((R)-1-(4-(3,5-dimethyl-1H-pyrazol-1-yl)phenyl)ethyl)amino)pyrimidin-4-yl)-4-isopropyloxazolidin-2-one and (S)-3-(2-(((S)-1-(4-(3,5-dimethyl-1H-pyrazol-1-yl)phenyl)ethyl)amino)pyrimidin-4-yl)-4-isopropyloxazolidin-2-one.<br>1st peak 343: $^1$H NMR (400 MHz, MeOD) δ 8.14 (d, J = 5.8 Hz, 1H), 7.56-7.48 (m, 2H), 7.41-7.34 (m, 3H), 6.06 (s, 1H), 5.07-5.02 (m, 1H), 4.46 (br s, 1H), 4.39-4.22 (m, 2H), 2.79-2.60 (m, 1H), 2.26 (s, 3H), 2.24 (s, 3H), 1.58 (d, J = 7.0 Hz, 3H), 1.02 (d, J = 7.1 Hz, 3H), 0.88 (d, J = 6.9 Hz, 3H). HRMS(B) (M + H) 421.2332 Calc'd (M + H) 421.2352<br>2nd peak 344: $^1$H NMR (400 MHz, MeOD) δ 8.15 (d, J = 5.8 Hz, 1H), 7.55-7.47 (m, 2H), 7.41-7.33 (m, 3H), 6.06 (s, 1H), 5.17 (q, J = 7.0 Hz, 1H), 4.74 (br s, 1H), 4.45-4.19 (m, 2H), 2.26 (s, 3H), 2.25 (s, 3H), 2.07 (br s, 1H), 1.56 (d, J = 7.0 Hz, 3H), 0.80 (br s, 3H), 0.65 (br s, 3H). HRMS(B) (M + H) 421.2335 Calc'd (M + H) 421.2352 |
| 345 & 346: (S)-4-isopropyl-3-(2-((1-(5-methyl-1,3,4-oxadiazol-2-yl)ethyl)amino)pyrimidin-4-yl)oxazolidin-2-one | Chiral separation was achieved by chiral SFC column chromatography (AD-H, 5 uM, 20 × 250 mm column, 80 ml/min, 99 bar, eluting 10% MeOH/CO2) to give (S)-4-isopropyl-3-(2-(((R)-1-(5-methyl-1,3,4-oxadiazol-2-yl)ethyl)amino)pyrimidin-4-yl)oxazolidin-2-one and (S)-4-isopropyl-3-(2-(((S)-1-(5-methyl-1,3,4-oxadiazol-2-yl)ethyl)amino)pyrimidin-4-yl)oxazolidin-2-one.<br>1st peak 345: HRMS(B) m/z 333.1668 (M + H)+.<br>RT = 1.96 min.<br>2nd peak 346: HRMS(B) m/z 333.1668 (M + H)+.<br>RT = 1.58 min. |
| 347 & 348: (S)-4-isopropyl-3-(2-((1-(1-methyl-1H-1,2,4-triazol-5-yl)ethyl)amino)pyrimidin-4-yl)oxazolidin-2-one. | Chiral separation was achieved by chiral SFC column chromatography (AD-H, 5 uM, 20 × 250 mm column, 80 ml/min, 99 bar, eluting 10% MeOH/CO2) to give (S)-4-isopropyl-3-(2-(((R)-1-(1-methyl-1H-1,2,4-triazol-5-yl)ethyl)amino)pyrimidin-4-yl)oxazolidin-2-one and (S)-4-isopropyl-3-(2-(((S)-1-(1-methyl-1H-1,2,4-triazol-5-yl)ethyl)amino)pyrimidin-4-yl)oxazolidin-2-one.<br>1st peak 347: HRMS(B) m/z 332.1831 (M + H)+.<br>RT = 1.68 min.<br>2nd peak 348: HRMS(B) m/z 332.1833 (M + H)+.<br>RT = 1.57 min. |
| 349 & 350: (S)-3-(2-((1-(imidazo[2,1-b][1,3,4]thiadiazol-6-yl)ethyl)amino)pyrimidin-4-yl)-4-isopropyloxazolidin-2-one. | Chiral separation was achieved by chiral SFC column chromatography (AD-H, 5 uM, 20 × 250 mm column, 80 ml/min, 99 bar, eluting 10% MeOH/CO2) to give (S)-3-(2-(((R)-1-(imidazo[2,1-b][1,3,4]thiadiazol-6-yl)ethyl)amino)pyrimidin-4-yl)-4-isopropyloxazolidin-2-one and (S)-3-(2-(((S)-1-(imidazo[2,1-b][1,3,4]thiadiazol-6-yl)ethyl)amino)pyrimidin-4-yl)-4-isopropyloxazolidin-2-one.<br>1st peak 349: HRMS(B) m/z 374.1384 (M + H)+.<br>RT = 2.01 min.<br>2nd peak 350: $^1$H NMR (400 MHz, CDCl$_3$) δ 8.43 (s, 1H), 8.12 (d, J = 5.8 Hz, 1H), 7.60 (s, 1H), 7.38 (d, J = 5.8 Hz, 1H), 5.13 (s, 1H), 4.60 (dt, J = 8.3, 3.3 Hz, 1H), 4.33-4.07 (m, 2H), 2.25 (b, 1H), 1.57 (d, J = 6.8 Hz, |

TABLE 10-continued

Chemical name, NMR chemical shifts, chiral separation conditions and LCMS signal for each compound listed in Table 9.

| Example: Name | Chiral separation conditions, peak identification and analytical data |
|---|---|
| | 3H), 0.84-0.52 (b, 6H). HRMS(B) m/z 373.1321 (M+), RT = 1.88 min. |
| 351 & 352: (S)-3-(2-((1-(1-ethyl-1H-1,2,4-triazol-5-yl)ethyl)amino)pyrimidin-4-yl)-4-isopropyloxazolidin-2-one | Chiral separation was achieved by chiral SFC column chromatography (AD-H, 5 uM, 20 × 250 mm column, 80 ml/min, 99 bar, eluting 10% MeOH/CO2) to give (S)-3-(2-(((R)-1-(1-ethyl-1H-1,2,4-triazol-5-yl)ethyl)amino)pyrimidin-4-yl)-4-isopropyloxazolidin-2-one and (S)-3-(2-(((S)-1-(1-ethyl-1H-1,2,4-triazol-5-yl)ethyl)amino)pyrimidin-4-yl)-4-isopropyloxazolidin-2-one<br>1st peak 351: HRMS(B) m/z 346.1985 (M + H)+. RT = 1.89 min.<br>2nd peak 352: HRMS(B) m/z 346.1983 (M + H)+, RT = 1.75 min. |
| 353 & 354: (S)-3-(2-((1-(4-ethyl-4H-1,2,4-triazol-3-yl)ethyl)amino)pyrimidin-4-yl)-4-isopropyloxazolidin-2-one | Chiral separation was achieved by chiral SFC column chromatography (AD-H, 5 uM, 20 × 250 mm column, 80 ml/min, 99 bar, eluting 10% MeOH/CO2) to give (S)-3-(2-(((R)-1-(4-ethyl-4H-1,2,4-triazol-3-yl)ethyl)amino)pyrimidin-4-yl)-4-isopropyloxazolidin-2-one and (S)-3-(2-(((S)-1-(4-ethyl-4H-1,2,4-triazol-3-yl)ethyl)amino)pyrimidin-4-yl)-4-isopropyloxazolidin-2-one<br>1st peak 353: HRMS(B) m/z 346.1984 (M + H)+. RT = 1.80 min.<br>2nd peak 354: HRMS(B) m/z 346.1982 (M + H)+, RT = 1.77 min. |
| 355 & 356: (S)-3-(2-((1-(imidazo[2,1-b]thiazol-6-yl)ethyl)amino)pyrimidin-4-yl)-4-isopropyloxazolidin-2-one | Chiral separation was achieved by chiral SFC column chromatography (AD-H, 5 uM, 20 × 250 mm column, 75 ml/min, 120 bar, eluting 20-30% MeOH/CO2) to give (S)-3-(2-(((R)-1-(imidazo[2,1-b]thiazol-6-yl)ethyl)amino)pyrimidin-4-yl)-4-isopropyloxazolidin-2-one and (S)-3-(2-(((S)-1-(imidazo[2,1-b]thiazol-6-yl)ethyl)amino)pyrimidin-4-yl)-4-isopropyloxazolidin-2-one<br>1st peak 355: HRMS(B) m/z 373.1436 (M + H)+. RT = 1.92 min.<br>2nd peak 356: HRMS(B) m/z 373.1439 (M + H)+, RT = 1.84 min. |
| 357 & 358: N-(4-(1-((4-((S)-4-isopropyl-2-oxooxazolidin-3-yl)pyrimidin-2-yl)amino)ethyl)phenyl)methanesulfonamide | Chiral separation was achieved by chiral SFC column chromatography (AD-H, 5 uM, 20 × 250 mm column, 80 ml/min, 96 bar, eluting 25% MeOH/CO2) to give N-(4-((R)-1-((4-((S)-4-isopropyl-2-oxooxazolidin-3-yl)pyrimidin-2-yl)amino)ethyl)phenyl)methanesulfonamide and N-(4-((S)-1-((4-((S)-4-isopropyl-2-oxooxazolidin-3-yl)pyrimidin-2-yl)amino)ethyl)phenyl)methanesulfonamide<br>1st peak 357: HRMS(B) m/z 420.1689 (M + H)+. RT = 2.08 min.<br>2nd peak 358: HRMS(B) m/z 420.1687 (M + H)+, RT = 1.98 min. |
| 359 & 360: (S)-4-isopropyl-3-(2-((1-(3-(pyridin-2-yl)-1,2,4-oxadiazol-5-yl)ethyl)amino)pyrimidin-4-yl)oxazolidin-2-one | Separation was achieved by silica gel chromatography (10 to 40% EtOAc/heptane) to give (S)-4-isopropyl-3-(2-(((R)-1-(3-(pyridin-2-yl)-1,2,4-oxadiazol-5-yl)ethyl)amino)pyrimidin-4-yl)oxazolidin-2-one and (S)-4-isopropyl-3-(2-(((S)-1-(3-(pyridin-2-yl)-1,2,4-oxadiazol-5-yl)ethyl)amino)pyrimidin-4-yl)oxazolidin-2-one<br>1st peak 359: HRMS(B) m/z 396.1784 (M + H)+. RT = 2.26 min.<br>2nd peak 360: HRMS(B) m/z 396.1784 (M + H)+, RT = 2.20 min. |
| 361 & 362: (S)-4-isopropyl-3-(2-((1-(3-(p-tolyl)-1,2,4-oxadiazol-5-yl)ethyl)amino)pyrimidin-4-yl)oxazolidin-2-one | Separation was achieved by silica gel chromatography (10 to 40% EtOAc/heptane) to give (S)-4-isopropyl-3-(2-(((R)-1-(3-(p-tolyl)-1,2,4-oxadiazol-5-yl)ethyl)amino)pyrimidin-4-yl)oxazolidin-2-one and (S)-4-isopropyl-3-(2-(((S)-1-(3-(p-tolyl)-1,2,4-oxadiazol-5-yl)ethyl)amino)pyrimidin-4-yl)oxazolidin-2-one.<br>1st peak 361: HRMS(B) m/z 409.1985 (M + H)+. RT = 2.88 min.<br>2nd peak 362: $^1$H NMR (400 MHz, CDCl$_3$) δ 8.24 (d, J = 5.8 Hz, 1H), 8.03 (d, J = 5.9 Hz, 2H), 7.59 (d, J = 5.8 Hz, 1H), 7.28 (d, J = 8.0 Hz, 2H), 5.41 (b, 1H), 4.67 (dt, J = 8.2, 3.3 Hz, 1H), 4.36-4.18 (m, 2H), 2.42 (s, 3H), 2.29-2.13 (m, 1H), 1.78 (d, J = 7.2 Hz, 3H), 0.81 (d, J = |

TABLE 10-continued

Chemical name, NMR chemical shifts, chiral separation conditions
and LCMS signal for each compound listed in Table 9.

| Example: Name | Chiral separation conditions, peak identification and analytical data |
|---|---|
| | 7.1 Hz, 3H), 0.73 (d, J = 7.0 Hz, 3H). HRMS(B) m/z 409.1985 (M + H)+, RT = 2.85 min. |
| 363 & 364: (S)-4-isopropyl-3-(2-((1-(4-(methylsulfonyl)phenyl)ethyl)amino)pyrimidin-4-yl)oxazolidin-2-one | Chiral separation was achieved by chiral SFC column chromatography (AD-H, 5 uM, 20 × 250 mm column, 74 ml/min, 100 bar, eluting 25% MeOH/CO2) to give (S)-4-isopropyl-3-(2-(((R)-1-(4-(methylsulfonyl)phenyl)ethyl)amino)pyrimidin-4-yl)oxazolidin-2-one and (S)-4-isopropyl-3-(2-(((S)-1-(4-(methylsulfonyl)phenyl)ethyl)amino)pyrimidin-4-yl)oxazolidin-2-one<br>1st peak 363: HRMS(B) m/z 405.1594 (M + H)+, RT = 2.26 min.<br>2nd peak 364: HRMS(B) m/z 405.1595 (M + H)+, RT = 2.14 min. |
| 365 & 366: (S)-4-isopropyl-3-(2-((1-(3-methyl-1,2,4-oxadiazol-5-yl)ethyl)amino)pyrimidin-4-yl)oxazolidin-2-one | Chiral separation was achieved by chiral SFC column chromatography (AD-H, 5 uM, 20 × 250 mm column, 80 ml/min, 100 bar, eluting 20% IPA/CO2) to give (S)-4-isopropyl-3-(2-(((R)-1-(3-methyl-1,2,4-oxadiazol-5-yl)ethyl)amino)pyrimidin-4-yl)oxazolidin-2-one and (S)-4-isopropyl-3-(2-(((S)-1-(3-methyl-1,2,4-oxadiazol-5-yl)ethyl)amino)pyrimidin-4-yl)oxazolidin-2-one<br>1st peak 365: HRMS(B) m/z 333.1679 (M + H)+, RT = 2.19 min.<br>2nd peak 366: HRMS(B) m/z 333.1680 (M + H)+, RT = 2.12 min. |
| 367 & 368: (S)-3-(2-((1-(3-ethylisoxazol-5-yl)ethyl)amino)pyrimidin-4-yl)-4-isopropyloxazolidin-2-one | Chiral separation was achieved by chiral SFC column chromatography (AD-H, 5 uM, 20 × 250 mm column, 79 ml/min, 100 bar, eluting 20% IPA/CO2) to give (S)-3-(2-(((R)-1-(3-ethylisoxazol-5-yl)ethyl)amino)pyrimidin-4-yl)-4-isopropyloxazolidin-2-one and (S)-3-(2-(((S)-1-(3-ethylisoxazol-5-yl)ethyl)amino)pyrimidin-4-yl)-4-isopropyloxazolidin-2-one<br>1st peak 367: HRMS(B) m/z 346.1886 (M + H)+, RT = 2.51 min.<br>2nd peak 368: HRMS(B) m/z 346.1882 (M + H)+, RT = 2.45 min. |
| 369 & 370: (S)-4-isopropyl-3-(2-((1-(3-propyl-1,2,4-oxadiazol-5-yl)ethyl)amino)pyrimidin-4-yl)oxazolidin-2-one | Chiral separation was achieved by chiral SFC column chromatography (AD-H, 5 uM, 20 × 250 mm column, 75 ml/min, 100 bar, eluting 20% IPA/CO2) to give (S)-4-isopropyl-3-(2-(((R)-1-(3-propyl-1,2,4-oxadiazol-5-yl)ethyl)amino)pyrimidin-4-yl)oxazolidin-2-one and (S)-4-isopropyl-3-(2-(((S)-1-(3-propyl-1,2,4-oxadiazol-5-yl)ethyl)amino)pyrimidin-4-yl)oxazolidin-2-one<br>1st peak 369: HRMS(B) m/z 361.1989 (M + H)+, RT = 2.52 min.<br>2nd peak 370: HRMS(B) m/z 361.1985 (M + H)+, RT = 2.49 min. |
| 371 & 372: (S)-3-(2-((1-(3-cyclopropyl-1,2,4-oxadiazol-5-yl)ethyl)amino)pyrimidin-4-yl)-4-isopropyloxazolidin-2-one | Chiral separation was achieved by chiral SFC column chromatography (AD-H, 5 uM, 20 × 250 mm column, 80 ml/min, 100 bar, eluting 15% IPA/CO2) to give (S)-3-(2-(((R)-1-(3-cyclopropyl-1,2,4-oxadiazol-5-yl)ethyl)amino)pyrimidin-4-yl)-4-isopropyloxazolidin-2-one and (S)-3-(2-(((S)-1-(3-cyclopropyl-1,2,4-oxadiazol-5-yl)ethyl)amino)pyrimidin-4-yl)-4-isopropyloxazolidin-2-one<br>1st peak 371: HRMS(B) m/z 359.1830 (M + H)+, RT = 2.42 min.<br>2nd peak 372: HRMS(B) m/z 359.1833 (M + H)+, RT = 2.37 min. |
| 373 & 374: (S)-4-isopropyl-3-(2-((1-(3-isopropyl-1,2,4-oxadiazol-5-yl)ethyl)amino)pyrimidin-4-yl)oxazolidin-2-one | Chiral separation was achieved by chiral SFC column chromatography (AD-H, 5 uM, 20 × 250 mm column, 80 ml/min, 100 bar, eluting 20% IPA/CO2) to give (S)-4-isopropyl-3-(2-(((R)-1-(3-isopropyl-1,2,4-oxadiazol-5-yl)ethyl)amino)pyrimidin-4-yl)oxazolidin-2-one and (S)-4-isopropyl-3-(2-(((S)-1-(3-isopropyl-1,2,4-oxadiazol-5-yl)ethyl)amino)pyrimidin-4-yl)oxazolidin-2-one<br>1st peak 373: HRMS(B) m/z 361.1990 (M + H)+, RT = 2.58 min.<br>2nd peak 374: HRMS(B) m/z 361.1987 (M + H)+, RT = 2.54 min. |
| 375 & 376: (S)-3-(2-((1-(1-ethyl-1H-pyrazol-3-yl)ethyl)amino)pyrimidin-4- | Chiral separation was achieved by chiral SFC column chromatography (AD-H, 5 uM, 20 × 250 mm column, 78 ml/min, 100 bar, eluting 20% IPA/CO2) to give (S)-3-(2- |

TABLE 10-continued

Chemical name, NMR chemical shifts, chiral separation conditions and LCMS signal for each compound listed in Table 9.

| Example: Name | Chiral separation conditions, peak identification and analytical data |
|---|---|
| yl)-4-isopropyloxazolidin-2-one | (((R)-1-(1-ethyl-1H-pyrazol-3-yl)ethyl)amino)pyrimidin-4-yl)-4-isopropyloxazolidin-2-one and (S)-3-(2-(((S)-1-(1-ethyl-1H-pyrazol-3-yl)ethyl)amino)pyrimidin-4-yl)-4-isopropyloxazolidin-2-one<br>1st peak 375: HRMS(B) m/z 345.2046 (M + H)+.<br>RT = 2.31 min.<br>2nd peak 376: HRMS(B) m/z 345.2050 (M + H)+,<br>RT = 2.26 min. |
| 377 & 378: (S)-3-(2-((1-(2-hydroxyphenyl)ethyl)amino)pyrimidin-4-yl)-4-isopropyloxazolidin-2-one | Chiral separation was achieved by chiral column chromatography (OJ-H, 4.6 × 250 mm column, 1 ml/min, eluting 25% ethanol/Heptane) to give (S)-3-(2-(((R)-1-(2-hydroxyphenyl)ethyl)amino)pyrimidin-4-yl)-4-isopropyloxazolidin-2-one and (S)-3-(2-(((S)-1-(2-hydroxyphenyl)ethyl)amino)pyrimidin-4-yl)-4-isopropyloxazolidin-2-one<br>1st peak 377: HRMS(B) m/z 343.1767 (M + H)+.<br>RT = 2.41 min.<br>2nd peak 378: HRMS(B) m/z 343.1767 (M + H)+,<br>RT = 2.36 min. |
| 379 & 380: (S)-4-isopropyl-3-(2-((1-(5-methyl-1-phenyl-1H-1,2,3-triazol-4-yl)ethyl)amino)pyrimidin-4-yl)oxazolidin-2-one | Chiral separation was achieved by chiral SFC column chromatography (AD-H, 5 uM, 20 × 250 mm column, 874 ml/min, 100 bar, eluting 30% IPA/CO2) to give (S)-4-isopropyl-3-(2-(((R)-1-(5-methyl-1-phenyl-1H-1,2,3-triazol-4-yl)ethyl)amino)pyrimidin-4-yl)oxazolidin-2-one and (S)-4-isopropyl-3-(2-(((S)-1-(5-methyl-1-phenyl-1H-1,2,3-triazol-4-yl)ethyl)amino)pyrimidin-4-yl)oxazolidin-2-one<br>1st peak 379: HRMS(B) m/z 408.2135 (M + H)+.<br>RT = 2.37 min.<br>2nd peak 380: HRMS(B) m/z 408.2140 (M + H)+,<br>RT = 2.31 min. |
| 381 & 382: (S)-4-isopropyl-3-(2-((1-(3-phenyl-1,2,4-oxadiazol-5-yl)ethyl)amino)pyrimidin-4-yl)oxazolidin-2-one | Chiral separation was achieved by chiral SFC column chromatography (AD-H, 5 uM, 20 × 250 mm column, 74 ml/min, 100 bar, eluting 20%-35% IPA/CO2) to give (S)-4-isopropyl-3-(2-(((R)-1-(3-phenyl-1,2,4-oxadiazol-5-yl)ethyl)amino)pyrimidin-4-yl)oxazolidin-2-one and (S)-4-isopropyl-3-(2-(((S)-1-(3-phenyl-1,2,4-oxadiazol-5-yl)ethyl)amino)pyrimidin-4-yl)oxazolidin-2-one<br>1st peak 381: HRMS(B) m/z 395.1792 (M + H)+.<br>RT = 2.63 min.<br>2nd peak 382: HRMS(B) m/z 395.1818(M + H)+,<br>RT = 2.58 min. |
| 383 & 384: (S)-3-(2-(((R)-1-(1H-pyrrolo[2,3-b]pyridin-5-yl)ethyl)amino)pyrimidin-4-yl)-4-isopropyloxazolidin-2-one | Chiral separation was achieved by chiral SFC column chromatography (IA, 20 × 250 mm column, 74 ml/min, 99 bar, eluting 45% MeOH with 5 mM NH4OH/CO2) to give (S)-3-(2-(((R)-1-(1H-pyrrolo[2,3-b]pyridin-5-yl)ethyl)amino)pyrimidin-4-yl)-4-isopropyloxazolidin-2-one and (S)-3-(2-(((S)-1-(1H-pyrrolo[2,3-b]pyridin-5-yl)ethyl)amino)pyrimidin-4-yl)-4-isopropyloxazolidin-2-one<br>1st peak 383: HRMS(B) m/z 367.1862 (M + H)+.<br>RT = 2.10 min.<br>2nd peak 384: $^1$H NMR (400 MHz, CDCl$_3$) δ 8.32 (d, J = 2.2 Hz, 1H), 8.19 (d, J = 5.8 Hz, 1H), 7.94 (d, J = 2.1 Hz, 1H), 7.47 (d, J = 5.8 Hz, 1H), 7.38 (d, J = 3.5 Hz, 1H), 6.46 (d, J = 3.5 Hz, 1H), 5.30-5.08 (m, 1H), 4.73-4.51 (m, 1H), 4.28 (t, J = 8.8 Hz, 1H), 4.19 (dd, J = 9.0, 3.1 Hz, 1H), 1.78 (dd, J = 31.8, 17.0 Hz, 1H), 1.66 (d, J = 6.9 Hz, 3H), 0.56 (s, 6H). HRMS(B) m/z 367.1870(M + H)+, RT = 2.00 min. |
| 385 & 386: (S)-4-isopropyl-3-(2-((1-(1-methyl-1H-benzo[d]imidazol-5-yl)ethyl)amino)pyrimidin-4-yl)oxazolidin-2-one | Chiral separation was achieved by chiral SFC column chromatography (AD-H, 5 uM, 20 × 250 mm column, 80 ml/min, 99 bar, eluting 20% IPA/CO2) to give (S)-4-isopropyl-3-(2-(((R)-1-(1-methyl-1H-benzo[d]imidazol-5-yl)ethyl)amino)pyrimidin-4-yl)oxazolidin-2-one and (S)-4-isopropyl-3-(2-(((S)-1-(1-methyl-1H-benzo[d]imidazol-5-yl)ethyl)amino)pyrimidin-4-yl)oxazolidin-2-one<br>1st peak 385: HRMS(B) m/z 381.2026 (M + H)+.<br>RT = 2.05 min.<br>2nd peak 386: HRMS(B) m/z 381.2022(M + H)+,<br>RT = 1.96 min. |
| 387 & 388: (S)-4-isopropyl-3-(2-((1-(2-oxo-2,3-dihydro-1H- | Chiral separation was achieved by chiral SFC column chromatography (AD-H, 5 uM, 20 × 250 mm column, 80 ml/min, 100 bar, eluting 25% IPA/CO2) to give (S)-4- |

TABLE 10-continued

Chemical name, NMR chemical shifts, chiral separation conditions and LCMS signal for each compound listed in Table 9.

| Example: Name | Chiral separation conditions, peak identification and analytical data |
|---|---|
| benzo[d]imidazol-5-yl)ethyl)amino)pyrimidin-4-yl)oxazolidin-2-one | isopropyl-3-(2-(((R)-1-(2-oxo-2,3-dihydro-1H-benzo[d]imidazol-5-yl)ethyl)amino)pyrimidin-4-yl)oxazolidin-2-one and (S)-4-isopropyl-3-(2-(((S)-1-(2-oxo-2,3-dihydro-1H-benzo[d]imidazol-5-yl)ethyl)amino)pyrimidin-4-yl)oxazolidin-2-one<br>1st peak 387: HRMS(B) m/z 383.1811 (M + H)+. RT = 1.90 min.<br>2nd peak 388: HRMS(B) m/z 383.1815(M + H)+, RT = 1.85 min. |
| 389 & 390: (S)-3-(2-((1-(benzo[d]thiazol-2-yl)ethyl)amino)pyrimidin-4-yl)-4-isopropyloxazolidin-2-one | Chiral separation was achieved by chiral SFC column chromatography (ID, 5 uM, 20 × 250 mm column, 74 ml/min, 100 bar, eluting 35% MeOH/CO2) to give (S)-3-(2-(((R)-1-(benzo[d]thiazol-2-yl)ethyl)amino)pyrimidin-4-yl)-4-isopropyloxazolidin-2-one and (S)-3-(2-(((S)-1-(benzo[d]thiazol-2-yl)ethyl)amino)pyrimidin-4-yl)-4-isopropyloxazolidin-2-one<br>1st peak 389: HRMS(B) m/z 384.1488 (M + H)+. RT = 2.44 min.<br>2nd peak 390: HRMS(B) m/z 384.1473(M + H)+, RT = 2.36 min. |
| 391 & 392: (S)-3-(2-((1-(indolizin-2-yl)ethyl)amino)pyrimidin-4-yl)-4-isopropyloxazolidin-2-one | Chiral separation was achieved by chiral SFC column chromatography (OJ, 5 uM, 20 × 250 mm column, 75 ml/min, 120 bar, eluting 15-55% MeOH/CO2) to give (S)-3-(2-(((R)-1-(indolizin-2-yl)ethyl)amino)pyrimidin-4-yl)-4-isopropyloxazolidin-2-one and (S)-3-(2-(((S)-1-(indolizin-2-yl)ethyl)amino)pyrimidin-4-yl)-4-isopropyloxazolidin-2-one<br>1st peak 391: HRMS(B) m/z 366.1926 (M + H)+. RT = 2.66 min.<br>2nd peak 392: HRMS(B) m/z 366.1918(M + H)+, RT = 2.63 min. |
| 393 & 394: (S)-4-isopropyl-3-(2-((1-(3-(2-methoxyphenyl)-1,2,4-oxadiazol-5-yl)ethyl)amino)pyrimidin-4-yl)oxazolidin-2-one | Chiral separation was achieved by chiral SFC column chromatography (AD-H, 5 uM, 20 × 250 mm column, 80 ml/min, 100 bar, eluting 5-55% MeOH/CO2) to give (S)-4-isopropyl-3-(2-(((R)-1-(3-(2-methoxyphenyl)-1,2,4-oxadiazol-5-yl)ethyl)amino)pyrimidin-4-yl)oxazolidin-2-one and (S)-4-isopropyl-3-(2-(((S)-1-(3-(2-methoxyphenyl)-1,2,4-oxadiazol-5-yl)ethyl)amino)pyrimidin-4-yl)oxazolidin-2-one<br>1st peak 393: HRMS(B) m/z 425.1925 (M + H)+. RT = 2.57 min.<br>2nd peak 394: HRMS(B) m/z 425.1916(M + H)+, RT = 2.52 min. |
| 395 & 396: (S)-4-isopropyl-3-(2-((1-(3-(3-methoxyphenyl)-1,2,4-oxadiazol-5-yl)ethyl)amino)pyrimidin-4-yl)oxazolidin-2-one | Chiral separation was achieved by chiral SFC column chromatography (IA, 5 uM, 20 × 250 mm column, 74 ml/min, 100 bar, eluting m25% MeOH/CO2) to give (S)-4-isopropyl-3-(2-(((R)-1-(3-(3-methoxyphenyl)-1,2,4-oxadiazol-5-yl)ethyl)amino)pyrimidin-4-yl)oxazolidin-2-one and (S)-4-isopropyl-3-(2-(((S)-1-(3-(3-methoxyphenyl)-1,2,4-oxadiazol-5-yl)ethyl)amino)pyrimidin-4-yl)oxazolidin-2-one<br>1st peak 395: HRMS(B) m/z 425.1924 (M + H)+. RT = 2.60 min.<br>2nd peak 396: $^1$H NMR (400 MHz, CDCl$_3$) δ 7.56 (dt, J = 7.7, 1.2 Hz, 1H), 7.49 (dt, J = 3.7, 1.8 Hz, 2H), 7.29 (t, J = 8.0 Hz, 2H), 6.96 (ddd, J = 8.3, 2.7, 0.9 Hz, 1H), 5.34 (b, 1H), 4.58 (dt, J = 8.2, 3.3 Hz, 1H), 4.37-4.03 (m, 2H), 3.78 (s, 3H), 2.12 (b, 1H), 1.68 (d, J = 7.1 Hz, 3H), 0.73 (d, J = 7.1 Hz, 3H), 0.65 (d, J = 7.0 Hz, 3H). HRMS(B) m/z 425.1924(M + H)+, RT = 2.54 min. |
| 397 & 398: (S)-3-(2-((1-(3-(3-fluorophenyl)-1,2,4-oxadiazol-5-yl)ethyl)amino)pyrimidin-4-yl)-4-isopropyloxazolidin-2-one | Chiral separation was achieved by chiral SFC column chromatography (AD-H, 5 uM, 20 × 250 mm column, 75 ml/min, 100 bar, eluting 20% MeOH/CO2) to give (S)-3-(2-(((R)-1-(3-(3-fluorophenyl)-1,2,4-oxadiazol-5-yl)ethyl)amino)pyrimidin-4-yl)-4-isopropyloxazolidin-2-one and (S)-3-(2-(((S)-1-(3-(3-fluorophenyl)-1,2,4-oxadiazol-5-yl)ethyl)amino)pyrimidin-4-yl)-4-isopropyloxazolidin-2-one<br>1st peak 397: HRMS(B) m/z 413.1729 (M + H)+. RT = 2.66 min.<br>2nd peak 398: $^1$H NMR (400 MHz, CDCl$_3$) δ 7.86 (dt, J = 7.8, 1.2 Hz, 1H), 7.77 (ddd, J = 9.4, 2.7, 1.5 Hz, 2H), 7.60 (d, J = 5.3 Hz, 1H), 7.46 (td, J = 8.0, 5.7 Hz, 1H), 7.22 (tdd, J = 8.4, 2.6, 1.0 Hz, 1H), 5.44 (b, 1H), 4.68 |

TABLE 10-continued

Chemical name, NMR chemical shifts, chiral separation conditions and LCMS signal for each compound listed in Table 9.

| Example: Name | Chiral separation conditions, peak identification and analytical data |
|---|---|
| | (dt, J = 8.3, 3.3 Hz, 1H), 4.44-4.11 (m, 2H), 2.18 (d, J = 8.4 Hz, 1H), 1.78 (d, J = 7.1 Hz, 3H), 0.83 (d, J = 6.9 Hz, 3H), 0.75 (d, J = 6.9 Hz, 3H). HRMS(B) m/z 413.1732(M + H)+, RT = 2.61 min. |
| 399 & 400: (S)-3-(2-((1-(3-cyclopentyl-1,2,4-oxadiazol-5-yl)ethyl)amino)pyrimidin-4-yl)-4-isopropyloxazolidin-2-one | Chiral separation was achieved by chiral SFC column chromatography (IA, 5 uM, 20 × 250 mm column, 74 ml/min, 99 bar, eluting 15% MeOH/CO2) to give (S)-3-(2-(((R)-1-(3-cyclopentyl-1,2,4-oxadiazol-5-yl)ethyl)amino)pyrimidin-4-yl)-4-isopropyloxazolidin-2-one and (S)-3-(2-(((S)-1-(3-cyclopentyl-1,2,4-oxadiazol-5-yl)ethyl)amino)pyrimidin-4-yl)-4-isopropyloxazolidin-2-one<br>1st peak 399: HRMS(B) m/z 387.2133 (M + H)+.<br>RT = 2.54 min.<br>2nd peak 400: HRMS(B) m/z 387.2117(M + H)+, RT = 2.50 min. |
| 401 & 402: (S)-3-(2-((1-(3-cyclohexyl-1,2,4-oxadiazol-5-yl)ethyl)amino)pyrimidin-4-yl)-4-isopropyloxazolidin-2-one | Chiral separation was achieved by chiral SFC column chromatography (IA, 5 uM, 20 × 250 mm column, 74 ml/min, 99 bar, eluting 30% MeOH/CO2) to give (S)-3-(2-(((R)-1-(3-cyclohexyl-1,2,4-oxadiazol-5-yl)ethyl)amino)pyrimidin-4-yl)-4-isopropyloxazolidin-2-one and (S)-3-(2-(((S)-1-(3-cyclohexyl-1,2,4-oxadiazol-5-yl)ethyl)amino)pyrimidin-4-yl)-4-isopropyloxazolidin-2-one<br>1st peak 401: HRMS(B) m/z 401.2277 (M + H)+.<br>RT = 2.71 min.<br>2nd peak 402: HRMS(B) m/z 401.2288(M + H)+, RT = 2.68 min. |
| 403 & 404: (S)-3-(2-((1-(3-(tert-butyl)-1,2,4-oxadiazol-5-yl)ethyl)amino)pyrimidin-4-yl)-4-isopropyloxazolidin-2-one | Chiral separation was achieved by chiral SFC column chromatography (IA, 5 uM, 20 × 250 mm column, 74 ml/min, 100 bar, eluting 15% MeOH/CO2) to give (S)-3-(2-(((R)-1-(3-(tert-butyl)-1,2,4-oxadiazol-5-yl)etnyl)amino)pyrimidin-4-yl)-4-isopropyloxazolidin-2-one and (S)-3-(2-(((S)-1-(3-(tert-butyl)-1,2,4-oxadiazol-5-yl)ethyl)amino)pyrimidin-4-yl)-4-isopropyloxazolidin-2-one<br>1st peak 403: HRMS(B) m/z 375.2131 (M + H)+.<br>RT = 2.47 min.<br>2nd peak 404: HRMS(B) m/z375.2130 (M + H)+, RT = 2.44 min. |
| 405 & 406: (S)-3-(2-((1-(3-isobutyl-1,2,4-oxadiazol-5-yl)ethyl)amino)pyrimidin-4-yl)-4-isopropyloxazolidin-2-one | Chiral separation was achieved by chiral SFC column chromatography (IA, 5 uM, 20 × 250 mm column, 74 ml/min, 100 bar, eluting 15% MeOH/CO2) to give (S)-3-(2-(((R)-1-(3-isobutyl-1,2,4-oxadiazol-5-yl)ethyl)amino)pyrimidin-4-yl)-4-isopropyloxazolidin-2-one and (S)-3-(2-(((S)-1-(3-isobutyl-1,2,4-oxadiazol-5-yl)ethyl)amino)pyrimidin-4-yl)-4-isopropyloxazolidin-2-one<br>1st peak 405: HRMS(B) m/z 375.2120 (M + H)+.<br>RT = 2.45 min.<br>2nd peak 406: HRMS(B) m/z 375.2135 (M + H)+, RT = 2.44 min. |
| 407 & 408: (S)-3-(2-((1-(5-(4-fluorophenyl)-1,3,4-oxadiazol-2-yl)ethyl)amino)pyrimidin-4-yl)-4-isopropyloxazolidin-2-one | Chiral separation was achieved by chiral SFC column chromatography (IA, 5 uM, 20 × 250 mm column, 74 ml/min, 99 bar, eluting 30% IPA/CO2) to give (S)-3-(2-(((R)-1-(5-(4-fluorophenyl)-1,3,4-oxadiazol-2-yl)ethyl)amino)pyrimidin-4-yl)-4-isopropyloxazolidin-2-one and (S)-3-(2-(((S)-1-(5-(4-fluorophenyl)-1,3,4-oxadiazol-2-yl)ethyl)amino)pyrimidin-4-yl)-4-isopropyloxazolidin-2-one<br>1st peak 407: HRMS(B) m/z 413.1713 (M + H)+.<br>RT = 2.31 min.<br>2nd peak 408: HRMS(B) m/z 413.1721 (M + H)+, RT = 2.25 min. |
| 409 & 410: (S)-3-(2-((1-(benzo[d]oxazol-2-yl)ethyl)amino)pyrimidin-4-yl)-4-isopropyloxazolidin-2-one | Chiral separation was achieved by chiral SFC column chromatography (IA, 5 uM, 20 × 250 mm column, 74 ml/min, 99 bar, eluting 25% MeOH/CO2) to give (S)-3-(2-(((R)-1-(benzo[d]oxazol-2-yl)ethyl)amino)pyrimidin-4-yl)-4-isopropyloxazolidin-2-one and (S)-3-(2-(((S)-1-(benzo[d]oxazol-2-yl)ethyl)amino)pyrimidin-4-yl)-4-isopropyloxazolidin-2-one<br>1st peak 409: HRMS(B) m/z 368.1729 (M + H)+.<br>RT = 2.66 min.<br>2nd peak 410: $^1$H NMR (400 MHz, CDCl$_3$) δ 7.80-7.61 |

TABLE 10-continued

Chemical name, NMR chemical shifts, chiral separation conditions and LCMS signal for each compound listed in Table 9.

| Example: Name | Chiral separation conditions, peak identification and analytical data |
|---|---|
| | (m, 1H), 7.54 (s, 1H), 7.51-7.42 (m, 2H), 7.40-7.21 (m, 2H), 6.40 (b, 1H), 5.39 (s, 1H), 4.64 (dt, J = 8.1, 3.2 Hz, 1H), 4.36-4.17 (m, 2H), 2.11 (b, 1H), 1.77 (d, J = 6.9 Hz, 3H), 0.64 (b, 6H). HRMS(B) m/z 368.1727 (M + H)+, RT = 2.60 min. |
| 411 & 412: (S)-3-(2-((1-(4-(4-chlorophenyl)-5-methylthiazol-2-yl)ethyl)amino)pyrimidin-4-yl)-4-isopropyloxazolidin-2-one | Separation was achieved by silica gel chromatography (10 to 50% EtOAc/heptane) to give (S)-3-(2-(((R)-1-(4-(4-chlorophenyl)-5-methylthiazol-2-yl)ethyl)amino)pyrimidin-4-yl)-4-isopropyloxazolidin-2-one and (S)-3-(2-(((S)-1-(4-(4-chlorophenyl)-5-methylthiazol-2-yl)ethyl)amino)pyrimidin-4-yl)-4-isopropyloxazolidin-2-one<br>1st peak 411: HRMS(B) m/z 458.1401 (M + H)+. RT = 3.02 min.<br>2nd peak 412: HRMS(B) m/z 458.1401 (M + H)+, RT = 2.92 min. |
| 413 & 414: (S)-3-(2-((1-(3-ethyl-1,2,4-oxadiazol-5-yl)ethyl)amino)pyrimidin-4-yl)-4-isopropyloxazolidin-2-one | Chiral separation was achieved by chiral SFC column chromatography (AD-H column (80 g/min, 80 bar, 20 × 250 mm) eluting 15% MeOH/CO2) to give (S)-3-(2-(((R)-1-(3-ethyl-1,2,4-oxadiazol-5-yl)ethyl)amino)pyrimidin-4-yl)-4-isopropyloxazolidin-2-one and (S)-3-(2-(((S)-1-(3-ethyl-1,2,4-oxadiazol-5-yl)ethyl)amino)pyrimidin-4-yl)-4-isopropyloxazolidin-2-one<br>1st peak 413: HRMS(B) m/z 346.1753 RT = 2.13 min.<br>2nd peak 414: HRMS(B) m/z 346.1753 RT = 2.05 min. |
| 415 & 416: (S)-4-isopropyl-3-(2-((1-(4-methylthiazol-2-yl)ethyl)amino)pyrimidin-4-yl)oxazolidin-2-one | Chiral separation was achieved by chiral SFC column chromatography (AD-H column (75 ml/min, 120 bar, 20 × 250 mm) eluting 10-25% MeOH/CO2) to give (S)-4-isopropyl-3-(2-(((R)-1-(4-methylthiazol-2-yl)ethyl)amino)pyrimidin-4-yl)oxazolidin-2-one and (S)-4-isopropyl-3-(2-(((S)-1-(4-methylthiazol-2-yl)ethyl)amino)pyrimidin-4-yl)oxazolidin-2-one<br>1st peak 415: HRMS(B) m/z 347.1416 RT = 2.25 min.<br>2nd peak 416: HRMS(B) m/z 347.1416 RT = 2.17 min. |
| 417 & 418: (S)-4-isopropyl-3-(2-((1-(thiophen-2-yl)ethyl)amino)pyrimidin-4-yl)oxazolidin-2-one | Chiral separation was achieved by chiral SFC column chromatography (AD-H column (75 ml/min, 120 bar, 20 × 250 mm) eluting 10-25% MeOH/CO2) to give (S)-4-isopropyl-3-(2-(((R)-1-(thiophen-2-yl)ethyl)amino)pyrimidin-4-yl)oxazolidin-2-one and (S)-4-isopropyl-3-(2-(((S)-1-(thiophen-2-yl)ethyl)amino)pyrimidin-4-yl)oxazolidin-2-one<br>1st peak 417: HRMS(B) m/z 332.1307 RT = 2.54 min.<br>2nd peak 418: HRMS(B) m/z 332.1307 RT = 2.53 min. |
| 419 & 420: (S)-3-(2-((1-(furan-2-yl)ethyl)amino)pyrimidin-4-yl)-4-isopropyloxazolidin-2-one | Chiral separation was achieved by chiral SFC column chromatography (AD-H column (75 ml/min, 120 bar, 20 × 250 mm) eluting 10-25% MeOH/CO2) to give (S)-3-(2-(((S)-1-(furan-2-yl)ethyl)amino)pyrimidin-4-yl)-4-isopropyloxazolidin-2-one and (S)-3-(2-(((R)-1-(furan-2-yl)ethyl)amino)pyrimidin-4-yl)-4-isopropyloxazolidin-2-one<br>1st peak 419: HRMS(B) m/z 316.1535 RT = 2.37 min.<br>2nd peak 420: HRMS(B) m/z 316.1535 RT = 2.39 min. |
| 421 & 422: (S)-4-isopropyl-3-(2-((1-(3-(pyridin-4-yl)-1,2,4-oxadiazol-5-yl)ethyl)amino)pyrimidin-4-yl)oxazolidin-2-one | Chiral separation was achieved by chiral SFC column chromatography (IA column (75 ml/min, 120 bar, 20 × 250 mm) eluting 15-25% MeOH/CO2) to give (S)-4-isopropyl-3-(2-(((R)-1-(3-(pyridin-4-yl)-1,2,4-oxadiazol-5-yl)ethyl)amino)pyrimidin-4-yl)oxazolidin-2-one and (S)-4-isopropyl-3-(2-(((S)-1-(3-(pyridin-4-yl)-1,2,4-oxadiazol-5-yl)ethyl)amino)pyrimidin-4-yl)oxazolidin-2-one<br>1st peak 421: HRMS(B) m/z 395.1706 RT = 1.75 min.<br>2nd peak 422: HRMS(B) m/z 395.1706 RT = 2.25 min. |
| 423 & 424: (S)-3-(2-((1-(3-(2-chlorophenyl)-1,2,4-oxadiazol-5-yl)ethyl)amino)pyrimidin-4-yl)-4-isopropyloxazolidin-2-one | Chiral separation was achieved by chiral SFC column chromatography (IA column (75 ml/min, 120 bar, 20 × 250 mm) eluting 15-25% MeOH/CO2) to give (S)-3-(2-(((R)-1-(3-(2-chlorophenyl)-1,2,4-oxadiazol-5-yl)ethyl)amino)pyrimidin-4-yl)-4-isopropyloxazolidin-2-one and (S)-3-(2-(((S)-1-(3-(2-chlorophenyl)-1,2,4-oxadiazol-5-yl)ethyl)amino)pyrimidin-4-yl)-4-isopropyloxazolidin-2-one<br>1st peak 423: HRMS(B) m/z 428.1364 RT = 3.01 min.<br>2nd peak 424: HRMS(B) m/z 428.1364 RT = 2.79 min. |
| 425 & 426: (S)-3-(2-((1-(3-(4-chlorophenyl)-1,2,4- | Chiral separation was achieved by chiral SFC column chromatography (IA column (75 ml/min, 120 bar, 20 × |

TABLE 10-continued

Chemical name, NMR chemical shifts, chiral separation conditions
and LCMS signal for each compound listed in Table 9.

| Example: Name | Chiral separation conditions, peak identification and analytical data |
|---|---|
| oxadiazol-5-yl)ethyl)amino)pyrimidin-4-yl)-4-isopropyloxazolidin-2-one | 250 mm) eluting 15-25% MeOH/CO2 to give (S)-3-(2-(((R)-1-(3-(4-chlorophenyl)-1,2,4-oxadiazol-5-yl)ethyl)amino)pyrimidin-4-yl)-4-isopropyloxazolidin-2-one and (S)-3-(2-(((S)-1-(3-(4-chlorophenyl)-1,2,4-oxadiazol-5-yl)ethyl)amino)pyrimidin-4-yl)-4-isopropyloxazolidin-2-one<br>1st peak 425: HRMS(B) m/z 428.1364 RT = 2.65 min.<br>2nd peak 426: $^1$H NMR (400 MHz, MeOD) δ 8.22 (d, J = 5.8 Hz, 1.0H), 8.08-7.97 (m, 2.07 H), 7.63-7.40 (m, 3.09 H), 5.41 (q, J = 7.2 Hz, 1.04 H), 4.75-4.63 (m, 0.97 H), 4.33 (d, J = 6.3 Hz, 2.18 H), 1.76 (d, J = 7.2 Hz, 3.31 H), 1.07-0.85 (m, 0.95 H), 0.70 (d, J = 38.0 Hz, 5.81 H). HRMS(B) m/z 428.1364 |
| 427: (S)-4-isopropyl-3-(2-((1-(3-(pyridin-3-yl)-1,2,4-oxadiazol-5-yl)ethyl)amino)pyrimidin-4-yl)oxazolidin-2-one | Chiral separation was achieved by chiral SFC column chromatography (IA column (75 ml/min, 120 bar, 20 × 250 mm) eluting 15-25% MeOH/CO2 to give (S)-4-isopropyl-3-(2-(((R)-1-(3-(pyridin-3-yl)-1,2,4-oxadiazol-5-yl)ethyl)amino)pyrimidin-4-yl)oxazolidin-2-one and (S)-4-isopropyl-3-(2-(((S)-1-(3-(pyridin-3-yl)-1,2,4-oxadiazol-5-yl)ethyl)amino)pyrimidin-4-yl)oxazolidin-2-one<br>2nd peak 427: HRMS(B) m/z 395.1706 RT = 2.24 min. |
| 428 & 429: (S)-3-(2-((1-(1-ethyl-1H-pyrazol-5-yl)ethyl)amino)pyrimidin-4-yl)-4-isopropyloxazolidin-2-one | Chiral separation was achieved by chiral SFC column chromatography (AD column (75 g/min, 120 bar, 20 × 250 mm) eluting 25% IPA/0.2% DEA/CO2) to give (S)-3-(2-(((R)-1-(1-ethyl-1H-pyrazol-5-yl)ethyl)amino)pyrimidin-4-yl)-4-isopropyloxazolidin-2-one and (S)-3-(2-(((S)-1-(1-ethyl-1H-pyrazol-5-yl)ethyl)amino)pyrimidin-4-yl)-4-isopropyloxazolidin-2-one<br>1st peak 428: HRMS(B) m/z 345.2005 (M + H) RT = 2.28 min.<br>2nd peak 429: HRMS(B) m/z 345.2044 (M + H) RT = 2.21 min. |
| 430: (S)-4-isopropyl-3-(2-(((S)-1-(3-(m-tolyl)-1,2,4-oxadiazol-5-yl)ethyl)amino)pyrimidin-4-yl)oxazolidin-2-one | Chiral separation was achieved by chiral SFC column chromatography (AD column (75 g/min, 120 bar, 20 × 250 mm) eluting 25-35% IPA/0.2% DEA/CO2) to give (S)-4-isopropyl-3-(2-(((R)-1-(3-(m-tolyl)-1,2,4-oxadiazol-5-yl)ethyl)amino)pyrimidin-4-yl)oxazolidin-2-one and (S)-4-isopropyl-3-(2-(((S)-1-(3-(m-tolyl)-1,2,4-oxadiazol-5-yl)ethyl)amino)pyrimidin-4-yl)oxazolidin-2-one<br>2nd peak 430: HRMS(B) m/z 345.2044 (M + H) RT = 2.82 min. |
| 431 & 432: (S)-4-isopropyl-3-(2-((1-(2-phenylthiazol-5-yl)ethyl)amino)pyrimidin-4-yl)oxazolidin-2-one | Chiral separation was achieved by chiral SFC column chromatography (AD column (75 g/min, 120 bar, 20 × 250 mm) eluting 40% IPA/0.2% DEA/CO2) to give (S)-4-isopropyl-3-(2-(((R)-1-(2-phenylthiazol-5-yl)ethyl)amino)pyrimidin-4-yl)oxazolidin-2-one and (S)-4-isopropyl-3-(2-(((S)-1-(2-phenylthiazol-5-yl)ethyl)amino)pyrimidin-4-yl)oxazolidin-2-one<br>1st peak 431: HRMS(B) m/z 409.1573 RT = 2.33 min.<br>2nd peak 432: $^1$H NMR (400 MHz, MeOD) δ 8.19 (d, J = 5.8 Hz, 1H), 7.92-7.78 (m, 2H), 7.65 (d, J = 1.1 Hz, 1H), 7.53-7.27 (m, 4H), 5.43 (q, J = 6.9 Hz, 1H), 4.74 (dt, J = 7.8, 3.7 Hz, 1H), 4.41-4.20 (m, 2H), 2.16 (s, 1H), 1.69 (d, J = 7.0 Hz, 3H), 1.15 (d, J = 6.1 Hz, 1H), 0.88-0.49 (m, 6H). HRMS(B) m/z 409.1573 |
| 433 & 434: (S)-4-isopropyl-3-(2-((1-(3-(o-tolyl)-1,2,4-oxadiazol-5-yl)ethyl)amino)pyrimidin-4-yl)oxazolidin-2-one | Chiral separation was achieved by chiral SFC column chromatography (AD column (75 g/min, 120 bar, 20 × 250 mm) eluting 25-40% IPA/0.2% DEA/CO2) to give (S)-4-isopropyl-3-(2-(((R)-1-(3-(o-tolyl)-1,2,4-oxadiazol-5-yl)ethyl)amino)pyrimidin-4-yl)oxazolidin-2-one and (S)-4-isopropyl-3-(2-(((S)-1-(3-(o-tolyl)-1,2,4-oxadiazol-5-yl)ethyl)amino)pyrimidin-4-yl)oxazolidin-2-one<br>1st peak 433: HRMS(B) m/z 409.1 (M + H) RT = 2.25 min.<br>2nd peak 434: $^1$H NMR (400 MHz, MeOD) δ 8.20 (d, J = 5.8 Hz, 1H), 7.90 (dd, J = 7.7, 1.4 Hz, 1H), 7.47 (d, J = 5.8 Hz, 1H), 7.41-7.25 (m, 3H), 5.40 (q, J = 7.2 Hz, 1H), 4.69 (s, 1H), 4.44-4.22 (m, 2H), 3.34 (s, 2H), 2.54 (s, 3H), 1.75 (d, J = 7.2 Hz, 3H), 1.15 (d, J = 6.1 Hz, 1H), 0.69 (d, J = 35.0 Hz, 6H). HRMS(B) m/z 409.1 (M + H) |
| 435 & 436: 4-(1-((4-((S)-4-isopropyl-2-oxooxazolidin-3-yl)pyrimidin-2- | Chiral separation was achieved by chiral SFC column chromatography (AS-H column (80 g/min, 120 bar, 20 × 250 mm) eluting 15% IPA/0.2% DEA/CO2) to give 4- |

TABLE 10-continued

Chemical name, NMR chemical shifts, chiral separation conditions
and LCMS signal for each compound listed in Table 9.

| Example: Name | Chiral separation conditions, peak identification and analytical data |
|---|---|
| yl)amino)ethyl)-N,N-dimethylbenzenesulfonamide | ((R)-1-((4-((S)-4-isopropyl-2-oxooxazolidin-3-yl)pyrimidin-2-yl)amino)ethyl)-N,N-dimethylbenzenesulfonamide and 4-((S)-1-((4-((S)-4-isopropyl-2-oxooxazolidin-3-yl)pyrimidin-2-yl)amino)ethyl)-N,N-dimethylbenzenesulfonamide<br>1st peak 435: HRMS(B) m/z 433.1784 RT = 2.45 min.<br>2nd peak 436: HRMS(B) m/z 433.1784 RT = 2.32 min. |
| 437 & 438: (S)-4-isopropyl-3-(2-((1-(thiazol-4-yl)ethyl)amino)pyrimidin-4-yl)oxazolidin-2-one | Chiral separation was achieved by chiral SFC column chromatography (IC column (75 g/min, 120 bar, 20 × 250 mm) eluting 25% IPA/0.2% DEA/CO2) to give (S)-4-isopropyl-3-(2-(((S)-1-(thiazol-4-yl)ethyl)amino)pyrimidin-4-yl)oxazolidin-2-one and (S)-4-isopropyl-3-(2-(((R)-1-(thiazol-4-yl)ethyl)amino)pyrimidin-4-yl)oxazolidin-2-one<br>1st peak 437: HRMS(B) m/z 333.1259 RT = 1.88 min.<br>2nd peak 438: HRMS(B) m/z 333.1259 RT = 1.98 min. |
| 439 & 440: (S)-4-isopropyl-3-(2-((1-(3-(4-methoxyphenyl)-1,2,4-oxadiazol-5-yl)ethyl)amino)pyrimidin-4-yl)oxazolidin-2-one | Chiral separation was achieved by chiral SFC column chromatography (AI column (70 g/min, 120 bar, 20 × 250 mm) eluting 20% IPA/0.2% DEA/CO2) to give (S)-4-isopropyl-3-(2-(((R)-1-(3-(4-methoxyphenyl)-1,2,4-oxadiazol-5-yl)etnyl)amino)pyrimidin-4-yl)oxazolidin-2-one and (S)-4-isopropyl-3-(2-(((S)-1-(3-(4-methoxyphenyl)-1,2,4-oxadiazol-5-yl)ethyl)amino)pyrimidin-4-yl)oxazolidin-2-one<br>1st peak 438: HRMS(B) m/z 425.1921 (M + H) RT = 2.49 min.<br>2nd peak 439: HRMS(B) m/z 425.1923 (M + H) RT = 2.42 min. |
| 441 & 442: (S)-3-(2-((1-(3-(4-fluorophenyl)-1,2,4-oxadiazol-5-yl)ethyl)amino)pyrimidin-4-yl)-4-isopropyloxazolidin-2-one | Chiral separation was achieved by chiral SFC column chromatography (AI column (70 g/min, 120 bar, 20 × 250 mm) eluting 25% IPA/0.2% DEA/CO2) to give (S)-3-(2-(((R)-1-(3-(4-fluorophenyl)-1,2,4-oxadiazol-5-yl)ethyl)amino)pyrimidin-4-yl)-4-isopropyloxazolidin-2-one and (S)-3-(2-(((S)-1-(3-(4-fluorophenyl)-1,2,4-oxadiazol-5-yl)ethyl)amino)pyrimidin-4-yl)-4-isopropyloxazolidin-2-one<br>1st peak 441: HRMS(B) m/z 413.1719 (M + H) RT = 2.58 min.<br>2nd peak 442: HRMS(B) m/z 413.1719 (M + H) RT = 2.52 min. |
| 443: (S)-3-(2-(((S)-1-(5-(4-chlorophenyl)-1,2,4-oxadiazol-3-yl)ethyl)amino)pyrimidin-4-yl)-4-isopropyloxazolidin-2-one | Chiral separation was achieved by chiral SFC column chromatography (ID-H column (80 g/min, 120 bar, 20 × 250 mm) eluting 30% MeOH/CO2) to give (S)-3-(2-(((R)-1-(5-(4-chlorophenyl)-1,2,4-oxadiazol-3-yl)ethyl)amino)pyrimidin-4-yl)-4-isopropyloxazolidin-2-one and (S)-3-(2-(((S)-1-(5-(4-chlorophenyl)-1,2,4-oxadiazol-3-yl)ethyl)amino)pyrimidin-4-yl)-4-isopropyloxazolidin-2-one<br>2nd peak 443: $^1$H NMR (400 MHz, MeOD) δ 8.25-8.03 (m, 6H), 7.71-7.55 (m, 4H), 7.44 (d, J = 5.7 Hz, 2H), 5.26 (d, J = 5.6 Hz, 2H), 4.71 (d, J = 7.9 Hz, 2H), 4.46-4.26 (m, 4H), 3.37 (s, 1H), 2.66 (heptd, J = 7.0, 3.3 Hz, 2H), 1.69 (d, J = 7.1 Hz, 6H), 1.17 (d, J = 6.2 Hz, 1H), 1.04 (d, J = 7.1 Hz, 6H), 0.88 (d, J = 6.9 Hz, 6H). HRMS(B) m/z 428.1364 RT = 2.77 min. |
| 444 & 445: (S)-3-(2-(1-(5-(4-fluoro-3-methylphenyl)pyridin-2-yl)ethylamino)pyrimidin-4-yl)-4-isopropyloxazolidin-2-one | Separation was achieved by silica gel chromatography (10 to 100% EtOAc/heptane) to give (S)-3-(2-((R)-1-(5-(4-fluoro-3-methylphenyl)pyridin-2-yl)ethylamino)pyrimidin-4-yl)-4-isopropyloxazolidin-2-one and (S)-3-(2-((S)-1-(5-(4-fluoro-3-methylphenyl)pyridin-2-yl)ethylamino)pyrimidin-4-yl)-4-isopropyloxazolidin-2-one<br>1st peak 444: HRMS(B) m/z 436.2126 (M + H)+, RT = 2.78 min<br>2nd peak 445: $^1$H NMR (400 MHz, CDCl$_3$) δ 8.75 (dd, J = 2.3, 0.9 Hz, 1H), 8.23 (d, J = 5.8 Hz, 1H), 7.78 (dd, J = 8.1, 2.4 Hz, 1H), 7.49 (d, J = 5.7 Hz, 1H), 7.41-7.27 (m, 3H), 7.12 (dd, J = 9.4, 8.4 Hz, 1H), 5.95 (d, J = 6.5 Hz, 1H), 5.16 (br s, 1H), 4.66 (br s, 1H), 4.34-4.19 (m, 2H), 2.37 (d, J = 1.9 Hz, 3H), 1.93 (br s, 1H), 1.65-1.61 (m, 3H), 0.71 (br s, 6H). HRMS(B) m/z 436.2131 (M + H)+. |
| 446 & 447: (S)-3-(2-(1-(5-(4- | Chiral separation was achieved by chiral SFC column chromatography (Column IA 20 × 250 mm column 30% |

TABLE 10-continued

Chemical name, NMR chemical shifts, chiral separation conditions and LCMS signal for each compound listed in Table 9.

| Example: Name | Chiral separation conditions, peak identification and analytical data |
| --- | --- |
| fluorophenoxy)pyrimidin-2-yl)ethylamino)pyrimidin-4-yl)-4-isopropyloxazolidin-2-one | IPA, 70% $CO_2$ to give (S)-3-(2-((S)-1-(5-(4-fluorophenoxy)pyrimidin-2-yl)ethylamino)pyrimidin-4-yl)-4-isopropyloxazolidin-2-one and (S)-3-(2-((R)-1-(5-(4-fluorophenoxy)pyrimidin-2-yl)ethylamino)pyrimidin-4-yl)-4-isopropyloxazolidin-2-one<br>1st peak 446: $^1$H NMR (400 MHz, $CDCl_3$) δ 8.42 (s, 2H), 8.21 (d, J = 5.8 Hz, 1H), 7.49 (d, J = 5.7 Hz, 1H), 7.18-6.99 (m, 4H), 6.18 (br s 1H), 5.28 (br s, 1H), 4.75 (dt, J = 8.2, 3.4 Hz, 1H), 4.39-4.25 (m, 2H), 2.34 (br s, 1H), 1.65-1.59 (m, 3H), 0.95-0.86 (d, J = 6.9 Hz, 3H), 0.82 (d, J = 6.9 Hz, 3H). HRMS(B) m/z 439.1876 (M + H)+.<br>2nd peak 447: HRMS(B) m/z 439.1883 (M + H)+, RT = 3.37 min |
| 448 & 449: (S)-3-(2-(1-(5-(4-fluorophenoxy)pyridin-2-yl)ethylamino)pyrimidin-4-yl)-4-isopropyloxazolidin-2-one | Separation was achieved by silica gel chromatography (20 to 100% EtOAc/heptane) to give (S)-3-(2-((R)-1-(5-(4-fluorophenoxy)pyridin-2-yl)ethylamino)pyrimidin-4-yl)-4-isopropyloxazolidin-2-one and (S)-3-(2-((S)-1-(5-(4-fluorophenoxy)pyridin-2-yl)ethylamino)pyrimidin-4-yl)-4-isopropyloxazolidin-2-one<br>1st peak 448: HRMS(B) m/z 438.1922 (M + H)+. RT = 2.62 min<br>2nd peak 449: $^1$H NMR (400 MHz, $CDCl_3$) δ 8.34 (dd, J = 2.7, 0.8 Hz, 1H), 8.21 (d, J = 5.8 Hz, 1H), 7.49 (d, J = 5.8 Hz, 1H), 7.33-7.18 (m, 3H), 7.14-6.95 (m, 3H), 5.95 (d, J = 7.1 Hz, 1H), 5.14 (br s, 1H), 4.68 (d, J = 7.8 Hz, 1H), 4.36-4.22 (m, 2H), 1.75 (br s, 1H), 1.61-1.57 (m, 3H), 0.95-0.75 (m, 6H). HRMS(B) m/z 438.1950 (M + H)+. |
| 450 & 451: (R)-3-(5-fluoro-2-(1-(5-(4-fluorophenoxy)pyridin-2-yl)ethylamino)pyrimidin-4-yl)-5,5-dimethyl-4-phenyloxazolidin-2-one | Separation was achieved by silica gel chromatography (10 to 100% EtOAc/heptane) to give (R)-3-(5-fluoro-2-((S)-1-(5-(4-fluorophenoxy)pyridin-2-yl)ethylamino)pyrimidin-4-yl)-5,5-dimethyl-4-phenyloxazolidin-2-one and (R)-3-(5-fluoro-2-((R)-1-(5-(4-fluorophenoxy)pyridin-2-yl)ethylamino)pyrimidin-4-yl)-5,5-dimethyl-4-phenyloxazolidin-2-one<br>1st peak 450: $^1$H NMR (400 MHz, $CDCl_3$) δ 8.27-8.17 (m, 1H), 8.08 (d, J = 2.8 Hz, 1H), 7.31-6.86 (m, 11H), 5.83 (d, J = 7.2 Hz, 1H), 5.28 (s, 1H), 4.69 (br s, 1H), 1.58 (s, 3H), 1.29-1.11 (m, 3H), 0.98 (s, 3H). HRMS(B) m/z 518.2005 (M + H)+.<br>2nd peak 451: HRMS(B) m/z 518.2003 (M + H)+, RT = 3.08 min |
| 452 & 453: (S)-3-(2-(1-(5-(4-fluorophenoxy)pyrazin-2-yl)ethylamino)pyrimidin-4-yl)-4-isopropyloxazolidin-2-one. | Separation was achieved by silica gel chromatography (25 to 100% EtOAc/heptane) to give (S)-3-(2-((R)-1-(5-(4-fluorophenoxy)pyrazin-2-yl)ethylamino)pyrimidin-4-yl)-4-isopropyloxazolidin-2-one and (S)-3-(2-((S)-1-(5-(4-fluoropnenoxy)pyrazin-2-yl)ethylamino)pyrimidin-4-yl)-4-isopropyloxazolidin-2-one.<br>1st peak 452: HRMS(B) m/z 439.1877 (M + H)+, RT = 2.66 min<br>2nd peak 453: $^1$H NMR (400 MHz, $CDCl_3$) δ 8.38 (d, J = 1.4 Hz, 1H), 8.20 (d, J = 5.8 Hz, 1H), 8.09 (s, 1H), 7.49 (d, J = 5.8 Hz, 1H), 7.12 (d, J = 6.3 Hz, 4H), 5.71 (s, 1H), 5.20 (br s, 1H), 4.66 (dt, J = 7.7, 2.9 Hz, 1H), 4.36-4.22 (m,2H), 2.10 (br s, 1H), 1.61 (d, J = 6.9 Hz, 3H), 0.94-0.78 (m, 6H). HRMS(B) m/z 439.1882 (M + H)+. |
| 454 & 455: (S)-3-(2-(1-(2-(4-fluorophenoxy)pyrimidin-5-yl)ethylamino)pyrimidin-4-yl)-4-isopropyloxazolidin-2-one. | Separation was achieved by silica gel chromatography (25 to 100% EtOAc/heptane) to give (S)-3-(2-((R)-1-(2-(4-fluorophenoxy)pyrimidin-5-yl)ethylamino)pyrimidin-4-yl)-4-isopropyloxazolidin-2-one and (S)-3-(2-((S)-1-(2-(4-fluorophenoxy)pyrimidin-5-yl)ethylamino)pyrimidin-4-yl)-4-isopropyloxazolidin-2-one.<br>1st peak 454: HRMS(B) m/z 439.1904 (M + H)+, RT = 3.09 min<br>2nd peak 455: HRMS(B) m/z 439.1897 (M + H)+, RT = 3.17 min |
| 456: (S)-3-(2-(1-(5-(2,4-difluorophenoxy)pyrimidin-2-yl)ethylamino)pyrimidin-4-yl)-4-isopropyloxazolidin-2-one. | Separation was achieved on a normal phase silica gel column with 20 to 100% ethylacetate/heptane to give (S)-3-(2-((R)-1-(5-(2,4-difluorophenoxy)pyrimidin-2-yl)ethylamino)pyrimidin-4-yl)-4-isopropyloxazolidin-2-one and (S)-3-(2-((S)-1-(5-(2,4-difluorophenoxy)pyrimidin-2-yl)ethylamino)pyrimidin-4-yl)-4-isopropyloxazolidin-2-one. |

TABLE 10-continued

Chemical name, NMR chemical shifts, chiral separation conditions and LCMS signal for each compound listed in Table 9.

| Example: Name | Chiral separation conditions, peak identification and analytical data |
|---|---|
| | 2$^{nd}$ Peak 456: $^1$H NMR (400 MHz, CDCl$_3$) δ 8.30 (s, 2H), 8.09 (d, J = 5.9 Hz, 1H), 7.42 (d, J = 5.9 Hz, 1H), 7.08 (td, J = 8.9, 5.4 Hz, 1H), 6.98-6.81 (m, 2H), 5.18 (br s, 1H), 4.64 (dt, J = 7.9, 3.1 Hz, 1H), 4.30-4.16 (m, 2H), 2.11 (br s, 1H), 1.53-1.49 (m, 3H), 0.85-0.77 (m, 3H), 0.71 (d, J = 6.8 Hz, 3H). HRMS(B) m/z 457.1797 (M + H)+. |
| 457: (S)-4-isopropyl-3-(2-(1-(5-(3-(trifluoromethyl)phenyl)pyrimidin-2-yl)ethylamino)pyrimidin-4-yl)oxazolidin-2-one. | Separation was achieved on a normal phase silica gel column with 25 to 100% gradient of (25% methanol in ethylacetate) and heptane to give (S)-4-isopropyl-3-(2-((R)-1-(5-(3-(trifluoromethyl)phenyl)pyrimidin-2-yl)ethylamino)pyrimidin-4-yl)oxazolidin-2-one and (S)-4-isopropyl-3-(2-((S)-1-(5-(3-(trifluoromethyl)phenyl)pyrimidin-2-yl)ethylamino)pyrimidin-4-yl)oxazolidin-2-one. Peak 2 457: $^1$H NMR (400 MHz, CDCl$_3$) δ 8.85 (s, 2H), 8.14 (d, J = 5.7 Hz, 1H), 7.77-7.54 (m, 4H), 7.40 (d, J = 5.7 Hz, 1H), 6.11 (br s, 1H), 5.25 (br s, 1H), 4.67 (dt, J = 7.8, 3.2 Hz, 1H), 4.33-4.15 (m, 2H), 2.92 2.15 (br s, 1H), 1.55 (d, J = 8.6 Hz, 3H), 0.85-0.76 (m, 3H), 0.70 (br s, 3H). HRMS(B) m/z 473.1897 (M + H)+. |
| 458: (S)-3-(2-((S)-1-(5-(4-fluoro-2-methylphenyl)pyrimidin-2-yl)ethylamino)pyrimidin-4-yl)-4-isopropyloxazolidin-2-one | The chiral separation was carried out with SFC (IA, 5 μm, 20 × 250 mm) using 35% MeOH in CO2 to give (S)-3-(2-((S)-1-(5-(4-fluoro-2-methylphenyl)pyrimidin-2-yl)ethylamino)pyrimidin-4-yl)-4-isopropyloxazolidin-2-one and (S)-3-(2-((R)-1-(5-(4-fluoro-2-methylphenyl)pyrimidin-2-yl)ethylamino)pyrimidin-4-yl)-4-isopropyloxazolidin-2-one 1st Peak 458: $^1$H NMR (400 MHz, CDCl$_3$) δ 8.68 (s, 2H), 8.24 (d, J = 5.8 Hz, 1H), 7.49 (d, J = 5.7 Hz, 1H), 7.17 (dd, J = 8.4, 5.8 Hz, 1H), 7.10-6.98 (m, 2H), 6.28 (br s, 1H), 5.34 (br s, 1H), 4.78 (dt, J = 8.2, 3.3 Hz, 1H), 4.40-4.25 (m, 2H), 2.30 (s, 3H), 1.79 (br s, 1H), 1.73 (d, J = 7.1 Hz, 3H), 0.95-0.75 (m, 6H). HRMS(B) m/z 437.2086 (M + H)+. |

Example 459

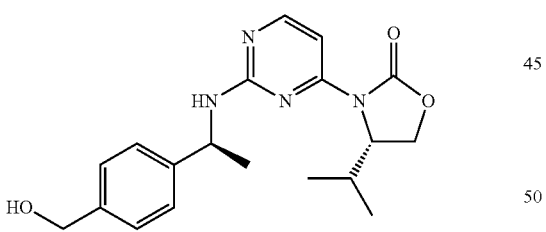

A solution of (S)-(4-(1-aminoethyl)phenyl)methanol hydrochloride (4.0301 g, 21.47 mmol, purchased from NetChem), (S)-3-(2-fluoropyrimidin-4-yl)-4-isopropyloxazolidin-2-one (5.3648 g, 23.82 mmol, 1.11 equiv) and DIPEA (38.0 mL, 218 mmol, 10.1 equiv) in DMSO (40 mL) was heated at 110° C. for 135 min. The reaction mixture was diluted with EtOAc (200 mL) and washed with water (200 mL). After separation, the aqueous phase was washed with EtOAc (2×150 mL). Combined organics were dried over Na$_2$SO$_4$, filtered and concentrated. Silica gel column chromatography (EtOAc/heptane 30 to 100%) provided (S)-3-(2-((S)-1-(4-(hydroxymethyl)phenyl)ethylamino)pyrimidin-4-yl)-4-isopropyloxazolidin-2-one (6.42 g) in 84% yield.

$^1$H NMR (400 MHz, CD$_3$OD) δ 8.13 (d, J=5.8 Hz, 1H), 7.36-7.28 (m, 5H), 5.06 (q, J=7.0 Hz, 1H), 4.68 (br s, 1H), 4.58 (s, 2H), 4.37-4.29 (m, 2H), 1.80 (br s, 1H), 1.52 (d, J=7.1 Hz, 3H), 0.74 (br s, 3H), 0.61 (br s, 3H); MS m/z 355.1 (M−H)

Example 460

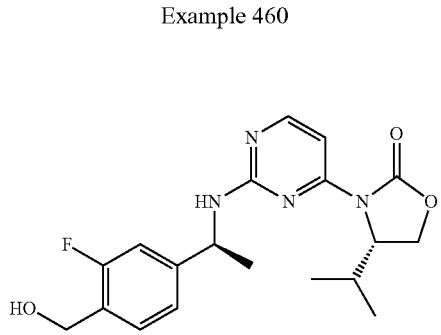

S)-3-(2-((S)-1-(3-fluoro-4-(hydroxymethyl)phenyl)ethylamino)pyrimidin-4-yl)-4-isopropyloxazolidin-2-one was prepared using a method similar to that described for the preparation of Example 459. $^1$H NMR (400 MHz, CDCl$_3$) δ 8.15 (d, J=5.9 Hz, 1H), 7.51-7.49 (m, 1H), 7.37 (t, J=7.7 Hz, 1H), 7.11 (d, J=7.8 Hz, 1H), 7.01 (d, J=11, Hz, 1H), 6.09 (br s, 1H), 5.00 (br s, 1H), 4.73 (s, 2H), 4.61-4.55 (m, 1H), 4.30 (t, J=8.7 Hz, 1H), 4.25-4.21 (m, 1H), 3.00 (s, 1H), 1.89 (br s, 1H), 1.54 (d, J=7.1 Hz, 3H), 0.67 (br s, 6H); MS m/z 375.0 (M+H)

Example 461

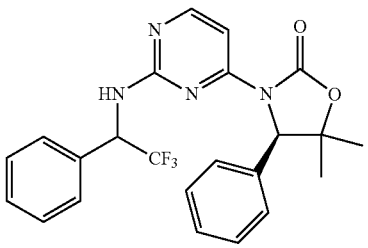 [SMILES: CC1(C)OC(=O)N(c2ccnc(NC(c3ccccc3)C(F)(F)F)n2)[C@@H]1c1ccccc1]

A solution of (S)-3-(2-chloropyrimidin-4-yl)-4-isopropyloxazolidin-2-one (50 mg, 0.165 mmol), 2,2,2-trifluoro-1-phenylethanamine (160 mg, 0.913 mmol) and pTsOH (78 mg, 0.412 mmol) in 2-BuOH was heated at 110° C. for 2.5 h. LCMS shows starting material as well as product. Another 78 mg of pTsOH was added followed by 98 mg of 2,2,2-trifluoro-1-phenylethanamine and heated at 110 C for 1.5 h. Mostly product some SM.

After cooling down mixture solidified. Added acetonitrial and sonicated. Filtered off solids (pTsOH salt of 2,2,2-trifluoro-1-phenylethanamine). The mother liquor was concentrated and purified by column chromatography (0-40% EtOAc/Hept followed by reverse HPLC (XBridge C18 5 uM 10-85% ACN/Water over 12 minutes with 0.01% NH4OH modifier) to give (4R)-5,5-dimethyl-4-phenyl-3-(2-(2,2,2-trifluoro-1-phenylethylamino)pyrimidin-4-yl)oxazolidin-2-one (28 mg, 0.063 mmol).

$^1$H NMR (400 MHz, MeOD) δ 8.20 (d, J=5.8 Hz, 1H), 7.58 (dd, J=11.4, 5.8 Hz, 1H), 7.51 (br d, J=6.8 Hz, 1H), 7.40 (dtd, J=15.9, 9.2, 4.5 Hz, 5H), 7.33-7.22 (m, 3H), 7.10 (br s, 1H), 5.50 (s, 0.5H), 5.38 (s, 0.5H), 5.29 (br s, 1H), 1.70 (s, 1.5H), 1.64 (s, 1.5H), 1.04 (s, 1.5H), 1.03 (s, 1.5H). HRMS(B) (M+H) 443.1682 Calc'd (M+H) 443.1695

Example 462 & 463

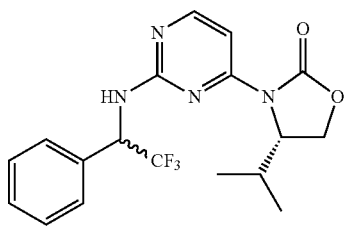 [SMILES: CC(C)[C@H]1COC(=O)N1c1ccnc(NC(c2ccccc2)C(F)(F)F)n1]

A solution of (S)-3-(2-chloropyrimidin-4-yl)-4-isopropyloxazolidin-2-one (163 mg, 0.674 mmol), 2,2,2-trifluoro-1-phenylethanamine (624 mg, 3.56 mmol, 5.3 equiv) and p-toluenesulfonic acid monohydrate (321 mg, 1.69 mmol, 2.5 equiv) in n-BuOH (3 mL) was heated at 110° C. for 2 h and treated with additional p-toluenesulfonic acid monohydrate (321 mg, 1.69 mmol, 2.5 equiv), then heated at 110° C. for 1½ h. After cooling, the solid reaction mixture was treated with MeCN, sonicated and filtered. The filtrated was concentrated and purified by silica gel column chromatography (EtOAc/Heptane 0 to 30%) to give (4S)-4-isopropyl-3-(2-(2,2,2-trifluoro-1-phenylethylamino)pyrimidin-4-yl)oxazolidin-2-one (65 mg) in 25% yield. HRMS(B) m/z 381.1545 (M+H)+. Anal. RP-HPLC tR=4.31//4.46 min (1.0 mL/min flow rate with gradient from 5% to 15% acetonitrile with 0.05% formic acid in 5.00 min and then 15% to 95% acetonitrile with 0.05% formic acid from 5.00 min to 9.50 min, aqueous phase modified with 0.1% formic acid. Silica gel column chromatography separated the two diastereomers (S)-4-isopropyl-3-(2-((R)-2,2,2-trifluoro-1-phenylethylamino)pyrimidin-4-yl)oxazolidin-2-one and (S)-4-isopropyl-3-(2-((S)-2,2,2-trifluoro-1-phenylethylamino)pyrimidin-4-yl)oxazolidin-2-one.

$1^{st}$ Peak: $^1$H NMR (400 MHz, MeOD) δ 8.23 (d, J=5.8 Hz, 1H), 7.62-7.53 (m, 2H), 7.50 (d, J=5.8 Hz, 1H), 7.42 (qt, J=5.0, 2.2 Hz, 3H), 5.93-5.86 (m, 1H), 4.80 (dt, J=7.5, 3.9 Hz, 1H), 4.48-4.33 (m, 2H), 2.65 (ddp, J=10.4, 7.0, 3.4 Hz, 1H), 1.05 (d, J=7.0 Hz, 3H), 0.89 (d, J=7.0 Hz, 3H).

$2^{nd}$ Peak: $^1$H NMR (400 MHz, MeOD) δ 8.23 (d, J=5.8 Hz, 1H), 7.55 (dd, J=7.3, 2.1 Hz, 2H), 7.49 (d, J=5.8 Hz, 1H), 7.45-7.32 (m, 3H), 5.92-5.86 (m, 1H), 4.86-4.82 (m, 1H), 4.44-4.38 (m, 2H), 2.26 (br s, 1H), 0.94 (d, J=7.0 Hz, 3H), 0.74 (br s, 3H).

Example 464

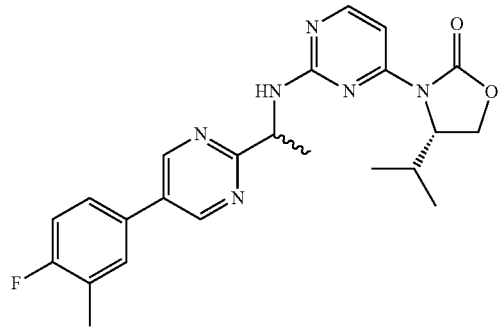 [SMILES: Cc1cc(-c2cnc(C(C)Nc3nccc(N4C(=O)OC[C@@H]4C(C)C)n3)nc2)ccc1F]

A solution of (S)-3-(2-fluoropyrimidin-4-yl)-4-isopropyloxazolidin-2-one (1055 mg, 4.68 mmol), 1-(5-(4-fluoro-3-methylphenyl)pyrimidin-2-yl)ethanamine (1300 mg, 5.62 mmol, 1.2 equiv) and diisopropylethylamine (908 mg, 7.03 mmol, 1.5 equiv) in DMSO (20 mL) was heated at 110° C. for 1 h. The reaction mixture was poured into water (60 mL) and extracted with EtOAc (2×50 mL). Combined organics were washed with water (40 mL), brine (40 mL), dried over Na$_2$SO$_4$, filtered and concentrated directly onto silica gel. Silica gel chromatography provided the mixed distereomers of (S)-3-(2-(1-(5-(4-fluoro-3-methylphenyl)pyrimidin-2-yl)ethylamino) pyrimidin-4-yl)-4-isopropyloxazolidin-2-one (560 mg). Chiral separation was carried out with SFC (ID, 5 μm, 20×250 mm) using 35% MeOH in CO2 to give (S)-3-(2-((S)-1-(5-(4-fluoro-3-methylphenyl)pyrimidin-2-yl)ethylamino)pyrimidin-4-yl)-4-isopropyloxazolidin-2-one and (S)-3-(2-((R)-1-(5-(4-fluoro-3-methylphenyl)pyrimidin-2-yl)ethylamino)pyrimidin-4-yl)-4-isopropyloxazolidin-2-one.

Example 464 first eluted product (302 mg) $^1$H NMR (400 MHz, CDCl$_3$) δ 8.87 (s, 2H), 8.23 (d, J=5.8 Hz, 1H), 7.49 (d, J=5.7 Hz, 1H), 7.43-7.30 (m, 2H), 7.21-7.11 (m, 1H), 6.26 (br s, 1H), 5.31 (br s, 1H), 4.75 (dt, J=7.9, 3.3 Hz, 1H), 4.39-4.24 (m, 2H), 2.38 (s, 3H), 2.09 (br s, 1H), 1.66-1.62 (m, 3H), 0.90 (dd, J=9.8, 6.0 Hz, 3H), 0.78 (br s, 3H). HRMS(B) m/z 437.2093 (M+H)+.

Example 465

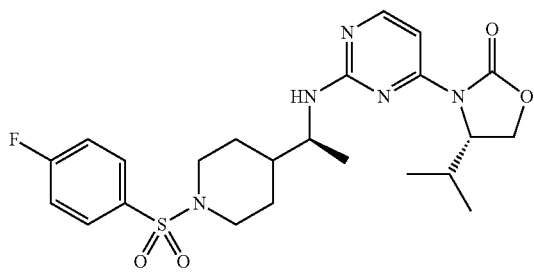 [SMILES: CC(C)[C@H]1COC(=O)N1c1ccnc(N[C@@H](C)C2CCN(S(=O)(=O)c3ccc(F)cc3)CC2)n1]

A solution of (S)-4-isopropyl-3-(2-((S)-1-(piperidin-4-yl)ethylamino)pyrimidin-4-yl)oxazolidin-2-one (225 mg, 0.675 mmol), 4-fluorobenzene-1-sulfonyl chloride (146 mg, 0.750 mmol) and DIPEA (1 ml) in CH$_2$Cl$_2$ was stirred at room temperature for 2 h. The reaction mixture was diluted with CH$_2$Cl$_2$ and washed with water. Aqueous layer was extracted with CH$_2$Cl$_2$. Combined organics were washed with brine, dried over Na$_2$SO$_4$, filtered and concentrated. The residue was purified by column chromatography to give (S)-3-(2-((S)-1-(1-(4-fluorophenylsulfonyl)piperidin-4-yl)ethylamino)pyrimidin-4-yl)-4-isopropyloxazolidin-2-one (4.5 mg, 0.009 mmol).

$^1$H NMR (400 MHz, MeOD) δ 8.45 (d, J=6.0 Hz, 1H), 8.23-8.15 (m, 2H), 7.73-7.63 (m, 3H), 5.13 (dt, J=7.4, 3.7 Hz, 1H), 4.78-4.69 (m, 2H), 4.26 (p, J=6.7 Hz, 1H), 4.17 (dddd, J=11.8, 6.4, 4.7, 2.3 Hz, 2H), 2.89 (ddq, J=10.7, 7.1, 3.5 Hz, 1H), 2.69 (tdd, J=11.6, 8.9, 2.6 Hz, 2H), 2.27-2.11 (m, 2H), 1.82 (dddt, J=11.9, 9.0, 5.8, 2.9 Hz, 1H), 1.77-1.64 (m, 2H), 1.52 (d, J=6.8 Hz, 3H), 1.30 (d, J=7.1 Hz, 3H), 1.21 (d, J=6.9 Hz, 3H). HRMS(B) (M+H) 492.2069 Calc'd (M+H) 492.2081

The following examples were prepared using methods substantially similar to those described for Example 465:

Example 466

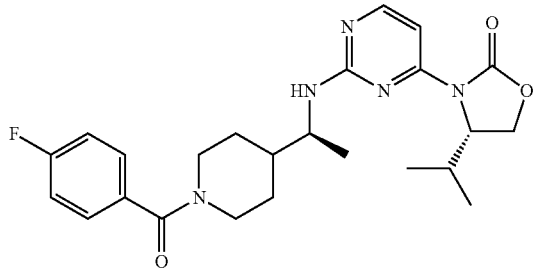 [SMILES: CC(C)[C@H]1COC(=O)N1c1ccnc(N[C@@H](C)C2CCN(C(=O)c3ccc(F)cc3)CC2)n1]

Purified by column chromatography (20% to 100% EtOAc/Hept), followed by reverse phase preparative chromatography (C18 column, 10-85% ACN/Water 0.1% NH4OH modifier over 12 min.) to give (S)-3-(2-((S)-1-(1-(4-fluorobenzoyl)piperidin-4-yl)ethylamino)pyrimidin-4-yl)-4-isopropyloxazolidin-2-one (12 mg, 0.026 mmol).

$^1$H NMR (400 MHz, MeOD) δ 8.12 (d, J=5.8 Hz, 1H), 7.51-7.41 (m, 2H), 7.36 (d, J=5.8 Hz, 1H), 7.25-7.15 (m, 2H), 4.82 (td, J=5.9, 3.6 Hz, 1H), 4.68 (br s, 1H), 4.41 (d, J=5.7 Hz, 2H), 3.98 (p, J=6.7 Hz, 1H), 3.78 (br s, 1H), 3.12 (br s, 1H), 2.82 (br s, 1H), 2.60 (pd, J=7.1, 6.5, 3.7 Hz, 1H), 1.92 (br s, 1H), 1.80 (dtd, J=15.3, 9.4, 7.0, 3.6 Hz, 2H), 1.31 (br s, 2H), 1.22 (d, J=6.8 Hz, 3H), 0.99 (d, J=7.1 Hz, 3H), 0.88 (d, J=6.9 Hz, 3H). HRMS(B) (M+H) 456.2384 Calc'd (M+H) 456.2411

Example 467

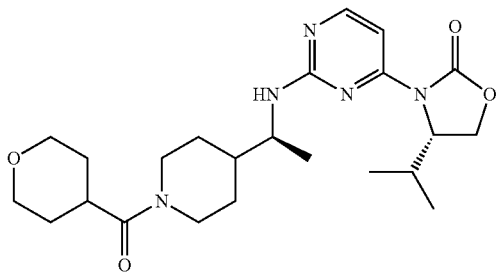 [SMILES: CC(C)[C@H]1COC(=O)N1c1ccnc(N[C@@H](C)C2CCN(C(=O)C3CCOCC3)CC2)n1]

Purified by column chromatography (MeOH/CH$_2$Cl$_2$ 0 to 20%) to give (S)-4-isopropyl-3-(2-((S)-1-(1-(tetrahydro-2H-pyran-4-carbonyl)piperidin-4-yl)ethylamino)pyrimidin-4-yl)oxazolidin-2-one (15 mg, 0.034 mmol).

$^1$H NMR (400 MHz, MeOD) δ 8.12 (d, J=5.8 Hz, 1H), 7.36 (d, J=5.8 Hz, 1H), 4.81 (td, J=5.6, 3.3 Hz, 1H), 4.59 (br s, 1H), 4.41 (d, J=5.7 Hz, 2H), 4.13 (br s, 1H), 3.96 (ddd, J=11.6, 4.3, 2.2 Hz, 3H), 3.51 (tq, J=11.8, 2.8 Hz, 2H), 3.15-2.89 (m, 2H), 2.69-2.48 (m, 2H), 1.99-1.68 (m, 5H), 1.61 (ddt, J=10.7, 4.0, 2.3 Hz, 2H), 1.35-1.23 (m, 1H), 1.21 (d, J=6.7 Hz, 3H), 1.19-1.09 (m, 1H), 0.98 (dd, J=7.0, 1.5 Hz, 3H), 0.88 (d, J=7.0 Hz, 3H). HRMS(B) (M+H) 446.2748 Calc'd (M+H) 446.2767

Example 468

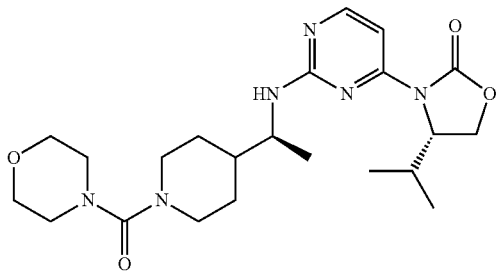 [SMILES: CC(C)[C@H]1COC(=O)N1c1ccnc(N[C@@H](C)C2CCN(C(=O)N3CCOCC3)CC2)n1]

Purified by column chromatography (50% to 100% EtOAc/Heptane followed by 0% to 20% MeOH/CH$_2$Cl$_2$) to give (S)-4-isopropyl-3-(2-((S)-1-(1-(morpholine-4-carbonyl)piperidin-4-yl)ethylamino)pyrimidin-4-yl)oxazolidin-2-one (21 mg, 0.047 mmol).

$^1$H NMR (400 MHz, MeOD) δ 8.11 (d, J=5.8 Hz, 1H), 7.36 (d, J=5.8 Hz, 1H), 4.81 (td, J=5.8, 3.4 Hz, 1H), 4.41 (d, J=5.7 Hz, 2H), 3.95 (p, J=6.8 Hz, 1H), 3.84-3.70 (m, 2H), 3.68-3.65 (m, 4H), 3.26-3.23 (m, 4H), 2.80 (tt, J=12.9, 3.1 Hz, 2H), 2.60 (ddq, J=10.4, 7.0, 3.5 Hz, 1H), 1.88-1.73 (m, 2H), 1.67 (ddt, J=18.5, 10.4, 3.5 Hz, 1H), 1.37-1.23 (m, 2H), 1.21 (d, J=6.8 Hz, 3H), 0.99 (d, J=7.1 Hz, 3H), 0.88 (d, J=7.0 Hz, 3H). HRMS(B) (M+H) 447.2690 Calc'd (M+H) 447.2720

Example 469

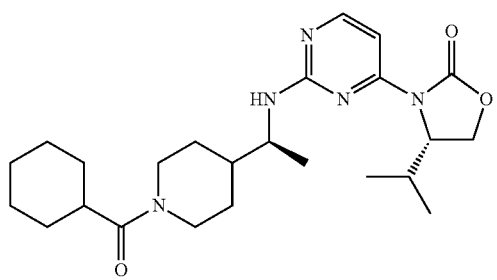 [SMILES: CC(C)[C@H]1COC(=O)N1c1ccnc(N[C@@H](C)C2CCN(C(=O)C3CCCCC3)CC2)n1]

Purified by column chromatography to give (S)-3-(2-((S)-1-(1-(cyclohexanecarbonyl) piperidin-4-yl)ethylamino)pyrimidin-4-yl)-4-isopropyloxazolidin-2-one $^1$H NMR (400 MHz, MeOD) δ 8.12 (d, J=5.7 Hz, 1H), 7.36 (d, J=5.6 Hz, 1H), 4.80 (dt, J=5.8, 2.9 Hz, 1H), 4.59 (br s, 1H), 4.40 (d, J=5.6 Hz, 2H), 4.18-4.03 (m, 1H), 3.95 (p, J=6.8 Hz, 1H), 3.05 (ddd, J=14.1, 10.1, 6.6 Hz, 1H), 2.58 (td, J=25.1, 23.5, 13.0 Hz, 3H), 1.97-1.63 (m, 8H), 1.54-1.08 (m, 7H), 1.21 (d, J=6.8 Hz, 3H), 0.98 (d, J=6.8 Hz, 3H), 0.88 (d, J=6.9 Hz, 3H). HRMS(B) (M+H) 444.2953 Calc'd (M+H) 444.2975

Examples 470

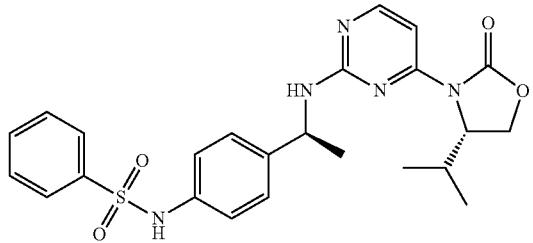 [SMILES: CC(C)[C@H]1COC(=O)N1c1ccnc(N[C@@H](C)c2ccc(NS(=O)(=O)c3ccccc3)cc2)n1]

A solution of (S)-3-(2-(((S)-1-(4-aminophenyl)ethyl)amino)pyrimidin-4-yl)-4-isopropyloxazolidin-2-one (100 mg, 0.30 mmol), benzenesulfonyl chloride (65 mg, 0.36 mmol, 1.2 equiv) and pyridine (35 mg, 0.45 mmol, 1.5 equiv) in DCM (5 mL) was stirred at room temperature for 15 h. The reaction mixture was quenched with MeOH, the solvent was removed to yield the crude product, which was purified by silica gel column chromatography (EA:MeOH=1:0 to 9:1), the solvent was removed to afford the pure product (46.8 mg, white solid) in a 31.5% yield. N-(4-((S)-1-((4-((S)-4-isopropyl-2-oxooxazolidin-3-yl)pyrimidin-2-yl)amino)ethyl)phenyl)benzenesulfonamide. $^1$H NMR (400 MHz, CDCl$_3$) δ 8.18-7.90 (m, 2H), 7.74 (d, J=7.8 Hz, 2H), 7.45 (t, J=7.4 Hz, 1H), 7.39-7.35 (m, 2H), 7.10 (d, J=8.1 Hz, 2H), 6.96 (d, J=8.0 Hz, 2H), 6.41 (s, 1H), 4.99-4.79 (m, 1H), 4.62-4.39 (m, 1H), 4.28-3.99 (m, 2H), 1.91-1.65 (b, 1H), 1.40 (d, J=7.0 Hz, 3H), 0.53 (b, J=21.1 Hz, 6H). HRMS(B) m/z 482.1847 (M+H)$^+$. RT=2.60 min.

Examples 471

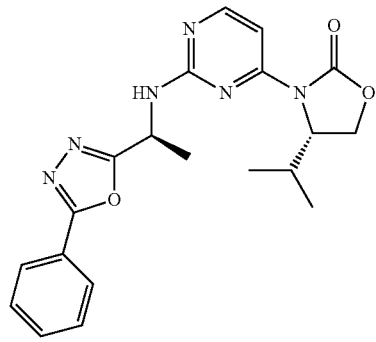 [SMILES: CC(C)[C@H]1COC(=O)N1c1ccnc(N[C@@H](C)c2nnc(-c3ccccc3)o2)n1]

A solution of (triethoxymethyl)benzene (360 mg, 1.6 mmol, 5.0 equiv. in 5 mL of benzene and 0.5 mL of glacial AcOH) was added to (S)-2-((4-((S)-4-isopropyl-2-oxooxazolidin-3-yl)pyrimidin-2-yl)amino)propanehydrazide (99 mg, 0.30 mmol, 1.0 equiv.), the reaction mixture was stirred at reflux for 1.5 hours, the solvent was removed to yield the crude product. Silica gel column chromatography (ethyl acetate in heptane 10 to 90%) to yield (S)-4-isopropyl-3-(2-(((S)-1-(5-phenyl-1,3,4-oxadiazol-2-yl)ethyl)amino)pyrimidin-4-yl)oxazolidin-2-one (21.2 mg, white solid) in 15.9% yield. HRMS(B) m/z 395.1820, (M+H)+, RT=2.42 min

Examples 472

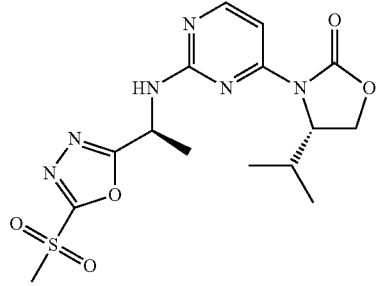 [SMILES: CC(C)[C@H]1COC(=O)N1c1ccnc(N[C@@H](C)c2nnc(S(C)(=O)=O)o2)n1]

To a solution of (S)-4-isopropyl-3-(2-(((S)-1-(5-(methylthio)-1,3,4-oxadiazol-2-yl)ethyl)amino)pyrimidin-4-yl)oxazolidin-2-one (102 mg, 0.28 mmol in 1.5 ml of CH$_3$COOH), was added a solution of KMnO$_4$ (66.4 mg, 0.42 mmol, 1.5 eq in 2.5 ml of water) dropwise. The solution was stirred at room temperature for 25 min, the mixture was decolorized with sodium bisulfite, the resulting solution was extracted with DCM, washed with sat. NaHCO$_3$, dried over Na$_2$SO$_4$, the solvent was removed to yield the pure desired product as a white solid. (S)-4-isopropyl-3-(2-(((S)-1-(5-(methylsulfonyl)-1,3,4-oxadiazol-2-yl)ethyl)amino)pyrimidin-4-yl)oxazolidin-2-one (83 mg, white solid) in 71% yield. HRMS(B) m/z 397.1281 (M+H)$^+$. RT=1.80 min.

Example 473 & 474

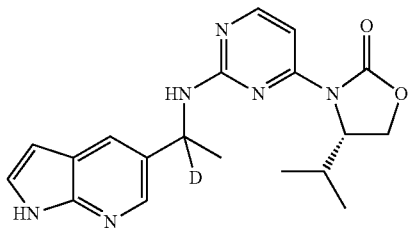 [SMILES: [2H]C(C)(Nc1nccc(N2C(=O)OC[C@@H]2C(C)C)n1)c1cnc2[nH]ccc2c1]

1-(1H-Pyrrolo[2,3-b]pyridin-5-yl)-ethanone (75 mg, 0.468 mmol), ammonium acetate (722 mg, 9.36 mmol, 20.0 eq) and sodium cyanoborodeuteride (131 mg, 1.999 mmol, 4.25 eq) were combined in propan-2-ol (5 ml) and heated under infrared irradiation at 130° C. for 4 min. The reaction was diluted with EtOAc (15 ml) and water (15 ml) and treated with 6M NaOH solution (1 ml) to ~10 pH. The product, 1-deutero-1-(1H-pyrrolo[2,3-b]pyridin-5-yl)ethanamine, was carried to the next step without further purification.

A solution of 3-(2-fluoropyrimidin-4-yl)oxazolidin-2-one (99 mg, 0.441 mmol), 1-deutero-1-(1H-pyrrolo[2,3-b]pyridin-5-yl)ethanamine (72 mg, 0.441 mmol, 1.0 equiv), and DIEA (0.154 mL, 0.882 mmol, 2.0 equiv) in DMSO (1 mL) was heated at 130° C. for 120 min. The reaction mixture was diluted with EtOAc (20 mL) and washed with water (10 mL) and concentrated in vacuo. Resolution of (4S)-3-(2-((1-deutero-1-(1H-pyrrolo[2,3-b]pyridin-5-yl)ethyl)amino)pyrimidin-4-yl)-4-isopropyloxazolidin-2-one via chiral SFC chromatography on a AI column (75 g/min, 120 bar, 20×250 mm) eluting 40-50% MeOH/0.2% DEA/CO2 (v/v) to give (4S)-3-(2-(((R)-1-deutero-1-(1H-pyrrolo[2,3-b]pyridin-5-yl)ethyl)amino)pyrimidin-4-yl)-4-isopropyloxazolidin-2-one and (4S)-3-(2-(((S)-1-deutero-1-(1H-pyrrolo[2,3-b]pyridin-5-yl)ethyl)amino)pyrimidin-4-yl)-4-isopropyloxazolidin-2-one 1st Peak 473
$^1$H NMR (400 MHz, CDCl$_3$) δ 10.10 (s, 1H), 8.33 (d, J=2.2 Hz, 1H), 8.21 (d, J=5.7 Hz, 1H), 7.92 (d, J=2.3 Hz, 1H), 7.46 (d, J=5.7 Hz, 1H), 7.35 (dd, J=3.5, 2.0 Hz, 1H), 6.47 (dd, J=3.4, 1.7 Hz, 1H), 5.82 (s, 1H), 1.66-1.58 (m, 3H), 4.59 (dt, J=7.7, 3.2 Hz, 1H), 4.28 (t, J=8.8 Hz, 1H), 4.19 (dd, J=9.2, 3.1 Hz, 1H), 3.51 (s, 1H), 1.78 (d, J=28.5 Hz, 2H), 1.30-1.15 (m, 1H), 0.57 (s, 6H). LCMS m/z 368.1 (M+H) RT=2.36 min.

2nd Peak 474
LCMS m/z 368.1 (M+H) RT=2.66 min.

Example 475

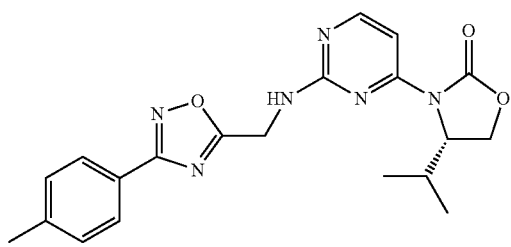 [SMILES: Cc1ccc(-c2noc(CNc3nccc(N4C(=O)OC[C@@H]4C(C)C)n3)n2)cc1]

A solution of 3-(2-fluoropyrimidin-4-yl)oxazolidin-2-one (100 mg, 0.444 mmol), (3-(p-tolyl)-1,2,4-oxadiazol-5-yl)methanamine (84 mg, 0.444 mmol, 1.0 equiv), and TEA (0.186 mL, 1.332 mmol, 3.0 equiv) in butan-1-ol (2 mL) was heated at 100° C. for 90 min. Addition of propan-1-ol (1 ml) and heated at 150° C. for 60 min. The reaction mixture was concentrated in vacuo. Flash column (silica, 24 g) eluting w/0-30% EtOAc/DCM afforded (S)-4-Isopropyl-3-{2-[(3-p-tolyl-[1,2,4]oxadiazol-5-ylmethyl)-amino]-pyrimidin-4-yl}-oxazolidin-2-one (95 mg, white foam) in 54.2% yield. HRMS (B) m/z 394.1753 2.38 Min.

Example 476

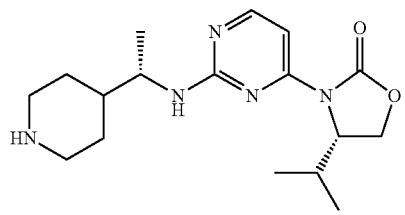 [SMILES: CC(C)[C@H]1COC(=O)N1c1ccnc(N[C@@H](C)C2CCNCC2)n1]

To a solution of 4-{(S)-1-[4-((S)-4-Isopropyl-2-oxo-oxazolidin-3-yl)-pyrimidin-2-ylamino]-ethyl}-piperidine-1-carboxylic acid benzyl ester (22 mg) in methanol (5 mL) was added palladium hydroxide on carbon (7 mg, 0.05 mmol). The reaction was then stirred at room temperature for 16 hours. The reaction is then filtered and then concentrated under vacuum. The crude material was then purified using reverse phase C18 ODB column water-acetonitrile 0.1% TFA modifier to give (S)-4-isopropyl-3-[2-((S)-1-piperidin-4-yl-ethylamino)-pyrimidin-4-yl]-oxazolidin-2-one (11 mg) in 70% yield.

HRMS(B) m/z 333.2165 (M+H)+; RT.: 1.09 min.

Example 477

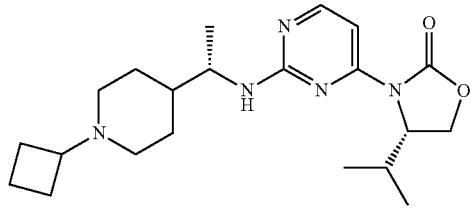 [SMILES: CC(C)[C@H]1COC(=O)N1c1ccnc(N[C@@H](C)C2CCN(C3CCC3)CC2)n1]

A solution of (S)-4-Isopropyl-3-[2-((S)-1-piperidin-4-yl-ethylamino)-pyrimidin-4-yl]-oxazolidin-2-one (28 mg, 0.084 mmol) in THF (2 mL) was added cyclobutanone (14 mg, 0.20 mmol) and sodium triacetoxyborohydride (28 mg, 0.13 mmol). The reaction was stirred at room temperature for 18 hours. The solvent is then removed under vacuum. The crude material was then purified using reverse phase C18 ODB column water-acetonitrile 0.1% TFA modifier to give (S)-3-{2-[(S)-1-(1-Cyclobutyl-piperidin-4-yl)-ethylamino]-pyrimidin-4-yl}-4-isopropyl-oxazolidin-2-one (20 mg) in 62% yield.

HRMS(B) m/z 388.2717 (M+H)+; RT.: 2.32 min.

Example 478

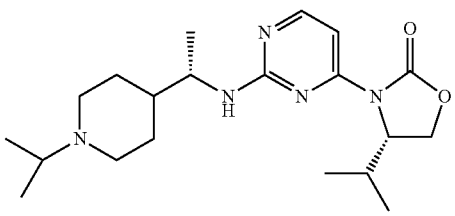 [SMILES: CC(C)[C@H]1COC(=O)N1c1ccnc(N[C@@H](C)C2CCN(C(C)C)CC2)n1]

A solution of (S)-4-Isopropyl-3-[2-((S)-1-piperidin-4-yl-ethylamino)-pyrimidin-4-yl]-oxazolidin-2-one (20 mg, 0.060 mmol) in THF (2 mL) was added cyclobutanone (10 mg, 0.17 mmol) and sodium triacetoxyborohydride (20 mg, 0.09 mmol). The reaction was stirred at room temperature for 18 hours. The solvent is then removed under vacuum. The crude material was then purified using reverse phase C18 ODB column water-acetonitrile 0.1% TFA modifier to give (S)-4-Isopropyl-3-{2-[(S)-1-(1-isopropyl-piperidin-4-yl)-ethylamino]-pyrimidin-4-yl}-oxazolidin-2-one (20 mg) in 62% yield.

HRMS(B) m/z 376.2705 (M+H)+; RT.: 1.24 min.

Example 479

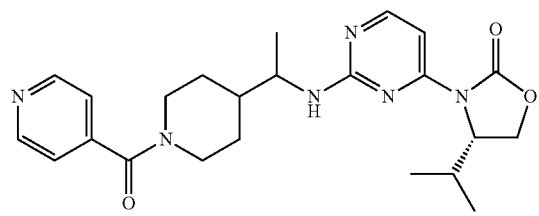 [SMILES: CC(Nc1nccc(N2C(=O)OC[C@@H]2C(C)C)n1)C1CCN(C(=O)c2ccncc2)CC1]

To a solution of S)-4-Isopropyl-3-[2-((S)-1-piperidin-4-yl-ethylamino)-pyrimidin-4-yl]-oxazolidin-2-one (20 mg, 0.48 mmol) in dichloromethane (1 mL) and DMF (1 mL) was added HATU (23 mg, 0.06 mmol) and DIPEA (0.03 mL, 0.18 mmol) The reaction was stirred at room temperature for 18 hours. The solvent is then removed under vacuum. The crude material was then purified using reverse phase C18 ODB column water-acetonitrile 0.1% TFA modifier to give (S)-4-Isopropyl-3-(2-{(S)-1-[1-(pyridine-4-carbonyl)-piperidin-4-yl]-ethylamino}-pyrimidin-4-yl)-oxazolidin-2-one (2 mg) in 8% yield.

HRMS(B) m/z 438.2379 (M+H)+; RT.: 1.82 min.

Example 480

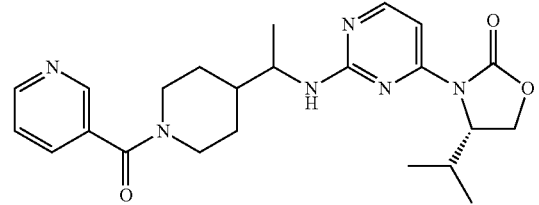 [SMILES: CC(Nc1nccc(N2C(=O)OC[C@@H]2C(C)C)n1)C1CCN(C(=O)c2cccnc2)CC1]

To a solution of S)-4-Isopropyl-3-[2-((S)-1-piperidin-4-yl-ethylamino)-pyrimidin-4-yl]-oxazolidin-2-one (16 mg, 0.48 mmol) in dichloromethane (1 mL) and DMF (1 mL) was added HATU (20 mg, 0.05 mmol) and DiPEA (0.03 mL, 0.15 mmol) The reaction was stirred at room temperature for 18 hours. The solvent is then removed under vacuum. The crude material was then purified using reverse phase C18 ODB column water-acetonitrile 0.1% TFA modifier to give (S)-4-Isopropyl-3-(2-{(S)-1-[1-(pyridine-4-carbonyl)-piperidin-4-yl]-ethylamino}-pyrimidin-3-yl)-oxazolidin-2-one (2 mg) in 8% yield.

HRMS(B) m/z 438.2379 (M+H)+; RT.: 1.83 min.

Example 481 & 482

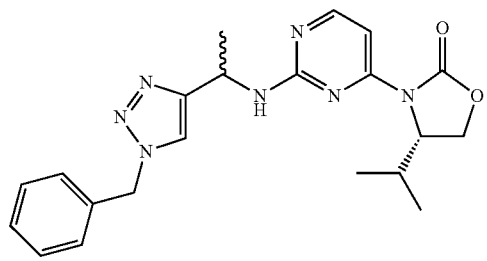 [SMILES: CC(Nc1nccc(N2C(=O)OC[C@@H]2C(C)C)n1)c1cn(Cc2ccccc2)nn1]

To a solution of (S)-4-Isopropyl-3-[2-((S)-1-methyl-prop-2-ynylamino)-pyrimidin-4-yl]-oxazolidin-2-one (60 mg, 0.22 mmol) and benzyl azide (30 mg, 0.23 mmol) in water (0.5 mL) and DMSO (3 mL) was added copper sulfate pentahydrate (56 mg, 0.23 mmol) and L-ascorbic acid sodium salt (45 mg, 0.23 mmol). The reaction was stirred for 48 hours at room temperature. The reaction mixture was diluted with EtOAc (75 mL) and washed with water (15 mL) and 1N solution sodium bicarbonate (15 mL). The organic layer was dried over MgSO4, filtered and concentrated. The crude material was then purified on reverse phase using a C18 column water-acetonitrile TFA as a modifier, which also effected separation of the two diastereomer products (S)-3-{2-[(S)-1-(1-benzyl-1H-[1,2,3]triazol-4-yl)-ethylamino]-pyrimidin-4-yl}-4-isopropyl-oxazolidin-2-one and (S)-3-{2-[(R)-1-(1-benzyl-1H-[1,2,3]triazol-4-yl)-ethylamino]-pyrimidin-4-yl}-4-isopropyl-oxazolidin-2-one First Peak 481: HRMS(B) m/z 407.2070 (M+H)+; RT.: 2.26 min.

Second Peak 482: HRMS(B) m/z 407.2070 (M+H)+; RT.: 2.32 min.

Example 483 & 484

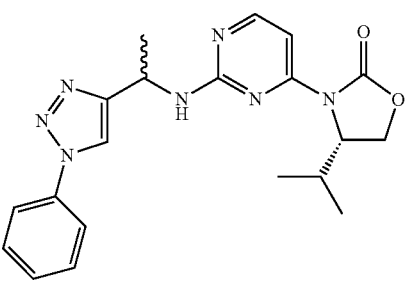 [SMILES: CC(Nc1nccc(N2C(=O)OC[C@@H]2C(C)C)n1)c1cn(-c2ccccc2)nn1]

To a solution of (S)-4-Isopropyl-3-[2-((S)-1-methyl-prop-2-ynylamino)-pyrimidin-4-yl]-oxazolidin-2-one (82 mg, 0.30 mmol) and azidobenzene (36 mg, 0.30 mmol) in water (0.5 mL) and DMSO (3 mL) was added copper sulfate pentahydrate (75 mg, 0.23 mmol) and L-ascorbic acid sodium salt (60 mg, 0.23 mmol). The reaction was stirred for 48 hours at room temperature. The reaction mixture was diluted with EtOAc (75 mL) and washed with water (15 mL) and 1N solution sodium bicarbonate (15 mL). The organic layer was dried over MgSO4, filtered and concentrated. The crude material was then purified on reverse phase using a C18 column water-acetonitrile TFA as a modifier, which also effected separation of the two diastereomer products (S)-4-isopropyl-3-{2-[(S)-1-(1-phenyl-1H-[1,2,3]triazol-4-yl)-ethylamino]-pyrimidin-4-yl}-oxazolidin-2-one and (S)-4-isopropyl-3-{2-[(R)-1-(1-phenyl-1H-[1,2,3]triazol-4-yl)-ethylamino]-pyrimidin-4-yl}-oxazolidin-2-one First Peak 483: HRMS(B) m/z 393.1913 (M+H)+; RT.: 2.31 min.

Second Peak 484: HRMS(B) m/z 393.1913 (M+H)+; RT.: 2.40 min.

Example 485

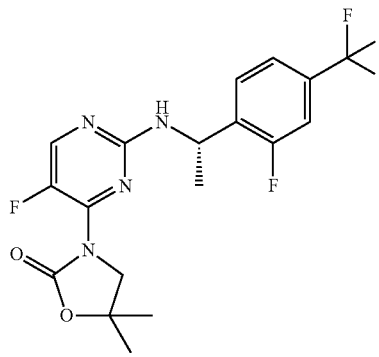

To a room temperature solution of 3-(2-chloro-5-fluoropyrimidin-4-yl)-5,5-dimethyloxazolidin-2-one (30 mg, 0.122 mmol) in DMSO (300 μL) was treated with DIPEA (68 μL, 0.366 mmol) followed by addition of (S)-1-(2-fluoro-4-(trifluoromethyl)phenyl)ethanamine (41.4 mg, 0.2 mmol). The reaction was sealed, heated at 95° C. for ~18 hr. Purification by reverse phase HPLC provided the trifluoroacetate salt of (S)-3-(5-fluoro-2-(1-(2-fluoro-4-(trifluoromethyl)phenyl) ethylamino)pyrimidin-4-yl)-5,5-dimethyloxazolidin-2-one. (6.0 mg, white solid). $^1$H NMR (400 MHz, METHANOL-d4) δ ppm 1.44-1.58 (m, 12H) 3.50-3.74 (m, 1H) 3.88 (d, J=9.8 Hz 1H) 5.29 (d, J=7.04 Hz, 1H) 7.38-7.45 (m, 2H) 7.6 (t, J=8.22 Hz 1H) 8.16 (d, J=3.13 Hz, 1H); HRMS(A) m/z 417.1360 (M+H)$^+$, Rt 2.29 min.

The compounds in Table 11 were prepared using methods similar to those described for the preparation of Example 485.

TABLE 11

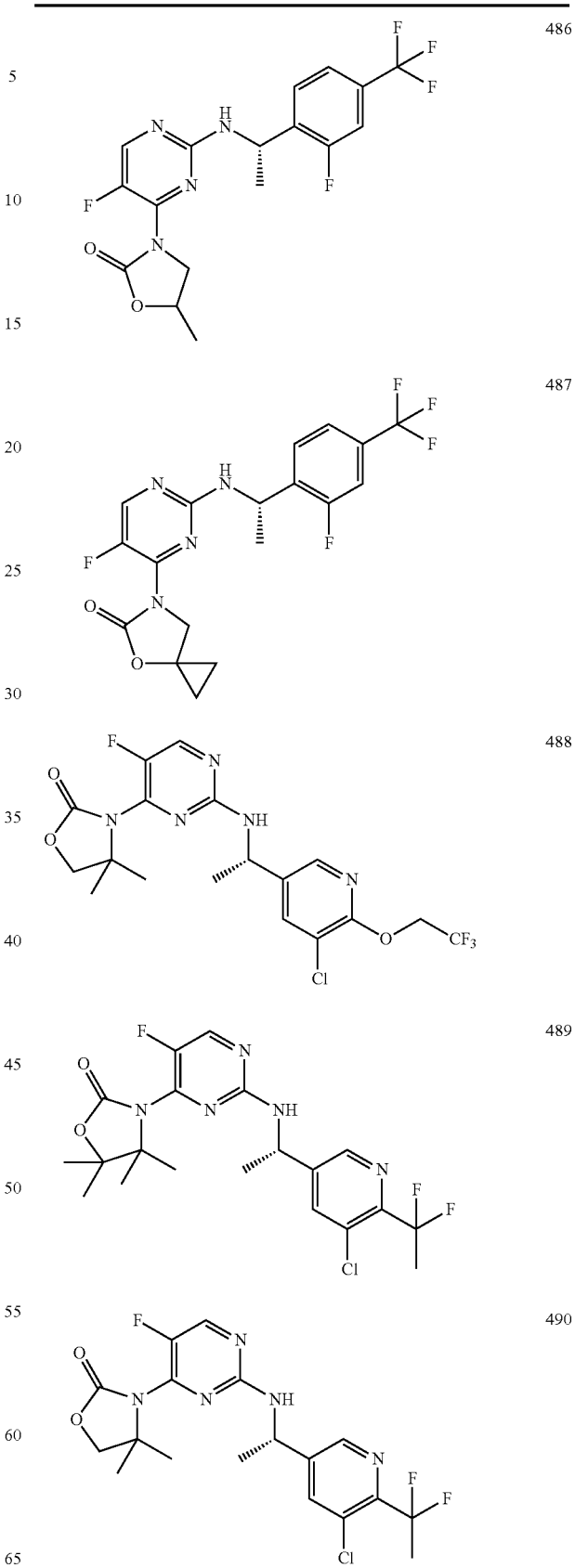

TABLE 11-continued
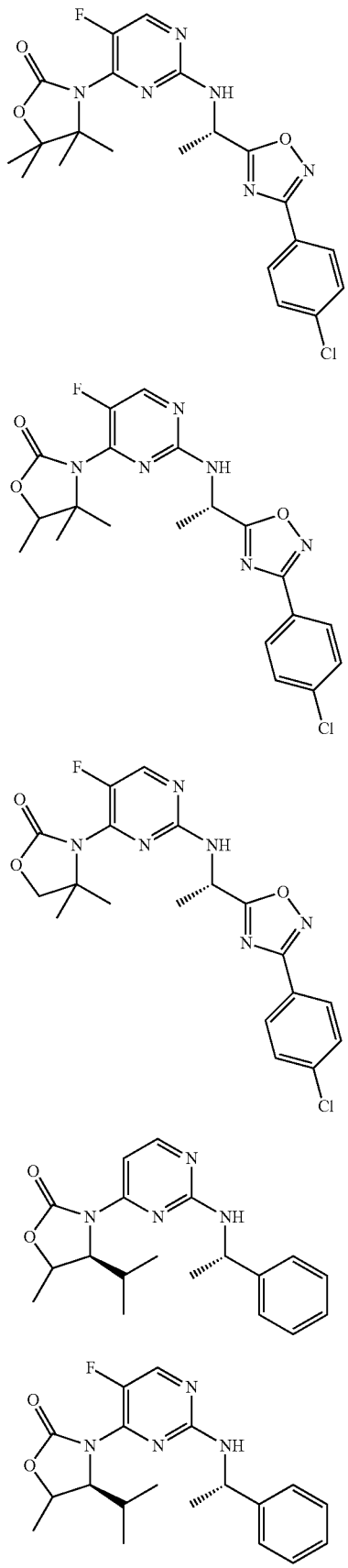
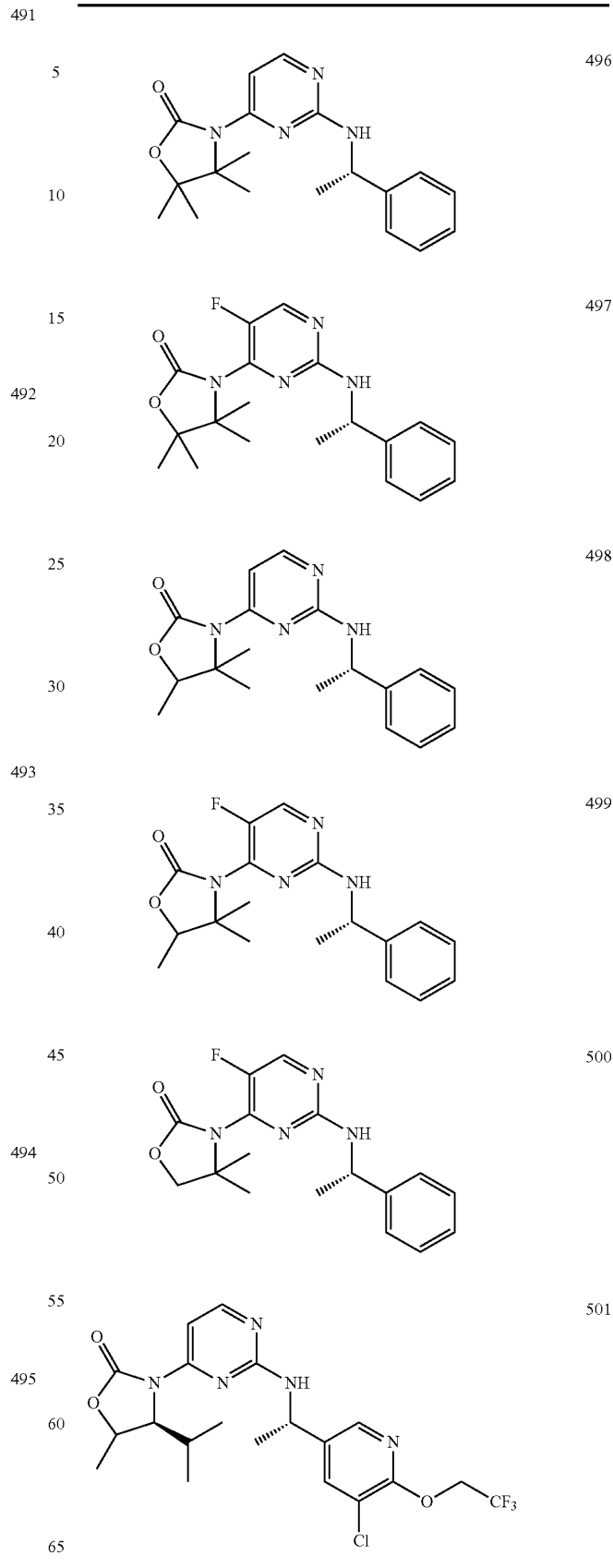

TABLE 11-continued

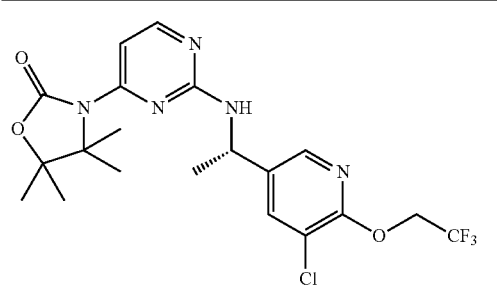
502

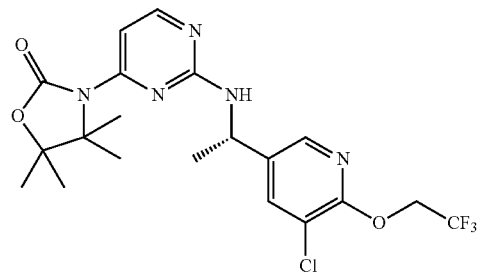 [SMILES: C[C@H](Nc1nccc(N2C(=O)OC(C)(C)C2(C)C)n1)c1cnc(OCC(F)(F)F)c(Cl)c1]
503

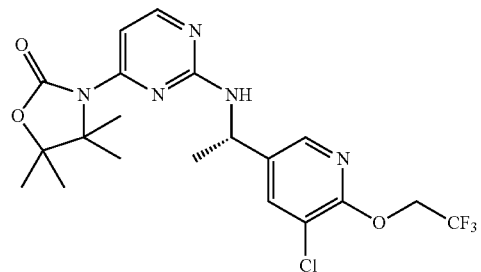
504

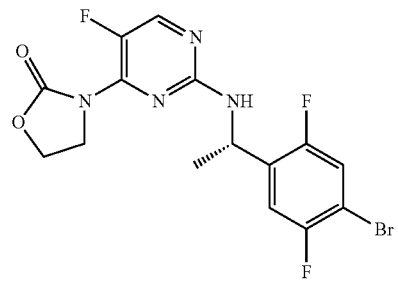 [SMILES: C[C@H](Nc1ncc(F)c(N2CCOC2=O)n1)c1cc(F)c(Br)cc1F]
505

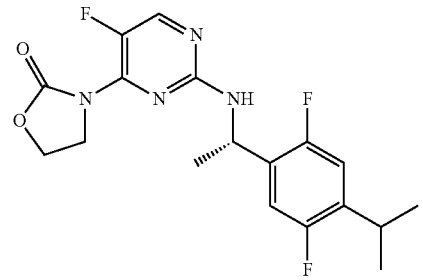 [SMILES: CC(C)c1cc(F)c([C@H](C)Nc2ncc(F)c(N3CCOC3=O)n2)cc1F]
506

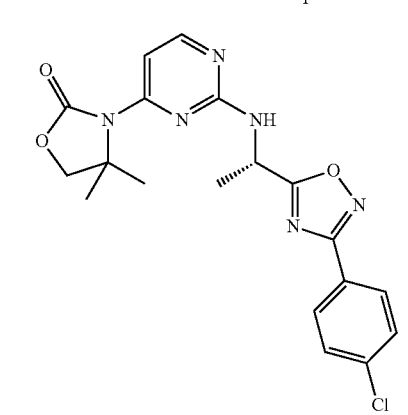
507

TABLE 12

Chemical name, NMR chemical shifts and LCMS signal for each compound listed in Table 11.

| Example: Name | $^1$H NMR (400 MHz) ppm | LCMS |
| --- | --- | --- |
| 486: 3-(5-fluoro-2-((S)-1-(2-fluoro-4-(trifluoromethyl)phenyl)ethylamino)pyrimidin-4-yl)-5-methyloxazolidin-2-one | (CD$_3$OD) 1.41-1.58 (m, 8 H) 3.55 (br. s., 1 H) 3.74-3.80 (m, 1 H) 4.17 (dd, J = 9.59, 7.63 Hz, 1 H) 5.26-5.33 (m, 1 H) 7.39-7.45 (m, 2 H) 7.60 (t, J = 7.83 Hz, 1 H) 8.15 (d, J = 3.52 Hz, 1 H) | HRMS(A) m/z 403.1198 (M + H)$^+$, Rt 2.20 min |
| 487: (S)-6-(5-fluoro-2-(1-(2-fluoro-4-(trifluoromethyl)phenyl)ethylamino)pyrimidin-4-yl)-4-oxa-6-azaspiro[2.4]heptan-5-one | (CD$_3$OD) 0.90 (m, 2 H) 1.18-1.27 (m, 2 H) 1.53 (d, J = 7.04 Hz, 3 H) 4.21 (d, J = 9.39 Hz, 1 H) 5.30 (d, J = 7.04 Hz, 1 H) 7.38-7.45 (m, 2 H) 7.60 (t, J = 7.83 Hz 1 H) 8.17 (d, J = 3.52 Hz, 1 H) | HRMS(A) m/z 415.1204 (M + H)$^+$, Rt 2.31 min |
| 488: (S)-3-(2-(1-(5-chloro-6-(2,2,2-trifluoroethoxy)pyridin-3-yl)ethylamino)-5-fluoropyrimidin-4-yl)-4,4-dimethyloxazolidin-2-one | (CD$_3$OD) 8.22 (d, J = 3.13 Hz, 1 H) 8.08 (d, J = 1.96 Hz, 1 H) 7.84 (d, J = 1.96 Hz, 1 H) 5.26-5.27 (m, 1 H) 4.90 (q, J = 8.61 Hz, 3 H) 4.13-4.22 (m, 2 H) 1.47-1.59 (m, 9H) | HRMS(A) m/z 464.1125 (M + H)$^+$, Rt 2.28 min |
| 489: (S)-3-(2-(1-(5-chloro-6-(1,1-difluoroethyl)pyridin-3-yl)ethylamino)-5- | (CD$_3$OD) 8.51 (d, J = 1.57 Hz, 1 H) 8.23 (d, J = 2.35 Hz, 1 H) 7.93 (d, J = 1.56 Hz, 1 H) 4.99 (q, J = 6.52 Hz, 1 H) 2.02 (t, J = 18.78 Hz, 3 H) 1.57 (d, J = 7.43 Hz, 3 H) | HRMS(A) m/z 458.1573 (M + H)$^+$, |

TABLE 12-continued

Chemical name, NMR chemical shifts and LCMS signal for each compound listed in Table 11.

| Example: Name | ¹H NMR (400 MHz) ppm | LCMS |
|---|---|---|
| fluoropyrimidin-4-yl)-4,4,5,5-tetramethyloxazolidin-2-one | 1.34-1.42 (m, 12 H) | Rt 2.02 min |
| 490: (S)-3-(2-(1-(5-chloro-6-(1,1-difluoroethyl)pyridin-3-yl)ethylamino)-5-fluoropyrimidin-4-yl)-4,4-dimethyloxazolidin-2-one | (CD₃OD) 8.50 (d, J = 1.17 Hz, 1 H) 8.24 (d, J = 2.35 Hz, 1 H) 7.93 (d, J = 1.57 Hz, 1 H) 4.99 (q, J = 6.65 Hz, 1 H) 4.12-4.21 (m, 2 H) 2.01 (t, J = 18.78 Hz, 3 H) 1.57 (d, J = 7.04 Hz, 3 H) 1.47 (s, 6 H) | HRMS(A) m/z 430.1265 (M + H)⁺, Rt 2.05 min |
| 491: (S)-3-(2-(1-(3-(4-chlorophenyl)-1,2,4-oxadiazol-5-yl)ethylamino)-5-fluoropyrimidin-4-yl)-4,4,5,5-tetramethyloxazolidin-2-one | (CD₃OD) 8.27 (br. s., 1 H) 8.00 (d, J = 8.61 Hz, 3 H) 7.52 (d, J = 8.61 Hz, 4 H) 5.29 (d, J = 7.04 Hz, 1 H) 1.73 (s, 3 H) 1.44 (s, 3 H) 1.38 (s, 3 H) 1.28 (s, 3 H) | HRMS(A) m/z 461.1512 (M + H)⁺, Rt 2.37 min |
| 492: 3-(2-((S)-1-(3-(4-chlorophenyl)-1,2,4-oxadiazol-5-yl)ethylamino)-5-fluoropyrimidin-4-yl)-4,4,5-trimethyloxazolidin-2-one (1:1 mixture of diastereomers) | (CD₃OD) 8.27 (d, J = 1.57 Hz, 1 H) 8.00 (d, J = 8.61 Hz, 2 H) 7.52 (d, J = 8.61 Hz, 2 H) 5.29 (m, 1 H) 4.44 (m, 1 H) 1.73 (d, J = 7.43 Hz, 3 H) 1.44 (br. s., 3 H) 1.26-1.35 (m, 6 H) | HRMS(A) m/z 477.1349 (M + H)⁺, Rt 2.3 min |
| 493: (S)-3-(2-(1-(3-(4-chlorophenyl)-1,2,4-oxadiazol-5-yl)ethylamino)-5-fluoropyrimidin-4-yl)-4,4-dimethyloxazolidin-2-one | (CD₃OD) 8.28 (d, J = 2.35 Hz, 1 H) 8.00 (d, J = 8.61 Hz, 2 H) 7.51 (d, J = 8.61 Hz, 2 H) 5.29 (m, 1 H) 4.11-4.24 (m, 2 H) 1.73 (d, J = 7.04 Hz, 3 H) 1.53 (s, 3 H) 1.30 (br. s., 3 H) | HRMS(A) m/z 433.1201 (M + H)⁺, Rt 2.21 min |
| 494: (4S)-4-isopropyl-5-methyl-3-(2-((S)-1-phenylethylamino)pyrimidin-4-yl)oxazolidin-2-one (1:1 mixture of diastereomers) | (CD₃OD) 8.11 (d, J = 6.26 Hz, 1 H) 7.71 (d, J = 7.43 Hz, 1 H) 7.29-7.40 (m, 4 H) 7.22-7.28 (m, 1 H) 5.23 (br. s., 1 H) 4.82-4.91 (m, 1 H) 4.78 (br. s., 1 H) 2.01 (br. s., 1 H) 1.59 (d, J = 7.04 Hz, 3 H) 1.54 (d, J = 6.65 Hz, 3 H) 0.76 (br. s., 6 H) | HRMS(A) m/z 341.1985 (M + H)⁺, Rt 1.78 min |
| 495: (4S)-3-(5-fluoro-2-((S)-1-phenylethylamino)pyrimidin-4-yl)-4-isopropyl-5-methyloxazolidin-2-one (1:1 mixture of diastereomers) | (CD₃OD) 7.87 (d, J = 3.13 Hz, 1 H) 6.95-7.02 (m, 2 H) 6.91 (t, J = 7.63 Hz, 2 H) 6.75-6.85 (m, 1 H) 4.52-4.61 (m, 2H) 4.00 (br. s., 1 H) 1.49 (br. s., 1 H) 1.11 (dd, J = 9.59, 6.85 Hz, 6 H) 0.38 (d, J = 4.30 Hz, 6 H) | HRMS(A) m/z 359.1891 (M + H)⁺, Rt 2.19 min |
| 496: (S)-4,4,5,5-tetramethyl-3-(2-(1-phenylethylamino)pyrimidin-4-yl)oxazolidin-2-one | (CD₃OD) 8.08 (d, J = 6.26 Hz, 1 H) 7.28-7.40 (m, 5 H) 7.18-7.25 (m, 1 H) 5.05 (q, J = 7.04 Hz, 1 H) 1.55-1.62 (m, 6H) 1.37 (s, 3 H) 1.32 (s, 3H) | HRMS(A) m/z 341.1984 (M + H)⁺, Rt 1.73 min |
| 497: (S)-3-(5-fluoro-2-(1-phenylethylamino)pyrimidin-4-yl)-4,4,5,5-tetramethyloxazolidin-2-one | (CD₃OD) 8.18 (d, J = 2.74 Hz, 1 H) 7.30-7.39 (m, 2 H) 7.23-7.30 (m, 2 H) 7.12-7.21 (m, 1 H) 4.90 (q, J = 6.91 Hz, 1 H) 1.50 (d, J = 7.04 Hz, 3 H) 1.42 (s, 3 H) 1.36 (s, 3 H) 1.33 (s, 3H) | HRMS(A) m/z 359.1891 (M + H)⁺, Rt 2.16 min |
| 498: 4,4,5-trimethyl-3-(2-((S)-1-phenylethylamino)pyrimidin-4-yl)oxazolidin-2-one (1:1 mixture of diastereomers) | (CD₃OD) 8.09 (d, J = 6.65 Hz, 1 H) 7.53 (d, J = 7.04 Hz, 1 H) 7.45 (d, J = 7.04 Hz, 1 H) 7.30-7.40 (m, 8 H) 7.20-7.28 (m, 2 H) 5.09 (t, J = 7.04 Hz, 2 H) 4.27-4.42 (m, 2 H) 1.52-1.69 (m, 12 H) 1.32 (dd, J = 11.15, 6.46 Hz, 6 H) 0.82-1.20 (m, 6 H) | HRMS(A) m/z 327.1826 (M + H)⁺, Rt 1.66 min |
| 499: 3-(5-fluoro-2-((S)-1-phenylethylamino)pyrimidin-4-yl)-4,4,5-trimethyloxazolidin-2-one (1:1 mixture of diastereomers) | (CD₃OD) 8.18 (d, J = 2.74 Hz, 1 H) 7.30-7.37 (m, 2 H) 7.24-7.30 (m, 2 H) 7.11-7.21 (m, 1 H) 4.87-4.97 (m, 1 H) 4.31-4.46 (m, 1 H) 1.50 (d, J = 7.04 Hz, 3 H) 1.41 (d, J = 10.96 Hz, 3 H) 1.29 (dd, J = 6.46, 3.33 Hz, 3 H) 0.84-1.16 (br. s, 3 H) | HRMS(A) m/z 345.1735 (M + H)⁺, Rt 2.09 min |
| 500: (S)-3-(5-fluoro-2-(1-phenylethylamino)pyrimidin-4-yl)-4,4-dimethyloxazolidin-2-one | (CD₃OD) 8.19 (d, J = 2.35 Hz, 1 H) 7.30-7.37 (m, 2 H) 7.24-7.30 (m, 2 H) 7.13-7.21 (m, 1 H) 4.91 (q, J = 7.30 Hz, 1 H) 4.12 (q, J = 8.22 Hz, 2 H) 1.45-1.55 (m, 6 H) 1.08 (br. s., 3 H) | HRMS(A) m/z 331.1573 (M + H)⁺, Rt 1.98 min |

TABLE 12-continued

Chemical name, NMR chemical shifts and LCMS signal for each compound listed in Table 11.

| Example: Name | ¹H NMR (400 MHz) ppm | LCMS |
|---|---|---|
| 501: (4S)-3-(2-((S)-1-(5-chloro-6-(2,2,2-trifluoroethoxy)pyridin-3-yl)ethylamino)pyrimidin-4-yl)-4-isopropyl-5-methyloxazolidin-2-one (1:1 mixture of diastereomers) | ¹H NMR (400 MHz, CD₃OD) δ ppm 8.14 (d, J = 6.65 Hz, 1 H) 8.10 (d, J = 1.96 Hz, 1 H) 7.86 (d, J = 2.35 Hz, 1 H) 7.57 (d, J = 6.26 Hz, 1 H) 5.17 (d, J = 6.65 Hz, 1 H) 4.92 (q, J = 8.87 Hz, 1 H) 4.80-4.84 (m, 1H) 2.04 (br. s., 2 H) 1.55 (dd, J = 15.85, 6.85 Hz, 6 H) 0.79 (br. s., 6 H) | HRMS(A) m/z 474.1523 (M + H)⁺, Rt 2.18 min |
| 502: (S)-3-(2-(1-(5-chloro-6-(2,2,2-trifluoroethoxy)pyridin-3-yl)ethylamino)pyrimidin-4-yl)-4,4,5,5-tetramethyloxazolidin-2-one | (CD₃OD) 8.07-8.16 (m, 1 H) 7.89 (d, J = 1.96 Hz, 1 H) 7.32 (d, J = 6.26 Hz, 1 H) 5.08 (q, J = 6.78 Hz, 1 H) 1.55-1.65 (m, 8 H) 1.37 (d, J = 11.35 Hz, 6 H) 1.20 (d, J = 11.35 Hz, 3 H) | HRMS(A) m/z 474.1534 (M + H)⁺, Rt 2.16 min |
| 503: 3-(2-((S)-1-(5-chloro-6-(2,2,2-trifluoroethoxy)pyridin-3-yl)ethylamino)pyrimidin-4-yl)-4,4,5-trimethyloxazolidin-2-one (1:2 mixture of diastereomers) | (CD₃OD) 8.47 (d, J = 5.87 Hz, 1 H) 8.11 (d, J = 2.35 Hz, 3H) 7.99 (d, J = 6.26 Hz, 1 H) 7.88 (d, J = 1.96 Hz, 3 H) 7.39 (d, J = 6.26 Hz, 2 H) 7.32 (d, J = 6.65 Hz, 2 H) 5.04-5.13 (m, 1 H) 4.87-4.98 (m, 2 H) 4.45 (d, J = 6.65 Hz, 1 H) 4.35 (dd, J = 13.69, 6.65 Hz, 2 H) 1.67(d, J = 4.70 Hz, 9 H) 1.59 (d, J = 7.04 Hz, 12 H) 1.39 (d, J = 6.65 Hz, 3 H) 1.33 (t, J = 6.06 Hz, 6 H) 0.99-1.27 (m, 9 H) | HRMS(A) m/z 460.1375 (M + H)⁺, Rt 2.08, 2.11 min |
| 504: (S)-3-(2-(1-(5-chloro-6-(2,2,2-trifluoroethoxy)pyridin-3-yl)ethylamino)pyrimidin-4-yl)-4,4-dimethyloxazolidin-2-one | (CD₃OD) 8.09-8.17 (m, 1 H) 7.88 (d, J = 2.35 Hz, 1 H) 7.38 (d, J = 6.26 Hz, 1 H) 4.91 (q, J = 8.61 Hz, 1 H) 4.06-4.16(m, 2 H) 1.71 (m, 5 H) 1.58 (d, J = 7.04 Hz, 3 H) 1.28 (br. s., 3 H) | HRMS(A) m/z 446.1219 (M + H)⁺, Rt 2.01 min |
| 505: (S)-3-(2-(1-(2,5-difluoro-4-isopropylphenyl)ethylamino)-5-fluoropyrimidin-4-yl)oxazolidin-2-one | (CD₃OD) 8.15 (d, J = 3.13 Hz, 1 H) 6.92-7.08 (m, 2 H) 5.21 (q, J = 6.78 Hz, 1 H) 4.44-4.58 (m, 2 H) 4.10-4.22 (m, 1H) 3.96 (m, 1 H) 3.07-3.23 (m, 1 H) 1.48 (d, J = 7.04 Hz, 5 H) 1.21 (m, 6 H) | HRMS(A) m/z 381.1544 (M + H)⁺, Rt 2.26 min |
| 506: (S)-3-(2-(1-(4-bromo-2,5-difluorophenyl)ethylamino)-5-fluoropyrimidin-4-yl)oxazolidin-2-one | (CD₃OD) 8.15 (d, J = 3.52 Hz, 1 H) 7.39 (dd, J = 9.00, 5.48 Hz, 1 H) 7.24 (dd, J = 9.19, 6.46 Hz, 1 H) 5.19 (q, J = 7.04 Hz,1 H) 4.44-4.58 (m, 2 H) 4.09-4.23 (m, 1 H) 3.94 (br. s., 1 H) 1.48 (d, J = 7.04 Hz, 3 H) | HRMS(A) m/z 417.018 (M + H)⁺, t 2.07 min |
| 507: (S)-3-(2-(1-(3-(4-chlorophenyl)-1,2,4-oxadiazol-5-yl)ethylamino)pyrimidin-4-yl)-4,4-dimethyloxazolidin-2-one | (CD₃OD) 8.09 (d, J = 6.26 Hz, 1 H) 7.91 (d, J = 8.61 Hz, 2 H) 7.43 (d, J = 8.61 Hz, 3 H) 5.35 (q, J = 7.30 Hz, 1 H) 3.97-4.09 (m, 2 H) 1.69 (d, J = 7.43 Hz, 3 H) 1.62 (s, 3 H) 1.14-1.45 (m, 3 H) | HRMS(A) m/z 415.1287 (M + H)⁺, Rt 2.14 min |

Example 508

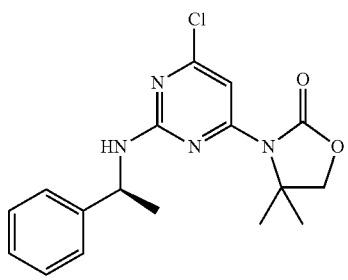 [SMILES: C[C@H](Nc1nc(Cl)cc(N2C(=O)OCC2(C)C)n1)c1ccccc1]

A solution of 3-(2,6-dichloropyrimidin-4-yl)-4,4-dimethyloxazolidin-2-one (70.0 mg, 0.267 mmol), (S)-(−)-1-phenylethanamine (0.034 mL, 0.267 mmol, 1.0 equiv), and N-ethyl-N-isopropylpropan-2-amine (0.070 mL, 0.401 mmol, 1.5 equiv) in DMSO (1.5 mL) was heated at 85° C. for 2-4 h. Purification by reverse phase HPLC provided the trifluoroacetate salt of (S)-3-(6-chloro-2-(1-phenylethylamino) pyrimidin-4-yl)-4,4-dimethyloxazolidin-2-one (20.0 mg, white solid) in 16% yield. ¹H NMR (300 MHz, CDCl₃) δ 7.36 (s, 1H), 7.33-7.31 (m, 4H), 7.26-7.21 (m, 1H), 5.48 (br m, 1H), 4.02-3.94 (m, 2H), 1.65 (s, 3H), 1.55 (d, J=6.9 Hz, 3H), 1.26 (s, 3H); HRMS(A) m/z 347.1274 (M+H)⁺, Rt 2.32 min.

The compounds in Table 13 were prepared using methods similar to those described for the preparation of Example 508.

TABLE 13

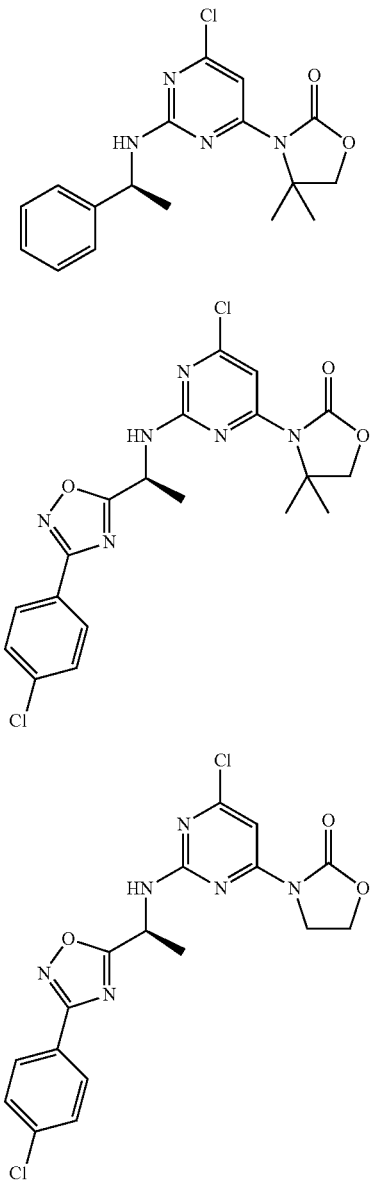

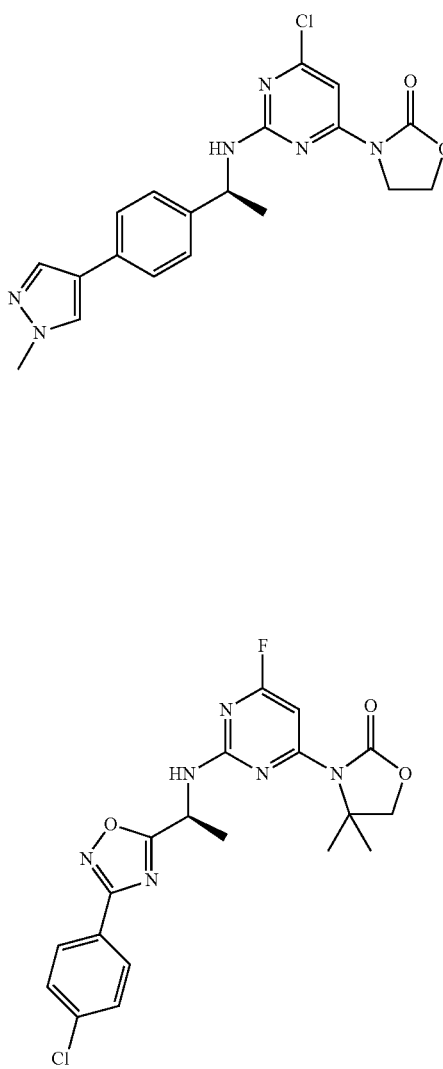

TABLE 14

Chemical name, NMR chemical shifts and LCMS signal for each compound listed in Table 13.

| Example: Name | $^1$H NMR (400 MHz) δ ppm | LCMS |
|---|---|---|
| 509: (S)-3-(6-chloro-2-(1-phenylethylamino)pyrimidin-4-yl)-4,4-dimethyloxazolidin-2-one | (CDCl$_3$) 7.36 (s, 1H), 7.33-7.31 (m, 4H), 7.26-7.21 (m, 1H), 5.48 (br m, 1H), 4.02-3.94 (m, 2H), 1.65 (s, 3H), 1.55 (d, J = 6.9 Hz, 3H), 1.26(s, 3H) | HRMS(A) m/z 347.1274 (M + H)$^+$, Rt 2.32 min |
| 510: (S)-3-(6-chloro-2-(1-(3-(4-chlorophenyl)-1,2,4-oxadiazol-5-yl)ethylamino)pyrimidin-4-yl)-4,4-dimethyloxazolidin-2-one | (CDCl$_3$) 8.00 (d, J = 8.4 Hz, 2 H), 7.53 (s, 1H), 7.47 (d, J = 8.4 Hz, 2H), 5.44-5.29 (br m, 1H), 4.09-4.02 (m, 2H), 1.78 (d, J = 7.1 Hz, 3H), 1.72 (s, 3H), 1.40 (br s, 3H) | HRMS(A) m/z 449.0905 (M + H)$^+$, Rt 2.51 min |
| 511: (S)-3-(6-chloro-2-(1-(3-(4-chlorophenyl)-1,2,4-oxadiazol-5- | (CDCl$_3$) 8.00 (d, J = 8.7 Hz, 2H), 7.62 (s, 1H), 7.47 (d, J = 8.7 Hz, 2H), 5.32 (br m, 1H), 4.49-4.43 (m, 2H), 4.17-4.14 (m, | HRMS(A) m/z 421.0585 |

TABLE 14-continued

Chemical name, NMR chemical shifts and LCMS signal for each compound listed in Table 13.

| Example: Name | ¹H NMR (400 MHz) δ ppm | LCMS |
|---|---|---|
| yl)ethylamino)pyrimidin-4-yl)oxazolidin-2-one | 1H), 3.95-3.60 (br m, 1H), 1.77 (d, J = 7.1 Hz, 3H) | (M + H)⁺, Rt 2.32 min |
| 512: (S)-3-(6-chloro-2-(1-(2-fluoro-4-(1-methyl-1H-pyrazol-4-yl)phenyl)ethylamino)pyrimidin-4-yl)oxazolidin-2-one | (CDCl₃) 7.76 (s, 1H), 7.60 (s, 1H), 7.50 (s, 1H), 7.34-7.28 (m, 1H), 7.20 (dd, J = 7.8, 1.6 Hz, 1H), 7.15-7.09 (m, 1H), 5.30 (br m, 1H), 4.49-4.42 (m, 2H), 4.28-4.23 (m, 1H), 3.97 (s, 3H), 3.92 (br m, 1H), 1.56 (d, J = 6.7 Hz, 3H) | LCMS m/z 417.2 (M + H)+ |
| 513: (S)-3-(2-(1-(3-(4-chlorophenyl)-1,2,4-oxadiazol-5-yl)ethylamino)-6-fluoropyrimidin-4-yl)-4,4-dimethyloxazolidin-2-one | (CDCl₃) 7.99 (d, J = 8.4 Hz, 2H), 7.45 (d, J = 8.4 Hz, 2H), 7.11 (s, 1H), 5.38 (br m, 1H), 4.08-4.03 (m, 2H), 1.78 (d, J = 7.0 Hz, 3H), 1.73 (s, 3H), 1.38 (brs, 3H) | HRMS(A) m/z 433.1201 (M + H)⁺, Rt 2.42 min |

Example 514

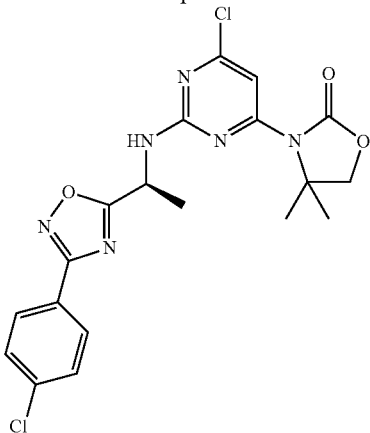

A solution of (S)-3-(2-(1-(3-(4-chlorophenyl)-1,2,4-oxadiazol-5-yl)ethylamino)-6-fluoropyrimidin-4-yl)-4,4-dimethyloxazolidin-2-one (29.0 mg, 0.053 mmol) and 1 N aqueous hydrochloric acid (0.70 mL) in 1,4-dioxane (0.7 mL) was heated at 100° C. for 4 h. After cooling to room temperature, the reaction mixture was diluted with dichloromethane (10 mL), washed with saturated aqueous sodium bicarbonate solution (10 mL), dried over Na₂SO₄, filtered and concentrated. Purification by reverse phase HPLC provided the trifluoroacetate salt of (S)-3-(2-(1-(3-(4-chlorophenyl)-1,2,4-oxadiazol-5-yl)ethylamino)-6-hydroxypyrimidin-4-yl)-4,4-dimethyloxazolidin-2-one (16 mg, white solid) in 55% yield. ¹H NMR (400 MHz, CDCl₃) δ 8.00 (d, J=8.5 Hz, 2H), 7.46 (d, J=8.5 Hz, 2H), 6.71 (br s, 1H), 5.33 (br m, 1H), 4.02-3.99 (m, 2H), 1.83 (d, J=7.1 Hz, 3H), 1.68 (s, 3H), 1.31 (s, 3H); HRMS(A) m/z 431.1245 (M+H)⁺, Rt 1.80 min.

Example 515

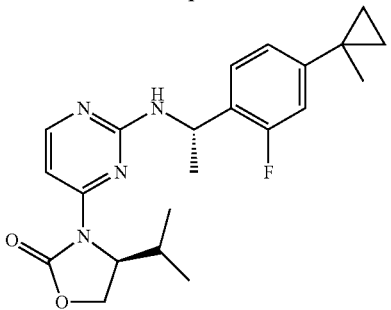

Step 1

To round bottom flask containing (R)—N—((S)-1-(2-fluoro-4-(1-methylcyclopropyl)phenyl)ethyl)-2-methylpropane-2-sulfinamide (87 mg, 0.29 mmol) was added dioxane (2 mL). To this solution was added hydrochloric acid in dioxane (4.0M, 0.15 ml, 0.59 mmol) and the solution allowed to stir 10 min at room temperature.

Volatiles were removed. Et₂O (10 mL) was added and the reaction mixture sonnicated. The volatiles were removed again. Et₂O (10 ml) was again added and the suspension sonnicated. Solid material was collected and washed with Et₂O to afford an HCl salt of (S)-1-(2-fluoro-4-(1-methylcyclopropyl)phenyl)ethanamine (42 mg, 0.18 mmol, 63% yield) as a white solid. LCMS m/z 194.1 (M+H)⁺, Rt 0.60 min.

Step 2

To a microwave vial with stir bar was added (S)-3-(2-chloropyrimidin-4-yl)-4-isopropyloxazolidin-2-one (30 mg, 0.12 mmol) and DMSO (1 mL). To this reaction mixture was added (S)-1-(2-fluoro-4-(1-methylcyclopropyl)phenyl)ethanamine (51 mg, 0.22 mmol) and DIEA (0.09 ml, 0.50 mmol). The vial was capped and the reaction mixture was heated in a preheated oil bath at 110° C. for 18 hr. Solution was purified by reverse phase HPLC. Product fractions combined, frozen and lyophilized to afford (S)-3-(2-((S)-1-(2-fluoro-4-(1-methylcyclopropyl)phenyl)ethylamino)pyrimidin-4-yl)-4-isopropyloxazolidin-2-one (3.3 mg, 6.3 μmol, 5% yield) as a TFA salt. ¹H NMR (400 MHz, CD₃OD) δ 0.58 (br. s., 3H) 0.77 (td, J=5.23, 1.76 Hz, 5H) 0.80-0.86 (m, 2H) 1.38 (s, 3H) 1.57 (d, J=6.94 Hz, 3H) 4.34-4.41 (m, 2H) 4.67 (br. s., 1H) 5.33 (d, J=7.97 Hz, 1H) 6.95-7.05 (m, 2H) 7.22 (t, J=7.97 Hz, 1H) 7.67 (d, J=6.85 Hz, 1H) 8.14 (d, J=6.65 Hz, 1H). LCMS m/z 399.4 (M+H)⁺, Rt 0.93 min. HRMS(A) m/z 399.2202 (M+H)⁺, Rt 2.23 min.

The compounds in Table 15 were prepared using methods similar to those described for the preparation of Examples 515.

TABLE 15
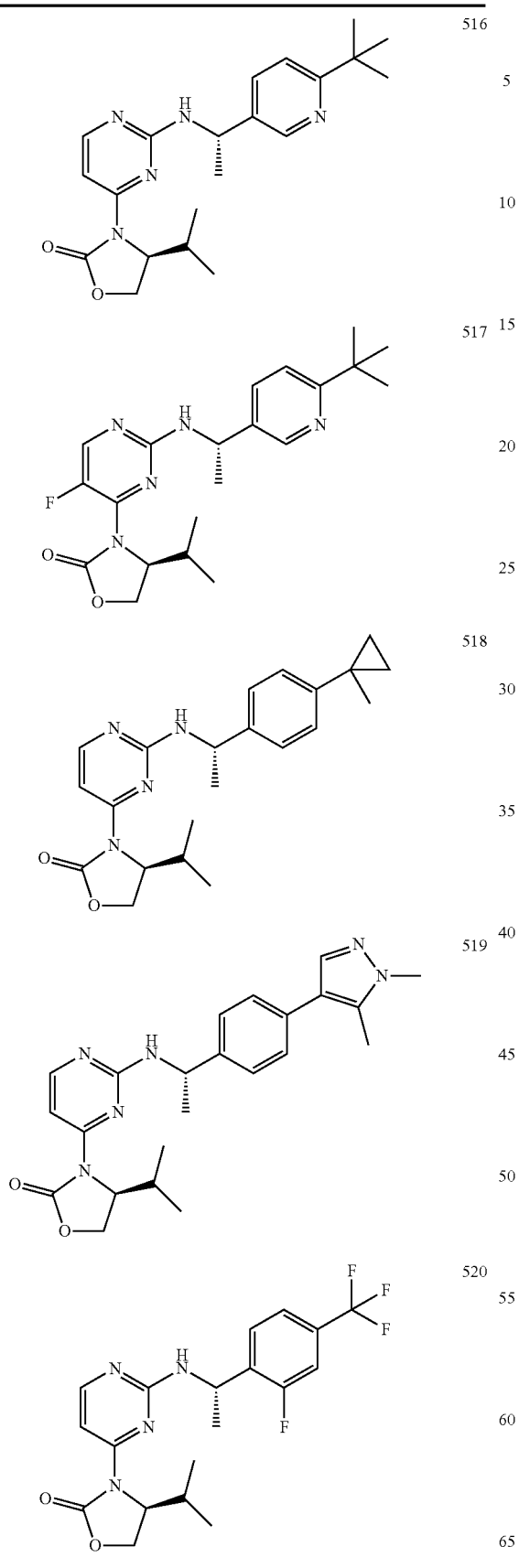
TABLE 15-continued
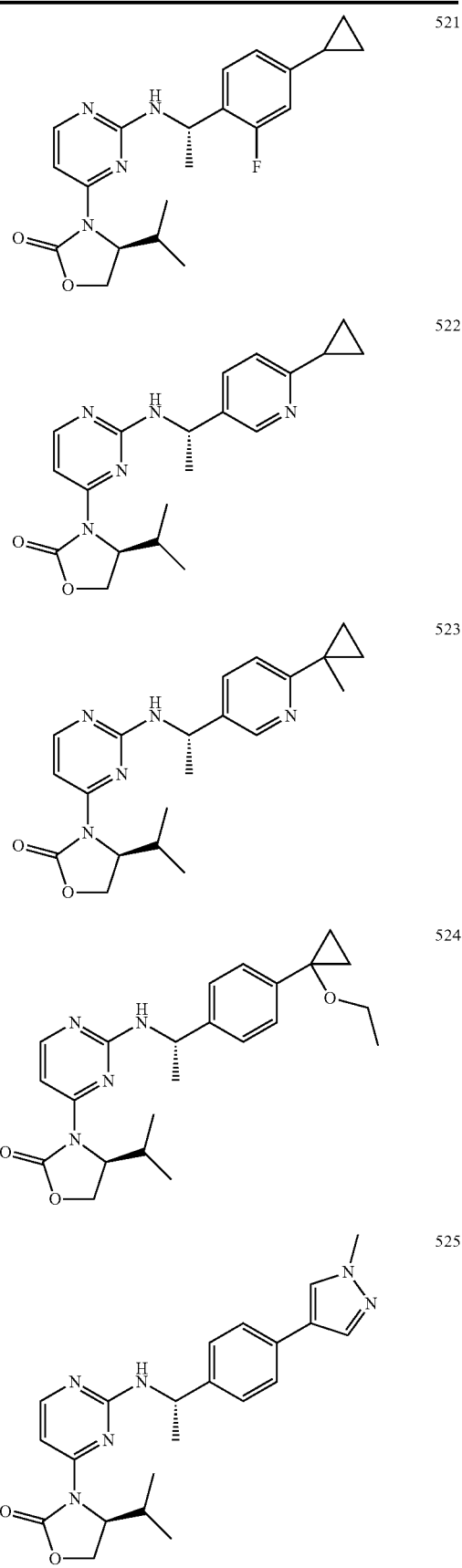

TABLE 15-continued
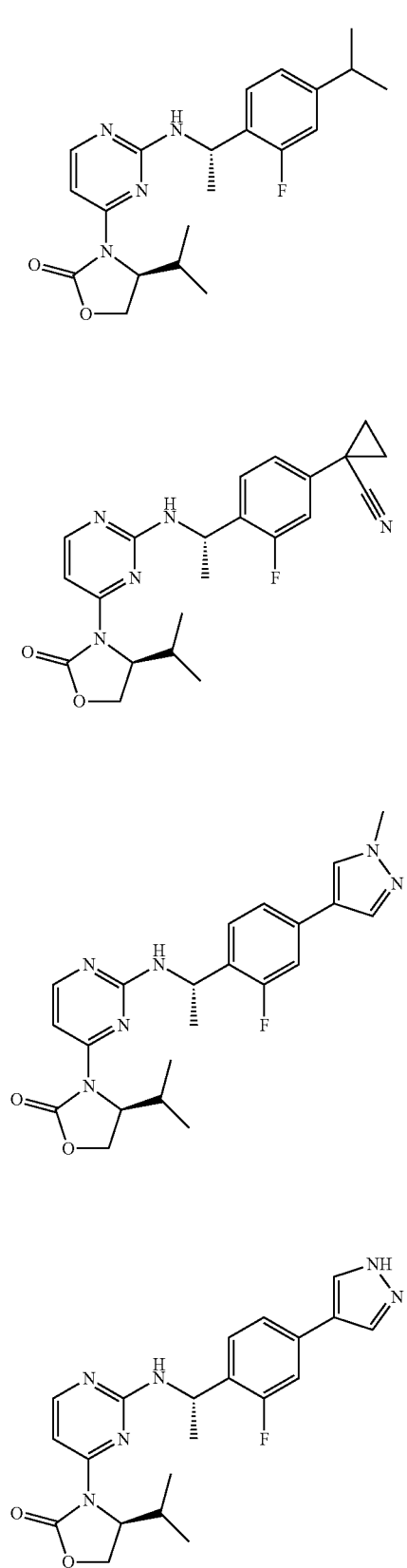
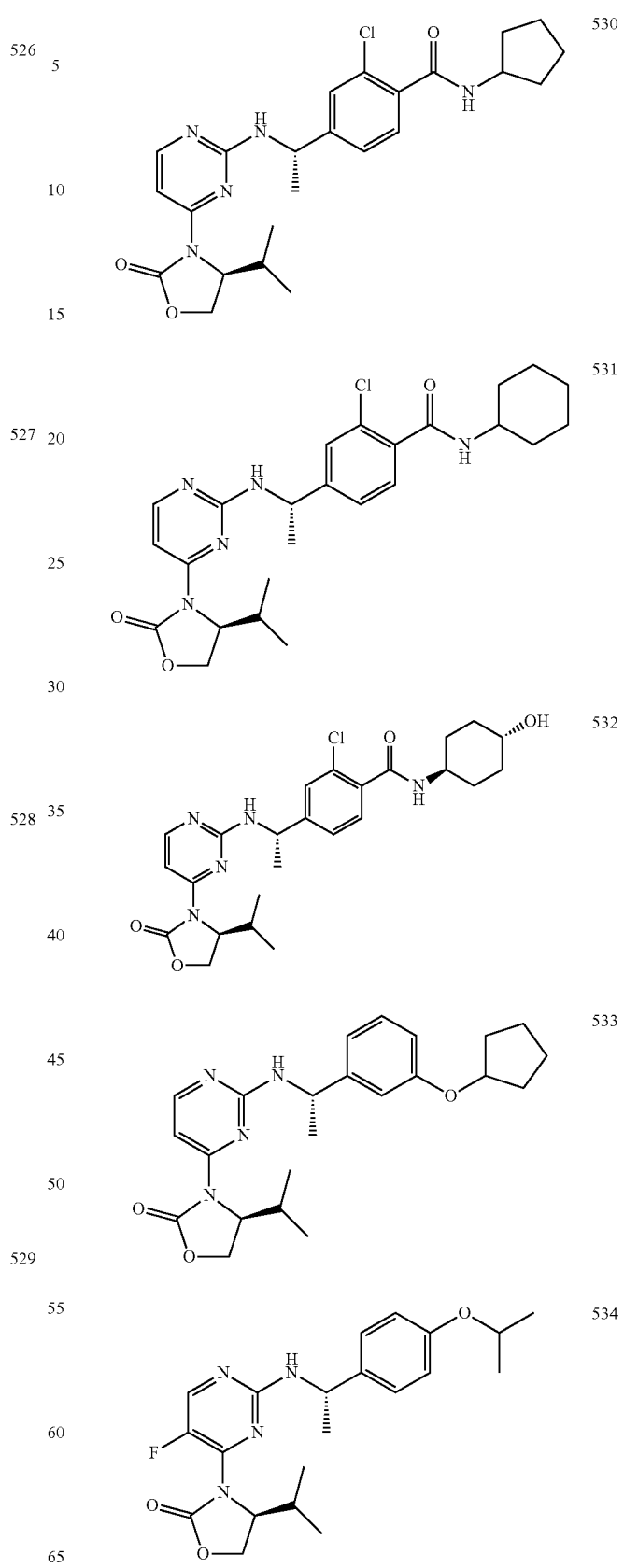

TABLE 15-continued
535 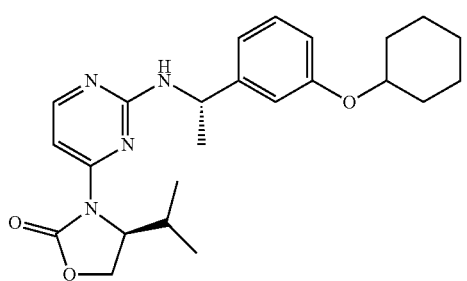 [SMILES: CC(C)[C@H]1COC(=O)N1c1ccnc(N[C@@H](C)c2cccc(OC3CCCCC3)c2)n1]
536 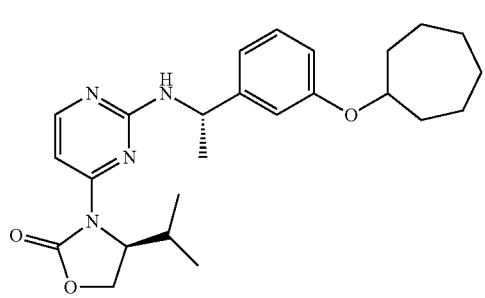 [SMILES: CC(C)[C@H]1COC(=O)N1c1ccnc(N[C@@H](C)c2cccc(OC3CCCCCC3)c2)n1]
537 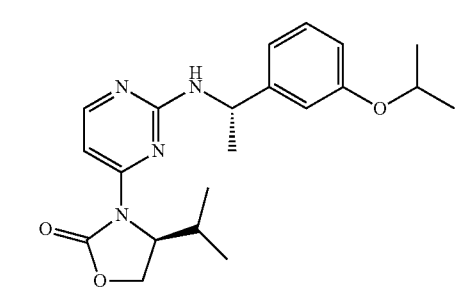 [SMILES: CC(C)Oc1cccc([C@H](C)Nc2nccc(N3C(=O)OC[C@@H]3C(C)C)n2)c1]
538 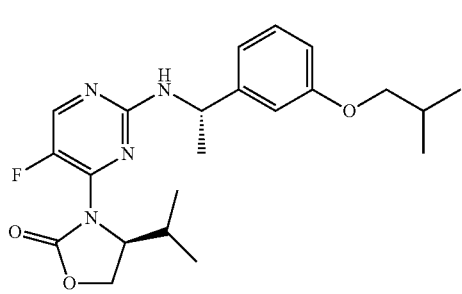 [SMILES: CC(C)COc1cccc([C@H](C)Nc2ncc(F)c(N3C(=O)OC[C@@H]3C(C)C)n2)c1]
539 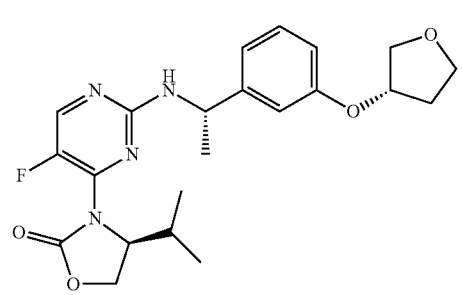 [SMILES: CC(C)[C@H]1COC(=O)N1c1nc(N[C@@H](C)c2cccc(O[C@H]3CCOC3)c2)ncc1F]
TABLE 15-continued
540 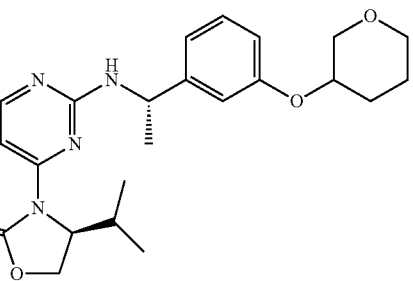
541 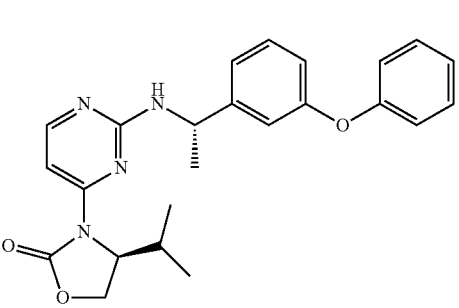 [SMILES: CC(C)[C@H]1COC(=O)N1c1ccnc(N[C@@H](C)c2cccc(Oc3ccccc3)c2)n1]
542 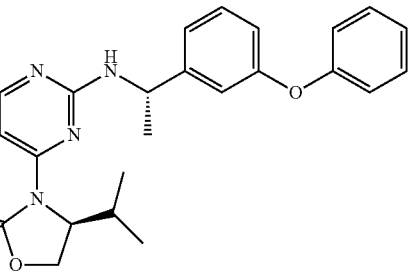
543 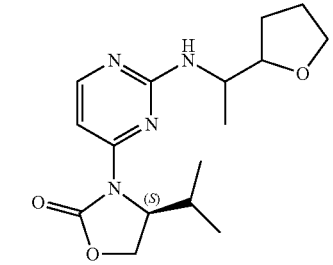
544 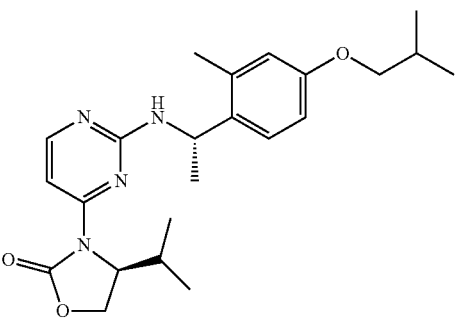 [SMILES: Cc1cc(OCC(C)C)ccc1[C@H](C)Nc1nccc(N2C(=O)OC[C@@H]2C(C)C)n1]

TABLE 15-continued

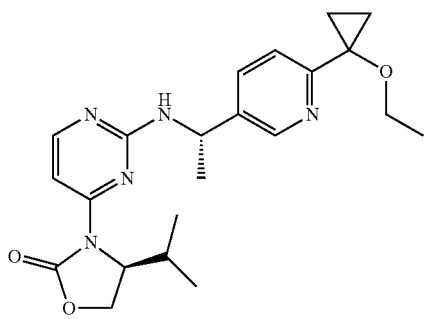 [SMILES: CCOC1(c2ccc([C@H](C)Nc3nccc(N4C(=O)OC[C@@H]4C(C)C)n3)cn2)CC1]

545

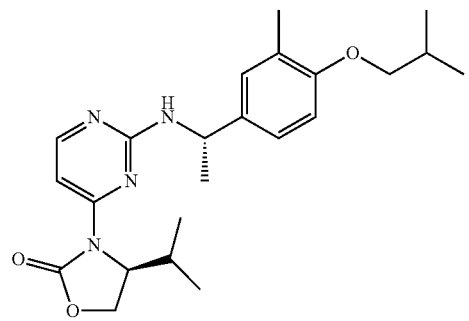 [SMILES: Cc1cc([C@H](C)Nc2nccc(N3C(=O)OC[C@@H]3C(C)C)n2)ccc1OCC(C)C]

546

TABLE 16

Table 16. Chemical name, NMR chemical shifts and LCMS signal for each compound listed in Table 15.

| Example: Name | $^1$H NMR (400 MHz) δ ppm | LCMS |
|---|---|---|
| 516: (S)-3-(2-((S)-1-(6-tert-butylpyridin-3-yl)ethylamino)pyrimidin-4-yl)-4-isopropyloxazolidin-2-one | (DMSO) 0.46 (br. s., 3 H) 0.63 (br. s., 3 H) 1.35 (s, 9 H) 1.50 (d, J = 6.99 Hz, 3 H) 4.34 (d, J = 7.92 Hz, 2 H) 4.59 (br. s., 1 H) 5.14 (br. s., 1 H) 7.32 (d, J = 5.92 Hz, 1 H) 7.70 (br. s., 1 H) 8.03 (br. s., 1 H) 8.24 (br. s., 2 H) 8.59 (br. s., 1 H) | HRMS(A) m/z 384.2410 (M + H)$^+$, Rt 1.34 |
| 517: (S)-3-(2-((S)-1-(6-tert-butylpyridin-3-yl)ethylamino)-5-fluoropyrimidin-4-yl)-4-isopropyloxazolidin-2-one | (DMSO) 0.55 (br. s., 6 H) 1.25-1.38 (s, 9 H) 1.47 (d, J = 7.04 Hz, 3 H) 4.26 (br. s., 1 H) 4.45-4.59 (m, 2 H) 4.98 (br. s., 1 H) 7.66 (br. s., 1 H) 8.11 (br. s., 2 H) 8.41 (br. s., 1 H) 8.60 (br. s., 1 H) | HRMS(A) m/z 402.2314 (M + H)$^+$, Rt 1.45 |
| 518: (S)-4-isopropyl-3-(2-((S)-1-(4-(1-methylcyclopropyl)phenyl)ethylamino)pyrimidin-4-yl)oxazolidin-2-one | | HRMS(A) m/z 381.2295 (M + H)$^+$, Rt 2.10 |
| 519: (S)-3-(2-((S)-1-(4-(1,5-dimethyl-1H-pyrazol-4-yl)phenyl)ethylamino)pyrimidin-4-yl)-4-isopropyloxazolidin-2-one | (DMSO) 0.49 (br. s., 3 H) 0.68 (br. s., 3 H) 1.48 (d, J = 7.04 Hz, 6 H) 2.33 (s, 3 H) 3.76 (s, 3 H) 4.63 (br. s., 1 H) 4.75-4.82 (m, 1 H) 5.03 (br. s., 2 H) 7.30-7.37 (m, 4 H) 7.50 (s, 1 H) 8.22 (br. s., 1 H) 8.36 (br. s., 1H) | HRMS(A) m/z 421.2362 (M + H)$^+$, Rt 1.58 |
| 520: (S)-3-(2-((S)-1-(2-fluoro-4-(trifluoromethyl)phenyl)ethylamino)pyrimidin-4-yl)-4-isopropyloxazolidin-2-one | (DMSO) 0.40 (br. s., 3 H) 0.57 (br. s., 3 H) 1.40 (br. s., 1 H) 1.47 (d, J = 7.04 Hz, 3 H) 4.24-4.37 (m, 2 H) 4.49 (br. s., 1 H) 5.23 (br. s., 1 H) 7.30 (d, J = 5.82 Hz, 1 H) 7.48-7.59 (m, 2 H) 7.65 (d, J = 10.56 Hz, 1 H) 8.21 (d, J = 18.58 Hz, 2 H) | HRMS(A) m/z 413.1602 (M + H)$^+$, Rt 2.16 |
| 521: (S)-3-(2-((S)-1-(4-cyclopropyl-2-fluorophenyl)ethylamino)pyrimidin-4-yl)-4-isopropyloxazolidin-2-one | (CD$_3$OD) 0.61 (br. s., 3 H) 0.64-0.69 (m, 3 H) 0.77 (br. s., 3 H) 0.96-1.04 (m, 2 H) 1.57 (d, J = 6.99 Hz, 3 H) 1.88-1.95 (m, 1 H) 4.39 (d, J = 5.97 Hz, 2 H) 4.69 (br. s., 1 H) 5.33 (br. s., 1 H) 6.82 (dd, J = 12.08, 1.71 Hz, 1 H) 6.88 (d, J = 7.97 Hz, 1 H) 7.19 (t, J = 8.31 Hz, 1 H) 7.70 (d, J = 6.90 Hz, 1 H) 8.14 (d, J = 7.04 Hz, 1 H) | HRMS(A) m/z 385.2042 (M + H)$^+$, Rt 2.06 |
| 522: (S)-3-(2-((S)-1-(6-cyclopropylpyridin-3-yl)ethylamino)pyrimidin-4-yl)-4-isopropyloxazolidin-2-one | (CD$_3$OD) 0.65-0.83 (m, 6 H) 1.14-1.20 (m, 2 H) 1.37-1.43 (m, 2 H) 1.64 (d, J = 7.09 Hz, 3 H) 2.26-2.37 (m, 1 H) 4.36-4.39 (m, 2 H) 4.68 (br. s., 1 H) 5.25 (q, J = 6.75 Hz, 1 H) 7.57 (d, J = 8.51 Hz, 1 H) 7.63 (br. s., 1 H) 8.18 (d, J = 5.92 Hz, 1 H) 8.33 (d, J = 7.24 Hz, 1 H) 8.57 (d, J = 2.10 Hz, 1 H) | HRMS(A) m/z 368.2097 (M + H)$^+$, Rt 1.12 |
| 523: (S)-4-isopropyl-3-(2-((S)-1-(6-(1-methylcyclopropyl)pyridin-3-yl)ethylamino)pyrimidin-4-yl)oxazolidin-2-one | (CD$_3$OD) 0.59-0.84 (m, 6 H) 1.08-1.15 (m, 2 H) 1.22-1.28 (m, 2 H) 1.56 (s, 3 H) 1.64 (d, J = 7.09 Hz, 3 H) 4.35-4.39 (m, 2 H) 4.69 (br. s., 1 H) 5.21-5.32 (m, 1 H) 7.62 (br. s., 1 H) 7.79 (d, J = 8.46 Hz, 1 H) 8.18 (d, J = 6.11 Hz, 1 H) 8.33 (d, J = 7.14 Hz, 1 H) 8.57 (d, J = 2.20 Hz, 1 H) | HRMS(A) m/z 382.2247 (M + H)$^+$, Rt 1.30 |
| 524: (S)-3-(2-((S)-1-(4-(1-ethoxycyclopropyl)-2-fluorophenyl)ethylami- | (CD$_3$OD) 0.60 (br. s., 3 H) 0.78 (br. s., 3 H) 0.92-0.98 (m, 2 H) 1.15 (t, J = 7.07 Hz, 3 H) 1.19-1.26 (m, 2 H) 1.59 (d, J = 6.99 Hz, | HRMS(A) m/z 429.2310 |

TABLE 16-continued

Table 16. Chemical name, NMR chemical shifts and
LCMS signal for each compound listed in Table 15.

| Example: Name | $^1$H NMR (400 MHz) δ ppm | LCMS |
|---|---|---|
| no)pyrimidin-4-yl)-4-isopropyloxazolidin-2-one | 3 H) 1.78 (br. s., 1 H) 3.43 (q, J = 7.09 Hz, 2 H) 4.40 (d, J = 5.72 Hz, 2 H) 4.70 (d, J = 3.91 Hz, 1 H) 5.38 (br. s., 1 H) 7.06 (s, 1 H) 7.07-7.12 (m, 1 H) 7.31 (t, J = 7.95 Hz, 1 H) 7.73 (d, J = 7.04 Hz, 1 H) 8.15 (d, J = 6.90 Hz, 1 H) | $(M + H)^+$, Rt 2.08 |
| 525: (S)-4-isopropyl-3-(2-((S)-1-(4-(1-methyl-1H-pyrazol-4-yl)phenyl)ethylamino)pyrimidin-4-yl)oxazolidin-2-one | (DMSO) 0.47 (br. s., 3 H) 0.69 (br. s., 3 H) 1.45 (d, J = 6.99 Hz, 3 H) 1.81 (br. s., 1 H) 3.84 (s, 3 H) 4.33 (d, J = 13.45 Hz, 2 H) 4.62 (br. s., 1 H) 4.99 (br. s., 1 H) 7.24-7.33 (m, 3 H) 7.46 (d, J = 8.27 Hz, 2 H) 7.79 (d, J = 0.73 Hz, 1 H) 8.06 (s, 1 H) 8.18 (br. s., 1 H) | HRMS(B) m/z 407.2179 $(M + H)^+$, Rt 2.44 min |
| 526: (S)-3-(2-((S)-1-(2-fluoro-4-isopropylphenyl)ethylamino)pyrimidin-4-yl)-4-isopropyloxazolidin-2-one | (CD$_3$OD) 0.59 (br. s., 3 H) 0.78 (br. s., 3 H) 1.23 (dd, J = 6.90, 1.03 Hz, 6 H) 1.58 (d, J = 6.99 Hz, 3 H) 2.91 (dt, J = 13.78, 6.93 Hz, 1 H) 4.39 (d, J = 5.97 Hz, 2 H) 4.69 (br. s., 1 H) 5.35 (br. s., 1 H) 6.97-7.06 (m, 2 H) 7.20-7.28 (m, 1 H) 7.73 (d, J = 6.99 Hz, 1 H) 8.15 (d, J = 6.90 Hz, 1 H) | HRMS(A) m/z 387.2207 $(M + H)^+$, Rt 2.20 |
| 527: 1-(3-fluoro-4-((S)-1-(4-((S)-4-isopropyl-2-oxooxazolidin-3-yl)pyrimidin-2-ylamino)ethyl)phenyl)cyclopropane carbonitrile | (CD$_3$OD) 0.61 (br. s., 3 H) 0.75 (br. s., 3 H) 1.40-1.50 (m, 2 H) 1.57 (d, J = 6.94 Hz, 3 H) 1.71-1.79 (m, 2 H) 4.37 (d, J = 6.50 Hz, 2 H) 4.66 (br. s., 1 H) 5.34 (d, J = 6.55 Hz, 1 H) 7.07-7.18 (m, 2 H) 7.36 (t, J = 8.19 Hz, 1 H) 7.64 (d, J = 6.65 Hz, 1 H) 8.15 (d, J = 6.60 Hz, 1 H) | HRMS(A) m/z 410.1999 $(M + H)^+$, Rt 1.82 |
| 528: (S)-3-(2-((S)-1-(2-fluoro-4-(1-methyl-1H-pyrazol-4-yl)phenyl)ethylamino)pyrimidin-4-yl)-4-isopropyloxazolidin-2-one | (CD$_3$OD) 0.58 (br. s., 3 H) 0.78 (br. s., 3 H) 1.62 (d, J = 7.04 Hz, 3 H) 1.82 (br. s., 1 H) 3.92 (s, 3 H) 4.40 (d, J = 6.26 Hz, 2 H) 4.70 (br. s., 1 H) 5.39 (br. s., 1 H) 7.29-7.39 (m, 3 H) 7.78 (d, J = 7.04 Hz, 1 H) 7.82 (s, 1 H) 7.99 (s, 1 H) 8.16 (d, J = 7.04 Hz, 1 H) | HRMS(A) m/z 425.2112 $(M + H)^+$, Rt 1.64 |
| 529: (S)-3-(2-((S)-1-(2-fluoro-4-(1H-pyrazol-4-yl)phenyl)ethylamino)pyrimidin-4-yl)-4-isopropyloxazolidin-2-one | (CD$_3$OD) 0.59 (br. s., 3 H) 0.79 (br. s., 3 H) 1.63 (d, J = 6.94 Hz, 3 H) 1.84 (br. s., 1 H) 4.40 (d, J = 6.26 Hz, 2 H) 4.71 (br. s., 1 H) 5.40 (br. s., 1 H) 7.29-7.36 (m, 1 H) 7.37-7.43 (m, 2 H) 7.78 (d, J = 7.09 Hz, 1 H) 7.99 (s, 2 H) 8.17 (dd, J = 6.36, 1.86 Hz, 1 H) | HRMS(A) m/z 411.1949 $(M + H)^+$, Rt 1.52 |
| 530: 2-chloro-N-cyclopentyl-4-((S)-1-(4-((S)-4-isopropyl-2-oxooxazolidin-3-yl)pyrimidin-2-ylamino)ethyl)benzamide | (DMSO) 0.55 (br. s., 3 H) 0.78 (br. s., 3 H) 1.42 (d, J = 7.09 Hz, 3 H) 1.50 (d, J = 4.65 Hz, 4 H) 1.64 (br. s., 2 H) 1.83 (d, J = 6.46 Hz, 3 H) 4.14 (dd, J = 12.72, 6.60 Hz, 1 H) 4.34 (br. s., 2 H) 4.64 (br. s., 1 H) 5.03 (br. s., 1 H) 7.25 (d, J = 5.77 Hz, 1 H) 7.31 (s, 2 H) 7.42 (s, 1 H) 8.19 (br. s., 1 H) 8.27 (br. s., 1 H) | HRMS(A) m/z 472.2117 $(M + H)^+$, Rt 1.82 |
| 531: 2-chloro-N-cyclohexyl-4-((S)-1-(4-((S)-4-isopropyl-2-oxooxazolidin-3-yl)pyrimidin-2-ylamino)ethyl)benzamide | (DMSO) 0.55 (br. s., 3 H) 0.78 (br. s., 4 H) 1.18-1.34 (m, 4 H) 1.42 (d, J = 7.04 Hz, 3 H) 1.56 (d, J = 12.08 Hz, 1 H) 1.69 (d, J = 12.86 Hz, 3 H) 1.81 (br. s., 3 H) 4.34 (br. s., 2 H) 4.63 (br. s., 1 H) 5.03 (br. s., 1 H) 7.26 (d, J = 5.82 Hz, 1 H) 7.31 (s, 2 H) 7.43 (s, 1 H) 8.03 (br. s., 1 H) 8.18 (br. s., 1 H) | HRMS(A) m/z 486.2275 $(M + H)^+$, Rt 1.94 |
| 532: 2-chloro-N-((1r,4S)-4-hydroxycyclohexyl)-4-((S)-1-(4-((S)-4-isopropyl-2-oxooxazolidin-3-yl)pyrimidin-2-ylamino)ethyl)benzamide | (DMSO) 0.54 (br. s., 3 H) 0.77 (br. s., 3 H) 1.18-1.30 (m, 5 H) 1.36 (s, 1 H) 1.42 (d, J = 7.04 Hz, 3 H) 1.81 (d, J = 9.19 Hz, 5 H) 3.36 (br. s., 1 H) 4.33 (br. s., 2 H) 4.63 (br. s., 1 H) 5.02 (br. s., 1 H) 7.25 (d, J = 5.77 Hz, 1 H) 7.30 (s, 2 H) 7.42 (s, 1 H) 8.17 (br. s., 2 H) | HRMS(A) m/z 502.2226 $(M + H)^+$, Rt 1.40 |
| 533: (S)-3-(2-((S)-1-(3-(cyclopentyloxy)phenyl)ethylamino)pyrimidin-4-yl)-4-isopropyloxazolidin-2-one | (DMSO) 0.40-0.73 (m, 6 H) 1.40 (d, J = 6.99 Hz, 3 H) 1.47-1.70 (m, 6 H) 1.83 (dd, J = 16.80, 6.72 Hz, 3 H) 4.31 (d, J = 8.75 Hz, 2 H) 4.58 (br. s., 1 H) 4.71 (br. s., 1 H) 4.94 (br. s., 1 H) 6.69 (dd, J = 7.95, 2.03 Hz, 1 H) 6.81 (d, J = 8.31 Hz, 2 H) 7.09-7.19 (m, 1 H) 7.27 (d, J = 6.06 Hz, 1 H) 8.16 (br. s., 2 H) | HRMS(A) m/z 411.2402 $(M + H)^+$, Rt 2.15 min |
| 534: (S)-3-(2-((S)-1-(3-(cyclohexyloxy)phenyl)ethylamino)pyrimidin-4-yl)-4-isopropyloxazolidin-2-one | (DMSO) 0.47 (br. s., 3 H) 0.65 (br. s., 3 H) 1.14-1.36 (m, 5 H) 1.40 (d, J = 7.04 Hz, 3 H) 1.44-1.54 (m, 1 H) 1.65 (d, J = 9.34 Hz, 2 H) 1.72-1.91 (m, 3 H) 4.11-4.39 (m, 3 H) 4.57 (br. s., 1 H) 4.94 (br. s., 1 H) 6.71 (dd, J = 7.85, 1.88 Hz, 1 H) 6.80 (br. s., 2 H) | HRMS(A) m/z 425.2565 $(M + H)^+$, Rt 2.26 min |

TABLE 16-continued

Table 16. Chemical name, NMR chemical shifts and
LCMS signal for each compound listed in Table 15.

| Example: Name | ¹H NMR (400 MHz) δ ppm | LCMS |
|---|---|---|
| | 7.14 (t, J = 8.07 Hz, 1 H) 7.26 (d, J = 6.02 Hz, 1 H) 8.16 (br. s., 2 H) | |
| 535: (S)-3-(2-((S)-1-(3-(cycloheptyloxy)phenyl)eth-ylamino)pyrimidin-4-yl)-4-isopropyloxazolidin-2-one | (DMSO) 0.50 (br. s., 3 H) 0.68 (br. s., 3 H) 1.43 (d, J = 7.04 Hz, 5 H) 1.53 (d, J = 2.98 Hz, 4 H) 1.58-1.71 (m, 4 H) 1.73-1.97 (m, 3 H) 4.34 (d, J = 8.46 Hz, 2 H) 4.38-4.46 (m, 1 H) 4.60 (br. s., 1 H) 4.98 (br. s., 1 H) 6.70 (dd, J = 8.14, 2.03 Hz, 1 H) 6.76-6.89 (m, 2 H) 7.18 (t, J = 7.87 Hz, 1 H) 7.30 (d, J = 6.02 Hz, 1 H) 8.20 (br. s., 2 H) | HRMS(A) m/z 439.2712 (M + H)⁺, Rt 2.41 min |
| 536: (S)-3-(2-((S)-1-(3-isopropoxyphenyl)ethylami-no)pyrimidin-4-yl)-4-isopropyloxazolidin-2-one | (DMSO) 0.49 (br. s., 3 H) 0.67 (br. s., 3 H) 1.09-1.28 (m, 7 H) 1.32-1.50 (m, 3 H) 4.23-4.39 (m, 2 H) 4.52 (dt, J = 12.04, 6.08 Hz, 1 H) 4.60 (br. s., 1 H) 4.96 (br. s., 1 H) 6.71 (dd, J = 8.00, 1.98 Hz, 1 H) 6.82 (br. s., 2H) 7.15 (t, J = 8.09 Hz, 1 H) 7.30 (d, J = 6.02 Hz, 1 H) 8.18 (br. s., 1 H) 8.28 (br. s., 1 H) | HRMS(A) m/z 385.2248 (M + H)⁺, Rt 1.92 min |
| 537: (S)-3-(5-fluoro-2-((S)-1-(3-isobutoxyphenyl)ethylami-no)pyrimidin-4-yl)-4-isopropyloxazolidin-2-one | (DMSO) 0.49 (br. s., 6 H) 0.92 (d, J = 6.7 Hz, 6 H) 1.37 (d, J = 7.04 Hz, 3 H) 1.93 (dquin, J = 13.25, 6.60, 6.60, 6.60, 6.60 Hz, 1 H) 3.59-3.70 (m, 2 H) 3.94-4.31 (m, 3 H) 4.45 (br. s., 1 H) 6.69 (dd, J = 8.17, 1.76 Hz, 1 H) 6.80-6.89 (m, 2 H) 7.13 (t, J = 7.83 Hz, 1H) 7.92 (br. s., 1 H) 8.34 (br. s., 1 H) | HRMS(A) m/z 417.231 (M + H)⁺, Rt 2.53 min |
| 538: (S)-3-(5-fluoro-2-((S)-1-(3-((S)-tetrahydrofuran-3-yloxy)phenyl)ethylami-no)pyrimidin-4-yl)-4-isopropyloxazolidin-2-one | (DMSO) 1.41 (d, J = 7.04 Hz, 6 H) 1.83-1.93 (m, 1 H) 2.11-2.23 (m, 1 H) 3.68-4.04 (m, 8 H) 4.25 (br. s., 1 H) 4.49 (br. s., 2 H) 4.80 (br. s., 1 H) 4.95 (dd, J = 6.06, 4.65 Hz, 1 H) 6.72 (dd, J = 8.02, 2.10 Hz, 1 H) 6.83-6.94 (m, 2 H) 7.19 (t, J = 7.87 Hz, 1 H) 7.96 (br. s., 1 H) 8.38 (br. s., 1 H) | HRMS(A) m/z 431.2098 (M + H)⁺, Rt 2.01 min |
| 539: (4S)-4-isopropyl-3-(2-((1S)-1-(3-(tetrahydro-2H-pyran-3-yloxy)phenyl)ethylami-no)pyrimidin-4-yl)oxazolidin-2-one | (DMSO) 0.47 (br. s., 3 H) 0.66 (br. s., 3 H) 1.39 (d, J = 6.99 Hz, 3 H) 1.44-2.00 (m, 5 H) 3.32-3.50 (m, 2 H) 3.54-3.88 (m, 3 H) 4.23-4.37 (m, 2 H) 4.61 (br. s., 1H) 4.90 (br. s., 1H) 6.74 (d, J = 8.36 Hz, 1 H) 6.85 (d, J = 13.55 Hz, 2 H) 7.15 (t, J = 7.87 Hz, 1 H) 7.25 (d, J = 5.97 Hz, 1 H) 8.06 (br. s., 1 H) 8.16 (br. s., 1 H) | HRMS(A) m/z 427.2353 (M + H)⁺, Rt 1.75 min |
| 540: (S)-4-isopropyl-3-(2-((S)-1-(3-phenoxyphenyl)ethylami-no)pyrimidin-4-yl)oxazolidin-2-one | (DMSO) 0.50 (br. s., 3 H) 0.66 (br. s., 3 H) 1.42 (d, J = 7.04 Hz, 3 H) 1.75 (br. s., 1 H) 4.27-4.37 (m, 2 H) 4.55-4.62 (m, 1 H) 4.97-5.07 (m, 1 H) 6.78 (dd, J = 8.02, 1.81 Hz, 1 H) 6.87 (d, J = 7.53 Hz, 2 H) 6.96 (br. s., 1 H) 7.04-7.14 (m, 2 H) 7.25-7.37 (m, 4 H) 8.17 (d, J = 4.99 Hz, 1 H) 8.36 (br. s., 1 H) | HRMS(A) m/z 419.2092 (M + H)⁺, Rt 2.12 min |
| 541: (S)-3-(5-fluoro-2-((S)-1-(3-phenoxyphenyl)ethylami-no)pyrimidin-4-yl)-4-isopropyloxazolidin-2-one | (DMSO) 0.44-0.65 (m, 6 H) 1.37 (d, J = 6.99 Hz, 3 H) 4.08-4.40 (m, 2 H) 4.45 (br. s., 1 H) 4.82 (br. s., 1 H) 6.75 (dd, J = 8.07, 1.37 Hz, 1 H) 6.86 (d, J = 7.48 Hz, 2 H) 6.95 (br. s., 1 H) 7.03-7.11 (m, 2 H) 7.28 (dt, J = 19.78, 7.86 Hz, 3 H) 7.94 (br. s., 1 H) 8.33 (br. s., 1 H) | HRMS(A) m/z 437.1992 (M + H)⁺, Rt 2.45 min |
| 542: (S)-3-(5-fluoro-2-((S)-1-(4-isopropoxyphenyl)ethylami-no)pyrimidin-4-yl)-4-isopropyloxazolidin-2-one | (DMSO) 0.56 (br. s., 6 H) 1.18 (d, J = 2.35 Hz, 3 H) 1.20 (d, J = 2.30 Hz, 3 H) 1.36 (d, J = 7.04 Hz, 3 H) 4.21 (br. s., 1H) 4.36-4.58 (m, 3 H) 4.75 (br. s., 1H) 6.77 (d, J = 8.71 Hz, 2 H) 7.18 (d, J = 8.56 Hz, 2 H) 7.87 (br. s., 1 H) 8.33 (d, J = 2.74 Hz, 1 H) | HRMS(A) m/z 403.2156 (M + H)⁺, Rt 2.30 min |
| 543: (4S)-4-isopropyl-3-(2-((1-(tetrahydrofuran-2-yl)ethyl)amino)pyrimidin-4-yl)oxazolidin-2-one | (CD₃OD) 8.00-8.17 (m, 1H), 7.71 (d, J = 7.04 Hz, 1H), 4.78-4.85 (m, 1H), 4.41-4.55 (m, 2H), 3.98-4.14 (m, 1H), 3.84-3.97 (m, 1H), 3.67-3.82 (m, 1H), 2.55-2.70 (m, 1H), 1.86-2.13 (m, 3H), 1.56-1.82 (m, 1H), 1.24-1.34 (m, 3H), 1.00-1.06 (m, 3H), 0.91 (t, J = 6.06 Hz, 3H) | HRMS(A) m/z 321.1935 (M + H)+, Rt 1.32 min |
| 544: (S)-3-(2-((S)-1-(4-isobutoxy-3-methylphenyl)ethylamino) pyrimidin-4-yl)-4-isopropyloxazolidin-2-one | (400 MHz, DMSO) δ ppm 0.54 (br. s., 3 H) 0.72 (br. s., 3 H) 0.96 (d, J = 6.70 Hz, 6 H) 1.41 (d, J = 6.99 Hz, 3 H) 1.89 (br. s., 1 H) 1.99 (dt, J = 13.24, 6.61 Hz, 1 H) 2.11 (s, 3 H) 3.68 (d, J = 6.41 Hz, 2 H) 4.31-4.41 (m, 2 H) 4.62 (dd, J = 6.99, 3.72 Hz, 1 H) 4.94 | HRMS(A) m/z 413.2561 (M + H)+, Rt 2.34 min |

TABLE 16-continued

Table 16. Chemical name, NMR chemical shifts and LCMS signal for each compound listed in Table 15.

| Example: Name | $^1$H NMR (400 MHz) δ ppm | LCMS |
|---|---|---|
| | (quin, J = 6.94 Hz, 1 H) 6.80 (d, J = 8.31 Hz, 1 H) 7.00-7.13 (m, 2 H) 7.34 (d, J = 6.06 Hz, 1 H) 8.19 (d, J = 4.94 Hz, 1 H) 8.42 (br. s., 1 H) | |
| 545: (S)-3-(2-((S)-1-(6-(1-ethoxycyclopropyl)pyridin-3-yl)ethylamino)pyrimidin-4-yl)-4-isopropyloxazolidin-2-one | $^1$H NMR (400 MHz, CD$_3$OD) d 0.65 (br. s., 3 H) 0.75 (br. s., 3 H) 1.23 (t, J = 7.04 Hz, 3 H) 1.28-1.45 (m, 4 H) 1.64 (d, J = 7.09 Hz, 3 H) 3.55 (q, J = 7.04 Hz, 2 H) 4.36-4.43 (m, 2 H) 4.70 (br. s., 1 H) 5.20-5.28 (m, 1 H) 7.66 (d, J = 8.41 Hz, 2 H) 8.04 (br. s., 1 H) 8.16 (d, J = 6.41 Hz, 1 H) | HRMS(A) m/z 412.2349 (M + H)+, Rt 1.55 min |
| 546: (S)-3-(2-((S)-1-(4-isobutoxy-3-methylphenyl)ethylamino)pyrimidin-4-yl)-4-isopropyloxazolidin-2-one | $^1$H NMR (400 MHz, DMSO) d ppm 0.54 (br. s., 3 H) 0.72 (br. s., 3 H) 0.96 (d, J = 6.70 Hz, 6 H) 1.41 (d, J = 6.99 Hz, 3 H) 1.89 (br. s., 1 H) 1.99 (dt, J = 13.24, 6.61 Hz, 1 H) 2.11 (s, 3 H) 3.68 (d, J = 6.41 Hz, 2 H) 4.31-4.41 (m, 2 H) 4.62 (dd, J = 6.99, 3.72 Hz, 1 H) 4.94 (quin, J = 6.94 Hz, 1 H) 6.80 (d, J = 8.31 Hz, 1 H) 7.00-7.13 (m, 2 H) 7.34 (d, J = 6.06 Hz, 1 H) 8.19 (d, J = 4.94 Hz, 1 H) 8.42 (br. s., 1 H) | HRMS m/z 413.2561 (M + H)+; Rt 2.34 min. |

Example 547

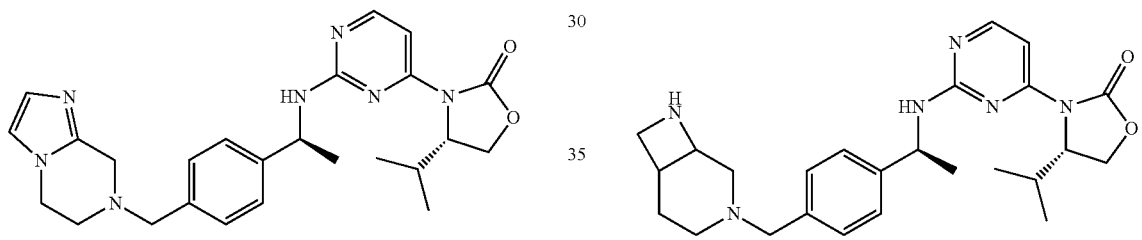

A solution of (S)-3-(2-((S)-1-(4-(chloromethyl)phenyl)ethylamino)pyrimidin-4-yl)-4-isopropyloxazolidin-2-one (75 mg, 0.2 mmol) and 5,6,7,8-tetrahydroimidazo[1,2-a]pyrazine (25 mg, 0.2 mmol) in DMSO (2 mL) was heated at 80° C. for 16 h. The reaction mixture was diluted with EtOAc (20 mL) and washed with water (20 mL). After separation, the aqueous phase was washed with EtOAc (2×15 mL). Combined organics were dried over Na2SO4, filtered and concentrated. Silica gel column chromatography (MeOH in CH$_2$Cl$_2$ 0 to 10%) provided (S)-3-(2-((S)-1-(4-((5,6-dihydroimidazo[1,2-a]pyrazin-7(8H)-yl)methyl)phenyl)ethylamino)pyrimidin-4-yl)-4-isopropyloxazolidin-2-one (58 mg, white solid) in 62.8% yield.

$^1$H NMR (400 MHz, MeOD) δ 8.12 (d, J=6.0 Hz, 1H), 7.34 (d, J=5.9 Hz, 1H), 7.33 (s, 4H), 6.99 (d, J=1.3 Hz, 1H), 6.89 (d, J=1.4 Hz, 1H), 5.07 (q, J=7.0 Hz, 1H), 4.68 (br s, 1H), 4.37-4.25 (m, 2H), 4.02 (t, J=5.5 Hz, 2H), 3.72 (s, 2H), 3.63 (s, 2H), 2.90 (td, J=5.4, 2.6 Hz, 2H), 1.84 (br s, 1H), 1.51 (d, J=7.0 Hz, 3H), 0.72 (br s, 3H), 0.57 (br s, 3H); HRMS m/z 462.2606 (M+H)+.

The following compounds were prepared using methods similar to those described for the preparation of Example 205.

Example 548

(4S)-3-(2-((1 S)-1-(4-(3,8-diazabicyclo[4.2.0]octan-3-yl-methyl)phenyl)ethylamino)pyrimidin-4-yl)-4-isopropyloxazolidin-2-one.

$^1$H NMR (400 MHz, MeOD) δ 8.12-8.08 (m, 1H), 7.37-7.22 (m, 5H), 5.10-5.01 (m, 1H), 4.66 (br s, 1H), 4.37-4.23 (m, 2H), 3.92-3.89 (m, 1H), 3.63-3.54 (m, 1H), 3.54-3.47 (m, 1H), 3.24-3.20 (m, 1H), 3.11-2.95 (m, 1H), 2.95-2.73 (m, 1H), 0.2.67-2.59 (m, 2H), 2.49 (ddd, J=16.2, 12.8, 5.3 Hz, 1H), 2.20-2.08 (m, 1H), 1.99-1.68 (m, 3H), 1.50 (d, J=7.0 Hz, 3H), 0.72 (br s, 1H), 0.56 (br s, 1H); HRMS m/z 451.2810 (M+H)+.

Example 549

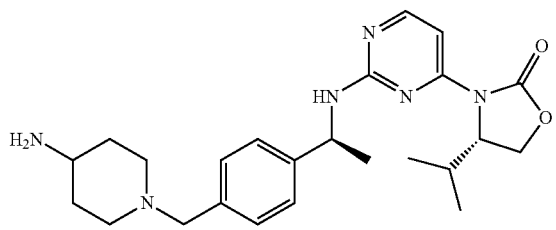 [SMILES: CC(C)[C@H]1COC(=O)N1c1ccnc(N[C@@H](C)c2ccc(CN3CCC(N)CC3)cc2)n1]

(S)-3-(2-((S)-1-(4-((4-aminopiperidin-1-yl)methyl)phenyl)ethylamino)pyrimidin-4-yl)-4-isopropyloxazolidin-2-one ¹H NMR (400 MHz, MeOD) d 8.12 (d, J=5.8 Hz, 1H), 7.34 (d, J=5.8 Hz, 1H), 7.27 (q, J=8.2 Hz, 4H), 5.05 (q, J=7.0 Hz, 1H), 4.67 (s, 1H), 4.38-4.25 (m, 2H), 3.48 (s, 2H), 2.86 (br d, J=11.8 Hz, 2H), 2.71 (tt, J=10.9, 4.2 Hz, 1H), 2.05 (tt, J=12.0, 2.5 Hz, 2H), 1.90-1.75 (m, 3H), 1.54-1.37 (m, 5H), 0.72 (br s, 4H), 0.55 (br s, 3H); HRMS m/z 439.2805 (M+H)+.

The following compounds were prepared using methods similar to those described for the preparation of Example 210.

Example 550

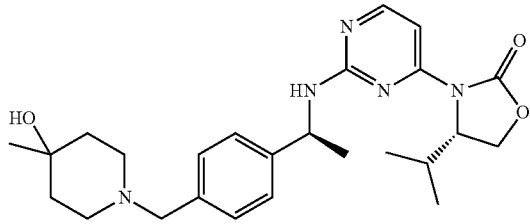 [SMILES: CC(C)[C@H]1COC(=O)N1c1ccnc(N[C@@H](C)c2ccc(CN3CCC(C)(O)CC3)cc2)n1]

(S)-3-(2-((S)-1-(4-((4-hydroxy-4-methylpiperidin-1-yl)methyl)phenyl)ethylamino)pyrimidin-4-yl)-4-isopropyloxazolidin-2-one ¹H NMR (400 MHz, MeOD) δ 8.12 (d, J=5.7 Hz, 1H), 7.34 (d, J=5.9 Hz, 1H), 7.27 (t, J=6.6 Hz, 4H), 5.06 (q, J=6.8 Hz, 1H), 4.67 (br s, 1H), 4.37-4.25 (m, 2H), 3.51 (d, J=3.2 Hz, 2H), 2.52 (br s, 2H), 2.44 (br s, 2H), 1.81 (br s, 1H), 1.59 (br s, 4H), 1.50 (d, J=7.0 Hz, 3H), 1.19 (s, 3H), 0.72 (br s, 3H), 0.56 (br s, 3H); HRMS m/z 454.2816 (M+H)+.

Example 552

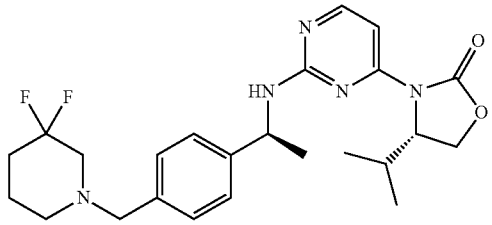 [SMILES: CC(C)[C@H]1COC(=O)N1c1ccnc(N[C@@H](C)c2ccc(CN3CCCC(F)(F)C3)cc2)n1]

(S)-3-(2-((S)-1-(4-((3,3-difluoropiperidin-1-yl)methyl)phenyl)ethylamino)pyrimidin-4-yl)-4-isopropyloxazolidin-2-one ¹H NMR (400 MHz, MeOD) δ 8.12 (d, J=5.8 Hz, 1H), 7.35 (d, J=5.8 Hz, 1H), 7.28 (q, J=8.2 Hz, 4H), 5.06 (q, J=7.0 Hz, 1H), 4.67 (br s, 1H), 4.39-4.25 (m, 2H), 3.55 (d, J=2.2 Hz, 2H), 2.56 (t, J=11.5 Hz, 2H), 2.51-2.40 (m, 2H), 1.91-1.81 (m, 3H), 1.78-1.70 (m, 2H), 1.50 (d, J=7.0 Hz, 3H), 0.71 (br s, 3H), 0.56 (br s, 3H); HRMS m/z 460.2537 (M+H)+.

Example 553

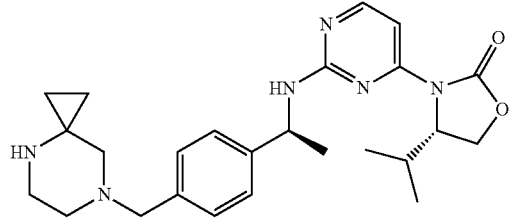 [SMILES: CC(C)[C@H]1COC(=O)N1c1ccnc(N[C@@H](C)c2ccc(CN3CCNC4(CC4)C3)cc2)n1]

(S)-3-(2-((S)-1-(4-(4,7-diazaspiro[2.5]octan-7-ylmethyl)phenyl)ethylamino)pyrimidin-4-yl)-4-isopropyloxazolidin-2-one ¹H NMR (400 MHz, MeOD) δ 8.12 (d, J=5.8 Hz, 1H), 7.34 (d, J=5.8 Hz, 1H), 7.32-7.24 (m, 4H), 5.06 (q, J=7.0 Hz, 1H), 4.68 (br s, 1H), 4.37-4.26 (m, 2H), 3.49 (s, 2H), 2.89 (t, J=5.0 Hz, 2H), 2.47 (br s, 2H), 2.28 (br s, 2H), 1.86 (br s, 1H), 1.49 (d, J=7.0 Hz, 3H), 0.72 (br s, 3H), 0.64-0.49 (m, 5H), 0.45 (t, J=3.2 Hz, 2H); HRMS m/z 451.2809 (M+H)+.

Example 554

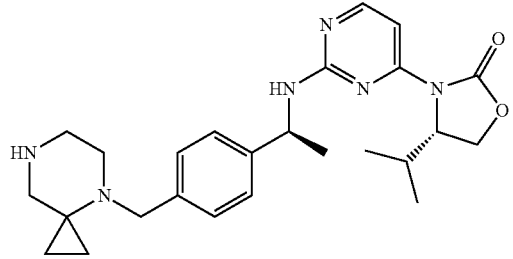 [SMILES: CC(C)[C@H]1COC(=O)N1c1ccnc(N[C@@H](C)c2ccc(CN3CCNCC34CC4)cc2)n1]

(S)-3-(2-((S)-1-(4-(4,7-diazaspiro[2.5]octan-4-ylmethyl)phenyl)ethylamino)pyrimidin-4-yl)-4-isopropyloxazolidin-2-one ¹H NMR (400 MHz, MeOD) δ 8.11 (d, J=5.8 Hz, 1H), 7.33 (d, J=5.8 Hz, 1H), 7.24 (q, J=8.3 Hz, 4H), 5.03 (q, J=7.0 Hz, 1H), 4.67 (br s, 1H), 4.37-4.25 (m, 2H), 3.85 (s, 2H), 2.85-2.65 (m, 6H), 1.87 (br s, 1H), 1.48 (d, J=7.0 Hz, 3H), 0.85-0.63 (m, 5H), 0.63-0.46 (m, 5H); HRMS m/z 451.2810 (M+H)+.

Example 555

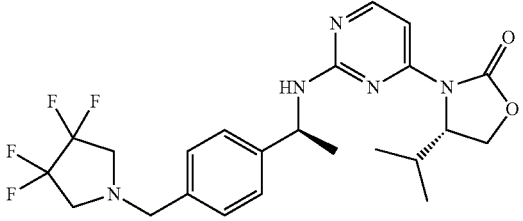 [SMILES: CC(C)[C@H]1COC(=O)N1c1ccnc(N[C@@H](C)c2ccc(CN3CC(F)(F)C(F)(F)C3)cc2)n1]

(S)-4-isopropyl-3-(2-((S)-1-(4-((3,3,4,4-tetrafluoropyrrolidin-1-yl)methyl)phenyl)ethylamino)pyrimidin-4-yl)oxazolidin-2-one HRMS m/z 482.2161 (M+H)+; RT=2.78 min.

Example 556

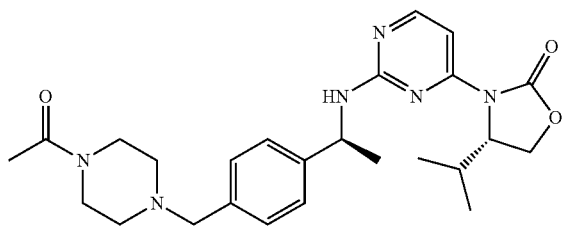 [SMILES: CC(=O)N1CCN(Cc2ccc([C@H](C)Nc3nccc(N4C(=O)OC[C@@H]4C(C)C)n3)cc2)CC1]

(S)-3-(2-((S)-1-(4-((4-acetylpiperazin-1-yl)methyl)phenyl)ethylamino)pyrimidin-4-yl)-4-isopropyloxazolidin-2-one HRMS m/z 467.2752 (M+H)+; RT=1.92 min.

Example 557

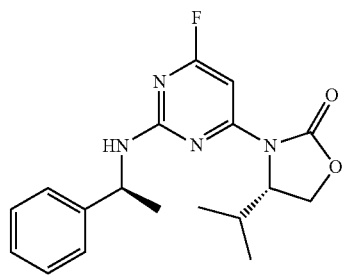 [SMILES: CC(C)[C@H]1COC(=O)N1c1cc(F)nc(N[C@@H](C)c2ccccc2)n1]

(S)-4,6-difluoro-N-(1-phenylethyl)pyrimidin-2-amine (48.8 mg, 0.21 mmol) was added to NaH (95%, 6.1 mg, 0.25 mmol, 1.2 equiv) in DMF (2 mL) at 0° C. After 5 min, (S)-4-isopropyl-2-oxazolidinone (27.9 mg, 0.22 mmol, 1.0 equiv) was added. The reaction was stirred for 10 min at 0° C. and then warmed to room temperature. After 4 h, the reaction mixture was quenched with water and poured into dilute brine (1:1 sat. brine:water) and EtOAc. The aqueous phase was extracted with EtOAc and the combined organic layers were washed with diluted brine. The organic layer was dried over $Na_2SO_4$, filtered and concentrated to a pink oil. Purification by reverse phase HPLC followed by lyopholization of the fractions containing product provided (S)-3-(6-fluoro-2-(((S)-1-phenylethyl)amino)pyrimidin-4-yl)-4-isopropyloxazolidin-2-one as a white solid (22.5 mg TFA salt) in 31% yield. $^1$H NMR (400 MHz, $CD_3OD$) δ 7.27-7.39 (m, 4H), 7.17-7.26 (m, 1H), 6.92 (s, 1H), 5.05 (q, J=7.04 Hz, 1H), 4.63 (br. s., 1H), 4.19-4.41 (m, 2H), 1.77 (br. s., 1H), 1.51 (d, J=7.04 Hz, 3H), 0.44-0.78 (m, 6H); LCMS m/z 345.1 (M+H)+. $R_t$ 1.00 min; UPLC $R_t$ 5.038 min.

The compounds in Table 17 were prepared using methods similar to those described for the preparation of Example 557.

TABLE 17

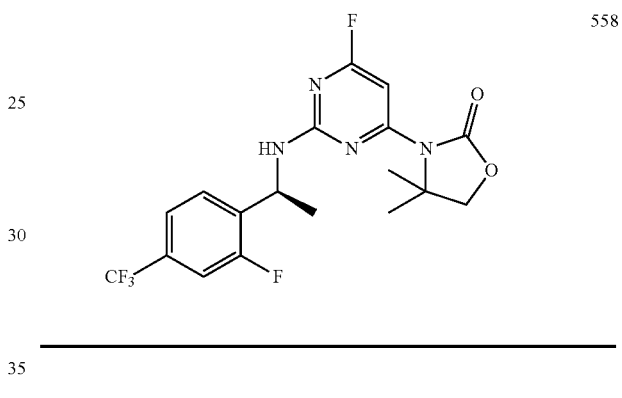

558

TABLE 18

Chemical name, NMR chemical shifts and LCMS signal for each compound listed in Table 17.

| Example: Name | $^1$H NMR (400 MHz) δ ppm | LCMS |
|---|---|---|
| 558: (S)-5,5-dimethyl-4-phenyl-3-(2-((S)-1-phenylethylamino)pyrimidin-4-yl)oxazolidin-2-one | ($CD_3OD$) 8.06 (d, J = 5.8 Hz, 1 H), 7.43 (d, J = 5.8 Hz, 1 H), 7.31-7.24 (m, 3 H), 7.19-7.11 (m, 5 H), 7.01 (br s 2 H), 5.48 (s, 1 H), 4.86-4.80 (m, 1 H), 1.65 (s, 3 H), 1.43 (d, J = 7.0 Hz, 3 H), 0.98 (s, 3 H) | HRMS(A) m/z 389.1987 (M + H)+ |

Example 559

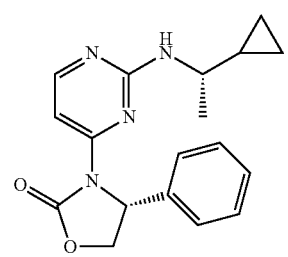 [SMILES: C[C@H](Nc1nccc(N2C(=O)OC[C@H]2c2ccccc2)n1)C1CC1]

A mixture of (R)-3-(2-chloropyrimidin-4-yl)-4-phenyloxazolidin-2-one (55.3 mg, 0.20 mmol), (S)-1-cyclopropylethylamine (40 μL, 0.26 mmol, 1.3 equiv) and $iPr_2Net$ (0.20 mL, 1.15 mmol, 5.7 equiv) in NMP (1 mL) was heated in the microwave at 180° C. for 20 min. The reaction mixture was filtered and purified by reverse phase HPLC to give (R)-3-(2-(((S)-1-cyclopropylethyl)amino)pyrimidin-4-yl)-4-phenyloxazolidin-2-one as a white solid (8.8 mg) in 10% yield. ¹H NMR (400 MHz, CD₃OD) δ 7.72 (d, J=6.26 Hz, 1H), 7.29-7.43 (m, 6H), 5.76 (dd, J=4.11, 8.80 Hz, 1H), 4.28 (dd, J=4.30, 8.61 Hz, 1H), 3.06-3.19 (m, 1H), 1.39 (dd, J=3.52, 6.65 Hz, 1H), 0.88-0.97 (m, 1H), 0.83 (br. s., 3H), 0.53-0.62 (m, 1H), 0.50 (dt, J=4.11, 8.51 Hz, 1H), 0.33 (qd, J=4.78, 9.54 Hz, 1H), 0.26 (td, J=4.60, 9.59 Hz, 1H); HRMS(A) m/z 325.1667 (M+H)⁺, Rt 1.54 min; UPLC 2.807 min.

The compounds in Table 19 were prepared using methods similar to those described for the preparation of Example 559.

TABLE 19-continued

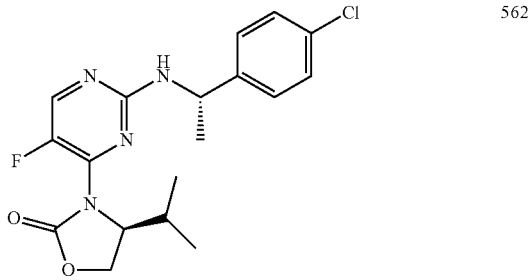

562

TABLE 20

Chemical name, NMR chemical shifts and LCMS signal for each compound listed in Table 19.

| Example: Name | ¹H NMR (400 MHz) δ ppm | LCMS |
| --- | --- | --- |
| 560: (S)-4-benzyl-3-(2-(((S)-1-cyclopropylethyl)amino)pyrimidin-4-yl)oxazolidin-2-one | (CD₃OD) 8.13 (d, J = 7.04 Hz, 1H), 7.71 (d, J = 7.04 Hz, 1H), 7.22-7.38 (m, 5H), 5.11 (tt, J = 3.03, 8.12 Hz, 1H), 4.23-4.53 (m, 2H), 3.08 (dd, J = 8.41, 13.50 Hz, 1H), 1.42 (d, J = 6.65 Hz, 3H), 1.04-1.23 (m, 1H), 0.47-0.73 (m, 2H), 0.17-0.47 (m, 2H). | HRMS(A) m/z 339.1822 (M + H)⁺, Rt 1.64 min |
| 561: (S)-3-(5-fluoro-2-(((S)-1-(3-isopropylphenyl)ethyl)amino)pyrimidin-4-yl)-4-isopropyloxazolidin-2-one | | HRMS(A) m/z 387.2203 (M + H)⁺, Rt 2.52 min |
| 562: (S)-3-(2-(((S)-1-(4-chlorophenyl)ethyl)amino)-5-fluoropyrimidin-4-yl)-4-isopropyloxazolidin-2-one | | HRMS(A) m/z 379.1341 (M + H)⁺, Rt 2.30 min |

TABLE 19

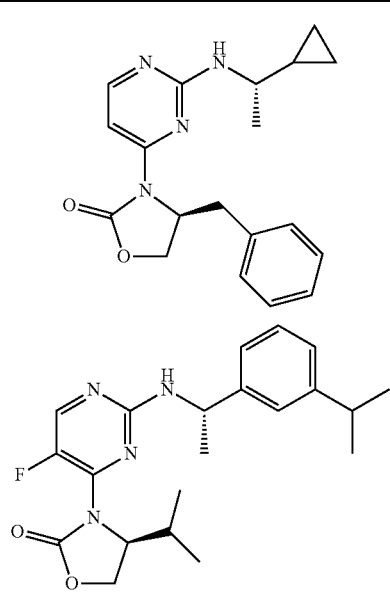

560

561

Example 563

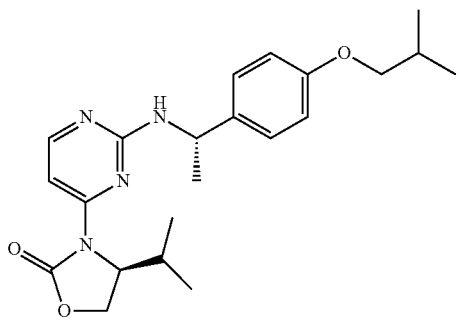 [SMILES: CC(C)COc1ccc([C@H](C)Nc2nccc(N3C(=O)OC[C@@H]3C(C)C)n2)cc1]

A mixture of (S)-3-(2-chloropyrimidin-4-yl)-4-isopropyloxazolidin-2-one (43.2 mg, 0.18 mmol), (1S)-1-[4-(2-Methylpropoxy)phenyl]ethan-1-amine (84.0 mg, 0.37 mmol, 2.0 equiv) and iPr₂Net (0.30 mL, 1.72 mmol, 4.7 equiv) in NMP (1 mL) was heated at 105° C. for 24 h. The reaction mixture was filtered and purified by reverse phase HPLC to give (S)-3-(2-(((S)-1-(4-isobutoxyphenyl)ethyl)amino)pyrimidin-4-yl)-4-isopropyloxazolidin-2-one as a white solid (5.3 mg, TFA salt) in 4% yield. ¹H NMR (400 MHz, CD₃OD) δ 7.68 (d, J=6.65 Hz, 1H), 7.25 (d, J=8.61 Hz, 2H), 6.90 (d, J=8.61 Hz, 2H), 4.41 (d, J=5.87 Hz, 2H), 3.74 (d, J=6.26 Hz, 2H), 1.96-2.15 (m, 1H), 1.58 (d, J=7.04 Hz, 3H), 1.03 (d, J=6.65 Hz, 6H); HRMS(A) m/z 399.2399 (M+H)⁺, Rt 2.60 min; UPLC 4.223 min.

The compounds in Table 21 were prepared using methods similar to those described for the preparation of Example 563.

TABLE 21

564

565

TABLE 22

Chemical name, NMR chemical shifts and LCMS signal for each compound listed in Table 21.

| Example: Name | ¹H NMR (400 MHz) δ ppm | LCMS |
|---|---|---|
| 564: (S)-3-(5-fluoro-2-(((S)-1-(4-isobutoxyphenyl)ethyl)amino)pyrimidin-4-yl)-4-isopropyloxazolidin-2-one | | HRMS(A) m/z 417.2314 (M + H)⁺, Rt 2.53 min |
| 565: (S)-3-(5-fluoro-2-(((S)-1-(2-fluoro-4-(1-methyl-1H-pyrazol-4-yl)phenyl)ethyl)amino)pyrimidin-4-yl)-4-isopropyloxazolidin-2-one | | HRMS(A) m/z 443.2012 (M + H)⁺, Rt 1.92 min |

Example 566

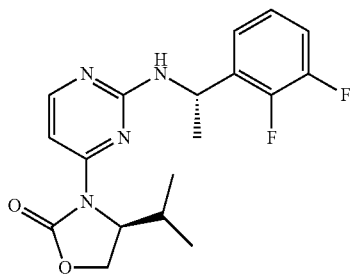 [SMILES: CC(C)[C@H]1COC(=O)N1c1ccnc(N[C@@H](C)c2cccc(F)c2F)n1]

To a microwave vial with stir bar was added (S)-3-(2-chloropyrimidin-4-yl)-4-isopropyloxazolidin-2-one (24.96 mg, 0.103 mmol) in DMSO (1653 μL). To this reaction mixture was added (S)-1-(2,3-difluorophenyl)ethanamine (40 mg, 0.207 mmol) and DIEA (144 μL, 0.826 mmol). The vial capped and heated at 110° C. over the weekend. The solution was filtered, then purified by reverse phase HPLC. Product fractions combined, frozen and lyopholyzed to afford ((S)-3-(2-((S)-1-(2,3-difluorophenyl)ethylamino)pyrimidin-4-yl)-4-isopropyloxazolidin-2-one (10.2 mg, 0.021 mmol, 10.26% yield) as a TFA salt. ¹H NMR (400 MHz, CD₃OD) δ ppm 0.59 (br. s., 3H) 0.75 (br. s., 3H) 1.59 (d, J=6.99 Hz, 3H) 1.69 (br. s., 1H) 4.37 (d, J=5.67 Hz, 2H) 4.66 (br. s., 1H) 5.40 (d, J=7.38 Hz, 1H) 7.06-7.23 (m, 3H) 7.70 (d, J=6.90 Hz, 1H) 8.14 (d, J=6.46 Hz, 1H); LCMS m/z 363.3 (M+H)⁺, Rt 0.77 min.; HRMS(A) m/z 363.1642 (M+H)⁺, Rt 1.89 min.

Example 567

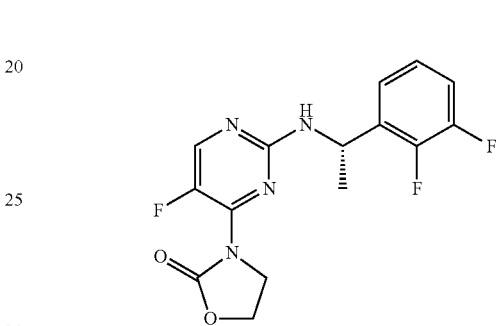

(S)-3-(2-(1-(2,3-difluorophenyl)ethylamino)-5-fluoropyrimidin-4-yl)oxazolidin-2-one was prepared using a method similar to that described for the preparation of Example 566. ¹H NMR (400 MHz, CD₃OD) δ ppm 1.50 (d, J=7.04 Hz, 3H) 3.91 (br. s., 1H) 4.09-4.20 (m, 1H) 4.42-4.56 (m, 2H) 5.26 (q, J=6.68 Hz, 1H) 6.99-7.12 (m, 2H) 7.16 (t, J=7.48 Hz, 1H) 8.13 (d, J=3.37 Hz, 1H). HRMS(A) m/z 339.1075 (M+H)+, Rt 1.86 min.

Example 568

2-fluoro-N-(trans-4-hydroxycyclohexyl)-4-((S)-1-(4-((S)-4-isopropyl-2-oxooxazolidin-3-yl)pyrimidin-2-ylamino)ethyl)benzamide

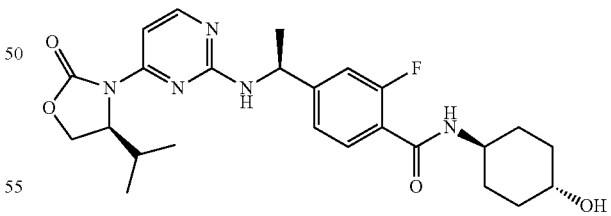

Step 1: Preparation of (S)-4-(1-(tert-butoxycarbonylamino)ethyl)-2-fluorobenzoic acid To (S)-4-(1-aminoethyl)-2-fluorobenzoic acid (900 mg, 4.10 mmol) was added, DCM (11 ml), Hunig's Base (2.147 ml, 12.29 mmol) and BOC-Anhydride (1.998 ml, 8.61 mmol). Then NMP (11.00 ml) was added to help solubility. The reaction was sonicated for 10 minutes and was stirred at room temperature for 22 hours, followed by LCMS. The DCM was mostly concentrated off. Then to the crude reaction was added 120 ml of water and basified with 10 ml of 5M NaOH. The basic aqueous solution was extracted with 2×50 ml of (15% ethyl acetate in heptane) solution. Then to the basic aqueous solution (with the product) was added 150 ml of ethyl acetate and with stirring acidified with 2M aqueous HCl solution to about pH 3. Then the ethyl acetate was extracted, saved and the acidic water extracted again with 100 ml of ethyl acetate. The organic layers were combined and washed with 0.5M aqueous HCl solution 1×40 ml, with water 3×40 ml, and concentrated to constant mass to give 1104 mg of (S)-4-(1-(tert-butoxycarbonylamino)ethyl)-2-fluorobenzoic acid, used as is. LCMS m/z BOC pattern of 269.0 (M+H-15 fragment) and weak 228.0 (M+H-56 fragment) compared to expected 284.0 (M+H)$^+$, Rt 0.72 min.

Step 2: Preparation of tert-butyl (S)-1-(3-fluoro-4-(trans-4-hydroxycyclohexylcarbamoyl)phenyl)ethylcarbamate To (S)-4-(1-(tert-butoxycarbonylamino)ethyl)-2-fluorobenzoic acid (40.8 mg, 0.144 mmol) was added NMP (0.5 ml), trans-4-aminocyclohexanol (41.5 mg, 0.360 mmol), Hunig's Base (0.101 ml, 0.576 mmol) and HATU (110 mg, 0.288 mmol) The reaction was stirred at room temperature for 6 hours, followed by LCMS. To the reaction was added 0.5 ml of NMP, filtered, purified by prep LC and lyophilized to give 33 mg of tert-butyl (S)-1-(3-fluoro-4-(trans-4-hydroxycyclohexylcarbamoyl)phenyl)ethylcarbamate as the TFA Salt. LCMS m/z 381.1 (M+H)+, Rt 0.70 min.

Step 3: Preparation of 4-((S)-1-aminoethyl)-2-fluoro-N-(trans-4-hydroxycyclohexyl)benzamide To tert-butyl (S)-1-(3-fluoro-4-(trans-4-hydroxycyclohexylcarbamoyl)phenyl)ethylcarbamate (33 mg, 0.087 mmol) was added, HCl 4M in Dioxane (2 mL, 8.00 mmol) and MeOH (0.2 ml). The reaction was stirred at room temperature for 1 hour, followed by LCMS. The solvent was concentrated off to residue to give 4-((S)-1-aminoethyl)-2-fluoro-N-(trans-4-hydroxycyclohexyl)benzamide in quantitative yield (0.087 mmol) as HCl salt. LCMS m/z 281.1 (M+H)$^+$, Rt 0.33 min.

Step 4: Preparation of 2-fluoro-N-(trans-4-hydroxycyclohexyl)-4-((S)-1-(4-((S)-4-isopropyl-2-oxooxazolidin-3-yl)pyrimidin-2-ylamino)ethyl)benzamide To 4-((S)-1-aminoethyl)-2-fluoro-N-((1r,4S)-4-hydroxycyclohexyl)benzamide (0.024 g, 0.087 mmol) was added (S)-3-(2-chloropyrimidin-4-yl)-4-isopropyloxazolidin-2-one (0.034 g, 0.139 mmol), DMSO (0.6 ml) and Hunig's Base (0.053 ml, 0.305 mmol). The reaction was heated at 100-105° C. for 16 hours or until done by LCMS. The reaction was let cool, 0.5 ml of DMSO added, filtered, purified by prep LC and lyophilized to give 10.1 mg of 2-fluoro-N-(trans-4-hydroxycyclohexyl)-4-((S)-1-(4-((S)-4-isopropyl-2-oxooxazolidin-3-yl)pyrimidin-2-ylamino)ethyl)benzamide as the TFA Salt. LCMS m/z 486.2 (M+H)$^+$, Rt 0.57 min.

$^1$H NMR (400 MHz, CD$_3$OD) δ ppm 8.13 (d, J=6.7 Hz, 1H), 7.70 (d, J=6.7 Hz, 1H), 7.64 (t, J=7.8 Hz, 1H), 7.13-7.28 (m, 2H), 5.16 (br. s., 1H), 4.67 (br. s., 1H), 4.37 (d, J=5.5 Hz, 2H), 3.82 (br. s., 1H), 3.53 (d, J=3.9 Hz, 1H), 1.97 (dd, J=5.1, 3.1 Hz, 4H), 1.57 (d, J=7.0 Hz, 3H), 1.38 (t, J=8.6 Hz, 4H), 0.50-0.88 (m, 6H); HRMS(A) m/z 486.2523 (M+H)$^+$.

Example 569

(S)-3-(2-((S)-1-(6-(4-fluorophenoxy)pyridin-3-yl)ethylamino)pyrimidin-4-yl)-4-isopropyloxazolidin-2-one

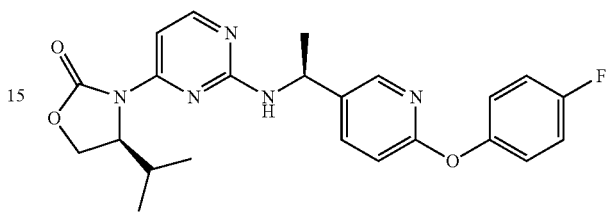

To (S)-3-(2-chloropyrimidin-4-yl)-4-isopropyloxazolidin-2-one (28 mg, 0.116 mmol) was added (S)-1-(6-(4-fluorophenoxy)pyridin-3-yl)ethanamine (46.7 mg, 0.174 mmol), DMSO (0.6 ml) and Hunig's Base (0.071 ml, 0.406 mmol). The reaction was heated at 105-110° C. for 24 hours or until done by LCMS. The reaction was let cool, 0.5 ml of DMSO was added, filtered, purified by prep LC and lyophilized to give 7.1 mg of (S)-3-(2-((S)-1-(6-(4-fluorophenoxy)pyridin-3-yl)ethylamino)pyrimidin-4-yl)-4-isopropyloxazolidin-2-one as the TFA Salt. LCMS m/z 438.2 (M+H)$^+$, Rt 0.82 min.

$^1$H NMR (400 MHz, CD$_3$OD) δ ppm 8.04 (d, J=6.3 Hz, 1H), 8.01 (d, J=2.0 Hz, 1H), 7.73 (dd, J=8.6, 2.3 Hz, 1H), 7.53 (d, J=6.3 Hz, 1H), 6.94-7.10 (m, 4H), 6.84 (d, J=8.6 Hz, 1H), 5.05 (d, J=7.0 Hz, 1H), 4.61 (d, J=3.9 Hz, 1H), 4.28 (d, J=5.5 Hz, 2H), 1.49 (d, J=7.0 Hz, 3H), 0.51-0.78 (m, 6H); HRMS (A) m/z 438.1946 (M+H)$^+$.

Example 570

(S)-3-(2-((S)-1-(3-fluoro-4-(piperidine-1-carbonyl)phenyl)ethylamino)pyrimidin-4-yl)-4-isopropyloxazolidin-2-one

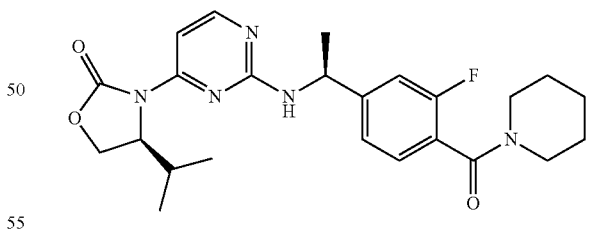

To (S)-(4-(1-aminoethyl)-2-fluorophenyl)(piperidin-1-yl)methanone (0.019 g, 0.076 mmol) was added (S)-3-(2-chloropyrimidin-4-yl)-4-isopropyloxazolidin-2-one (0.028 g, 0.114 mmol), NMP (0.5 ml) and Hunig's Base (0.033 ml, 0.190 mmol). The reaction was heated at 105-110° C. for 16 hours or until done by LCMS. The reaction was let cool, 0.5 ml of NMP was added, filtered, purified by prep LC and lyophilized to give 4.0 mg of (S)-3-(2-((S)-1-(3-fluoro-4-(piperidine-1-carbonyl)phenyl)ethylamino)pyrimidin-4-yl)-4-isopropyloxazolidin-2-one as TFA Salt. LCMS m/z 456.1 (M+H)$^+$, rt 0.74 min.

¹H NMR (400 MHz, CD₃OD) δ ppm 8.13 (d, J=6.7 Hz, 1H), 7.69 (d, J=7.0 Hz, 1H), 7.30-7.38 (m, 1H), 7.23-7.28 (m, 1H), 7.20 (d, J=10.6 Hz, 1H), 5.18 (br. s., 1H), 4.63-4.74 (m, 1H), 4.33-4.42 (m, 2H), 3.61-3.79 (m, 2H), 1.61-1.76 (m, 5H), 1.57 (d, J=7.0 Hz, 3H), 1.51 (br. s., 2H), 0.77 (br. s., 3H), 0.62 (br. s., 3H); HRMS(A) m/z 456.2416 (M+H)⁺.

Example 571

(S)-3-(5-fluoro-2-((S)-1-(3-fluoro-4-(piperidine-1-carbonyl)phenyl)ethylamino)pyrimidin-4-yl)-4-isopropyloxazolidin-2-one

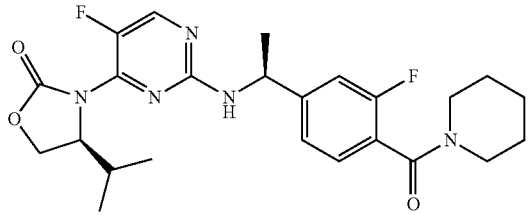 [SMILES: CC(C)[C@H]1COC(=O)N1c1nc(N[C@@H](C)c2ccc(C(=O)N3CCCCC3)c(F)c2)ncc1F]

To (S)-(4-(1-aminoethyl)-2-fluorophenyl)(piperidin-1-yl)methanone (0.019 g, 0.076 mmol) was added (S)-3-(2-chloro-5-fluoropyrimidin-4-yl)-4-isopropyloxazolidin-2-one (0.030 g, 0.114 mmol), NMP (0.5 ml) and Hunig's Base (0.033 ml, 0.190 mmol). The reaction was heated at 105-110° C. for 8 hours or until done by LCMS. The reaction was let cool, 0.5 ml of NMP added, filtered, purified by prep LC and lyophilized to give 4.5 mg of (S)-3-(5-fluoro-2-((S)-1-(3-fluoro-4-(piperidine-1-carbonyl)phenyl)ethylamino)pyrimidin-4-yl)-4-isopropyloxazolidin-2-one as TFA Salt. LCMS m/z 474.2 (M+H)⁺, Rt 0.91 min.
¹H NMR (400 MHz, CD₃OD) δ ppm 8.21 (d, J=2.7 Hz, 1H), 7.22-7.33 (m, 2H), 7.17 (d, J=11.0 Hz, 1H), 4.97 (q, J=7.0 Hz, 1H), 4.59 (br. s., 1H), 4.47 (t, J=8.8 Hz, 1H), 4.20-4.32 (m, 1H), 3.68 (br. s., 2H), 1.57-1.75 (m, 5H), 1.48 (d, J=7.0 Hz, 5H), 0.69 (br. s., 3H), 0.62 (br. s., 3H); HRMS(A) m/z 474.2330 (M+H)⁺.

Example 572

N-cyclohexyl-2-fluoro-4-((S)-1-(5-fluoro-4-((S)-4-isopropyl-2-oxooxazolidin-3-yl)pyrimidin-2-ylamino)ethyl)benzamide

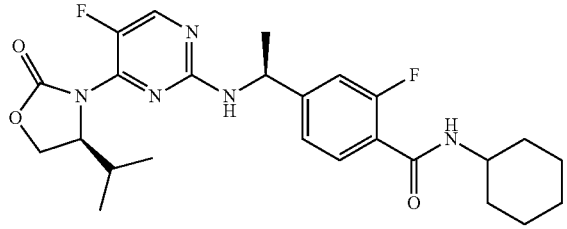 [SMILES: CC(C)[C@H]1COC(=O)N1c1nc(N[C@@H](C)c2ccc(C(=O)NC3CCCCC3)c(F)c2)ncc1F]

To (S)-4-(1-aminoethyl)-N-cyclohexyl-2-fluorobenzamide (16 mg, 0.061 mmol) was added (S)-3-(2-chloro-5-fluoropyrimidin-4-yl)-4-isopropyloxazolidin-2-one (31.4 mg, 0.121 mmol), NMP (0.5 ml) and Hunig's Base (0.032 ml, 0.182 mmol). The reaction was heated at 125° C. for 4 hours or until done by LCMS. The reaction was let cool, 0.5 ml of NMP added, filtered, purified by prep LC and lyophilized to give 2.5 mg of N-cyclohexyl-2-fluoro-4-((S)-1-(5-fluoro-4-((S)-4-isopropyl-2-oxooxazolidin-3-yl)pyrimidin-2-ylamino)ethyl)benzamide as the TFA Salt. LCMS m/z 488.2 (M+H)⁺, Rt 0.99 min.

¹H NMR (400 MHz, CD₃OD) δ ppm 8.21 (br. s., 1H), 7.62 (t, J=7.8 Hz, 1H), 7.24 (dd, J=8.0, 1.4 Hz, 1H), 7.16 (d, J=12.1 Hz, 1H), 4.39-4.54 (m, 2H), 4.23 (t, J=7.2 Hz, 1H), 3.83 (t, J=10.4 Hz, 1H), 1.86-1.97 (m, 2H), 1.76 (d, J=12.9 Hz, 2H), 1.64 (d, J=12.9 Hz, 1H), 1.48 (d, J=7.0 Hz, 3H), 1.12-1.42 (m, 6H), 0.61 (br. s., 6H); HRMS(A) m/z 488.2484 (M+H)⁺

Example 573

N-cyclohexyl-2-fluoro-4-((S)-1-(4-((S)-4-isopropyl-2-oxooxazolidin-3-yl)pyrimidin-2-ylamino)ethyl)benzamide

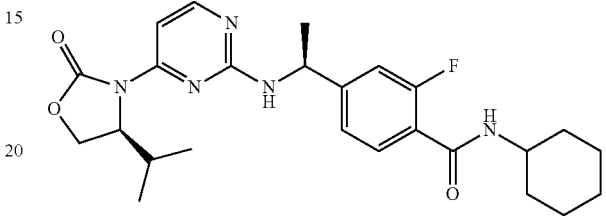

To (S)-4-(1-aminoethyl)-N-cyclohexyl-2-fluorobenzamide (16 mg, 0.061 mmol) was added (S)-3-(2-chloropyrimidin-4-yl)-4-isopropyloxazolidin-2-one (29.3 mg, 0.121 mmol), NMP (0.5 ml) and Hunig's Base (0.032 ml, 0.182 mmol). The reaction was heated at 125° C. for 4 hours or until done by LCMS. The reaction was let cool, 0.5 ml of NMP added, filtered, purified by prep LC and lyophilized to give 5.6 mg of N-cyclohexyl-2-fluoro-4-((S)-1-(4-((S)-4-isopropyl-2-oxooxazolidin-3-yl)pyrimidin-2-ylamino)ethyl)benzamide as the TFA Salt. LCMS m/z 470.2 (M+H)+, Rt 0.83 min.

¹H NMR (400 MHz, CD₃OD) δ ppm 8.12 (br. s., 1H), 7.57-7.73 (m, 2H), 7.13-7.27 (m, 2H), 5.15 (br. s., 1H), 4.66 (br. s., 1H), 4.36 (d, J=5.5 Hz, 2H), 3.76-3.94 (m, 1H), 1.87-1.99 (m, 2H), 1.77 (d, J=12.9 Hz, 2H), 1.65 (d, J=13.7 Hz, 1H), 1.57 (d, J=7.0 Hz, 3H), 1.12-1.50 (m, 6H), 0.73 (br. s., 3H), 0.62 (br. s., 3H); HRMS(A) m/z 470.2572 (M+H)⁺

Example 574

(S)-4-Isopropyl-3-(2-(((S)-1-(4-(pyrimidin-5-yloxy)phenyl)ethyl)amino)pyrimidin-4-yl)oxazolidin-2-one

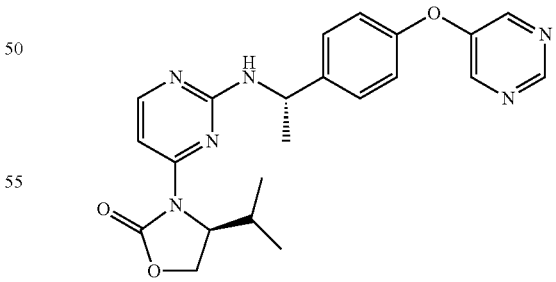

To the solution of (S)-3-(2-chloropyrimidin-4-yl)-4-isopropyloxazolidin-2-one (43 mg, 0.169 mmol) in NMP (0.7 mL) was added (S)-1-(4-(pyrimidin-5-yloxy)phenyl)ethanamine (41 mg, 0.169 mmol) and DIEA (88 μL, 0.507 mmol). The brown reaction mixture was stirred at 110° C. for 2 days. The reaction mixture was diluted with ethyl acetate and aqueous sodium bicarbonate solution. The separated organic layer was washed with saturated aqueous sodium bicarbonate solution, water and brine. The organic phase was dried over sodium sulfate, filtered off and concentrated under reduced pressure. The residue was purified by reverse phase column chromatography [C-18] to provide (S)-4-isopropyl-3-(2-(((S)-1-(4-(pyrimidin-5-yloxy)phenyl)ethyl)amino)pyrimidin-4-yl)oxazolidin-2-one (7 mg) as its trifluoroacetic acid salt.

MS m/z 421.3 (M+H)+, Rt 0.68 min.
HRMS(A) m/z 421.1996 (M+H)+, Rt 1.54 min.

Example 575

4-Phenyl-3-(2-((S)-1-phenylethylamino)pyrimidin-4-yl)-1,8-dioxa-3-azaspiro[4.5]decan-2-one

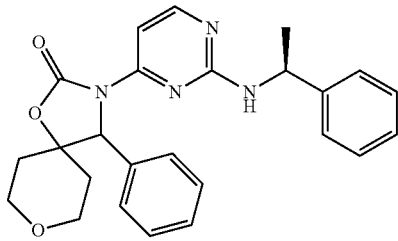 [SMILES: C[C@H](Nc1nccc(N2C(=O)OC3(CCOCC3)C2c2ccccc2)n1)c1ccccc1]

A mixture of crude 3-(2-chloropyrimidin-4-yl)-4-phenyl-1,8-dioxa-3-azaspiro[4.5]decan-2-one (330 mg, 0.954 mmol), (S)-1-phenylethanamine (810 mg, 6.68 mmol), Hunig's base (1.17 mL, 6.68 mmol) in DMA (3.5 mL) was heated in a sealed tube at 80° C. for ~16 hours. The mixture was allowed to cool to room temperature, diluted with DMSO and purified by reverse phase HPLC. Selected fractions were combined and lyophilized, providing 4-phenyl-3-(2-((S)-1-phenylethylamino)pyrimidin-4-yl)-1,8-dioxa-3-azaspiro[4.5]decan-2-one as its trifluoroacetic acid salt as a white solid. LCMS m/z 431.2 (M+H)+, Rt 0.83 min.

The solid was dissolved in ethyl acetate/saturated aqueous NaHCO$_3$ solution. The separated organic layer was washed with saturated aqueous NaHCO$_3$ solution (2×), brine, dried over sodium sulfate, filtered off and concentrated under reduced pressure providing 4-phenyl-3-(2-((S)-1-phenylethylamino)pyrimidin-4-yl)-1,8-dioxa-3-azaspiro[4.5]decan-2-one (120 mg).

Examples 576 & 577

(S)-4-phenyl-3-(2-((S)-1-phenylethylamino)pyrimidin-4-yl)-1,8-dioxa-3-azaspiro[4.5]decan-2-one and (R)-4-phenyl-3-(2-((S)-1-phenylethylamino)pyrimidin-4-yl)-1,8-dioxa-3-azaspiro[4.5]decan-2-one

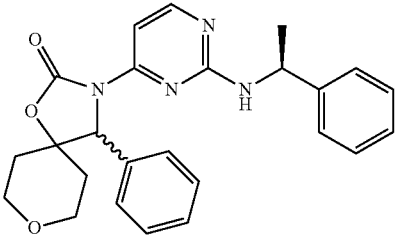 [SMILES: C[C@H](Nc1nccc(N2C(=O)OC3(CCOCC3)C2c2ccccc2)n1)c1ccccc1]

120 mg of 4-phenyl-3-(2-((S)-1-phenylethylamino)pyrimidin-4-yl)-1,8-dioxa-3-azaspiro[4.5]decan-2-one were dissolved in EtOH (10 mL).
Analytical Separation:
  Column: CHIRALPAK AD-H (5 um) 100×4.6 mm (Daicel Chemical Industries, LTD.).
  Solvent: n-heptane:ethyl alcohol=70:30
  Flow rate: 1.0 mL/min; detection: UV=220 nm.
  Fraction 1: Retention time: 5.84 min.
  Fraction 2: Retention time: 10.18 min.
Preparative Separation:
  Column: CHIRALPAK AD-prep (10 um) 2×25 cm.
  Solvent: n-heptane:ethyl alcohol=70:30
  Flow rate: 20 mL/min; 530 psi; injection: 4 mL; detection: UV=210 nm.
  Fractions were concentrated under reduce pressure. The residue was dissolved in acetonitrile and filtered through a syringe filter, diluted with water and lyophilized.
  Example 576: Peak 1: white powder. Yield: 52.0 mg; de=99% (UV, 220 nm).
  LCMS m/z 431.3 (M+H)+, Rt 0.81 min.
  Example 577: Peak 2: white powder. Yield: 47.8 mg; de=99% (UV, 220 nm).
  LCMS m/z 431.3 (M+H)+, Rt 0.81 min.

Examples 578 and 579

(R)-8-phenyl-7-(2-((S)-1-phenylethylamino)pyrimidin-4-yl)-2,5-dioxa-7-azaspiro[3.4]octan-6-one and (S)-8-phenyl-7-(2-((S)-1-phenylethylamino)pyrimidin-4-yl)-2,5-dioxa-7-azaspiro[3.4]octan-6-one were prepared using methods similar to those described for the preparation of Example 576 & 577.

TABLE 23

| Example No. | Structure | Chiral column for separation/ conditions | Chiral column for quality control/ conditions | Retention time |
|---|---|---|---|---|
| 578 (Peak 1) | 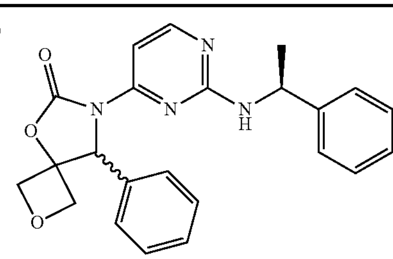 | AD column; 56 mg/ 6 mL EtOH; heptane:EtOH 75:25; 20 mL/min, 400 psi | AD-H column; heptane:EtOH 75:25; 1 mL/min | 5.4 min |

TABLE 23-continued

| Example No. | Structure | Chiral column for separation/ conditions | Chiral column for quality control/ conditions | Retention time |
|---|---|---|---|---|
| 579 (Peak 2) | | | AD-H column: heptane:EtOH 75:25; 1 mL/min | 8.9 min |

The compounds in Table 24 were prepared using methods similar to those described for the preparation of Example 569

TABLE 24

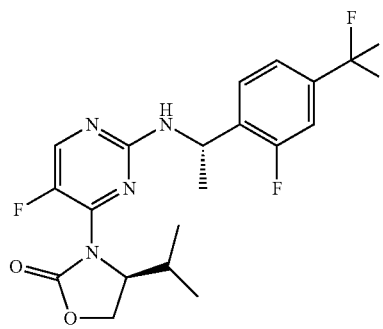

580

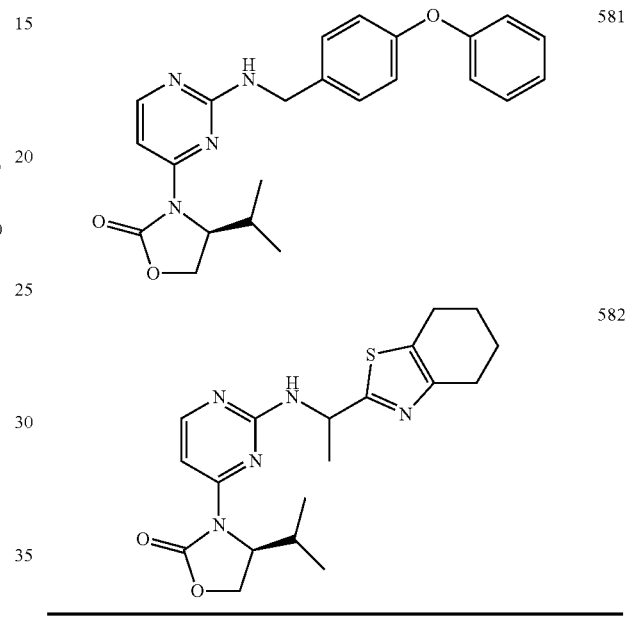

581

582

TABLE 25

Chemical name, NMR chemical shifts and LCMS signal for each compound listed in Table 24.

| Example: Name | $^1$H NMR (400 MHz) δ ppm | LCMS |
|---|---|---|
| 580: (S)-3-(5-fluoro-2-((S)-1-(2-fluoro-4-(trifluoromethyl)phenyl)eth-ylamino)pyrimidin-4-yl)-4-isopropyloxazolidin-2-one | (CD$_3$OD) 0.46-0.69 (m, 6 H) 0.81-0.91 (m, 1 H) 1.53 (d, J = 3.00 Hz, 3 H) 4.21-4.29 (m, 1 H) 4.43-4.53 (m, 2 H) 5.25 (m, J = 7.00, 7.00, 7.00 Hz, 1 H) 7.43 (m, J = 7.40 Hz, 2 H) 7.52-7.59 (m, 1 H) 8.21-8.27 (m, 1 H) | HRMS(A) m/z 431.1516 (M + H)+; Rt-2.40 min |
| 581: (S)-4-isopropyl-3-(2-(4-phenoxybenzylamino)pyrim-idin-4-yl)oxazolidin-2-one | (CD$_3$OD) 0.63-1.00 (m, 7 H) 4.37-4.49 (m, 2 H) 4.58-4.65 (m, 1 H) 4.66-4.78 (m, 2 H) 6.95-7.02 (m, 4 H) 7.10-7.16 (m, 1 H) 7.32-7.40 (m, 4 H) 7.75 (d, J = 7.04 Hz, 1 H) 8.16 (d, J = 6.65 Hz, 1 H) | HRMS(A) m/z 405.1935 (M + H)+; Rt-2.02 min |
| 582: (4S)-4-isopropyl-3-(2-(1-(4,5,6,7-tetrahydrobenzo[d]thiazol-2-yl)ethylamino)pyrimidin-4-yl)oxazolidin-2-one | | HRMS(A) m/z 388.1814 (M + H)+; Rt-1.82/1.88 min |

Examples 583 & 584

(S)-4-isopropyl-3-(2-((R)-1,1,1-trifluoropropan-2-ylamino)pyrimidin-4-yl)oxazolidin-2-one (S)-4-isopropyl-3-(2-((S)-1,1,1-trifluoropropan-2-ylamino)pyrimidin-4-yl)oxazolidin-2-one

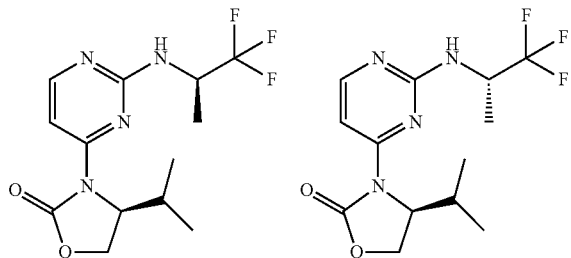 [SMILES: CC(C)[C@H]1COC(=O)N1c1ccnc(N[C@H](C)C(F)(F)F)n1 ; CC(C)[C@H]1COC(=O)N1c1ccnc(N[C@@H](C)C(F)(F)F)n1]

To a solution of (S)-3-(2-chloropyrimidin-4-yl)-4-isopropyloxazolidin-2-one (40 mg, 0.166 mmol) in 2-butanol was added 1,1,1-trifluoropropan-2-amine (74.9 mg, 0.662 mmol) and para-toluenesulfonic acid monohydrate (74.9 mg, 0.662 mmol). The mixture was heated under argon in a sealed vial for ~7 days at 115° C. Independently, to a solution of (S)-3-(2-chloropyrimidin-4-yl)-4-isopropyloxazolidin-2-one (100 mg, 0.414 mmol) in 2-butanol was added 1,1,1-trifluoropropan-2-amine (187 mg, 1.655 mmol) and para-toluenesulfonic acid monohydrate (157 mg, 0.828 mmol). The mixture was heated under argon in a sealed vial at 115° C. for ~4 days. The two reaction mixtures was combined and concentrated under reduced pressure. The residue was diluted with DMSO and water (~10 vol. % of DMSO), filtered through a syringe filter and purified by reverse phase HPLC. Selected fractions were collected and lyophilized providing two isomers as white solids as their trifluoroacetic acid salts.

1st Peak 583: Yield: 29.1 mg.
$^1$H NMR (400 MHz, CD$_3$OD) δ ppm 0.90 (d, J=7.04 Hz, 3H) 0.98-1.02 (m, 3H) 1.45 (d, J=7.04 Hz, 3H) 2.59 (dtd, J=13.89, 6.95, 6.95, 3.52 Hz, 1H) 4.43-4.47 (m, 2H) 4.76-4.83 (m, 2H) 7.70 (d, J=5.87 Hz, 1H) 8.20 (d, J=6.26 Hz, 1H)
LCMS m/z 319.3 (M+H)$^+$, Rt 0.73 min. HRMS(A) m/z 319.1391 (M+H)+, Rt 1.89 min 2nd Peak 584: Yield: 38.5 mg.
$^1$H NMR (400 MHz, CD$_3$OD) δ ppm 0.87 (d, J=7.04 Hz, 3H) 0.98 (d, J=7.04 Hz, 3H) 1.45 (d, J=7.04 Hz, 3H) 2.48-2.60 (m, 1H) 4.40-4.49 (m, 2H) 4.88-4.95 (m, 2H) 7.69 (d, J=5.87 Hz, 1H) 8.20 (d, J=6.65 Hz, 1H)
LCMS m/z 319.3 (M+H)$^+$, Rt 0.73 min. HRMS(A) m/z 319.1385 (M+H)+, Rt 1.88 min

Example 585

(4S)-4-phenyl-3-(2-(1,1,1-trifluoropropan-2-ylamino)pyrimidin-4-yl)oxazolidin-2-one

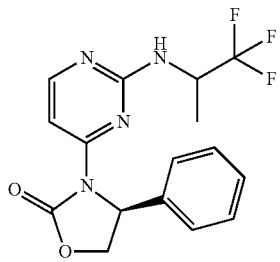 [SMILES: CC(Nc1nccc(N2C(=O)OC[C@@H]2c2ccccc2)n1)C(F)(F)F]

A mixture of (S)-3-(2-chloropyrimidin-4-yl)-4-phenyloxazolidin-2-one (40 mg, 0.145 mmol), 1,1,1-trifluoropropan-2-amine (82 mg, 0.725 mmol), Hunig's Base (0.038 mL, 0.218 mmol) in DMSO (0.4 mL) was heated under argon at 115° C. for ~3 days. Then mixture was allowed to cool to room temperature. The mixture was diluted with DMSO and water (~10 vol. % of DMSO), filtered through a syringe filter and purified by reverse phase HPLC. Selected fractions were collected and lyophilized providing (4S)-4-phenyl-3-(2-(1,1,1-trifluoropropan-2-ylamino)pyrimidin-4-yl)oxazolidin-2-one (ratio of two isomers: 7/3) as white solid as its trifluoroacetic acid salt. LCMS m/z 353.2 (M+H)+, Rt 0.78 min. HRMS(A) m/z 353.1231 (M+H)+, Rt 1.92/1.96 min.

Example 586

(S)-3-(2-((S)-1-cyclopropylethylamino)-5-fluoropyrimidin-4-yl)-4-phenyloxazolidin-2-one

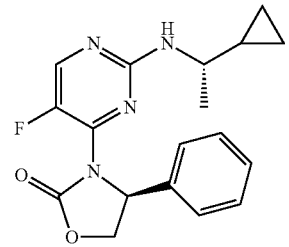 [SMILES: C[C@H](Nc1ncc(F)c(N2C(=O)OC[C@@H]2c2ccccc2)n1)C1CC1]

A mixture of (S)-3-(2-chloro-5-fluoropyrimidin-4-yl)-4-phenyloxazolidin-2-one (40 mg, 0.136 mmol), (S)-1-cyclopropylethanamine (34.8 mg, 0.409 mmol), Hunig's Base (0.119 mL, 0.681 mmol) in DMSO (0.4 mL) was heated under argon at 105-115° C. for ~18 hrs (alternative: 120-135° C. for ~90 min). Then mixture was allowed to cool to room temperature. The mixture was diluted with DMSO and water (~10 vol. % of DMSO), filtered through a syringe filter and purified by reverse phase HPLC. Selected fractions were collected and lyophilized providing (S)-3-(2-((S)-1-cyclopropylethylamino)-5-fluoropyrimidin-4-yl)-4-phenyloxazolidin-2-one (26 mg) as a white solid as its trifluoroacetic acid salt.

$^1$H NMR (400 MHz, CD$_3$OD) δ ppm −0.14-0.05 (m, 1H) 0.01-0.08 (m, 1H) 0.23-0.31 (m, 1H) 0.36-0.44 (m, 1H) 0.78-0.86 (m, 1H) 1.19 (d, J=6.65 Hz, 3H) 3.05-3.14 (m, 1H) 4.25-4.32 (m, 1H) 4.89-4.90 (m, 1H) 5.77 (t, J=8.61 Hz, 1H) 7.32-7.39 (m, 5H) 8.15 (d, J=3.52 Hz, 1H).

LCMS m/z 343.1 (M+H)$^+$, Rt 0.88 min. HRMS(A) m/z 343.1577 (M+H)$^+$, Rt 2.09 min The compounds in Table 26 were prepared using methods similar to those described for the preparation of Example 586.

TABLE 26

| | |
|---|---|
| 587 | 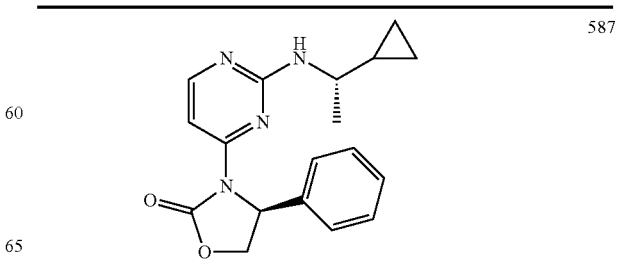 |

TABLE 26-continued

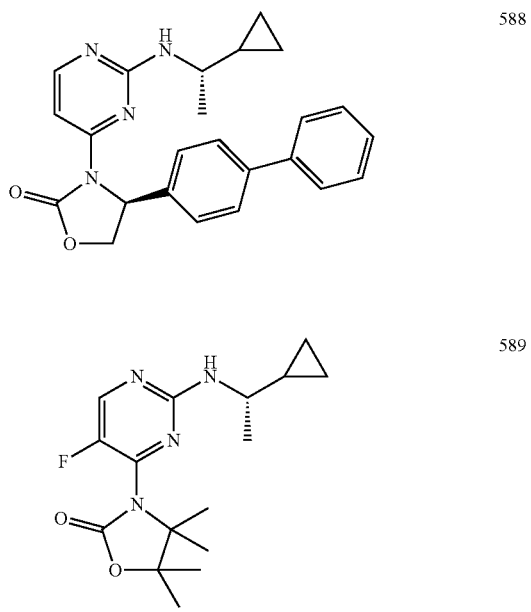

The compounds in Table 28 were prepared using methods similar to those described for the preparation of Example 568

TABLE 28

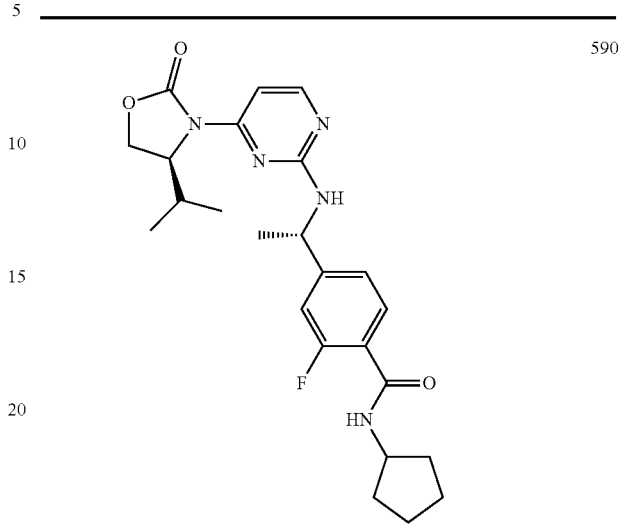

TABLE 27

Chemical name, NMR chemical shifts and LCMS signal for each compound listed in Table 26.

| Example: Name | $^1$H NMR (400 MHz) δ ppm | LCMS |
|---|---|---|
| 587: (S)-3-(2-((S)-1-cyclopropylethylamino)pyrimidin-4-yl)-4-phenyloxazolidin-2-one | (CD$_3$OD) −0.55-−0.27 (m, 1 H), −0.01 (m, J = 9.00, 4.30 Hz, 1 H), 0.12-0.32 (m, 1 H) 0.35-0.50 (m, 1 H) 0.64-0.93 (m, 1 H) 1.28 (d, J = 1.00 Hz, 3 H) 2.77-3.00 (m, 1 H) 4.26 (dd, J = 1.00 Hz, 1 H) 4.76-4.95 (m, 1-2 H; overlay with solvent) 5.75 (dd, J = 1.00 Hz, 1 H) 7.17-7.52 (m, 5 H) 7.78 (d, J = 1.00 Hz, 1 H) 8.08 (d, J = 7.04 Hz, 1 H) | MS m/z 325.2 (M + H)+; Rt-0.77 min. HRMS(A) m/z 325.1664 (M + H)+; Rt-1.53 min |
| 588: (S)-4-(biphenyl-4-yl)-3-(2-((S)-1-cyclopropylethylamino)pyrimidin-4-yl)oxazolidin-2-one | (CD$_3$OD) 0.01 (m, J = 4.30 Hz, 1 H) 0.14-0.26 (m, 1 H) 0.33-0.45 (m, 1 H) 0.73-0.85 (m, 1 H) 1.28 (d, J = 6.65 Hz, 3 H) 2.91-3.02 (m, 1 H) 4.32 (dd, J = 9.00, 4.30 Hz, 1 H) 4.89-4.96 (m, 1 H) 5.81 (dd, J = 9.00, 4.30 Hz, 1 H) 7.34-7.42 (m, 3 H) 7.45 (t, J = 7.63 Hz, 2 H) 7.59-7.64 (m, 2 H) 7.67 (m, J = 8.20 Hz, 2 H) 7.79 (d, J = 7.04 Hz, 1 H) 8.10 (d, J = 7.04 Hz, 1 H) | MS m/z 401.3 (M + H)+; Rt-0.89 min. HRMS(A) m/z 401.1988 (M + H)+; Rt-1.89 min |
| 589: (S)-3-(2-(1-cyclopropylethylamino)-5-fluoropyrimidin-4-yl)-4,4,5,5-tetramethyloxazolidin-2-one | (CD$_3$OD) 0.17-0.24 (m, 1 H) 0.31 (dq, J = 9.34, 4.71 Hz, 1 H) 0.41-0.55 (m, 2 H) 0.93-1.04 (m, 1 H) 1.26 (d, J = 6.65 Hz, 3 H) 1.42 (s, 6 H) 1.49 (s, 6 H) 3.34-3.42 (m, 1 H) 8.17 (d, J = 3.13 Hz, 1 H) MS m/z 323.6 (M + H)+; Rt-0.89 min. HRMS m/z 323.1891 (M + H)+; Rt-2.10 min | HRMS(A) m/z 464.1125 (M + H)+, Rt 2.28 mm |

TABLE 28-continued
591
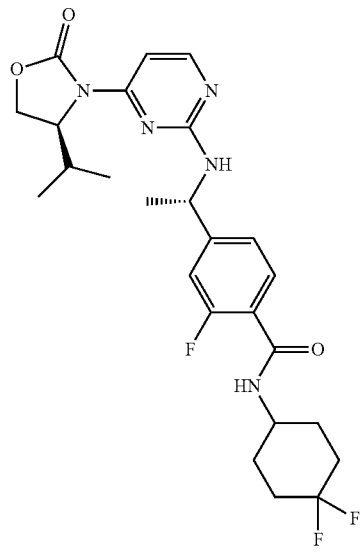 [SMILES: CC(C)[C@H]1COC(=O)N1c1ccnc(N[C@@H](C)c2ccc(C(=O)NC3CCC(F)(F)CC3)c(F)c2)n1]
592
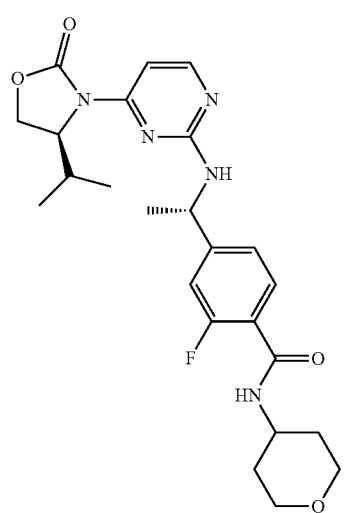 [SMILES: CC(C)[C@H]1COC(=O)N1c1ccnc(N[C@@H](C)c2ccc(C(=O)NC3CCOCC3)c(F)c2)n1]
593
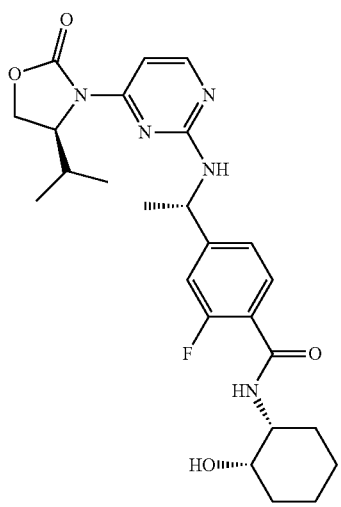 [SMILES: CC(C)[C@H]1COC(=O)N1c1ccnc(N[C@@H](C)c2ccc(C(=O)N[C@@H]3CCCC[C@@H]3O)c(F)c2)n1]
TABLE 28-continued
594
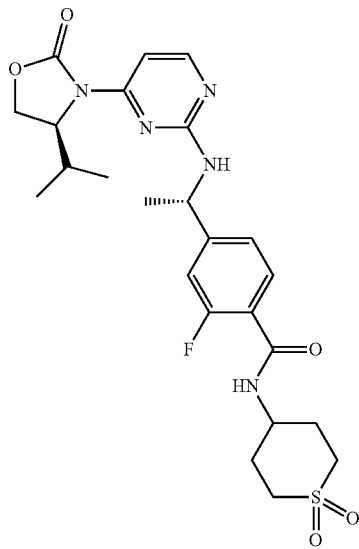 [SMILES: CC(C)[C@H]1COC(=O)N1c1ccnc(N[C@@H](C)c2ccc(C(=O)NC3CCS(=O)(=O)CC3)c(F)c2)n1]
595
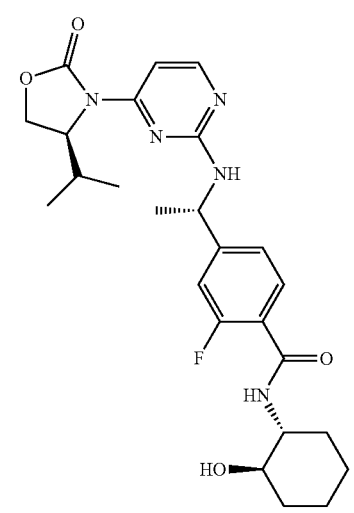 [SMILES: CC(C)[C@H]1COC(=O)N1c1ccnc(N[C@@H](C)c2ccc(C(=O)N[C@@H]3CCCC[C@H]3O)c(F)c2)n1]
596
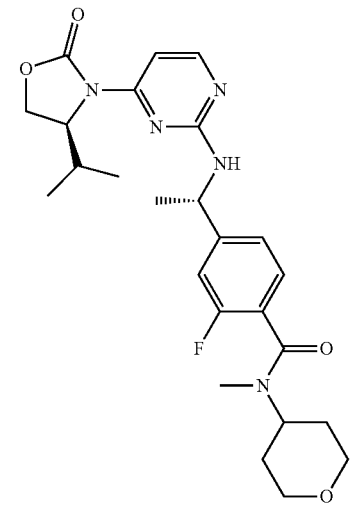 [SMILES: CC(C)[C@H]1COC(=O)N1c1ccnc(N[C@@H](C)c2ccc(C(=O)N(C)C3CCOCC3)c(F)c2)n1]

TABLE 28-continued
597 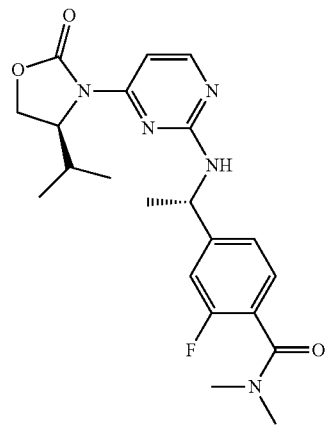 [SMILES: CC(C)[C@H]1COC(=O)N1c1ccnc(N[C@@H](C)c2ccc(C(=O)N(C)C)c(F)c2)n1]
598 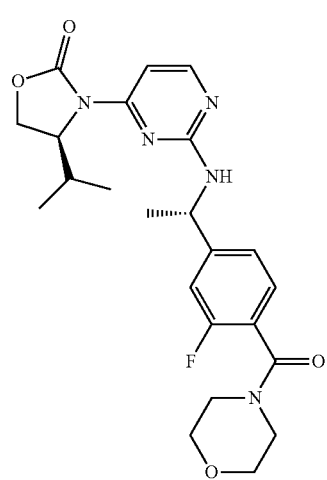 [SMILES: CC(C)[C@H]1COC(=O)N1c1ccnc(N[C@@H](C)c2ccc(C(=O)N3CCOCC3)c(F)c2)n1]
599 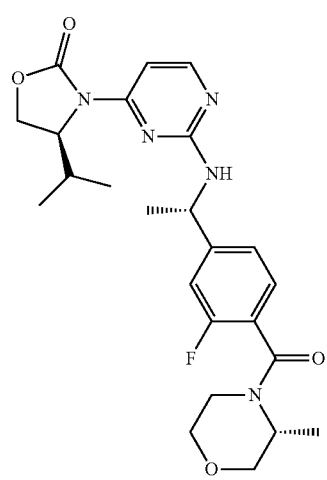 [SMILES: CC(C)[C@H]1COC(=O)N1c1ccnc(N[C@@H](C)c2ccc(C(=O)N3CCOC[C@H]3C)c(F)c2)n1]
TABLE 28-continued
600 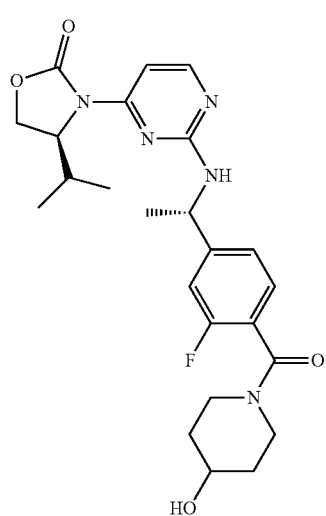 [SMILES: CC(C)[C@H]1COC(=O)N1c1ccnc(N[C@@H](C)c2ccc(C(=O)N3CCC(O)CC3)c(F)c2)n1]
601 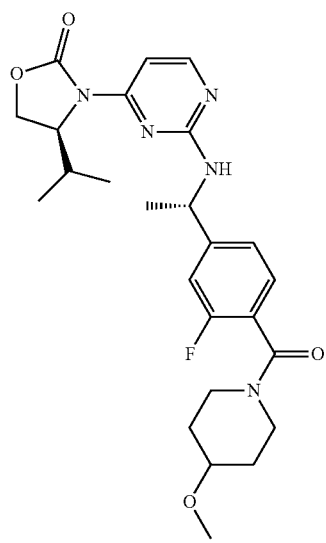 [SMILES: COC1CCN(C(=O)c2ccc([C@H](C)Nc3nccc(N4C(=O)OC[C@@H]4C(C)C)n3)cc2F)CC1]
602 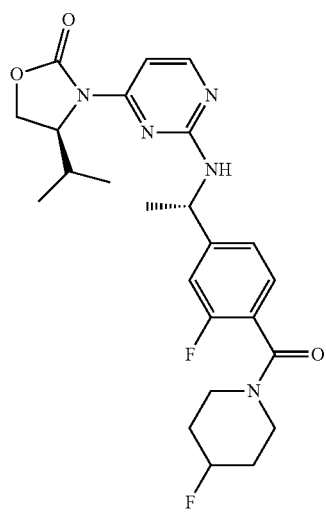 [SMILES: CC(C)[C@H]1COC(=O)N1c1ccnc(N[C@@H](C)c2ccc(C(=O)N3CCC(F)CC3)c(F)c2)n1]

TABLE 28-continued

603

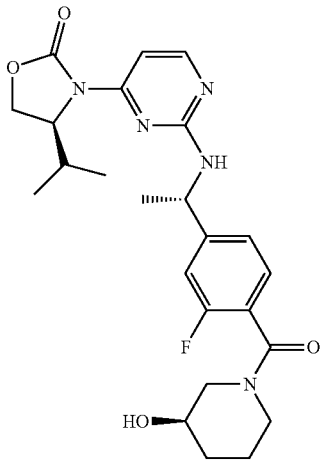 [SMILES: CC(C)[C@H]1COC(=O)N1c1ccnc(N[C@@H](C)c2ccc(C(=O)N3CCC[C@@H](O)C3)c(F)c2)n1]

TABLE 28-continued

604

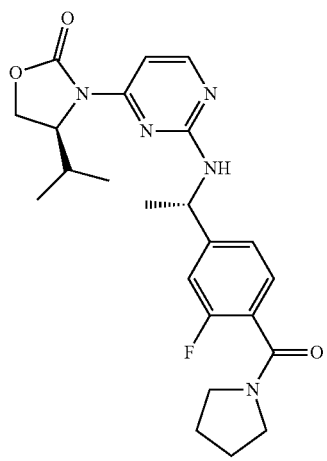 [SMILES: CC(C)[C@H]1COC(=O)N1c1ccnc(N[C@@H](C)c2ccc(C(=O)N3CCCC3)c(F)c2)n1]

TABLE 29

Chemical name, NMR chemical shifts and LCMS signal for each compound listed in Table 28.

| Example: Name | $^1$H NMR (400 MHz) δ ppm | LCMS |
| --- | --- | --- |
| 590: N-cyclopentyl-2-fluoro-4-((S)-1-(4-((S)-4-isopropyl-2-oxooxazolidin-3-yl)pyrimidin-2-ylamino)ethyl)benzamide | (CD$_3$OD) 8.14 (d, J = 6.3 Hz, 1H), 7.72 (d, J = 7.0 Hz, 1H), 7.64 (t, J = 7.6 Hz, 1H), 7.13-7.31 (m, 2H), 5.17 (br. s., 1H), 4.67 (br. s., 1H), 4.34-4.41 (m, 2H), 4.24-4.33 (m, 1H), 1.99 (dt, J = 11.7, 5.9 Hz, 2H), 1.73 (d, J = 6.7 Hz, 2H), 1.49-1.66 (m, 8H), 0.74 (br. s., 3H), 0.61 (br. s., 3H) | HRMS(A) m/z (M + H)+ 456.2422 |
| 591: N-(4,4-difluorocyclohexyl)-2-fluoro-4-((S)-1-(4-((S)-4-isopropyl-2-oxooxazolidin-3-yl)pyrimidin-2-ylamino)ethyl)benzamide | (CD$_3$OD) 8.14 (d, J = 6.3 Hz, 1H), 7.70 (d, J = 7.0 Hz, 1H), 7.64 (t, J = 7.8 Hz, 1H), 7.12-7.32 (m, 2H), 5.16 (br. s., 1H), 4.67 (br. s., 1H), 4.37 (d, J = 5.9 Hz, 2H), 4.00 (t, J = 10.0 Hz, 1H), 1.82-2.13 (m, 6H), 1.61-1.77 (m, 2H), 1.57 (d, J = 7.0 Hz, 3H), 0.73 (br. s., 3H), 0.61 (br. s., 3H) | HRMS(A) m/z (M + H)+ 506.2388 |
| 592: 2-fluoro-4-((S)-1-(4-((S)-4-isopropyl-2-oxooxazolidin-3-yl)pyrimidin-2-ylamino)ethyl)-N-(tetrahydro-2H-pyran-4-yl)benzamide | (CD$_3$OD) 8.13 (d, J = 5.9 Hz, 1H), 7.58-7.71 (m, 2H), 7.13-7.29 (m, 2H), 5.16 (br. s., 1H), 4.67 (br. s., 1H), 4.36 (d, J = 5.5 Hz, 2H), 4.01-4.16 (m, 1H), 3.94 (d, J = 11.3 Hz, 2H), 3.50 (td, J = 11.7, 2.0 Hz, 2H), 1.82-1.94 (m, 2H), 1.59-1.69 (m, 2H), 1.57 (d, J = 7.0 Hz, 3H), 0.73 (br. s., 3H), 0.61 (br. s., 3H) | HRMS(A) m/z (M + H)+ 472.2366 |
| 593: 2-fluoro-N-((1R,2S)-2-hydroxycyclohexyl)-4-((S)-1-(4-((S)-4-isopropyl-2-oxooxazolidin-3-yl)pyrimidin-2-ylamino)ethyl)benzamide | (CD$_3$OD) 8.14 (d, J = 6.3 Hz, 1H), 7.83 (t, J = 7.8 Hz, 1H), 7.69 (d, J = 7.0 Hz, 1H), 7.14-7.36 (m, 2H), 5.15 (d, J = 6.3 Hz, 1H), 4.65 (br. s., 1H), 4.36 (d, J = 5.5 Hz, 2H), 3.96-4.05 (m, 1H), 3.94 (d, J = 2.3 Hz, 1H), 1.79 (dd, J = 10.4, 4.5 Hz, 1H), 1.69 (d, J = 5.9 Hz, 4H), 1.54-1.64 (m, 5H), 1.28-1.48 (m, 2H), 0.70 (br. s., 3H), 0.60 (br. s., 3H) | HRMS(A) m/z (M + H)+ 486.2526 |
| 594: N-(1,1-dioxidotetrahydro-2H-thiopyran-4-yl)-2-fluoro-4-((S)-1-((4-((S)-4-isopropyl-2-oxooxazolidin-3-yl)pyrimidin-2-yl)amino)ethyl)benzamide | (CD$_3$OD) 8.14 (d, J = 6.3 Hz, 1H), 7.69 (d, J = 7.0 Hz, 1H), 7.64 (t, J = 7.6 Hz, 1H), 7.15-7.31 (m, 2H), 5.16 (br. s., 1H), 4.67 (br. s., 1H), 4.36 (d, J = 5.9 Hz, 2H), 4.13-4.27 (m, 1H), 3.08 (d, J = 13.7 Hz, 2H), 2.25-2.36 (m, 2H), 2.07-2.24 (m, 2H), 1.57 (d, J = 7.0 Hz, 3H), 0.73 (br. s., 3H), 0.61 (br. s., 3H) | HRMS(A) m/z (M + H)+ 520.203 |
| 595: 2-fluoro-N-((1R,2R)-2-hydroxycyclohexyl)-4-((S)-1-(4-((S)-4-isopropyl-2-oxooxazolidin-3-yl)pyrimidin-2-ylamino)ethyl)benzamide | (CD$_3$OD) 8.13 (d, J = 6.3 Hz, 1H), 7.63-7.78 (m, 2H), 7.14-7.30 (m, 2H), 5.15 (br. s., 1H), 4.67 (br. s., 1H), 4.36 (d, J = 5.5 Hz, 2H), 3.67-3.83 (m, 1H), 3.38-3.51 (m, 1H), 2.01 (d, J = 9.0 Hz, 2H), 1.64-1.81 (m, 3H), 1.57 (d, J = 7.0 Hz, 3H), 1.17-1.46 (m, 4H), 0.74 (br. s., 3H), 0.61 (br. s., 3H) | HRMS(A) m/z (M + H)+ 486.2521 |

TABLE 29-continued

Chemical name, NMR chemical shifts and LCMS
signal for each compound listed in Table 28.

| Example: Name | $^1$H NMR (400 MHz) δ ppm | LCMS |
| --- | --- | --- |
| 596: 2-fluoro-4-((S)-1-(4-((S)-4-isopropyl-2-oxooxazolidin-3-yl)pyrimidin-2-ylamino)ethyl)-N-methyl-N-(tetrahydro-2H-pyran-4-yl)benzamide | (CD$_3$OD) 8.14 (d, J = 6.7 Hz, 1 H), 7.76 (d, J = 7.4 Hz, 1H), 7.32-7.42 (m, 1H), 7.17-7.31 (m, 2H), 5.22 (br. s., 1H), 4.60-4.76 (m, 2H), 4.33-4.44 (m, 2H), 4.02 (dd, J = 11.3, 4.3 Hz, 1H), 3.91 (d, J = 8.6 Hz, 1H), 3.45-3.65 (m, 2H), 3.07-3.21 (m, 1H), 2.99 (s, 1H), 2.80 (s, 2H), 1.81-2.05 (m, 3H), 1.52-1.71 (m, 5H), 0.78 (br. s., 3H), 0.63 (br. s., 3H) | HRMS(A) m/z (M + H)+ 486.2528 |
| 597: 2-fluoro-4-((S)-1-(4-((S)-4-isopropyl-2-oxooxazolidin-3-yl)pyrimidin-2-ylamino)ethyl)-N,N-dimethylbenzamide | (CD$_3$OD) 8.14 (d, J = 7.0 Hz, 1H), 7.75 (d, J = 7.0 Hz, 1H), 7.32-7.43 (m, 1H), 7.13-7.31 (m, 2H), 5.20 (br. s., 1H), 4.70 (br. s., 1H), 4.33-4.45 (m, 2H), 3.09 (s, 3H), 2.92 (d, J = 0.8 Hz, 3H), 1.76 (br. s., 1H), 1.59 (d, J = 7.0 Hz, 3H), 0.78 (br. s., 3H), 0.62 (br. s., 3H) | HRMS(A) m/z (M + H)+ 416.2106 |
| 598: (S)-3-(2-((S)-1-(3-fluoro-4-(morpholine-4-carbonyl)phenyl)ethylamino)pyrimidin-4-yl)-4-isopropyloxazolidin-2-one | (CD$_3$OD) 8.14 (d, J = 6.7 Hz, 1H), 7.73 (d, J = 6.7 Hz, 1H), 7.35-7.43 (m, 1H), 7.28 (d, J = 7.8 Hz, 1H), 7.22 (d, J = 10.6 Hz, 1H), 5.18 (br. s., 1H), 4.69 (br. s., 1H), 4.30-4.42 (m, 2H), 3.73 (d, J = 3.1 Hz, 4H), 3.59 (t, J = 4.7 Hz, 2H), 1.58 (d, J = 7.0 Hz, 3H), 0.76 (br. s., 3H), 0.62 (br. s., 3H) | HRMS(A) m/z (M + H)+ 458.2209 |
| 599: (S)-3-(2-((S)-1-(3-fluoro-4-((R)-3-methylmorpholine-4-carbonyl)phenyl)ethylamino)pyrimidin-4-yl)-4-isopropyloxazolidin-2-one | (CD$_3$OD) 8.14 (d, J = 6.7 Hz, 1H), 7.76 (d, J = 7.0 Hz, 1H), 7.36 (d, J = 6.7 Hz, 1H), 7.14-7.31 (m, 2H), 5.20 (br. s., 1H), 4.70 (br. s., 1H), 4.65 (br. s., 1H), 4.34-4.45 (m, 2H), 4.29 (d, J = 13.3 Hz, 1H), 3.96 (d, J = 10.6 Hz, 1H), 3.75 (d, J = 11.3 Hz, 1H), 3.51-3.67 (m, 2H), 3.43-3.51 (m, 1H), 3.07-3.19 (m, 1H), 1.76 (br. s., 1H), 1.59 (d, J = 7.0 Hz, 3H), 1.36 (d, J = 6.7 Hz, 2H), 1.28 (br. s., 1H), 0.77 (br. s., 3H), 0.62 (br. s., 3H) | HRMS(A) m/z (M + H)+ 472.2366 |
| 600: (S)-3-(2-((S)-1-(3-fluoro-4-(4-hydroxypiperidine-1-carbonyl)phenyl)ethylamino)pyrimidin-4-yl)-4-isopropyloxazolidin-2-one | (CD$_3$OD) 8.14 (d, J = 6.7 Hz, 1H), 7.73 (d, J = 7.0 Hz, 1H), 7.31-7.40 (m, 1H), 7.16-7.29 (m, 2H), 5.18 (br. s., 1H), 4.70 (br. s., 1H), 4.31-4.45 (m, 2H), 4.16 (dd, J = 12.9, 5.5 Hz, 1H), 3.87 (br. s., 1H), 3.48 (d, J = 14.1 Hz, 1H), 3.35 (d, J = 3.5 Hz, 1H), 3.05-3.22 (m, 1H), 1.85-1.98 (m, 1 H), 1.70-1.83 (m, 2H), 1.58 (d, J = 7.0 Hz, 3H), 1.49-1.55 (m, 1H), 1.43 (br. s., 1H), 0.76 (br. s., 3H), 0.62 (br. s., 3H) | HRMS(A) m/z (M + H)+ 472.2369 |
| 601: (S)-3-(2-((S)-1-(3-fluoro-4-(4-methoxypiperidine-1-carbonyl)phenyl)ethylamino)pyrimidin-4-yl)-4-isopropyloxazolidin-2-one | (CD$_3$OD) 8.13 (d, J = 6.7 Hz, 1H), 7.70 (d, J = 6.7 Hz, 1H), 7.31-7.41 (m, 1H), 7.26 (d, J = 7.8 Hz, 1H), 7.21 (d, J = 10.6 Hz, 1H), 5.17 (br. s., 1H), 4.69 (br. s., 1H), 4.33-4.42 (m, 2H), 3.98 (dd, J = 10.8, 6.5 Hz, 1H), 3.40-3.60 (m, 3H), 3.34 (s, 3H), 3.18 (d, J = 8.6 Hz, 1H), 1.88-2.03 (m, 1H), 1.79 (br. s., 1H), 1.62 (br. s., 1H), 1.58 (d, J = 7.0 Hz, 3H), 1.49 (br. s., 1H), 0.76 (br. s., 3H), 0.62 (br. s., 3H) | HRMS(A) m/z (M + H)+ 486.2523 |
| 602: (S)-3-(2-((S)-1-(3-fluoro-4-(4-fluoropiperidine-1-carbonyl)phenyl)ethylamino)pyrimidin-4-yl)-4-isopropyloxazolidin-2-one | (CD$_3$OD) 8.14 (d, J = 6.7 Hz, 1H), 7.73 (d, J = 7.0 Hz, 1H), 7.34-7.44 (m, 1H), 7.16-7.31 (m, 2H), 5.18 (br. s., 1H), 4.93 (br. s., 1H), 4.70 (br. s., 1H), 4.29-4.43 (m, 2H), 3.91 (d, J = 11.3 Hz, 1H), 3.70 (br. s., 1H), 3.40-3.53 (m, 1H), 1.93-2.06 (m, 1H), 1.83-1.93 (m, 2H), 1.77 (dd, J = 10.2, 4.7 Hz, 2H), 1.58 (d, J = 7.0 Hz, 3H), 0.76 (br. s., 3H), 0.62 (br. s., 3H) | HRMS(A) m/z (M + H)+ 474.2324 |
| 603: (S)-3-(2-((S)-1-(3-fluoro-4-((R)-3-hydroxypiperidine-1-carbonyl)phenyl)ethylamino)pyrimidin-4-yl)-4-isopropyloxazolidin-2-one | (CD$_3$OD) 8.13 (d, J = 6.7 Hz, 1H), 7.72 (d, J = 7.0 Hz, 1H), 7.36 (t, J = 7.4 Hz, 1H), 7.14-7.30 (m, 2H), 5.19 (br. s., 1H), 4.70 (br. s., 1H), 4.30-4.44 (m, 2H), 3.71 (br. s., 1H), 3.38-3.52 (m, 1H), 3.08-3.19 (m, 1H), 3.02 (br. s., 1H), 1.96 (br. s., 1H), 1.87 (br. s., 1H), 1.66-1.81 (m, 1H), 1.49-1.62 (m, 5H), 1.43 (br. s., 1H), 0.78 (br. s., 3H), 0.63 (br. s., 3H) | HRMS(A) m/z (M + H)+ 472.2362 |

TABLE 29-continued

Chemical name, NMR chemical shifts and LCMS signal for each compound listed in Table 28.

| Example: Name | $^1$H NMR (400 MHz) δ ppm | LCMS |
|---|---|---|
| 604: (S)-3-(2-((S)-1-(3-fluoro-4-(pyrrolidine-1-carbonyl)phenyl)ethylamino)pyrimidin-4-yl)-4-isopropyloxazolidin-2-one | (CD$_3$OD) 8.13 (d, J = 6.3 Hz, 1H), 7.71 (d, J = 7.0 Hz, 1H), 7.34-7.43 (m, 1H), 7.14-7.30 (m, 2H), 5.18 (br. s., 1H), 4.70 (br. s., 1H), 4.28-4.43 (m, 2H), 3.57 (t, J = 6.8 Hz, 2H), 1.93-2.07 (m, 2H), 1.83-1.93 (m, 2H), 1.58 (d, J = 7.0 Hz, 3H), 0.77 (br. s., 3H), 0.63 (br. s., 3H) | HRMS(A) m/z (M + H)+ 442.2263 |

Biological Data

Mutant IDH1 Biochemical Assay: LC-MS Detection of 2-HG.

Mutant IDH1 R132H catalytic activity was monitored using the quantitative liquid chromatography/mass spectrometry (LC-MS) detection of 2-HG, a product of the NADPH-dependent alpha-KG reduction reaction.

More specifically, the biochemical reactions were performed at room temperature in 384-well Greiner flat-bottom plates (Costar, Cat. No. 781201) using a final reaction volume of 30 µL and the following assay buffer conditions: 50 mM HEPES pH 7.4, 10 mM MgCl$_2$, 50 mM KCl, 1 mM DTT, 0.02% BSA, 5 uM NADPH and 100 uM alpha-KG.

The final reaction mixture contained 3.3% DMSO and inhibitors with concentrations ranging 0.02-50 µM. The IDH1 enzyme was used at a final concentration of 0.25 nM. Following 45 minutes incubation, the reaction mixtures were quenched by the addition of 10 µL of 16% formic acid containing 800 nM of 5-carbon labeled $^{13}$C-2-HG). The protein was then precipitated by the addition of 2.5 volumes of acetonitrile followed by centrifugation (3000×g, 20 minutes). The concentration of 2-HG in the resulting supernatants was measured by LC-MS (see below).

LC-MS method. Reaction mixture supernatants were submitted to chromatographic separation on a BiobasicAX column (2.1 mm×20 mm, 5 µm particle, Thermo Scientific Inc.). The chromatographic mobile phases were A) 25 mM ammonium biocarbonate and B) acetonitrile (0.1% ammonium hydroxide). Nicotinamide was eluted at 1 ml/min using a 85-5% B gradient over 0.9 minutes (Agilent 1200SL LC system, Thermofisher LX-4 autosampler) and analyzed by multiple reaction monitoring (MRM) on a API4000 QTrap mass spectrometer (ABSciex, Framingham, Mass.) in the positive electrospray ionization (ESI+) mode. The mass transition for 2-HG and $^{13}$C-2-HG were 147→129 and 152→134, respectively. The relative responses (2-HG/$^{13}$C-2-HG) were measured at varied inhibitor concentrations and used to calculate inhibitory IC50 values (normalized IC50 regression curves).

R132 Protein Expression and Purification.

IDH1 R132H was cloned into the pET47b vector using the restriction sites XmaI/XhoI which yields an in frame, N-terminal His$_6$ (SEQ ID NO: 3) site cleavable with Prescission protease. This plasmid was transformed into Rosetta™ 2 (DE3) (Novagen) cells. In shake flasks, 8 L of cells were grown in Terrific Broth (Teknova) (plus kanamycin 50 µg/mL and chloramphenicol 34 µg/mL) at 37° C. to an OD$_{600}$ of 0.8 and protein expression was induced by addition of IPTG to a concentration of 0.20 mM. The cells were subsequently grown for 18 hours at 18° C.

```
                                         (SEQ ID NO: 1)
His6-IDH1 (R132H) Uncut protein ("His6" disclosed
as SEQ ID NO: 3)
MAHHHHHHSAALEVLFQGPGMSKKISGGSVVEMQGDEMTRIIWELIKEK

LIFPYVELDLHSYDLGIENRDATNDQVTKDAAEAIKKHNVGVKCATITP

DEKRVEEFKLKQMWKSPNGTIRNILGGTVFREAIICKNIPRLVSGWVKP

IIIGHHAYGDQYRATDFVVPGPGKVEITYTPSDGTQKVTYLVHNFEEGG

GVAMGMYNQDKSIEDFAHSSFQMALSKGWPLYLSTKNTILKKYDGRFKD

IFQEIYDKQYKSQFEAQKIWYEHRLIDDMVAQAMKSEGGFIWACKNYD

GDVQSDSVAQGYGSLGMMTSVLVCPDGKTVEAEAAHGTVTRHYRMYQKG

QETSTNPIASIFAWTRGLAHRAKLDNNKELAFFANALEEVSIETIEAGF

MTKDLAACIKGLPNVQRSDYLNTFEFMDKLGENLKIKLAQAKL (stop)
                                         (SEQ ID NO: 2)
IDH1 (R132H) Prescission Cut Protein (N-term gpg
is cloning artifact)
GPGMSKKISGGSVVEMQGDEMTRIIWELIKEKLIFPYVELDLHSYDLGI

ENRDATNDQVTKDAAEAIKKHNVGVKCATITPDEKRVEEFKLKQMWKSP

NGTIRNILGGTVFREAIICKNIPRLVSGWVKPIIIGHHAYGDQYRATDF

VVPGPGKVEITYTPSDGTQKVTYLVHNFEEGGGVAMGMYNQDKSIEDFA

HSSFQMALSKGWPLYLSTKNTILKKYDGRFKDIFQEIYDKQYKSQFEAQ

KIWYEHRLIDDMVAQAMKSEGGFIWACKNYDGDVQSDSVAQGYGSLGMM

TSVLVCPDGKTVEAEAAHGTVTRHYRMYQKGQETSTNPIASIFAWTRGL

AHRAKLDNNKELAFFANALEEVSIETIEAGFMTKDLAACIKGLPNVQRS

DYLNTFEFMDKLGENLKIKLAQAKL (stop)
```

Purification

The cells were homogenized in Lysis Buffer with protease inhibitors (complete EDTA-free protease inhibitor tablets (Roche), 1 tablet per 50 mL of buffer), DNAse, and to 200 µM PMSF and lysed in a Microfluidizer. After lysis, Triton X-100 was added to 0.1% and stirred at 4° C. for 30 minutes.

The cleared lysate was loaded onto 2×5 mL HisTrap FF crude columns (GE), washed extensively with Lysis Buffer until the A$_{280}$ stabilized and eluted with Ni Elution Buffer. Peak eluted fractions were concentrated to 30 mL, EDTA was added to 1 mM and GST-Prescission protease was added to 3 U/100 µg of protein. The sample was dialyzed against 2 L Dialysis Buffer I (MWCO 50 kDa) for 6 hours at 4° C. then dialyzed against 2 L of Dialysis Buffer II for at least 6 more hours. GST-Prescission cleaved sample was rocked with Glutathione Agarose Beads, spun down and then the supernatant was loaded through a 5 mL HisTrap HP column and the flow through was collected.

Flow through was then diluted with ice cold 20 mM Tris pH 7.4 and 1 mM TCEP until the conductivity dropped to less than 5 mS/cm (a roughly three fold dilution). This sample was then flowed through a HiTrap Q column and the flow through was concentrated to 10 mL and loaded onto an equilibrated 26/60 Superdex 200 column using SEC Buffer as the mobile phase. Peak fractions were collected, concentrated and aliquoted.

Lysis Buffer: 50 mM Tris pH=7.4, 500 mM NaCl, 20 mM Imidazole, and 1 mM TCEP

Ni Elution Buffer: 50 mM Tris pH=7.4, 150 mM NaCl, 200 mM Imidazole, and 1 mM TCEP Dialysis Buffer I: 20 mM Tris pH=7.4, 150 mM NaCl, 1 mM TCEP, and 50 mM Imidazole Dialysis Buffer II: 20 mM Tris pH=7.4, 150 mM NaCl, and 1 mM TCEP SEC Buffer: 20 mM Tris pH=7.4, 150 mM NaCl, and 1 mM TCEP The results of the mutant IDH1 biochemical assay (mIDH R132H) are given in Table 30. Some of the examples were run in the assay multiple times and therefore the $IC_{50}$ values are expressed as a range of activity.

Fluorescence Biochemical Assay

The IDH1 (R132H) mutant catalyzes the reduced form of NADP+ (NADPH) and α-ketoglutarate (α-KG) to form nicotinamide adenine dinucleotide phosphate (NADP+) and R(−)-2-hydroxyglutarate (2HG). The reaction can be monitored kinetically by following the oxidation of NADPH to NADP+ which is measured using fluorescence, excitation at 355 nm and emission at 530 nm. Reactions were monitored using the Perkin-Elmer Envision, Model 2101. More specifically, the biochemical reactions were performed at room temperature in 384-well Greiner flat-bottom plates (Cat. No. 781076) using a final reaction volume of 20 μL and the following assay buffer conditions: 50 mM HEPES pH 7.5, 10 mM $MgCl_2$, 1 mM DTT, 0.02% BSA, 0.02% Tween-20, 10 μM NADPH and 100 μM α-KG. The final reaction mixture contained 2.5% DMSO and test compounds with concentrations ranging 0.0000008-25 μM. The IDH1 (R132H) enzyme was used at a final concentration of 10 nM. Curve fitting for dose response IC50 determinations was done in the Helios module of the software package DAVID. The 4-parameter logistic model was used: $y=min+((max-min)/1+(x/IC_{50})^{slope})$

TABLE 30

Results of the LC-MS and fluorescence biochemical assays.

| Example Number | LC-MS biochemical assay $IC_{50}$ (μM) | Fluorescence biochemical assay IC50 (μM) |
|---|---|---|
| 1 | 0.084-0.236 | |
| 2 | >50 | |
| 3 | 0.086-0.575 | 0.091-0.501 |
| 4 | 4.612 | |
| 5 | 0.410-0.600 | |
| 6 | 12.175 | |
| 7 | 2.527 | |
| 8 | 13.011 | |
| 9 | 6.444 | |
| 10 | 0.355-0.419 | |
| 11 | 0.770-4.552 | |
| 12 | 1.990-2.391 | 9.55 |
| 13 | 18.344-29.100 | |
| 14 | 2.333-2.814 | |
| 15 | 5.383 | |
| 16 | >50 | |
| 17 | 7.625 | |
| 18 | >50 | |

TABLE 30-continued

Results of the LC-MS and fluorescence biochemical assays.

| Example Number | LC-MS biochemical assay $IC_{50}$ (μM) | Fluorescence biochemical assay IC50 (μM) |
|---|---|---|
| 19 | >50 | |
| 20 | >50 | |
| 21 | 4.169 | |
| 22 | 19.671 | |
| 23 | 0.502-0.591 | |
| 24 | 3.564 | |
| 25 | 18.182->50 | |
| 26 | >50 | |
| 27 | 2.486-2.730 | |
| 28 | 4.427-4.625 | |
| 29 | 4.630-11.566 | |
| 30 | 1.072 | |
| 31 | 1.721 | |
| 32 | 9.797 | |
| 33 | 3.483 | |
| 34 | 7.588 | |
| 35 | 0.222-0.273 | |
| 36 | 17.576 | |
| 37 | 4.595 | |
| 38 | >50 | |
| 39 | 8.806 | |
| 40 | 20.34 | |
| 41 | 0.291-0.581 | |
| 42 | 0.584 | |
| 43 | 7.686 | |
| 44 | 0.125 | |
| 45 | >50 | |
| 46 | 0.234 | |
| 47 | 7.481 | |
| 48 | 2.090-2.601 | 1.91 |
| 49 | 2.803 | |
| 50 | 0.076-0.100 | |
| 51 | 19.457 | |
| 52 | 23.847 | |
| 53 | 3.852 | |
| 54 | 0.141 | |
| 55 | 3.494 | |
| 56 | 9.502 | |
| 57 | 1.393-3.153 | 7.58 |
| 58 | >50 | |
| 59 | 0.575 | |
| 60 | 0.052 | 0.094 |
| 61 | 12.729 | |
| 62 | 0.117-0.178 | |
| 63 | 0.085-0.124 | |
| 64 | 6.79 | |
| 65 | 0.25 | |
| 66 | 0.073 | |
| 67 | 5.342 | |
| 68 | 6.302 | |
| 69 | 0.127-0.390 | |
| 70 | 0.195-0.230 | |
| 71 | 20.503 | |
| 72 | 37.361 | |
| 73 | 0.316 | |
| 74 | 2.569 | |
| 75 | 1.338 | 4.27 |
| 76 | 8.008 | |
| 77 | 11.26 | |
| 78 | 28.611 | |
| 79 | 0.09 | |
| 80 | 0.679 | |
| 81 | 0.103 | |
| 82 | 0.163-0.217 | |
| 83 | 0.238-0.462 | |
| 84 | 0.075 | |
| 85 | 1.061 | 17.9 |
| 86 | 9.767 | |
| 87 | 0.126 | 0.245 |
| 88 | 0.148-0.344 | |
| 89 | 0.203 | 0.308 |
| 90 | 0.272 | 0.275 |
| 91 | 2.875 | |
| 92 | 0.211-0.544 | 0.598 |

TABLE 30-continued

Results of the LC-MS and fluorescence biochemical assays.

| Example Number | LC-MS biochemical assay IC$_{50}$ (μM) | Fluorescence biochemical assay IC50 (μM) |
|---|---|---|
| 93 | 0.405-0.905 | |
| 94 | 4.487 | |
| 95 | 0.655 | 0.571 |
| 96 | >50 | |
| 97 | 0.195 | 0.166 |
| 98 | 0.628 | |
| 99 | 0.184 | |
| 100 | 0.169 | |
| 101 | 2.382 | |
| 102 | 0.401 | |
| 103 | 3.184 | |
| 104 | 0.207 | |
| 105 | 0.352 | 0.352 |
| 106 | 1.918 | |
| 107 | 3.445 | |
| 108 | >50 | |
| 109 | 0.542 | 0.939 |
| 110 | 0.188 | 0.284 |
| 111 | 0.125 | |
| 112 | 7.768 | |
| 113 | 1.925 | |
| 114 | 0.697 | 1.14 |
| 115 | 0.092 | 0.126 |
| 116 | 2.038 | |
| 117 | 0.163-0.217 | |
| 118 | 1.302-2.152 | |
| 119 | 0.117 | 0.149 |
| 120 | 0.258-0.847 | |
| 121 | 0.081-0.448 | |
| 122 | 0.157-0.379 | |
| 123 | 0.112 | 0.162 |
| 124 | 0.081-0.298 | 0.791 |
| 125 | 1.012 | |
| 126 | 0.118 | |
| 127 | 0.158 | 0.215 |
| 128 | 0.565 | |
| 129 | 0.467 | |
| 130 | 0.549-0.615 | |
| 131 | 14.319 | |
| 132 | 31.016 | |
| 133 | 7.115 | |
| 134 | 3.102 | |
| 135 | 11.6 | |
| 136 | 6.455 | |
| 137 | 3.14 | |
| 138 | 1.061 | |
| 139 | 1.252 | 2.5 |
| 140 | 0.089 | 0.114-0.181 |
| 141 | 0.095 | |
| 142 | 0.390-0.512 | |
| 143 | >50 | |
| 144 | >50 | |
| 145 | 6.807 | |
| 146 | 11.362 | |
| 147 | 6.445 | |
| 148 | 3.544 | |
| 149 | 0.647 | |
| 150 | 0.53 | 0.538 |
| 151 | 1.363 | |
| 152 | 0.385 | 0.598 |
| 153 | 0.759 | 0.582 |
| 154 | 0.049 | 0.091 |
| 155 | 0.04 | |
| 156 | 0.232 | 0.248 |
| 157 | >50 | |
| 158 | 0.873 | 1.41 |
| 159 | 0.287 | |
| 160 | 6.078 | |
| 161 | 6.502 | |
| 162 | 0.009-0.035 | 0.020-0.043 |
| 163 | 0.149 | |
| 164 | 0.067 | 0.0339 |
| 165 | 0.183 | 0.143 |
| 166 | 0.637 | 1.56 |
| 167 | 0.254 | |
| 168 | 0.102 | |
| 169 | 0.195 | |
| 170 | 1.083 | |
| 171 | 6.161 | |
| 172 | 0.245-0.274 | |
| 173 | 2.908 | |
| 174 | 0.056-0.118 | 0.283 |
| 175 | 8.156 | |
| 176 | 0.125 | 0.138 |
| 177 | 4.333 | |
| 178 | 0.097 | 0.0687 |
| 179 | 5.973 | |
| 180 | 0.194 | |
| 181 | 10.232 | |
| 182 | 0.309-0.370 | |
| 183 | 36.818 | |
| 184 | 0.696 | |
| 185 | 6.066 | |
| 186 | 0.04 | |
| 187 | 3.899 | |
| 188 | 0.089 | 0.17 |
| 189 | 0.117 | |
| 190 | 2.134 | |
| 191 | 6.969 | |
| 192 | 0.221 | 0.294 |
| 193 | 0.097 | |
| 194 | 4.333 | |
| 195 | 5.748 | |
| 196 | 0.083 | |
| 197 | 15.05 | |
| 198 | 0.173 | 0.179 |
| 199 | 2.435 | |
| 200 | 0.08 | 0.0665 |
| 201 | 0.927 | |
| 202 | 0.025 | 0.0541 |
| 203 | 1.856 | |
| 204 | 0.062 | 0.0955 |
| 205 | 0.199 | 0.219 |
| 206 | 1.458 | 0.81 |
| 207 | 0.069 | 0.0169 |
| 208 | 0.085 | 0.108-0.183 |
| 209 | 0.088 | 0.0881 |
| 210 | 0.576 | 0.343 |
| 211 | | 0.439 |
| 212 | 0.132 | 0.024 |
| 213 | 2.913 | |
| 214 | 0.298 | 0.791 |
| 215 | 0.390 | 0.419 |
| 216 | 0.031 | 0.0206 |
| 217 | 0.177-0.206 | 0.079-0.146 |
| 218 | 1.373 | 0.625 |
| 219 | 0.613 | |
| 220 | 0.529 | 0.247 |
| 221 | 0.098 | 0.0476 |
| 222 | 0.505 | 0.296 |
| 223 | 0.293 | 0.14 |
| 224 | <0.022 | 0.0166 |
| 225 | 0.026 | 0.0173 |
| 226 | 0.114 | 0.0832 |
| 227 | 0.065 | 0.0339 |
| 228 | 0.067 | 0.0463 |
| 229 | 0.113 | 0.0662 |
| 230 | 0.072 | 0.0415 |
| 231 | 0.327 | 0.242 |
| 232 | 0.251 | 0.755 |
| 233 | 0.147 | 0.0684 |
| 234 | >50 | >25 |
| 235 | 0.039 | 0.0141 |
| 236 | 0.372 | 0.338 |
| 237 | 0.877 | 0.219 |
| 238 | | 9.8 |
| 239 | 0.038 | 0.073 |
| 240 | 0.030 | 0.0506 |

TABLE 30-continued

Results of the LC-MS and fluorescence biochemical assays.

| Example Number | LC-MS biochemical assay IC$_{50}$(μM) | Fluorescence biochemical assay IC50 (μM) |
|---|---|---|
| 241 | 0.155 | 0.213 |
| 242 | 0.048 | 0.242 |
| 243 | 0.260-0.914 | 1.21-1.6 |
| 244 | 0.863 | 0.774 |
| 245 | 0.184 | 0.103 |
| 246 | 0.497-0.589 | 0.236-0.316 |
| 247 | 1.373 | 1.79 |
| 248 | 0.687 | 0.842 |
| 249 | 0.585 | 0.616 |
| 250 | 0.031 | 0.0468 |
| 251 | 0.064 | 0.0878 |
| 252 | 0.033 | 0.0608 |
| 253 | | 0.559 |
| 254 | 0.656 | 1.12 |
| 255 | 10.369 | |
| 256 | 0.197 | |
| 257 | 0.242-0.282 | 0.221-0.27 |
| 258 | 0.378 | |
| 259 | 2.569 | |
| 260 | 0.186 | |
| 261 | 0.040 | 0.0639 |
| 262 | 0.058 | 0.0991 |
| 263 | | 0.679 |
| 264 | 0.108 | |
| 265 | <0.022 | 0.0232 |
| 266 | 0.152 | |
| 267 | 3.308 | |
| 268 | 20.567 | |
| 269 | 0.467 | |
| 270 | 0.463 | |
| 271 | 0.100 | 0.108 |
| 272 | 1.717 | 2.28 |
| 273 | 0.202 | 0.143 |
| 274 | 0.104 | 0.0524 |
| 275 | 0.261 | 0.273 |
| 276 | 0.298 | 0.175 |
| 277 | 0.094 | 0.0899 |
| 278 | 0.241 | 0.29 |
| 279 | 0.312 | |
| 280 | 7.823 | |
| 281 | <0.022 | |
| 282 | 0.180 | |
| 283 | 0.538 | 0.635 |
| 284 | 2.023 | 1.38 |
| 285 | 0.390 | 0.375 |
| 286 | 1.807 | 2.54 |
| 287 | 34.794 | >25 |
| 288 | 0.053 | 0.269 |
| 289 | 0.316 | 0.19 |
| 290 | 2.222 | 0.414-0.975 |
| 291 | | 4.64 |
| 292 | 0.049 | 0.0645 |
| 293 | 2.696 | |
| 294 | 0.095 | 0.648 |
| 295 | 0.342 | 0.252 |
| 296 | 0.085 | |
| 297 | | 0.848 |
| 298 | 0.188 | 1.04 |
| 299 | 4.052 | 10.4 |
| 300 | 1.639 | 1.84 |
| 301 | | 0.0887 |
| 302 | 0.131 | |
| 303 | | 0.326 |
| 304 | 2.107 | |
| 305 | 0.065 | 0.0413 |
| 306 | 4.043 | 12.5 |
| 307 | | 0.225 |
| 308 | 0.259 | 0.703 |
| 309 | 0.868 | 1.66 |
| 310 | 36.281 | >25 |
| 311 | 4.139 | |
| 312 | 0.051 | 0.024 |
| 313 | 0.073 | 0.0799 |
| 314 | 1.311 | 1.59 |
| 315 | 5.916 | |
| 316 | 0.131 | |
| 317 | 0.050 | |
| 318 | 5.007 | |
| 319 | 0.705 | |
| 320 | 2.410 | |
| 321 | 1.214 | |
| 322 | 0.026 | 0.0666 |
| 323 | | 17.1 |
| 324 | | 0.483 |
| 325 | 15.718 | 18.5-21.4 |
| 326 | 0.115 | 0.268-0.369 |
| 327 | | 19.2 |
| 328 | 0.329-1.144 | 0.558-0.843 |
| 329 | 2.164 | 5.62 |
| 330 | 0.026 | 0.0545 |
| 331 | 6.083 | 7.65 |
| 332 | 0.052-0.072 | 0.0693 |
| 333 | 0.128 | 0.335 |
| 334 | 0.646 | |
| 335 | | 6.53 |
| 336 | | 0.236 |
| 337 | | 7.22 |
| 338 | 0.148 | 0.145 |
| 339 | 3.101 | 4.4 |
| 340 | <0.022 | 0.0276 |
| 341 | | 2.13 |
| 342 | 0.029 | 0.0278 |
| 343 | | 4.08 |
| 344 | | 0.265 |
| 345 | >50 | |
| 346 | 32.256 | |
| 347 | >50 | |
| 348 | >50 | |
| 349 | 4.010 | 24.2 |
| 350 | 0.583 | 0.731 |
| 351 | >50 | |
| 352 | >50 | |
| 353 | >50 | |
| 354 | >50 | |
| 355 | 33.589 | >25 |
| 356 | 1.642 | 4.53 |
| 357 | 13.229 | |
| 358 | 0.864 | 1.53 |
| 359 | >50 | >25 |
| 360 | 3.035 | 4.37-11.9 |
| 361 | 0.781 | 0.736 |
| 362 | 0.063 | 0.0621 |
| 363 | 14.441 | 23.3 |
| 364 | 0.964 | 1.06 |
| 365 | >50 | >25 |
| 366 | 2.602 | 20.2-21.7 |
| 367 | 20.809 | >25 |
| 368 | 0.706 | 0.862 |
| 369 | >50 | >25 |
| 370 | 6.649 | 3.01 |
| 371 | 25.036 | >25 |
| 372 | | 4.19 |
| 373 | 39.696 | >25 |
| 374 | 1.617 | 1.89-2.42 |
| 375 | >50 | >25 |
| 376 | 2.321 | 3.27-4.33 |
| 377 | | >25 |
| 378 | | 4.19 |
| 379 | | >25 |
| 380 | | 0.839 |
| 381 | | 20 |
| 382 | 0.203 | 0.349 |
| 383 | | 5.16 |
| 384 | 0.068 | 0.107 |
| 385 | | 22.5 |
| 386 | | 4.74 |
| 387 | | 20.6 |
| 388 | | 4.37 |

TABLE 30-continued

Results of the LC-MS and fluorescence biochemical assays.

| Example Number | LC-MS biochemical assay IC$_{50}$(μM) | Fluorescence biochemical assay IC50 (μM) |
|---|---|---|
| 389 | | 1.83 |
| 390 | 0.140 | 0.213 |
| 391 | | 2.35-5.33 |
| 392 | 0.694 | 0.355-0.697 |
| 393 | | 12.1 |
| 394 | 0.268 | 0.34 |
| 395 | | 9.36 |
| 396 | 0.189 | 0.224 |
| 397 | | 7.14 |
| 398 | 0.094-0.123 | 0.189 |
| 399 | | >25 |
| 400 | | 0.648 |
| 401 | | 19 |
| 402 | 0.362 | 0.39 |
| 403 | | >25 |
| 404 | | 0.964 |
| 405 | | 21.1 |
| 406 | | 1.82 |
| 407 | | 6.39 |
| 408 | 0.237 | 0.349 |
| 409 | | 1.35 |
| 410 | 0.340-0.440 | 0.098-0.521 |
| 411 | 2.907 | |
| 412 | 0.190 | |
| 413 | 21.616 | |
| 414 | 6.026-7.675 | 5.47-8.32 |
| 415 | 26.674 | |
| 416 | 1.592 | |
| 417 | 20.287 | |
| 418 | 0.808 | |
| 419 | 2.833 | |
| 420 | >50 | |
| 421 | 27.999 | >25 |
| 422 | 2.136 | 3.81 |
| 423 | 7.595 | 14.8 |
| 424 | 0.162 | 0.491-0.747 |
| 425 | 0.909 | 2.45 |
| 426 | <0.022-0.038 | 0.019-0.058 |
| 427 | 1.229 | 2.09 |
| 428 | >50 | >25 |
| 429 | 6.407 | 9.78 |
| 430 | 0.133 | 0.0908 |
| 431 | 0.568 | 0.811 |
| 432 | 0.040 | 0.0448 |
| 433 | 6.675 | 5.31 |
| 434 | 0.153 | 2.19-3.96 |
| 435 | | >25 |
| 436 | 0.291 | 0.364-0.373 |
| 437 | | 2.69-3.18 |
| 438 | | >25 |
| 439 | | 6.155 |
| 440 | 0.125 | 0.105-0.122 |
| 441 | 4.229 | 1.63-10.6 |
| 442 | 0.136 | 0.225 |
| 443 | 0.063-0.077 | 0.0414 |
| 444 | 0.040 | 0.0266 |
| 445 | 2.526 | 2.46 |
| 446 | 0.079-0.081 | 0.039 |
| 447 | 3.876 | |
| 448 | 0.034 | 0.0373 |
| 449 | | 5.43 |
| 450 | 0.062 | 0.0518 |
| 451 | 0.207 | 0.386 |
| 452 | 0.063-0.065 | 0.134 |
| 453 | 11.400 | 14.5 |
| 454 | 0.401 | 0.601 |
| 455 | 6.218 | >25 |
| 456 | 0.082 | 0.041 |
| 457 | <0.022 | 0.013 |
| 458 | 0.069 | 0.0588 |
| 459 | 0.991 | 1.16 |
| 460 | | |
| 461 | 2.275 | |
| 462 | 1.924 | 2.87 |
| 463 | >50 | |
| 464 | <0.022 | 0.020-0.055 |
| 465 | | 0.164 |
| 466 | 0.665 | 0.821 |
| 467 | | 9.82 |
| 468 | | 3.03-11.8 |
| 469 | 0.077 | 0.185-0.198 |
| 470 | 0.075 | 0.172 |
| 471 | 0.925 | 0.78 |
| 472 | | 14.8 |
| 473 | | 0.0986 |
| 474 | | 7.1 |
| 475 | 0.341 | 0.355 |
| 476 | >50 | |
| 477 | >50 | |
| 478 | >50 | |
| 479 | >50 | |
| 480 | >50 | |
| 481 | 0.780 | 2.52 |
| 482 | >50 | >25 |
| 483 | 0.096 | 0.202 |
| 484 | 5.160 | 21.3 |
| 485 | | 2.12 |
| 486 | | 0.873 |
| 487 | | 1 |
| 488 | 0.311 | 0.437 |
| 489 | | 4.15 |
| 490 | | 2.61 |
| 491 | | 0.821 |
| 492 | | 0.249 |
| 493 | 0.067 | 0.139 |
| 494 | 1.649 | 0.595 |
| 495 | 0.712 | 0.734 |
| 496 | 0.751 | 0.723 |
| 497 | | 1.13 |
| 498 | | 5.27 |
| 499 | | 2.39 |
| 500 | | 1.45 |
| 501 | | 0.494 |
| 502 | | 0.305 |
| 503 | 0.546 | 0.96 |
| 504 | 0.268 | 0.243 |
| 505 | | 0.275 |
| 506 | | 0.46 |
| 507 | | 0.0773 |
| 508 | 0.553 | 0.484 |
| 509 | 0.553 | 0.484 |
| 510 | | 0.0294 |
| 511 | 0.062 | |
| 512 | 0.450 | 0.38 |
| 513 | | 0.0336 |
| 514 | | |
| 515 | | 0.0287 |
| 516 | 0.082 | 0.0592 |
| 517 | | 1.58 |
| 518 | | 0.0785 |
| 519 | 0.123 | 0.363 |
| 520 | 0.080 | 0.053-0.321 |
| 521 | | 0.23 |
| 522 | | 0.745 |
| 523 | | 0.165 |
| 524 | 0.026 | 0.0211 |
| 525 | 0.085 | 0.108-0.183 |
| 526 | 0.088 | 0.0427 |
| 527 | | 0.0851 |
| 528 | 0.077 | 0.0613 |
| 529 | 0.117 | 0.0622 |
| 530 | <0.022 | 0.00835 |
| 531 | | 0.00812 |
| 532 | | 0.0727 |
| 533 | 0.307 | 0.227 |
| 534 | 0.188 | 0.331 |
| 535 | | 0.183 |
| 536 | | 0.104 |

TABLE 30-continued

Results of the LC-MS and fluorescence biochemical assays.

| Example Number | LC-MS biochemical assay IC$_{50}$(µM) | Fluorescence biochemical assay IC50 (µM) |
|---|---|---|
| 537 | 0.400 | 0.257 |
| 538 | 0.416 | 0.268 |
| 539 |  | 2.66 |
| 540 | 0.878 | 0.573 |
| 541 | 0.266 | 0.0899 |
| 542 | 0.090 | 0.0877 |
| 543 |  | >25 |
| 544 | 0.075 | 0.0477 |
| 545 |  | 0.0943 |
| 546 | 0.059 | 0.0423 |
| 547 | 0.158 | 0.146 |
| 548 | 0.184 |  |
| 549 | 1.840 |  |
| 550 | 0.791 | 0.276 |
| 552 | <0.022 | 0.0199 |
| 553 | 0.521 | 0.41 |
| 554 | 0.075 | 0.217 |
| 555 | <0.022 |  |
| 556 | <0.072 |  |
| 557 | 0.246 | 0.237 |
| 558 |  | 0.283 |
| 559 |  | 17.6 |
| 560 |  | 25 |
| 561 |  | 0.552 |
| 562 |  | 0.364 |
| 563 |  | 0.04 |
| 564 |  | 0.0501 |
| 565 |  | 0.309 |
| 566 | 0.135 | 0.13 |
| 567 |  | 5.41 |
| 568 | 0.086-0.141 | 0.067-0.161 |
| 569 |  | 0.0575 |
| 570 |  | 0.0446 |
| 571 |  | 0.0742 |
| 572 |  | 0.0781 |
| 573 |  | 0.00786 |
| 574 | 0.204 | 0.324 |
| 575 |  | 1.91 |
| 576 |  | 2.37 |
| 577 |  | 1.65 |
| 578 |  | 1.07 |
| 579 | 0.911 | 0.591 |
| 580 | 0.153 | 0.193 |
| 581 | 0.260 | 0.432 |
| 582 |  | 0.204 |
| 583 |  | >25 |
| 584 |  | 10.6 |
| 585 |  | 6.7 |
| 586 | 2.797 | 1.02 |
| 587 |  | 1.95 |
| 588 | 0.764 | 0.85 |
| 589 |  | 2.92 |
| 590 | <0.022 | 0.006-0.009 |
| 591 | <0.022 | 0.018 |
| 592 | 0.138 | 0.077 |
| 593 | 0.077 | 0.036 |
| 594 | 0.257 | 0.178 |
| 595 | 0.121 | 0.053 |
| 596 | 0.161 | 0.154 |
| 597 | 0.457 | 0.741 |
| 598 | 0.519 | 0.715 |
| 599 | 0.155 | 0.265 |
| 600 | 0.488 | 0.729 |
| 601 | 0.042 | 0.042 |
| 602 | 0.049 | 0.034 |
| 603 | 0.244 | 0.336 |
| 604 | 0.112 | 0.161 |

IDH Cellular Assay

The IDH cellular assay consists of two side-by-side comparator assays: 1) 2HG oncometabolite detection assay using LC-MS (See Mutant IDH1 biochemical assay for LC-MS detection details) and 2) Cell proliferation assay to monitor off-target killing of cells and to normalize 2HG level change. IDH1 cellular screens were run with the HCT-116 cell line (express endogenous level of IDH1mut R132H, available from Horizon Discoveries X-Man isogenic human cell lines, catalog # HD104-013). The cells were grown in DMEM (LONZA Cat#12-540F) with 10% Fetal bovine serum (Gibco cat #10099) and 1× non-essential amino acids (NEAA LONZA cat #13-114E). Panel assays were run periodically to test compound activity in cell lines with different endogenous mutations—HT1080 (IDH1mut R132C, EMEM+10% FBS), SNU-1079 (IDH1mut R132C, RPMI+10% FBS+1% sodium pyruvate), and SW1353 (IDH2mut R172S, RPMI+10% FBS+1% sodium pyruvate).

The assay process is as follows:

Day 1: cells were seeded in 384-well plates (Corning Cat#3707) in triplicates for both the cell proliferation and 2HG assay, and incubated at 37 C, 95% Rh, 5% CO2 overnight.

Day 2: compounds were serially diluted 1:3 (10 point dilution from 10 mM solutions in DMSO) and delivered to the cell assay plates via acoustic dispenser, with final concentration ranging from 30 uM to 1.5 nM. The plates were returned to the incubator after treatment and incubated for 48 hours.

Day 4 Proliferation assay: CTG (cell titer-glo, Promega part # G755B) was added to the assay plates and luminescence signal was read on the plate reader.

Day 4 2HG assay: Extraction sample preparation consisted of aspirating all media from the assay plates, adding 70 ul of 90% methanol in water, dry ice incubation for 15 minutes, centrifuging at 2000 rpm for 30 min to ensure all particulates have settled, and transferring 30 ul of the supernatant into LC-MS ready plates. LC-MS analysis follows.

Certain compounds of the invention have been tested in the IDH Cellular Assay.

What is claimed is:

1. A compound of formula (I)

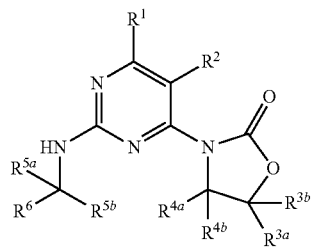

wherein:
$R^1$ and $R^2$ are each independently hydrogen, deuterium, halo, hydroxyl, $NH_2$, aryl, heteroaryl, or optionally substituted $C_{1-4}$ alkyl,
  wherein said $C_{1-4}$ alkyl is optionally substituted with one to three substituents each independently selected from the group consisting of: halo, hydroxyl, and $NH_2$;
$R^{3a}$ is hydrogen, deuterium, $C_{1-6}$ alkyl, phenyl, or benzyl and
$R^{3b}$ is hydrogen, deuterium, or $C_{1-6}$ alkyl; or
$R^{3a}$ and $R^{3b}$ are joined together forming an optionally substituted 3-7 membered cycloalkyl ring or an optionally substituted 4-7 membered heterocyclic ring,
  wherein said cycloalkyl and heterocyclic rings are each optionally substituted with one or two substituents each independently selected from the group consisting of: halo, hydroxyl, oxo, $NH_2$, and $C_{1-3}$ alkyl;
$R^{4a}$ is hydrogen, $C_{1-6}$ alkyl, optionally substituted phenyl, optionally substituted benzyl, optionally substituted heteroaryl, or methylene-dibenzene,
  wherein said phenyl, benzyl, and heteroaryl rings are optionally substituted with one to three substituents each independently selected from the group consisting of: halo, hydroxyl, cyano, nitro, $C_{1-4}$ alkoxy, $C_{1-3}$ haloalkyl, $C_{1-3}$ haloalkoxy, $C_{1-6}$ alkyl, $C_{3-6}$ cycloalkyl, phenyl, 5-6 membered heteroaryl, 5-6 membered heterocyclic, phenoxy, —$COOR^b$, —$SO_2R^b$, —$NHC(O)R^b$, and —$NR^bR^b$ and
$R^{4b}$ is hydrogen, deuterium, or $C_{1-3}$ alkyl; or
$R^{4a}$ and $R^{4b}$ are joined together forming an optionally substituted 3-7 membered cycloalkyl ring or an optionally substituted 4-7 membered heterocyclic ring,
  wherein said cycloalkyl and heterocyclic rings are optionally substituted with one or two substituents each independently selected from the group consisting of: halo, hydroxyl, oxo, $NH_2$, and $C_{1-3}$ alkyl,
  provided that only one of $R^{3a}$ and $R^{3b}$ and $R^{4a}$ and $R^{4b}$ are joined together forming a ring;
$R^{5a}$ is hydrogen or deuterium;
$R^{5b}$ is hydrogen, deuterium, methyl, ethyl, $CD_3$, $CF_3$, $CH_2F$, or $CHF_2$ and
$R^6$ is optionally substituted $C_{1-6}$ alkyl, optionally substituted aryl, optionally substituted heteroaryl, optionally substituted heterocyclic, or optionally substituted $C_{3-10}$ cycloalkyl,
  wherein said $C_{1-6}$ alkyl is optionally substituted with one substituent selected from the group consisting of hydroxyl, $C_{1-3}$ alkoxy and –$OR^a$,
  wherein said aryl, heteroaryl, heterocyclic and $C_{3-10}$ cycloalkyl are optionally substituted with one to three substituents each independently selected from the group consisting of: halo; hydroxyl; cyano; nitro; $C_{1-4}$ alkoxy; $C_{1-3}$ haloalkyl; $C_{1-3}$ haloalkoxy; $C_{1-6}$ alkyl; $C_{3-6}$ cycloalkyl optionally substituted with one to three substituents each independently selected from the group consisting of: hydroxyl, cyano, $C_{1-3}$ alkyl, $C_{1-3}$ alkoxy, and $C_{1-3}$ haloalkyl; phenyl optionally substituted with one to three substituents each independently selected from the group consisting of: halo, hydroxyl, cyano, nitro, $C_{1-3}$ alkoxy, $C_{1-3}$ haloalkyl, $C_{1-3}$ haloalkoxy, $C_{1-6}$ alkyl, $C_{3-6}$ cycloalkyl, 5-6 membered heteroaryl, 5-6 membered heterocyclic, phenoxy, —$COOR^b$, —$SO_2R^b$, —$NHC(O)R^b$, and $NR^bR^b$; 5-6 membered heteroaryl optionally substituted with one to three substituents each independently selected from the group consisting of: halo, hydroxyl, cyano, $C_{1-3}$ alkyl, $C_{1-3}$ alkoxy; 5-6 membered heterocyclic optionally substituted with one to three substituents each independently selected from the group consisting of: halo, hydroxyl, oxo, $NH_2$, and $C_{1-3}$ alkyl; —$CH_2R^a$; —$OR^a$; —$C(O)R^a$; —$NR^aR^b$; —$COOR^a$; —$SO_2R^a$; —$SO_2R^b$; —$NHC(O)R^a$; —$NHC(O)R^b$; —$C(O)NR^aR^b$; —$C(O)NHR^b$; and —$SO_2NR^bR^b$; or $R^{5b}$ and $R^6$ are joined together forming an optionally substituted $C_{3-7}$ cycloalkyl group or an optionally substituted group of formula (a):

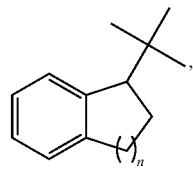

wherein n is 1, 2, or 3 and said $C_{3-7}$ cycloalkyl and group of formula (a) are optionally substituted with one to three substituents each independently selected from the group consisting of: halo, hydroxyl, cyano, nitro, $C_{1-3}$ alkoxy, $C_{1-3}$ haloalkyl, $C_{1-3}$ haloalkoxy, $C_{1-6}$ alkyl, $C_{3-6}$ cycloalkyl, 5-6 membered heteroaryl, 5-6 membered heterocyclic, benzyloxy, —$COOR^b$, —$SO_2R^b$, —$NHC(O)R^b$, and —$NR^bR^b$;

each $R^a$ is independently optionally substituted phenyl, optionally substituted heteroaryl, optionally substituted heterocyclic, or optionally substituted $C_{3-7}$ cycloalkyl, wherein said phenyl and heteroaryl are optionally substituted with one to three substituents each independently selected from the group consisting of halo, hydroxyl, cyano, nitro, $C_{1-3}$ alkoxy, $C_{1-3}$ haloalkyl, $C_{1-3}$ haloalkoxy, and $C_{1-3}$ alkyl, wherein said heterocyclic is optionally substituted with one to three substituents each independently selected from the group consisting of halo, hydroxyl, oxo, $C_{1-3}$ alkoxy, $C_{1-3}$ haloalkyl, $C_{1-3}$ haloalkoxy, $C_{1-4}$ alkyl, $C_{3-5}$ cycloalkyl, —$C(O)R^b$, and —$NR^bR^b$, and wherein said $C_{3-7}$ cycloalkyl is optionally substituted with one to three substituents each independently selected from the group consisting of halo, hydroxyl, oxo, $C_{1-3}$ alkoxy, $C_{1-3}$ haloalkyl, $C_{1-3}$ haloalkoxy, and $C_{1-3}$ alkyl; and each $R^b$ is independently hydrogen or $C_{1-6}$ alkyl; or a pharmaceutically acceptable salt thereof.

2. The compound according to claim 1 of the formula (III)

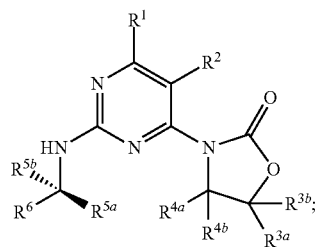

or a pharmaceutically acceptable salt thereof.

3. The compound according to claim 2 of the formula (IV)

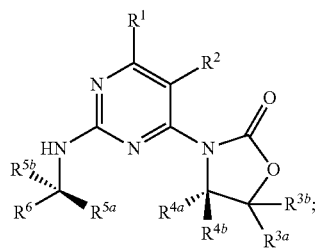

or a pharmaceutically acceptable salt thereof.

4. The compound according to claim 3 wherein $R^{3a}$ and $R^{3b}$ are both hydrogen; or a pharmaceutically acceptable salt thereof.

5. The compound according to claim 4 wherein $R^{5a}$ is hydrogen and $R^{5b}$ is hydrogen, methyl, ethyl, or $CF_3$; or a pharmaceutically acceptable salt thereof.

6. The compound according to claim 5 wherein $R^{5b}$ is methyl; or a pharmaceutically acceptable salt thereof.

7. The compound according to claim 6 wherein $R^1$ is hydrogen, fluoro or chloro and $R^2$ is hydrogen, fluoro, chloro, or methyl; or a pharmaceutically acceptable salt thereof.

8. The compound according to claim 7 wherein $R^1$ and $R^2$ are both hydrogen; or a pharmaceutically acceptable salt thereof.

9. The compound according to claim 8 wherein $R^{4a}$ is hydrogen, $C_{1-6}$ alkyl, optionally substituted phenyl, optionally substituted benzyl, optionally substituted heteroaryl, or methylene-dibenzene, wherein said phenyl, benzyl, and heteroaryl rings are optionally substituted with one to three substituents each independently selected from the group consisting of: halo, hydroxyl, cyano, nitro, $C_{1-3}$ alkoxy, $C_{1-3}$ haloalkyl, $C_{1-3}$ haloalkoxy, $C_{1-6}$ alkyl, $C_{3-6}$ cycloalkyl, 5-6 membered heteroaryl, 5-6 membered heterocyclic, phenoxy, —$COOR^b$, —$SO_2R^b$, —$NHC(O)R^b$, and —$NR^bR^b$ and $R^{4b}$ is hydrogen or $C_{1-3}$ alkyl; or a pharmaceutically acceptable salt thereof.

10. The compound according to claim 9 wherein $R^{4b}$ is hydrogen or methyl; or a pharmaceutically acceptable salt thereof.

11. The compound according to claim 10 wherein $R^{4b}$ is hydrogen; or a pharmaceutically acceptable salt thereof.

12. The compound according to claim 11 $R^{4a}$ is hydrogen, methyl, ethyl, isopropyl, phenyl, 4-fluorophenyl, 4-methoxyphenyl, biphenyl, benzyl, or pyridinyl; or a pharmaceutically acceptable salt thereof.

13. The compound according to claim 12 wherein $R^{4a}$ is isopropyl; or a pharmaceutically acceptable salt thereof.

14. The compound according to claim 1 wherein $R^6$ is methyl, $C_{5-10}$ cycloalkyl, optionally substituted phenyl, optionally substituted pyridinyl, optionally substituted pyrimidinyl, optionally substituted pyridazinyl, optionally substituted pyrazinyl, optionally substituted triazolyl, optionally substituted pyrazolyl, optionally substituted thiazolyl, optionally substituted 1,3,4-oxadiazolyl, optionally substituted 1,2,4-oxadiazolyl, optionally substituted isoxazolyl, thienyl, oxazolyl, quinolinyl, optionally substituted benzimidazolyl, benzthiazolyl, benzoxazolyl, tetrazolo[1,5-a]pyridinyl, imidazo[2,1-b][1,3,4]thiadiazolyl, optionally substituted piperidinyl, optionally substituted piperazinyl, tetrahydrofuranyl, tetrahydropyranyl, optionally substituted tetrahydrothiopyran1,1-dioxide, 1H-pyrrolo[2,3-b]pyridinyl, 2,3-dihydro-benzo[1,4]dioxinyl, 5,6,7,8-tetrahydro-[1,2,4]trazolo[4,3-a]pyrazinyl, 4,5,6,7-tetrahydro-benzothiazolyl, indolizinyl, cyclopropyl, cyclopentyl, or cyclohexyl, wherein said phenyl, pyridinyl, pyrimidinyl, pyridazinyl, pyrazinyl, triazolyl, pyrazolyl, thiazolyl, 1,3,4-oxadiazolyl, 1,2,4-oxadiazolyl, isoxazolyl, benzimidazolyl, piperidinyl, piperazinyl, and tetrahydro-thiopyran1,1-dioxide are each optionally substituted with one or two substituents as defined in formula (I).

15. The compound according to claim 14 wherein $R^6$ is optionally substituted with one or two substituents each independently selected from the group consisting of: halo; hydroxy; nitro; $C_{1-4}$ alkoxy; $C_{1-3}$ haloalkyl; $C_{1-3}$ haloalkoxy; $C_{1-6}$ alkyl; $C_{3-6}$ cycloalkyl optionally substituted with one substituent selected from the group consisting of: cyano, $C_{1-3}$ alkyl, and $C_{1-3}$ alkoxy; phenyl optionally substituted with one or two substituents each independently selected from the group consisting of: fluoro, chloro, methyl, cyano, and methoxy; and 5-6 membered heteroaryl optionally substituted with one or two methyl groups; or a pharmaceutically acceptable salt thereof.

16. The compound according to claim 15 wherein $R^6$ is optionally substituted 1,3,4-oxadiazolyl or optionally substituted 1,2,4-oxadiazolyl; or a pharmaceutically acceptable salt thereof.

17. The compound according to claim 14 wherein $R^6$ is substituted with one —$CH_2R^a$, —$C(O)R^a$, —$NHC(O)R^a$, —$NHC(O)R^b$, —$C(O)NHR^a$, $C(O)NHR^b$, —$OR^a$, —$NR^aR^b$, —$SO_2NR^bR^b$, —$SO_2R^a$, or —$SO_2R^b$ group; or a pharmaceutically acceptable salt thereof.

18. The compound according to claim 17 wherein Ra is
    (a) phenyl optionally substituted with one or two substituents each independently selected from the group consisting of fluoro, chloro and bromo;
    (b) optionally substituted 5-6 membered heteroaryl;
    (c) $C_{5-7}$ cycloalkyl optionally substituted with one or two substituents each independently selected from the group consisting of fluoro, hydroxy, methyl, and $C_{1-3}$ haloalkoxy; or
    (d) a heterocyclic group selected from the group consisting of: piperidinyl, piperazinyl, morpholinyl, tetrahydropyranyl, tetrahydro-thiopyran1,1-dioxide, 1,4-diazepanyl, 4,7-diaza-spiro[2.5]octanyl, 3,8-diaza-bicyclo[3.2.1]octanyl, 3,8-diaza-bicyclo[4.2.0]octanyl, octahydro-pyrrolo[1,2-a]pyrazinyl, octahydro-pyrido[1,2-a]pyrazinyl, octahydro-pyrrolo[3,4-c]pyrrolyl, and 5,6,7,8-tetrahydro-imidazo[1,2-a]pyrazinyl each of which is optionally substituted with one to three substituents each independently selected from the group consisting of: hydroxy, fluoro, amino, dimethylamino, $C_{1-3}$ haloalkoxy, $C_{1-3}$ alkyl, and $C_{3-5}$ cycloalkyl; or a pharmaceutically acceptable salt thereof.

19. The compound according to claim 18 wherein $R^6$ is optionally substituted phenyl; or a pharmaceutically acceptable salt thereof.

20. The compound according to claim 19 wherein the phenyl is substituted with one —$CH_2R^a$, —$C(O)R^a$, or —$C(O)NHR^a$ group in the para position; or a pharmaceutically acceptable salt thereof.

21. The compound according to claim 2 of the formula (V)

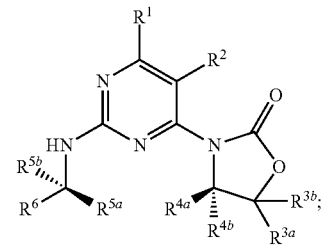

(V)

wherein $R^{4a}$ is phenyl and $R^{4b}$ is hydrogen; or a pharmaceutically acceptable salt thereof.

22. The compound according to claim 1 selected from the group consisting of:
(S)-4-isopropy-3-(2-(((S)-1-(4-(2-yl)phenyl)ethyl)amino)pyrimidin-4-yl)oxazolidin-2-one;
N-(4-((S)-1-(4-((S)-4-isopropyl-2-oxooxazolidin-3-yl)pyrimidin-2-ylamino)ethyl)phenyl)cyclohexanecarboxamide;
(S)-3-(2-(((S)-1-(3-fluoro-4-((4-methylpiperazin-1-yl)methyl)phenyl)ethyl)amino)pyrimidin-4-yl)-4-isopropyloxazolidin-2-one;
(S)-4-isopropyl-3-(2-(((S)-1-(4-((3,3,4-trimethylpiperazin-1-yl)methyl)phenyl)ethyl)amino)pyrimidin-4-yl)oxazolidin-2-one;
2-fluoro-N-(4-hydroxy-4-methylcyclohexyl)-4-((S)-1-((4-((S)-4-isopropyl-2-oxooxazolidin-3-yl)pyrimidin-2-yl)amino)ethyl)benzamide;
(S)-3-(2-((S)-1-(4-((4-amino-4-methylpiperidin-1-yl)methyl)phenyl)ethylamino)pyrimidin-4-yl)-4-isopropyloxazolidin-2-one;
(S)-3-(2-((S)-1-(4-((4-(dimethylamino)piperidin-1-yl)methyl)phenyl)ethylamino)pyrimidin-4-yl)-4-isopropyloxazolidin-2-one;
(S)-4-isopropyl-3-(2-((S)-1-(4-((4-methylpiperazin-1-yl)methyl)phenyl)ethylamino)pyrimidin-4-yl)oxazolidin-2-one;
(S)-4-isopropyl-4-methyl-3-(2-((S)-1-(4-((4-methylpiperazin-1-yl)methyl)phenyl)ethylamino)pyrimidin-4-yl)oxazolidin-2-one;
(S)-4-isopropyl-3-(2-((S)-1-(6-phenylpyridin-3-yl)ethylamino)pyrimidin-4-yl)oxazolidin-2-one;
(S)-3-(2-((S)-1-(4-benzoylphenyl)ethylamino)pyrimidin-4-yl)-4-isopropyloxazolidin-2-one;
(S)-4-isopropyl-3-(2-(((S)-1-(5-phenyl-1,3,4-thiadiazol-2-yl)ethyl)amino) pyrimidin-4-yl)oxazolidin-2-one;
(4S)-4-isopropyl-3-(2-(1-(5-phenylpyrimidin-2-yl)ethylamino)pyrimidin-4-yl)oxazolidin-2-one;
3-(5-fluoro-2-((1-(5-(4-fluoro-3-methylphenyl)pyridin-2-yl)ethyl)amino)pyrimidin-4-yl)oxazolidin-2-one;
(S)-4-isopropyl-3-(2-(((S)-1-(1-(3-methoxyphenyl)-1H-pyrazol-4-yl)ethyl)amino)pyrimidin-4-yl)oxazolidin-2-one;

(S)-3-(2-(((S)-1-(5-(4-fluorophenyl)-1,3,4-oxadiazol-2-yl)ethyl)amino)pyrimidin-4-yl)-4-isopropyloxazolidin-2-one;

(S)-3-(2-(((S)-1-(3-(4-chlorophenyl)-1,2,4-oxadiazol-5-yl)ethyl)amino)pyrimidin-4-yl)-4-isopropyloxazolidin-2-one;

(S)-4-isopropyl-3-(2-(((S)-1-(3-(m-tolyl)-1,2,4-oxadiazol-5-yl)ethyl)amino)pyrimidin-4-yl)oxazolidin-2-one;

(S)-3-(2-(((S)-1-(3-(4-fluorophenyl)-1,2,4-oxadiazol-5-yl)ethyl)amino)pyrimidin-4-yl)-4-isopropyloxazolidin-2-one;

(S)-3-(2-((S)-1-(5-(4-fluoro-2-methylphenyl)pyrimidin-2-yl)ethylamino)pyrimidin-4-yl)-4-isopropyloxazolidin-2-one;

(S)-4-Isopropyl-3-{2-[(3-p-tolyl-[1,2,4]oxadiazol-5-ylmethyl)-amino]-pyrimidin-4-yl}-oxazolidin-2-one;

(S)-4-isopropyl-3-(2-((S)-1-(4-(1-methyl-1H-pyrazol-4-yl)phenyl)ethylamino)pyrimidin-4-yl)oxazolidin-2-one;

(S)-3-(2-((S)-1-(2-fluoro-4-isopropylphenyl)ethylamino)pyrimidin-4-yl)-4-isopropyloxazolidin-2-one;

(S)-3-(2-((S)-1-(4-isobutoxy-3-methylphenyl)ethylamino)pyrimidin-4-yl)-4-isopropyloxazolidin-2-one;

(S)-3-(2-(((S)-1-(4-isobutoxyphenyl)ethyl)amino)pyrimidin-4-yl)-4-isopropyloxazolidin-2-one;

(S)-3-(5-fluoro-2-(((S)-1-(4-isobutoxyphenyl)ethyl)amino)pyrimidin-4-yl)-4-isopropyloxazolidin-2-one;

2-fluoro-N-(trans-4-hydroxycyclohexyl)-4-((S)-1-(4-((S)-4-isopropyl-2-oxooxazolidin-3-yl)pyrimidin-2-ylamino)ethyl)benzamide;

(S)-3-(5-fluoro-2-((S)-1-(3-fluoro-4-(piperidine-1-carbonyl)phenyl)ethylamino)pyrimidin-4-yl)-4-isopropyloxazolidin-2-one;

N-cyclohexyl-2-fluoro-4-((S)-1-(5-fluoro-4-((S)-4-isopropyl-2-oxooxazolidin-3-yl)pyrimidin-2-ylamino)ethyl)benzamide;

N-cyclohexyl-2-fluoro-4-((S)-1-(4-((S)-4-isopropyl-2-oxooxazolidin-3-yl)pyrimidin-2-ylamino)ethyl)benzamide; and (S)-3-(5-fluoro-2-((S)-1-(2-fluoro-4-(trifluoromethyl)phenyl)ethylami no)pyrimidin-4-yl)-4-isopropyloxazolidin-2-one; or a pharmaceutically acceptable salt thereof.

23. The compound according to claim 1 selected from the group consisting of:

(S)-3-(2-(((S)-1-(3-fluoro-4-((3,3,4-trimethylpiperazin-1-yl)methyl)phenyl)ethyl)amino)pyrimidin-4-yl)-4-isopropyloxazolidin-2-one;

(S)-3-(2-(((S)-1-(4-((4,4-difluoropiperidin-1-yl)methyl)phenyl)ethyl)amino)pyrimidin-4-yl)-4-isopropyloxazolidin-2-one;

(S)-3-(5-fluoro-2-(1-(4-phenoxyphenyl)ethylamino)pyrimidin-4-yl)oxazolidin-2-one;

(S)-3-(2-((S)-1-(4-(4-fluorophenoxy)phenyl)ethylamino)pyrimidin-4-yl)-4-isopropyloxazolidin-2-one;

(S)-3-(2-((S)-1-(4-(((2S,6R)-2,6-dimethylmorpholino)methyl)phenyl)ethylamino)pyrimidin-4-yl)-4-isopropyloxazolidin-2-one;

(S)-3-(2-(((S)-1-(3-(4-chlorophenyl)-1,2,4-oxadiazol-5-yl)ethyl)amino)pyrimidin-4-yl)-4-isopropyloxazolidin-2-one;

(S)-3-(2-(((S)-1-(5-(4-chlorophenyl)-1,2,4-oxadiazol-3-yl)ethyl)amino)pyrimidin-4-yl)-4-isopropyloxazolidin-2-one;

(S)-3-(2-((S)-1-(5-(4-fluoro-3-methylphenyl)pyridin-2-yl)ethylamino)pyrimidin-4-yl)-4-isopropyloxazolidin-2-one;

(S)-3-(2-((S)-1-(5-(4-fluorophenoxy)pyrimidin-2-yl)ethylamino)pyrimidin-4-yl)-4-isopropyloxazolidin-2-one;

(S)-3-(2-((S)-1-(5-(4-fluorophenoxy)pyrazin-2-yl)ethylamino)pyrimidin-4-yl)-4-isopropyloxazolidin-2-one;

(S)-4-isopropyl-3-(2-((S)-1-(5-(3-(trifluoromethyl)phenyl)pyrimidin-2-yl)ethylamino)pyrimidin-4-yl)oxazolidin-2-one; and (S)-3-(2-((S)-1-(5-(4-fluoro-3-methylphenyl)pyrimidin-2-yl)ethylamino)pyrimidin-4-yl)-4-isopropyloxazolidin-2-one; or a pharmaceutically acceptable salt thereof.

24. The compound according to claim 1 selected from the group consisting of:

(S)-3-(2-(1-(3-(4-chlorophenyl)-1,2,4-oxadiazol-5-yl)ethylamino)-5-fluoropyrimidin-4-yl)-4,4-dimethyloxazolidin-2-one;

(S)-3-(6-chloro-2-(1-(3-(4-chlorophenyl)-1,2,4-oxadiazol-5-yl)ethylamino)pyrimidin-4-yl)oxazolidin-2-one;

(S)-3-(2-((S)-1-(2-fluoro-4-(1-methylcyclopropyl)phenyl)ethylamino) pyrimidin-4-yl)-4-isopropyloxazolidin-2-one;

(S)-3-(2-((S)-1-(2-fluoro-4-(trifluoromethyl)phenyl)ethylamino)pyrimidin-4-yl)-4-isopropyloxazolidin-2-one;

2-chloro-N-cyclopentyl-4-((S)-1-(4-((S)-4-isopropyl-2-oxooxazolidin-3-yl)pyrimidin-2-ylamino)ethyl)benzamide;

(S)-3-(2-((S)-1-(4-((3,3-difluoropiperidin-1-yl)methyl)phenyl)ethylamino)pyrimidin-4-yl)-4-isopropyloxazolidin-2-one;

(S)-3-(2-((S)-1-(4-(4,7-diazaspiro[2.5]octan-4-ylmethyl)phenyl)ethylamino)pyrimidin-4-yl)-4-isopropyloxazolidin-2-one;

(S)-3-(2-((S)-1-(4-((4-acetylpiperazin-1-yl)methyl)phenyl)ethylamino)pyrimidin-4-yl)-4-isopropyloxazolidin-2-one;

(S)-3-(2-(((S)-1-(4-isobutoxyphenyl)ethyl)amino)pyrimidin-4-yl)-4-isopropyloxazolidin-2-one;

(S)-3-(5-fluoro-2-(((S)-1-(4-isobutoxyphenyl)ethyl)amino)pyrimidin-4-yl)-4-isopropyloxazolidin-2-one; and 2-fluoro-N-(trans-4-hydroxycyclohexyl)-4-((S)-1-(4-((S)-4-isopropyl-2-oxooxazolidin-3-yl)pyrimidin-2-ylamino)ethyl)benzamide; or a pharmaceutically acceptable salt thereof.

25. The compound according to claim 1 wherein each $R^1$ and $R^2$ is independently hydrogen, deuterium, halo, hydroxyl, $NH_2$, aryl, heteroaryl, or optionally substituted $C_{1-4}$ alkyl,
   wherein said $C_{1-4}$ alkyl is optionally substituted with one to three substituents each independently selected from the group consisting of: halo, hydroxyl, and $NH_2$;

$R^{3a}$ is hydrogen, deuterium, $C_{1-6}$ alkyl, phenyl, or benzyl and $R^{3b}$ is hydrogen, deuterium, or $C_{1-6}$ alkyl; or $R^{3a}$ and $R^{3b}$ are joined together forming an optionally substituted 3-7 membered cycloalkyl ring or an optionally substituted 4-7 membered heterocyclic ring,
   wherein said cycloalkyl and heterocyclic rings are each optionally substituted with one or two substituents each independently selected from the group consisting of: halo, hydroxyl, oxo, $NH_2$, and $C_{1-3}$ alkyl;

$R^{4a}$ is hydrogen, $C_{1-6}$ alkyl, optionally substituted phenyl, optionally substituted benzyl, optionally substituted heteroaryl, or methylene-dibenzene,
   wherein said phenyl, benzyl, and heteroaryl rings are optionally substituted with one to three substituents each independently selected from the group consisting of: halo, hydroxyl, cyano, nitro, $C_{1-3}$ alkoxy, $C_{1-3}$ haloalkyl, $C_{1-3}$ haloalkoxy, $C_{1-6}$ alkyl, $C_{3-6}$ cycloalkyl, 5-6 membered heteroaryl, 5-6 membered heterocyclic, phenoxy, $COOR^b$, $SO_2R^b$, $NHC(O)R^b$, and $NR^bR^b$ and $R^{4b}$ is hydrogen, deuterium, or $C_{1-3}$ alkyl; or $R^{4a}$ and $R^{4b}$ are joined together forming an optionally substituted 3-7 membered cycloalkyl ring or an optionally substituted 4-7 membered heterocyclic ring, wherein said cycloalkyl and heterocyclic rings are optionally substituted with one or two substituents each independently selected from the group consisting of: halo, hydroxyl, oxo, $NH_2$, and $C_{1-3}$ alkyl, provided that only one of $R^{3a}$ and $R^{3b}$ and $R^{4a}$ and $R^{4b}$ are joined together forming a ring;

$R^{5a}$ is hydrogen or deuterium;

$R^{5b}$ is hydrogen, deuterium, methyl, ethyl, $CD_3$, $CF_3$, $CH_2F$, or $CHF_2$ and $R^6$ is optionally substituted $C_{1-6}$ alkyl, optionally substituted aryl, optionally substituted heteroaryl, optionally substituted heterocyclic, or optionally substituted $C_{5-10}$ cycloalkyl, wherein said $C_{1-6}$ alkyl is optionally substituted with one substituent selected from the group consisting of hydroxyl, $C_{1-3}$ alkoxy and $-OR^a$;

wherein said aryl, heteroaryl, heterocyclic and $C_{5-10}$ cycloalkyl are optionally substituted with one to three substituents each independently selected from the group consisting of: halo; hydroxyl; cyano; nitro; $C_{1-3}$ alkoxy; $C_{1-3}$ haloalkyl; $C_{1-3}$ haloalkoxy; $C_{1-6}$ alkyl; $C_{3-6}$ cycloalkyl; phenyl optionally substituted with one to three substituents each independently selected from the group consisting of: halo, hydroxyl, cyano, nitro, $C_{1-3}$ alkoxy, $C_{1-3}$ haloalkyl, $C_{1-3}$ haloalkoxy, $C_{1-6}$ alkyl, $C_{3-6}$ cycloalkyl, 5-6 membered heteroaryl, 5-6 membered heterocyclic, phenoxy, $COOR^b$, $SO_2R^b$, $NHC(O)R^b$, and $NR^bR^b$; 5-6 membered heteroaryl; 5-6 membered heterocyclic optionally substituted with one to three substituents each independently selected from the group consisting of: halo, hydroxyl, oxo, $NH_2$, and $C_{1-3}$ alkyl; $-CH_2R^a$; $-OR^a$; $-C(O)R^a$; $-NR^aR^b$; $-COOR^a$; $-SO_2R^a$; $NHC(O)R^a$; and $-SO_2NR^bR^b$; or $R^{5b}$ and $R^6$ are joined together forming an optionally substituted $C_{3-7}$ cycloalkyl group or an optionally substituted group of formula (a):

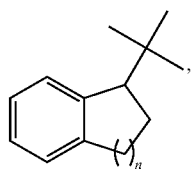

(a)

wherein n is 1, 2, or 3 and said $C_{3-7}$ cycloalkyl and group of formula (a) are optionally substituted with one to three substituents each independently selected from the group consisting of: halo, hydroxyl, cyano, nitro, $C_{1-3}$ alkoxy, $C_{1-3}$ haloalkyl, $C_{1-3}$ haloalkoxy, $C_{1-6}$ alkyl, $C_{3-6}$ cycloalkyl, 5-6 membered heteroaryl, 5-6 membered heterocyclic, benzyloxy, $COOR^b$, $SO_2R^b$, $NHC(O)R^b$, and $NR^bR^b$;

each $R^a$ is independently optionally substituted phenyl, optionally substituted heteroaryl, or optionally substituted 4-7 membered heterocyclic, wherein said phenyl and heteroaryl are optionally substituted with one to three substituents each independently selected from the group consisting of halo, hydroxyl, cyano, nitro, $C_{1-3}$ alkoxy, $C_{1-3}$ haloalkyl, $C_{1-3}$ haloalkoxy, and $C_{1-3}$ alkyl, wherein said 4-7 membered heterocyclic is optionally substituted with one to three substituents each independently selected from the group consisting of halo, hydroxyl, oxo, $C_{1-3}$ alkoxy, $C_{1-3}$ haloalkyl, $C_{1-3}$ haloalkoxy, and $C_{1-3}$ alkyl; and each $R^b$ is independently hydrogen or $C_{1-6}$ alkyl; or a pharmaceutically acceptabble salt thereof.

26. The compound according to claim 25 wherein $R^1$ is hydrogen, fluoro, chloro, or methyl;

$R^2$ is hydrogen;

$R^{3a}$ is hydrogen, methyl, or phenyl;

$R^{3b}$ is hydrogen or methyl;

$R^{4a}$ is hydrogen, $C_{1-4}$ alkyl, optionally substituted phenyl, optionally substituted benzyl, optionally substituted heteroaryl, or methylene-dibenzene;

$R^{4b}$ is hydrogen or methyl;

$R^{5a}$ is H; and $R^{5b}$ is hydrogen, methyl, ethyl, or $CF_3$; or a pharmaceutically acceptable salt thereof.

27. The compound according to claim 26 wherein $R^6$ is isopropyl, optionally substituted aryl, optionally substituted pyrazolyl, optionally substituted pyridinyl, 2,3-dihydrobenzofuranyl, 2,3-dihydrobenzo[b][1,4]dioxinyl, or optionally substituted $C_{5-10}$ cycloalkyl; or a pharmaceutically acceptable salt thereof.

28. A pharmaceutical composition comprising a compound according to claim 1, or a pharmaceutically acceptable salt thereof, and a pharmaceutically acceptable carrier or excipient.

* * * * *